US012606552B2

(12) United States Patent
Tong

(10) Patent No.: US 12,606,552 B2
(45) Date of Patent: Apr. 21, 2026

(54) BIFUNCTIONAL COMPOUND, PREPARATION METHOD THEREFOR, AND USE THEREOF

(71) Applicant: SUZHOU KINTOR PHARMACEUTICALS, INC., Suzhou (CN)

(72) Inventor: Youzhi Tong, New York, NY (US)

(73) Assignee: SUZHOU KINTOR PHARMACEUTICALS, INC., Suzhou (CN)

( * ) Notice: Subject to any disclaimer, the term of this patent is extended or adjusted under 35 U.S.C. 154(b) by 743 days.

(21) Appl. No.: 17/942,094

(22) Filed: Sep. 9, 2022

(65) Prior Publication Data

US 2023/0054270 A1 Feb. 23, 2023

Related U.S. Application Data

(63) Continuation of application No. PCT/CN2021/080167, filed on Mar. 11, 2021.

(30) Foreign Application Priority Data

Mar. 11, 2020 (CN) ......................... 202010165789.1
Dec. 29, 2020 (CN) ......................... 202011593015.5
Mar. 5, 2021 (CN) ......................... 202110246427.X

(51) Int. Cl.
*C07D 417/14* (2006.01)
*A61P 17/10* (2006.01)
*A61P 17/14* (2006.01)
*A61P 35/00* (2006.01)

(52) U.S. Cl.
CPC ............ *C07D 417/14* (2013.01); *A61P 17/10* (2018.01); *A61P 17/14* (2018.01); *A61P 35/00* (2018.01)

(58) Field of Classification Search
None
See application file for complete search history.

(56) References Cited

U.S. PATENT DOCUMENTS 10,584,101 B2 3/2020 Crew et al.
2014/0066425 A1 3/2014 Tong
2015/0291562 A1 10/2015 Crew et al.
2016/0214972 A1 7/2016 Jin et al.
2017/0008904 A1 1/2017 Crew et al.
2017/0281784 A1 10/2017 Wang et al.
2018/0346457 A1 12/2018 Zamboni et al.
2020/0199107 A1 6/2020 Crew et al.

FOREIGN PATENT DOCUMENTS

CN 107428734 7/2016
CN 106458993 2/2017
CN 107428734 A 12/2017
CN 108136044 6/2018
CN 108137507 6/2018
CN 110545853 12/2018
CN 110506039 A 11/2019
CN 110612297 12/2019
CN 110506039 3/2020
CN 110903345 3/2020
WO WO 2012/119559 9/2012
WO WO2016197032 A1 8/2016
WO WO2016197114 A1 8/2016
WO WO2017176708 A1 12/2017
WO WO2019023553 A1 1/2019
WO WO2019148055 A9 1/2019
WO WO2020142228 A1 9/2020

OTHER PUBLICATIONS

Patani and LaVoie "Bioisosterism: A Rational Approach in Drug Design" Chem. Rev. 1996, 96, 3147-3176 (Year: 1996).*
International Search Report issued in International Application No. PCT/CN2021/080167 mailed Jun. 15, 2021.
Han et al. "Discovery of ARD-69 as a Highly Potent Proteolysis Targeting Chimera (PROTAC) Degrader of Androgen Receptor (AR) for the Treatment of Prostate Cancer. J Med Chem," 62(2):941-964 (2019).

* cited by examiner

*Primary Examiner* — Kortney L. Klinkel
*Assistant Examiner* — Donna M Nestor
(74) *Attorney, Agent, or Firm* — pH IP Law

(57) ABSTRACT

The present invention relates to a bifunctional compound, a preparation method therefor, and a use thereof, wherein the bifunctional compound comprises an E3 ubiquitin ligase-binding moiety; a target protein-binding moiety that binds to an androgen receptor; and a linking moiety that links the E3 ubiquitin ligase-binding moiety and the target protein-binding moiety. The bifunctional compound of the present application allows the androgen receptor to be positioned adjacent to the ubiquitin ligase, so as to achieve the degradation or inhibition of the androgen receptor.

13 Claims, 5 Drawing Sheets

BIFUNCTIONAL COMPOUND, PREPARATION METHOD THEREFOR, AND USE THEREOF

This application is a continuation of PCT Application No. PCT/CN2021/080167, filed Mar. 11, 2021, entitled "Bifunctional compound, preparation method therefor, and use thereof", which claims priority to Chinese Patent Application No. 202010165789.1, titled "Bifunctional compound, preparation method therefor, and use thereof" and filed with the China National Intellectual Property Administration on Mar. 11, 2020, Chinese Patent Application No. 202011593015.5, titled "Bifunctional compound, preparation method therefor, and use thereof" and filed with the China National Intellectual Property Administration on Dec. 29, 2020, and Chinese Patent Application No. 202110246427.X, titled "Bifunctional compound, preparation method therefor, and use thereof" and filed with the China National Intellectual Property Administration on Mar. 5, 2021. The contents of each of the above-referenced priority applications are hereby incorporated by reference.

FIELD

The present invention relates to the technical field of medicine, and in particular to a bifunctional compound, a preparation method therefor, and a use thereof, wherein the bifunctional compound comprises an E3 ubiquitin ligase-binding moiety; a target protein-binding moiety that binds to an androgen receptor; and a linking moiety that connects the E3 ubiquitin ligase-binding moiety and the target protein-binding moiety. The bifunctional compound of the present application allows the androgen receptor to be positioned adjacent to the ubiquitin ligase, so as to achieve the degradation or inhibition of the androgen receptor.

BACKGROUND

The androgen receptor (AR) belongs to the nuclear hormone receptor family that is activated by androgen. In the absence of androgens, AR is bound by heat shock protein 90 (Hsp90) in the cytosol. When androgen binds AR, its conformation changes to release AR from Hsp90 and expose the nuclear localization signal (NLS). The latter enables the translocation of AR into the nucleus, where AR acts as a transcription factor to promote the expression of genes responsible for male sex characteristics. AR deficiency can lead to androgen insensitivity syndrome.

Although AR is responsible for the development of male sex characteristics, it is also a well-documented oncogene in some forms of cancer, such as prostate cancer. One commonly measured target gene for AR activity is the secreted prostate specific antigen (PSA) protein. Current treatment strategies for prostate cancer comprise two options. The first strategy relies on androgen reduction, and the second strategy aims at inhibition of AR function. Despite the development of effective targeted therapies, most patients develop drug resistance, and their disease continues to progress. An alternative for the treatment of prostate cancer involves eliminating the AR protein. Because AR is a key driver of tumorigenesis in many forms of prostate cancer, its elimination would result in a therapeutically beneficial response.

There continues to be a need in the art to find effective therapeutic modalities for diseases and disorders associated with aberrant AR regulation or activity (e.g., cancer, prostate cancer, and Kennedy's disease), especially those capable of achieving targeted ubiquitination and degradation of androgen receptor (AR) to treat diseases while reducing or avoiding the side effects of oral androgen signaling pathway inhibitors (as AR is responsible for the development of male sex characteristics).

SUMMARY

The present invention provides a bifunctional compound whose function is to recruit endogenous proteins to E3 ubiquitin ligase for degradation. Specifically, the present invention provides bifunctional compounds or proteolytic targeted chimeric (PROTAC) compounds for use as modulators of targeted ubiquitination and degradation of the androgen receptor (AR). Additionally, the present invention provides methods of treating or ameliorating disease conditions (including cancers, e.g., prostate cancer and Kennedy's disease) using an effective amount of the compounds as described herein.

In one aspect, the present invention provides compounds that function to recruit endogenous proteins (e.g., AR protein) to E3 ubiquitin ligases for ubiquitination and degradation.

In some certain embodiments, the bifunctional compounds represented by formula (I) or pharmaceutically acceptable salts, solvates, stereoisomers and prodrugs thereof:

ABM-L-ULM (I), wherein ABM has the structure of formula (IV), wherein ∿∿ represents the point of attachment of the linking moiety:

(IV)

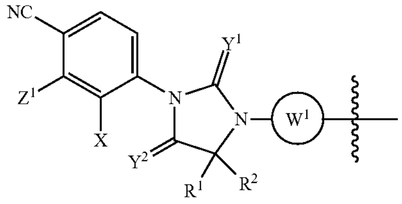

$Z^1$ is selected from: hydrogen, halogen, cyano, $C_{1-4}$ alkyl optionally substituted with one or more halogens, and $C_{1-4}$ alkoxy optionally substituted with one or more halogens;

X is selected from: halogen, hydroxy, cyano and $C_{1-4}$ alkoxy optionally substituted with one or more halogens;

$Y^1$ and $Y^2$ are each independently selected from: O, S;

$R^1$ and $R^2$ are each independently selected from: H, halogen, Ci-s alkyl or Ci-s alkoxy optionally substituted with halogen or Ci-s alkoxy, or $R^1$ and $R^2$ together with the atoms to which they are attached form 3 to 8 membered rings containing 0 to 2 heteroatoms;

$W^1$ is selected from: chemical bonds, $C_{6-10}$ aryl, 5-10 membered heteroaryl, bi-$C_{6-10}$ aryl or bi-5-10 membered heteroaryl, each optionally substituted with 1-10 $R^{W1}$;

each $R^{W1}$ is independently selected from: H, halogen, cyano, hydroxyl, amino, —$COOR^{W11}$, —$CONR^{W11}R^{W12}$, $C_{1-6}$ alkyl or $C_{1-6}$ alkoxy optionally substituted with halogen, hydroxyl, cyano and $C_{1-6}$ alkoxy, $C_{3-6}$ cycloalkyl, $C_{4-6}$ cycloheteroalkyl, $C_{6-10}$ aryl or 5-10 membered heteroaryl; $R^{W11}$ and $R^{W12}$ are each independently selected from: hydrogen, $C_{1-6}$ alkyl or $C_{3-6}$ cycloalkyl optionally substituted by halogen;

L is the chemical linking moiety connecting ABM and ULM;

ULM is the cerebron E3 ubiquitin ligase binding moiety (CLM) or the VHLE3 ligase binding moiety (VLM).

In some certain embodiments, the bifunctional compounds are bifunctional compounds of the following structures of formula I, and salts, polymorphs, and prodrugs thereof:

ABM-L-ULM (I), wherein ABM is the androgen receptor (AR) binding moiety, and L is the chemical linking moiety linking the ABM and ULM, and ULM is the E3 ligase binding moiety, e.g., cerebron E3 ubiquitin ligase binding moiety (CLM) or VHLE3 ligase binding moiety (VLM).

The ABM has the structure of formula (IV), wherein represents the point of attachment of the linking moiety:

(IV)

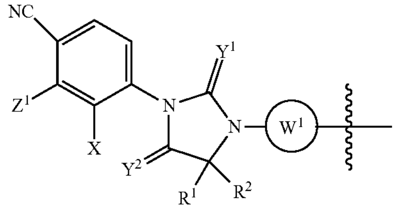

wherein:

$Z^1$ is selected from: hydrogen, halogen, cyano, $C_{1-4}$ alkyl optionally substituted with one or more halogens, and $C_{1-4}$ alkoxy optionally substituted with one or more halogens;

X is selected from: halogen, hydroxy, cyano and $C_{1-4}$ alkoxy optionally substituted with one or more halogens;

$Y^1$ and $Y^2$ are each independently selected from: O, S;

$R^1$ and $R^2$ are each independently selected from: hydrogen, halogen, $C_{1-6}$ alkyl or $C_{1-6}$ alkoxy optionally substituted with halogen or $C_{1-6}$ alkoxy, or $R^1$ and $R^2$ together with the atoms to which they are attached form 3 to 8 membered rings containing 0 to 2 heteroatoms;

$W^1$ is selected from: chemical bonds, $C_{6-10}$ aryl, 5-10 membered heteroaryl, bi-$C_{6-10}$ aryl or bi-5-10 membered heteroaryl, each optionally substituted with 1-10 $R^{W1}$;

each $R^{W1}$ is independently selected from: hydrogen, halogen, cyano, hydroxyl, amino, $C_{1-6}$ alkyl or $C_{1-6}$ alkoxy optionally substituted with halogen, hydroxyl, cyano and $C_{1-6}$ alkoxy, $C_{3-6}$ cycloalkyl, $C_{4-6}$ cycloheteroalkyl, $C_{6-10}$ aryl or 5-10 membered heteroaryl.

In some certain embodiments, $Z_1$ is selected from halogen, cyano, methyl, $CH_2F$, $CHF_2$, $CF_3$, methoxy and $CF_3O$;

X is selected from: halogen, hydroxyl, cyano, $C_{1-3}$ alkoxy and $CF_3O$;

$Y^1$ and $Y^2$ are each independently selected from: O, S;

$R^1$ and $R^2$ are each independently selected from: $C_{1-6}$ alkyl or $C_{1-6}$ alkoxy optionally substituted with halogen and $C_{1-6}$ alkoxy, or $R^1$ and $R^2$ together with the atoms to which they are attached form $C_{3-6}$ cycloalkyl;

$W^1$ is selected from: chemical bonds, $C_{6-10}$ aryl, 5-10 membered heteroaryl, bi-$C_{6-10}$ aryl or bi-5-10 membered heteroaryl, each optionally substituted with 1, 2 or 3 $R^{W1}$; and each $R^{W1}$ is independently selected from: hydrogen, halogen, cyano, and $C_{1-6}$ alkyl or $C_{1-6}$ alkoxy optionally substituted with halogen, hydroxyl and cyano.

In some certain embodiments of the present invention, $W^1$ is selected from: chemical bonds, phenyl, pyridyl, pyrimidinyl, pyrazinyl and pyridazinyl, each optionally substituted with 1, 2 or 3 $R^{W1}$; and each $R^{W1}$ is independently selected from: hydrogen, halogen, cyano, $C_{1-6}$ alkyl or $C_{1-6}$ alkoxy optionally substituted with halogen, hydroxyl and cyano, —CO-$OR^{W11}$, —$CONR^{W11}R^{W12}$; $R^{W11}$ and $R^{W12}$ are each independently selected from: hydrogen, $C_{1-6}$ alkyl optionally substituted with halogen.

In some certain embodiments, $Z_1$ is selected from: halogen, cyano, methyl, $CH_2F$, $CHF_2$, $CF_3$, methoxy and $CF_3O$;

X is selected from: halogen, hydroxyl, cyano, $C_{1-3}$ alkoxy and $CF_3O$;

$Y^1$ and $Y^2$ are each independently selected from: O, S;

$R^1$ and $R^2$ are each independently selected from: $C_{1-6}$ alkyl or $C_{1-6}$ alkoxy optionally substituted with halogen and $C_{1-6}$ alkoxy, or $R^1$ and $R^2$ together with the atoms to which they are attached form $C_{3-6}$ cycloalkyl;

$W^1$ is selected from: chemical bonds, $C_{6-10}$ aryl, 5-10 membered heteroaryl, bi-$C_{6-10}$ aryl or bi-5-10 membered heteroaryl, each optionally substituted by 1, 2 or 3 $R^{W1}$; and each $R^{W1}$ is independently selected from: hydrogen, halogen, cyano, $C_{1-6}$ alkyl or $C_{1-6}$ alkoxy optionally substituted with halogen, hydroxyl and cyano, —CO-$OR^{W11}$, —$CONR^{W11}R^{W12}$; $R^{W11}$ and $R^{W12}$ are each independently selected from: hydrogen, $C_{1-6}$ alkyl optionally substituted with halogen.

In some certain embodiments, $Z_1$ is selected from: halogen, cyano, methyl, $CH_2F$, $CHF_2$, $CF_3$, methoxy and $CF_3O$;

X is selected from: halogen;

$Y^1$ and $Y^2$ are each independently selected from: O, S;

$R^1$ and $R^2$ are each independently selected from: methyl, or $R^1$ and $R^2$ together with the atoms to which they are attached form $C_{3-6}$ cycloalkyl;

$W^1$ is selected from: chemical bonds,

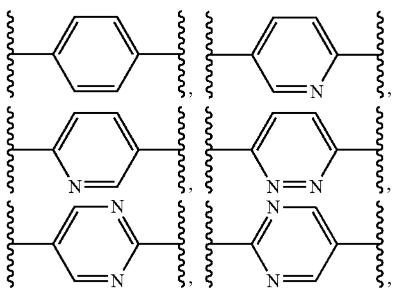

each optionally substituted by 1, 2 or 3 $R^{W1}$; and each $R^{W1}$ is independently selected from: hydrogen, halogen, cyano, $C_{1-3}$ alkyl or $C_{1-3}$ alkoxy optionally substituted with halogen.

In some certain embodiments, $Z_1$ is selected from: halogen, cyano, methyl, $CH_2F$, $CHF_2$, $CF_3$, methoxy and $CF_3O$;

X is selected from: halogen;

$Y^1$ and $Y^2$ are each independently selected from: O, S;

$R^1$ and $R^2$ are each independently selected from: methyl, or $R^1$ and $R^2$ together with the atoms to which they are attached form $C_{3-6}$ cycloalkyl;

$W^1$ is selected from: chemical bonds,

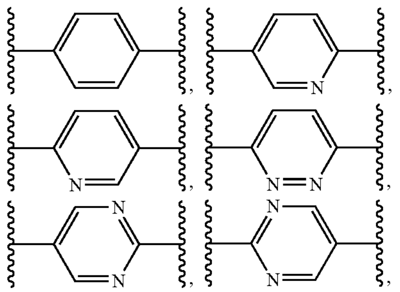

each optionally substituted by 1, 2 or 3 $R^{W1}$; and each $R^{W1}$ is independently selected from: hydrogen, halogen, cyano, $C_{1-3}$ alkyl or $C_{1-3}$ alkoxy optionally substituted with halogen, —$COOR^{W11}$, —$CONR^{W11}R^{W12}$; $R^{W11}$ and $R^{W12}$ are each independently selected from: hydrogen, $C_{1-6}$ alkyl optionally substituted with halogen.

In some certain embodiments, $Z_1$ is selected from: $CF_3$;

X is selected from: F;

$Y^1$ and $Y^2$ are each independently selected from: O, S;

$R^1$ and $R^2$ are each independently selected from: methyl, or $R^1$ and $R^2$ together with the atoms to which they are attached form $C_{3-4}$ cycloalkyl;

$W^1$ is selected from: chemical bonds,

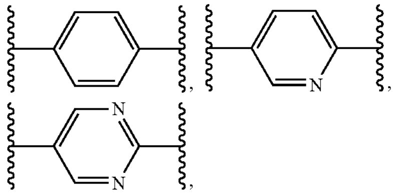

each optionally substituted by 1, 2 or 3 $R^{W1}$; and each $R^{W1}$ is independently selected from: hydrogen, halogen, cyano, $C_{1-3}$ alkyl or $C_{1-3}$ alkoxy optionally substituted with F.

In some certain embodiments, $Z_1$ is selected from: $CF_3$;

X is selected from: F;

$Y^1$ and $Y^2$ are each independently selected from: O, S;

$R^1$ and $R^2$ are each independently selected from: methyl, or $R^1$ and $R^2$ together with the atoms to which they are attached form $C_{3-4}$ cycloalkyl;

$W^1$ is selected from: chemical bonds,

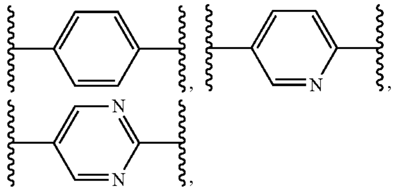

each optionally substituted by 1, 2 or 3 $R^{W1}$; and each $R^{W1}$ is independently selected from: hydrogen, halogen, cyano, $C_{1-3}$ alkyl or $C_{1-3}$ alkoxy optionally substituted with F, and —$CONH_2$ and —$COOC_{1-3}$ alkyl.

In some certain embodiments, ABM is selected from the following fragments of compounds, wherein  represents the point of attachment of the linking moiety:

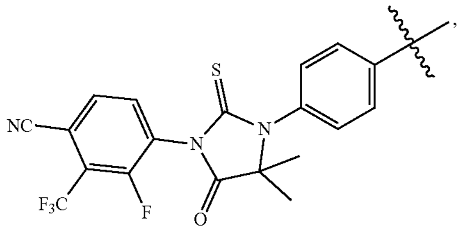

,

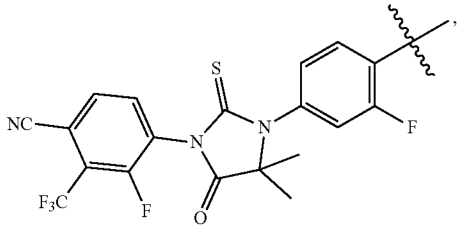

,

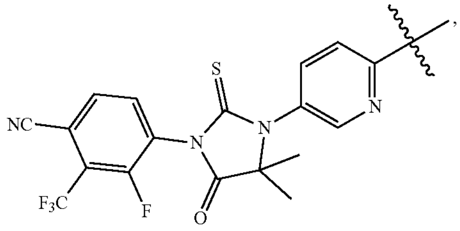

,

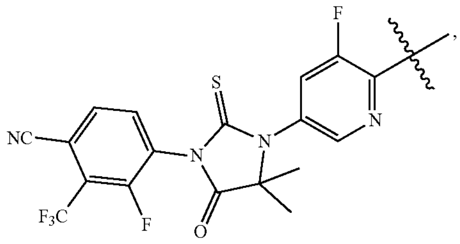

,

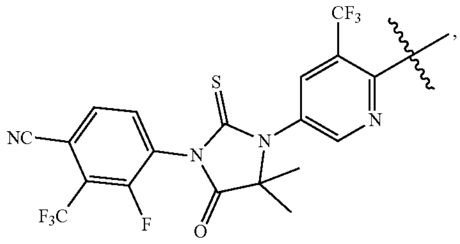

,

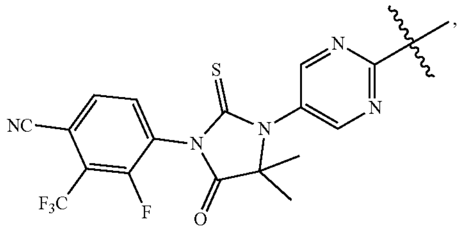

,

-continued

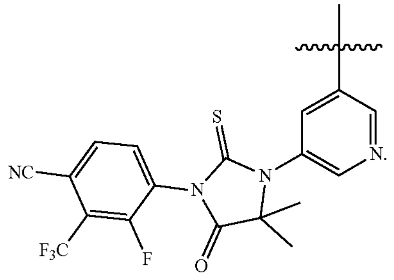

In some certain embodiments, ABM is selected from the following fragments of the compounds, wherein ∿∿∿ represents the point of attachment of the linking moiety:

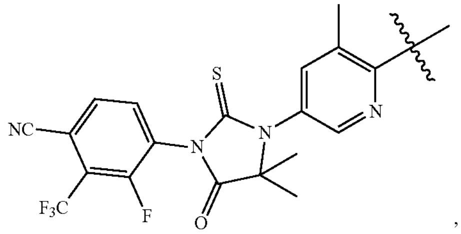

,

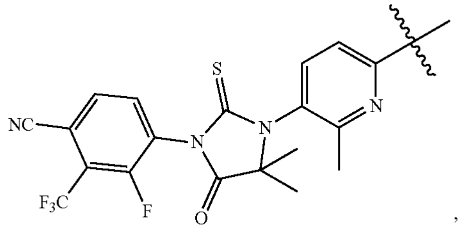

,

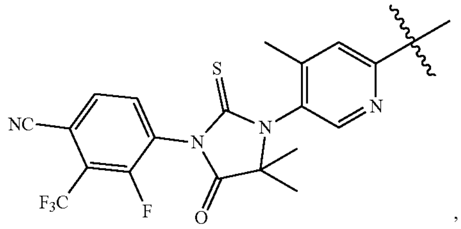

,

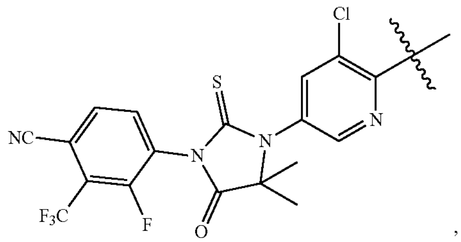

,

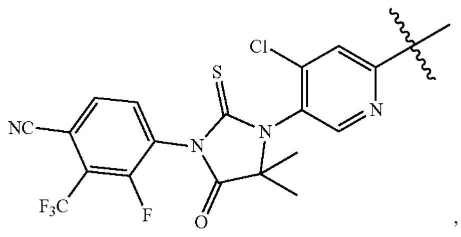

,

-continued

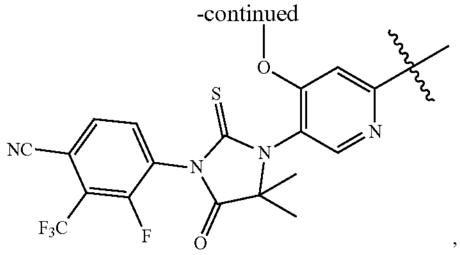

,

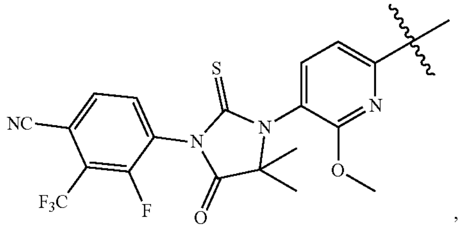

,

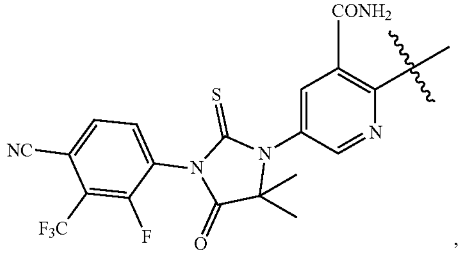

,

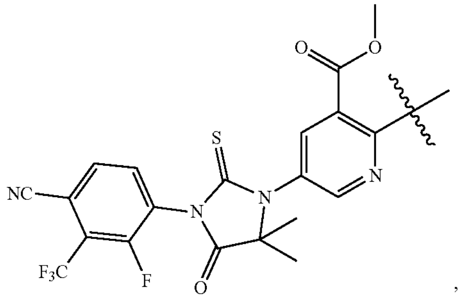

,

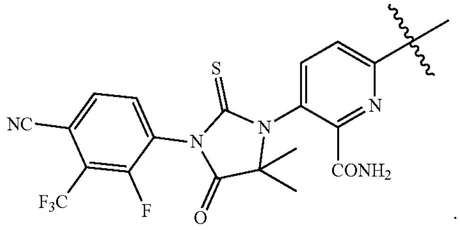

.

In the first aspect, the present invention provides bifunctional compounds having the structure of formula (II), and salts, polymorphs and prodrugs thereof:

ABM-L-CLM (II), wherein ABM is the androgen receptor (AR) binding moiety, L is the chemical linking moiety connecting ABM and CLM, and CLM is the cerebron E3 ubiquitin ligase binding moiety;

wherein, ABM is defined as above.

In some certain embodiments, CLM comprises chemical groups derived from imide, thioimide, amide or thioamide, which binds to the cerebron E3 ubiquitin ligase.

In some certain embodiments, CLM is a phthalimide group or an analog thereof.

In some certain embodiments, CLM is a structural fragment represented by formula (V) or a stereoisomer thereof, wherein ∿∿∿ represents the point of attachment of the linking moiety:

(V)

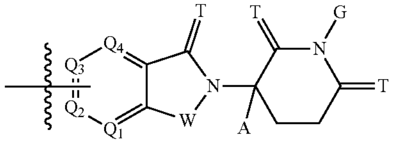

wherein

W is selected from: $CH_2$, $CHR^{11}$, C=O, NH or —N—$C_{1-6}$ alkyl;

each T is independently selected from: O or S;

G is selected from: hydrogen, $C_{1-6}$ alkyl or hydroxyl;

$Q_1$, $Q_2$, $Q_3$ and $Q_4$ are independently selected from: CR' or N;

A is selected from: hydrogen, $C_{1-6}$ alkyl, $C_{3-6}$ cycloalkyl, or halogen;

$R^{11}$ is selected from: halogen, cyano, $C_{1-6}$ alkyl or $C_{1-6}$ alkoxy optionally substituted by halogen, $C_{3-6}$ cycloalkyl, —CONR'R", —OR', or —NR'R";

R' and R" are each independently selected from: hydrogen, halogen, amino, cyano, $C_{1-6}$ alkyl or $C_{1-6}$ alkoxy optionally substituted by halogen, and $C_{3-6}$ cycloalkyl.

In some certain embodiments, W is selected from: $CH_2$, $CHR^{11}$, or C=O;

each T is independently selected from: O or S;

G is selected from: hydrogen or $C_{1-6}$ alkyl;

$Q_1$, $Q_2$, $Q_3$ and $Q_4$ are independently selected from: CH;

A is selected from: hydrogen, $C_{1-6}$ alkyl or halogen;

$R^{11}$ is selected from: halogen, cyano, —$CF_3$, $OCF_3$, methyl, —CONR'R", —OR', or —NR'R";

R' and R" are each independently selected from: hydrogen, halogen, cyano, amino, —$CF_3$, $OCF_3$ or methyl.

In some certain embodiments, CLM is a structural fragment represented by formula (V)-1 or a stereoisomer thereof, wherein ~~~~ represents the point of attachment of the linking moiety:

(V)-1

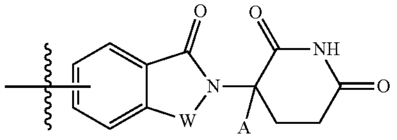

wherein:

W is selected from: $CH_2$ or C=O;

A is selected from: hydrogen or $C_{1-6}$ alkyl.

In some certain embodiments, CLM is a structural fragment represented by formula (V)-2 or (V)-3 or a stereoisomer thereof, wherein ~~~~ represents the point of attachment of the linking moiety:

(V)-2

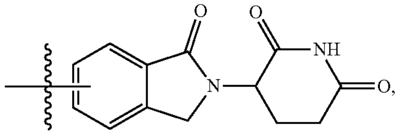

-continued (V)-3

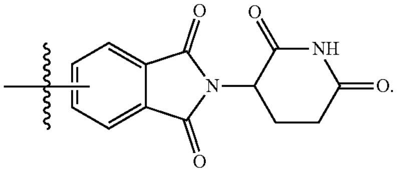

In some certain embodiments, CLM is a fragment of thalidomide, lenalidomide, pomalidomide, or an analog thereof.

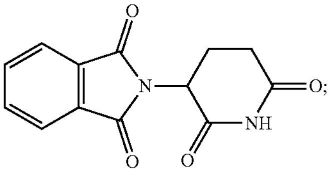

thalidomide

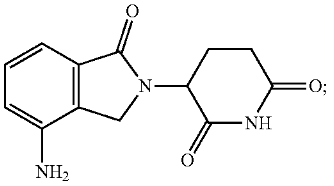

lenalidomide

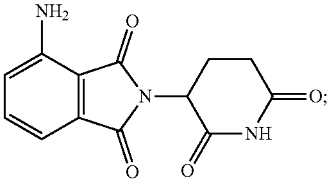

pomalidomide

In an embodiment of the present invention, the linking group (L) is selected from the groups represented by the following general structure:

$—(CH_2)_m—CO—N(R^{31})—(CH_2)_n—N(R^{31})—CO—(CH_2)_o—O—$;

$—(CH_2)_m—CO—N(R^{31})—(CH_2)_n—N(R^{31})—$;

$—(CH_2)_m—CO—N(R^{31})—$;

$—O—(CH_2)_n—N(R^{31})—CO—(CH_2)_o—O—$;

$-Cy-CO—N(R^{31})—(CH_2)_n—N(R^{31})—CO—(CH_2)_o—O—$;

$—C≡C-Cy-(CH_2)_n—N(R^{31})—CO—(CH_2)_o—O—$;

$—O—(CH_2)_n—N(R^{31})—$;

$—C≡C—(Cy)_p-CO—(CH_2)_o—O—$;

$—O-(Cy)_p-CO—(CH_2)_o—O—$;

$—O—(CH_2)_m—CO—N(R^{31})—(CH_2)_n—N(R^{31})—$;

$—(CH_2)_m—CO-Cy-CO—(CH_2)_o—O—$;

$-(Cy)_q-(CH_2)_m—CO—N(R^{31})—(CH_2)_n—N(R^{31})—CO—(CH_2)_o—O—$;

$-(Cy)_q-(CH_2)_m—CO—N(R^{31})—(CH_2)_n—N(R^{31})—$;

$-(Cy)_q-(CH_2)_m—CO—N(R^{31})—$;

$-(Cy)_q-O—(CH_2)_n—N(R^{31})—CO—(CH_2)_o—O—$;

$-(Cy)_q-Cy-CO—N(R^{31})—(CH_2)_n—N(R^{31})—CO—(CH_2)_o—O—$;

$-(Cy)_q-C≡C-Cy-(CH_2)_n—N(R^{31})—CO—(CH_2)_o—O—$;

$-(Cy)_q-O—(CH_2)_n—N(R^{31})—$;

$-(Cy)_q-(Cy)_q-C≡C—(Cy)_p-CO—(CH_2)_o—O—$;

$-(Cy)_q-O-(Cy)_p-CO—(CH_2)_o—O—$;

$-(Cy)_q-O—(CH_2)_m—CO—N(R^{31})—(CH_2)_n—N(R^{31})—$;

$-(Cy)_q-(CH_2)_m—CO-Cy-CO—(CH_2)_o—O—$;

$—(CH_2)_m—O—(CH_2)_n—CO—N(R^{31})—(CH_2)_o—N(R^{31})—CO—(CH_2)_t—O—$;

$—CO—N(R^{31})—(CH_2)_m—N(R^{31})—(CH_2)_n—CO—N(R^{31})—$;

$-(Cy)_q-O—(CH_2)_m—CO—N(R^{31})—(CH_2)_n—N(R^{31})—CO—(CH_2)_t—O—$;

wherein m, n, o, p, q and t are each independently selected from: 0, 1, 2, 3, 4, 5, 6, with the proviso that when said number is zero, no N—O or O—O bonds are present, and each $R^{31}$ is independently selected from group hydrogen, methyl or ethyl, and Cy is selected from $C_{6-10}$ aryl, $C_{3-6}$ heteroaryl, $C_{3-6}$ cycloalkyl, $C_{3-6}$ heterocycloalkyl, preferably

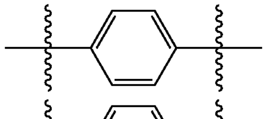,
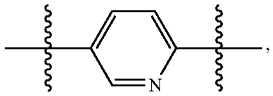, 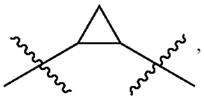,
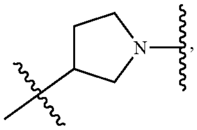, 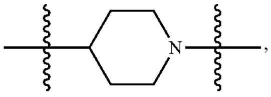,
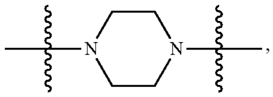, each optionally substituted with 1, 2 or 3 $R^{Cy}$; and each $R^{Cy}$ is independently selected from: hydrogen, halogen, cyano, and $C_{1-3}$ alkyl or $C_{1-3}$ alkoxy optionally substituted with halogen.

In preferred solution of the present invention, the linking group (L) is selected from the groups represented by the following general structure:

$—(CH_2)_m—CO—N(R^{31})—(CH_2)_n—N(R^{31})—CO—(CH_2)_o—O—$;

$—(CH_2)_m—CO—N(R^{31})—(CH_2)_n—N(R^{31})—$;

$—(CH_2)_m—CO—N(R^{31})—$;

$—O—(CH_2)_n—N(R^{31})—CO—(CH_2)_o—O—$;

$-Cy-CO—N(R^{31})—(CH_2)_n—N(R^{31})—CO—(CH_2)_o—O—$;

$—C≡C-Cy-(CH_2)_n—N(R^{31})—CO—(CH_2)_o—O—$;

$—O—(CH_2)_n—N(R^{31})—$;

$—C≡C—(Cy)_p-CO—(CH_2)_o—O—$;

$—O-(Cy)_p-CO—(CH_2)_o—O—$;

$—O—(CH_2)_m—CO—N(R^{31})—(CH_2)_n—N(R^{31})—$;

$—(CH_2)_m—CO-Cy-CO—(CH_2)_o—O—$;

$-(Cy)_q-(CH_2)_m—CO—N(R^{31})—(CH_2)_n—N(R^{31})—CO—(CH_2)_o—O—$;

$-(Cy)_q-(CH_2)_m—CO—N(R^{31})—(CH_2)_n—N(R^{31})—$;

$-(Cy)_q-(CH_2)_m—CO—N(R^{31})—$;

$-(Cy)_q-O—(CH_2)_n—N(R^{31})—CO—(CH_2)_o—O—$;

$-(Cy)_q-Cy-CO—N(R^{31})—(CH_2)_n—N(R^{31})—CO—(CH_2)_o—O—$;

$-(Cy)_q-C≡C-Cy-(CH_2)_n—N(R^{31})—CO—(CH_2)_o—O—$;

$-(Cy)_q-O—(CH_2)_n—N(R^{31})—$;

$-(Cy)_q-(Cy)_q-C≡C—(Cy)_p-CO—(CH_2)_o—O—$;

$-(Cy)_q-O-(Cy)_p-CO—(CH_2)_o—O—$;

$-(Cy)_q-O—(CH_2)_m—CO—N(R^{31})—(CH_2)_n—N(R^{31})—$;

$-(Cy)_q-(CH_2)_m—CO-Cy-CO—(CH_2)_o—O—$;

wherein m, n, o, p, and q are each independently selected from: 0, 1, 2, 3, 4, 5, 6, with the proviso that when said number is zero, no N—O or O—O bonds are present, and each $R^{31}$ is independently selected from group hydrogen, methyl or ethyl, and Cy is selected from $C_{3-6}$ aryl, $C_{3-6}$ heteroaryl, $C_{3-6}$ cycloalkyl, $C_{3-6}$ heterocycloalkyl, preferably

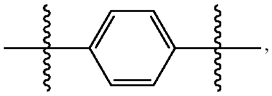,
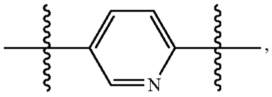, 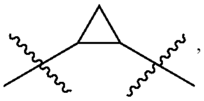,
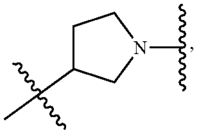, 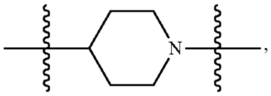,
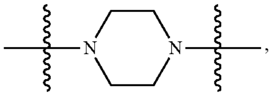, each optionally substituted with 1, 2 or 3 $R^{Cy}$; and each $R^{Cy}$ is independently selected from: hydrogen, halogen, cyano, and $C_{1-3}$ alkyl or $C_{1-3}$ alkoxy optionally substituted with halogen.

In some certain embodiments, the linking group (L) is selected from the groups:

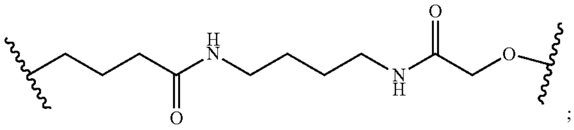;

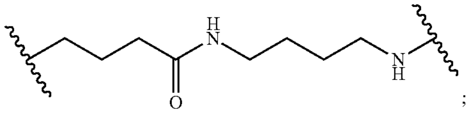;

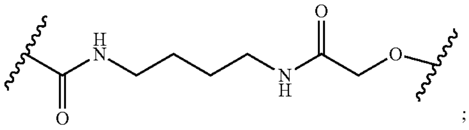;

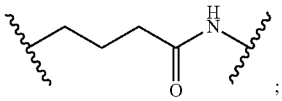;

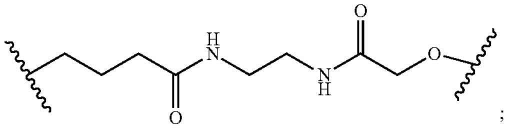;

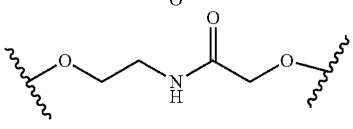;

-continued
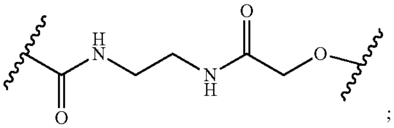
;
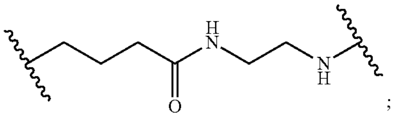
;
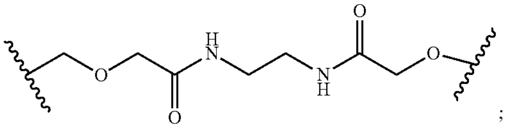
;
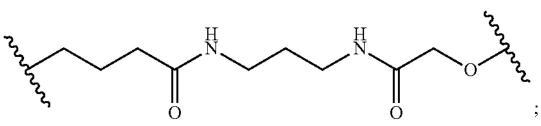
;
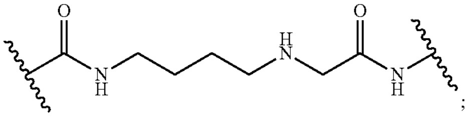
;
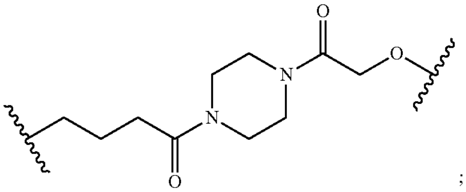
;
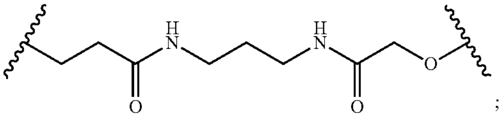
;
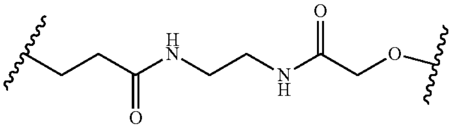
;
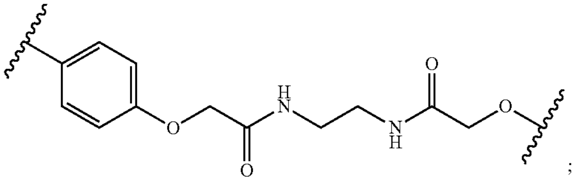
;
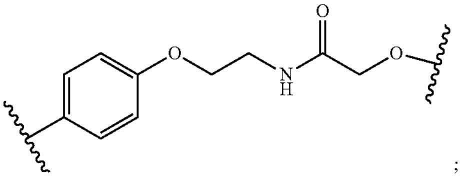
;
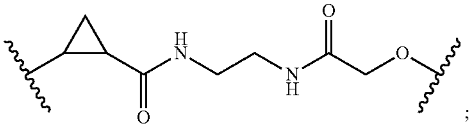
;
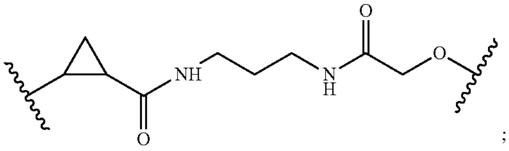
;
-continued
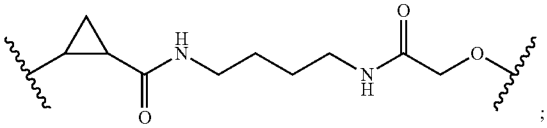
;
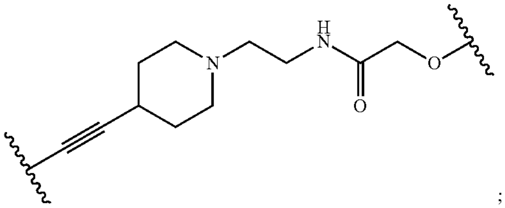
;
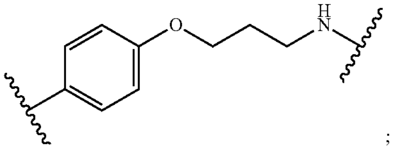
;
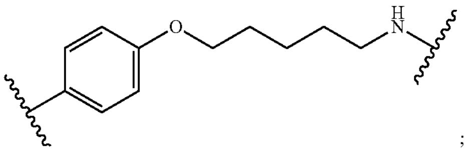
;
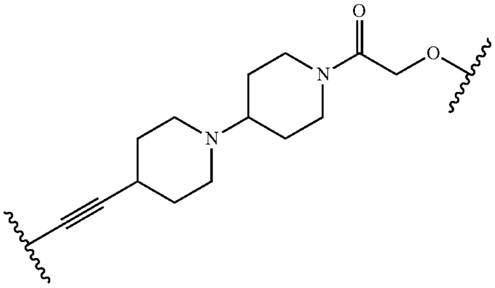
;
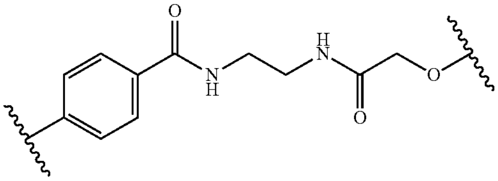
;
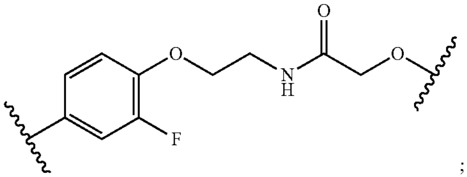
;
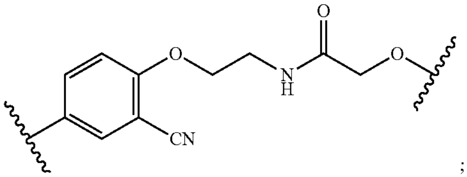
;
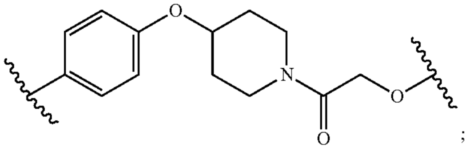
;

-continued

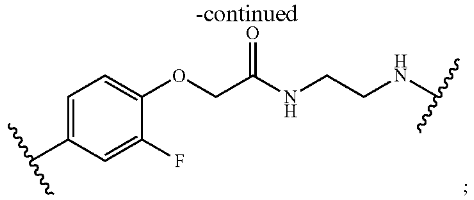
;

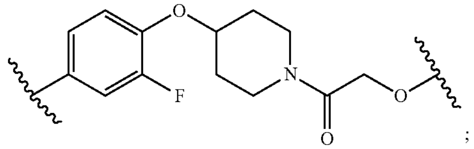
;

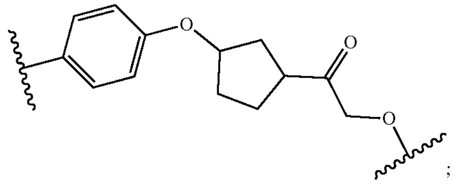
;

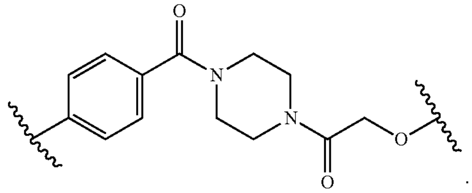
.

In some certain embodiments, the linking group (L) is selected from the groups:

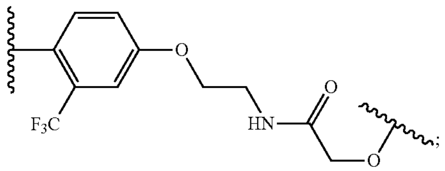

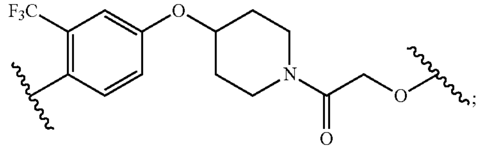

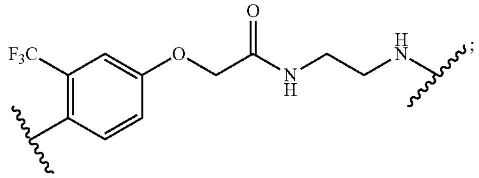

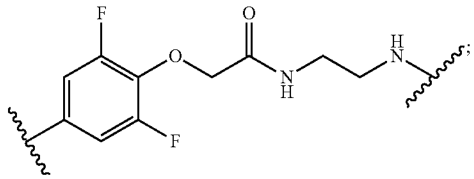

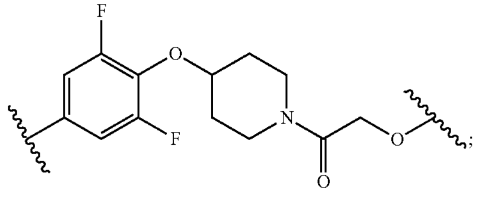

-continued

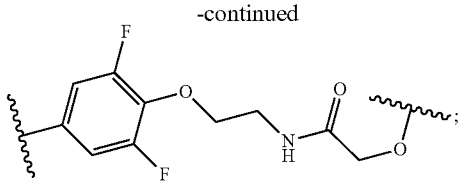

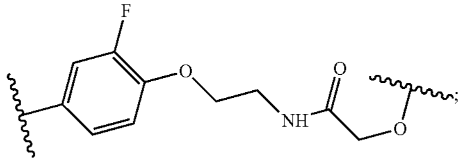

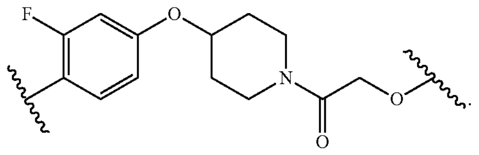

In the second aspect of the present invention, the present invention provides compounds having the structure of formula (III), and salts, polymorphs and prodrugs thereof:

ABM-L-VLM (III), wherein ABM is defined as above;

VLM is a structural fragment represented by formula (VI) or a stereoisomer thereof:

(VI)

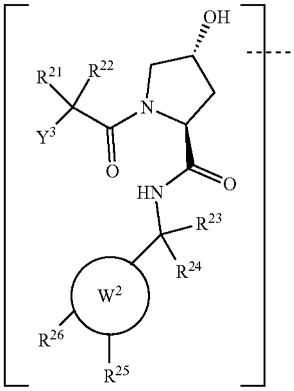

$Y^3$ is $NR^{Y3}R^{Y4}$, $OR^{Y3}$, $SR^{Y3}$,

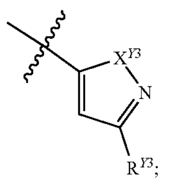

$R^{21}$ and $R^{22}$ are independently selected from: hydrogen, $C_{1-6}$ alkyl optionally substituted with halogen, hydroxyl and cyano, $C_{3-6}$ cycloalkyl optionally substituted with halogen, hydroxyl and cyano;

$R^{Y3}$ and $R^{Y4}$ are independently selected from: hydrogen, $C_{1-6}$ alkyl optionally substituted with halogen, hydroxyl and cyano, $C_{3-6}$ cycloalkyl optionally substituted with halogen, hydroxyl and cyano, $C_{1-6}$ alkyl-CO— optionally substituted with halogen, hydroxyl and cyano, $C_{3-6}$ cycloalkyl-CO-optionally substituted with halogen, hydroxyl and cyano; or $R^{Y3}$ and $R^{21}$ together with the carbon atoms and nitrogen atoms to which they are attached form optionally substituted 5-6 membered heterocycloalkyl;

$X^{Y3}$ is O or S;

$R^{23}$ and $R^{24}$ are each independently selected from: H, $C_{1-6}$ alkyl optionally substituted by halogen, hydroxyl and cyano;

$W^2$ is $C_{6-10}$ aryl or 5-10 membered heteroaryl;

$R^{25}$ is hydrogen, halogen, cyano, hydroxy, nitro, $C_{1-6}$ alkyl optionally substituted with halogen, hydroxyl and cyano, $C_{1-6}$ alkoxy optionally substituted with halogen, hydroxyl and cyano, $NR^{25a}R^{25b}$, $CONR^{25a}R^{25b}$, $C_{6-10}$ aryl, 6-10 membered heteroaryl, thienyl, or

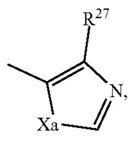

wherein $R^{25a}$ and $R^{25b}$ are each independently selected from: H, $C_{1-6}$ alkyl optionally substituted with halogen, hydroxyl, and cyano; $R^{27}$ is H, halogen, $C_{1-6}$ alkyl optionally substituted with halogen, hydroxy, cyano, and Xa is S, O or $NR^{28}$; $R^{28}$ is hydrogen, $C_{1-6}$ alkyl optionally substituted with halogen; the $C_{6-10}$ aryl, 6-10-membered heteroaryl and thienyl are optionally substituted with one or more groups selected from hydrogen, halogen, $C_{1-6}$ alkyl optionally substituted with halogen, hydroxyl, and cyano, $C_{3-6}$ cycloalkyl optionally substituted with halogen, hydroxyl and cyano, —$CONHC_{1-6}$ alkyl, —$COOC_{1-6}$ alkyl;

$R^{26}$ is hydrogen, halogen, cyano, hydroxy, nitro, $C_{1-6}$ alkyl optionally substituted with halogen, hydroxyl and cyano, $C_{1-6}$ alkoxy optionally substituted with halogen, hydroxyl and cyano;

"- - - " means that the linking group L is connected with the group after any H atom in the above structural formula is removed.

In a preferred second aspect of the present invention, the present invention provides compounds having the structure of formula (III), and salts, polymorphs and prodrugs thereof:

ABM-L-VLM (III), wherein ABM is the AR binding moiety, L is the chemical linking moiety connecting ABM and VLM, and VLM is the VHLE3 ligase binding moiety. In some certain embodiments, the VLM comprises a hydroxyprolyl moiety;

wherein ABM is defined as above;

VLM is a structural fragment represented by formula (VI) or a stereoisomer thereof:

(VI)

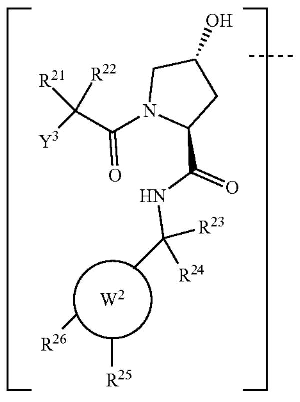

wherein $Y^3$ is $NR^{Y3}R^{Y4}$ $OR^{Y3}$, —$SR^{Y3}$;

$R^{21}$ and $R^{22}$ are independently selected from: hydrogen, $C_{1-6}$ alkyl optionally substituted with halogen, hydroxyl and cyano, $C_{3-6}$ cycloalkyl optionally substituted with halogen, hydroxyl and cyano;

$R^{Y3}$ and $R^{Y4}$ are independently selected from: hydrogen, $C_{1-6}$ alkyl optionally substituted with halogen, hydroxyl and cyano, $C_{3-6}$ cycloalkyl optionally substituted with halogen, hydroxyl and cyano, $C_{1-6}$ alkyl-CO— optionally substituted with halogen, hydroxyl and cyano, $C_{3-6}$ cycloalkyl-CO-optionally substituted with halogen, hydroxyl and cyano; or $R^{Y3}$ and $R^{21}$ together with the carbon atoms and nitrogen atoms to which they are attached form optionally substituted 5-6 membered heterocycloalkyl;

$R^{23}$ and $R^{24}$ are each independently selected from: hydrogen, $C_{1-6}$ alkyl optionally substituted by halogen, hydroxyl, cyano;

$W^2$ is $C_{6-10}$ aryl or 5-10 membered heteroaryl;

$R^{25}$ is hydrogen, halogen, cyano, hydroxy, nitro, $C_{1-6}$ alkyl optionally substituted with halogen, hydroxyl and cyano, $C_{1-6}$ alkoxy optionally substituted with halogen, hydroxyl and cyano, $NR^{25a}R^{25b}$, $CONR^{25a}R^{25b}$, $C_{6-10}$ aryl, or

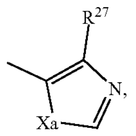

wherein $R^{25a}$ and $R^{25b}$ are each independently selected from: hydrogen, $C_{1-6}$ alkyl optionally substituted with halogen, hydroxyl, cyano; $R^{27}$ is hydrogen, halogen, $C_{1-6}$ alkyl optionally substituted with halogen, hydroxyl, cyano, and Xa is S or O;

$R^{26}$ is hydrogen, halogen, cyano, hydroxy, nitro, $C_{1-6}$ alkyl optionally substituted with halogen, hydroxyl and cyano, $C_{1-6}$ alkoxy optionally substituted with halogen, hydroxyl, cyano;

"- - - " means that the linking group L is connected with the group after any H atom in the above structural formula is removed.

In some certain embodiments, $Y^3$ is $NR^{Y3}R^{Y4}$, $OR^{Y3}$;

$R^{21}$ and $R^{22}$ are independently selected from: hydrogen, $C_{1-6}$ alkyl;

$R^{Y3}$ and $R^{Y4}$ are independently selected from: hydrogen, $C_{1-6}$ alkyl optionally substituted with halogen, hydroxyl and cyano, $C_{3-6}$ cycloalkyl-CO— optionally substituted with halogen, hydroxy, cyano; or $R^{Y3}$ and $R^{21}$ together with the carbon atoms and nitrogen atoms to which they are attached form optionally substituted 5-6 membered heterocycloalkyl;

$R^{23}$ and $R^{24}$ are each independently selected from: hydrogen, $C_{1-6}$ alkyl;

$W^2$ is phenyl;

$R^{25}$ is hydrogen, halogen, $C_{1-6}$ alkyl, $CONR^{25a}R^{25b}$ or,

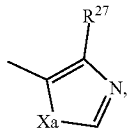

wherein $R^{25a}$, $R^{25b}$ are each independently selected from: H, $C_{1-6}$ alkyl; $R^{27}$ is H, $C_{1-6}$ alkyl, and Xa is S;

$R^{26}$ is hydrogen, $C_{1-6}$ alkyl.

In some certain embodiments, $Y^3$ is $NR^{Y3}R^{Y4}$, $OR^{Y3}$;

$R^{21}$ and $R^{22}$ are independently selected from: hydrogen, $C_{1-6}$ alkyl;

$R^{Y3}$ and $R^{Y4}$ are independently selected from: hydrogen, $C_{1-6}$ alkyl, $C_{3-6}$ cycloalkyl-CO-optionally substituted with halogen, hydroxy, cyano; or $R^{Y3}$ and $R^{21}$ together with the carbon atoms and nitrogen atoms to which they are attached form optionally substituted 5 membered heterocycloalkyl;

$R^{23}$ and $R^{24}$ are each independently selected from: hydrogen, $C_{1-6}$ alkyl;

$W^2$ is phenyl;

$R^{25}$ is $CONR^{25a}R^{25b}$, or

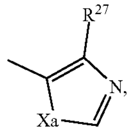

wherein $R^{25a}$, $R^{25b}$ are each independently selected from: hydrogen, $C_{1-6}$ alkyl; $R^{27}$ is $C_{1-6}$ alkyl, and Xa is S;

$R^{26}$ is hydrogen.

In some certain embodiments, $Y^3$ is

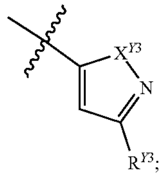

$R^{Y3}$ is selected from: hydrogen, $C_{1-6}$ alkyl optionally substituted with halogen, hydroxyl and cyano, $C_{3-6}$ cycloalkyl optionally substituted with halogen, hydroxy, cyano;

$X^{Y3}$ is O or S.

In some certain embodiments, wherein $Y^3$ is

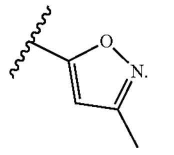 [SMILES: *c1cc(C)no1]

In some certain embodiments, the VLM is selected from the following structural fragment or the stereoisomer thereof, wherein  represents the point of attachment of the linking moiety:

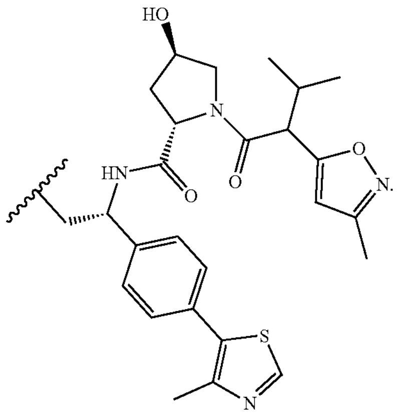 [SMILES: *C[C@H](NC(=O)[C@@H]1C[C@@H](O)CN1C(=O)C(c1cc(C)no1)C(C)C)c1ccc(-c2scnc2C)cc1]

In some certain embodiments, VLM is a structural fragment represented by formula (VI)-1 or a stereoisomer thereof:

(VI)-1

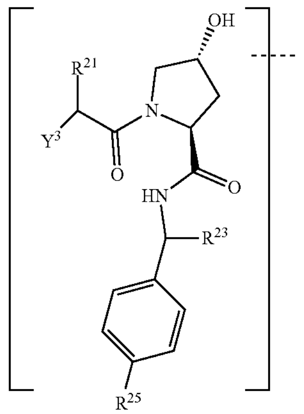

wherein $Y^3$, $R^{21}$, $R^{23}$ and $R^{25}$ are defined as above.

In some certain embodiments, VLM is a structural fragment represented by formula (VI)-2 or a stereoisomer thereof:

(VI)-2

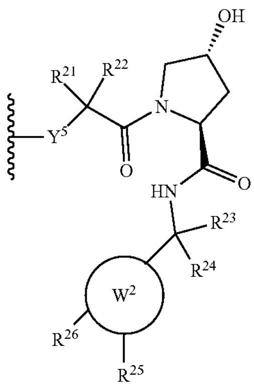

$Y^5$ is $NR^{Y5}$, O;

$R^{21}$ and $R^{22}$ are independently selected from: hydrogen, $C_{1-6}$ alkyl optionally substituted with halogen, hydroxyl and cyano, $C_{3-6}$ cycloalkyl optionally substituted with halogen, hydroxy, cyano;

$R^{Y5}$ is hydrogen, $C_{1-6}$ alkyl optionally substituted with halogen, hydroxyl and cyano, $C_{3-6}$ cycloalkyl optionally substituted with halogen, hydroxyl and cyano, $C_{1-6}$ alkyl-CO— optionally substituted with halogen, hydroxyl and cyano, $C_{3-6}$ cycloalkyl-CO— optionally substituted with halogen, hydroxyl, cyano; or $R^{Y5}$ and $R^{21}$ together with the carbon atoms and nitrogen atoms to which they are attached form optionally substituted 5-6 membered heterocycloalkyl;

$R^{23}$ and $R^{24}$ are each independently selected from: hydrogen, $C_{1-6}$ alkyl optionally substituted with halogen, hydroxyl, cyano;

$W^2$ is $C_{6-10}$ aryl or 5-10 membered heteroaryl;

$R^{25}$ is hydrogen, halogen, cyano, hydroxy, nitro, $C_{1-6}$ alkyl optionally substituted with halogen, hydroxyl and cyano, $C_{1-6}$ alkoxy optionally substituted with halogen, hydroxyl and cyano, $NR^{25a}R^{25b}$, $CONR^{25a}R^{25b}$, $C_{6-10}$ aryl, or

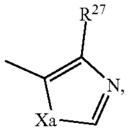

wherein $R^{25a}$ and $R^{25b}$ are each independently selected from: hydrogen, $C_{1-6}$ alkyl optionally substituted with halogen, hydroxyl, cyano; $R^{27}$ is H, halogen, $C_{1-6}$ alkyl optionally substituted with halogen, hydroxy, cyano, and Xa is S or O;

$R^{26}$ is hydrogen, halogen, cyano, hydroxy, nitro, $C_{1-6}$ alkyl optionally substituted with halogen, hydroxyl and cyano, $C_{1-6}$ alkoxy optionally substituted with halogen, hydroxy, cyano.

In some certain embodiments, VLM is a structural fragment represented by formula (VI)-2 or a stereoisomer thereof:

(VI)-2

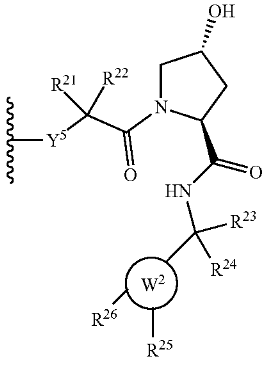

$Y^5$ is $NR^{Y5}$, O;

$R^{21}$ and $R^{22}$ are independently selected from: hydrogen, $C_{1-6}$ alkyl optionally substituted with halogen, hydroxyl and cyano, $C_{3-6}$ cycloalkyl optionally substituted with halogen, hydroxy, cyano;

$R^{Y5}$ is hydrogen, $C_{1-6}$ alkyl optionally substituted with halogen, hydroxyl and cyano, $C_{3-6}$ cycloalkyl optionally substituted with halogen, hydroxyl and cyano, $C_{1-6}$ alkyl-CO— optionally substituted with halogen, hydroxyl and cyano, $C_{3-6}$ cycloalkyl-CO— optionally substituted with halogen, hydroxyl, cyano; or $R^{Y5}$ and $R^{21}$ together with the carbon atoms and nitrogen atoms to which they are attached form optionally substituted 5-6 membered heterocycloalkyl;

$R^{23}$ and $R^{24}$ are each independently selected from: hydrogen, $C_{1-6}$ alkyl optionally substituted with halogen, hydroxyl, cyano;

$W^2$ is 5-6 membered heteroaryl;

$R^{25}$ is hydrogen, halogen, cyano, hydroxy, nitro, $C_{1-6}$ alkyl optionally substituted with halogen, hydroxyl and cyano, $C_{1-6}$ alkoxy optionally substituted with halogen, hydroxyl and cyano, $NR^{25a}R^{25b}$, $CONR^{25a}R^{25b}$, $C_{6-10}$ aryl, 6-10 membered heteroaryl, thienyl, or

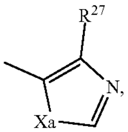

wherein $R^{25a}$ and $R^{25b}$ are each independently selected from: hydrogen, $C_{1-6}$ alkyl optionally substituted with halogen, hydroxyl, cyano; $R^{27}$ is H, halogen, $C_{1-6}$ alkyl optionally substituted with halogen, hydroxy, cyano, and Xa is S, O or $NR^{28}$; $R^{28}$ is hydrogen, $C_{1-6}$ alkyl optionally substituted by halogen; the $C_{6-10}$ aryl, 6-10 membered heteroaryl and thienyl are optionally substituted with one or more groups selected from hydrogen, halogen, $C_{1-6}$ alkyl optionally substituted with halogen, $C_{3-6}$ cycloalkyl optionally substituted with halogen, —$CONHC_{1-6}$ alkyl and —$COOC_{1-6}$ alkyl;

$R^{26}$ is hydrogen, halogen, cyano, hydroxy, nitro, $C_{1-6}$ alkyl optionally substituted with halogen, hydroxyl and cyano, $C_{1-6}$ alkoxy optionally substituted with halogen, hydroxy, cyano.

In some certain embodiments, $Y^5$ is $NR^{Y5}$, O;

$R^{21}$ and $R^{22}$ are independently selected from: hydrogen, $C_{1-6}$ alkyl;

$R^{Y5}$ is hydrogen, $C_{1-6}$ alkyl; or $R^{Y5}$ and $R^{21}$ together with the carbon atoms and nitrogen atoms to which they are attached form optionally substituted 5 membered heterocycloalkyl;

$R^{23}$ and $R^{24}$ are each independently selected from: hydrogen, $C_{1-6}$ alkyl;

$W^2$ is phenyl;

$R^{25}$ is $CONR^{25a}R^{25b}$, or

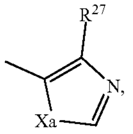

wherein $R^{25a}$ and $R^{25b}$ are each independently selected from: hydrogen, $C_{1-6}$ alkyl; $R^{27}$ is $C_{1-6}$ alkyl, and Xa is S;

$R^{26}$ is hydrogen.

In some certain embodiments of the present invention, $R^{21}$ is selected from: methyl, ethyl, n-propyl, isopropyl, n-butyl, 2-methylpropyl, sec-butyl, tert-butyl, n-pentyl, isopentyl or neopentyl.

In some certain embodiments, $Y^5$ is $NR^{Y5}$, O;

$R^{21}$ is selected from: methyl, ethyl, n-propyl, isopropyl, n-butyl, 2-methylpropyl, sec-butyl, tert-butyl, n-pentyl, isopentyl or neopentyl;

$R^{22}$ is selected from: hydrogen;

$R^{Y5}$ is hydrogen, $C_{1-6}$ alkyl;

$R^{23}$ and $R^{24}$ are each independently selected from: hydrogen, $C_{1-6}$ alkyl;

$W^2$ is

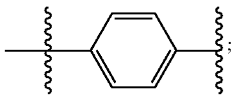

$R^{25}$ is

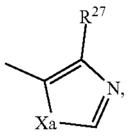

wherein $R^{27}$ is $C_{1-3}$ alkyl, and Xa is S;

$R^{26}$ is hydrogen.

In some certain embodiments, $Y^5$ is $NR^{Y5}$, O;

$R^{21}$ and $R^{22}$ are independently selected from: hydrogen, $C_{1-6}$ alkyl;

$R^{Y5}$ is hydrogen, $C_{1-6}$ alkyl; or $R^{Y5}$ and $R^{21}$ together with the carbon atoms and nitrogen atoms to which they are attached form optionally substituted 5 membered heterocycloalkyl;

$R^{23}$ and $R^{24}$ are each independently selected from: hydrogen, $C_{1-6}$ alkyl;

$W^2$ is oxazolyl or thiazolyl;

$R^{25}$ is hydrogen;

$R^{26}$ is hydrogen.

In some certain embodiments, $Y^5$ is $NR^{Y5}$, O;

$R^{21}$ is selected from: methyl, ethyl, n-propyl, isopropyl, n-butyl, 2-methylpropyl, sec-butyl, tert-butyl, n-pentyl, isopentyl or neopentyl;

$R^{22}$ is selected from: hydrogen;

$R^{Y5}$ is hydrogen, $C_{1-6}$ alkyl;

$R^{23}$ and $R^{24}$ are each independently selected from: hydrogen, $C_{1-6}$ alkyl;

$W^2$ is oxazolyl or thiazolyl;

$R^{25}$ is hydrogen;

$R^{26}$ is hydrogen.

In some certain embodiments, the VLM is selected from the following structural fragments or the stereoisomers thereof, wherein  represents the point of attachment of the linking moiety:

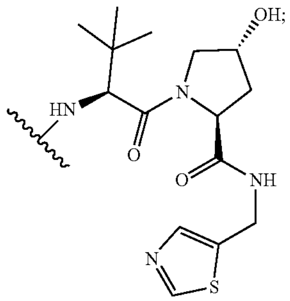

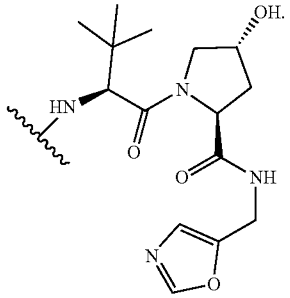

In some certain embodiments, VLM is a structural fragment represented by formula (VI)-3 or a stereoisomer thereof:

(VI)-3

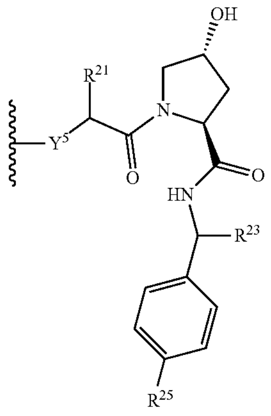

wherein, $Y^5$, $R^{21}$, $R^{23}$ and $R^{25}$ are defined as above.

In another example, VLM is a structural fragment represented by formula (VI)-4 or (VI)-5 or a stereoisomer thereof:

(VI)-4
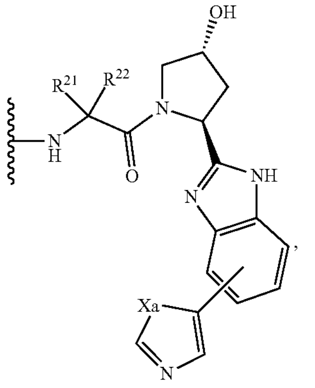
(VI)-5
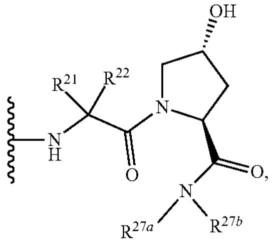
wherein, $R^{21}$, $R^{22}$ and Xa are defined as above; $R^{27a}$ and $R^{27b}$ are each independently selected from: hydrogen, $C_{1-6}$ alkyl.
In some certain embodiments, the VLM is selected from the following structural fragments or the stereoisomers thereof, wherein  represents the point of attachment of the linking moiety:
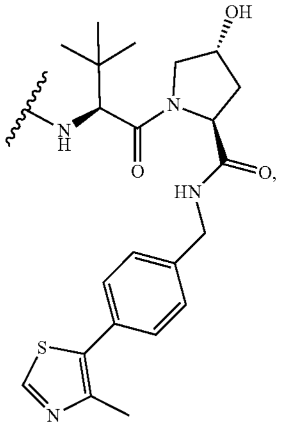
-continued
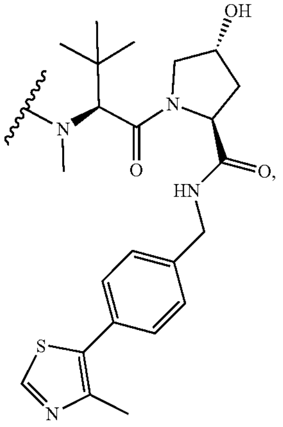
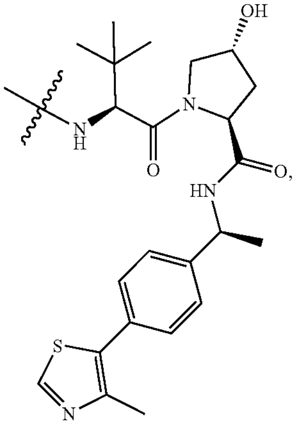
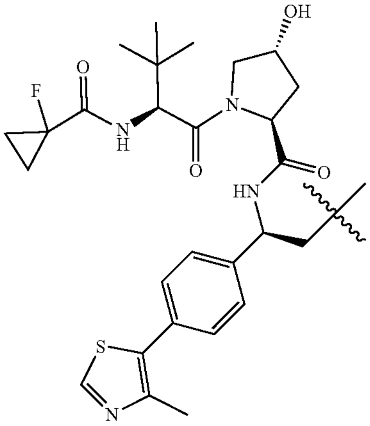
,
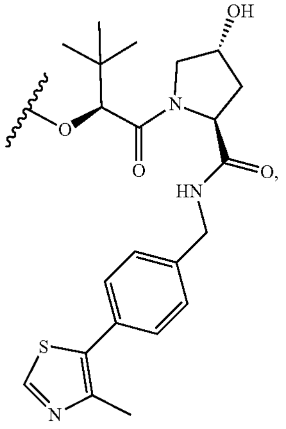

-continued

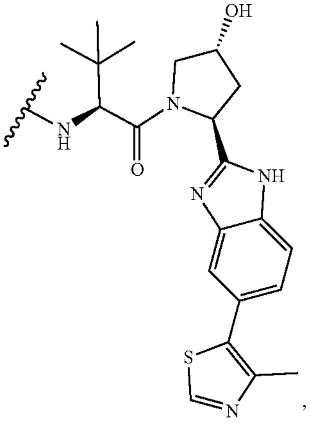

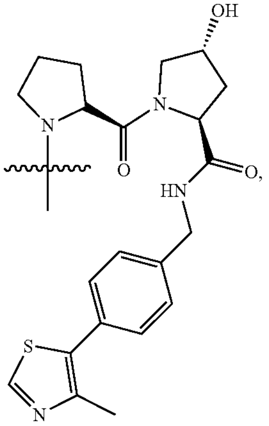

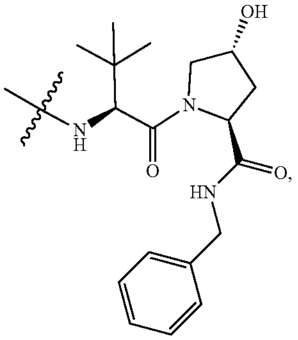

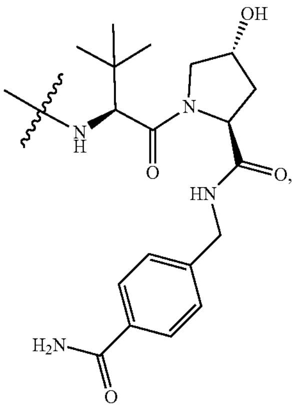

-continued

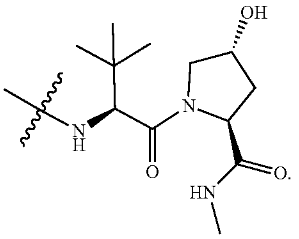

In some certain embodiments, VLM is a structural fragment represented by formula (VI)-5 or a stereoisomer thereof:

(VI)-5

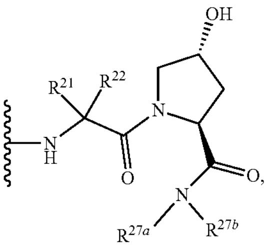

$R^{21}$ and $R^{22}$ are independently selected from: hydrogen, $C_{1-6}$ alkyl;

$R^{27a}$ and $R^{27b}$ are each independently selected from: H, 5-6 membered heteroaryl, preferably H, thiazolyl.

In some certain embodiments, the VLM is selected from the following structural fragments or the stereoisomers thereof, wherein ∿∿∿ represents the point of attachment of the linking moiety:

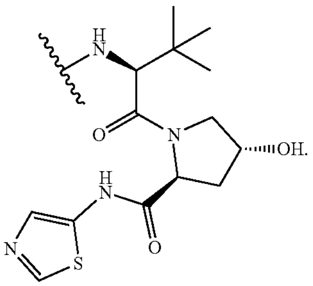 [SMILES: *N[C@H](C(=O)N1C[C@H](O)C[C@H]1C(=O)Nc1cncs1)C(C)(C)C]

In some certain embodiments, VLM is a structural fragment represented by formula (VI)-61 or a stereoisomer thereof:

(VI)-61

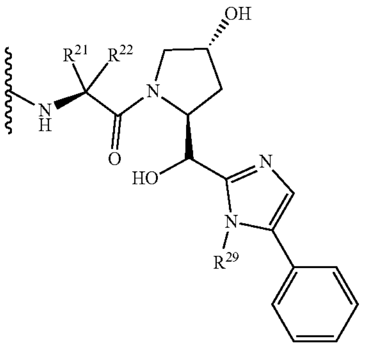

$R^{21}$ and $R^{22}$ are independently selected from: hydrogen, $C_{1-6}$ alkyl;

$R^{29}$ is $C_{1-6}$ alkyl optionally substituted with halogen.

In some certain embodiments, the VLM is selected from the following structural fragments or the stereoisomers thereof, wherein represents the point of attachment of the linking moiety:

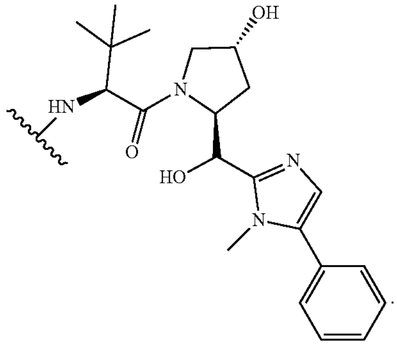 [SMILES: *N[C@H](C(=O)N1C[C@H](O)C[C@H]1C(O)c1ncc(-c2ccccc2)n1C)C(C)(C)C]

In some certain embodiments, VLM is a structural fragment represented by formula (VI)-71 or formula (VI)-81 or a stereoisomer thereof:

(VI)-71

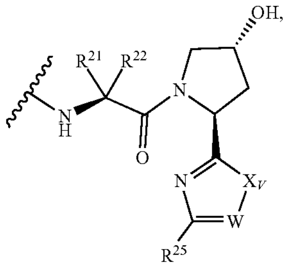

-continued (VI)-81

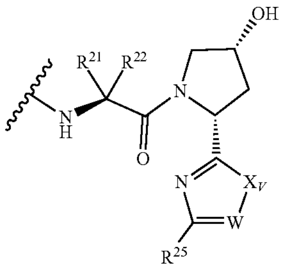

$R^{21}$ and $R^{22}$ are independently selected from: hydrogen, $C_{1-6}$ alkyl;

$R^{25}$ is phenyl, pyridyl, pyrimidinyl, thienyl, or

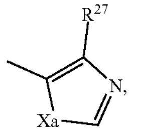

and $R^{27}$ is $C_{1-6}$ alkyl, and Xa is S, O or $NR^{28}$; $R^{28}$ is $C_{1-6}$ alkyl; the phenyl, pyridyl, pyrimidinyl and thienyl are optionally substituted with one or more groups selected from halogen, $C_{1-6}$ alkyl and —$CONHC_{1-6}$ alkyl;

Xv is S, O or $NR^{29}$; $R^{29}$ is hydrogen, $C_{1-6}$ alkyl; W is $CH_2$.

In some certain embodiments, the VLM is selected from the following structural fragments or the stereoisomers thereof, wherein represents the point of attachment of the linking moiety:

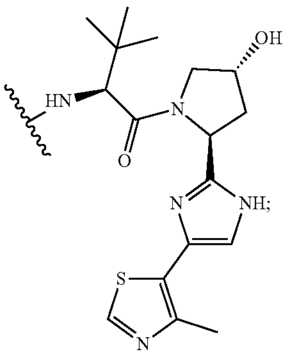

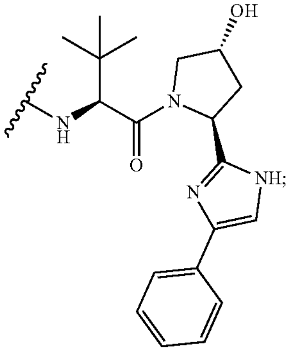

-continued
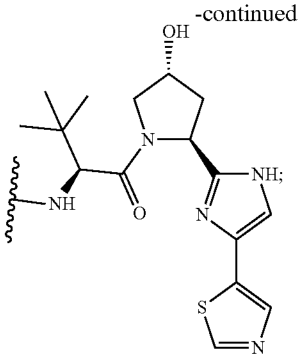
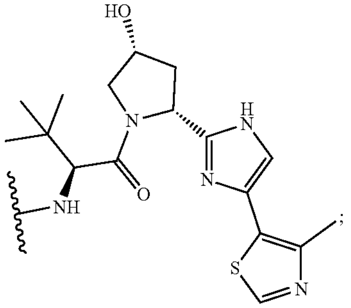
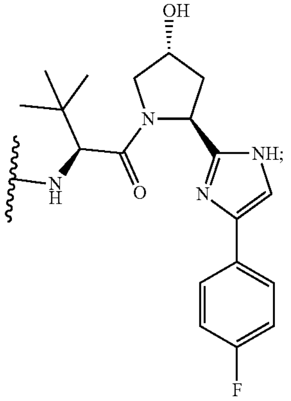
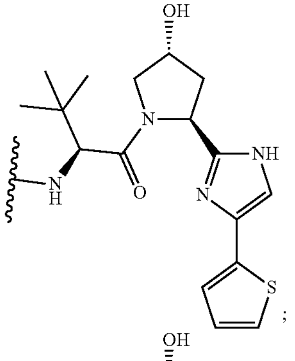
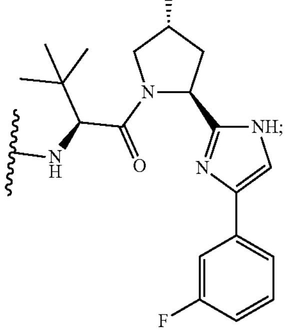
-continued
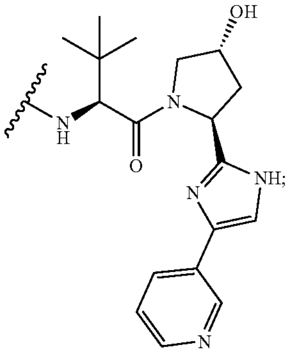
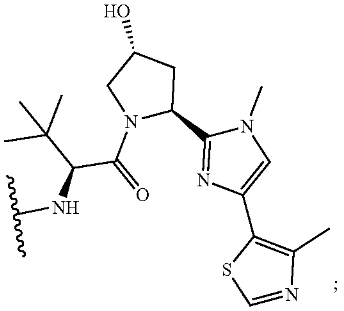
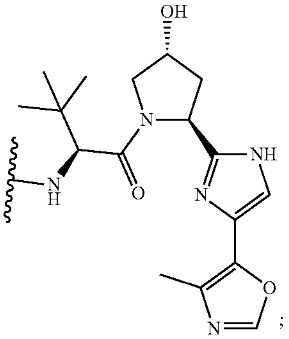
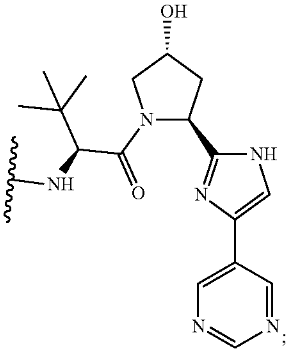
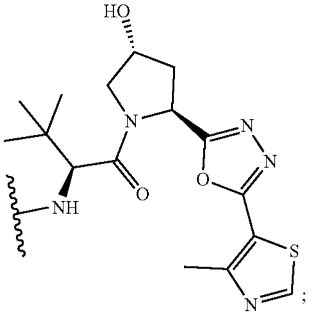

-continued

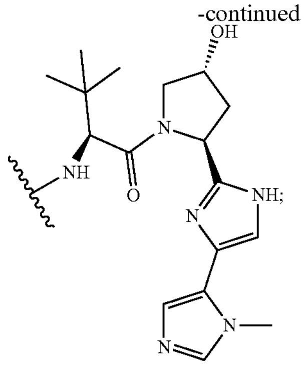

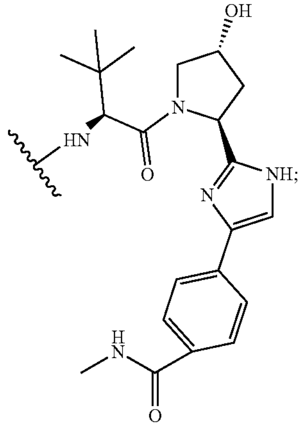

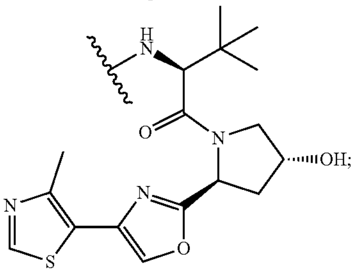

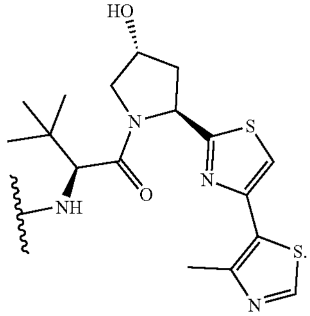 [SMILES: *N[C@H](C(=O)N1C[C@H](O)C[C@H]1c1nc(-c2scnc2C)cs1)C(C)(C)C]

In some certain embodiments, the linking group (L) is selected from groups represented by the following general structure:

$—(CH_2)_m—CO—N(R^{31})—(CH_2)_n—CO—$;
$—O—(CH_2)_m—O—(CH_2)_n—CO—$;
$—O—(CH_2)_m—CO—$;
$—C≡C—(Cy)_p-(CH_2)_m—CO—$;
$—CO—N(R^{31})—(CH_2)_m-(Cy)_p-(CH_2)_n—CO—$;
$—CO-(Cy)_p-(CH_2)_n—CO—$;
$—O—(CH_2)_m-(Cy)_p-(CH_2)_n—CO—$;
$—N(R^{31})—CO—(CH_2)_m—O—(CH_2)_n—CO—$;
$—N(R^{31})—(CH_2)_m—O—(CH_2)_n—CO—$;
$—(CH_2)_m-(Cy)_p-(CH_2)_n—CO—$;
$—O—(CH_2)_m—O—(CH_2)_n—O—(CH_2)_o—CO—$;
$-(Cy)_p-(CH_2)_n—O—(CH_2)_o—CO—$;
$—C≡C—(CH_2)_m—CO—$;
$—(CH_2)_m—CO—N(R^{31})—(CH_2)_n-(Cy)_p-CO—$;
$—C≡C—(Cy)_p-(CH_2)_m—N(R^{31})—CO—$;
$-(Cy)_q-(CH_2)_m—CO—N(R^{31})—(CH_2)_n—CO—$;
$-(Cy)_q-O—(CH_2)_m—O—(CH_2)_n—CO—$;
$-(Cy)_q-O—(CH_2)_m—CO—$;
$-(Cy)_q-C≡C—(Cy)_p-(CH_2)_m—CO—$;
$-(Cy)_q-CO—N(R^{31})—(CH_2)_m-(Cy)_p-(CH_2)_n—CO—$;
$-(Cy)_q-CO-(Cy)_p-(CH_2)_n—CO—$;
$-(Cy)_q-O—(CH_2)_m-(Cy)_p-(CH_2)_n—CO—$;
$-(Cy)_q-N(R^{31})—CO—(CH_2)_m—O—(CH_2)_n—CO—$;
$-(Cy)_q-N(R^{31})—(CH_2)_m—O—(CH_2)_n—CO—$;
$-(Cy)_q-(CH_2)_m-(Cy)_p-(CH_2)_n—CO—$;
$-(Cy)_q-O—(CH_2)_m—O—(CH_2)_n—O—(CH_2)_o—CO—$;
$-(Cy)_q-(Cy)_p-(CH_2)_n—O—(CH_2)_o—CO—$;
$-(Cy)_q-C≡C—(CH_2)_m—CO—$;
$-(Cy)_q-(CH_2)_m—CO—N(R^{31})—(CH_2)_n-(Cy)_p-CO—$;
$-(Cy)_q-C≡C—(Cy)_p-(CH_2)_m—N(R^{31})—CO—$;
$—O—(CH_2)_m—O—(CH_2)_n—$;
$—CH═CH—CO—N(R^{31})—(CH_2)_m—O—(CH_2)_n—CO—$;
$-(Cy)_q-O—(CH_2)_m—N(R^{31})—CO—$;
$-(Cy)_q-O-(Cy)_p-(CH_2)_m—N(R^{31})—CO—$;
$-(Cy)_q-N(R^{31})—CO—(CH_2)_m-(Cy)_p-(CH_2)_n—CO—$;
$-(Cy)_q-O—(CH_2)_m-(Cy)_p-CO—$;
$—O—(CH_2)_m—O—(CH_2)_n—O—(CH_2)_o—O—(CH_2)_t—CO—$;
$—O-(Cy)_q-CO—N(R^{31})—(CH_2)_m—O—(CH_2)_n—CO—$;
$—O-(Cy)_q-O—(CH_2)_m—O—(CH_2)_n—CO—$;
$—O—(CH_2)_m—O—(CH_2)_n—O—(CH_2)_o-(Cy)_q-CO—$;
$—O—(CH_2)_m—O—(CH_2)_n-(Cy)_q-CO—$;

wherein m, n, o, p, q and t are each independently selected from: 0, 1, 2, 3, 4, 5, 6, with the proviso that when said number is zero, no N—O or O—O bonds are present, and one or two hydrogen atoms in each $—CH_2—$ can be replaced by fluorine atoms, and each $R^{31}$ is independently selected from group hydrogen, methyl, ethyl, or benzyl, and Cy is selected from $C_{6-10}$ aryl, $C_{3-6}$ heteroaryl, $C_{3-6}$ cycloalkyl, $C_{3-6}$ heterocycloalkyl, preferably N

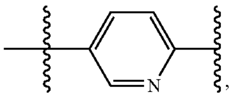, 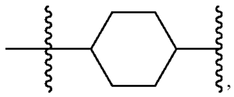, 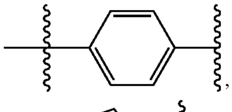, 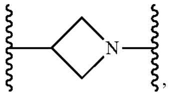, 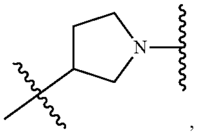, 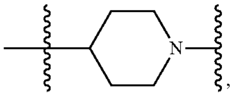, 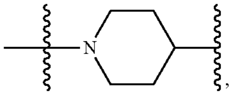, 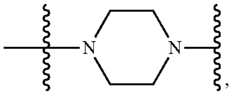, 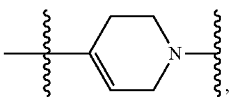, 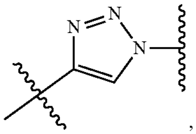, -continued

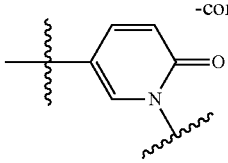
,
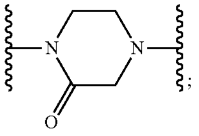
;

each optionally substituted with 1, 2 or 3 $R^{Cy}$; and each $R^{Cy}$ is independently selected from: hydrogen, halogen, cyano, $C_{1-3}$ alkyl or $C_{1-3}$ alkoxy optionally substituted with halogen.

In some certain embodiments, the linking group (L) is selected from groups represented by the following general structure:

—$(CH_2)_m$—CO—N($R^{31}$)—$(CH_2)_n$—CO—;
—O—$(CH_2)_m$—O—$(CH_2)_n$—CO—;
—O—$(CH_2)_m$—CO—;
—C≡C—$(Cy)_p$-$(CH_2)_m$—CO—;
—CO—N($R^{31}$)—$(CH_2)_m$-$(Cy)_p$-$(CH_2)_n$—CO—;
—CO-$(Cy)_p$-$(CH_2)_n$—CO—;
—O—$(CH_2)_m$-$(Cy)_p$-$(CH_2)_n$—CO—;
—N($R^{31}$)—CO—$(CH_2)_m$—O—$(CH_2)_n$—CO—;
—N($R^{31}$)—$(CH_2)_m$—O—$(CH_2)_n$—CO—;
—$(CH_2)_m$-$(Cy)_p$-$(CH_2)_n$—CO—;
—O—$(CH_2)_m$—O—$(CH_2)_n$—O—$(CH_2)_o$—CO—;
-$(Cy)_p$-$(CH_2)_n$—O—$(CH_2)_o$—CO—;
—C≡C—$(CH_2)_m$—CO—;
—$(CH_2)_m$—CO—N($R^{31}$)—$(CH_2)_n$-$(Cy)_p$-CO—;
—C≡C—$(Cy)_p$-$(CH_2)_m$—N($R^{31}$)—CO—;
-$(Cy)_q$-$(CH_2)_m$—CO—N($R^{31}$)—$(CH_2)_n$—CO—;
-$(Cy)_q$-O—$(CH_2)_m$—O—$(CH_2)_n$—CO—;
-$(Cy)_q$-O—$(CH_2)_m$—CO—;
-$(Cy)_q$-C≡C—$(Cy)_p$-$(CH_2)_m$—CO—;
-$(Cy)_q$-CO—N($R^{31}$)—$(CH_2)_m$-$(Cy)_p$-$(CH_2)_n$—CO—;
-$(Cy)_q$-CO-$(Cy)_p$-$(CH_2)_n$—CO—;
-$(Cy)_q$-O—$(CH_2)_m$-$(Cy)_p$-$(CH_2)_n$—CO—;
-$(Cy)_q$-N($R^{31}$)—CO—$(CH_2)_m$—O—$(CH_2)_n$—CO—;
-$(Cy)_q$-N($R^{31}$)—$(CH_2)_m$—O—$(CH_2)_n$—CO—;
-$(Cy)_q$-$(CH_2)_m$-$(Cy)_p$-$(CH_2)_n$—CO—;
-$(Cy)_q$-O—$(CH_2)_m$—O—$(CH_2)_n$—O—$(CH_2)_o$—CO—;
-$(Cy)_q$-$(Cy)_p$-$(CH_2)_n$—O—$(CH_2)_o$—CO—;
-$(Cy)_q$-C≡C—$(CH_2)_m$—CO—;
-$(Cy)_q$-$(CH_2)_m$—CO—N($R^{31}$)—$(CH_2)_n$-$(Cy)_p$-CO—;
-$(Cy)_q$-C≡C—$(Cy)_p$-$(CH_2)_m$—N($R^{31}$)—CO—;

wherein m, n, o, p, and q are each independently selected from: 0, 1, 2, 3, 4, 5, 6, with the proviso that when said number is zero, no N—O or O—O bonds are present, and each $R^{31}$ is independently selected from group hydrogen, methyl, ethyl, or benzyl, and Cy is selected from $C_{3-6}$ cycloalkyl, $C_{3-6}$ heterocycloalkyl, preferably

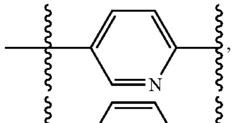
,
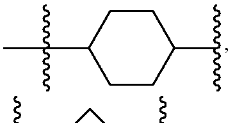
,
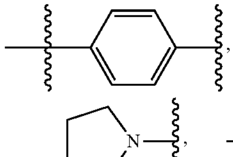
,
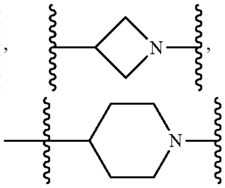
,
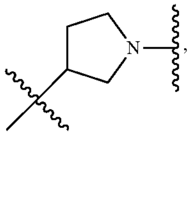
,
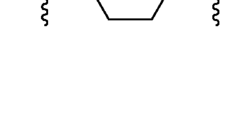
, -continued

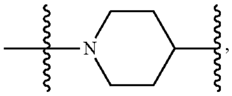
,
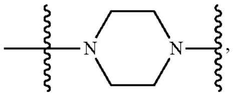
,
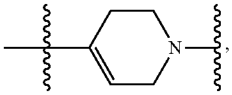
,
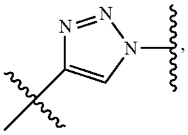
,
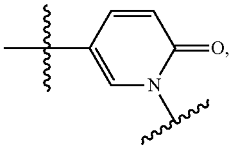

each optionally substituted with 1, 2 or 3 $R^{Cy}$; and each $R^{Cy}$ is independently selected from: hydrogen, halogen, cyano, $C_{1-3}$ alkyl or $C_{1-3}$ alkoxy optionally substituted with halogen.

In some certain embodiments of the present invention, Cy is selected from $C_{6-10}$ aryl, $C_{3-6}$ heteroaryl, $C_{3-6}$ cycloalkyl, $C_{3-6}$ heterocycloalkyl, preferably phenyl, pyridyl, triazolyl, azetidinyl, tetrahydropyrrolyl, piperidinyl, piperazinyl, oxopiperazinyl, tetrahydropyridyl, oxodihydropyridyl, further preferably

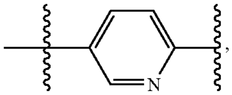
,
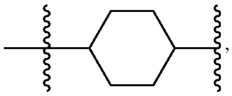
,
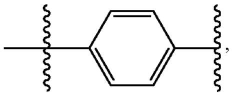
,
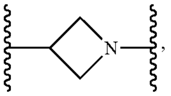
,
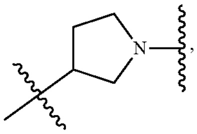
,
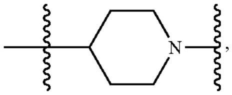
,
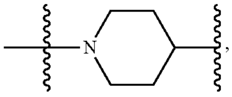
,
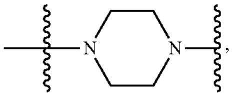
,
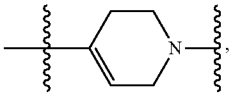
, -continued

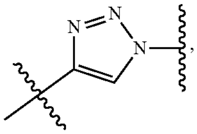

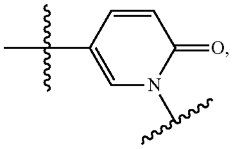

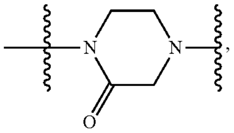

each optionally substituted with 1, 2 or 3 $R^{Cy}$; and each $R^{Cy}$ is independently selected from: hydrogen, halogen, cyano, $C_{1-3}$ alkyl optionally substituted with halogen.

In some certain embodiments, the linking group (L) is selected from the following groups:

—O—$(CH_2)_m$—O—$(CH_2)_n$—CO—;

—O—$(CH_2)_m$—CO—;

—O—$(CH_2)_m$—O—$(CH_2)_n$—O—$(CH_2)_o$—CO—;

-$(Cy)_p$-$(CH_2)_n$—O—$(CH_2)_o$—CO—;

-$(Cy)_q$-O—$(CH_2)_m$—O—$(CH_2)_n$—CO—;

-$(Cy)_q$-O—$(CH_2)_m$—CO—;

-$(Cy)_q$-O—$(CH_2)_m$—O—$(CH_2)_n$—O—$(CH_2)_o$—CO—;

—O-$(Cy)_q$-O—$(CH_2)_m$—O—$(CH_2)_n$—CO—;

—O—$(CH_2)_m$—O—$(CH_2)_n$—O—$(CH_2)_o$-$(Cy)_q$-CO—;

—O—$(CH_2)_m$—O—$(CH_2)_n$-$(Cy)_q$-CO—;

wherein m, n and o are each independently selected from: 1, 2, 3, 4, 5, 6, and q is selected from: 1, and Cy is selected from $C_{6-10}$ aryl, $C_{3-6}$ heteroaryl, $C_{3-6}$ cycloalkyl, $C_{3-6}$ heterocycloalkyl, preferably phenyl, pyridyl, triazolyl, azetidinyl, tetrahydropyrrolyl, piperidinyl, piperazinyl, oxopiperazinyl, tetrahydropyridyl, oxodihydropyridyl, further preferably

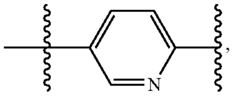 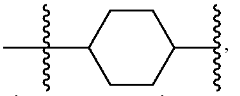

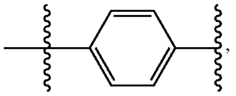 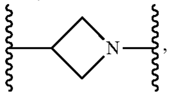

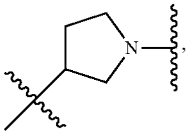 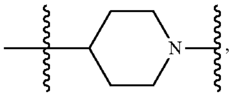

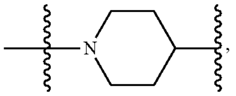 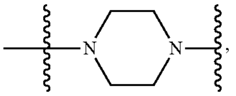

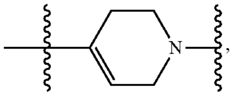 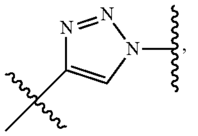

-continued

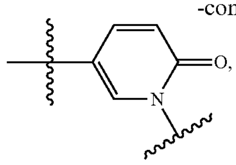 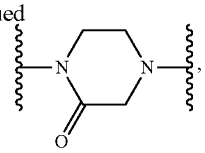

each optionally substituted with 1, 2 or 3 $R^{Cy}$; and each $R^{Cy}$ is independently selected from: hydrogen, halogen, cyano, $C_{1-3}$ alkyl optionally substituted with halogen.

In some certain embodiments, the linking group (L) is selected from groups:

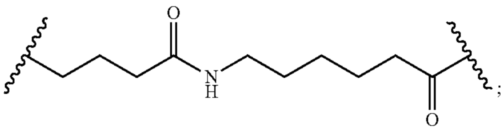

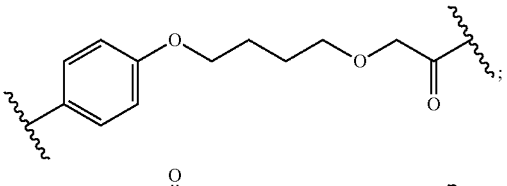

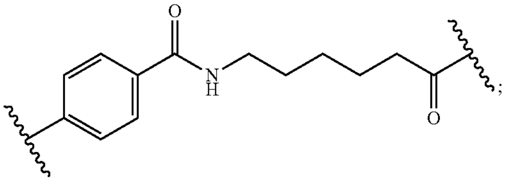

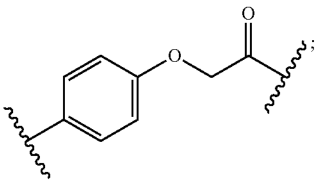

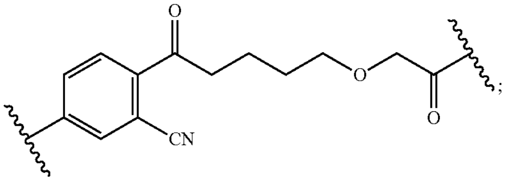

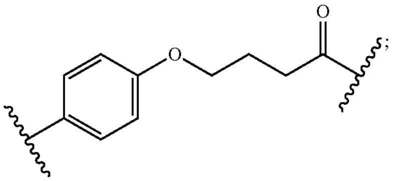

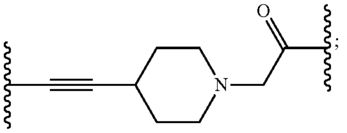

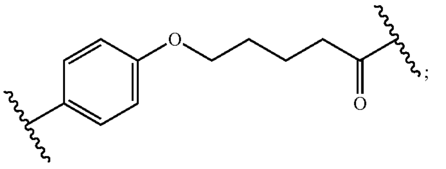

-continued
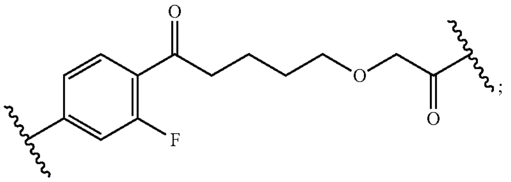
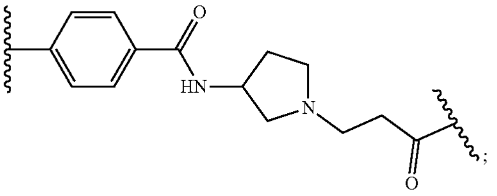
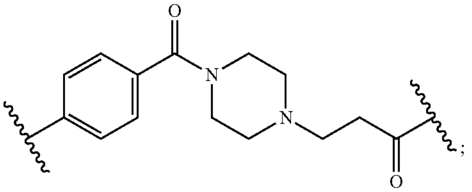
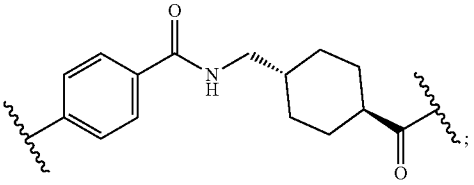
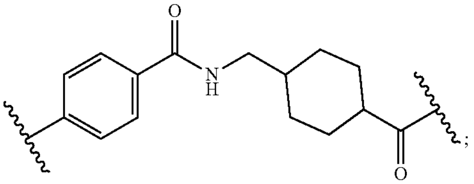
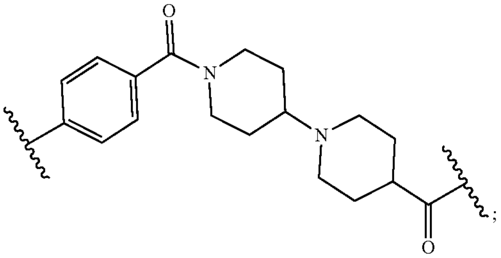
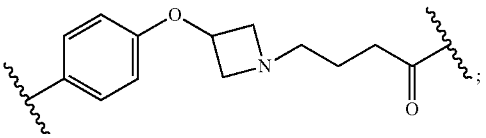
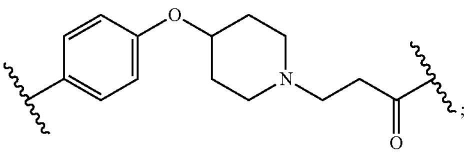
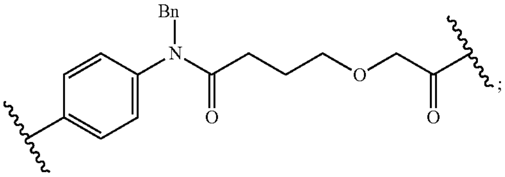
-continued
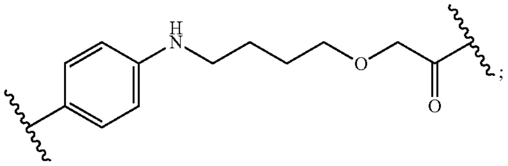
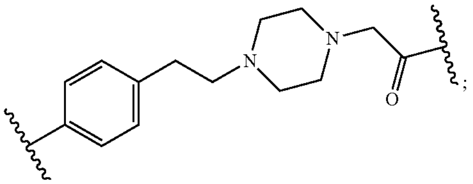
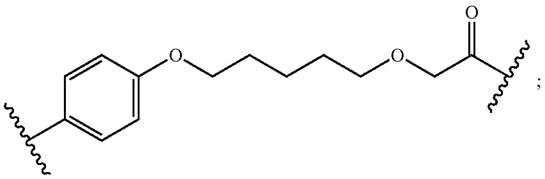
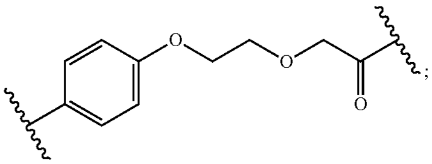
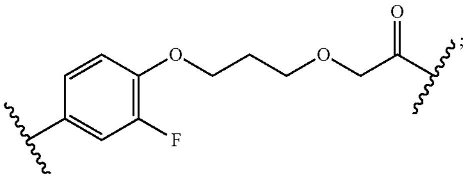
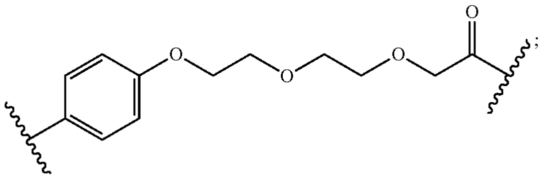
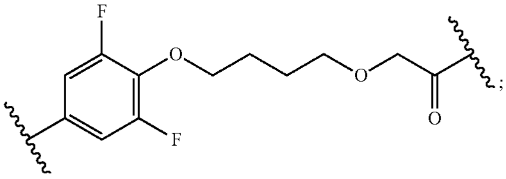
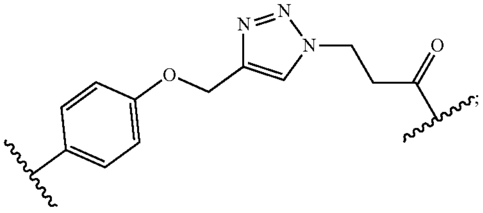
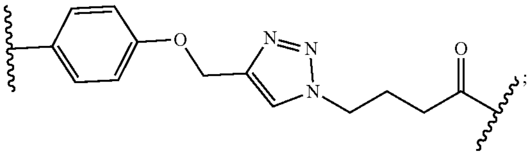

-continued
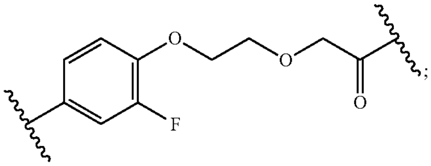
;
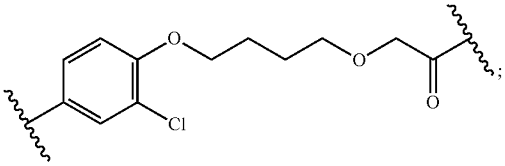
;
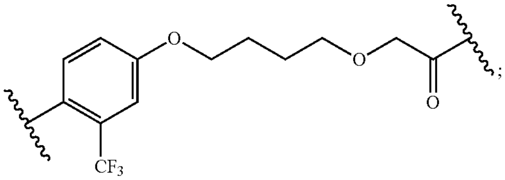
;
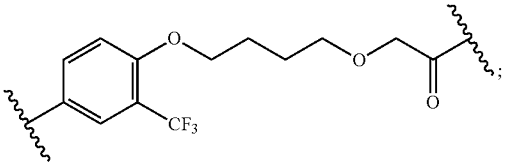
;
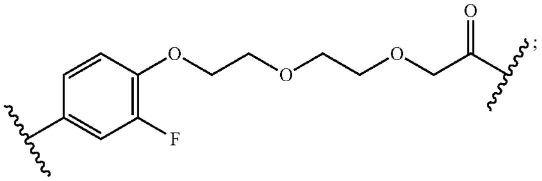
;
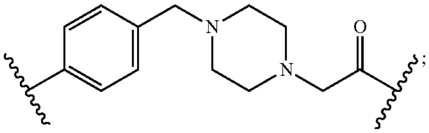
;
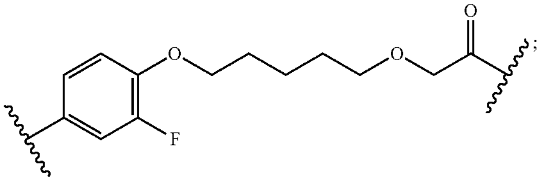
;
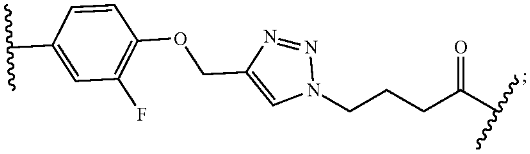
;
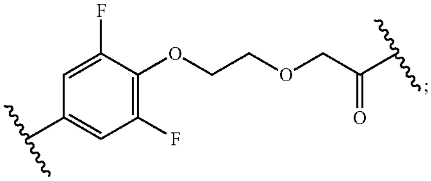
;
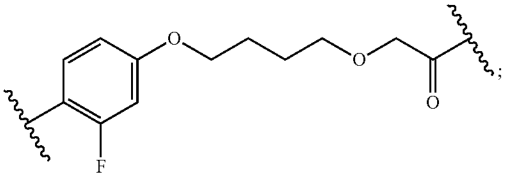
;
-continued
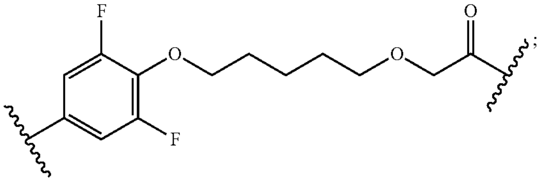
;
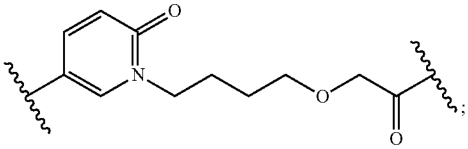
;
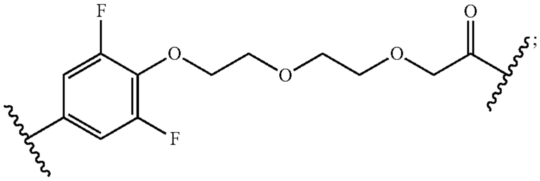
;
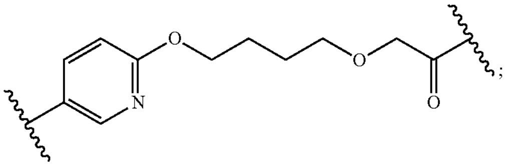
;
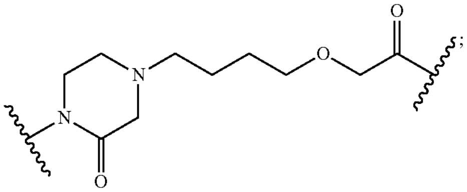
;
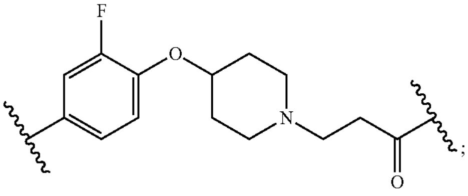
;
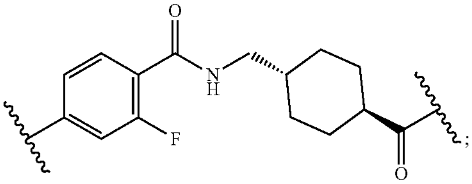
;
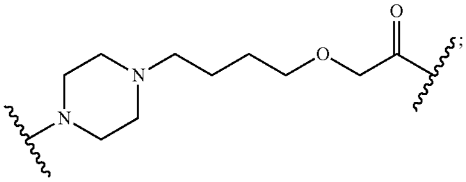
;
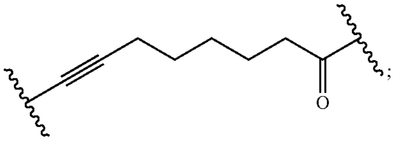
;
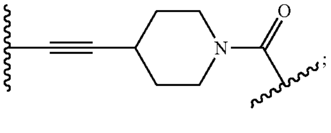
;

-continued
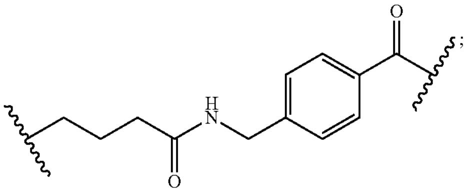
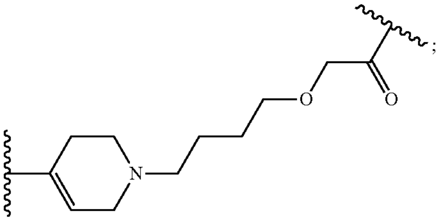
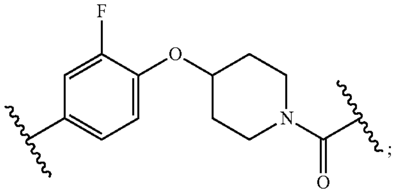
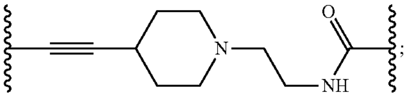
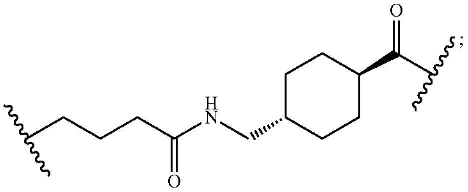
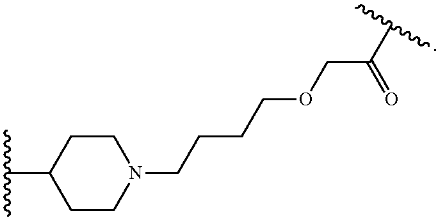
In some certain embodiments, the linking group (L) is selected from groups:
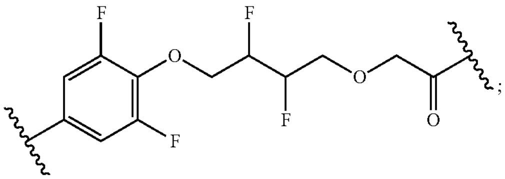
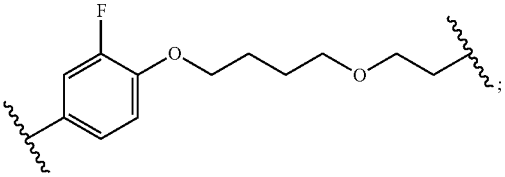
-continued
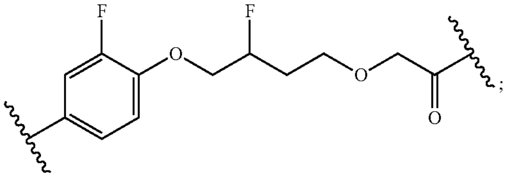
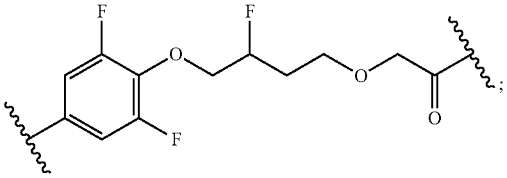
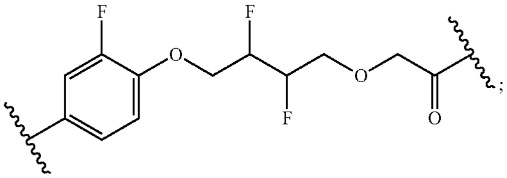
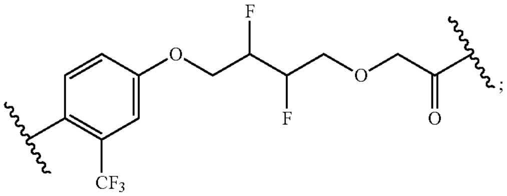
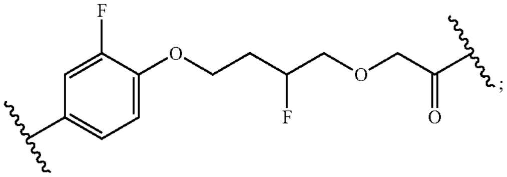
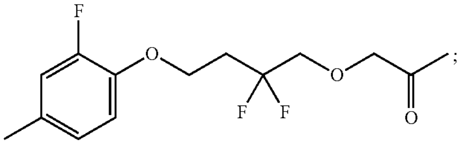
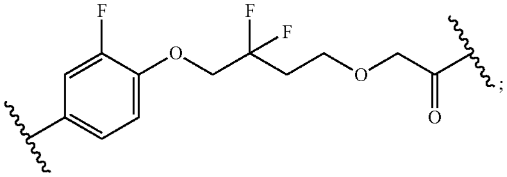
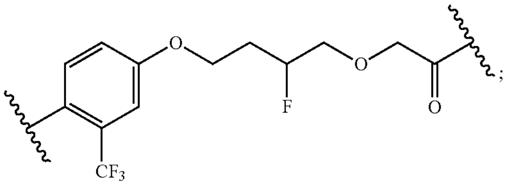
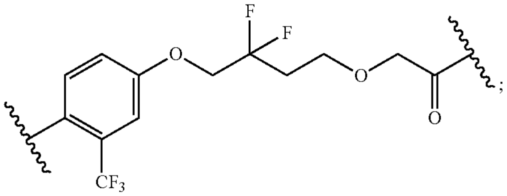

-continued
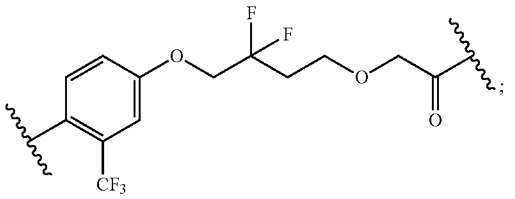
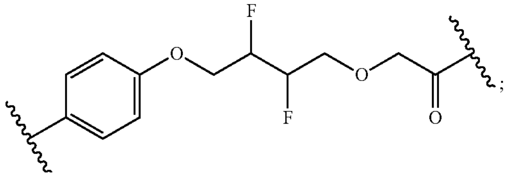
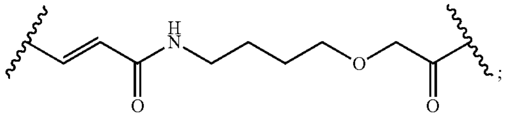
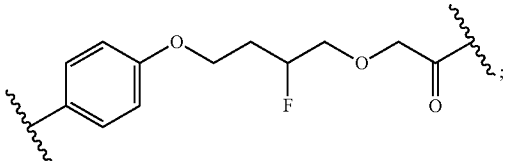
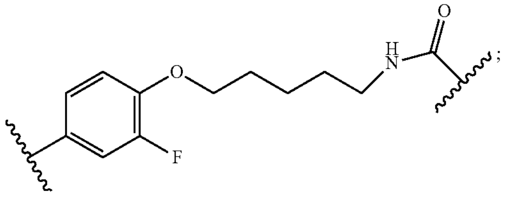
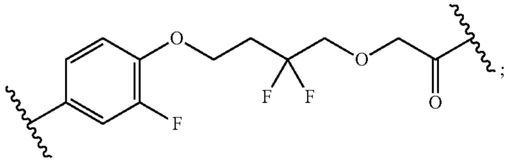
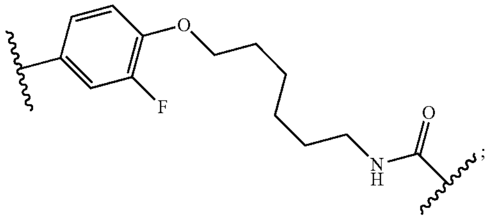
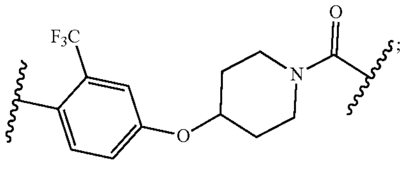
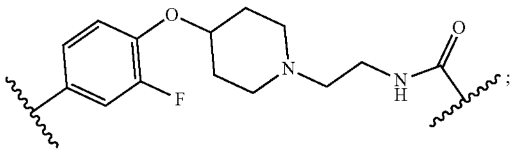
-continued
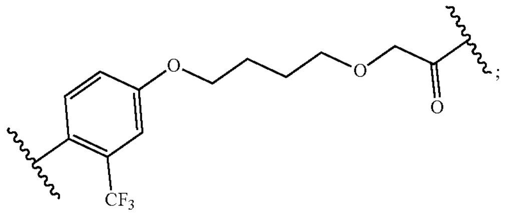
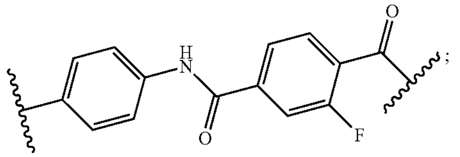
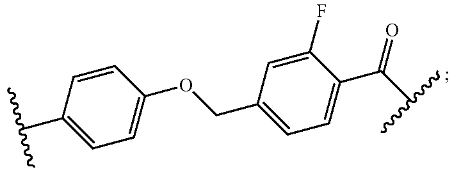
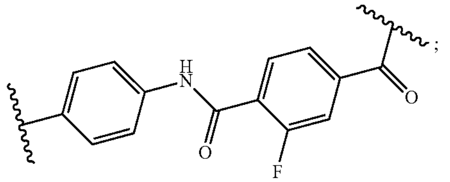
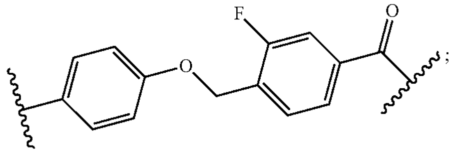
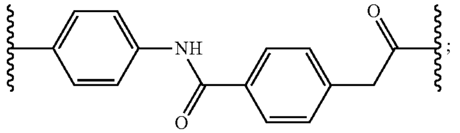
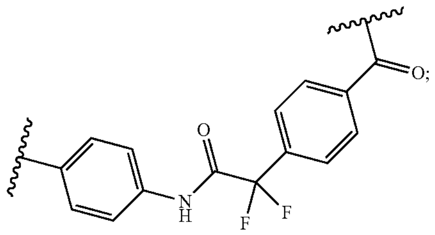
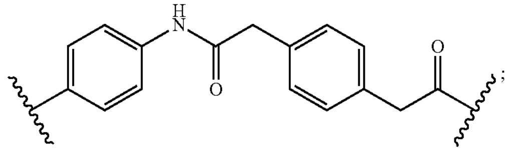
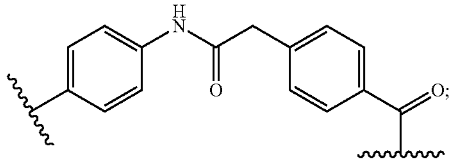
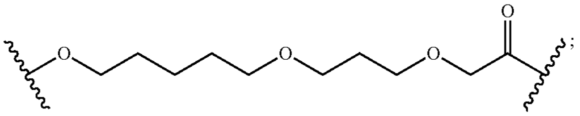

-continued
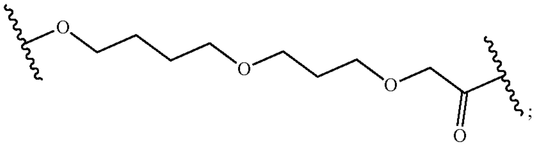
;
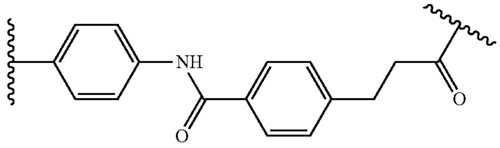
;
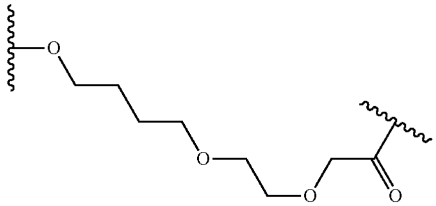
;
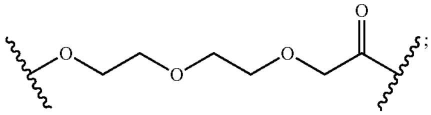
;
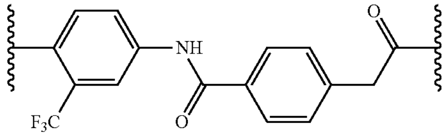
;
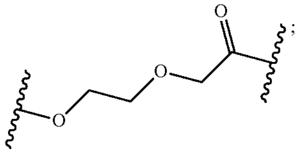
;
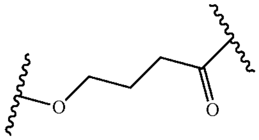
;
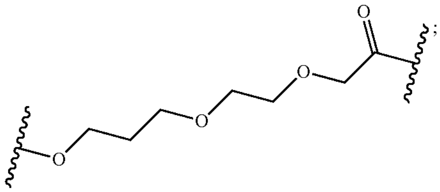
;
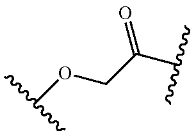
;
-continued
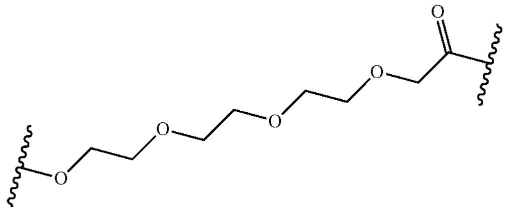
;
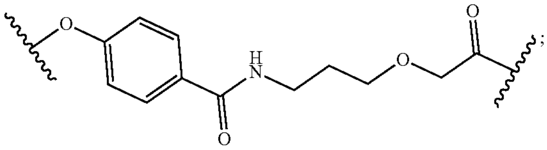
;
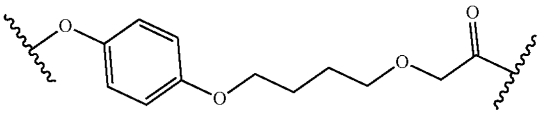
;
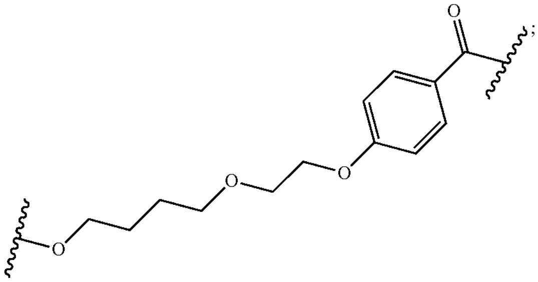
;
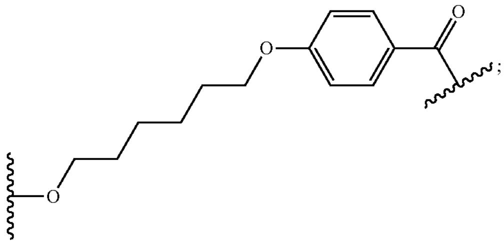
;
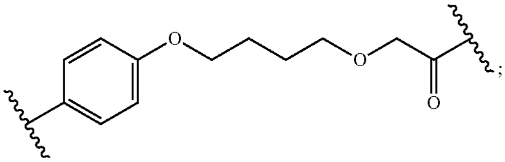
;
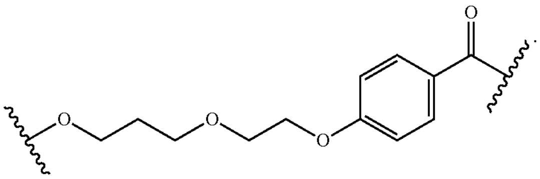 [SMILES: *OCCCOCCOc1ccc(C(*)=O)cc1]
.
The specific compounds of the present invention are as follows:

| Compound number | Compound structure |
|---|---|
| A1 | 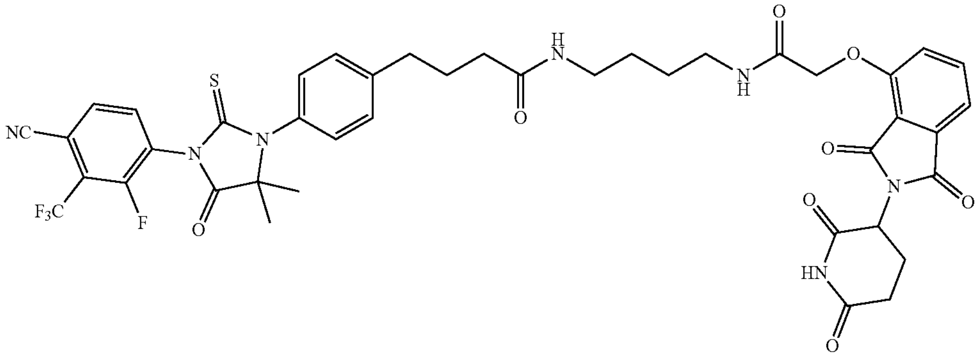 [SMILES: CC1(C)C(=O)N(c2ccc(C#N)c(C(F)(F)F)c2F)C(=S)N1c1ccc(CCCC(=O)NCCCCNC(=O)COc2cccc3c2C(=O)N(C2CCC(=O)NC2=O)C3=O)cc1] |
| A2 | 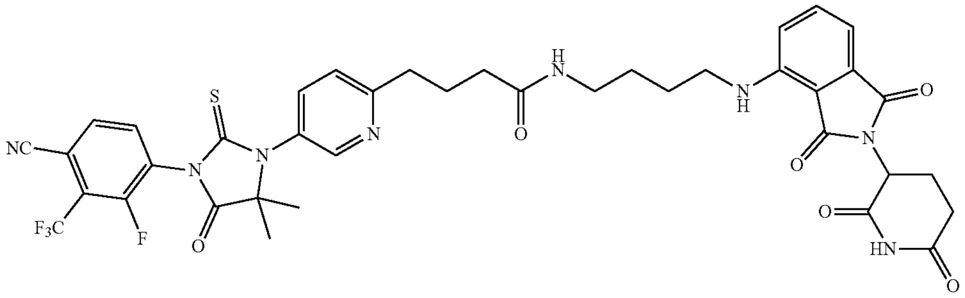 [SMILES: CC1(C)C(=O)N(c2ccc(C#N)c(C(F)(F)F)c2F)C(=S)N1c1ccc(CCCC(=O)NCCCCNc2cccc3c2C(=O)N(C2CCC(=O)NC2=O)C3=O)nc1] |
| A3 | |
| A4 | |
| A5 | |
| A6 | |
| A7 | 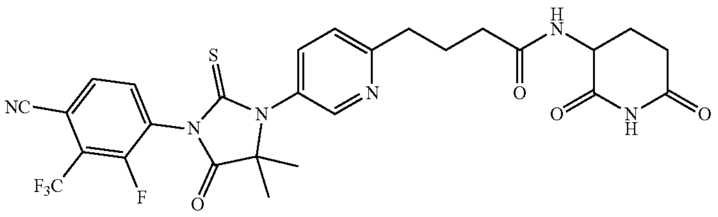 [SMILES: CC1(C)C(=O)N(c2ccc(C#N)c(C(F)(F)F)c2F)C(=S)N1c1ccc(CCCC(=O)NC2CCC(=O)NC2=O)nc1] |
| A8 | 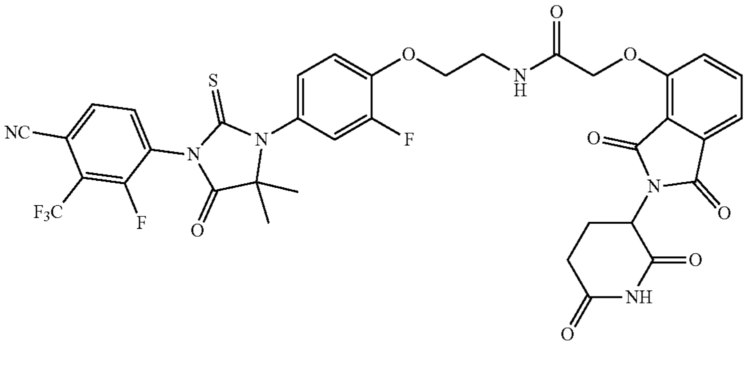 [SMILES: CC1(C)C(=O)N(c2ccc(C#N)c(C(F)(F)F)c2F)C(=S)N1c1ccc(OCCNC(=O)COc2cccc3c2C(=O)N(C2CCC(=O)NC2=O)C3=O)c(F)c1] |

-continued
| Compound number | Compound structure |
| --- | --- |
| A9 | 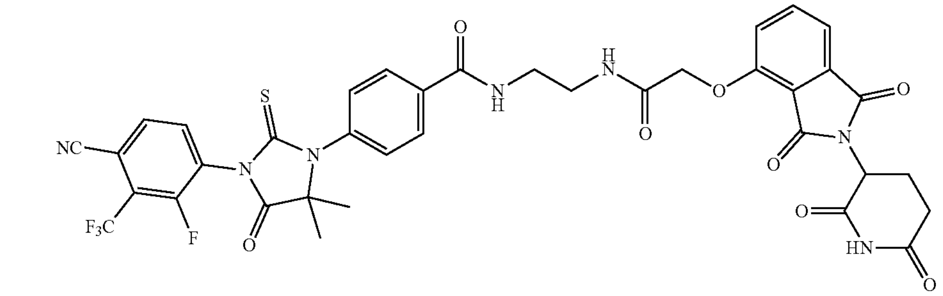 [SMILES: CC1(C)C(=O)N(c2ccc(C#N)c(C(F)(F)F)c2F)C(=S)N1c1ccc(C(=O)NCCNC(=O)COc2cccc3c2C(=O)N(C2CCC(=O)NC2=O)C3=O)cc1] |
| A10 | 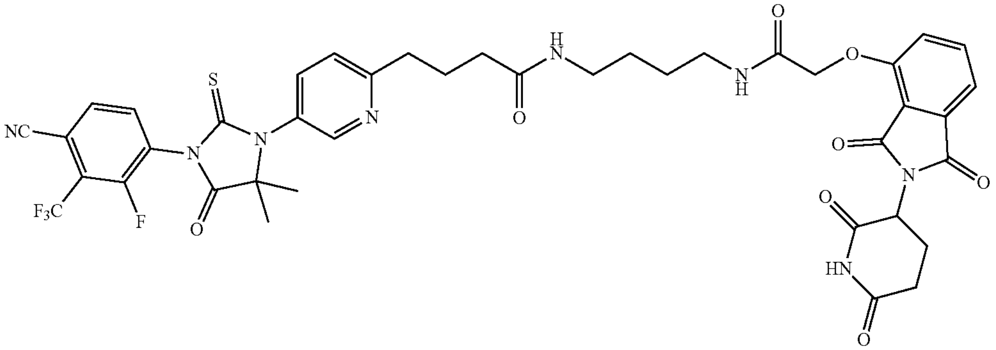 [SMILES: CC1(C)C(=O)N(c2ccc(C#N)c(C(F)(F)F)c2F)C(=S)N1c1ccc(CCCC(=O)NCCCCNC(=O)COc2cccc3c2C(=O)N(C2CCC(=O)NC2=O)C3=O)nc1] |
| A11 | 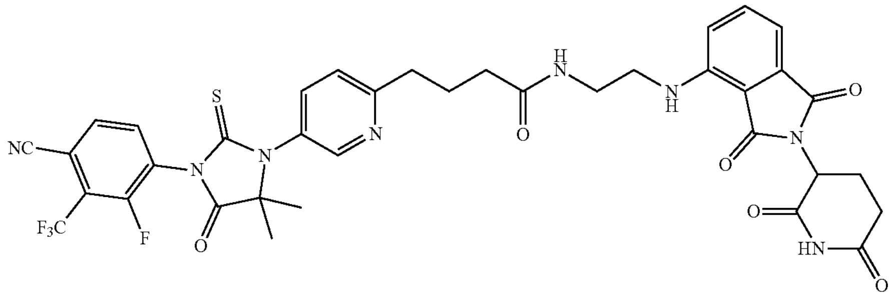 [SMILES: CC1(C)C(=O)N(c2ccc(C#N)c(C(F)(F)F)c2F)C(=S)N1c1ccc(CCCC(=O)NCCNc2cccc3c2C(=O)N(C2CCC(=O)NC2=O)C3=O)nc1] |
| A12 | 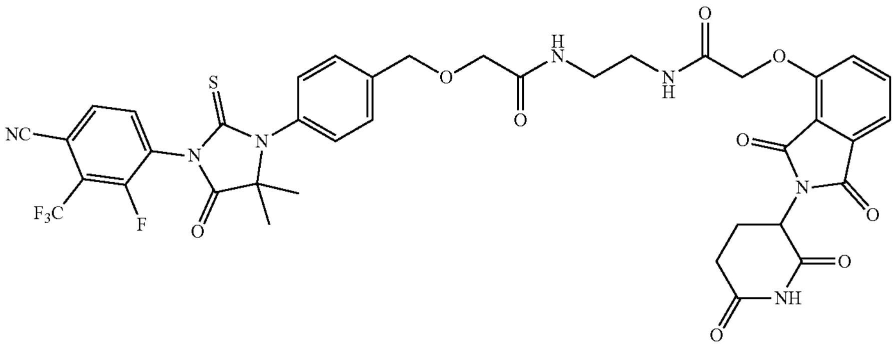 [SMILES: CC1(C)C(=O)N(c2ccc(C#N)c(C(F)(F)F)c2F)C(=S)N1c1ccc(COCC(=O)NCCNC(=O)COc2cccc3c2C(=O)N(C2CCC(=O)NC2=O)C3=O)cc1] |

-continued
| Compound number | Compound structure |
|---|---|
| A13 | 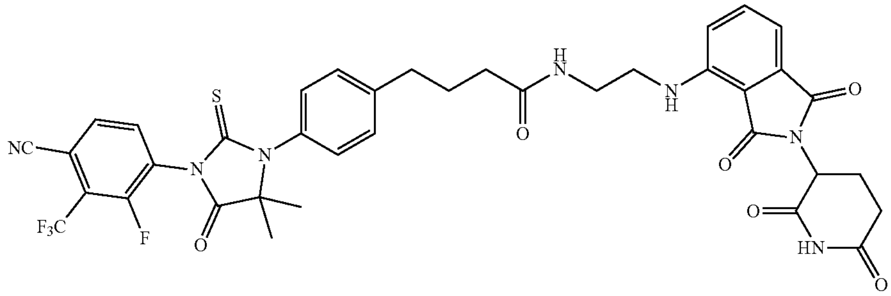 [SMILES: CC1(C)C(=O)N(c2ccc(C#N)c(C(F)(F)F)c2F)C(=S)N1c1ccc(CCCC(=O)NCCNc2cccc3c2C(=O)N(C2CCC(=O)NC2=O)C3=O)cc1] |
| A14 | 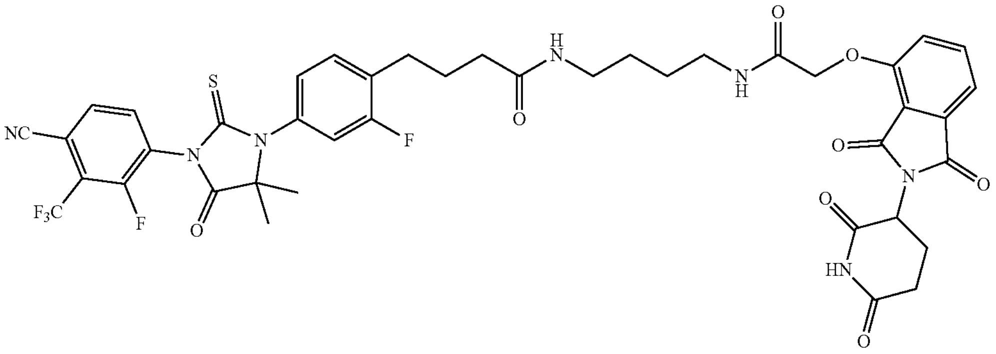 [SMILES: CC1(C)C(=O)N(c2ccc(C#N)c(C(F)(F)F)c2F)C(=S)N1c1ccc(CCCC(=O)NCCCCNC(=O)COc2cccc3c2C(=O)N(C2CCC(=O)NC2=O)C3=O)c(F)c1] |
| A15 | 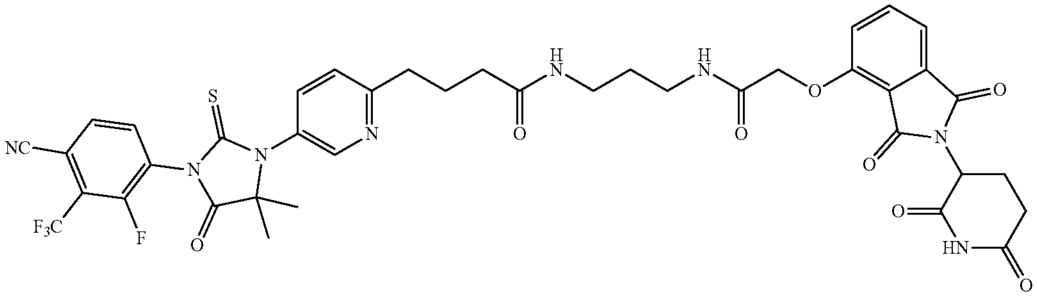 [SMILES: CC1(C)C(=O)N(c2ccc(C#N)c(C(F)(F)F)c2F)C(=S)N1c1ccc(CCCC(=O)NCCCNC(=O)COc2cccc3c2C(=O)N(C2CCC(=O)NC2=O)C3=O)nc1] |
| A16 | 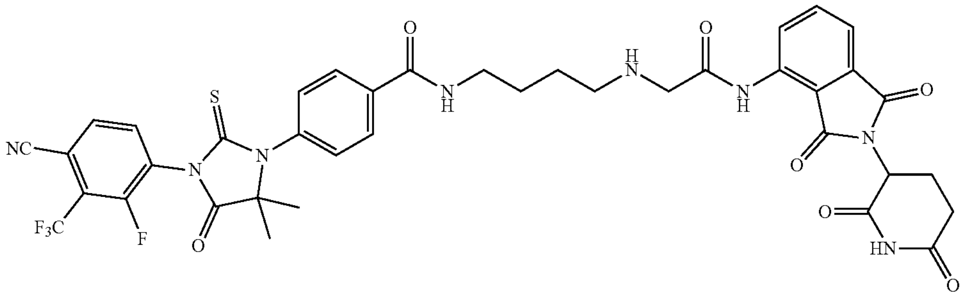 [SMILES: CC1(C)C(=O)N(c2ccc(C#N)c(C(F)(F)F)c2F)C(=S)N1c1ccc(C(=O)NCCCCNCC(=O)Nc2cccc3c2C(=O)N(C2CCC(=O)NC2=O)C3=O)cc1] |

-continued
| Compound number | Compound structure |
| --- | --- |
| A17 | 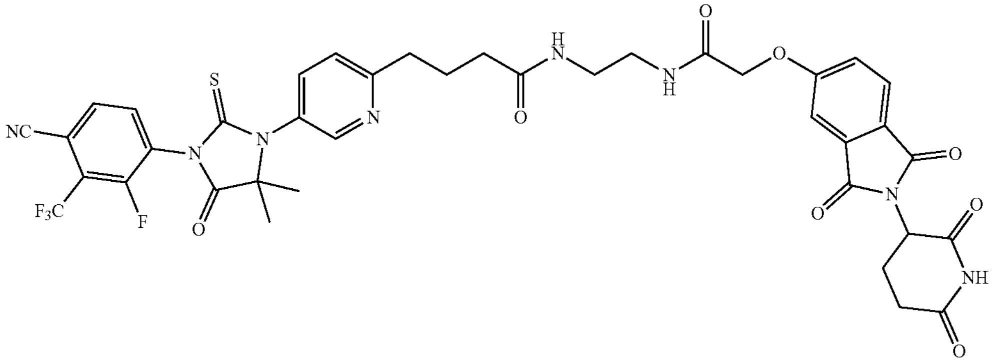 [SMILES: CC1(C)C(=O)N(c2ccc(C#N)c(C(F)(F)F)c2F)C(=S)N1c1ccc(CCCC(=O)NCCNC(=O)COc2ccc3c(c2)C(=O)N(C2CCC(=O)NC2=O)C3=O)nc1] |
| A18 | 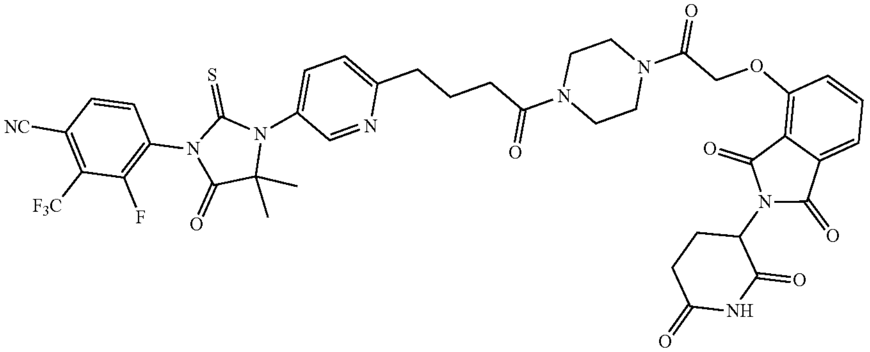 [SMILES: CC1(C)C(=O)N(c2ccc(C#N)c(C(F)(F)F)c2F)C(=S)N1c1ccc(CCCC(=O)N2CCN(C(=O)COc3cccc4c3C(=O)N(C3CCC(=O)NC3=O)C4=O)CC2)nc1] |
| A19 | 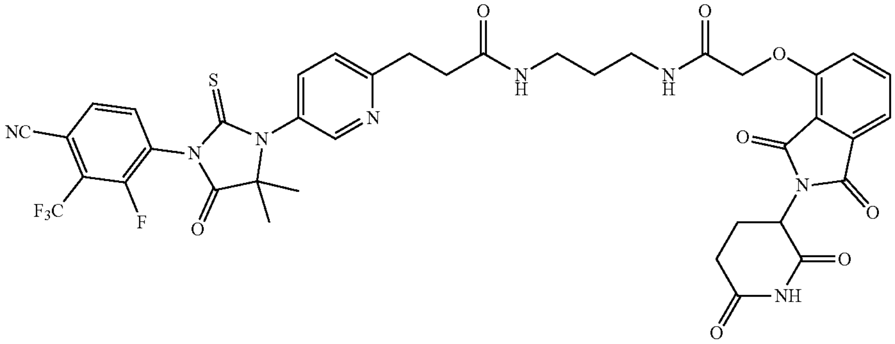 [SMILES: CC1(C)C(=O)N(c2ccc(C#N)c(C(F)(F)F)c2F)C(=S)N1c1ccc(CCC(=O)NCCCNC(=O)COc2cccc3c2C(=O)N(C2CCC(=O)NC2=O)C3=O)nc1] |
| A20 | 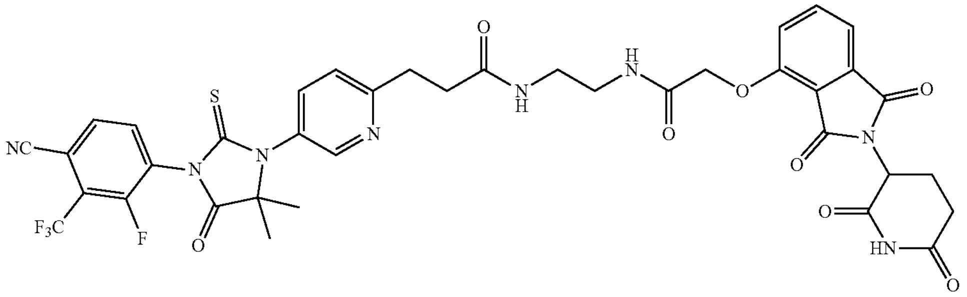 [SMILES: CC1(C)C(=O)N(c2ccc(C#N)c(C(F)(F)F)c2F)C(=S)N1c1ccc(CCC(=O)NCCNC(=O)COc2cccc3c2C(=O)N(C2CCC(=O)NC2=O)C3=O)nc1] |

-continued
| Compound number | Compound structure |
|---|---|
| A21 | 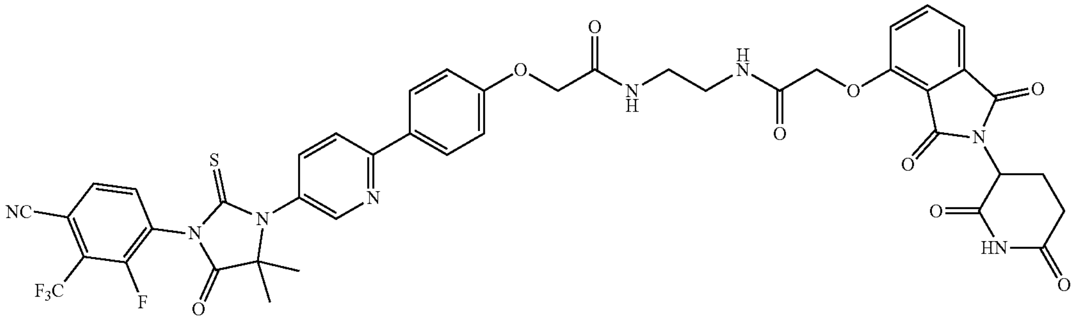 [SMILES: CC1(C)C(=O)N(c2ccc(C#N)c(C(F)(F)F)c2F)C(=S)N1c1ccc(-c2ccc(OCC(=O)NCCNC(=O)COc3cccc4c3C(=O)N(C3CCC(=O)NC3=O)C4=O)cc2)nc1] |
| A22 | 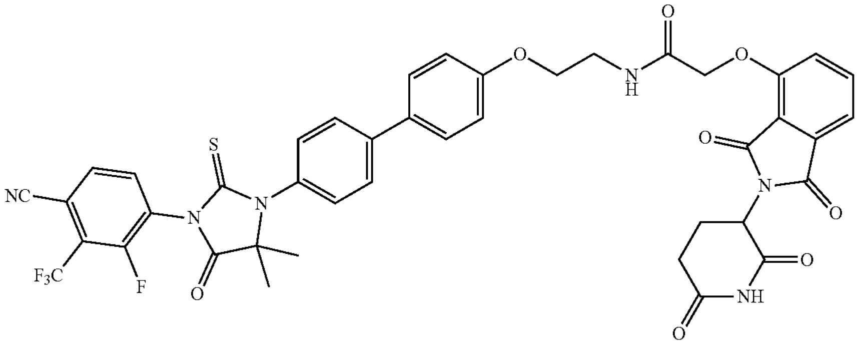 [SMILES: CC1(C)C(=O)N(c2ccc(C#N)c(C(F)(F)F)c2F)C(=S)N1c1ccc(-c2ccc(OCCNC(=O)COc3cccc4c3C(=O)N(C3CCC(=O)NC3=O)C4=O)cc2)cc1] |
| A23 | 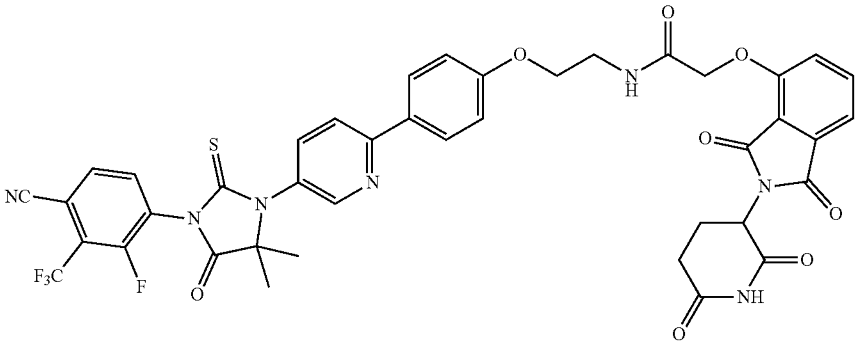 [SMILES: CC1(C)C(=O)N(c2ccc(C#N)c(C(F)(F)F)c2F)C(=S)N1c1ccc(-c2ccc(OCCNC(=O)COc3cccc4c3C(=O)N(C3CCC(=O)NC3=O)C4=O)cc2)nc1] |
| A24 | 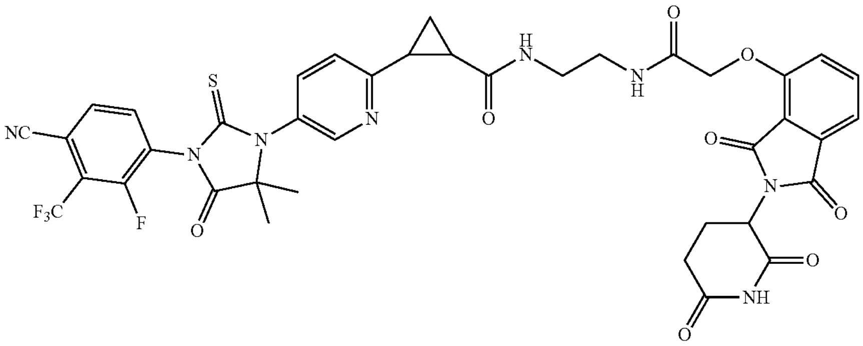 [SMILES: CC1(C)C(=O)N(c2ccc(C#N)c(C(F)(F)F)c2F)C(=S)N1c1ccc(C2CC2C(=O)NCCNC(=O)COc2cccc3c2C(=O)N(C2CCC(=O)NC2=O)C3=O)nc1] |

-continued
| Compound number | Compound structure |
|---|---|
| A25 | 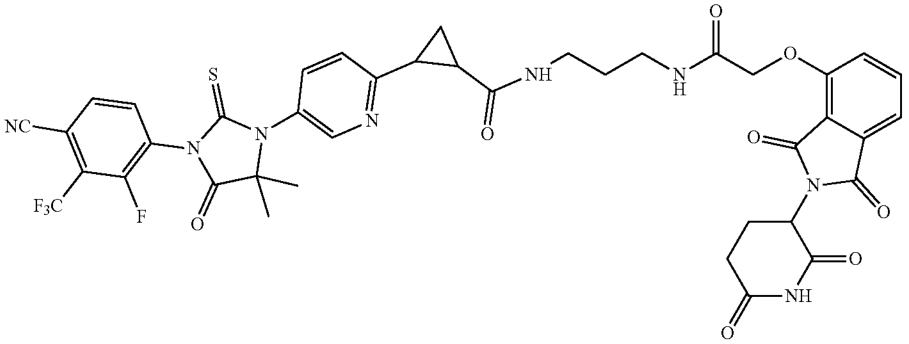 [SMILES: CC1(C)C(=O)N(c2ccc(C#N)c(C(F)(F)F)c2F)C(=S)N1c1ccc(C2CC2C(=O)NCCCNC(=O)COc2cccc3c2C(=O)N(C2CCC(=O)NC2=O)C3=O)nc1] |
| A26 | 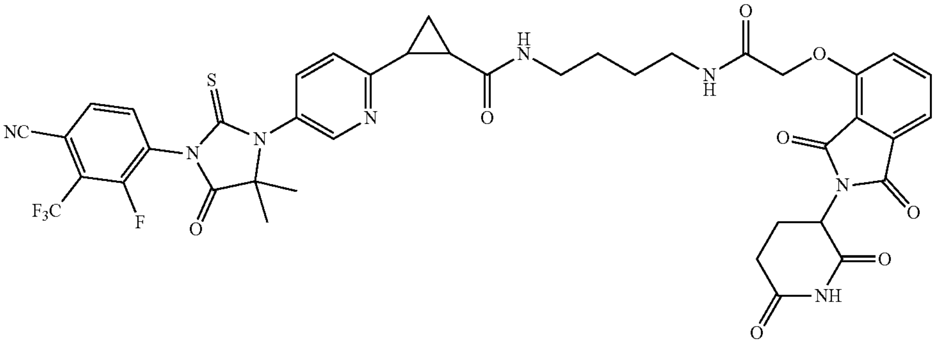 [SMILES: CC1(C)C(=O)N(c2ccc(C#N)c(C(F)(F)F)c2F)C(=S)N1c1ccc(C2CC2C(=O)NCCCCNC(=O)COc2cccc3c2C(=O)N(C2CCC(=O)NC2=O)C3=O)nc1] |
| A27 | 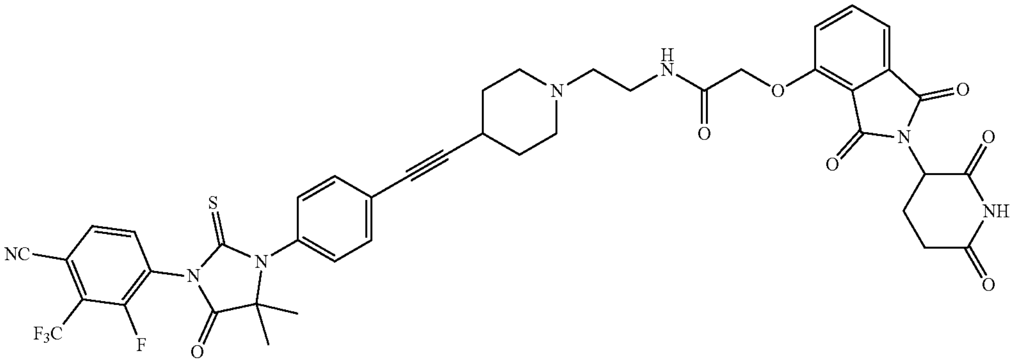 [SMILES: CC1(C)C(=O)N(c2ccc(C#N)c(C(F)(F)F)c2F)C(=S)N1c1ccc(C#CC2CCN(CCNC(=O)COc3cccc4c3C(=O)N(C3CCC(=O)NC3=O)C4=O)CC2)cc1] |
| A28 | 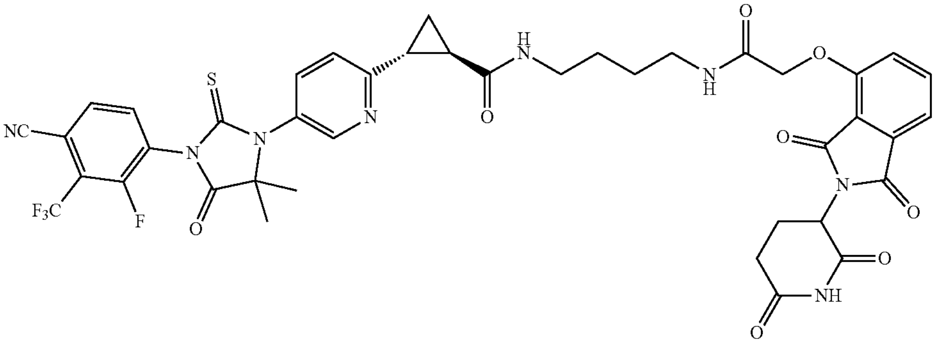 [SMILES: CC1(C)C(=O)N(c2ccc(C#N)c(C(F)(F)F)c2F)C(=S)N1c1ccc([C@@H]2C[C@H]2C(=O)NCCCCNC(=O)COc2cccc3c2C(=O)N(C2CCC(=O)NC2=O)C3=O)nc1] |

-continued
| Compound number | Compound structure |
|---|---|
| A29 | 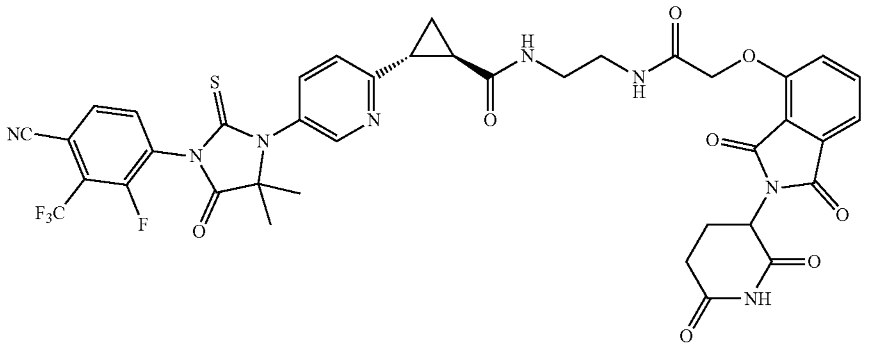 [SMILES: CC1(C)C(=O)N(c2ccc(C#N)c(C(F)(F)F)c2F)C(=S)N1c1ccc([C@@H]2C[C@H]2C(=O)NCCNC(=O)COc2cccc3c2C(=O)N(C2CCC(=O)NC2=O)C3=O)nc1] |
| A30 | 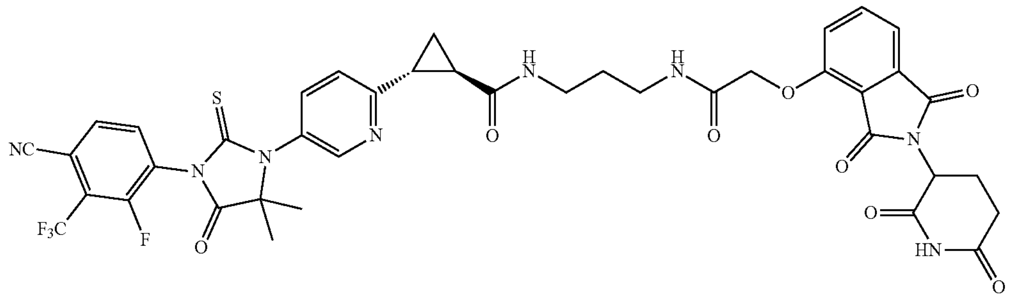 [SMILES: CC1(C)C(=O)N(c2ccc(C#N)c(C(F)(F)F)c2F)C(=S)N1c1ccc([C@@H]2C[C@H]2C(=O)NCCCNC(=O)COc2cccc3c2C(=O)N(C2CCC(=O)NC2=O)C3=O)nc1] |
| A31 | 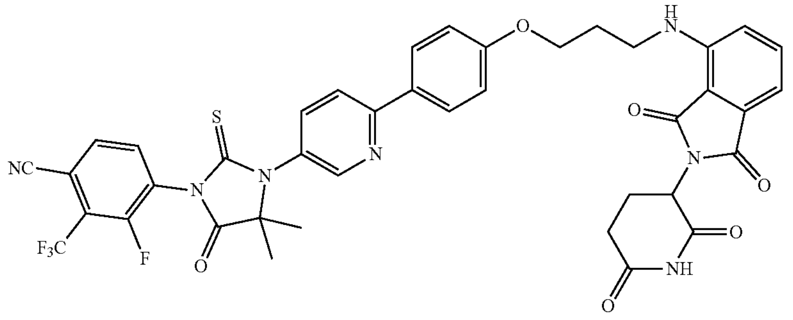 [SMILES: CC1(C)C(=O)N(c2ccc(C#N)c(C(F)(F)F)c2F)C(=S)N1c1ccc(-c2ccc(OCCCNc3cccc4c3C(=O)N(C3CCC(=O)NC3=O)C4=O)cc2)nc1] |
| A32 | 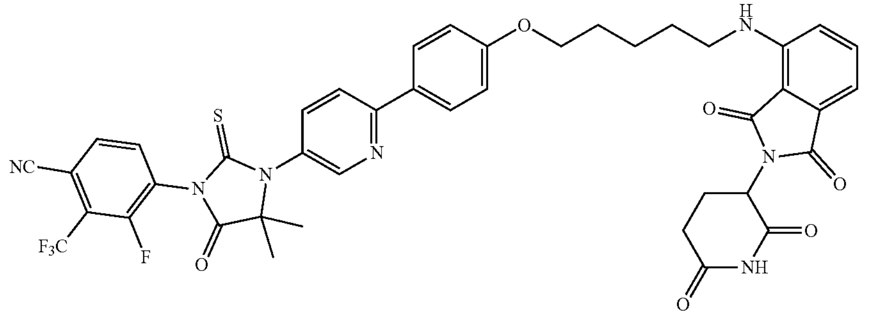 [SMILES: CC1(C)C(=O)N(c2ccc(C#N)c(C(F)(F)F)c2F)C(=S)N1c1ccc(-c2ccc(OCCCCCNc3cccc4c3C(=O)N(C3CCC(=O)NC3=O)C4=O)cc2)nc1] |

-continued
| Compound number | Compound structure |
|---|---|
| A33 | 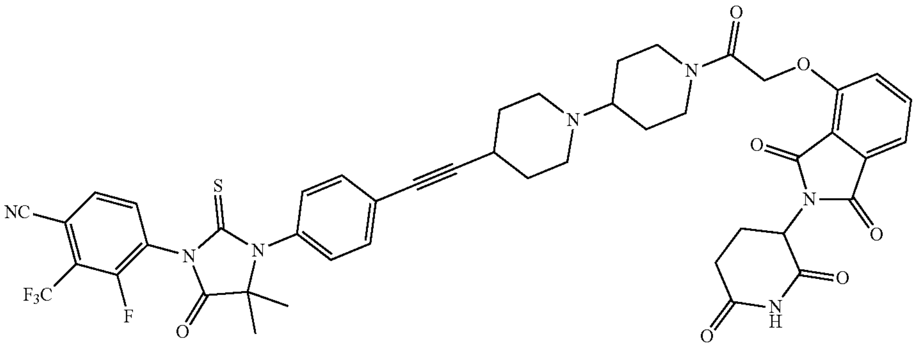 [SMILES: CC1(C)C(=O)N(c2ccc(C#N)c(C(F)(F)F)c2F)C(=S)N1c1ccc(C#CC2CCN(C3CCN(C(=O)COc4cccc5c4C(=O)N(C4CCC(=O)NC4=O)C5=O)CC3)CC2)cc1] |
| A34 | 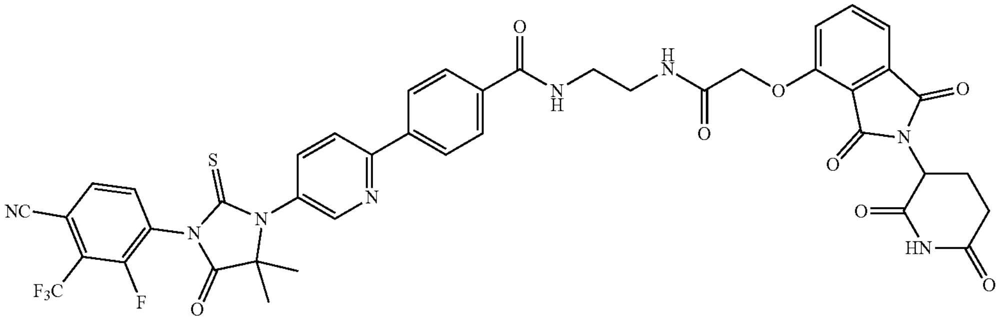 [SMILES: CC1(C)C(=O)N(c2ccc(C#N)c(C(F)(F)F)c2F)C(=S)N1c1ccc(-c2ccc(C(=O)NCCNC(=O)COc3cccc4c3C(=O)N(C3CCC(=O)NC3=O)C4=O)cc2)nc1] |
| A35 | 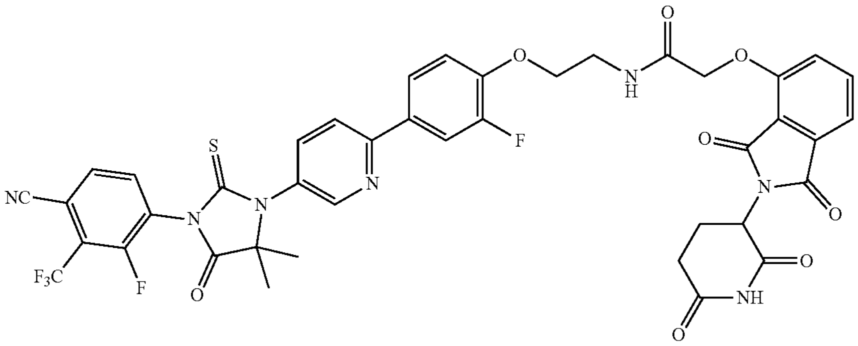 [SMILES: CC1(C)C(=O)N(c2ccc(C#N)c(C(F)(F)F)c2F)C(=S)N1c1ccc(-c2ccc(OCCNC(=O)COc3cccc4c3C(=O)N(C3CCC(=O)NC3=O)C4=O)c(F)c2)nc1] |
| A36 | 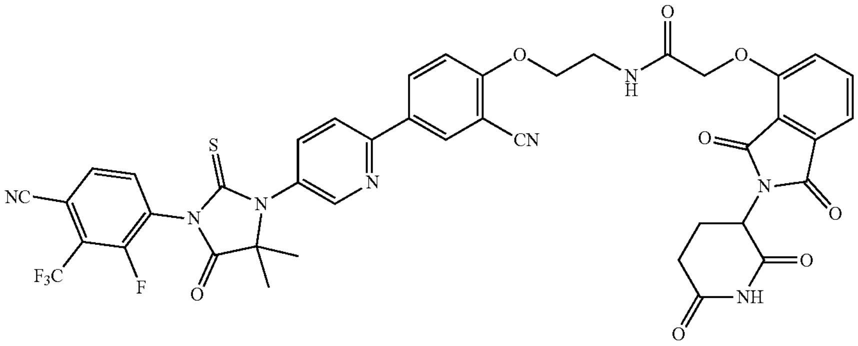 [SMILES: CC1(C)C(=O)N(c2ccc(C#N)c(C(F)(F)F)c2F)C(=S)N1c1ccc(-c2ccc(OCCNC(=O)COc3cccc4c3C(=O)N(C3CCC(=O)NC3=O)C4=O)c(C#N)c2)nc1] |

-continued
| Compound number | Compound structure |
|---|---|
| A37 | 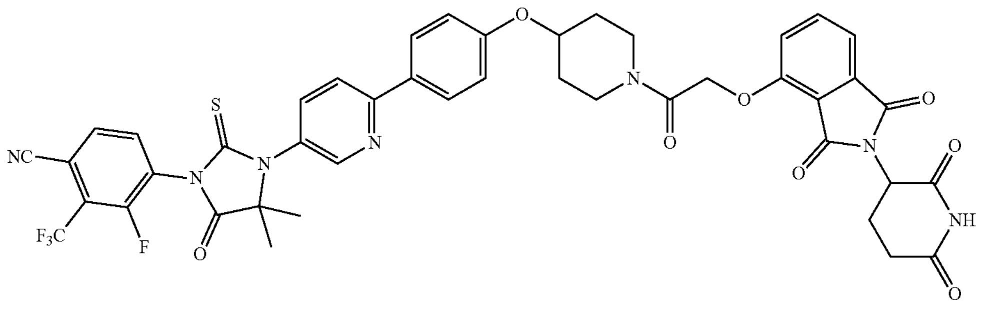 [SMILES: CC1(C)C(=O)N(c2ccc(C#N)c(C(F)(F)F)c2F)C(=S)N1c1ccc(-c2ccc(OC3CCN(C(=O)COc4cccc5c4C(=O)N(C4CCC(=O)NC4=O)C5=O)CC3)cc2)nc1] |
| A38 | 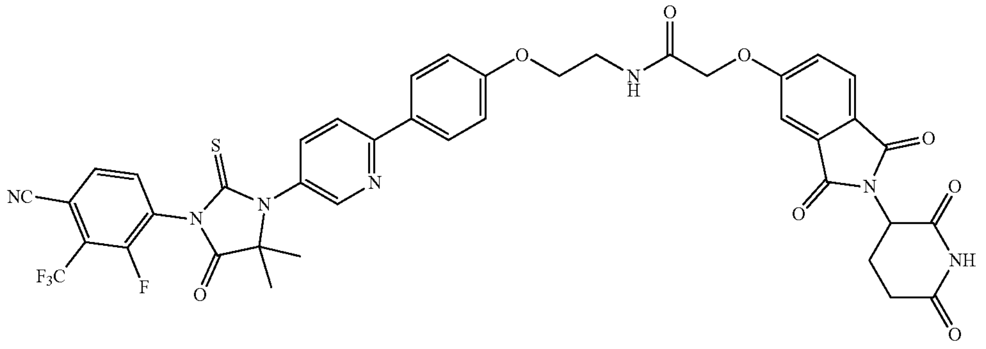 [SMILES: CC1(C)C(=O)N(c2ccc(C#N)c(C(F)(F)F)c2F)C(=S)N1c1ccc(-c2ccc(OCCNC(=O)COc3ccc4c(c3)C(=O)N(C3CCC(=O)NC3=O)C4=O)cc2)nc1] |
| A39 | 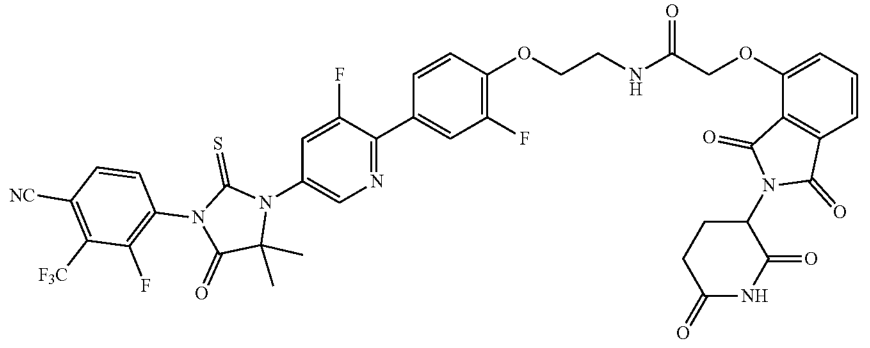 [SMILES: CC1(C)C(=O)N(c2ccc(C#N)c(C(F)(F)F)c2F)C(=S)N1c1cnc(-c2ccc(OCCNC(=O)COc3cccc4c3C(=O)N(C3CCC(=O)NC3=O)C4=O)c(F)c2)c(F)c1] |
| A40 | 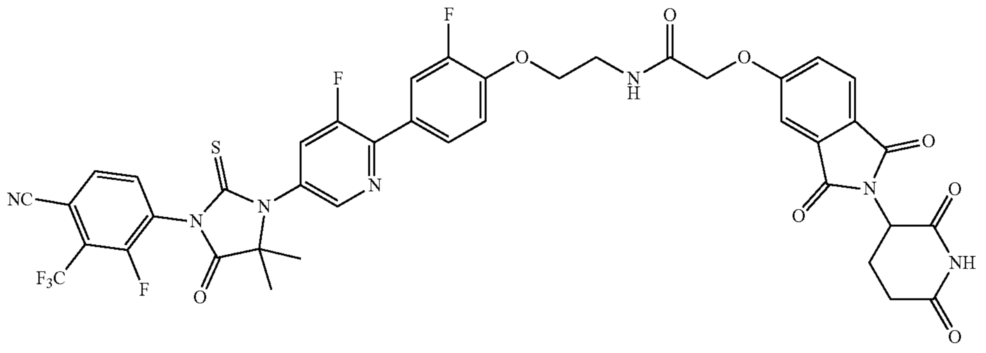 [SMILES: CC1(C)C(=O)N(c2ccc(C#N)c(C(F)(F)F)c2F)C(=S)N1c1cnc(-c2ccc(OCCNC(=O)COc3ccc4c(c3)C(=O)N(C3CCC(=O)NC3=O)C4=O)c(F)c2)c(F)c1] |

-continued
| Compound number | Compound structure |
|---|---|
| A41 | 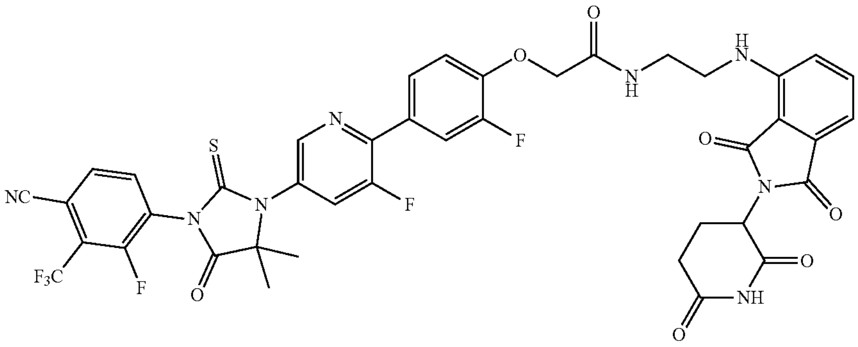 [SMILES: CC1(C)C(=O)N(c2ccc(C#N)c(C(F)(F)F)c2F)C(=S)N1c1cnc(-c2ccc(OCC(=O)NCCNc3cccc4c3C(=O)N(C3CCC(=O)NC3=O)C4=O)c(F)c2)c(F)c1] |
| A42 | 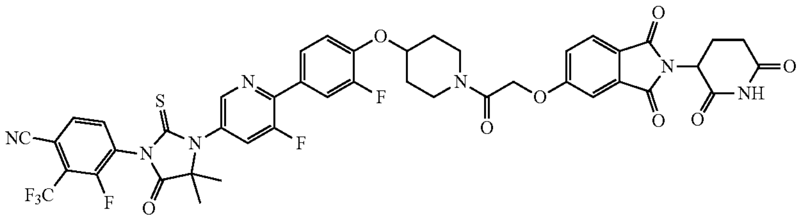 [SMILES: CC1(C)C(=O)N(c2ccc(C#N)c(C(F)(F)F)c2F)C(=S)N1c1cnc(-c2ccc(OC3CCN(C(=O)COc4ccc5c(c4)C(=O)N(C4CCC(=O)NC4=O)C5=O)CC3)c(F)c2)c(F)c1] |
| A43 | 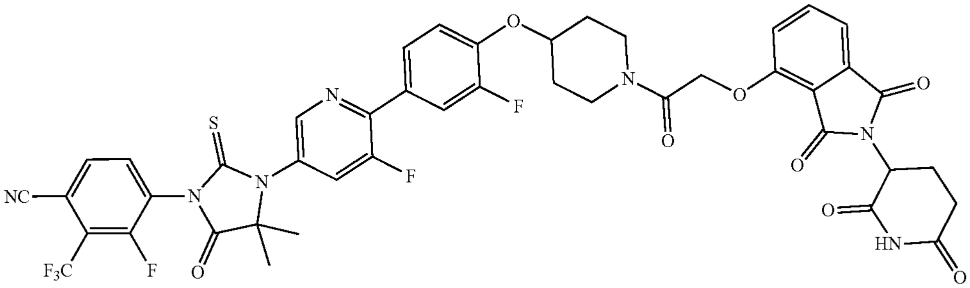 [SMILES: CC1(C)C(=O)N(c2ccc(C#N)c(C(F)(F)F)c2F)C(=S)N1c1cnc(-c2ccc(OC3CCN(C(=O)COc4cccc5c4C(=O)N(C4CCC(=O)NC4=O)C5=O)CC3)c(F)c2)c(F)c1] |
| A44 | 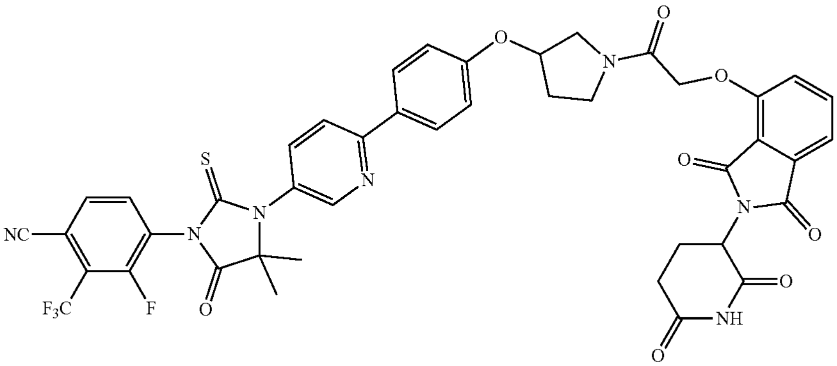 [SMILES: CC1(C)C(=O)N(c2ccc(C#N)c(C(F)(F)F)c2F)C(=S)N1c1ccc(-c2ccc(OC3CCN(C(=O)COc4cccc5c4C(=O)N(C4CCC(=O)NC4=O)C5=O)C3)cc2)nc1] |

-continued
| Compound number | Compound structure |
| --- | --- |
| A45 | 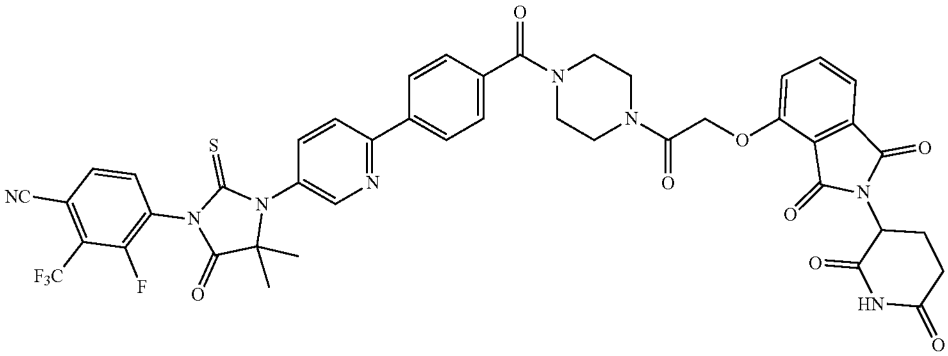 [SMILES: CC1(C)C(=O)N(c2ccc(C#N)c(C(F)(F)F)c2F)C(=S)N1c1ccc(-c2ccc(C(=O)N3CCN(C(=O)COc4cccc5c4C(=O)N(C4CCC(=O)NC4=O)C5=O)CC3)cc2)nc1] |
| A46 | 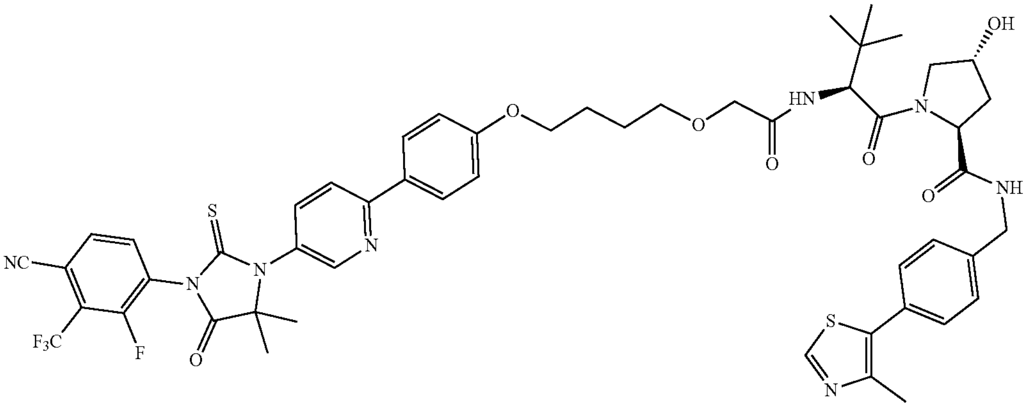 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2)C(C)(C)C)cc1] |
| A47 | 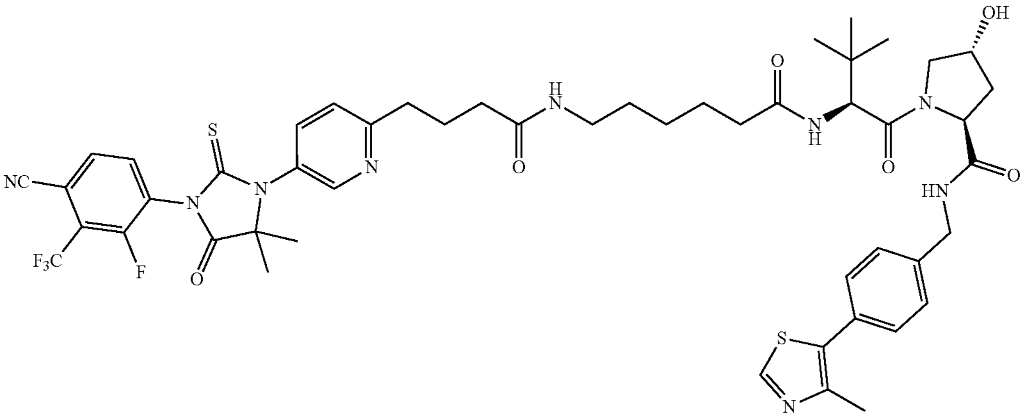 [SMILES: Cc1ncsc1-c1ccc(CNC(=O)[C@@H]2C[C@@H](O)CN2C(=O)[C@@H](NC(=O)CCCCCNC(=O)CCCc2ccc(N3C(=S)N(c4ccc(C#N)c(C(F)(F)F)c4F)C(=O)C3(C)C)cn2)C(C)(C)C)cc1] |

-continued
| Compound number | Compound structure |
|---|---|
| A48 | 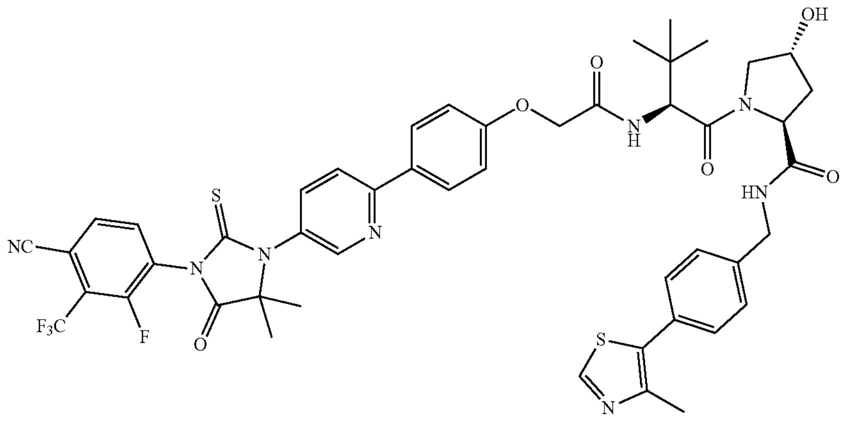 [SMILES: Cc1ncsc1-c1ccc(CNC(=O)[C@@H]2C[C@@H](O)CN2C(=O)[C@@H](NC(=O)COc2ccc(-c3ccc(N4C(=S)N(c5ccc(C#N)c(C(F)(F)F)c5F)C(=O)C4(C)C)cn3)cc2)C(C)(C)C)cc1] |
| A49 | 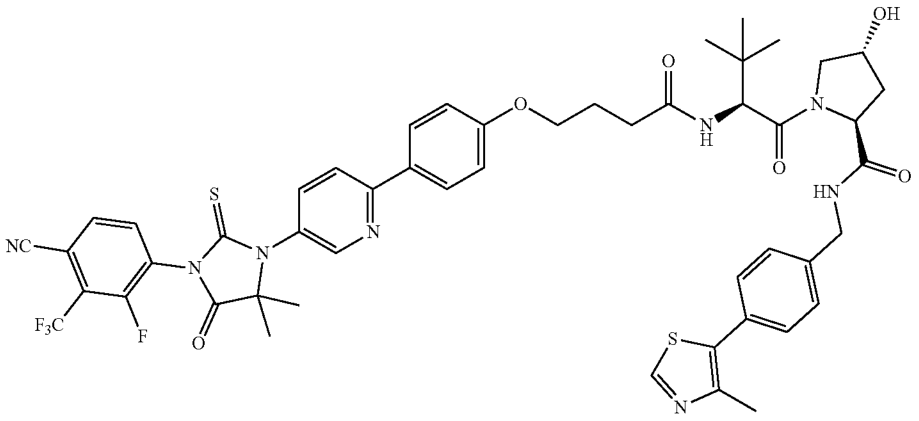 [SMILES: Cc1ncsc1-c1ccc(CNC(=O)[C@@H]2C[C@@H](O)CN2C(=O)[C@@H](NC(=O)CCCOc2ccc(-c3ccc(N4C(=S)N(c5ccc(C#N)c(C(F)(F)F)c5F)C(=O)C4(C)C)cn3)cc2)C(C)(C)C)cc1] |
| A50 | 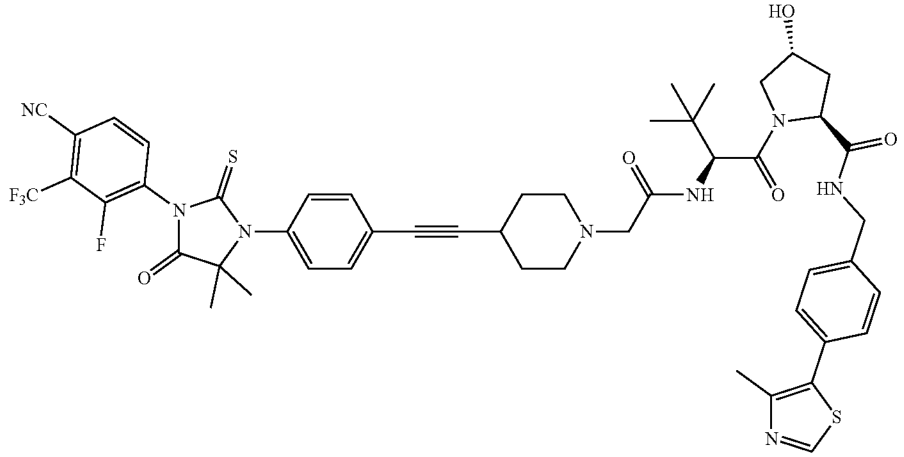 [SMILES: Cc1ncsc1-c1ccc(CNC(=O)[C@@H]2C[C@@H](O)CN2C(=O)[C@@H](NC(=O)CN2CCC(C#Cc3ccc(N4C(=S)N(c5ccc(C#N)c(C(F)(F)F)c5F)C(=O)C4(C)C)cc3)CC2)C(C)(C)C)cc1] |

-continued
| Compound number | Compound structure |
|---|---|
| A51 | 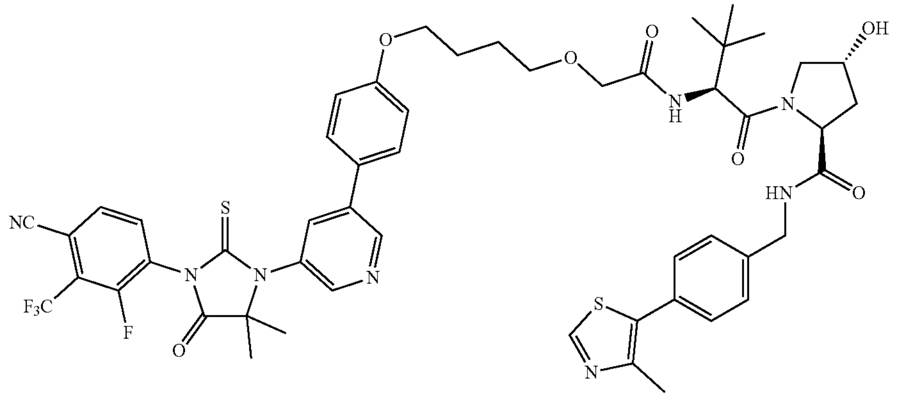 [SMILES: Cc1ncsc1-c1ccc(CNC(=O)[C@@H]2C[C@@H](O)CN2C(=O)[C@@H](NC(=O)COCCCCOc2ccc(-c3cncc(N4C(=S)N(c5ccc(C#N)c(C(F)(F)F)c5F)C(=O)C4(C)C)c3)cc2)C(C)(C)C)cc1] |
| A52 | 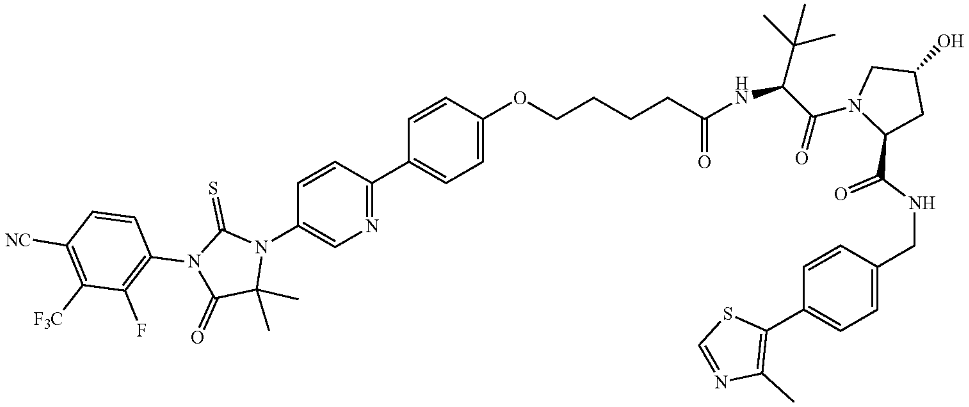 [SMILES: Cc1ncsc1-c1ccc(CNC(=O)[C@@H]2C[C@@H](O)CN2C(=O)[C@@H](NC(=O)CCCCOc2ccc(-c3ccc(N4C(=S)N(c5ccc(C#N)c(C(F)(F)F)c5F)C(=O)C4(C)C)cn3)cc2)C(C)(C)C)cc1] |
| A53 | 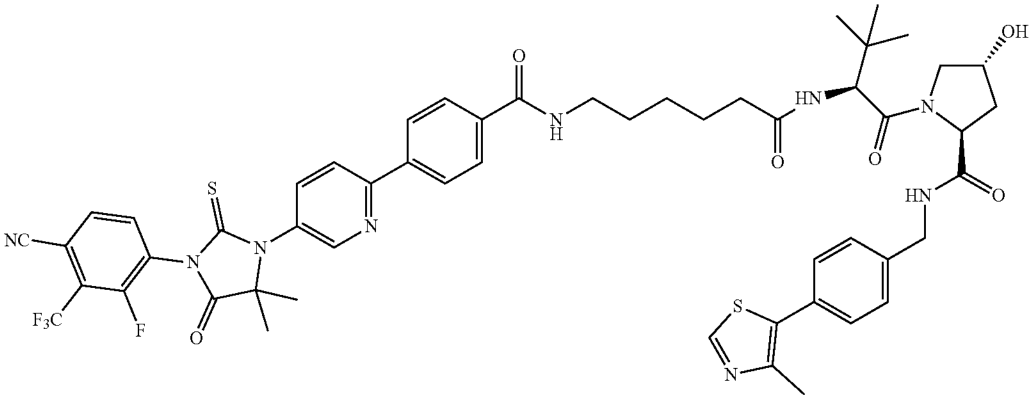 [SMILES: Cc1ncsc1-c1ccc(CNC(=O)[C@@H]2C[C@@H](O)CN2C(=O)[C@@H](NC(=O)CCCCCNC(=O)c2ccc(-c3ccc(N4C(=S)N(c5ccc(C#N)c(C(F)(F)F)c5F)C(=O)C4(C)C)cn3)cc2)C(C)(C)C)cc1] |

-continued
| Compound number | Compound structure |
|---|---|
| A54 | 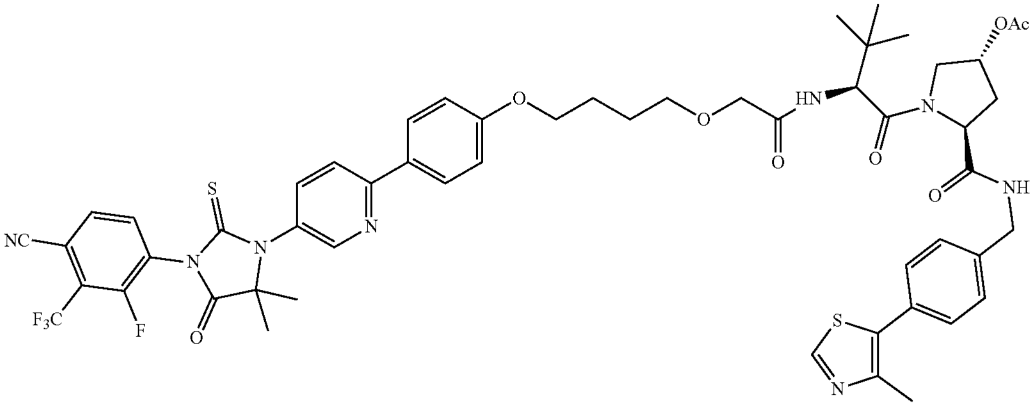 [SMILES: CC(=O)O[C@@H]1C[C@@H](C(=O)NCc2ccc(-c3scnc3C)cc2)N(C(=O)[C@@H](NC(=O)COCCCCOc2ccc(-c3ccc(N4C(=S)N(c5ccc(C#N)c(C(F)(F)F)c5F)C(=O)C4(C)C)cn3)cc2)C(C)(C)C)C1] |
| A55 | 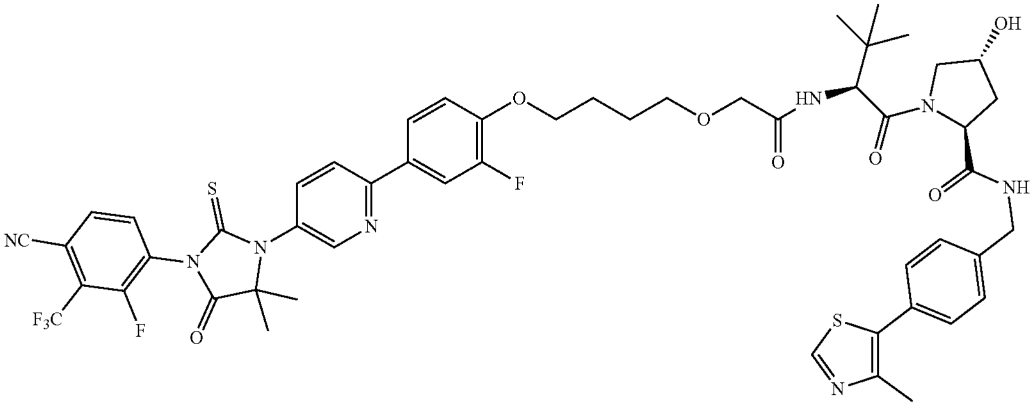 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2F)C(C)(C)C)cc1] |
| A56 | 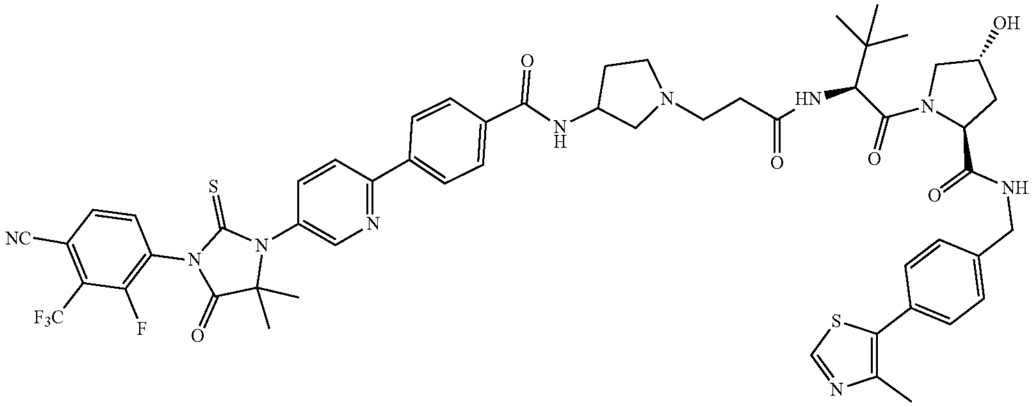 [SMILES: Cc1ncsc1-c1ccc(CNC(=O)[C@@H]2C[C@@H](O)CN2C(=O)[C@@H](NC(=O)CCN2CCC(NC(=O)c3ccc(-c4ccc(N5C(=S)N(c6ccc(C#N)c(C(F)(F)F)c6F)C(=O)C5(C)C)cn4)cc3)C2)C(C)(C)C)cc1] |

-continued
| Compound number | Compound structure |
|---|---|
| A57 | 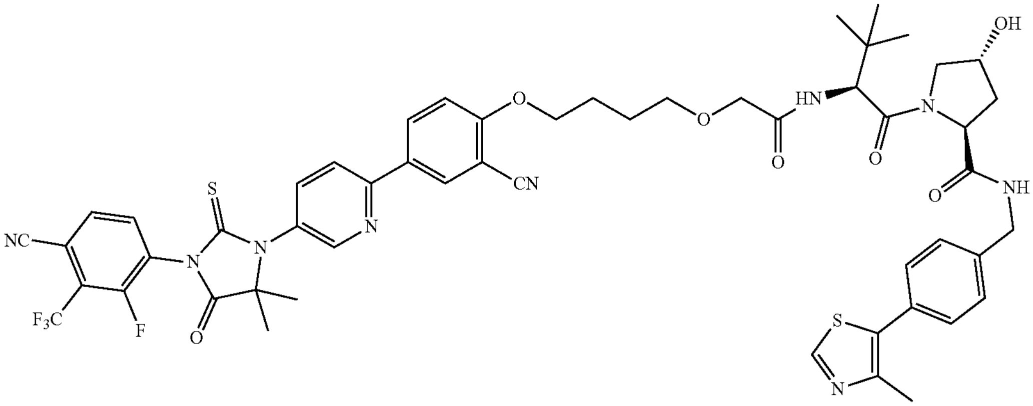 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2C#N)C(C)(C)C)cc1] |
| A58 | 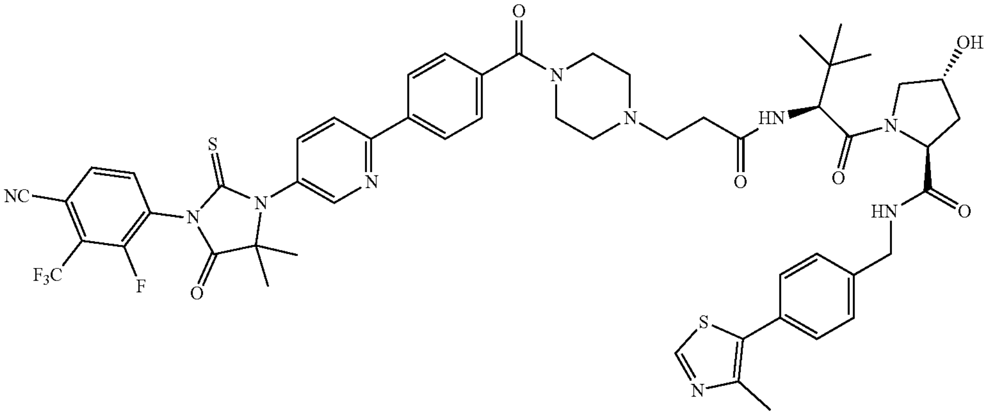 [SMILES: Cc1ncsc1-c1ccc(CNC(=O)[C@@H]2C[C@@H](O)CN2C(=O)[C@@H](NC(=O)CCN2CCN(C(=O)c3ccc(-c4ccc(N5C(=S)N(c6ccc(C#N)c(C(F)(F)F)c6F)C(=O)C5(C)C)cn4)cc3)CC2)C(C)(C)C)cc1] |
| A59 | 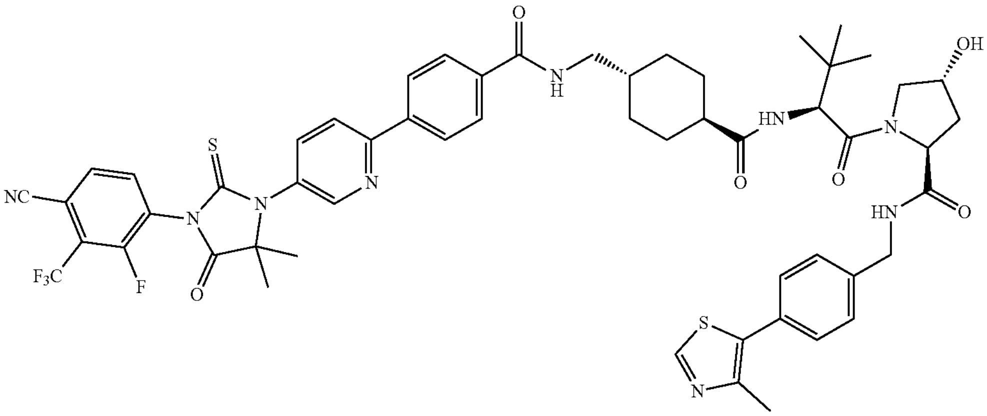 [SMILES: Cc1ncsc1-c1ccc(CNC(=O)[C@@H]2C[C@@H](O)CN2C(=O)[C@@H](NC(=O)[C@H]2CC[C@H](CNC(=O)c3ccc(-c4ccc(N5C(=S)N(c6ccc(C#N)c(C(F)(F)F)c6F)C(=O)C5(C)C)cn4)cc3)CC2)C(C)(C)C)cc1] |

-continued
| Compound number | Compound structure |
| --- | --- |
| A60 | 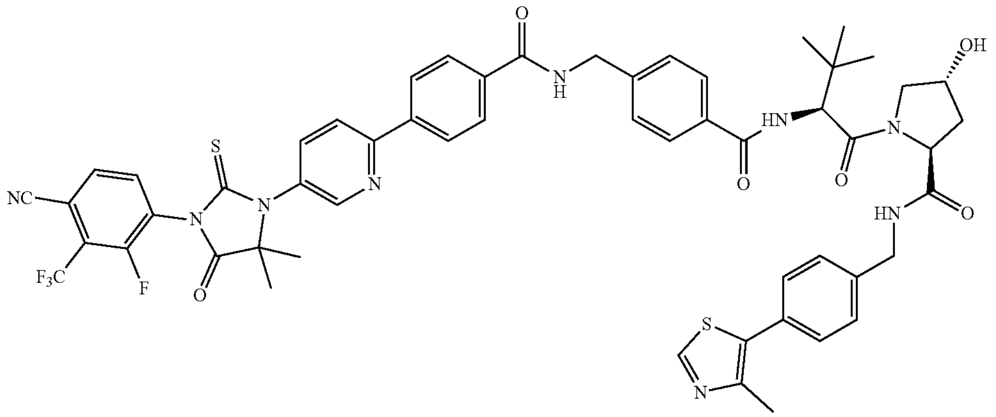 [SMILES: Cc1ncsc1-c1ccc(CNC(=O)[C@@H]2C[C@@H](O)CN2C(=O)[C@@H](NC(=O)c2ccc(CNC(=O)c3ccc(-c4ccc(N5C(=S)N(c6ccc(C#N)c(C(F)(F)F)c6F)C(=O)C5(C)C)cn4)cc3)cc2)C(C)(C)C)cc1] |
| A61 | 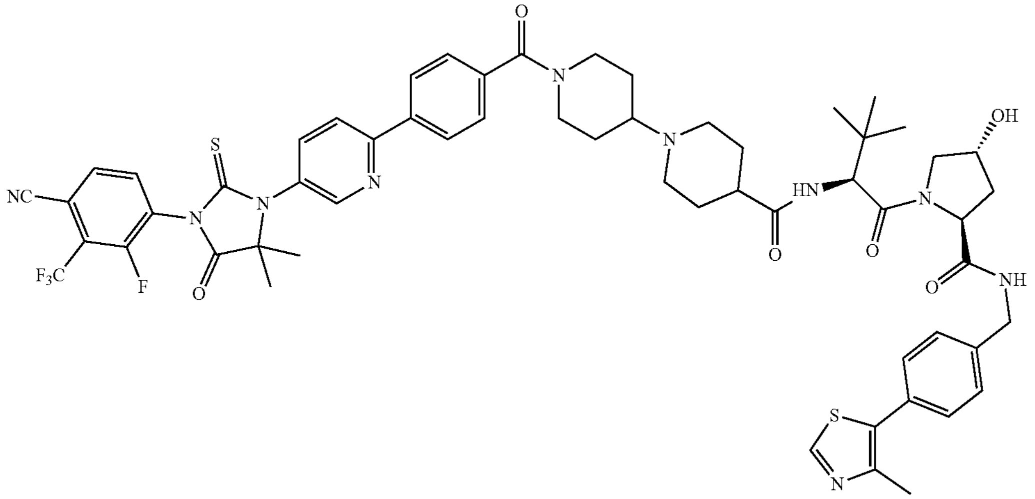 [SMILES: Cc1ncsc1-c1ccc(CNC(=O)[C@@H]2C[C@@H](O)CN2C(=O)[C@@H](NC(=O)C2CCN(C3CCN(C(=O)c4ccc(-c5ccc(N6C(=S)N(c7ccc(C#N)c(C(F)(F)F)c7F)C(=O)C6(C)C)cn5)cc4)CC3)CC2)C(C)(C)C)cc1] |
| A62 | 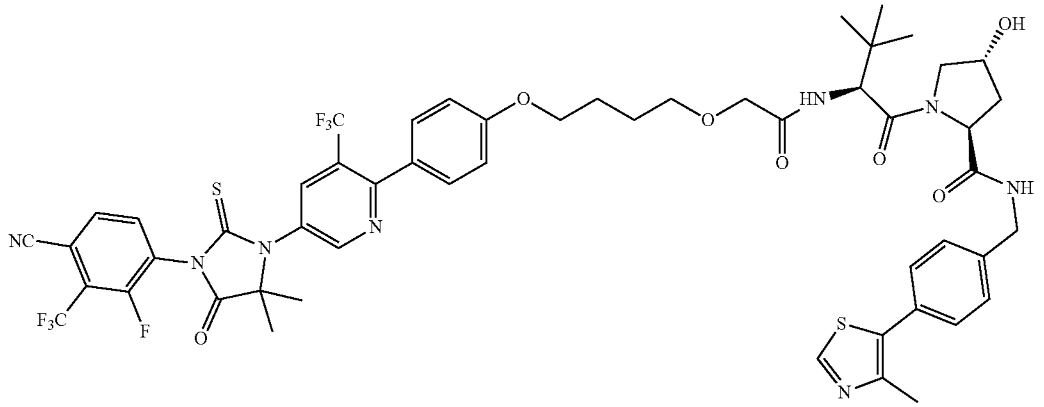 [SMILES: Cc1ncsc1-c1ccc(CNC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3C(F)(F)F)cc2)C(C)(C)C)cc1] |

-continued
| Compound number | Compound structure |
| --- | --- |
| A63 | 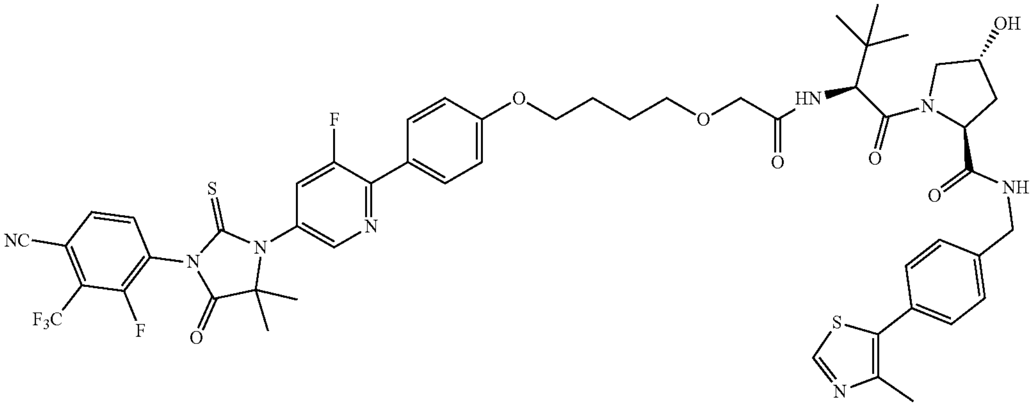 [SMILES: Cc1ncsc1-c1ccc(CNC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)cc2)C(C)(C)C)cc1] |
| A64 | 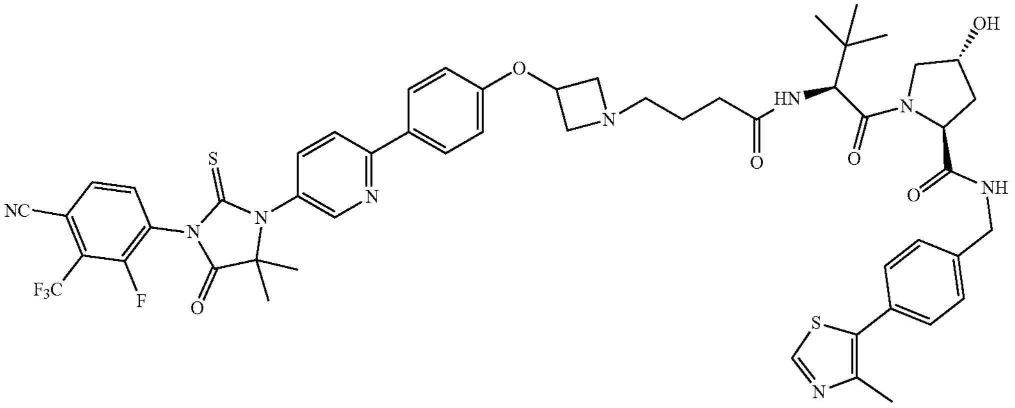 [SMILES: Cc1ncsc1-c1ccc(CNC(=O)[C@@H]2C[C@@H](O)CN2C(=O)[C@@H](NC(=O)CCCN2CC(Oc3ccc(-c4ccc(N5C(=S)N(c6ccc(C#N)c(C(F)(F)F)c6F)C(=O)C5(C)C)cn4)cc3)C2)C(C)(C)C)cc1] |
| A65 | 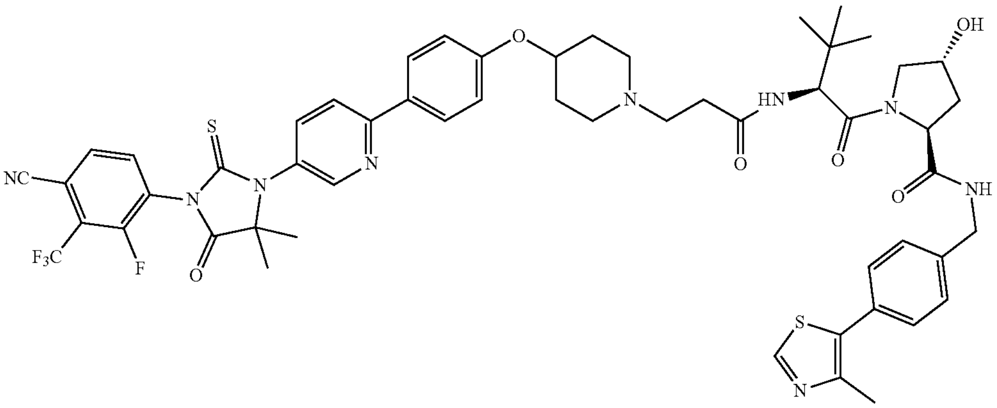 [SMILES: Cc1ncsc1-c1ccc(CNC(=O)[C@@H]2C[C@@H](O)CN2C(=O)[C@@H](NC(=O)CCN2CCC(Oc3ccc(-c4ccc(N5C(=S)N(c6ccc(C#N)c(C(F)(F)F)c6F)C(=O)C5(C)C)cn4)cc3)CC2)C(C)(C)C)cc1] |

-continued
| Compound number | Compound structure |
|---|---|
| A66 | 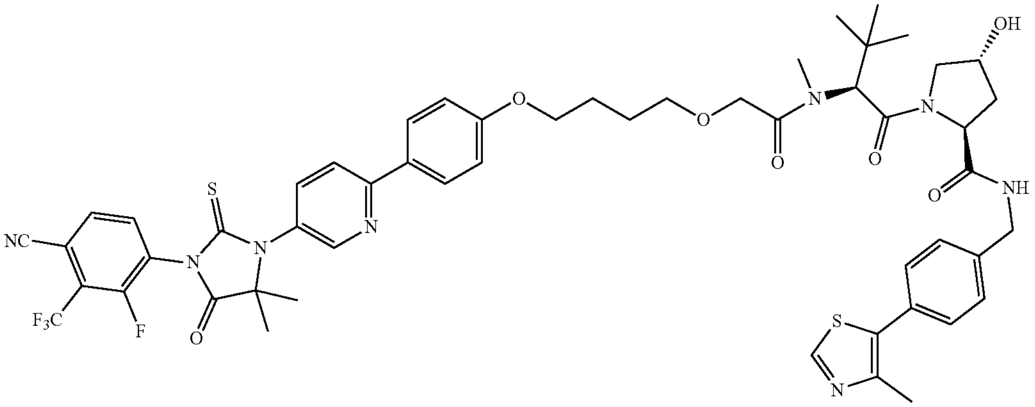 [SMILES: Cc1ncsc1-c1ccc(CNC(=O)[C@@H]2C[C@@H](O)CN2C(=O)[C@@H](N(C)C(=O)COCCCCOc2ccc(-c3ccc(N4C(=S)N(c5ccc(C#N)c(C(F)(F)F)c5F)C(=O)C4(C)C)cn3)cc2)C(C)(C)C)cc1] |
| A67 | 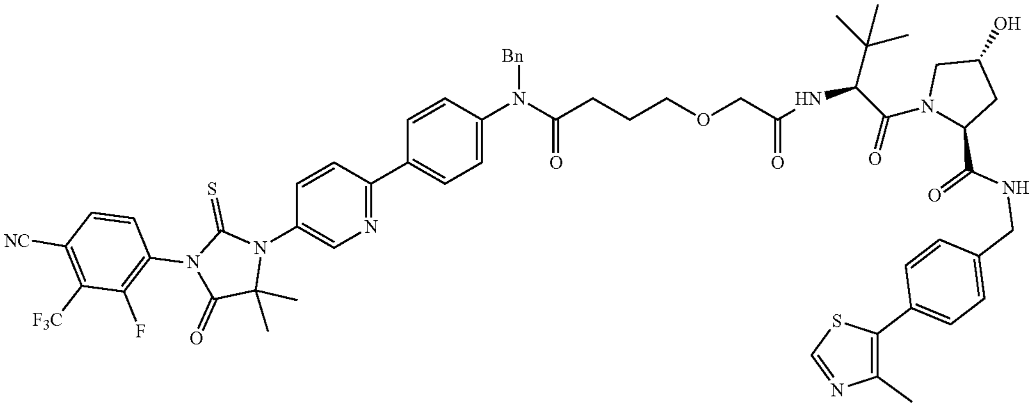 [SMILES: Cc1ncsc1-c1ccc(CNC(=O)[C@@H]2C[C@@H](O)CN2C(=O)[C@@H](NC(=O)COCCCC(=O)N(Cc2ccccc2)c2ccc(-c3ccc(N4C(=S)N(c5ccc(C#N)c(C(F)(F)F)c5F)C(=O)C4(C)C)cn3)cc2)C(C)(C)C)cc1] |
| A68 | 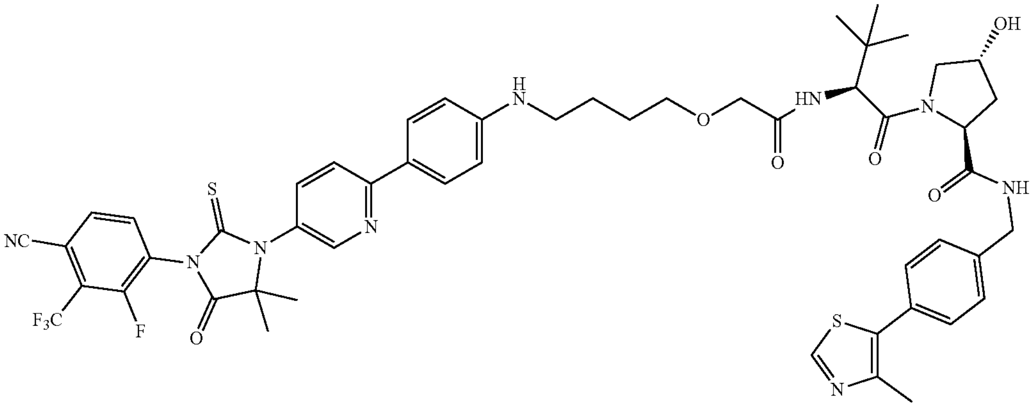 [SMILES: Cc1ncsc1-c1ccc(CNC(=O)[C@@H]2C[C@@H](O)CN2C(=O)[C@@H](NC(=O)COCCCCNc2ccc(-c3ccc(N4C(=S)N(c5ccc(C#N)c(C(F)(F)F)c5F)C(=O)C4(C)C)cn3)cc2)C(C)(C)C)cc1] |

-continued
| Compound number | Compound structure |
|---|---|
| A69 | 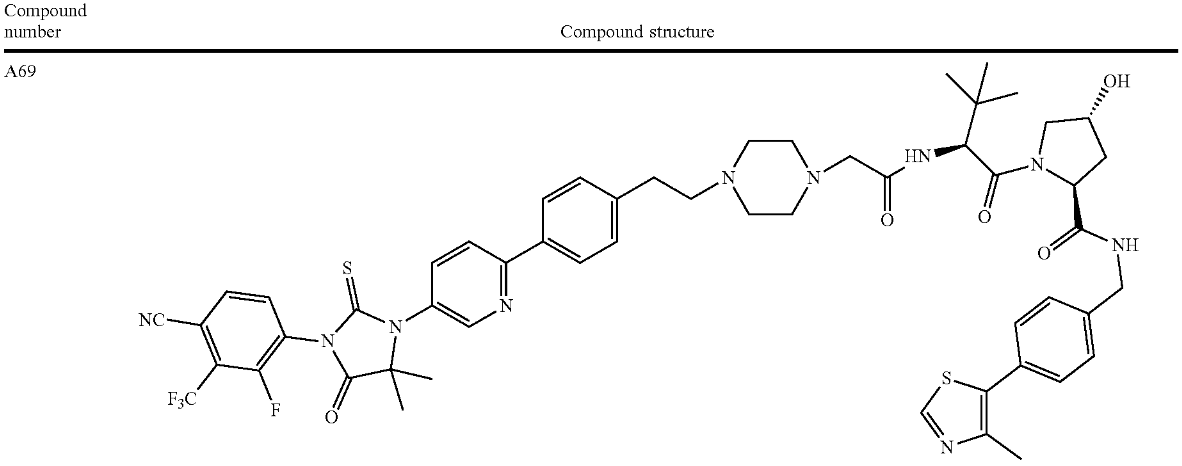 |
| A70 | 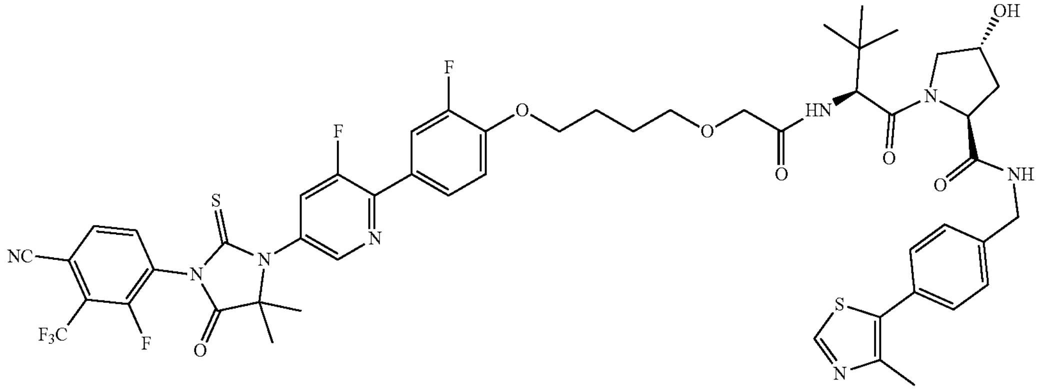 [SMILES: Cc1ncsc1-c1ccc(CNC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)cc2F)C(C)(C)C)cc1] |
| A71 | 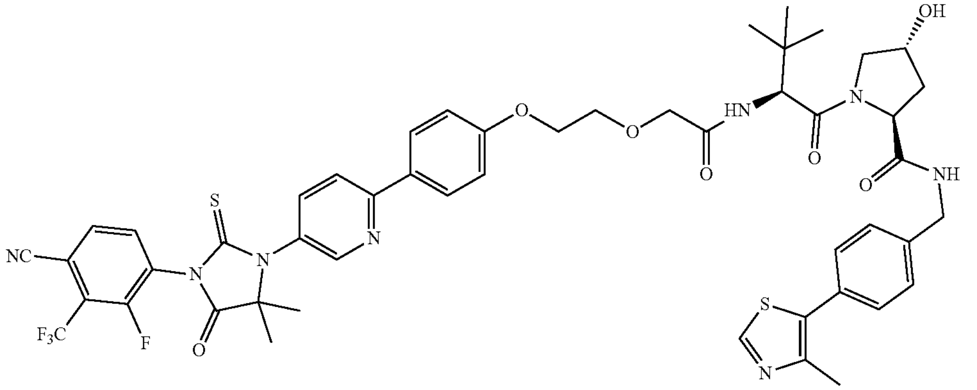 [SMILES: Cc1ncsc1-c1ccc(CNC(=O)[C@@H]2C[C@@H](O)CN2C(=O)[C@@H](NC(=O)COCCOc2ccc(-c3ccc(N4C(=S)N(c5ccc(C#N)c(C(F)(F)F)c5F)C(=O)C4(C)C)cn3)cc2)C(C)(C)C)cc1] |
| A72 | 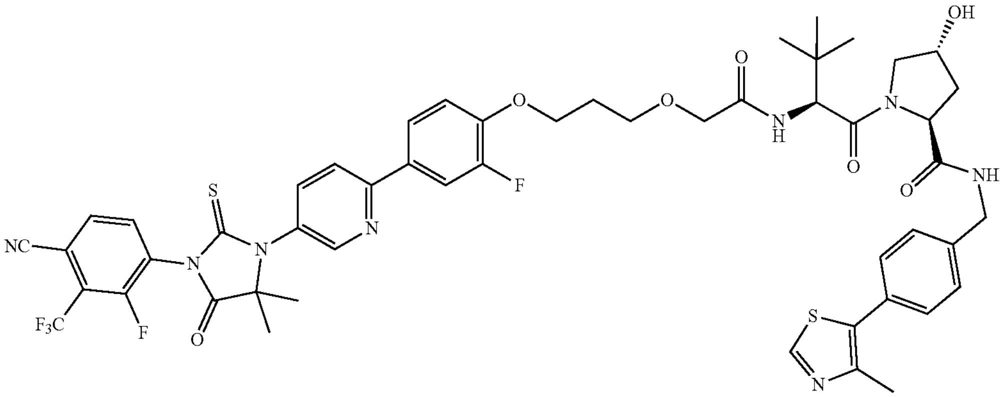 [SMILES: Cc1ncsc1-c1ccc(CNC(=O)[C@@H]2C[C@@H](O)CN2C(=O)[C@@H](NC(=O)COCCCOc2ccc(-c3ccc(N4C(=S)N(c5ccc(C#N)c(C(F)(F)F)c5F)C(=O)C4(C)C)cn3)cc2F)C(C)(C)C)cc1] |

-continued
| Compound number | Compound structure |
| --- | --- |
| A73 | 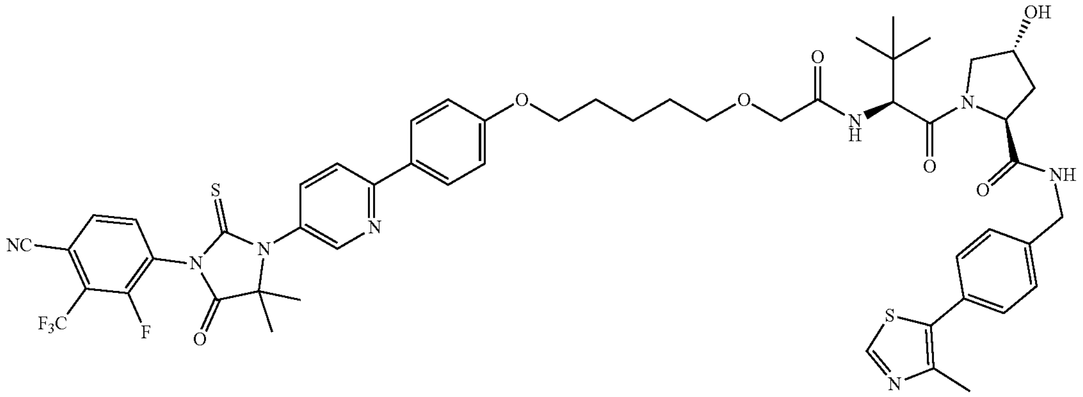 [SMILES: Cc1ncsc1-c1ccc(CNC(=O)[C@@H]2C[C@@H](O)CN2C(=O)[C@@H](NC(=O)COCCCCCOc2ccc(-c3ccc(N4C(=S)N(c5ccc(C#N)c(C(F)(F)F)c5F)C(=O)C4(C)C)cn3)cc2)C(C)(C)C)cc1] |
| A74 | 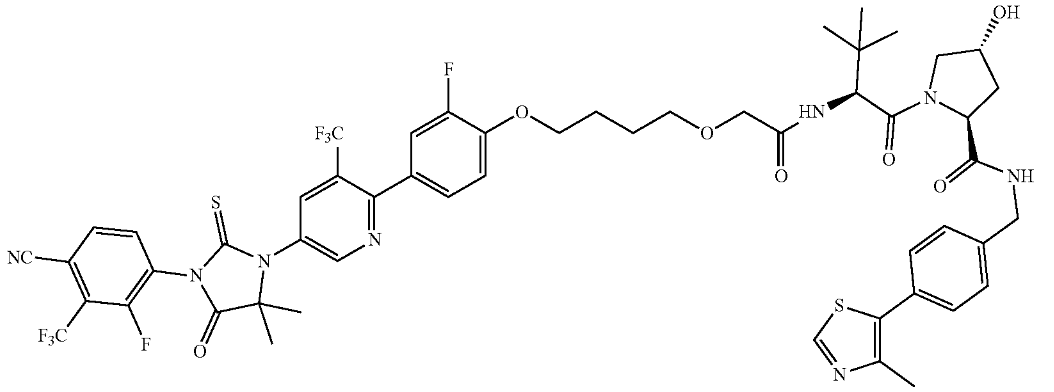 [SMILES: Cc1ncsc1-c1ccc(CNC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3C(F)(F)F)cc2F)C(C)(C)C)cc1] |
| A75 | 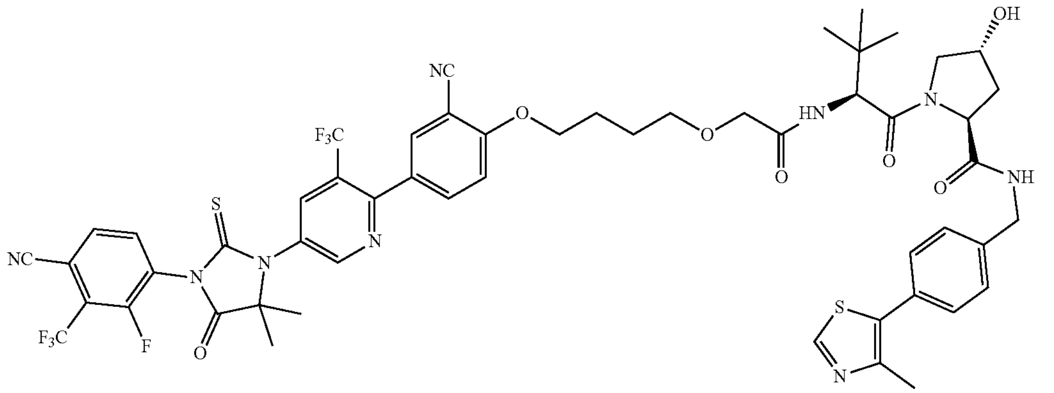 [SMILES: Cc1ncsc1-c1ccc(CNC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3C(F)(F)F)cc2C#N)C(C)(C)C)cc1] |

-continued
| Compound number | Compound structure |
|---|---|
| A76 | 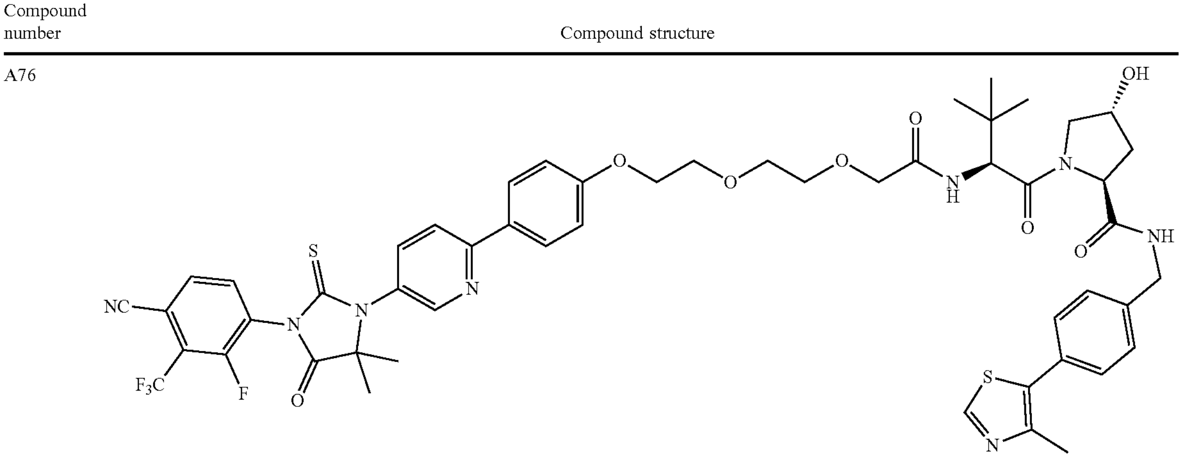 |
| A77 | 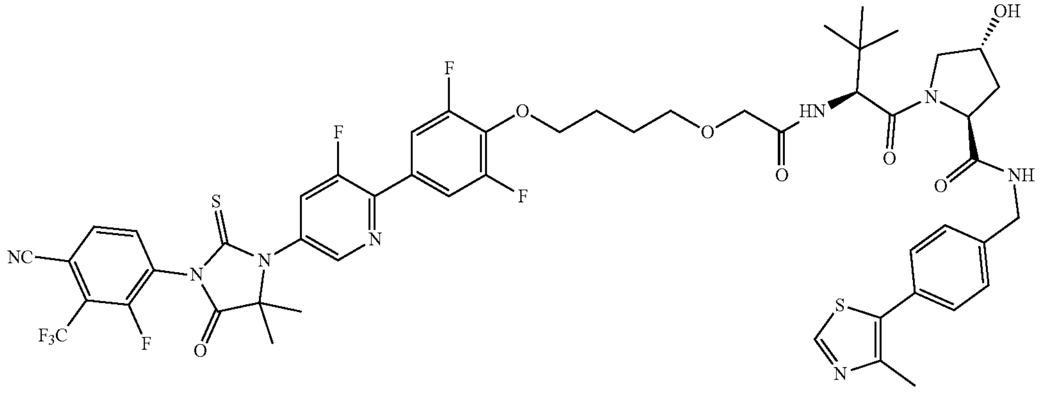 [SMILES: Cc1ncsc1-c1ccc(CNC(=O)[C@@H]2C[C@@H](O)CN2C(=O)[C@@H](NC(=O)COCCCCOc2c(F)cc(-c3ncc(N4C(=S)N(c5ccc(C#N)c(C(F)(F)F)c5F)C(=O)C4(C)C)cc3F)cc2F)C(C)(C)C)cc1] |
| A78 | 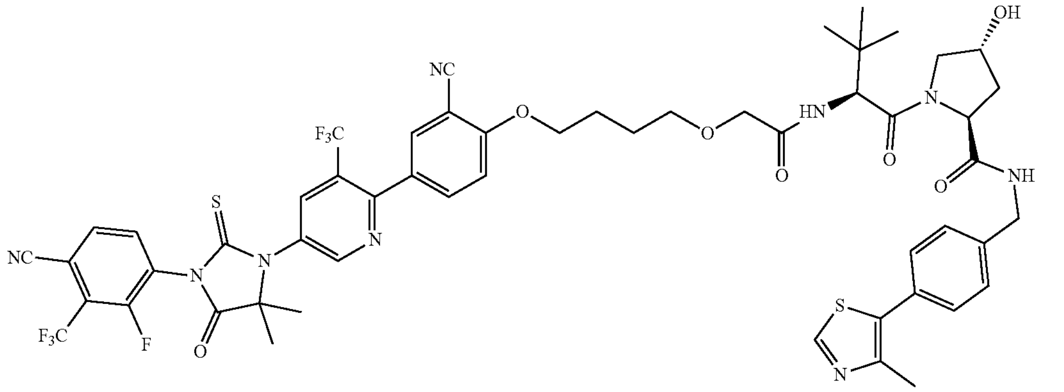 [SMILES: Cc1ncsc1-c1ccc(CNC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3C(F)(F)F)cc2C#N)C(C)(C)C)cc1] |
| A79 | 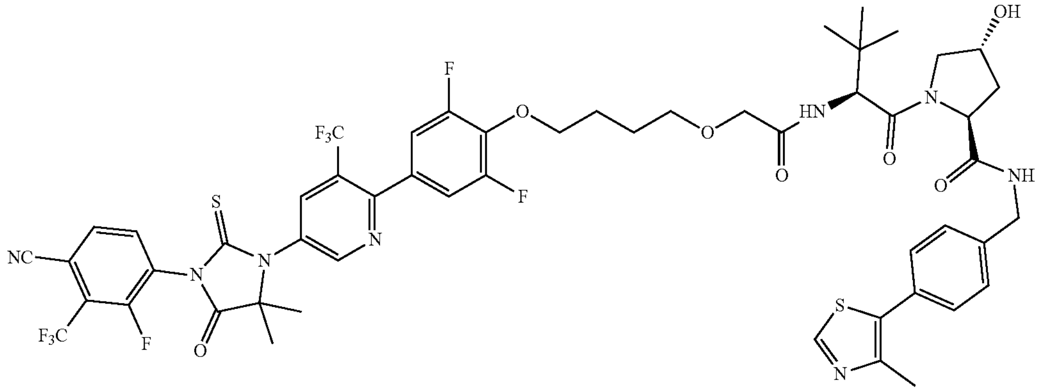 [SMILES: Cc1ncsc1-c1ccc(CNC(=O)[C@@H]2C[C@@H](O)CN2C(=O)[C@@H](NC(=O)COCCCCOc2c(F)cc(-c3ncc(N4C(=S)N(c5ccc(C#N)c(C(F)(F)F)c5F)C(=O)C4(C)C)cc3C(F)(F)F)cc2F)C(C)(C)C)cc1] |

-continued
| Compound number | Compound structure |
| --- | --- |
| A80 | 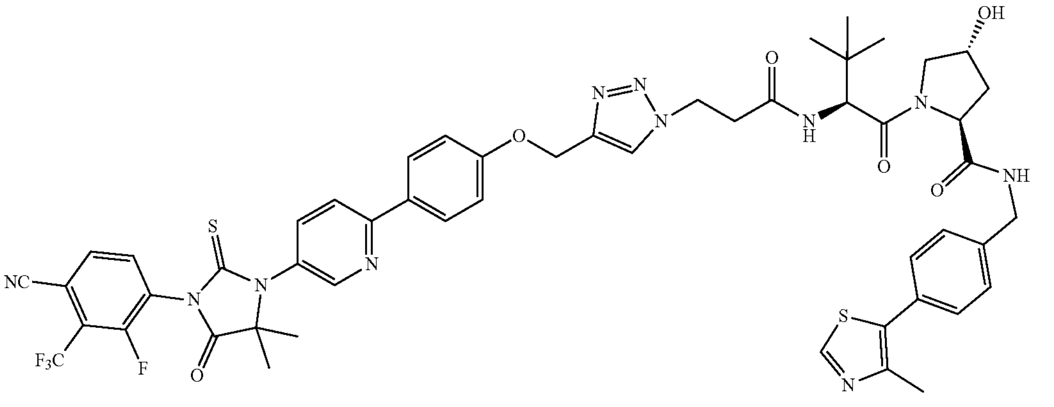 [SMILES: Cc1ncsc1-c1ccc(CNC(=O)[C@@H]2C[C@@H](O)CN2C(=O)[C@@H](NC(=O)CCn2cc(COc3ccc(-c4ccc(N5C(=S)N(c6ccc(C#N)c(C(F)(F)F)c6F)C(=O)C5(C)C)cn4)cc3)nn2)C(C)(C)C)cc1] |
| A81 | 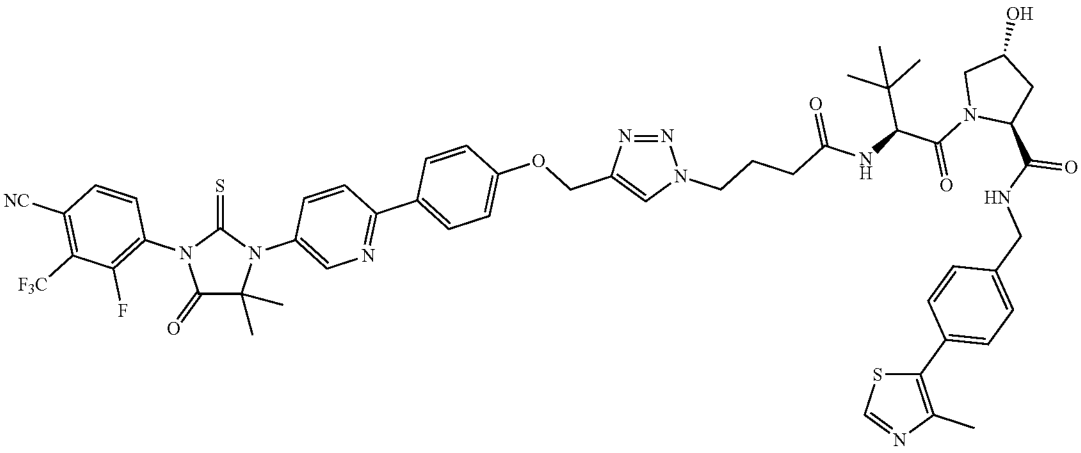 [SMILES: Cc1ncsc1-c1ccc(CNC(=O)[C@@H]2C[C@@H](O)CN2C(=O)[C@@H](NC(=O)CCCn2cc(COc3ccc(-c4ccc(N5C(=S)N(c6ccc(C#N)c(C(F)(F)F)c6F)C(=O)C5(C)C)cn4)cc3)nn2)C(C)(C)C)cc1] |
| A82 | 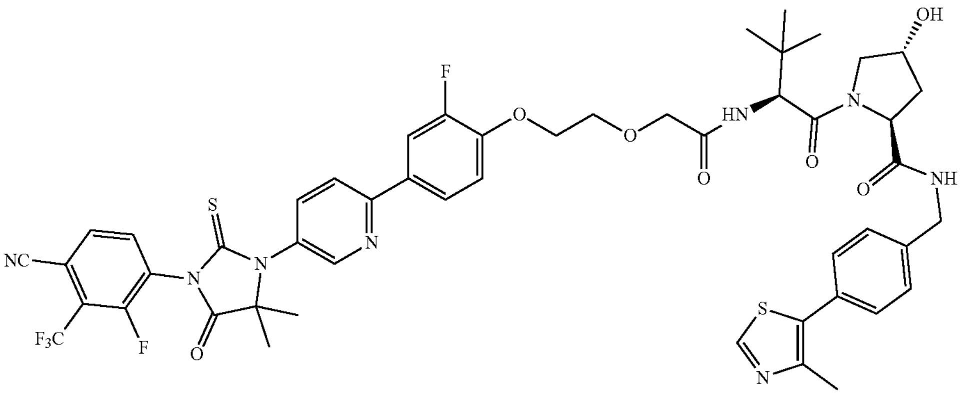 [SMILES: Cc1ncsc1-c1ccc(CNC(=O)[C@@H]2C[C@@H](O)CN2C(=O)[C@@H](NC(=O)COCCOc2ccc(-c3ccc(N4C(=S)N(c5ccc(C#N)c(C(F)(F)F)c5F)C(=O)C4(C)C)cn3)cc2F)C(C)(C)C)cc1] |

-continued
| Compound number | Compound structure |
|---|---|
| A83 | 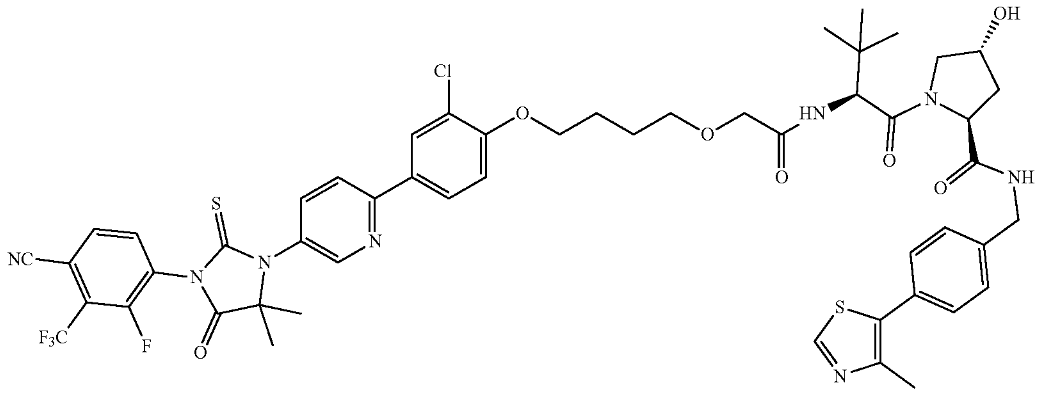 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2Cl)C(C)(C)C)cc1] |
| A84 | 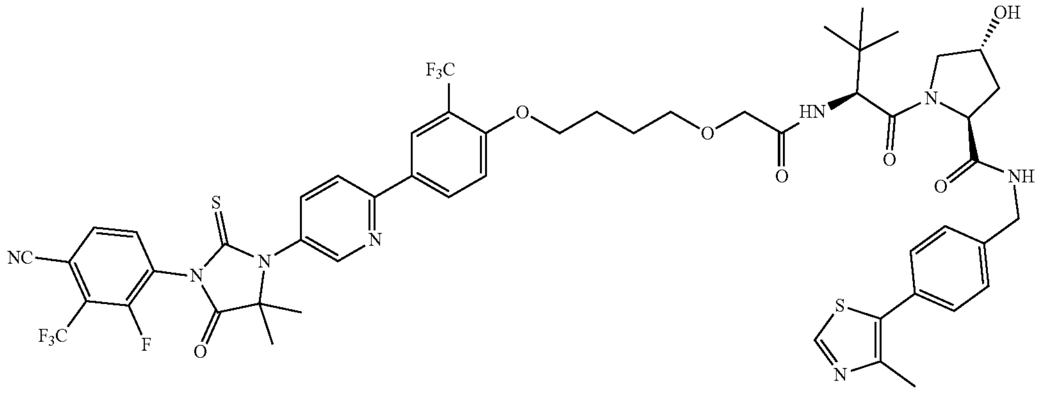 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2C(F)(F)F)C(C)(C)C)cc1] |
| A85 | 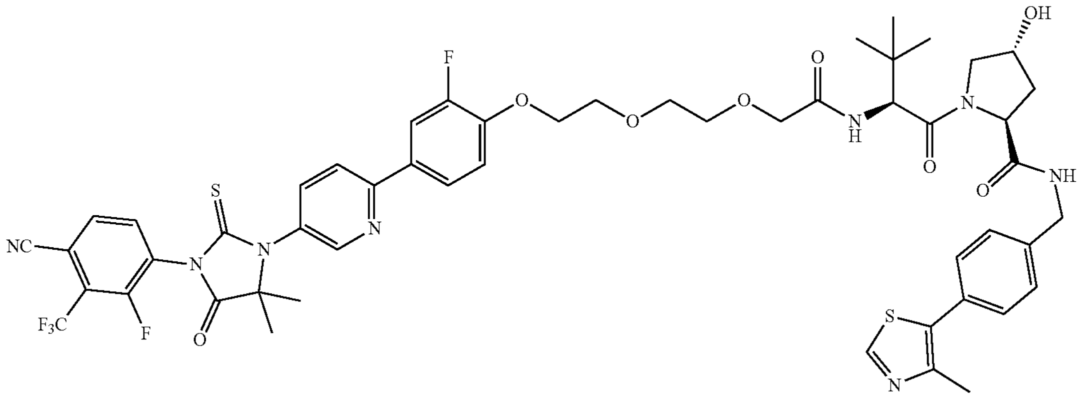 [SMILES: Cc1ncsc1-c1ccc(CNC(=O)[C@@H]2C[C@@H](O)CN2C(=O)[C@@H](NC(=O)COCCOCCOc2ccc(-c3ccc(N4C(=S)N(c5ccc(C#N)c(C(F)(F)F)c5F)C(=O)C4(C)C)cn3)cc2F)C(C)(C)C)cc1] |
| A86 | 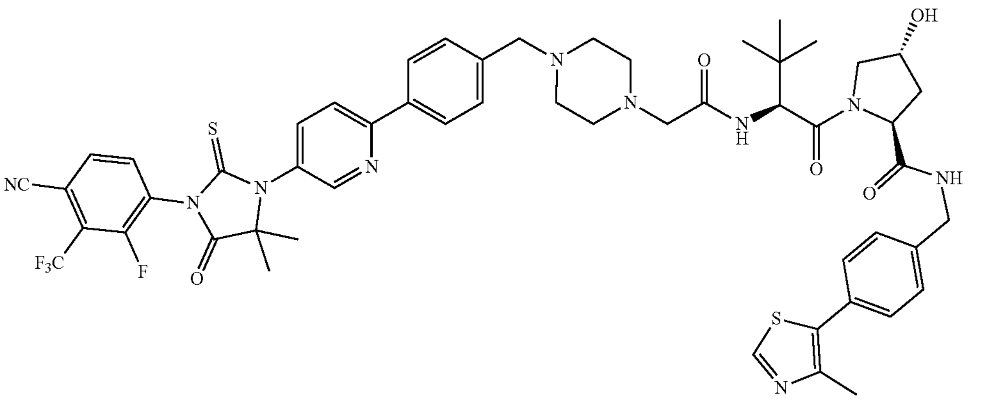 [SMILES: Cc1ncsc1-c1ccc(CNC(=O)[C@@H]2C[C@@H](O)CN2C(=O)[C@@H](NC(=O)CN2CCN(Cc3ccc(-c4ccc(N5C(=S)N(c6ccc(C#N)c(C(F)(F)F)c6F)C(=O)C5(C)C)cn4)cc3)CC2)C(C)(C)C)cc1] |

-continued
| Compound number | Compound structure |
| --- | --- |
| A87 | 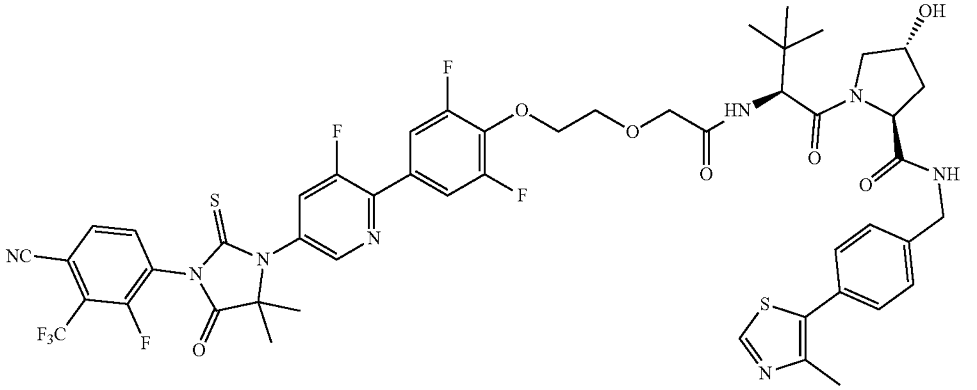 [SMILES: Cc1ncsc1-c1ccc(CNC(=O)[C@@H]2C[C@@H](O)CN2C(=O)[C@@H](NC(=O)COCCOc2c(F)cc(-c3ncc(N4C(=S)N(c5ccc(C#N)c(C(F)(F)F)c5F)C(=O)C4(C)C)cc3F)cc2F)C(C)(C)C)cc1] |
| A88 | 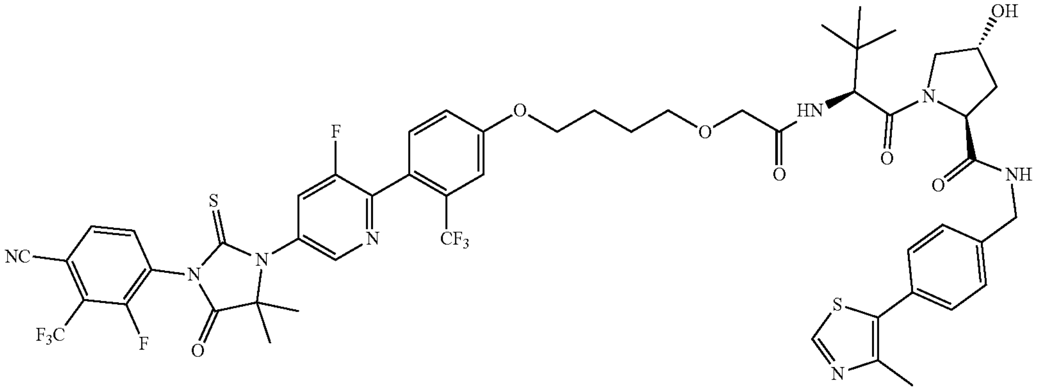 [SMILES: Cc1ncsc1-c1ccc(CNC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)c(C(F)(F)F)c2)C(C)(C)C)cc1] |
| A89 | 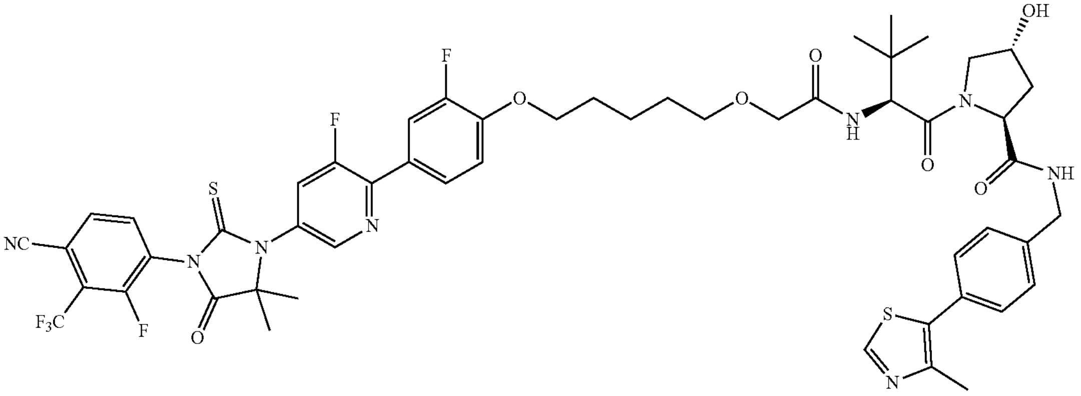 [SMILES: Cc1ncsc1-c1ccc(CNC(=O)[C@@H]2C[C@@H](O)CN2C(=O)[C@@H](NC(=O)COCCCCCOc2ccc(-c3ncc(N4C(=S)N(c5ccc(C#N)c(C(F)(F)F)c5F)C(=O)C4(C)C)cc3F)cc2F)C(C)(C)C)cc1] |

-continued
| Compound number | Compound structure |
| --- | --- |
| A90 | 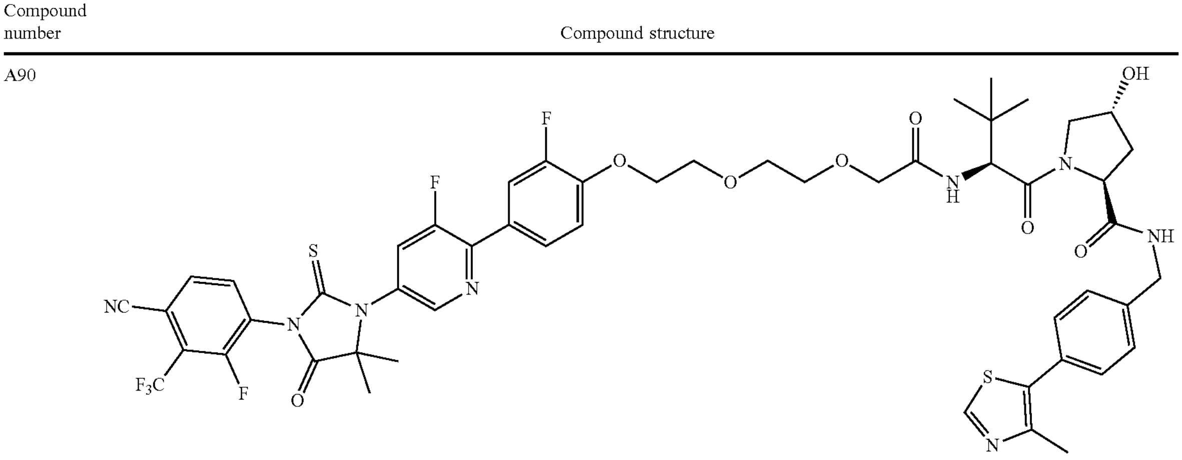 |
| A91 | 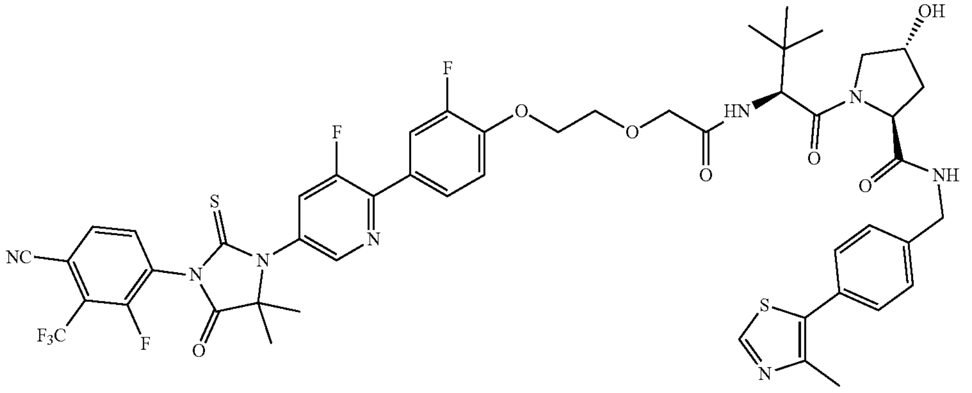 [SMILES: Cc1ncsc1-c1ccc(CNC(=O)[C@@H]2C[C@@H](O)CN2C(=O)[C@@H](NC(=O)COCCOc2ccc(-c3ncc(N4C(=S)N(c5ccc(C#N)c(C(F)(F)F)c5F)C(=O)C4(C)C)cc3F)cc2F)C(C)(C)C)cc1] |
| A92 | 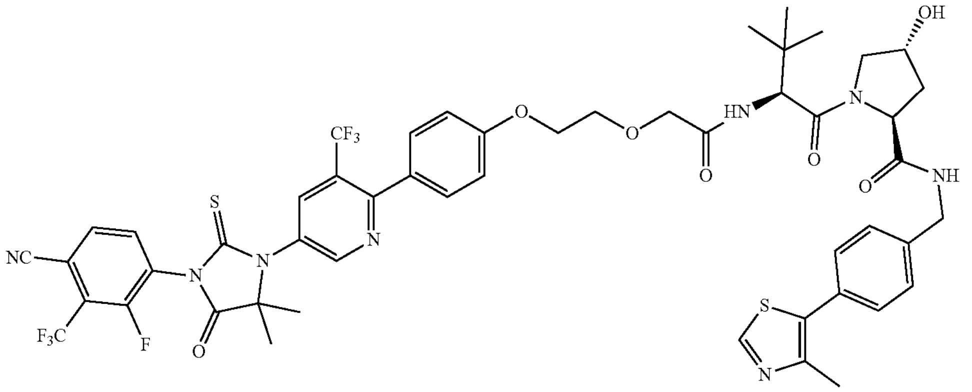 [SMILES: Cc1ncsc1-c1ccc(CNC(=O)[C@@H]2C[C@@H](O)CN2C(=O)[C@@H](NC(=O)COCCOc2ccc(-c3ncc(N4C(=S)N(c5ccc(C#N)c(C(F)(F)F)c5F)C(=O)C4(C)C)cc3C(F)(F)F)cc2)C(C)(C)C)cc1] |
| A93 | 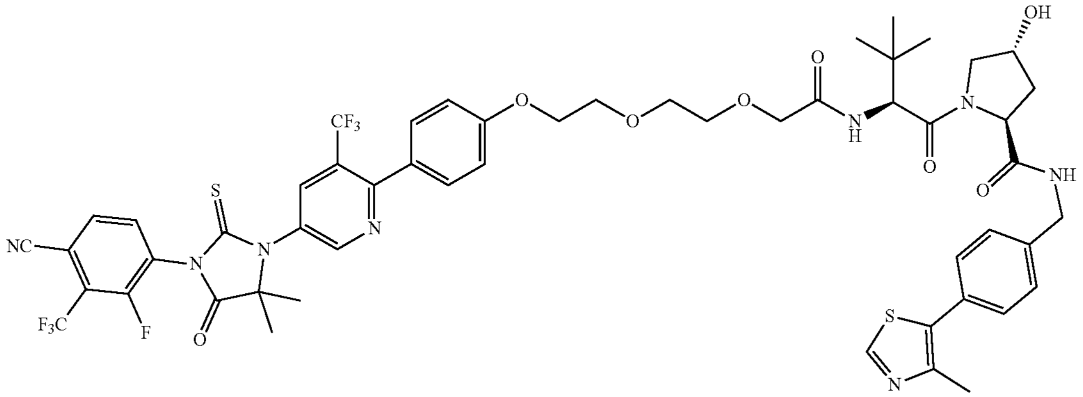 [SMILES: Cc1ncsc1-c1ccc(CNC(=O)[C@@H]2C[C@@H](O)CN2C(=O)[C@@H](NC(=O)COCCOCCOc2ccc(-c3ncc(N4C(=S)N(c5ccc(C#N)c(C(F)(F)F)c5F)C(=O)C4(C)C)cc3C(F)(F)F)cc2)C(C)(C)C)cc1] |

-continued
| Compound number | Compound structure |
| --- | --- |
| A94 | 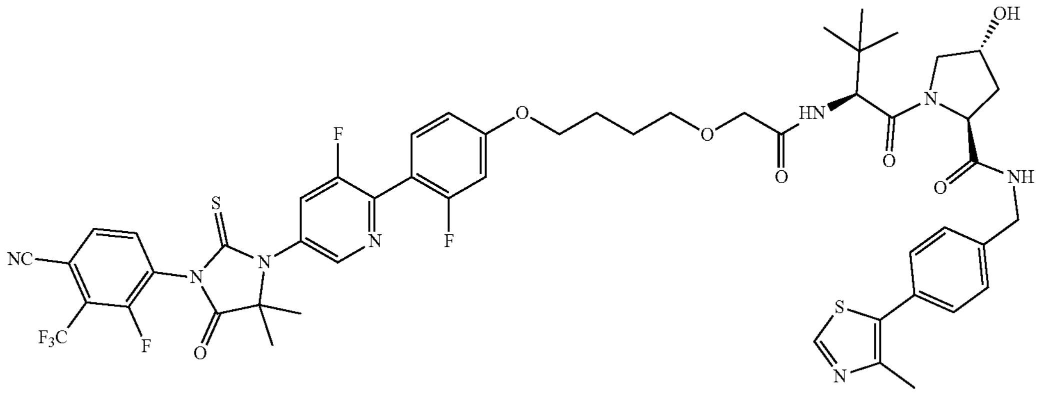 [SMILES: Cc1ncsc1-c1ccc(CNC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)c(F)c2)C(C)(C)C)cc1] |
| A95 | 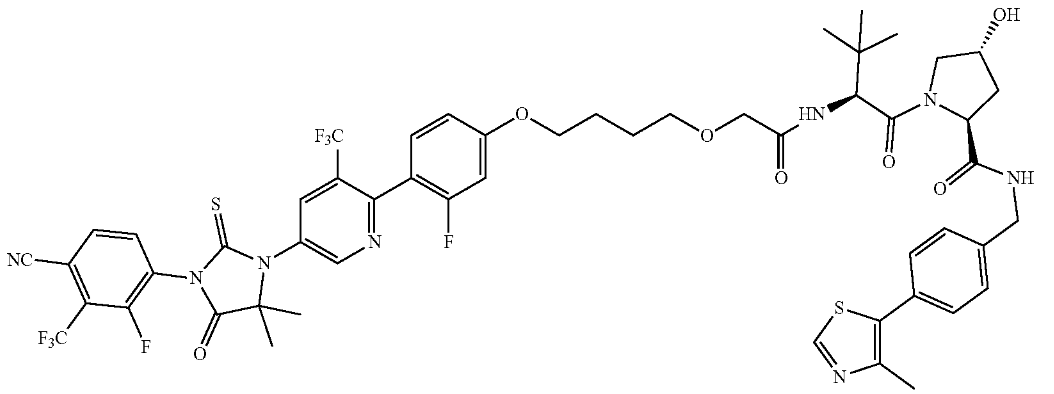 [SMILES: Cc1ncsc1-c1ccc(CNC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3C(F)(F)F)c(F)c2)C(C)(C)C)cc1] |
| A96 | 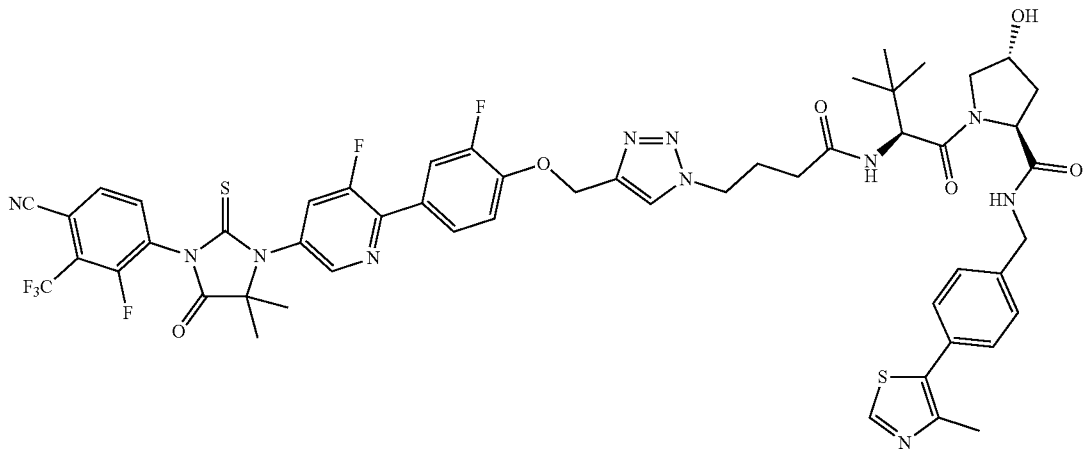 [SMILES: Cc1ncsc1-c1ccc(CNC(=O)[C@@H]2C[C@@H](O)CN2C(=O)[C@@H](NC(=O)CCCn2cc(COc3ccc(-c4ncc(N5C(=S)N(c6ccc(C#N)c(C(F)(F)F)c6F)C(=O)C5(C)C)cc4F)cc3F)nn2)C(C)(C)C)cc1] |

-continued
| Compound number | Compound structure |
|---|---|
| A97 | 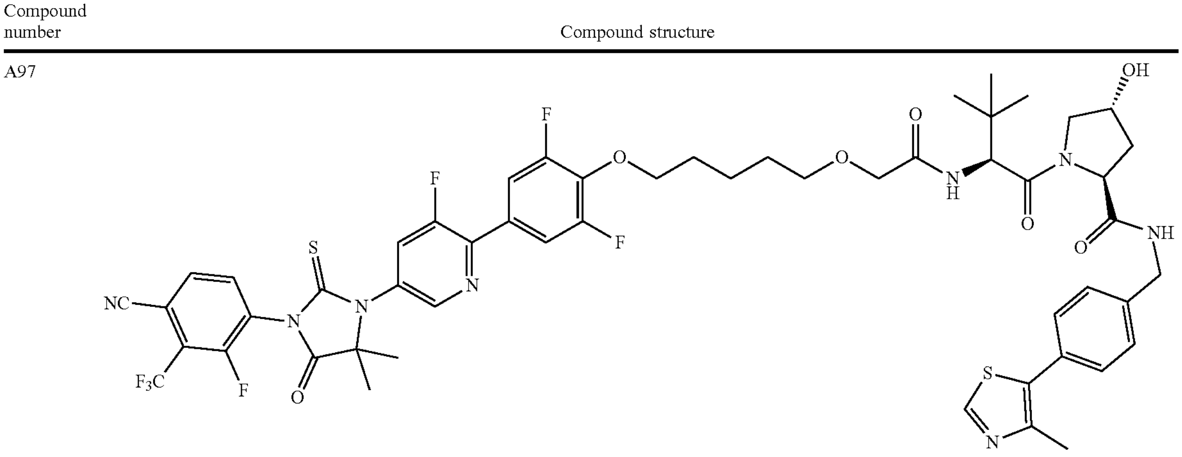 |
| A98 | 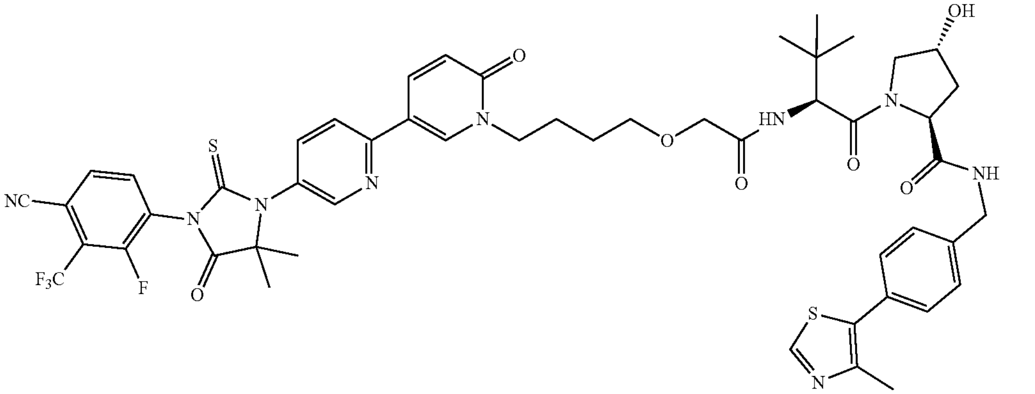 [SMILES: Cc1ncsc1-c1ccc(CNC(=O)[C@@H]2C[C@@H](O)CN2C(=O)[C@@H](NC(=O)COCCCCn2cc(-c3ccc(N4C(=S)N(c5ccc(C#N)c(C(F)(F)F)c5F)C(=O)C4(C)C)cn3)ccc2=O)C(C)(C)C)cc1] |
| A99 | 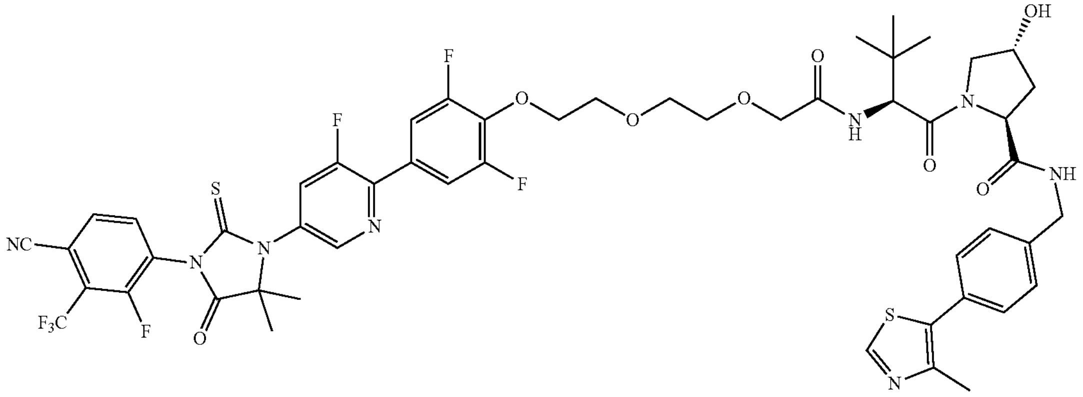 [SMILES: Cc1ncsc1-c1ccc(CNC(=O)[C@@H]2C[C@@H](O)CN2C(=O)[C@@H](NC(=O)COCCOCCOc2c(F)cc(-c3ncc(N4C(=S)N(c5ccc(C#N)c(C(F)(F)F)c5F)C(=O)C4(C)C)cc3F)cc2F)C(C)(C)C)cc1] |
| A100 | 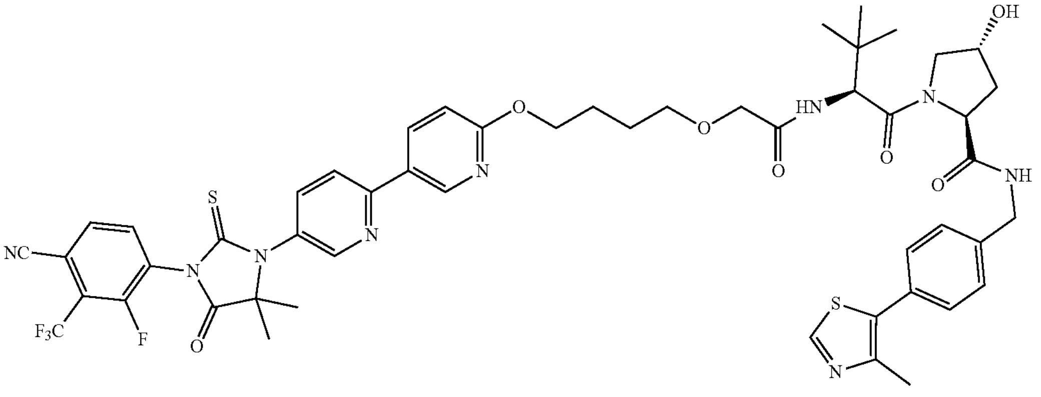 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cn2)C(C)(C)C)cc1] |

-continued
| Compound number | Compound structure |
|---|---|
| A101 | 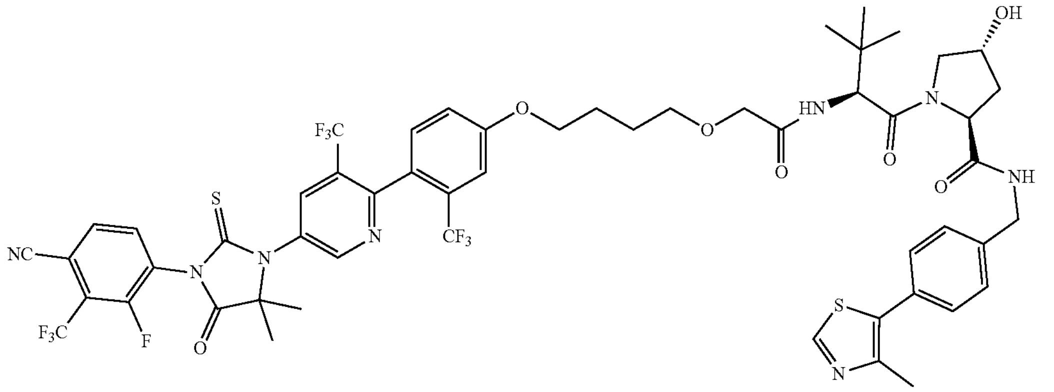 [SMILES: Cc1ncsc1-c1ccc(CNC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3C(F)(F)F)c(C(F)(F)F)c2)C(C)(C)C)cc1] |
| A102 | 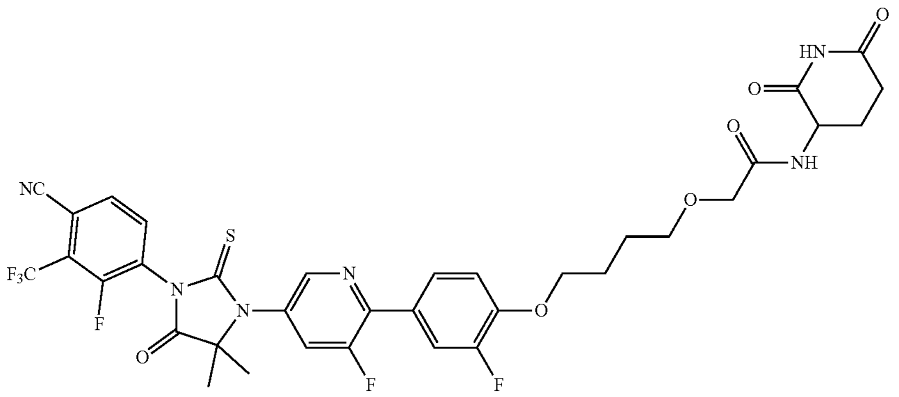 [SMILES: CC1(C)C(=O)N(c2ccc(C#N)c(C(F)(F)F)c2F)C(=S)N1c1cnc(-c2ccc(OCCCCOCC(=O)NC3CCC(=O)NC3=O)c(F)c2)c(F)c1] |
| A103 | 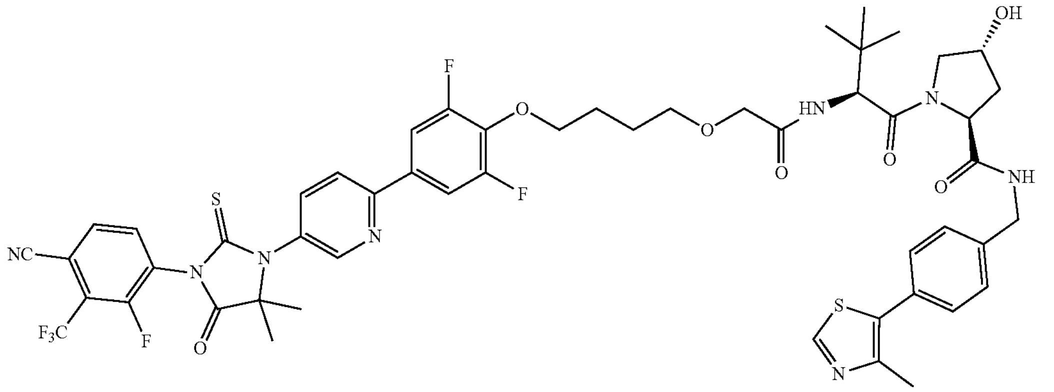 [SMILES: Cc1ncsc1-c1ccc(CNC(=O)[C@@H]2C[C@@H](O)CN2C(=O)[C@@H](NC(=O)COCCCCOc2c(F)cc(-c3ccc(N4C(=S)N(c5ccc(C#N)c(C(F)(F)F)c5F)C(=O)C4(C)C)cn3)cc2F)C(C)(C)C)cc1] |

-continued
| Compound number | Compound structure |
| --- | --- |
| A104 | 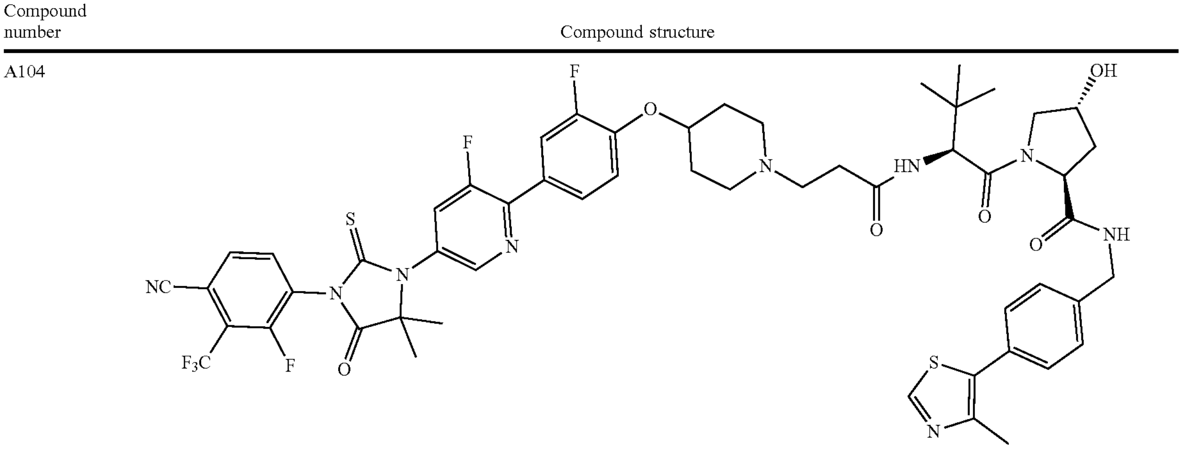 |
| A105 | 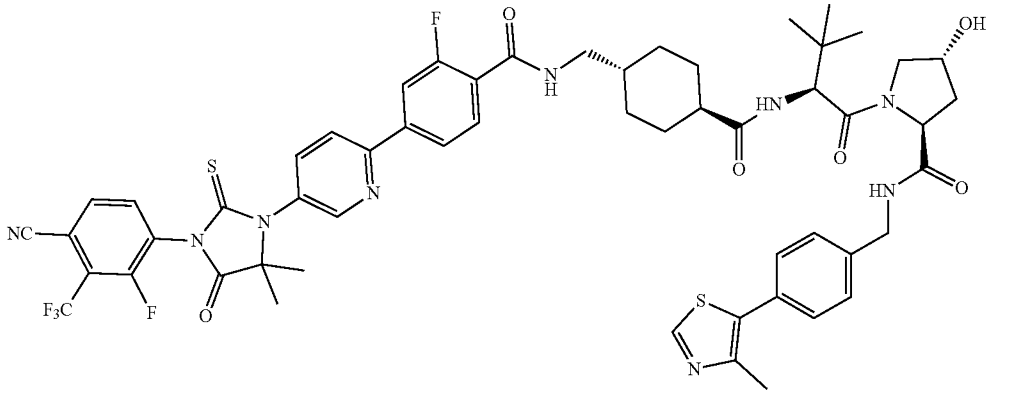 [SMILES: Cc1ncsc1-c1ccc(CNC(=O)[C@@H]2C[C@@H](O)CN2C(=O)[C@@H](NC(=O)[C@H]2CC[C@H](CNC(=O)c3ccc(-c4ccc(N5C(=S)N(c6ccc(C#N)c(C(F)(F)F)c6F)C(=O)C5(C)C)cn4)cc3F)CC2)C(C)(C)C)cc1] |
| A106 | 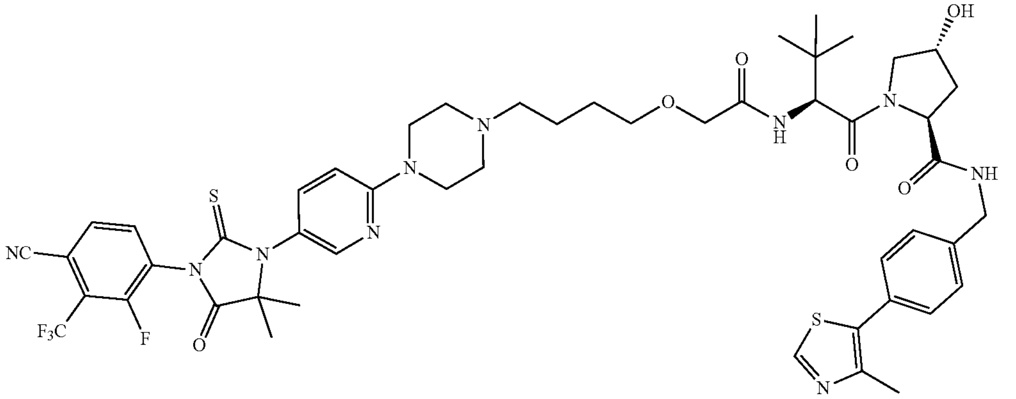 [SMILES: Cc1ncsc1-c1ccc(CNC(=O)[C@@H]2C[C@@H](O)CN2C(=O)[C@@H](NC(=O)COCCCCN2CCN(c3ccc(N4C(=S)N(c5ccc(C#N)c(C(F)(F)F)c5F)C(=O)C4(C)C)cn3)CC2)C(C)(C)C)cc1] |
| A107 | 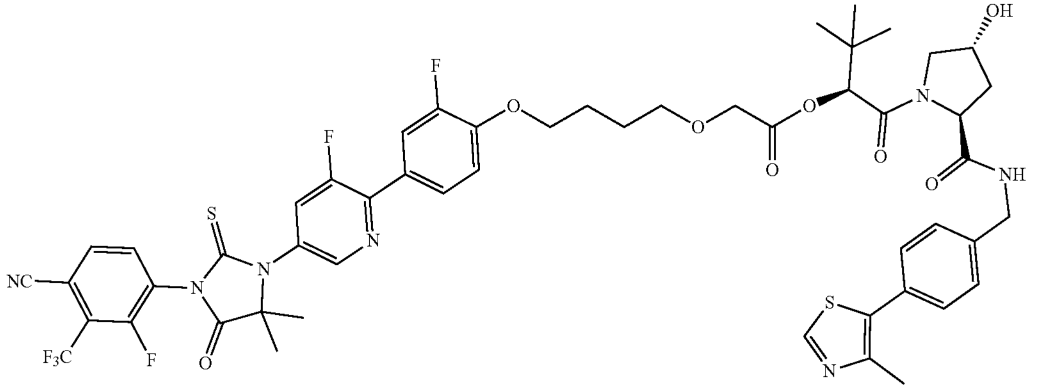 [SMILES: Cc1ncsc1-c1ccc(CNC(=O)[C@@H]2C[C@@H](O)CN2C(=O)[C@@H](OC(=O)COCCCCOc2ccc(-c3ncc(N4C(=S)N(c5ccc(C#N)c(C(F)(F)F)c5F)C(=O)C4(C)C)cc3F)cc2F)C(C)(C)C)cc1] |

-continued
| Compound number | Compound structure |
|---|---|
| A108 | 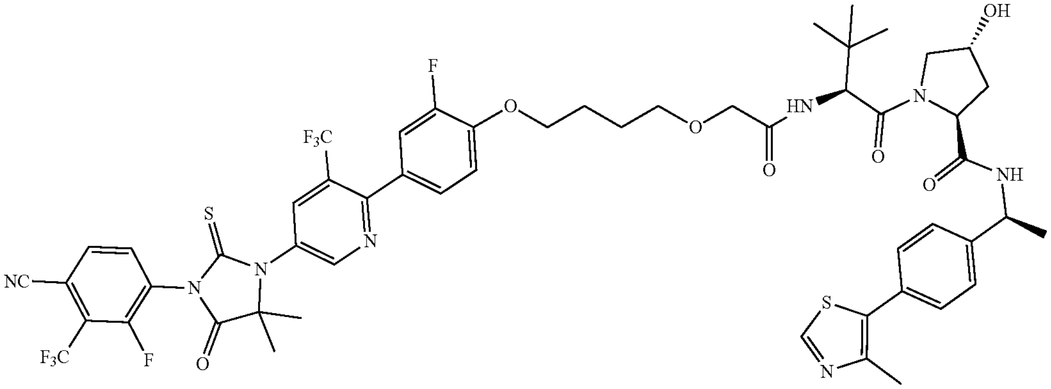 [SMILES: Cc1ncsc1-c1ccc([C@H](C)NC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3C(F)(F)F)cc2F)C(C)(C)C)cc1] |
| A109 | 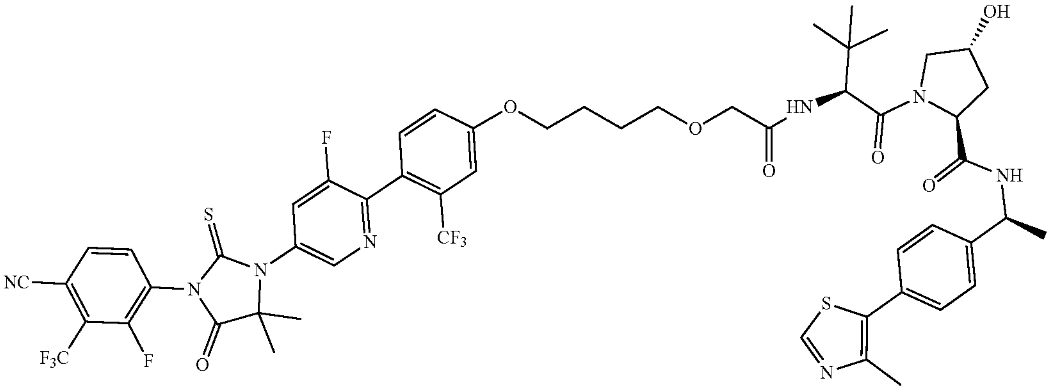 [SMILES: Cc1ncsc1-c1ccc([C@H](C)NC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)c(C(F)(F)F)c2)C(C)(C)C)cc1] |
| A110 | 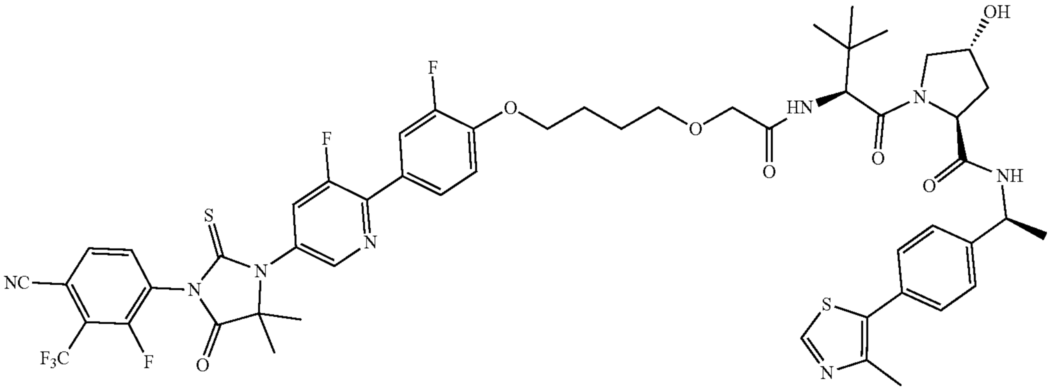 [SMILES: Cc1ncsc1-c1ccc([C@H](C)NC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)cc2F)C(C)(C)C)cc1] |
| A111 | 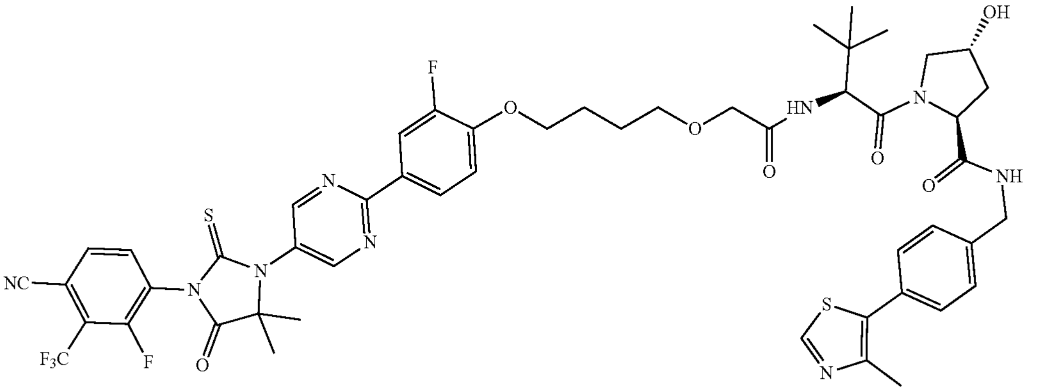 [SMILES: Cc1ncsc1-c1ccc(CNC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cn3)cc2F)C(C)(C)C)cc1] |

-continued
| Compound number | Compound structure |
|---|---|
| A112 | 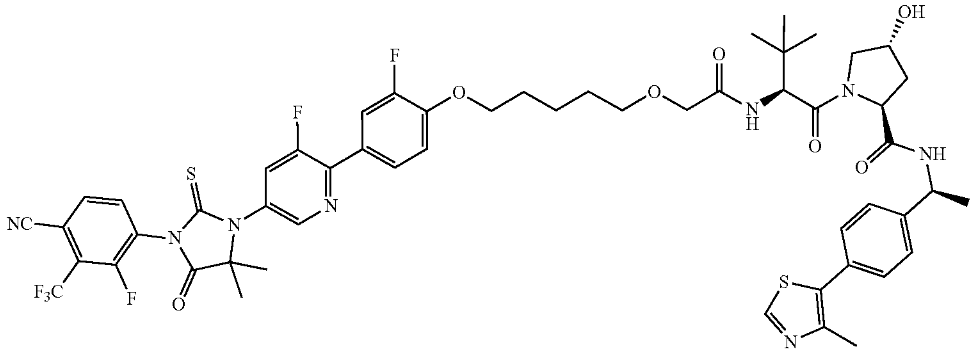 [SMILES: Cc1ncsc1-c1ccc([C@H](C)NC(=O)[C@@H]2C[C@@H](O)CN2C(=O)[C@@H](NC(=O)COCCCCCOc2ccc(-c3ncc(N4C(=S)N(c5ccc(C#N)c(C(F)(F)F)c5F)C(=O)C4(C)C)cc3F)cc2F)C(C)(C)C)cc1] |
| A113 | 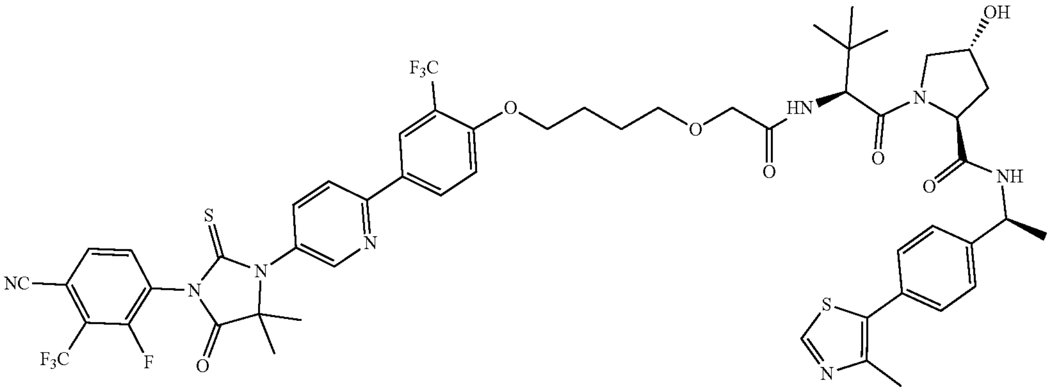 [SMILES: Cc1ncsc1-c1ccc([C@H](C)NC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2C(F)(F)F)C(C)(C)C)cc1] |
| A114 | 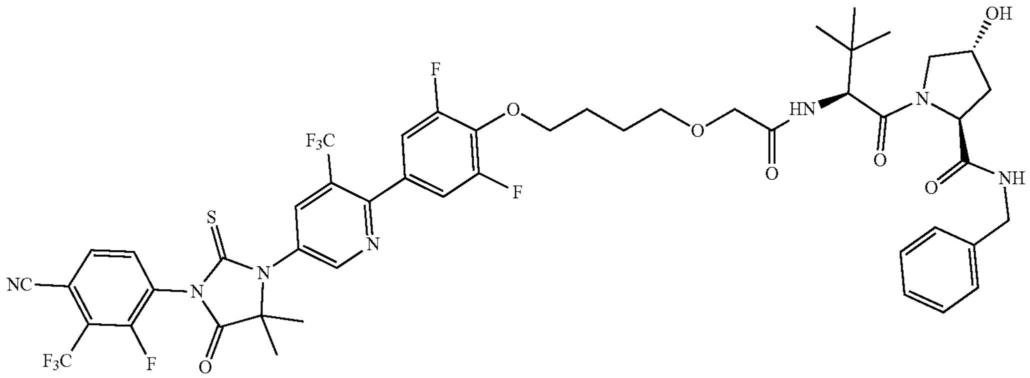 [SMILES: CC(C)(C)[C@H](NC(=O)COCCCCOc1c(F)cc(-c2ncc(N3C(=S)N(c4ccc(C#N)c(C(F)(F)F)c4F)C(=O)C3(C)C)cc2C(F)(F)F)cc1F)C(=O)N1C[C@H](O)C[C@H]1C(=O)NCc1ccccc1] |
| A115 | 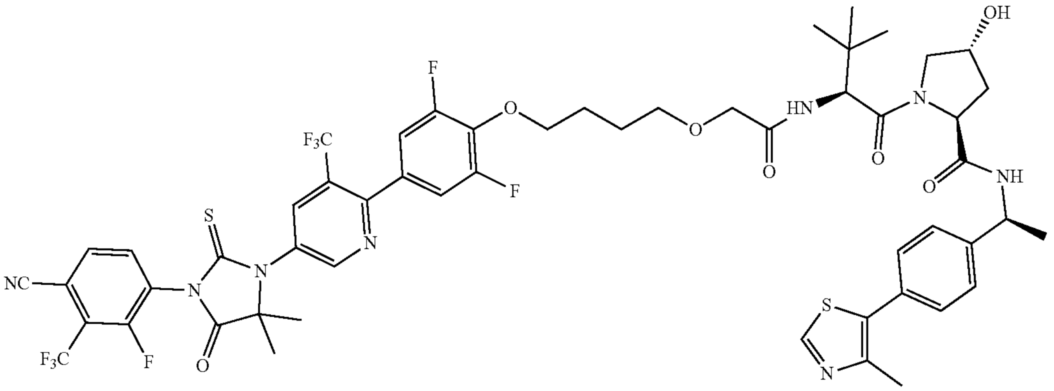 [SMILES: Cc1ncsc1-c1ccc([C@H](C)NC(=O)[C@@H]2C[C@@H](O)CN2C(=O)[C@@H](NC(=O)COCCCCOc2c(F)cc(-c3ncc(N4C(=S)N(c5ccc(C#N)c(C(F)(F)F)c5F)C(=O)C4(C)C)cc3C(F)(F)F)cc2F)C(C)(C)C)cc1] |

-continued
| Compound number | Compound structure |
|---|---|
| A116 | 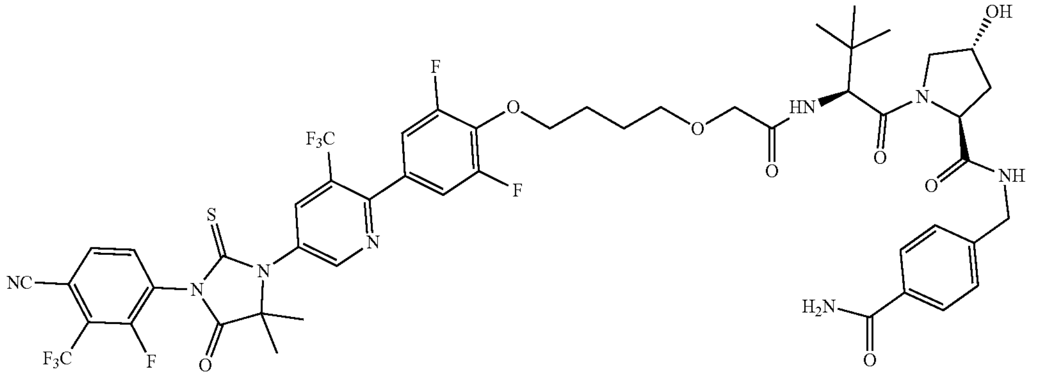 [SMILES: CC(C)(C)[C@H](NC(=O)COCCCCOc1c(F)cc(-c2ncc(N3C(=S)N(c4ccc(C#N)c(C(F)(F)F)c4F)C(=O)C3(C)C)cc2C(F)(F)F)cc1F)C(=O)N1C[C@H](O)C[C@H]1C(=O)NCc1ccc(C(N)=O)cc1] |
| A117 | 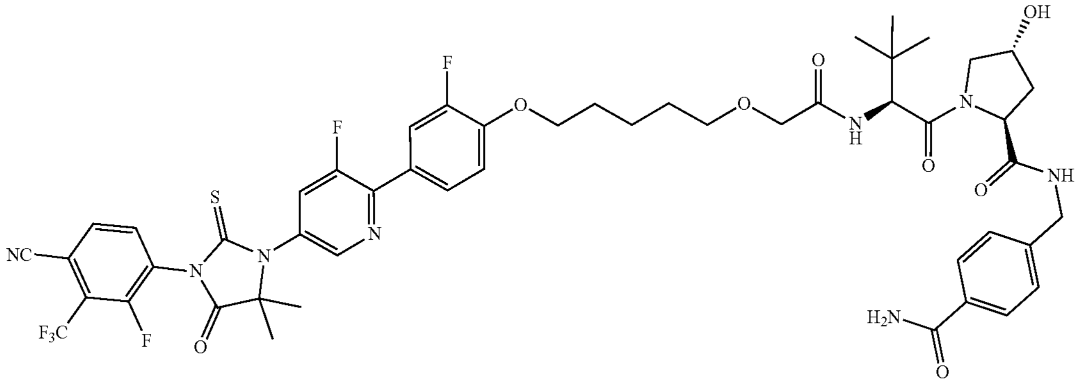 [SMILES: CC(C)(C)[C@H](NC(=O)COCCCCCOc1ccc(-c2ncc(N3C(=S)N(c4ccc(C#N)c(C(F)(F)F)c4F)C(=O)C3(C)C)cc2F)cc1F)C(=O)N1C[C@H](O)C[C@H]1C(=O)NCc1ccc(C(N)=O)cc1] |
| A118 | 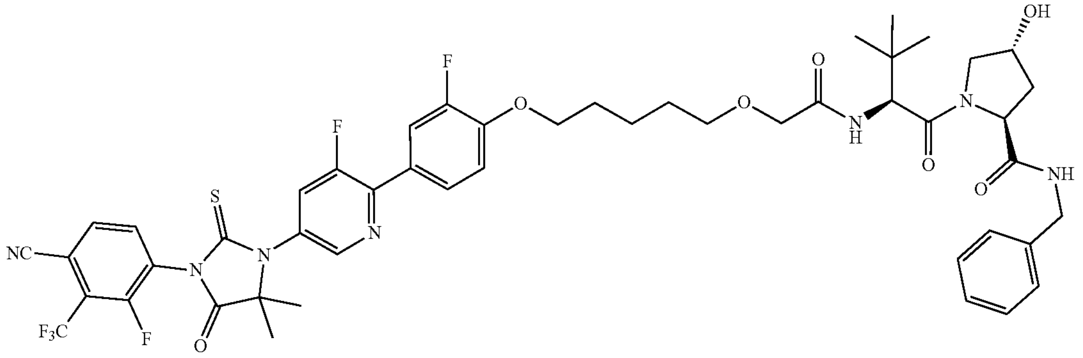 [SMILES: CC(C)(C)[C@H](NC(=O)COCCCCCOc1ccc(-c2ncc(N3C(=S)N(c4ccc(C#N)c(C(F)(F)F)c4F)C(=O)C3(C)C)cc2F)cc1F)C(=O)N1C[C@H](O)C[C@H]1C(=O)NCc1ccccc1] |
| A119 | 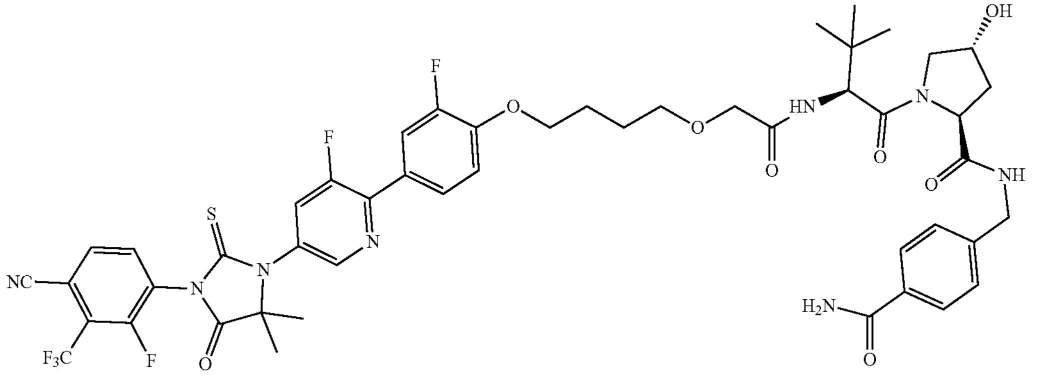 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)cc1F)C(=O)N1C[C@H](O)C[C@H]1C(=O)NCc1ccc(C(N)=O)cc1] |

-continued
| Compound number | Compound structure |
|---|---|
| A120 | 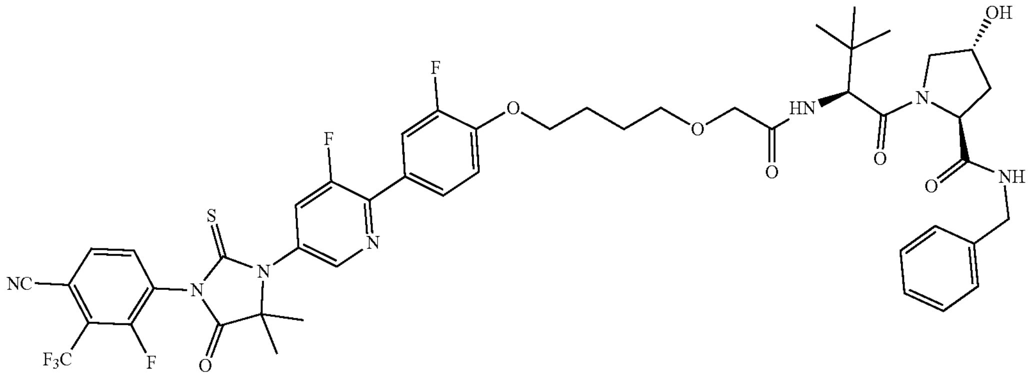 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)cc1F)C(=O)N1C[C@H](O)C[C@H]1C(=O)NCc1ccccc1] |
| A121 | 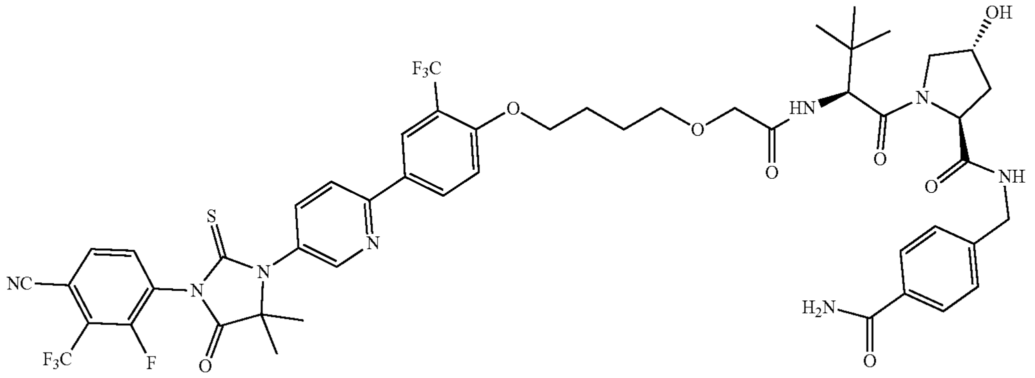 [SMILES: CC(C)(C)[C@H](NC(=O)COCCCCOc1ccc(-c2ccc(N3C(=S)N(c4ccc(C#N)c(C(F)(F)F)c4F)C(=O)C3(C)C)cn2)cc1C(F)(F)F)C(=O)N1C[C@H](O)C[C@H]1C(=O)NCc1ccc(C(N)=O)cc1] |
| A122 | 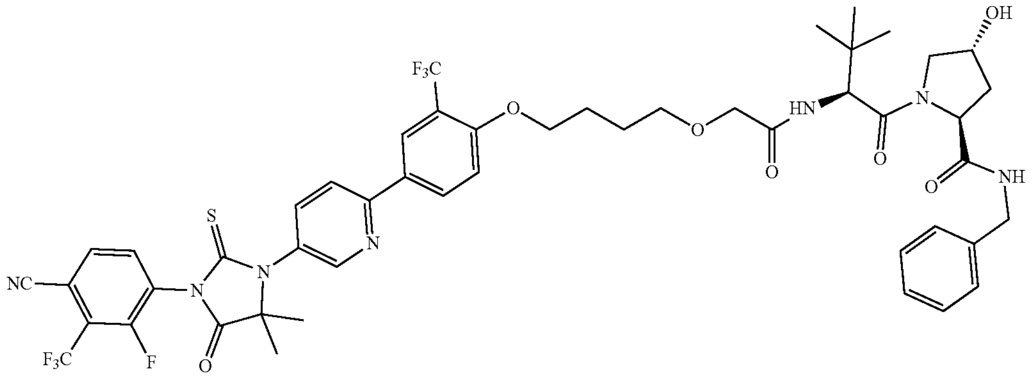 [SMILES: CC(C)(C)[C@H](NC(=O)COCCCCOc1ccc(-c2ccc(N3C(=S)N(c4ccc(C#N)c(C(F)(F)F)c4F)C(=O)C3(C)C)cn2)cc1C(F)(F)F)C(=O)N1C[C@H](O)C[C@H]1C(=O)NCc1ccccc1] |
| A123 | 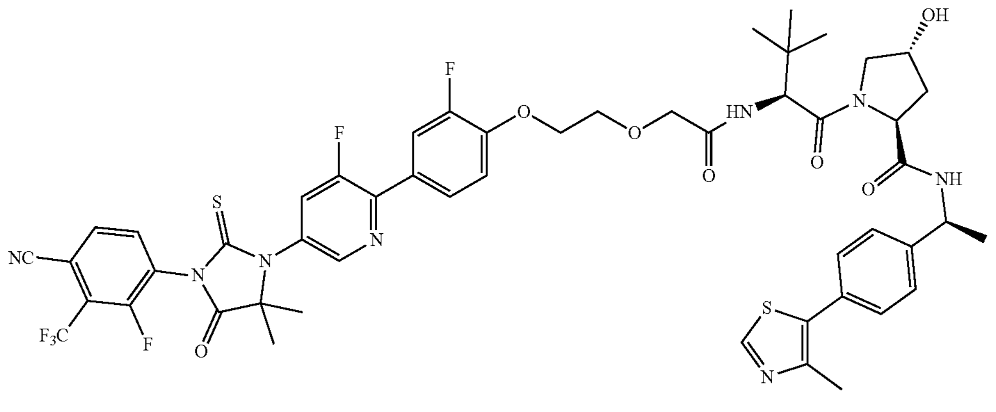 [SMILES: Cc1ncsc1-c1ccc([C@H](C)NC(=O)[C@@H]2C[C@@H](O)CN2C(=O)[C@@H](NC(=O)COCCOc2ccc(-c3ncc(N4C(=S)N(c5ccc(C#N)c(C(F)(F)F)c5F)C(=O)C4(C)C)cc3F)cc2F)C(C)(C)C)cc1] |

-continued
| Compound number | Compound structure |
|---|---|
| A124 | 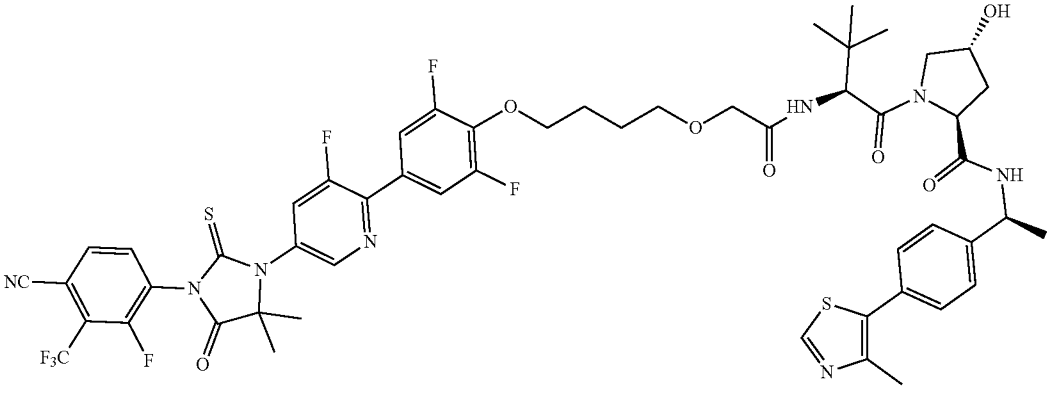 [SMILES: Cc1ncsc1-c1ccc([C@H](C)NC(=O)[C@@H]2C[C@@H](O)CN2C(=O)[C@@H](NC(=O)COCCCCOc2c(F)cc(-c3ncc(N4C(=S)N(c5ccc(C#N)c(C(F)(F)F)c5F)C(=O)C4(C)C)cc3F)cc2F)C(C)(C)C)cc1] |
| A125 | 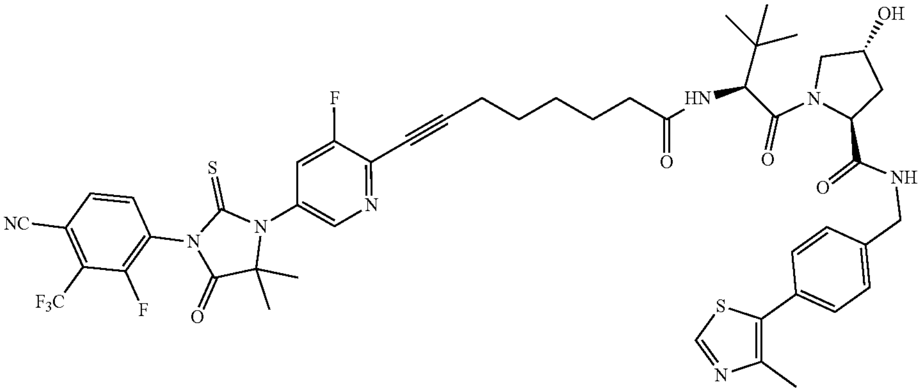 [SMILES: Cc1ncsc1-c1ccc(CNC(=O)[C@@H]2C[C@@H](O)CN2C(=O)[C@@H](NC(=O)CCCCCC#Cc2ncc(N3C(=S)N(c4ccc(C#N)c(C(F)(F)F)c4F)C(=O)C3(C)C)cc2F)C(C)(C)C)cc1] |
| A126 | 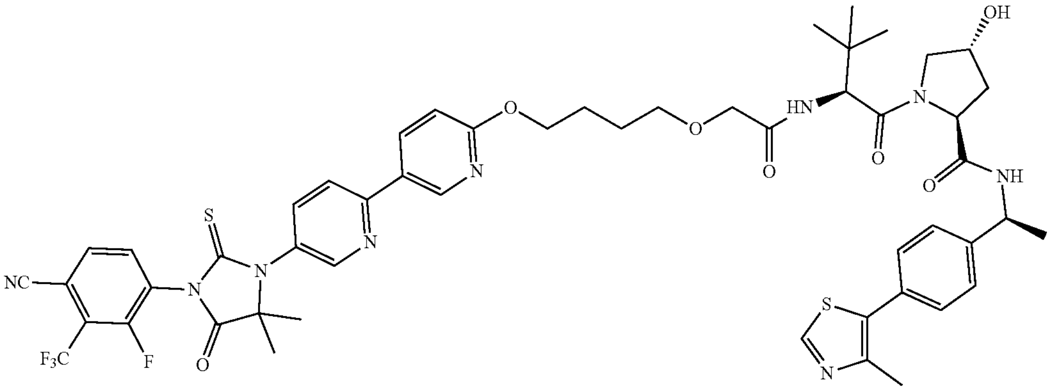 [SMILES: Cc1ncsc1-c1ccc([C@H](C)NC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cn2)C(C)(C)C)cc1] |
| A127 | 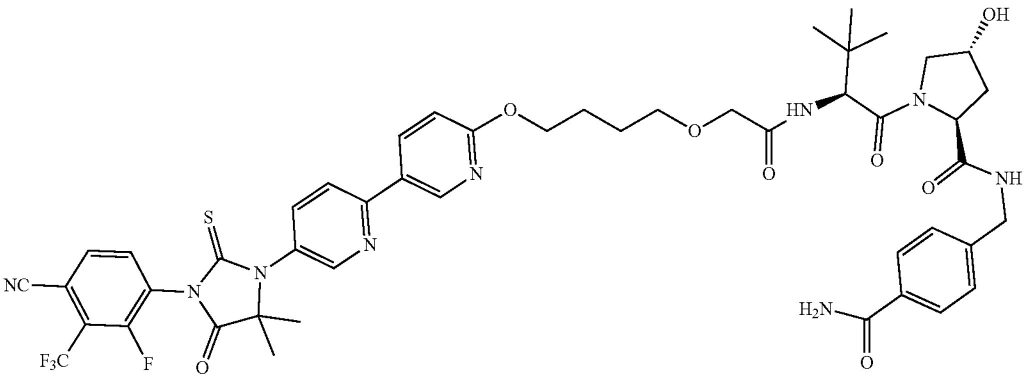 [SMILES: CC(C)(C)[C@H](NC(=O)COCCCCOc1ccc(-c2ccc(N3C(=S)N(c4ccc(C#N)c(C(F)(F)F)c4F)C(=O)C3(C)C)cn2)cn1)C(=O)N1C[C@H](O)C[C@H]1C(=O)NCc1ccc(C(N)=O)cc1] |

-continued
| Compound number | Compound structure |
|---|---|
| A128 | 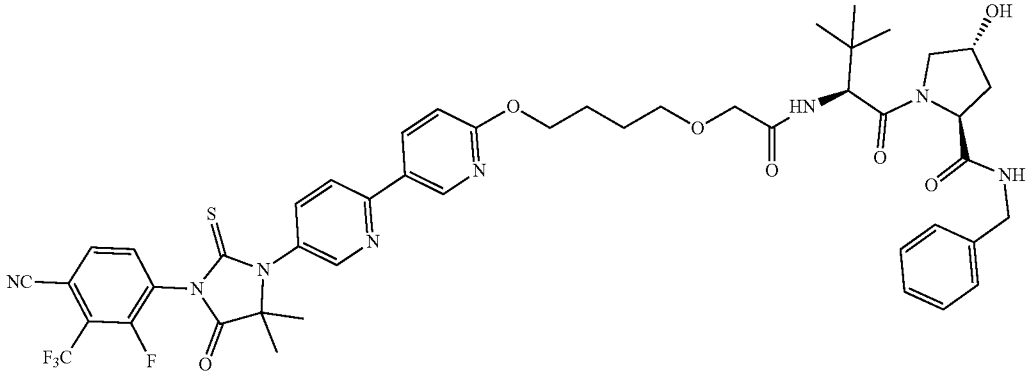 [SMILES: CC(C)(C)[C@H](NC(=O)COCCCCOc1ccc(-c2ccc(N3C(=S)N(c4ccc(C#N)c(C(F)(F)F)c4F)C(=O)C3(C)C)cn2)cn1)C(=O)N1C[C@H](O)C[C@H]1C(=O)NCc1ccccc1] |
| A129 | 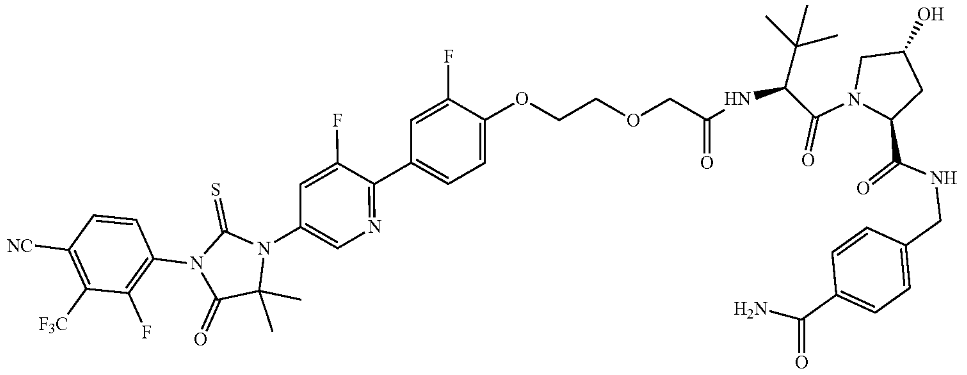 [SMILES: CC(C)(C)[C@H](NC(=O)COCCOc1ccc(-c2ncc(N3C(=S)N(c4ccc(C#N)c(C(F)(F)F)c4F)C(=O)C3(C)C)cc2F)cc1F)C(=O)N1C[C@H](O)C[C@H]1C(=O)NCc1ccc(C(N)=O)cc1] |
| A130 | 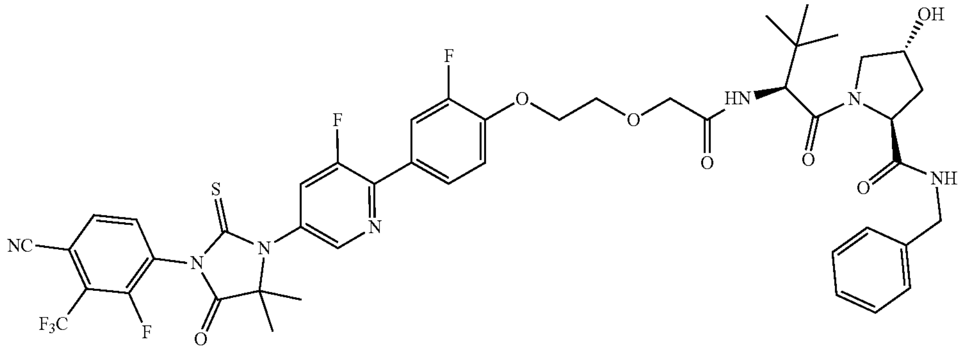 [SMILES: CC(C)(C)[C@H](NC(=O)COCCOc1ccc(-c2ncc(N3C(=S)N(c4ccc(C#N)c(C(F)(F)F)c4F)C(=O)C3(C)C)cc2F)cc1F)C(=O)N1C[C@H](O)C[C@H]1C(=O)NCc1ccccc1] |
| A131 | 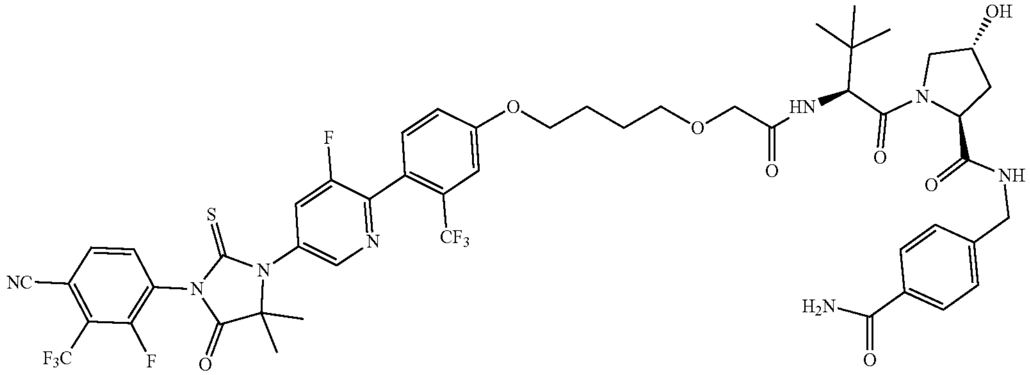 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)c(C(F)(F)F)c1)C(=O)N1C[C@H](O)C[C@H]1C(=O)NCc1ccc(C(N)=O)cc1] |

-continued
| Compound number | Compound structure |
|---|---|
| A132 | 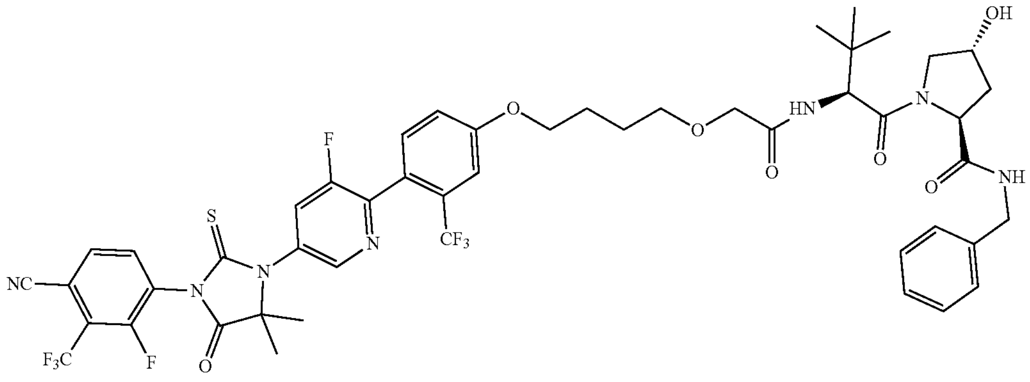 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)c(C(F)(F)F)c1)C(=O)N1C[C@H](O)C[C@H]1C(=O)NCc1ccccc1] |
| A133 | 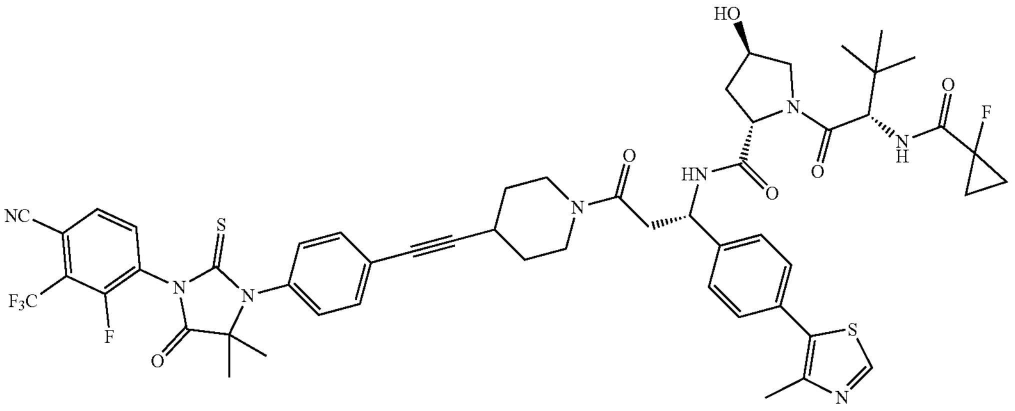 [SMILES: Cc1ncsc1-c1ccc([C@H](CC(=O)N2CCC(C#Cc3ccc(N4C(=S)N(c5ccc(C#N)c(C(F)(F)F)c5F)C(=O)C4(C)C)cc3)CC2)NC(=O)[C@@H]2C[C@@H](O)CN2C(=O)[C@@H](NC(=O)C2(F)CC2)C(C)(C)C)cc1] |
| A134 | 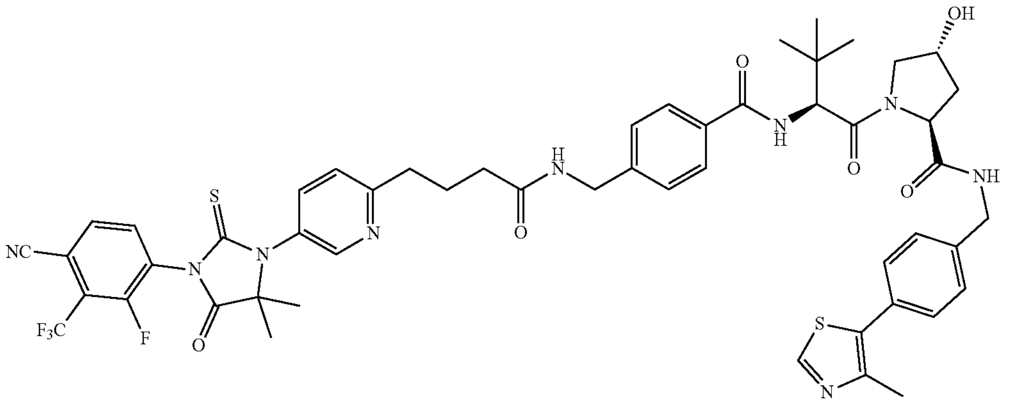 [SMILES: Cc1ncsc1-c1ccc(CNC(=O)[C@@H]2C[C@@H](O)CN2C(=O)[C@@H](NC(=O)c2ccc(CNC(=O)CCCc3ccc(N4C(=S)N(c5ccc(C#N)c(C(F)(F)F)c5F)C(=O)C4(C)C)cn3)cc2)C(C)(C)C)cc1] |

-continued
| Compound number | Compound structure |
|---|---|
| A135 | 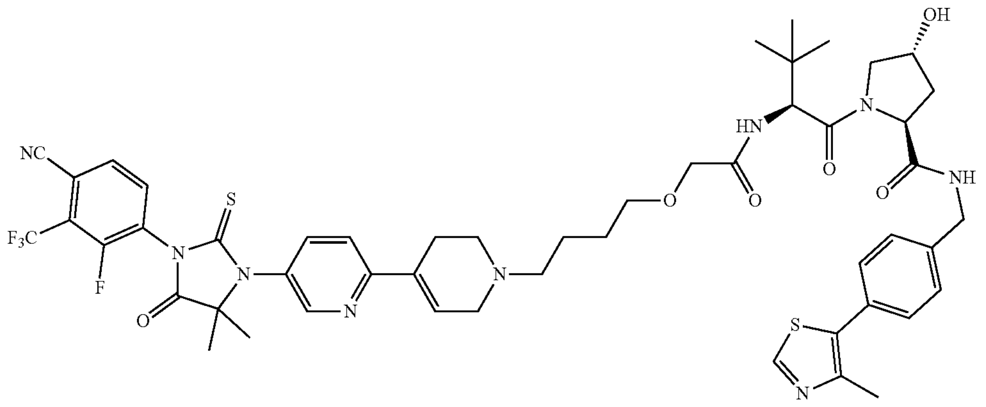 [SMILES: Cc1ncsc1-c1ccc(CNC(=O)[C@@H]2C[C@@H](O)CN2C(=O)[C@@H](NC(=O)COCCCCN2CC=C(c3ccc(N4C(=S)N(c5ccc(C#N)c(C(F)(F)F)c5F)C(=O)C4(C)C)cn3)CC2)C(C)(C)C)cc1] |
| A136 | 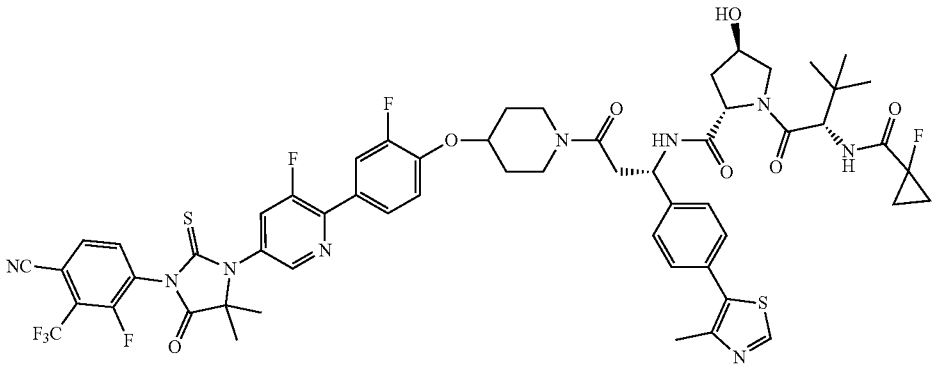 [SMILES: Cc1ncsc1-c1ccc([C@H](CC(=O)N2CCC(Oc3ccc(-c4ncc(N5C(=S)N(c6ccc(C#N)c(C(F)(F)F)c6F)C(=O)C5(C)C)cc4F)cc3F)CC2)NC(=O)[C@@H]2C[C@@H](O)CN2C(=O)[C@@H](NC(=O)C2(F)CC2)C(C)(C)C)cc1] |
| A137 | 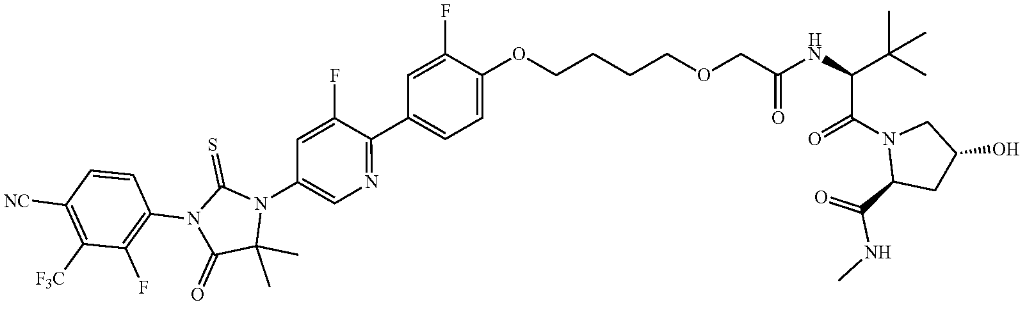 [SMILES: CNC(=O)[C@@H]1C[C@@H](O)CN1C(=O)[C@@H](NC(=O)COCCCCOc1ccc(-c2ncc(N3C(=S)N(c4ccc(C#N)c(C(F)(F)F)c4F)C(=O)C3(C)C)cc2F)cc1F)C(C)(C)C] |
| A138 | 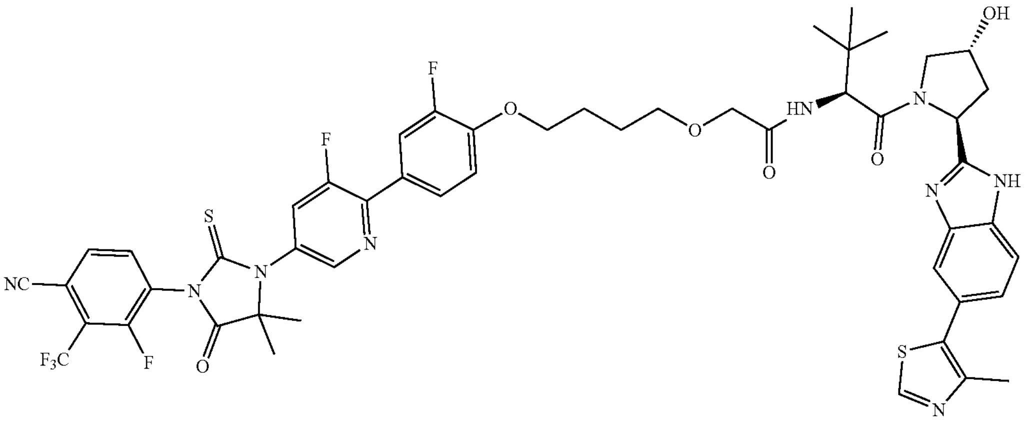 [SMILES: Cc1ncsc1-c1ccc2[nH]c([C@@H]3C[C@@H](O)CN3C(=O)[C@@H](NC(=O)COCCCCOc3ccc(-c4ncc(N5C(=S)N(c6ccc(C#N)c(C(F)(F)F)c6F)C(=O)C5(C)C)cc4F)cc3F)C(C)(C)C)nc2c1] |

-continued
| Compound number | Compound structure |
|---|---|
| A139 | 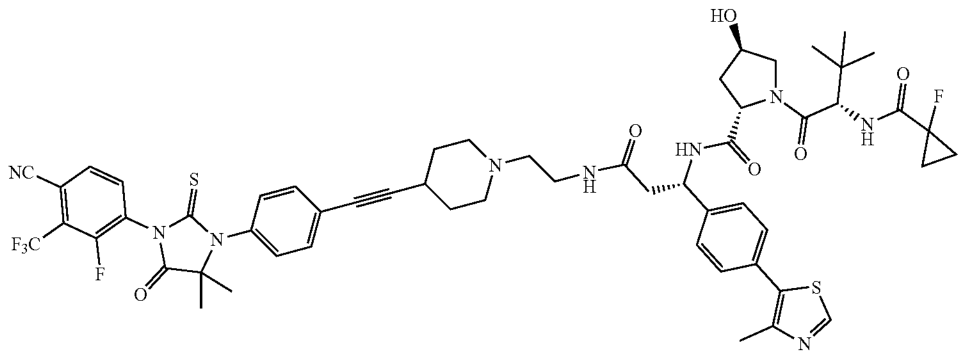 [SMILES: Cc1ncsc1-c1ccc([C@H](CC(=O)NCCN2CCC(C#Cc3ccc(N4C(=S)N(c5ccc(C#N)c(C(F)(F)F)c5F)C(=O)C4(C)C)cc3)CC2)NC(=O)[C@@H]2C[C@@H](O)CN2C(=O)[C@@H](NC(=O)C2(F)CC2)C(C)(C)C)cc1] |
| A140 | 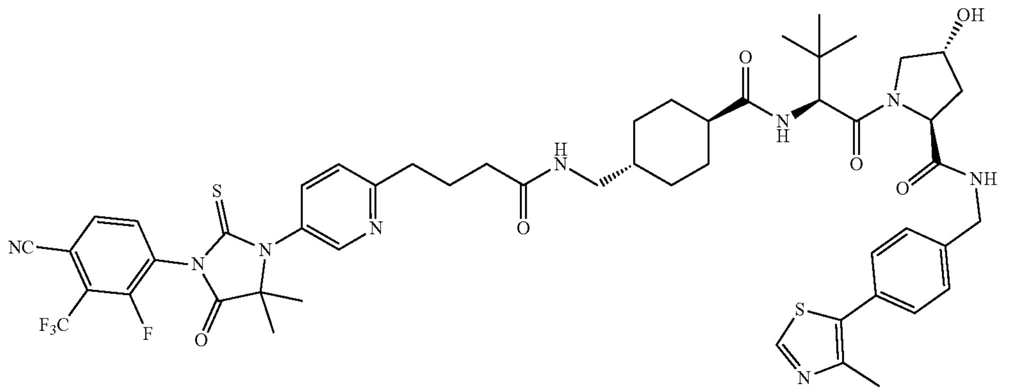 [SMILES: Cc1ncsc1-c1ccc(CNC(=O)[C@@H]2C[C@@H](O)CN2C(=O)[C@@H](NC(=O)[C@H]2CC[C@H](CNC(=O)CCCc3ccc(N4C(=S)N(c5ccc(C#N)c(C(F)(F)F)c5F)C(=O)C4(C)C)cn3)CC2)C(C)(C)C)cc1] |
| A141 | 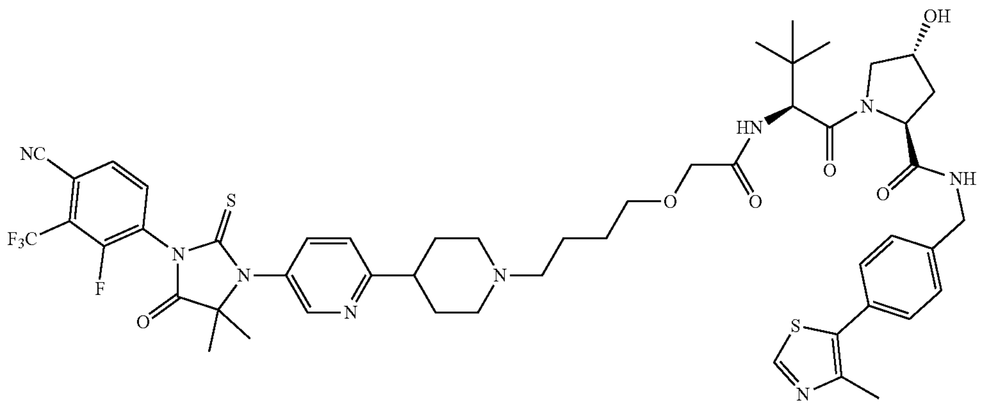 [SMILES: Cc1ncsc1-c1ccc(CNC(=O)[C@@H]2C[C@@H](O)CN2C(=O)[C@@H](NC(=O)COCCCCN2CCC(c3ccc(N4C(=S)N(c5ccc(C#N)c(C(F)(F)F)c5F)C(=O)C4(C)C)cn3)CC2)C(C)(C)C)cc1] |
| A142 | 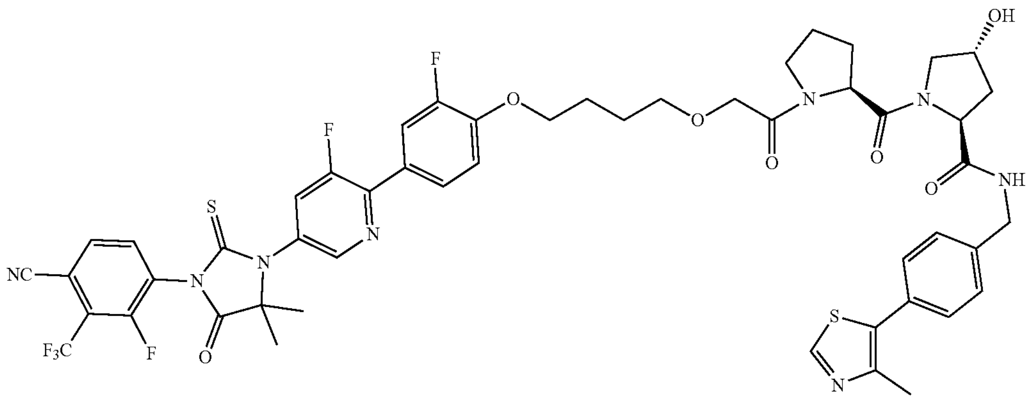 [SMILES: Cc1ncsc1-c1ccc(CNC(=O)[C@@H]2C[C@@H](O)CN2C(=O)[C@@H]2CCCN2C(=O)COCCCCOc2ccc(-c3ncc(N4C(=S)N(c5ccc(C#N)c(C(F)(F)F)c5F)C(=O)C4(C)C)cc3F)cc2F)cc1] |

-continued
| Compound number | Compound structure |
| --- | --- |
| A143 | 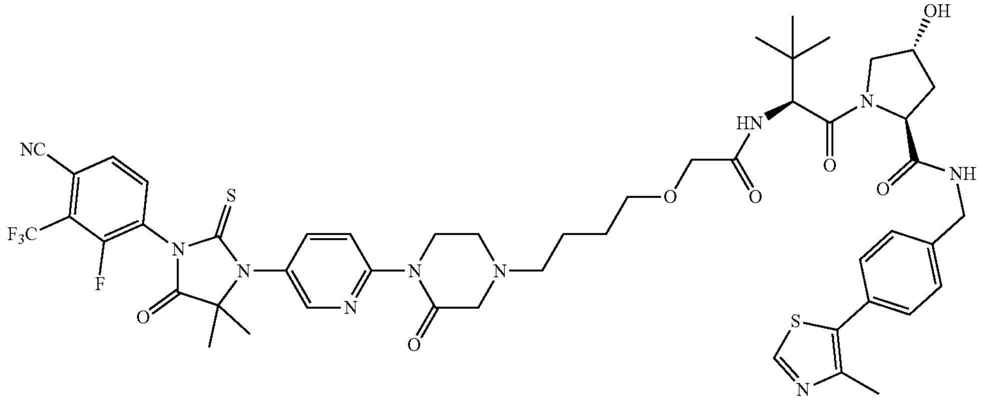 [SMILES: Cc1ncsc1-c1ccc(CNC(=O)[C@@H]2C[C@@H](O)CN2C(=O)[C@@H](NC(=O)COCCCCN2CCN(c3ccc(N4C(=S)N(c5ccc(C#N)c(C(F)(F)F)c5F)C(=O)C4(C)C)cn3)C(=O)C2)C(C)(C)C)cc1] |
| A144 | 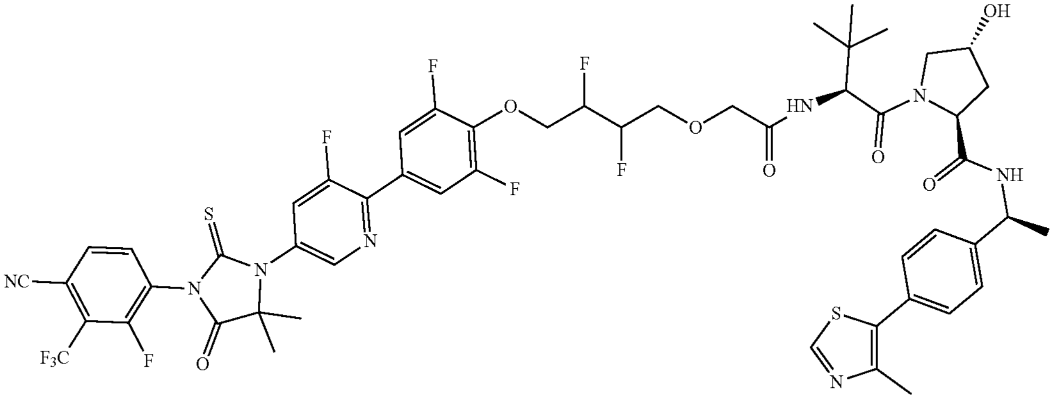 [SMILES: Cc1ncsc1-c1ccc([C@H](C)NC(=O)[C@@H]2C[C@@H](O)CN2C(=O)[C@@H](NC(=O)COCC(F)C(F)COc2c(F)cc(-c3ncc(N4C(=S)N(c5ccc(C#N)c(C(F)(F)F)c5F)C(=O)C4(C)C)cc3F)cc2F)C(C)(C)C)cc1] |
| A145 | 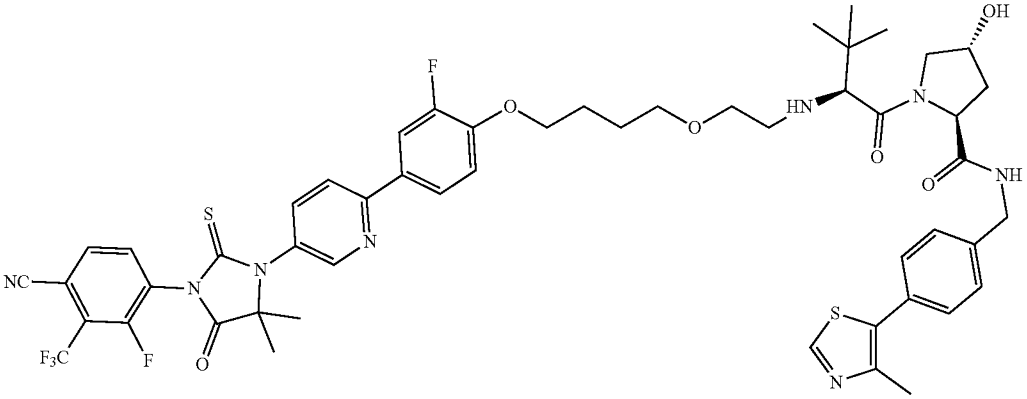 [SMILES: Cc1ncsc1-c1ccc(CNC(=O)[C@@H]2C[C@@H](O)CN2C(=O)[C@@H](NCCOCCCCOc2ccc(-c3ccc(N4C(=S)N(c5ccc(C#N)c(C(F)(F)F)c5F)C(=O)C4(C)C)cn3)cc2F)C(C)(C)C)cc1] |

-continued
| Compound number | Compound structure |
|---|---|
| A146 | 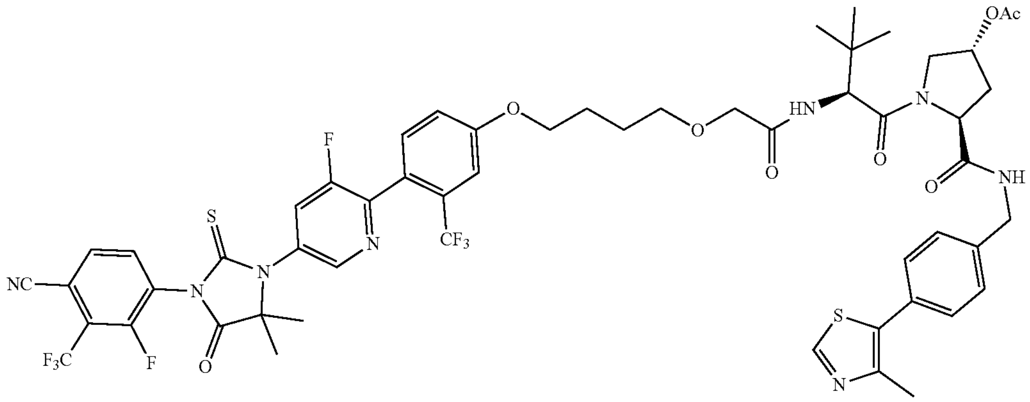 [SMILES: CC(=O)O[C@@H]1C[C@@H](C(=O)NCc2ccc(-c3scnc3C)cc2)N(C(=O)[C@@H](NC(=O)COCCCCOc2ccc(-c3ncc(N4C(=S)N(c5ccc(C#N)c(C(F)(F)F)c5F)C(=O)C4(C)C)cc3F)c(C(F)(F)F)c2)C(C)(C)C)C1] |
| A147 | 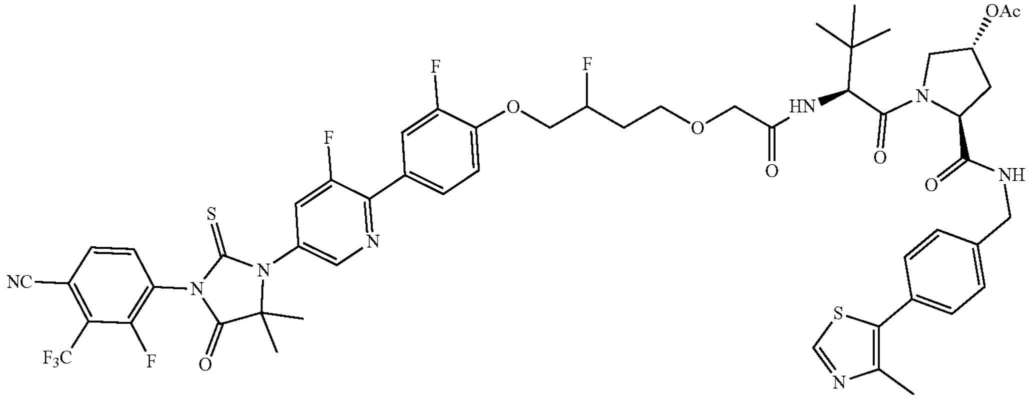 [SMILES: CC(=O)O[C@@H]1C[C@@H](C(=O)NCc2ccc(-c3scnc3C)cc2)N(C(=O)[C@@H](NC(=O)COCCC(F)COc2ccc(-c3ncc(N4C(=S)N(c5ccc(C#N)c(C(F)(F)F)c5F)C(=O)C4(C)C)cc3F)cc2F)C(C)(C)C)C1] |
| A148 | 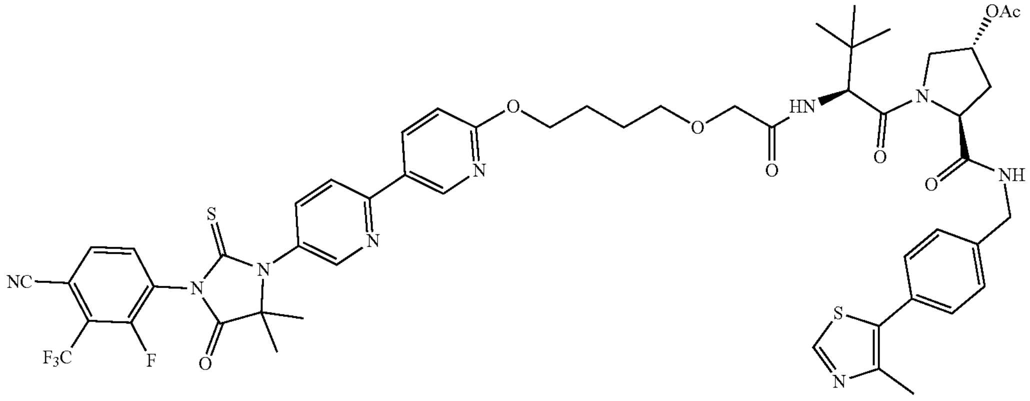 [SMILES: CC(=O)O[C@@H]1C[C@@H](C(=O)NCc2ccc(-c3scnc3C)cc2)N(C(=O)[C@@H](NC(=O)COCCCCOc2ccc(-c3ccc(N4C(=S)N(c5ccc(C#N)c(C(F)(F)F)c5F)C(=O)C4(C)C)cn3)cn2)C(C)(C)C)C1] |

-continued
| Compound number | Compound structure |
| --- | --- |
| A149 | 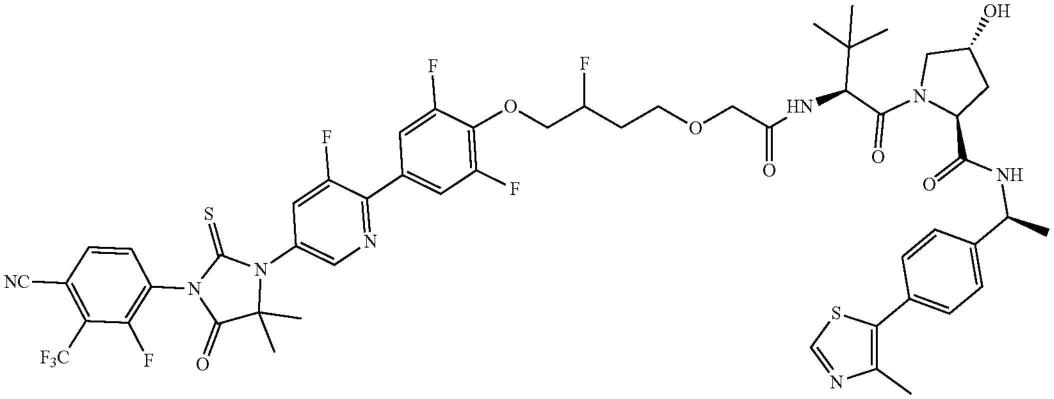 [SMILES: Cc1ncsc1-c1ccc([C@H](C)NC(=O)[C@@H]2C[C@@H](O)CN2C(=O)[C@@H](NC(=O)COCCC(F)COc2c(F)cc(-c3ncc(N4C(=S)N(c5ccc(C#N)c(C(F)(F)F)c5F)C(=O)C4(C)C)cc3F)cc2F)C(C)(C)C)cc1] |
| A150 | 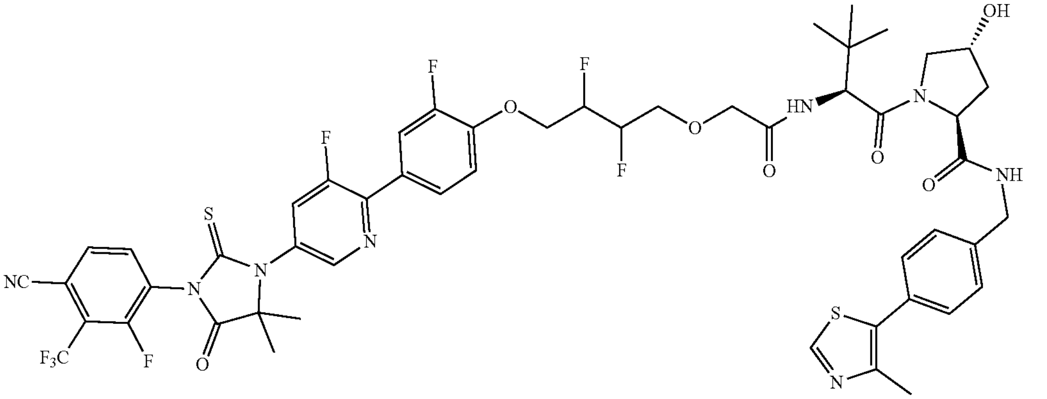 [SMILES: Cc1ncsc1-c1ccc(CNC(=O)[C@@H]2C[C@@H](O)CN2C(=O)[C@@H](NC(=O)COCC(F)C(F)COc2ccc(-c3ncc(N4C(=S)N(c5ccc(C#N)c(C(F)(F)F)c5F)C(=O)C4(C)C)cc3F)cc2F)C(C)(C)C)cc1] |
| A151 | 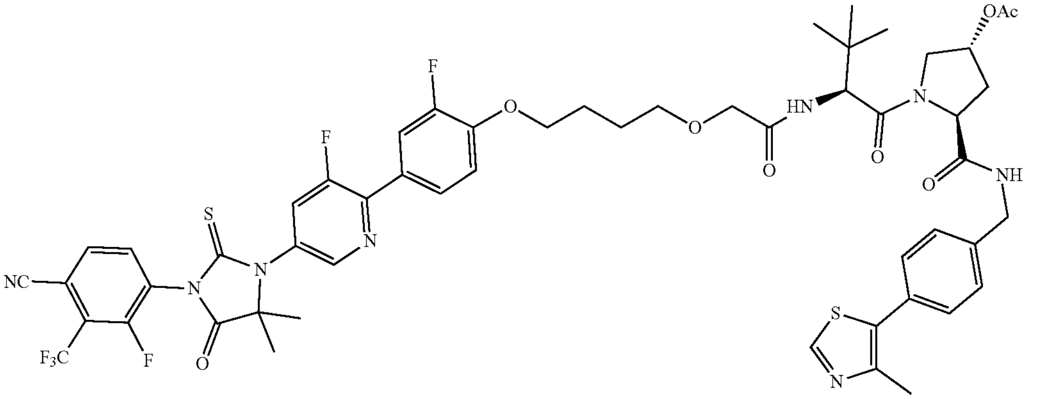 [SMILES: CC(=O)O[C@@H]1C[C@@H](C(=O)NCc2ccc(-c3scnc3C)cc2)N(C(=O)[C@@H](NC(=O)COCCCCOc2ccc(-c3ncc(N4C(=S)N(c5ccc(C#N)c(C(F)(F)F)c5F)C(=O)C4(C)C)cc3F)cc2F)C(C)(C)C)C1] |

-continued
| Compound number | Compound structure |
| --- | --- |
| A152 | 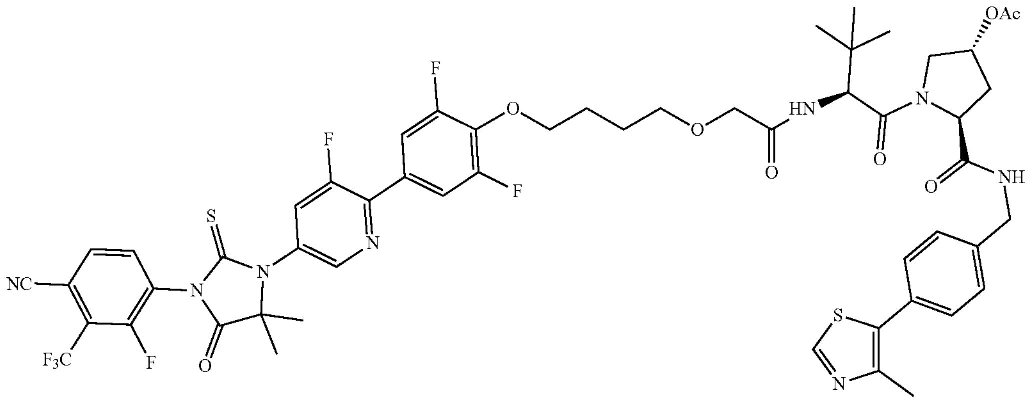 [SMILES: CC(=O)O[C@@H]1C[C@@H](C(=O)NCc2ccc(-c3scnc3C)cc2)N(C(=O)[C@@H](NC(=O)COCCCCOc2c(F)cc(-c3ncc(N4C(=S)N(c5ccc(C#N)c(C(F)(F)F)c5F)C(=O)C4(C)C)cc3F)cc2F)C(C)(C)C)C1] |
| A153 | 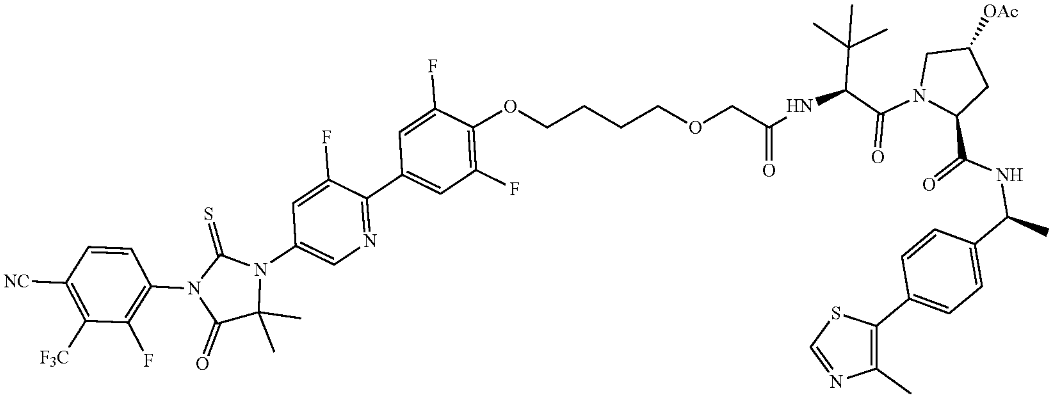 [SMILES: CC(=O)O[C@@H]1C[C@@H](C(=O)N[C@@H](C)c2ccc(-c3scnc3C)cc2)N(C(=O)[C@@H](NC(=O)COCCCCOc2c(F)cc(-c3ncc(N4C(=S)N(c5ccc(C#N)c(C(F)(F)F)c5F)C(=O)C4(C)C)cc3F)cc2F)C(C)(C)C)C1] |
| A154 | 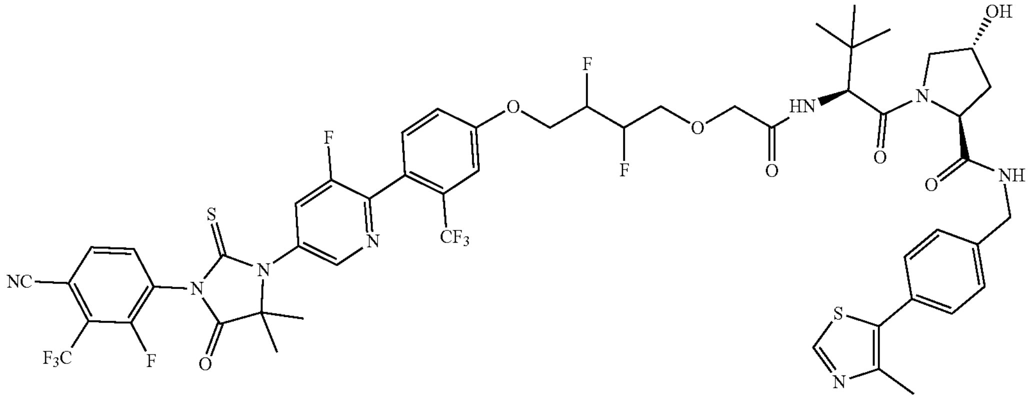 [SMILES: Cc1ncsc1-c1ccc(CNC(=O)[C@@H]2C[C@@H](O)CN2C(=O)[C@@H](NC(=O)COCC(F)C(F)COc2ccc(-c3ncc(N4C(=S)N(c5ccc(C#N)c(C(F)(F)F)c5F)C(=O)C4(C)C)cc3F)c(C(F)(F)F)c2)C(C)(C)C)cc1] |
| A155 | 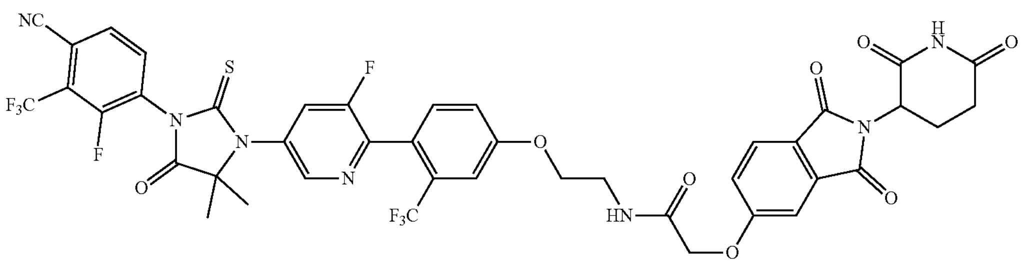 [SMILES: CC1(C)C(=O)N(c2ccc(C#N)c(C(F)(F)F)c2F)C(=S)N1c1cnc(-c2ccc(OCCNC(=O)COc3ccc4c(c3)C(=O)N(C3CCC(=O)NC3=O)C4=O)cc2C(F)(F)F)c(F)c1] |

-continued
| Compound number | Compound structure |
| --- | --- |
| A156 | 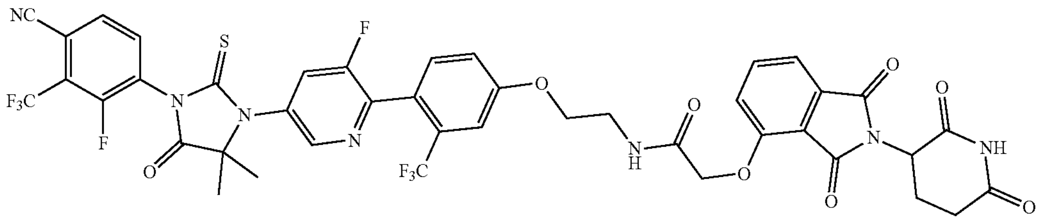 [SMILES: CC1(C)C(=O)N(c2ccc(C#N)c(C(F)(F)F)c2F)C(=S)N1c1cnc(-c2ccc(OCCNC(=O)COc3cccc4c3C(=O)N(C3CCC(=O)NC3=O)C4=O)cc2C(F)(F)F)c(F)c1] |
| A157 | 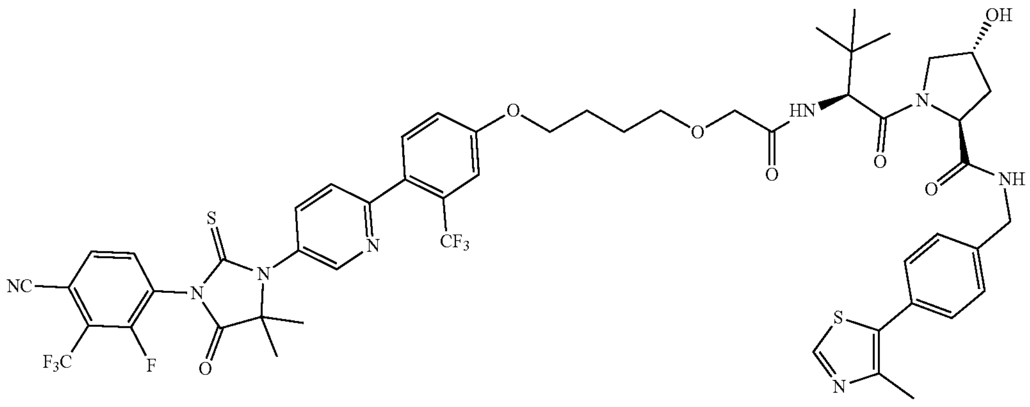 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)c(C(F)(F)F)c2)C(C)(C)C)cc1] |
| A158 | 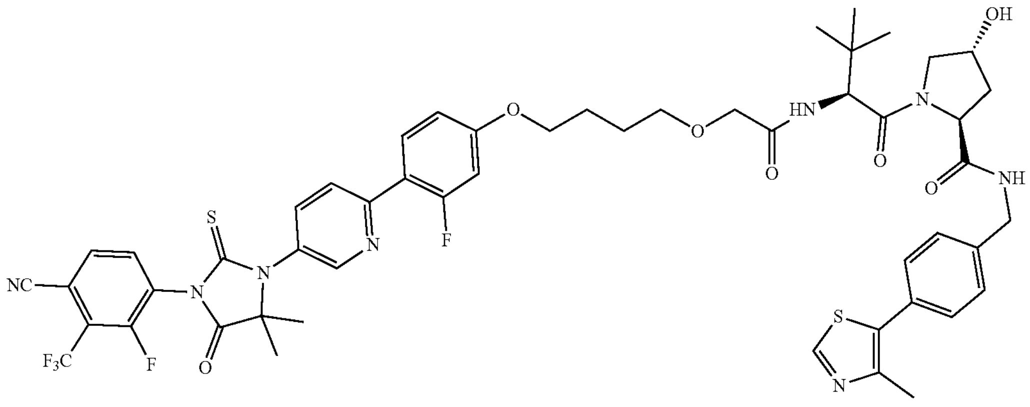 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)c(F)c2)C(C)(C)C)cc1] |
| A159 | 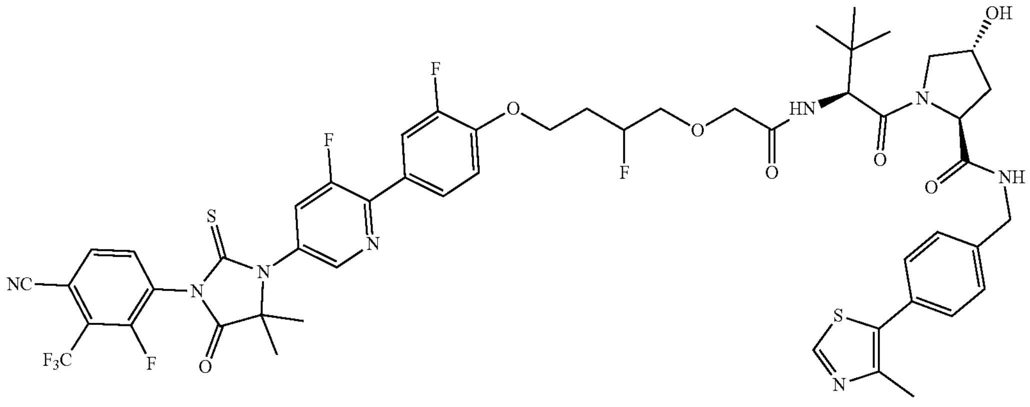 [SMILES: Cc1ncsc1-c1ccc(CNC(=O)[C@@H]2C[C@@H](O)CN2C(=O)[C@@H](NC(=O)COCC(F)CCOc2ccc(-c3ncc(N4C(=S)N(c5ccc(C#N)c(C(F)(F)F)c5F)C(=O)C4(C)C)cc3F)cc2F)C(C)(C)C)cc1] |

-continued
| Compound number | Compound structure |
|---|---|
| A160 | 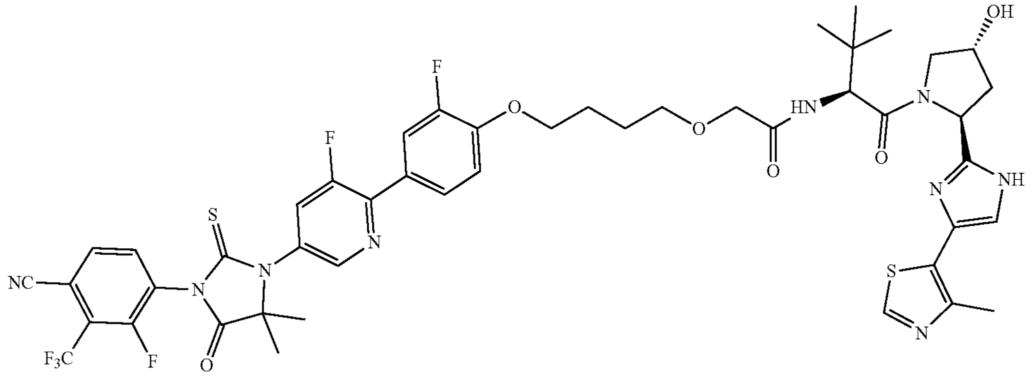 [SMILES: Cc1ncsc1-c1c[nH]c([C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)cc2F)C(C)(C)C)n1] |
| A161 | 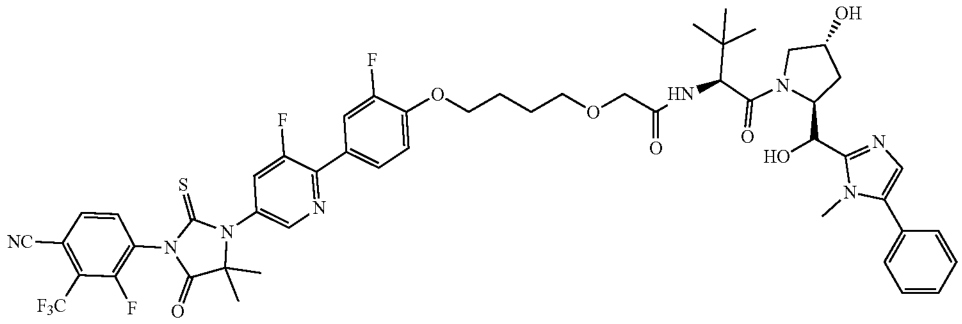 [SMILES: Cn1c(-c2ccccc2)cnc1C(O)[C@@H]1C[C@@H](O)CN1C(=O)[C@@H](NC(=O)COCCCCOc1ccc(-c2ncc(N3C(=S)N(c4ccc(C#N)c(C(F)(F)F)c4F)C(=O)C3(C)C)cc2F)cc1F)C(C)(C)C] |
| A162 | 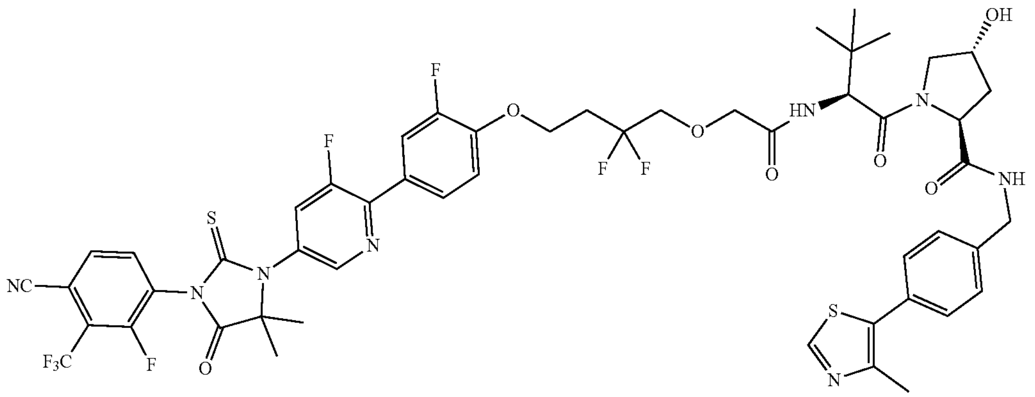 [SMILES: Cc1ncsc1-c1ccc(CNC(=O)[C@@H]2C[C@@H](O)CN2C(=O)[C@@H](NC(=O)COCC(F)(F)CCOc2ccc(-c3ncc(N4C(=S)N(c5ccc(C#N)c(C(F)(F)F)c5F)C(=O)C4(C)C)cc3F)cc2F)C(C)(C)C)cc1] |
| A163 | 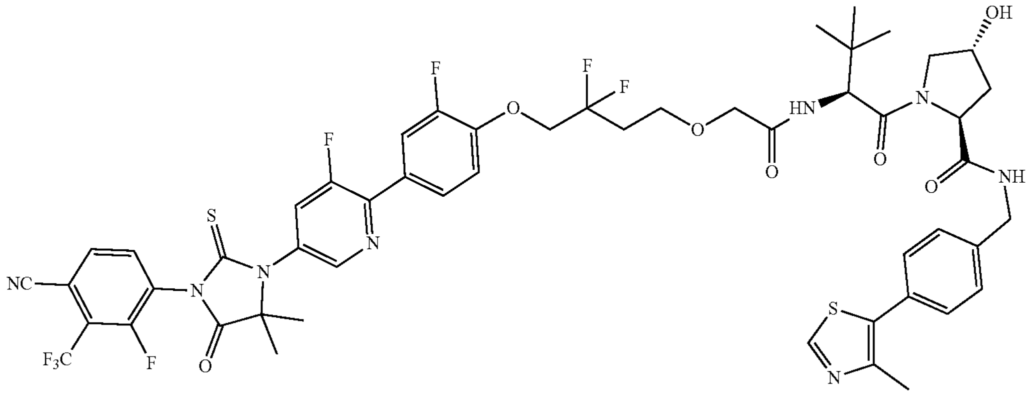 [SMILES: Cc1ncsc1-c1ccc(CNC(=O)[C@@H]2C[C@@H](O)CN2C(=O)[C@@H](NC(=O)COCCC(F)(F)COc2ccc(-c3ncc(N4C(=S)N(c5ccc(C#N)c(C(F)(F)F)c5F)C(=O)C4(C)C)cc3F)cc2F)C(C)(C)C)cc1] |

-continued
| Compound number | Compound structure |
| --- | --- |
| A164 | 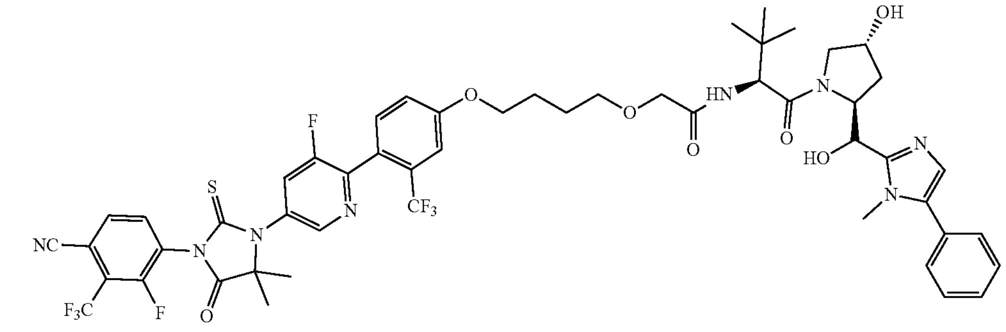 [SMILES: Cn1c(-c2ccccc2)cnc1C(O)[C@@H]1C[C@@H](O)CN1C(=O)[C@@H](NC(=O)COCCCCOc1ccc(-c2ncc(N3C(=S)N(c4ccc(C#N)c(C(F)(F)F)c4F)C(=O)C3(C)C)cc2F)c(C(F)(F)F)c1)C(C)(C)C] |
| A165 | 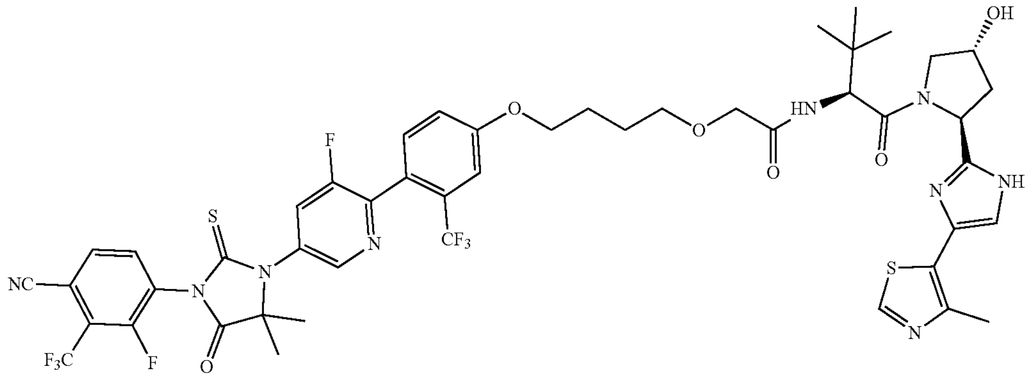 [SMILES: Cc1ncsc1-c1c[nH]c([C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)c(C(F)(F)F)c2)C(C)(C)C)n1] |
| A166 | 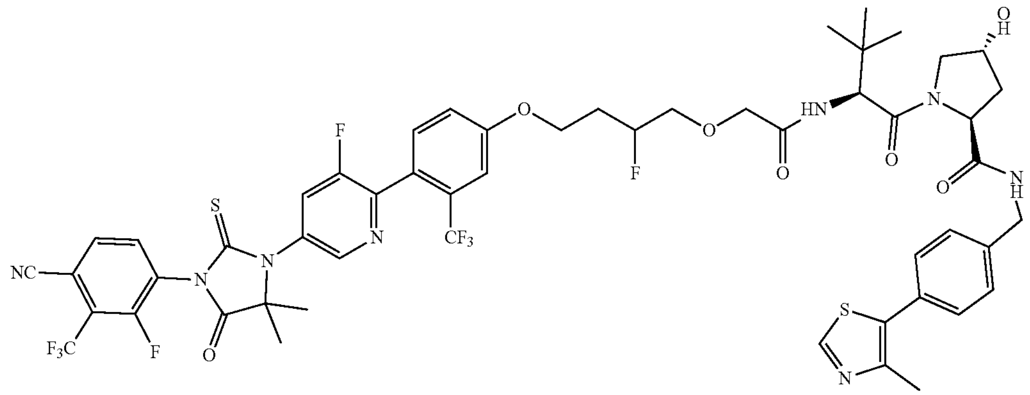 [SMILES: Cc1ncsc1-c1ccc(CNC(=O)[C@@H]2C[C@@H](O)CN2C(=O)[C@@H](NC(=O)COCC(F)CCOc2ccc(-c3ncc(N4C(=S)N(c5ccc(C#N)c(C(F)(F)F)c5F)C(=O)C4(C)C)cc3F)c(C(F)(F)F)c2)C(C)(C)C)cc1] |
| A167 | 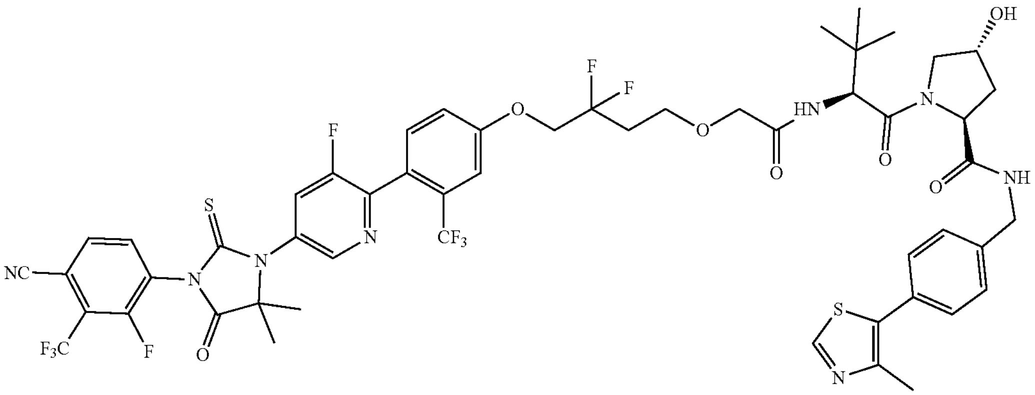 [SMILES: Cc1ncsc1-c1ccc(CNC(=O)[C@@H]2C[C@@H](O)CN2C(=O)[C@@H](NC(=O)COCCC(F)(F)COc2ccc(-c3ncc(N4C(=S)N(c5ccc(C#N)c(C(F)(F)F)c5F)C(=O)C4(C)C)cc3F)c(C(F)(F)F)c2)C(C)(C)C)cc1] |

-continued
| Compound number | Compound structure |
| --- | --- |
| A168 | 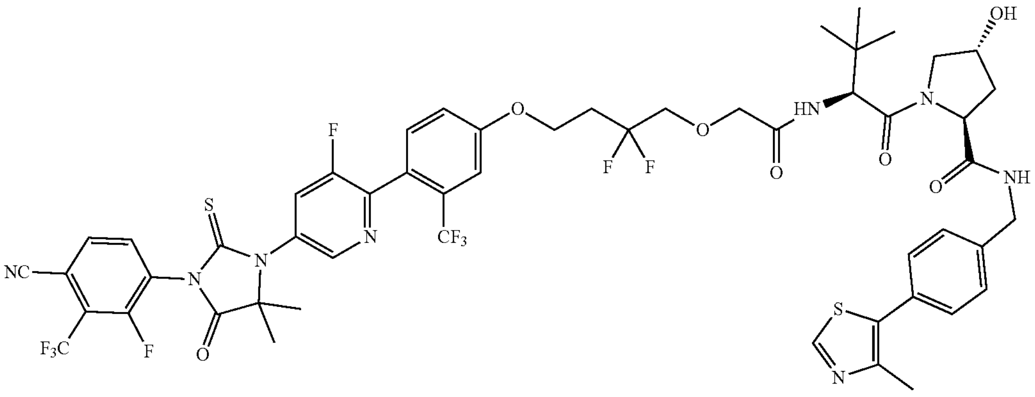 [SMILES: Cc1ncsc1-c1ccc(CNC(=O)[C@@H]2C[C@@H](O)CN2C(=O)[C@@H](NC(=O)COCC(F)(F)CCOc2ccc(-c3ncc(N4C(=S)N(c5ccc(C#N)c(C(F)(F)F)c5F)C(=O)C4(C)C)cc3F)c(C(F)(F)F)c2)C(C)(C)C)cc1] |
| A169 | 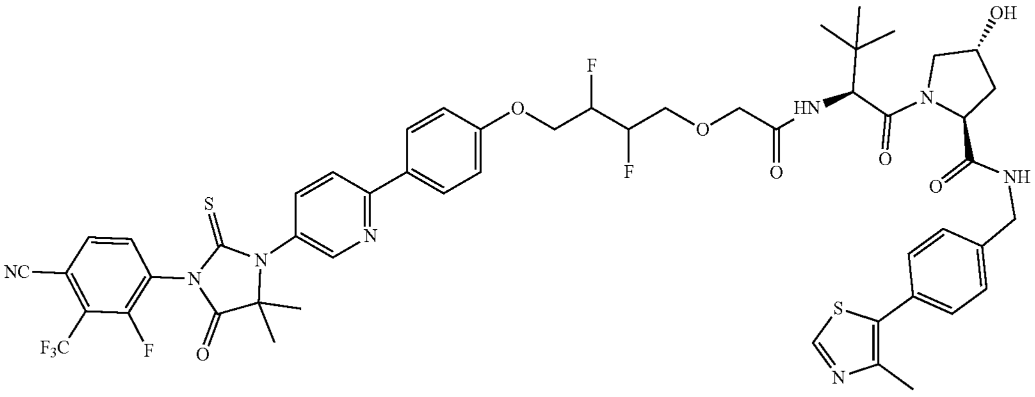 [SMILES: Cc1ncsc1-c1ccc(CNC(=O)[C@@H]2C[C@@H](O)CN2C(=O)[C@@H](NC(=O)COCC(F)C(F)COc2ccc(-c3ccc(N4C(=S)N(c5ccc(C#N)c(C(F)(F)F)c5F)C(=O)C4(C)C)cn3)cc2)C(C)(C)C)cc1] |
| A170 | 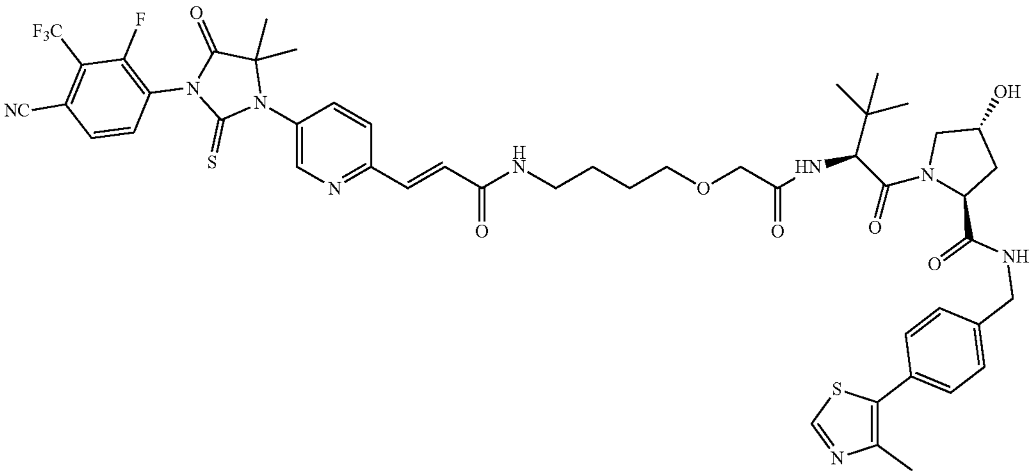 [SMILES: Cc1ncsc1-c1ccc(CNC(=O)[C@@H]2C[C@@H](O)CN2C(=O)[C@@H](NC(=O)COCCCCNC(=O)/C=C/c2ccc(N3C(=S)N(c4ccc(C#N)c(C(F)(F)F)c4F)C(=O)C3(C)C)cn2)C(C)(C)C)cc1] |

-continued
| Compound number | Compound structure |
|---|---|
| A171 | 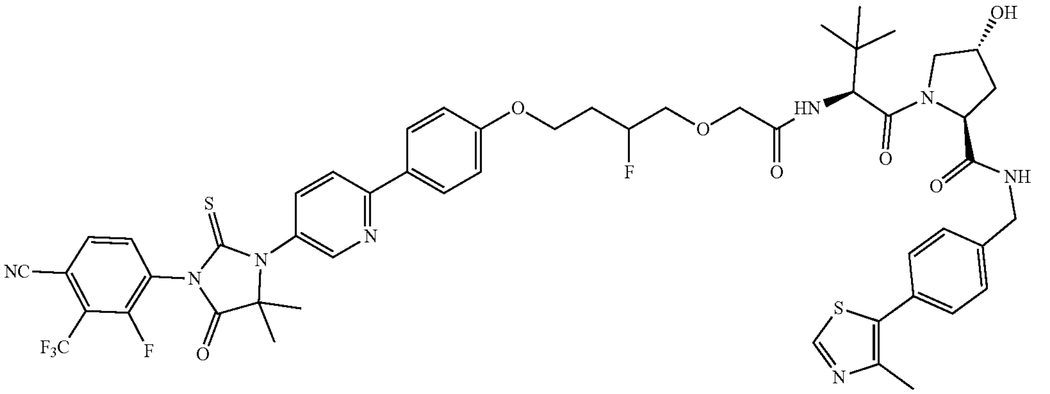 [SMILES: Cc1ncsc1-c1ccc(CNC(=O)[C@@H]2C[C@@H](O)CN2C(=O)[C@@H](NC(=O)COCC(F)CCOc2ccc(-c3ccc(N4C(=S)N(c5ccc(C#N)c(C(F)(F)F)c5F)C(=O)C4(C)C)cn3)cc2)C(C)(C)C)cc1] |
| A172 | 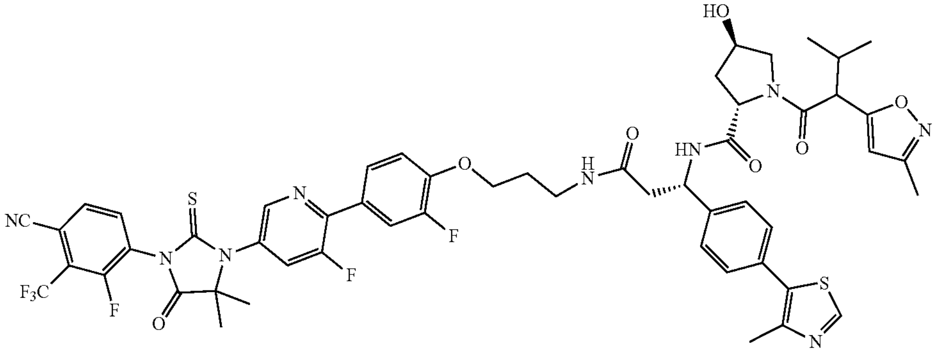 [SMILES: Cc1cc(C(C(=O)N2C[C@H](O)C[C@H]2C(=O)N[C@@H](CC(=O)NCCCOc2ccc(-c3ncc(N4C(=S)N(c5ccc(C#N)c(C(F)(F)F)c5F)C(=O)C4(C)C)cc3F)cc2F)c2ccc(-c3scnc3C)cc2)C(C)C)on1] |
| A173 | 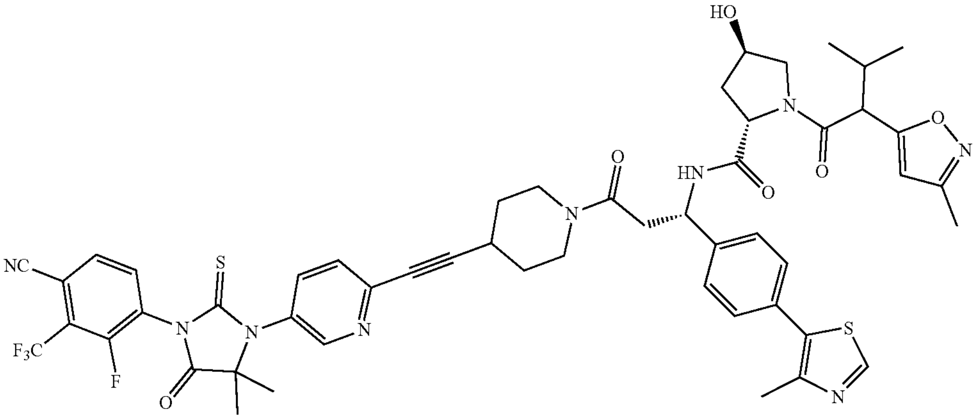 [SMILES: Cc1cc(C(C(=O)N2C[C@H](O)C[C@H]2C(=O)N[C@@H](CC(=O)N2CCC(C#Cc3ccc(N4C(=S)N(c5ccc(C#N)c(C(F)(F)F)c5F)C(=O)C4(C)C)cn3)CC2)c2ccc(-c3scnc3C)cc2)C(C)C)on1] |
| A174 | 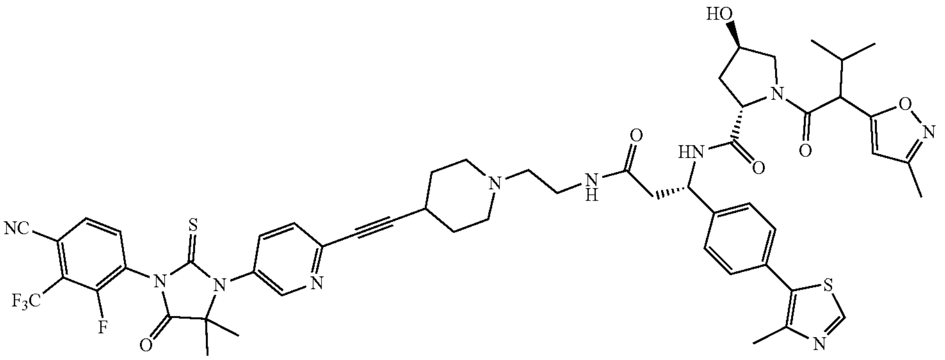 [SMILES: Cc1cc(C(C(=O)N2C[C@H](O)C[C@H]2C(=O)N[C@@H](CC(=O)NCCN2CCC(C#Cc3ccc(N4C(=S)N(c5ccc(C#N)c(C(F)(F)F)c5F)C(=O)C4(C)C)cn3)CC2)c2ccc(-c3scnc3C)cc2)C(C)C)on1] |

-continued
| Compound number | Compound structure |
| --- | --- |
| A175 | 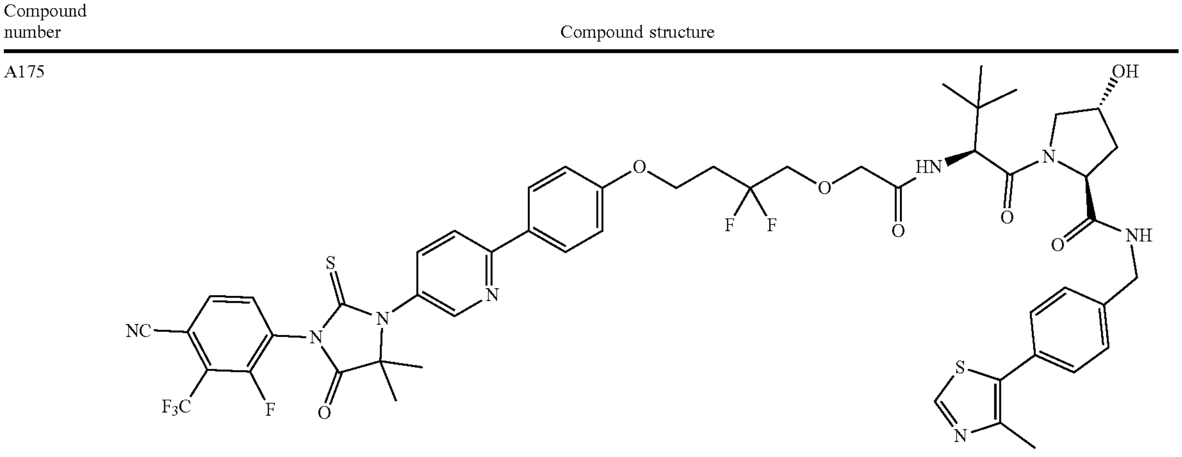 |
| A176 | 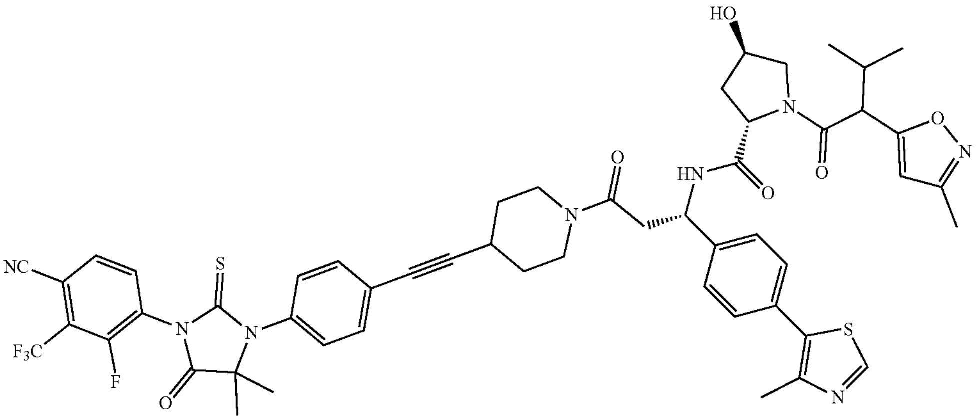 [SMILES: Cc1cc(C(C(=O)N2C[C@H](O)C[C@H]2C(=O)N[C@@H](CC(=O)N2CCC(C#Cc3ccc(N4C(=S)N(c5ccc(C#N)c(C(F)(F)F)c5F)C(=O)C4(C)C)cc3)CC2)c2ccc(-c3scnc3C)cc2)C(C)C)on1] |
| A177 | 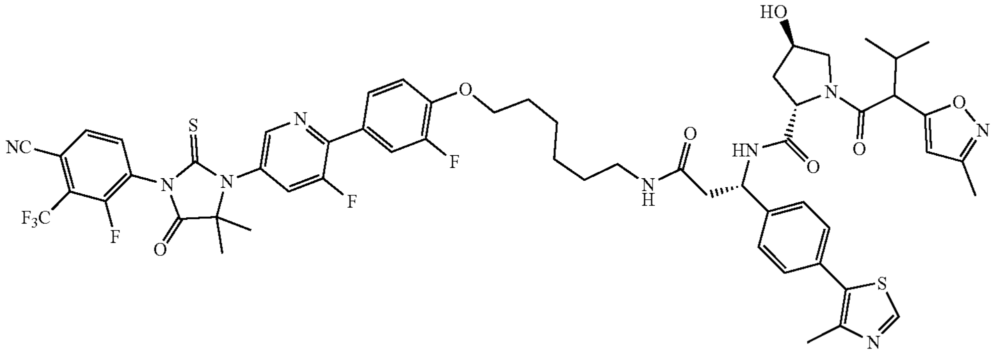 [SMILES: Cc1cc(C(C(=O)N2C[C@H](O)C[C@H]2C(=O)N[C@@H](CC(=O)NCCCCCCOc2ccc(-c3ncc(N4C(=S)N(c5ccc(C#N)c(C(F)(F)F)c5F)C(=O)C4(C)C)cc3F)cc2F)c2ccc(-c3scnc3C)cc2)C(C)C)on1] |
| A178 | 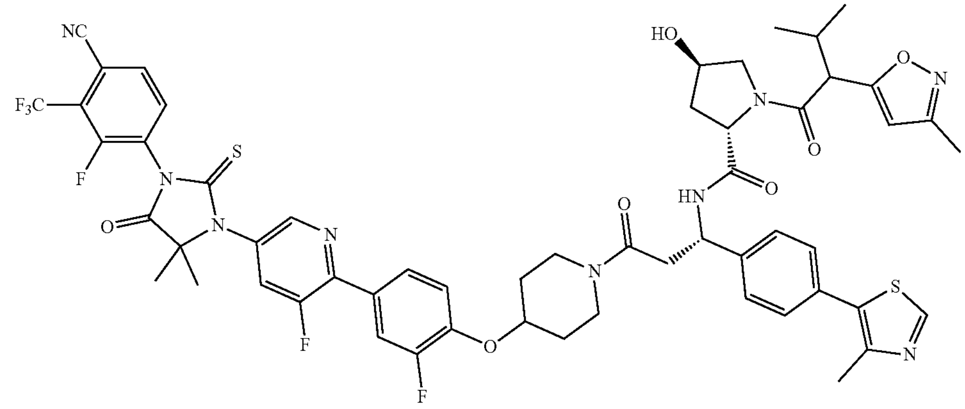 [SMILES: Cc1cc(C(C(=O)N2C[C@H](O)C[C@H]2C(=O)N[C@@H](CC(=O)N2CCC(Oc3ccc(-c4ncc(N5C(=S)N(c6ccc(C#N)c(C(F)(F)F)c6F)C(=O)C5(C)C)cc4F)cc3F)CC2)c2ccc(-c3scnc3C)cc2)C(C)C)on1] |

-continued
| Compound number | Compound structure |
|---|---|
| A179 | 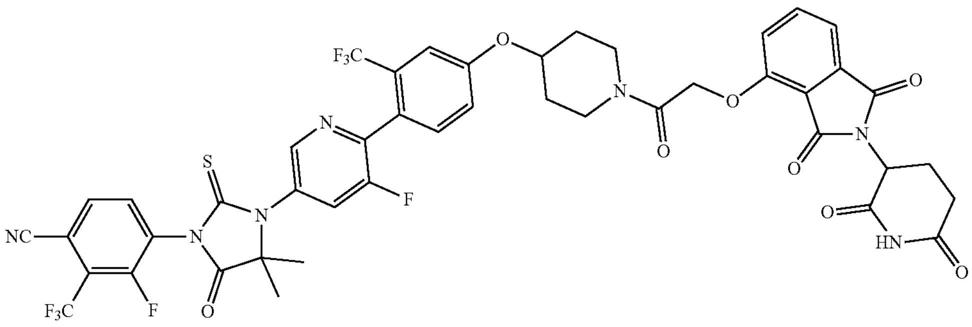 [SMILES: CC1(C)C(=O)N(c2ccc(C#N)c(C(F)(F)F)c2F)C(=S)N1c1cnc(-c2ccc(OC3CCN(C(=O)COc4cccc5c4C(=O)N(C4CCC(=O)NC4=O)C5=O)CC3)cc2C(F)(F)F)c(F)c1] |
| A180 | 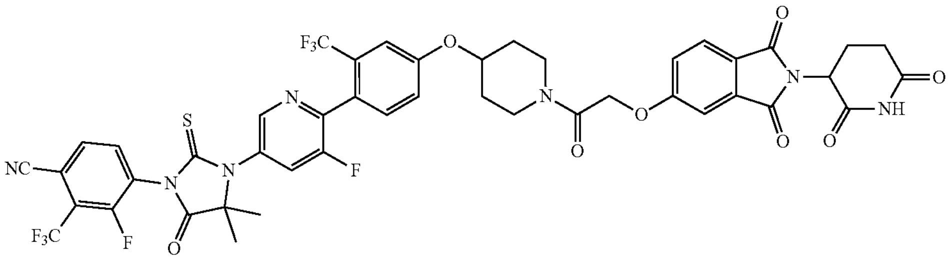 [SMILES: CC1(C)C(=O)N(c2ccc(C#N)c(C(F)(F)F)c2F)C(=S)N1c1cnc(-c2ccc(OC3CCN(C(=O)COc4ccc5c(c4)C(=O)N(C4CCC(=O)NC4=O)C5=O)CC3)cc2C(F)(F)F)c(F)c1] |
| A181 | 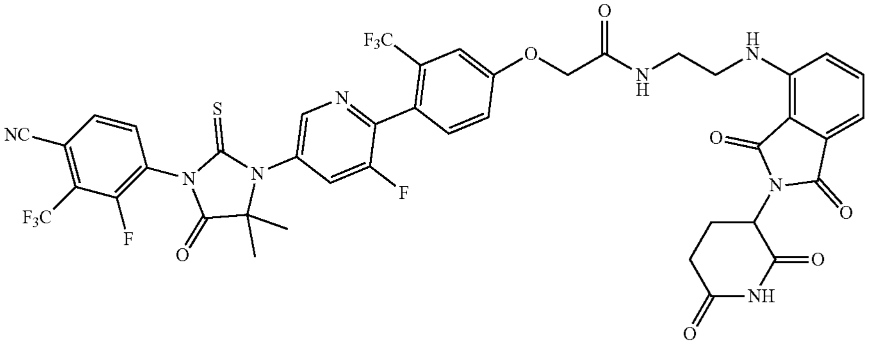 [SMILES: CC1(C)C(=O)N(c2ccc(C#N)c(C(F)(F)F)c2F)C(=S)N1c1cnc(-c2ccc(OCC(=O)NCCNc3cccc4c3C(=O)N(C3CCC(=O)NC3=O)C4=O)cc2C(F)(F)F)c(F)c1] |
| A182 | 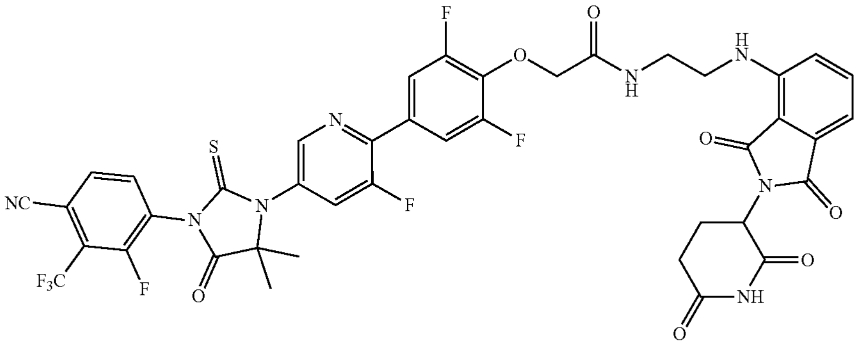 [SMILES: CC1(C)C(=O)N(c2ccc(C#N)c(C(F)(F)F)c2F)C(=S)N1c1cnc(-c2cc(F)c(OCC(=O)NCCNc3cccc4c3C(=O)N(C3CCC(=O)NC3=O)C4=O)c(F)c2)c(F)c1] |

-continued
| Compound number | Compound structure |
|---|---|
| A183 | 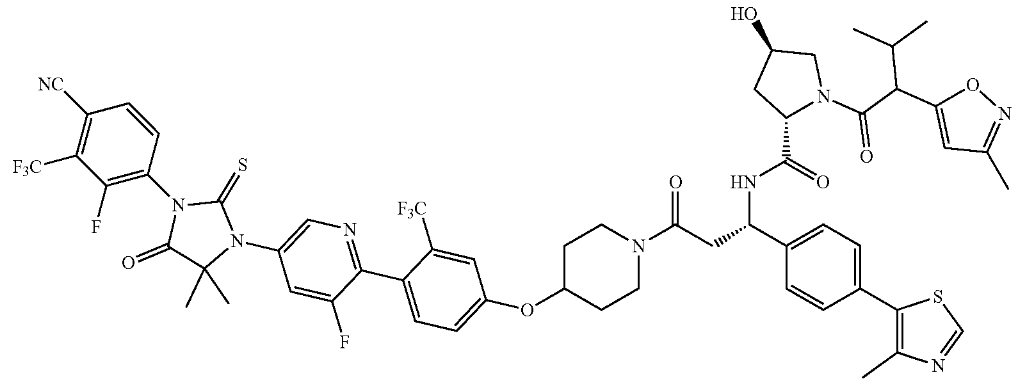 [SMILES: Cc1cc(C(C(=O)N2C[C@H](O)C[C@H]2C(=O)N[C@@H](CC(=O)N2CCC(Oc3ccc(-c4ncc(N5C(=S)N(c6ccc(C#N)c(C(F)(F)F)c6F)C(=O)C5(C)C)cc4F)c(C(F)(F)F)c3)CC2)c2ccc(-c3scnc3C)cc2)C(C)C)on1] |
| A184 | 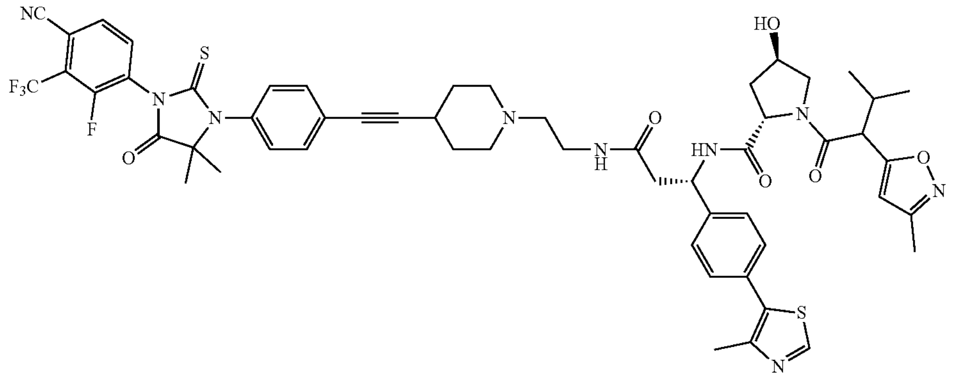 [SMILES: Cc1cc(C(C(=O)N2C[C@H](O)C[C@H]2C(=O)N[C@@H](CC(=O)NCCN2CCC(C#Cc3ccc(N4C(=S)N(c5ccc(C#N)c(C(F)(F)F)c5F)C(=O)C4(C)C)cc3)CC2)c2ccc(-c3scnc3C)cc2)C(C)C)on1] |
| A185 | 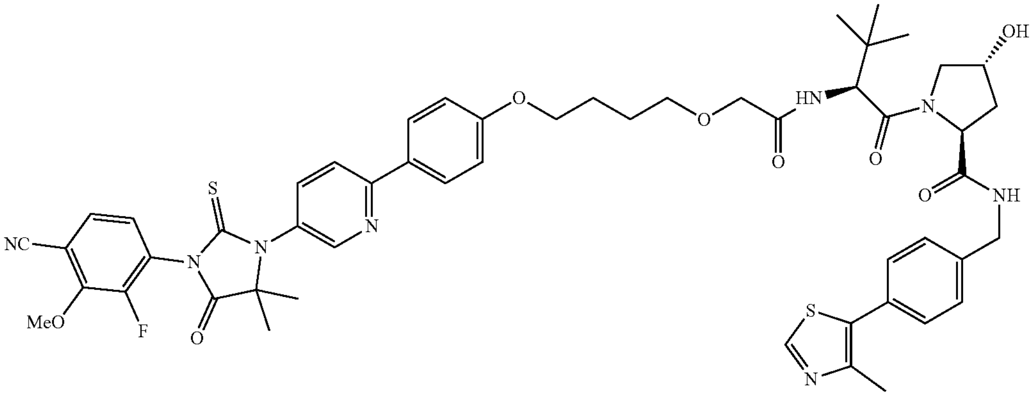 [SMILES: COc1c(C#N)ccc(N2C(=O)C(C)(C)N(c3ccc(-c4ccc(OCCCCOCC(=O)N[C@H](C(=O)N5C[C@H](O)C[C@H]5C(=O)NCc5ccc(-c6scnc6C)cc5)C(C)(C)C)cc4)nc3)C2=S)c1F] |
| A186 | 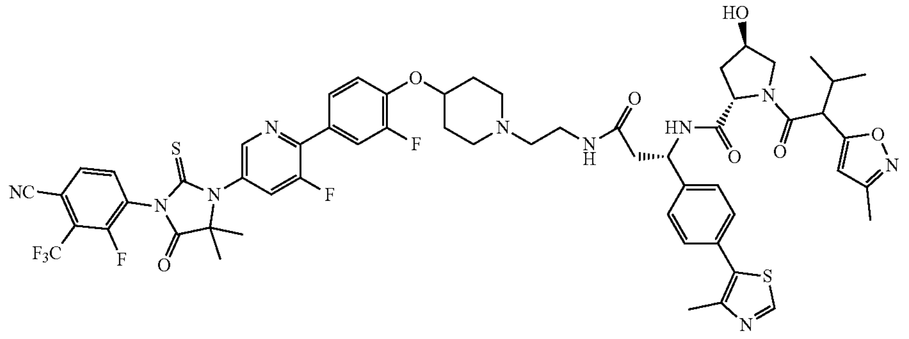 [SMILES: Cc1cc(C(C(=O)N2C[C@H](O)C[C@H]2C(=O)N[C@@H](CC(=O)NCCN2CCC(Oc3ccc(-c4ncc(N5C(=S)N(c6ccc(C#N)c(C(F)(F)F)c6F)C(=O)C5(C)C)cc4F)cc3F)CC2)c2ccc(-c3scnc3C)cc2)C(C)C)on1] |

-continued
| Compound number | Compound structure |
|---|---|
| A187 | 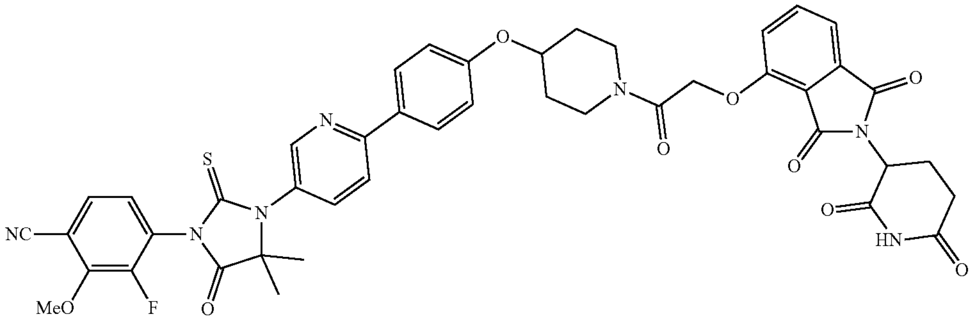 [SMILES: COc1c(C#N)ccc(N2C(=O)C(C)(C)N(c3ccc(-c4ccc(OC5CCN(C(=O)COc6cccc7c6C(=O)N(C6CCC(=O)NC6=O)C7=O)CC5)cc4)nc3)C2=S)c1F] |
| A188 | 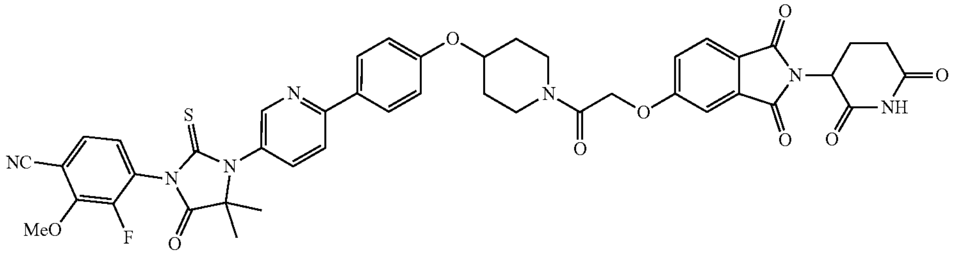 [SMILES: COc1c(C#N)ccc(N2C(=O)C(C)(C)N(c3ccc(-c4ccc(OC5CCN(C(=O)COc6ccc7c(c6)C(=O)N(C6CCC(=O)NC6=O)C7=O)CC5)cc4)nc3)C2=S)c1F] |
| A189 | 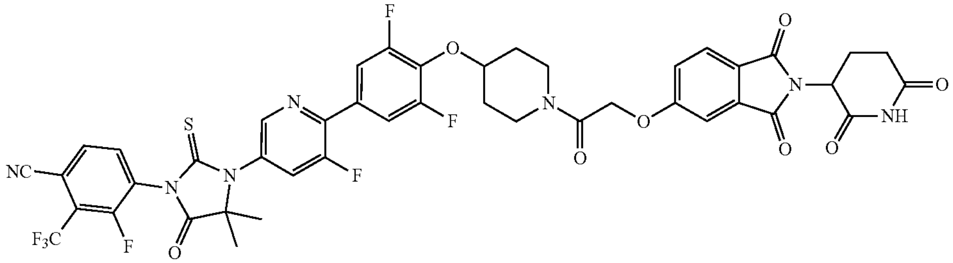 [SMILES: CC1(C)C(=O)N(c2ccc(C#N)c(C(F)(F)F)c2F)C(=S)N1c1cnc(-c2cc(F)c(OC3CCN(C(=O)COc4ccc5c(c4)C(=O)N(C4CCC(=O)NC4=O)C5=O)CC3)c(F)c2)c(F)c1] |
| A190 | 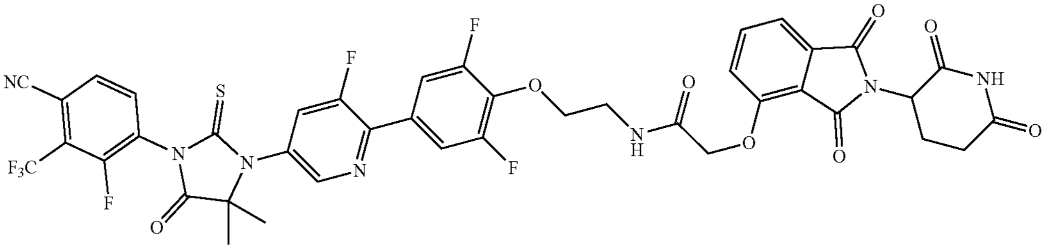 [SMILES: CC1(C)C(=O)N(c2ccc(C#N)c(C(F)(F)F)c2F)C(=S)N1c1cnc(-c2cc(F)c(OCCNC(=O)COc3cccc4c3C(=O)N(C3CCC(=O)NC3=O)C4=O)c(F)c2)c(F)c1] |
| A191 | 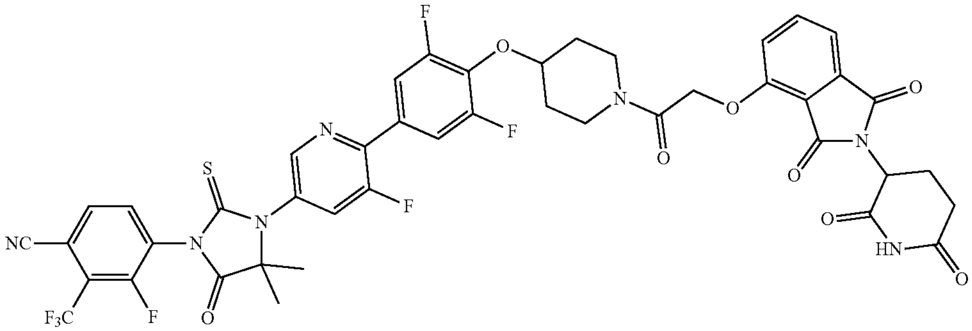 [SMILES: CC1(C)C(=O)N(c2ccc(C#N)c(C(F)(F)F)c2F)C(=S)N1c1cnc(-c2cc(F)c(OC3CCN(C(=O)COc4cccc5c4C(=O)N(C4CCC(=O)NC4=O)C5=O)CC3)c(F)c2)c(F)c1] |

-continued
| Compound number | Compound structure |
| --- | --- |
| A192 | 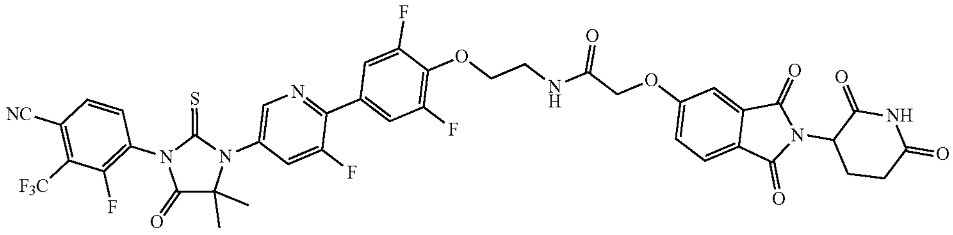 [SMILES: CC1(C)C(=O)N(c2ccc(C#N)c(C(F)(F)F)c2F)C(=S)N1c1cnc(-c2cc(F)c(OCCNC(=O)COc3ccc4c(c3)C(=O)N(C3CCC(=O)NC3=O)C4=O)c(F)c2)c(F)c1] |
| A193 | 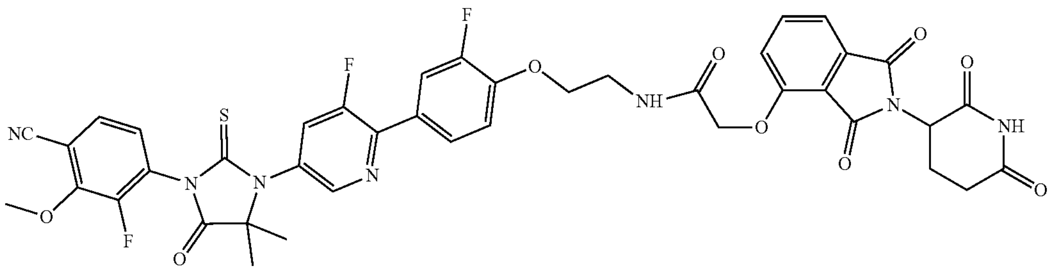 [SMILES: COc1c(C#N)ccc(N2C(=O)C(C)(C)N(c3cnc(-c4ccc(OCCNC(=O)COc5cccc6c5C(=O)N(C5CCC(=O)NC5=O)C6=O)c(F)c4)c(F)c3)C2=S)c1F] |
| A194 | 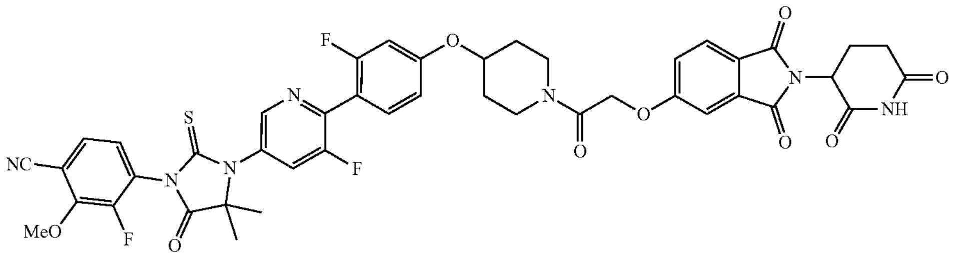 [SMILES: COc1c(C#N)ccc(N2C(=O)C(C)(C)N(c3cnc(-c4ccc(OC5CCN(C(=O)COc6ccc7c(c6)C(=O)N(C6CCC(=O)NC6=O)C7=O)CC5)cc4F)c(F)c3)C2=S)c1F] |
| A195 | 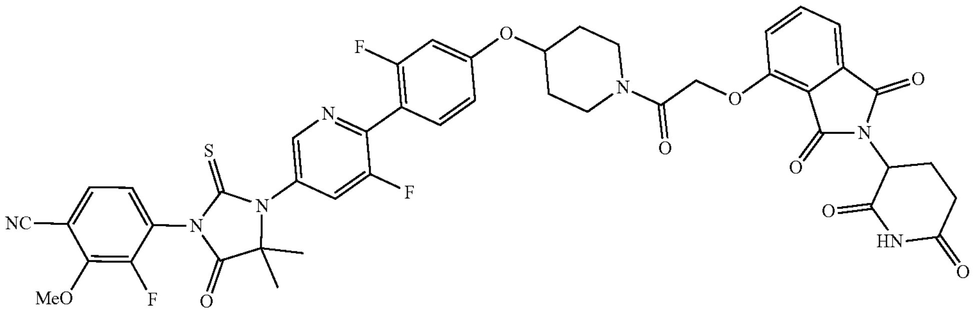 [SMILES: COc1c(C#N)ccc(N2C(=O)C(C)(C)N(c3cnc(-c4ccc(OC5CCN(C(=O)COc6cccc7c6C(=O)N(C6CCC(=O)NC6=O)C7=O)CC5)cc4F)c(F)c3)C2=S)c1F] |
| A196 | 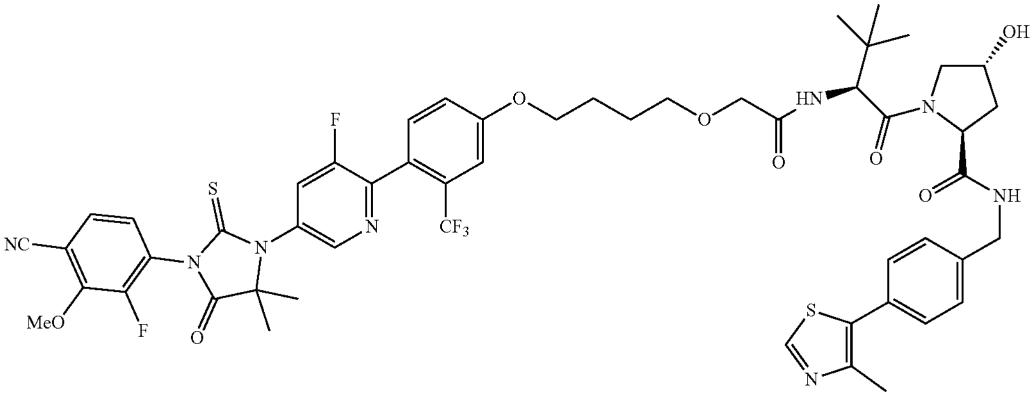 [SMILES: COc1c(C#N)ccc(N2C(=O)C(C)(C)N(c3cnc(-c4ccc(OCCCCOCC(=O)N[C@H](C(=O)N5C[C@H](O)C[C@H]5C(=O)NCc5ccc(-c6scnc6C)cc5)C(C)(C)C)cc4C(F)(F)F)c(F)c3)C2=S)c1F] |

-continued
| Compound number | Compound structure |
|---|---|
| A197 | 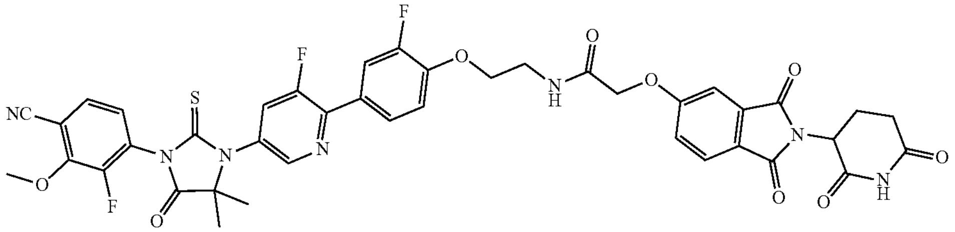 [SMILES: COc1c(C#N)ccc(N2C(=O)C(C)(C)N(c3cnc(-c4ccc(OCCNC(=O)COc5ccc6c(c5)C(=O)N(C5CCC(=O)NC5=O)C6=O)c(F)c4)c(F)c3)C2=S)c1F] |
| A198 | 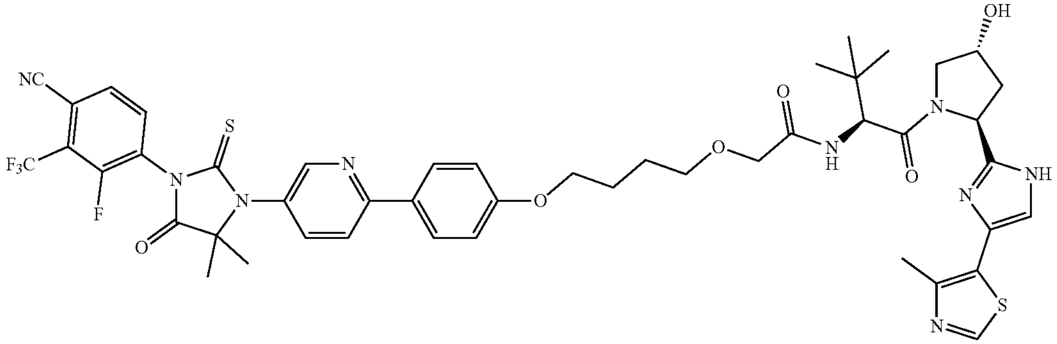 [SMILES: Cc1ncsc1-c1c[nH]c([C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2)C(C)(C)C)n1] |
| A199 | 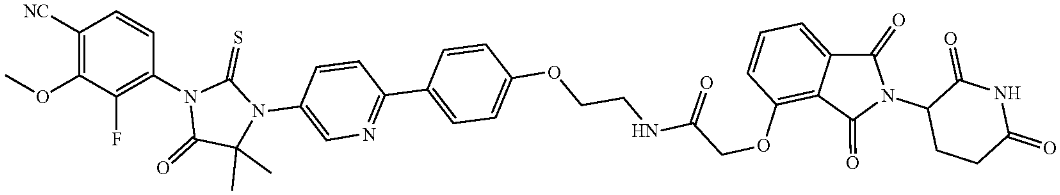 [SMILES: COc1c(C#N)ccc(N2C(=O)C(C)(C)N(c3ccc(-c4ccc(OCCNC(=O)COc5cccc6c5C(=O)N(C5CCC(=O)NC5=O)C6=O)cc4)nc3)C2=S)c1F] |
| A200 | 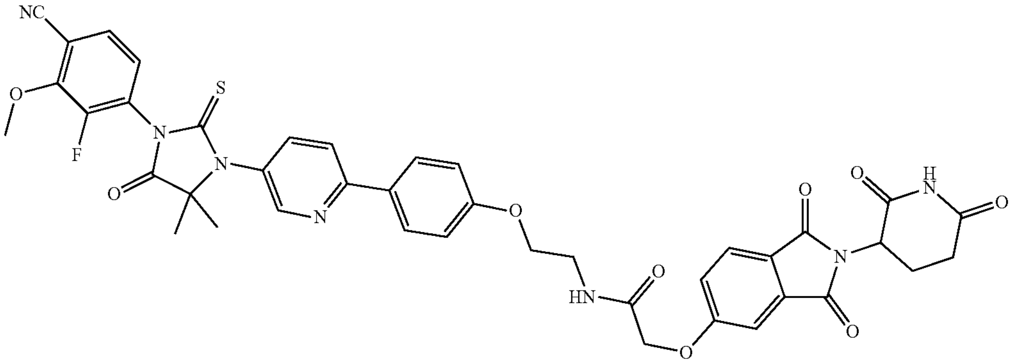 [SMILES: COc1c(C#N)ccc(N2C(=O)C(C)(C)N(c3ccc(-c4ccc(OCCNC(=O)COc5ccc6c(c5)C(=O)N(C5CCC(=O)NC5=O)C6=O)cc4)nc3)C2=S)c1F] |
| A201 | 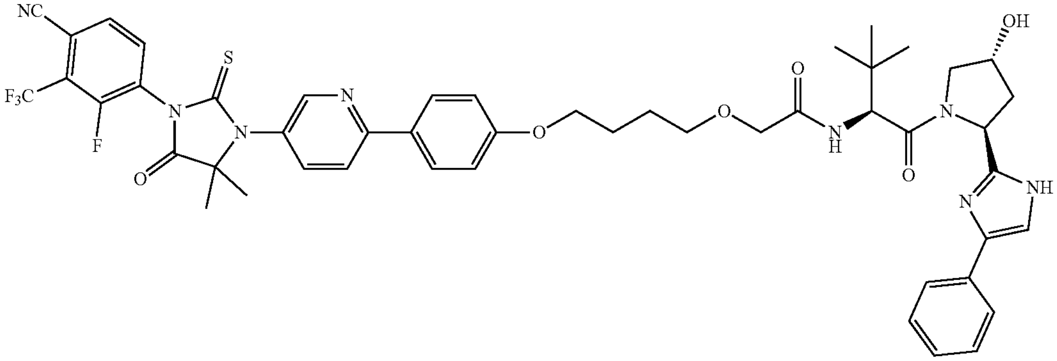 [SMILES: CC(C)(C)[C@H](NC(=O)COCCCCOc1ccc(-c2ccc(N3C(=S)N(c4ccc(C#N)c(C(F)(F)F)c4F)C(=O)C3(C)C)cn2)cc1)C(=O)N1C[C@H](O)C[C@H]1c1nc(-c2ccccc2)c[nH]1] |

-continued
| Compound number | Compound structure |
| --- | --- |
| A202 | 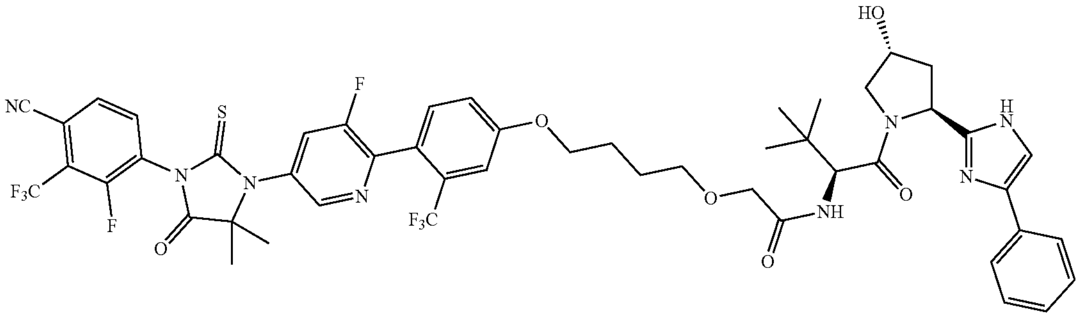 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)c(C(F)(F)F)c1)C(=O)N1C[C@H](O)C[C@H]1c1nc(-c2ccccc2)c[nH]1] |
| A203 | 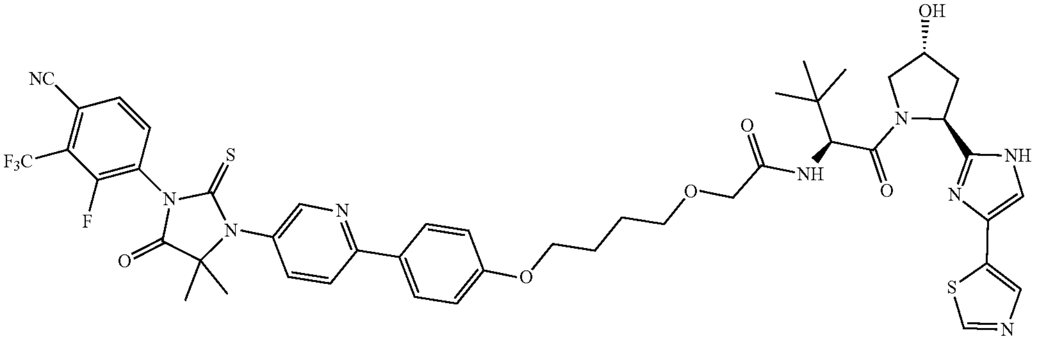 [SMILES: CC(C)(C)[C@H](NC(=O)COCCCCOc1ccc(-c2ccc(N3C(=S)N(c4ccc(C#N)c(C(F)(F)F)c4F)C(=O)C3(C)C)cn2)cc1)C(=O)N1C[C@H](O)C[C@H]1c1nc(-c2cncs2)c[nH]1] |
| A204 | 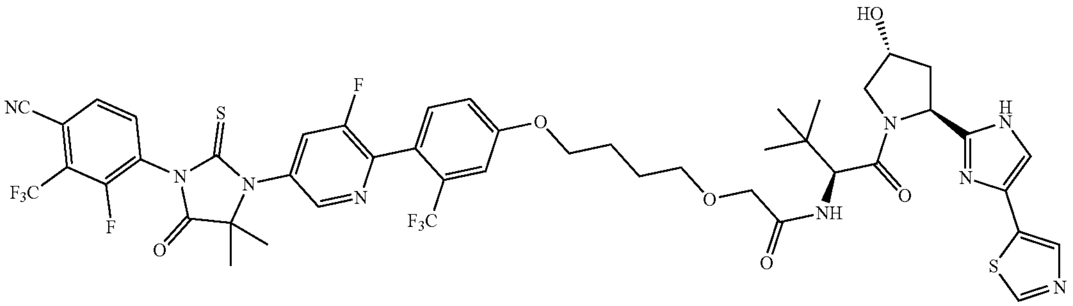 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)c(C(F)(F)F)c1)C(=O)N1C[C@H](O)C[C@H]1c1nc(-c2cncs2)c[nH]1] |
| A205 | 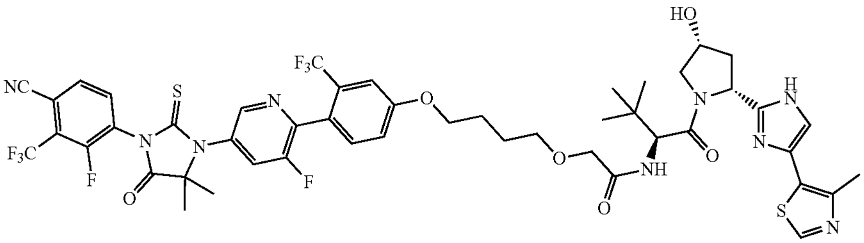 [SMILES: Cc1ncsc1-c1c[nH]c([C@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)c(C(F)(F)F)c2)C(C)(C)C)n1] |
| A206 | 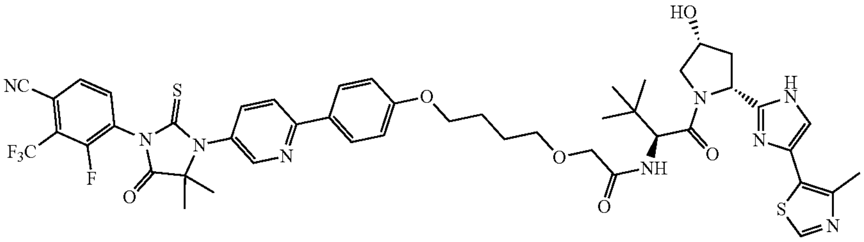 [SMILES: Cc1ncsc1-c1c[nH]c([C@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2)C(C)(C)C)n1] |

-continued
| Compound number | Compound structure |
|---|---|
| A207 | 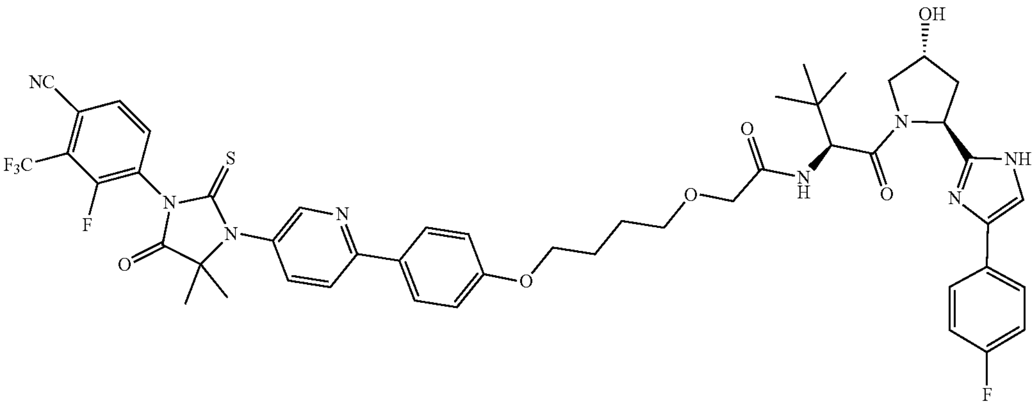 [SMILES: CC(C)(C)[C@H](NC(=O)COCCCCOc1ccc(-c2ccc(N3C(=S)N(c4ccc(C#N)c(C(F)(F)F)c4F)C(=O)C3(C)C)cn2)cc1)C(=O)N1C[C@H](O)C[C@H]1c1nc(-c2ccc(F)cc2)c[nH]1] |
| A208 | 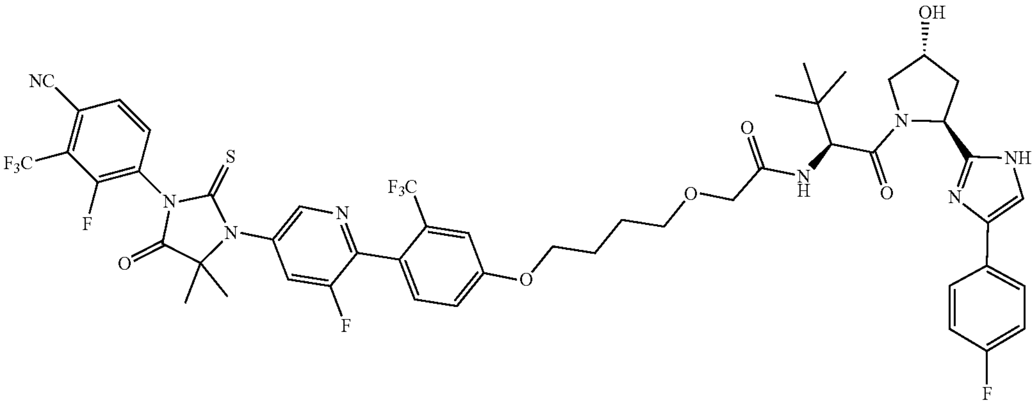 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)c(C(F)(F)F)c1)C(=O)N1C[C@H](O)C[C@H]1c1nc(-c2ccc(F)cc2)c[nH]1] |
| A209 | 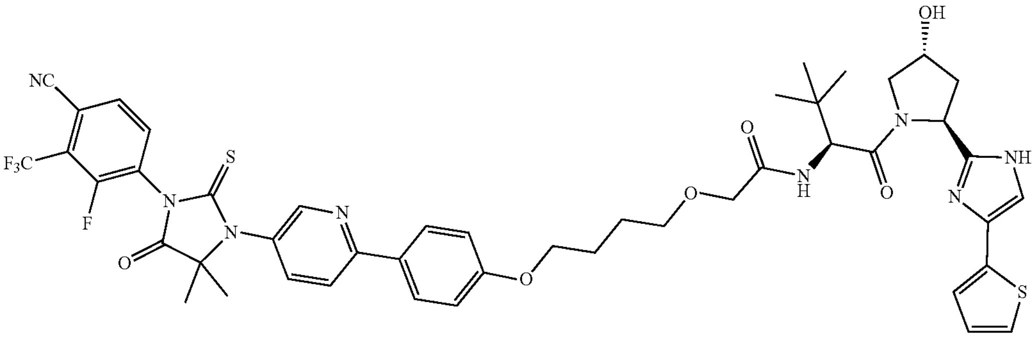 [SMILES: CC(C)(C)[C@H](NC(=O)COCCCCOc1ccc(-c2ccc(N3C(=S)N(c4ccc(C#N)c(C(F)(F)F)c4F)C(=O)C3(C)C)cn2)cc1)C(=O)N1C[C@H](O)C[C@H]1c1nc(-c2cccs2)c[nH]1] |
| A210 | 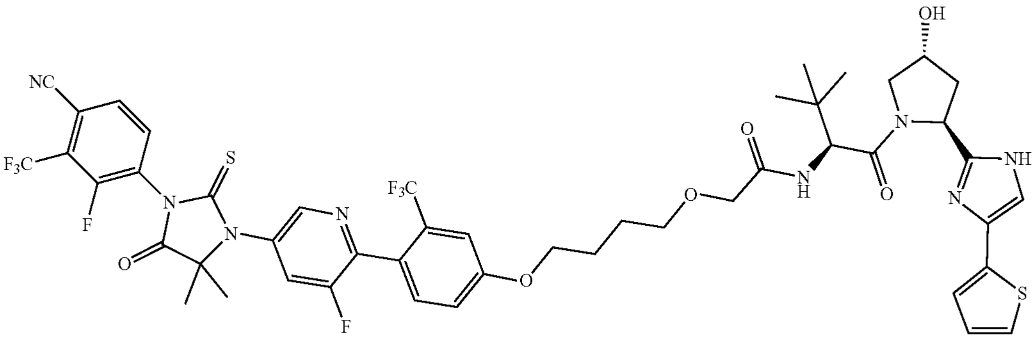 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)c(C(F)(F)F)c1)C(=O)N1C[C@H](O)C[C@H]1c1nc(-c2cccs2)c[nH]1] |

-continued
| Compound number | Compound structure |
|---|---|
| A211 | 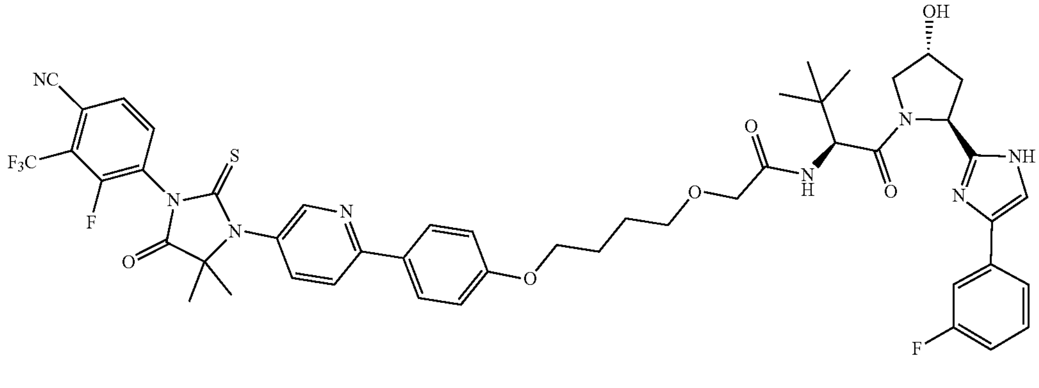 [SMILES: CC(C)(C)[C@H](NC(=O)COCCCCOc1ccc(-c2ccc(N3C(=S)N(c4ccc(C#N)c(C(F)(F)F)c4F)C(=O)C3(C)C)cn2)cc1)C(=O)N1C[C@H](O)C[C@H]1c1nc(-c2cccc(F)c2)c[nH]1] |
| A212 | 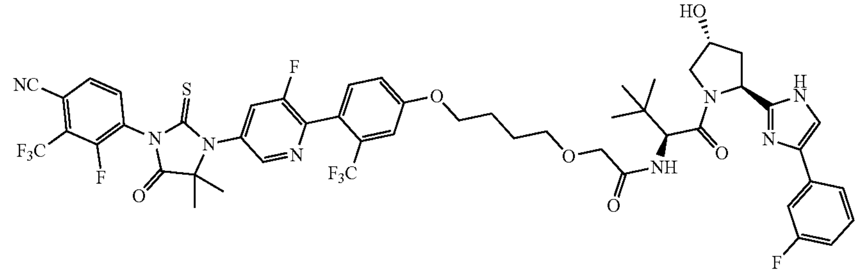 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)c(C(F)(F)F)c1)C(=O)N1C[C@H](O)C[C@H]1c1nc(-c2cccc(F)c2)c[nH]1] |
| A213 | 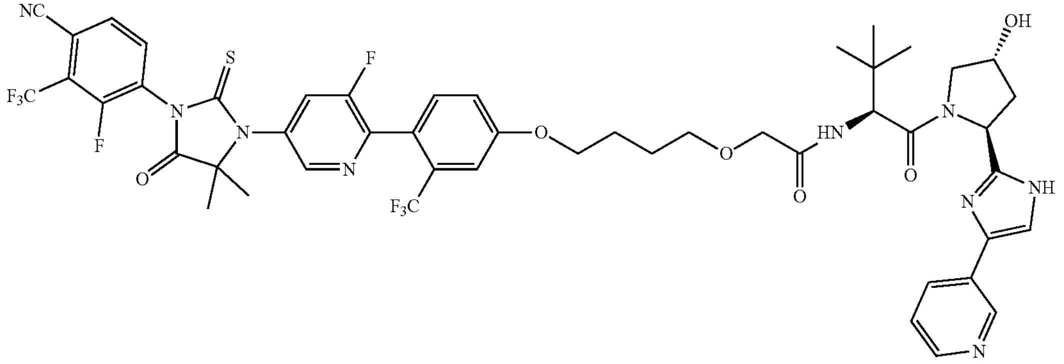 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)c(C(F)(F)F)c1)C(=O)N1C[C@H](O)C[C@H]1c1nc(-c2cccnc2)c[nH]1] |
| A214 | 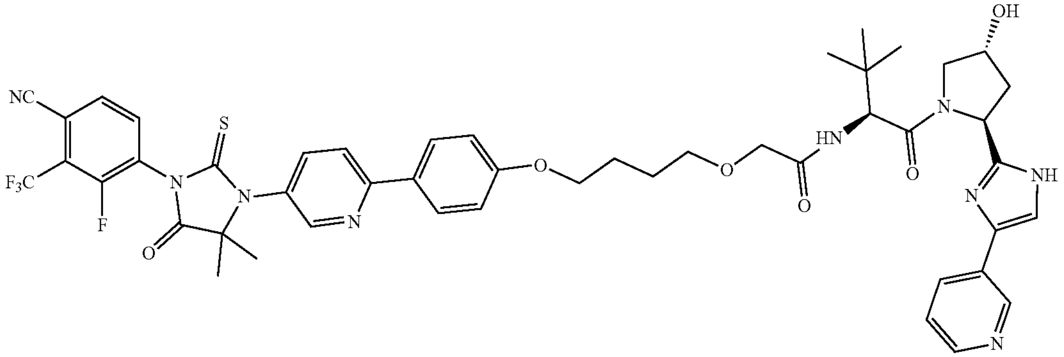 [SMILES: CC(C)(C)[C@H](NC(=O)COCCCCOc1ccc(-c2ccc(N3C(=S)N(c4ccc(C#N)c(C(F)(F)F)c4F)C(=O)C3(C)C)cn2)cc1)C(=O)N1C[C@H](O)C[C@H]1c1nc(-c2cccnc2)c[nH]1] |

-continued
| Compound number | Compound structure |
| --- | --- |
| A215 | 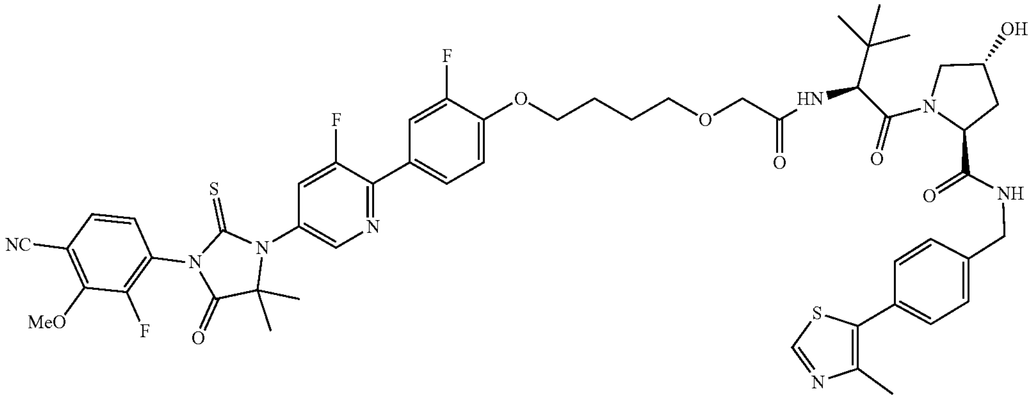 [SMILES: COc1c(C#N)ccc(N2C(=O)C(C)(C)N(c3cnc(-c4ccc(OCCCCOCC(=O)N[C@H](C(=O)N5C[C@H](O)C[C@H]5C(=O)NCc5ccc(-c6scnc6C)cc5)C(C)(C)C)c(F)c4)c(F)c3)C2=S)c1F] |
| A216 | 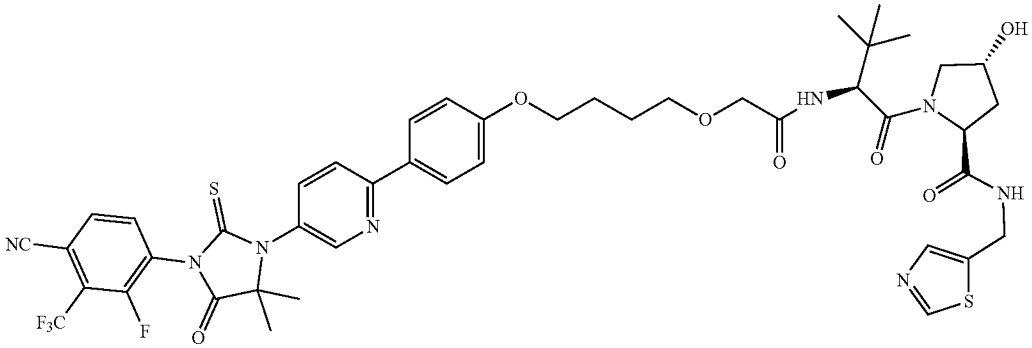 [SMILES: CC(C)(C)[C@H](NC(=O)COCCCCOc1ccc(-c2ccc(N3C(=S)N(c4ccc(C#N)c(C(F)(F)F)c4F)C(=O)C3(C)C)cn2)cc1)C(=O)N1C[C@H](O)C[C@H]1C(=O)NCc1cncs1] |
| A217 | 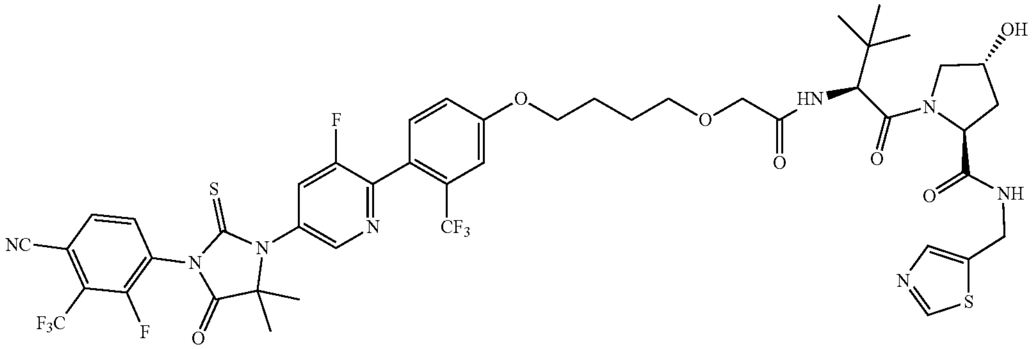 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)c(C(F)(F)F)c1)C(=O)N1C[C@H](O)C[C@H]1C(=O)NCc1cncs1] |
| A218 | 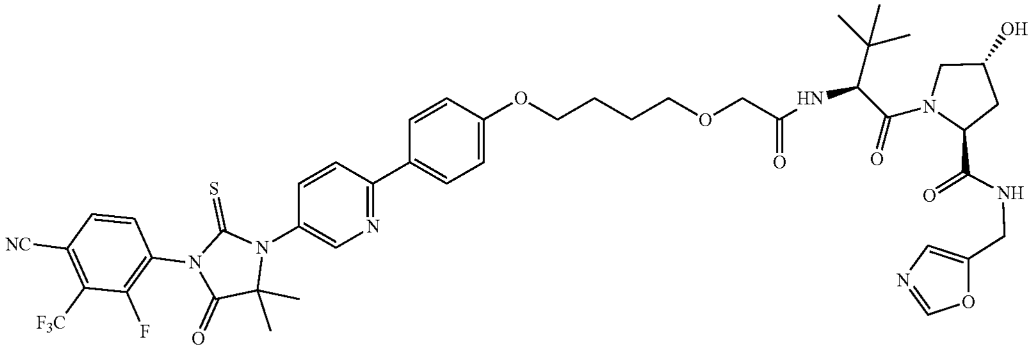 |

-continued
| Compound number | Compound structure |
| --- | --- |
| A219 | 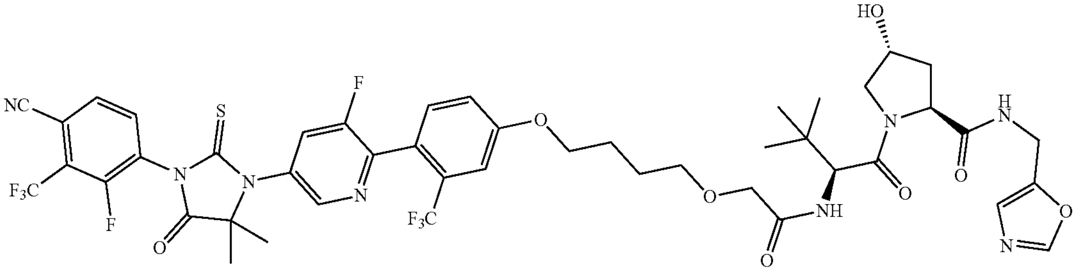 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)c(C(F)(F)F)c1)C(=O)N1C[C@H](O)C[C@H]1C(=O)NCc1cnco1] |
| A220 | 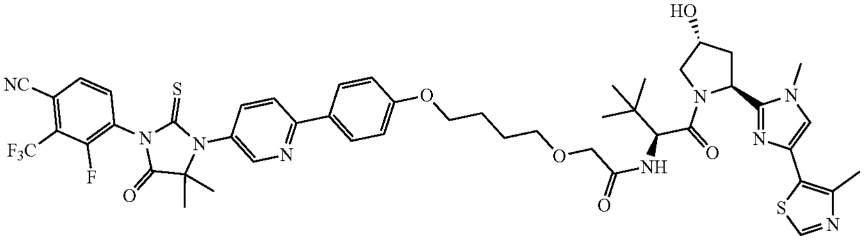 [SMILES: Cc1ncsc1-c1cn(C)c([C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2)C(C)(C)C)n1] |
| A221 | 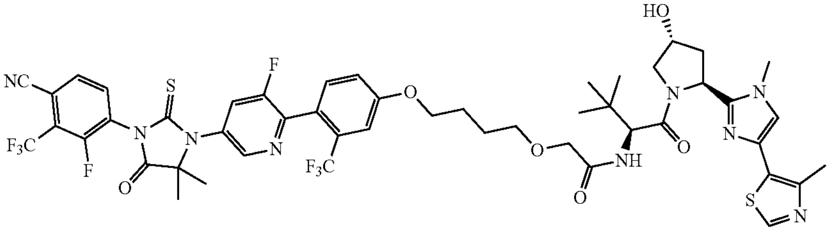 [SMILES: Cc1ncsc1-c1cn(C)c([C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)c(C(F)(F)F)c2)C(C)(C)C)n1] |
| A222 | 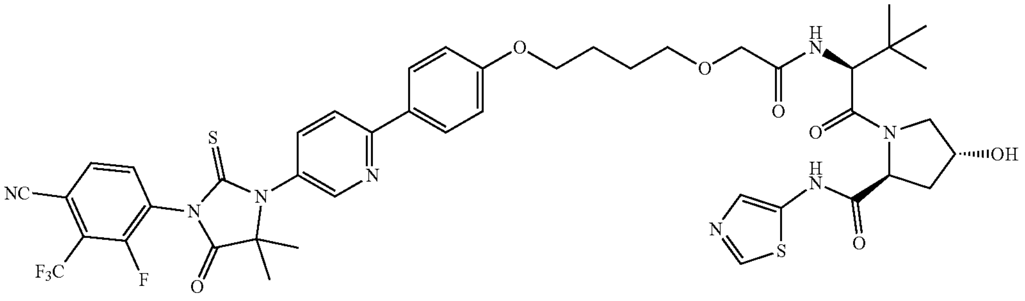 [SMILES: CC(C)(C)[C@H](NC(=O)COCCCCOc1ccc(-c2ccc(N3C(=S)N(c4ccc(C#N)c(C(F)(F)F)c4F)C(=O)C3(C)C)cn2)cc1)C(=O)N1C[C@H](O)C[C@H]1C(=O)Nc1cncs1] |
| A223 | 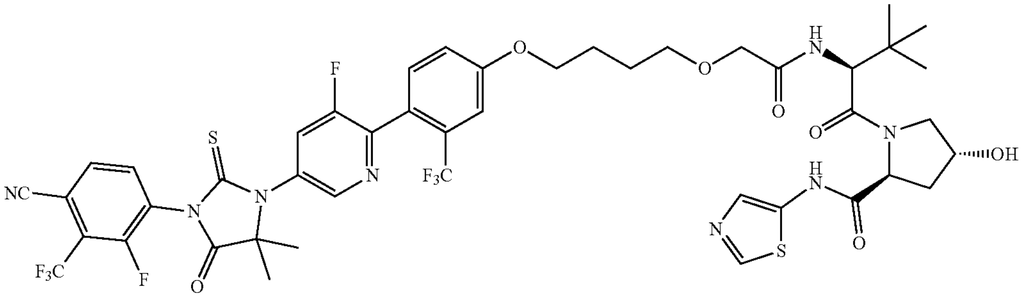 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)c(C(F)(F)F)c1)C(=O)N1C[C@H](O)C[C@H]1C(=O)Nc1cncs1] |

-continued
| Compound number | Compound structure |
| --- | --- |
| A224 | 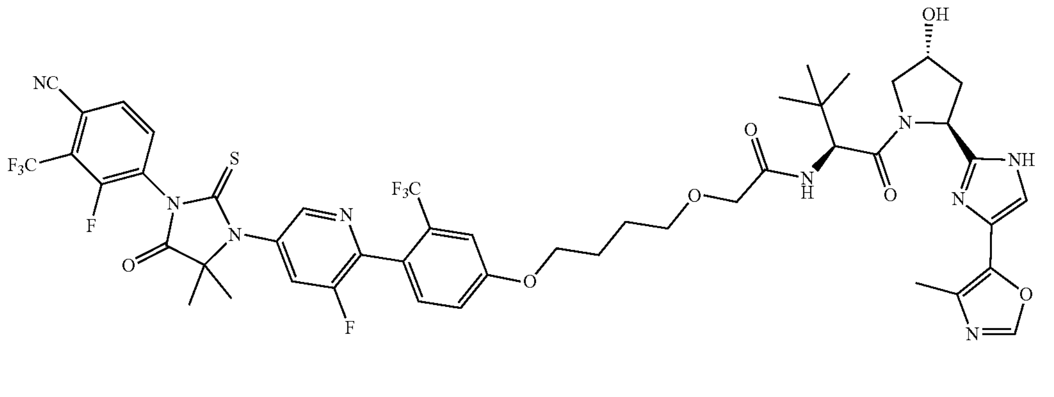 [SMILES: Cc1ncoc1-c1c[nH]c([C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)c(C(F)(F)F)c2)C(C)(C)C)n1] |
| A225 | 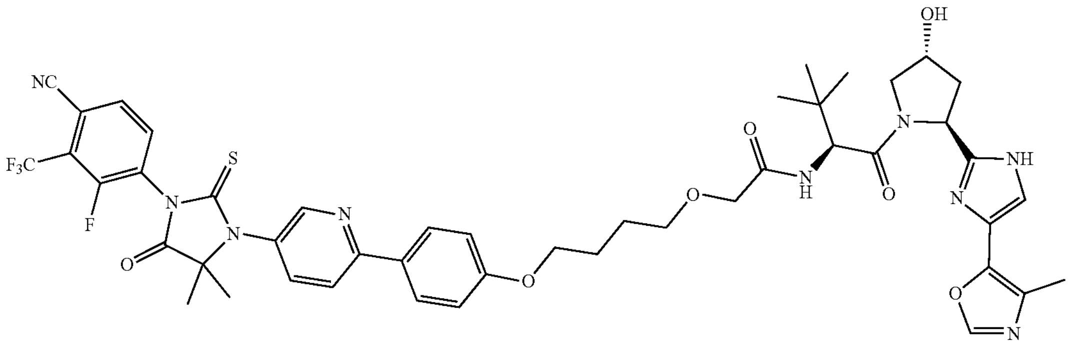 [SMILES: Cc1ncoc1-c1c[nH]c([C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2)C(C)(C)C)n1] |
| A226 | 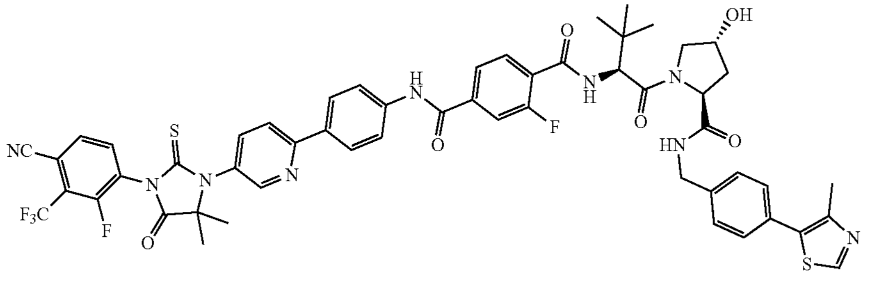 [SMILES: Cc1ncsc1-c1ccc(CNC(=O)[C@@H]2C[C@@H](O)CN2C(=O)[C@@H](NC(=O)c2ccc(C(=O)Nc3ccc(-c4ccc(N5C(=S)N(c6ccc(C#N)c(C(F)(F)F)c6F)C(=O)C5(C)C)cn4)cc3)cc2F)C(C)(C)C)cc1] |
| A227 | 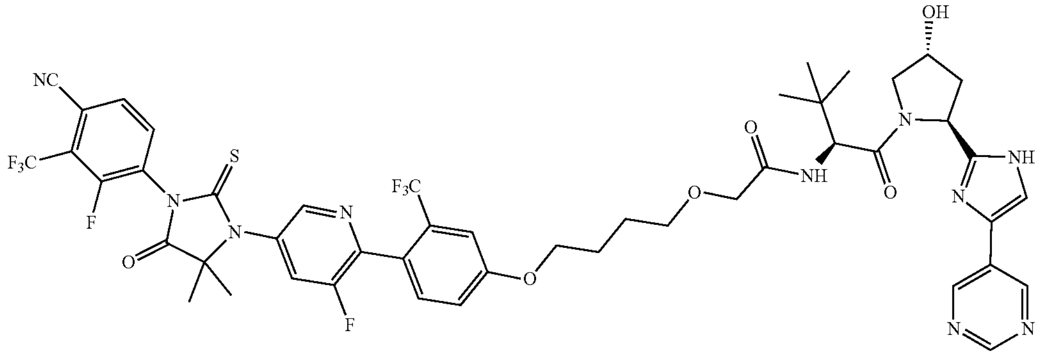 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)c(C(F)(F)F)c1)C(=O)N1C[C@H](O)C[C@H]1c1nc(-c2cncnc2)c[nH]1] |

-continued
| Compound number | Compound structure |
|---|---|
| A228 | 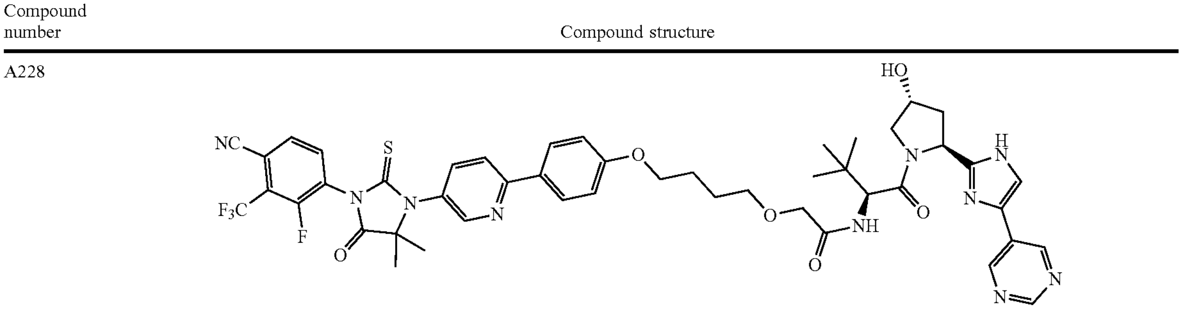 |
| A229 | 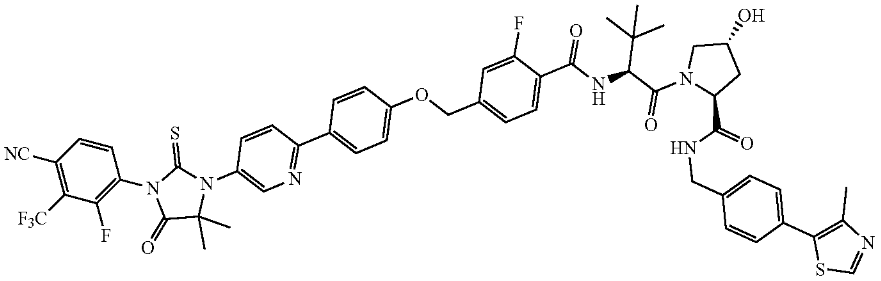 [SMILES: Cc1ncsc1-c1ccc(CNC(=O)[C@@H]2C[C@@H](O)CN2C(=O)[C@@H](NC(=O)c2ccc(COc3ccc(-c4ccc(N5C(=S)N(c6ccc(C#N)c(C(F)(F)F)c6F)C(=O)C5(C)C)cn4)cc3)cc2F)C(C)(C)C)cc1] |
| A230 | 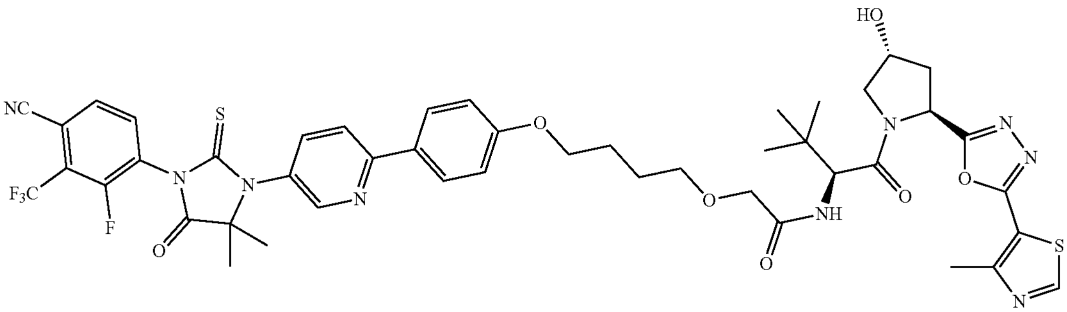 [SMILES: Cc1ncsc1-c1nnc([C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2)C(C)(C)C)o1] |
| A231 | 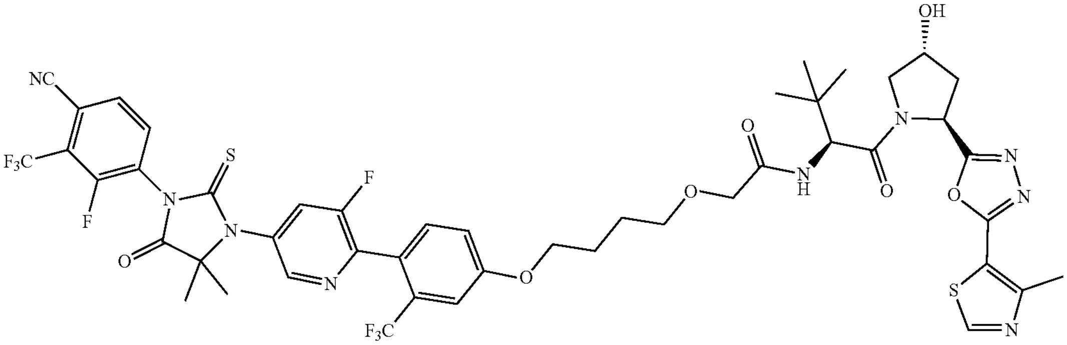 [SMILES: Cc1ncsc1-c1nnc([C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)c(C(F)(F)F)c2)C(C)(C)C)o1] |
| A232 | 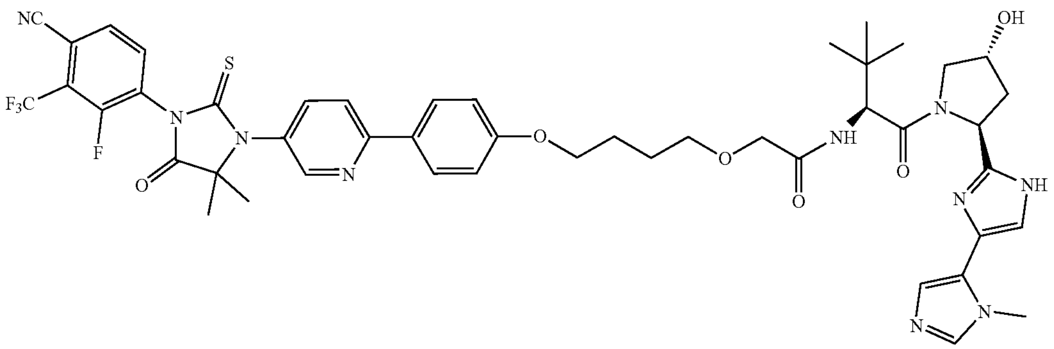 [SMILES: Cn1cncc1-c1c[nH]c([C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2)C(C)(C)C)n1] |

-continued
| Compound number | Compound structure |
| --- | --- |
| A233 | 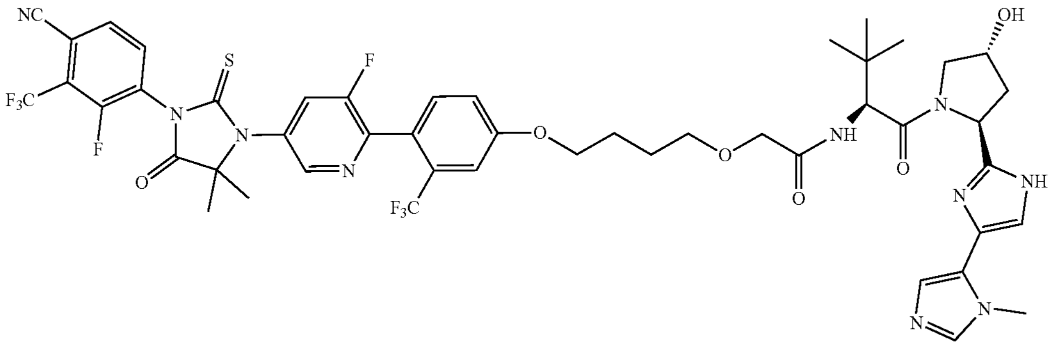 [SMILES: Cn1cncc1-c1c[nH]c([C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)c(C(F)(F)F)c2)C(C)(C)C)n1] |
| A234 | 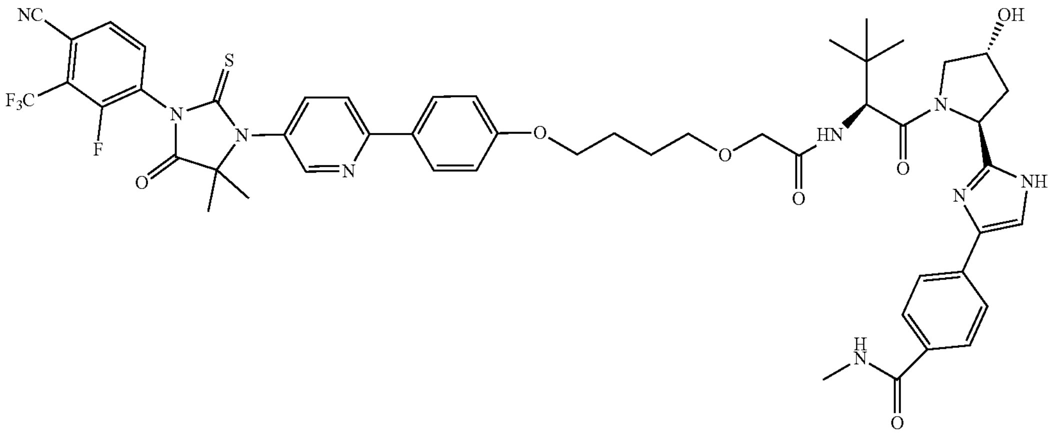 [SMILES: CNC(=O)c1ccc(-c2c[nH]c([C@@H]3C[C@@H](O)CN3C(=O)[C@@H](NC(=O)COCCCCOc3ccc(-c4ccc(N5C(=S)N(c6ccc(C#N)c(C(F)(F)F)c6F)C(=O)C5(C)C)cn4)cc3)C(C)(C)C)n2)cc1] |
| A235 | 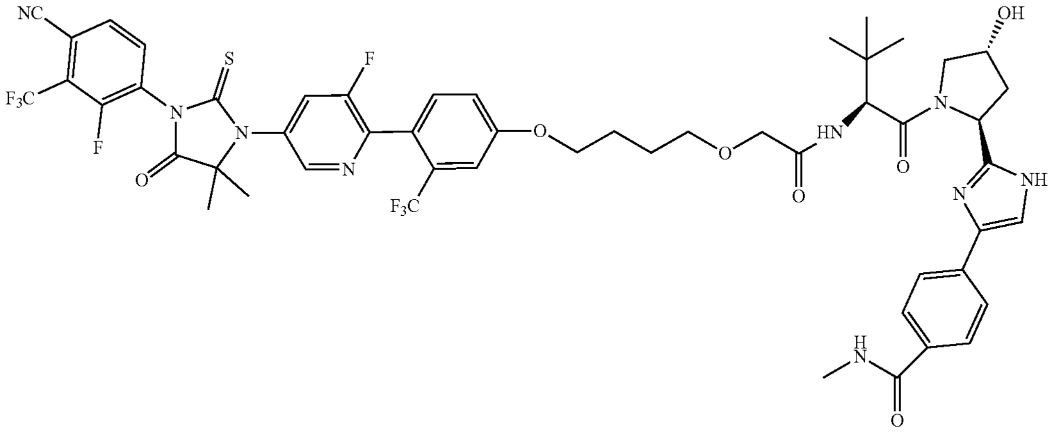 [SMILES: CNC(=O)c1ccc(-c2c[nH]c([C@@H]3C[C@@H](O)CN3C(=O)[C@@H](NC(=O)COCCCCOc3ccc(-c4ncc(N5C(=S)N(c6ccc(C#N)c(C(F)(F)F)c6F)C(=O)C5(C)C)cc4F)c(C(F)(F)F)c3)C(C)(C)C)n2)cc1] |
| A236 | 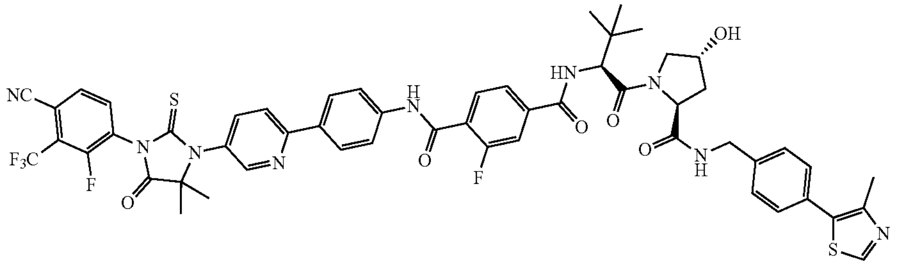 [SMILES: Cc1ncsc1-c1ccc(CNC(=O)[C@@H]2C[C@@H](O)CN2C(=O)[C@@H](NC(=O)c2ccc(C(=O)Nc3ccc(-c4ccc(N5C(=S)N(c6ccc(C#N)c(C(F)(F)F)c6F)C(=O)C5(C)C)cn4)cc3)c(F)c2)C(C)(C)C)cc1] |

-continued
| Compound number | Compound structure |
| --- | --- |
| A237 | 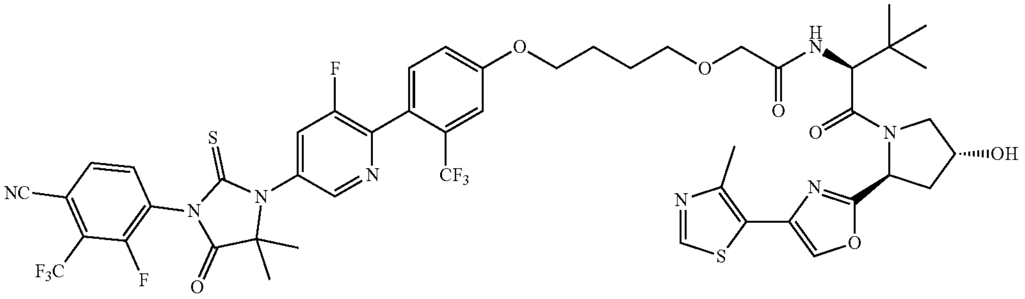 [SMILES: Cc1ncsc1-c1coc([C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)c(C(F)(F)F)c2)C(C)(C)C)n1] |
| A238 | 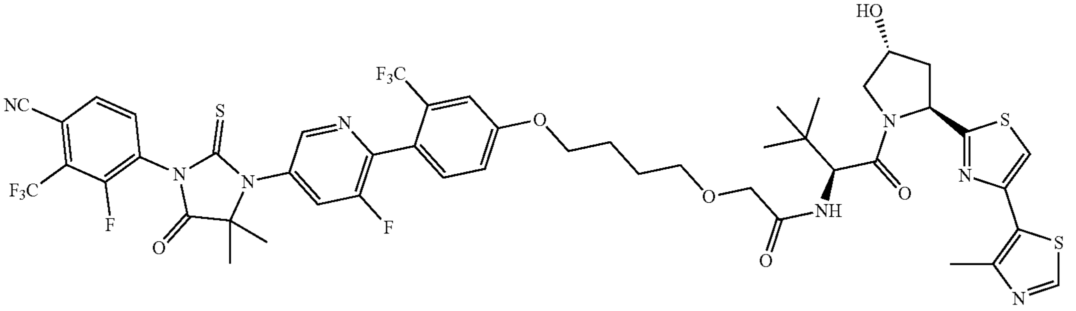 [SMILES: Cc1ncsc1-c1csc([C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)c(C(F)(F)F)c2)C(C)(C)C)n1] |
| A239 | 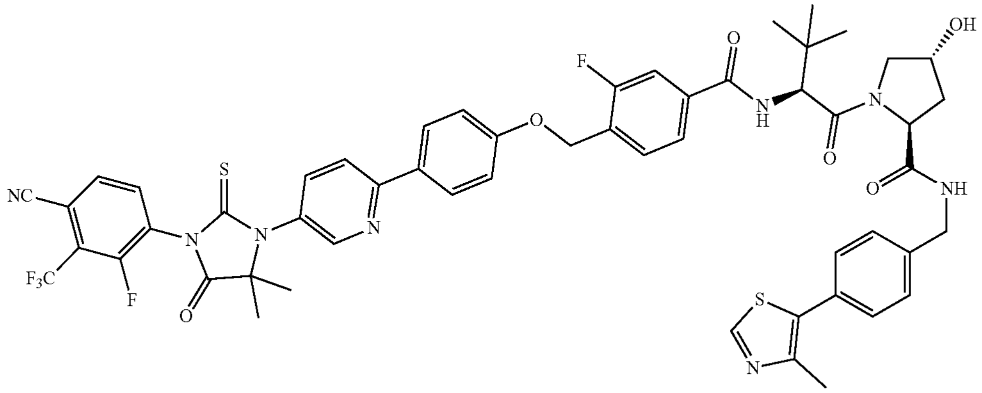 [SMILES: Cc1ncsc1-c1ccc(CNC(=O)[C@@H]2C[C@@H](O)CN2C(=O)[C@@H](NC(=O)c2ccc(COc3ccc(-c4ccc(N5C(=S)N(c6ccc(C#N)c(C(F)(F)F)c6F)C(=O)C5(C)C)cn4)cc3)c(F)c2)C(C)(C)C)cc1] |
| A240 | 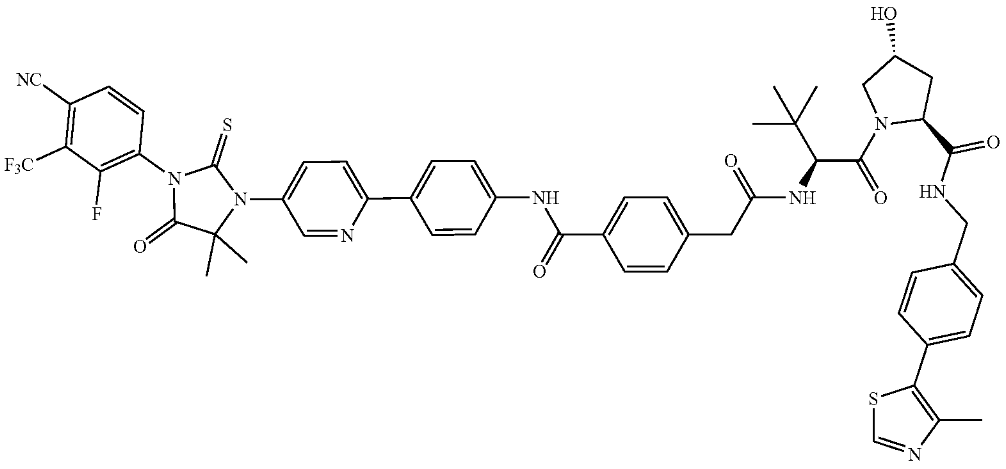 [SMILES: Cc1ncsc1-c1ccc(CNC(=O)[C@@H]2C[C@@H](O)CN2C(=O)[C@@H](NC(=O)Cc2ccc(C(=O)Nc3ccc(-c4ccc(N5C(=S)N(c6ccc(C#N)c(C(F)(F)F)c6F)C(=O)C5(C)C)cn4)cc3)cc2)C(C)(C)C)cc1] |

-continued
| Compound number | Compound structure |
|---|---|
| A241 | 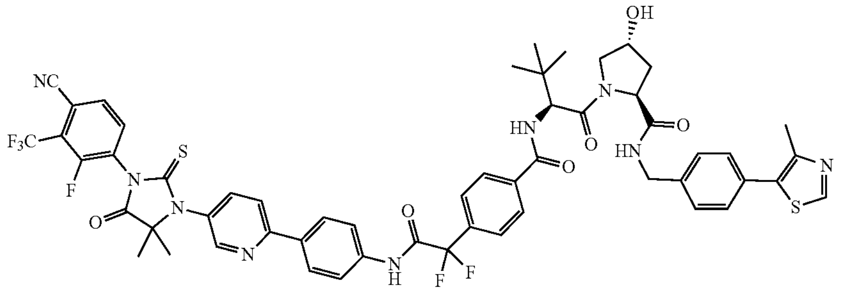 [SMILES: Cc1ncsc1-c1ccc(CNC(=O)[C@@H]2C[C@@H](O)CN2C(=O)[C@@H](NC(=O)c2ccc(C(F)(F)C(=O)Nc3ccc(-c4ccc(N5C(=S)N(c6ccc(C#N)c(C(F)(F)F)c6F)C(=O)C5(C)C)cn4)cc3)cc2)C(C)(C)C)cc1] |
| A242 | 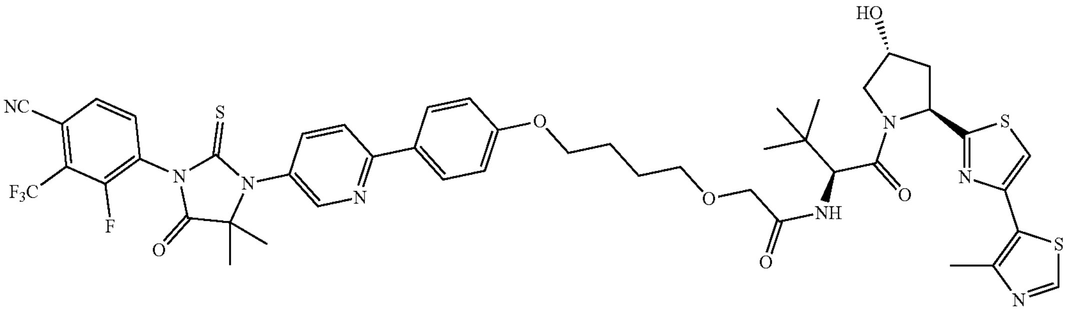 [SMILES: Cc1ncsc1-c1csc([C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2)C(C)(C)C)n1] |
| A243 | 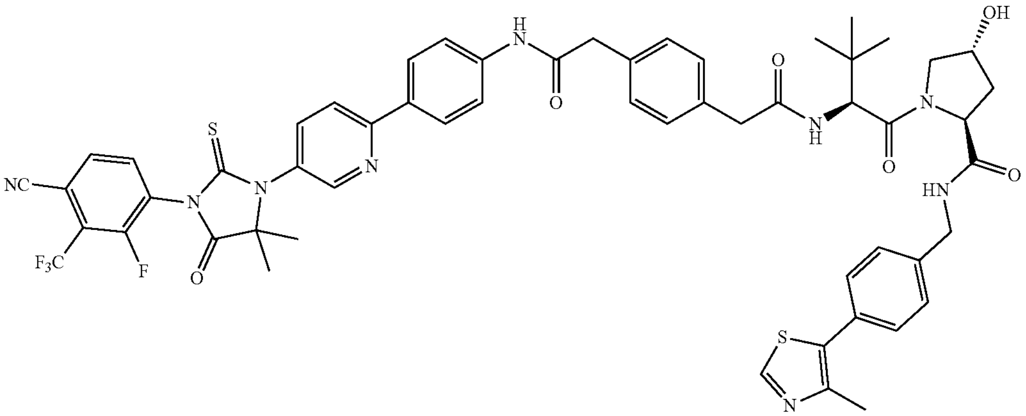 [SMILES: Cc1ncsc1-c1ccc(CNC(=O)[C@@H]2C[C@@H](O)CN2C(=O)[C@@H](NC(=O)Cc2ccc(CC(=O)Nc3ccc(-c4ccc(N5C(=S)N(c6ccc(C#N)c(C(F)(F)F)c6F)C(=O)C5(C)C)cn4)cc3)cc2)C(C)(C)C)cc1] |
| A244 | 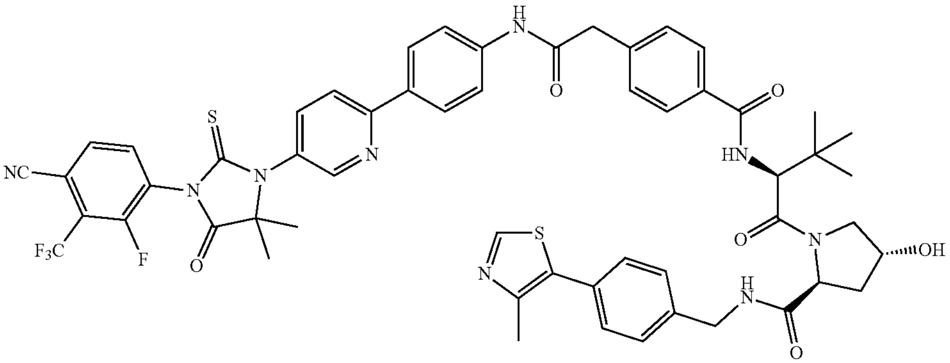 [SMILES: Cc1ncsc1-c1ccc(CNC(=O)[C@@H]2C[C@@H](O)CN2C(=O)[C@@H](NC(=O)c2ccc(CC(=O)Nc3ccc(-c4ccc(N5C(=S)N(c6ccc(C#N)c(C(F)(F)F)c6F)C(=O)C5(C)C)cn4)cc3)cc2)C(C)(C)C)cc1] |

-continued
| Compound number | Compound structure |
| --- | --- |
| A245 | 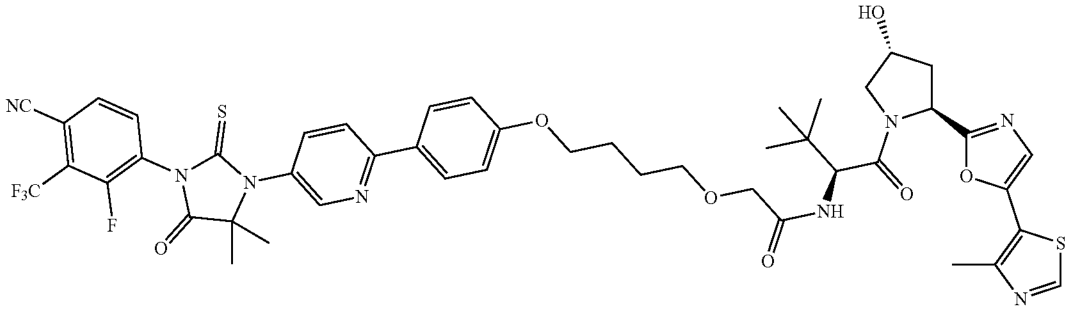 [SMILES: Cc1ncsc1-c1cnc([C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2)C(C)(C)C)o1] |
| A246 | 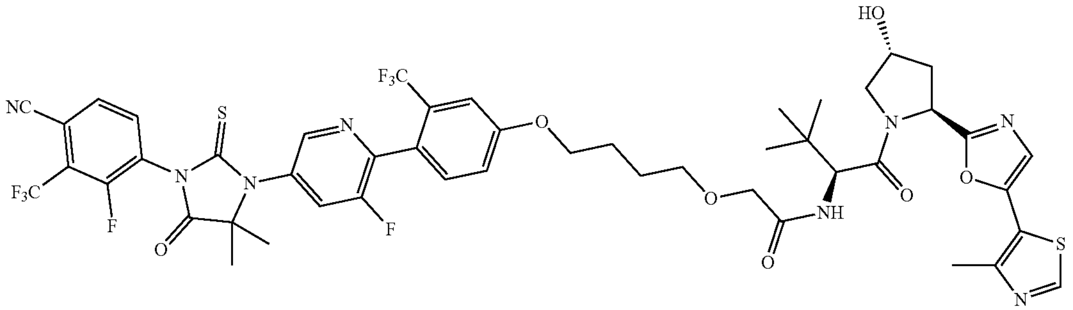 [SMILES: Cc1ncsc1-c1cnc([C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)c(C(F)(F)F)c2)C(C)(C)C)o1] |
| A247 | 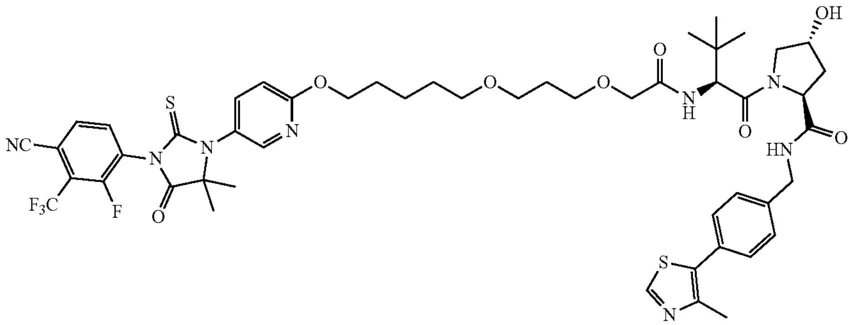 [SMILES: Cc1ncsc1-c1ccc(CNC(=O)[C@@H]2C[C@@H](O)CN2C(=O)[C@@H](NC(=O)COCCCOCCCCCOc2ccc(N3C(=S)N(c4ccc(C#N)c(C(F)(F)F)c4F)C(=O)C3(C)C)cn2)C(C)(C)C)cc1] |
| A248 | 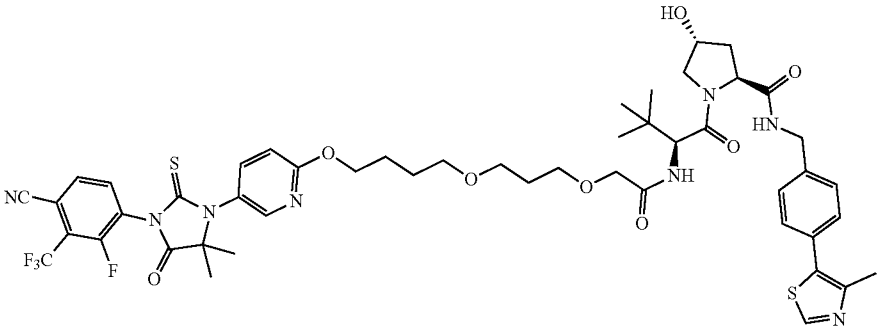 [SMILES: Cc1ncsc1-c1ccc(CNC(=O)[C@@H]2C[C@@H](O)CN2C(=O)[C@@H](NC(=O)COCCCOCCCCOc2ccc(N3C(=S)N(c4ccc(C#N)c(C(F)(F)F)c4F)C(=O)C3(C)C)cn2)C(C)(C)C)cc1] |
| A252 | 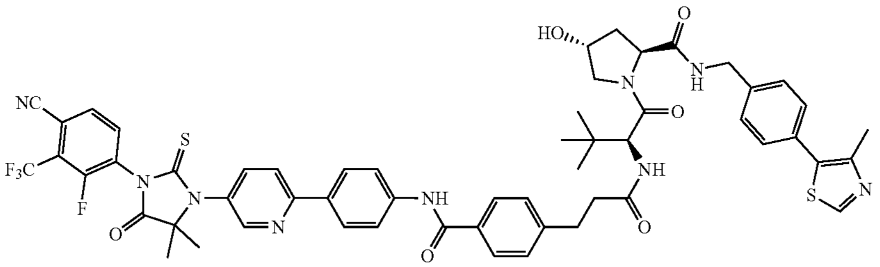 [SMILES: Cc1ncsc1-c1ccc(CNC(=O)[C@@H]2C[C@@H](O)CN2C(=O)[C@@H](NC(=O)CCc2ccc(C(=O)Nc3ccc(-c4ccc(N5C(=S)N(c6ccc(C#N)c(C(F)(F)F)c6F)C(=O)C5(C)C)cn4)cc3)cc2)C(C)(C)C)cc1] |

-continued
| Compound number | Compound structure |
|---|---|
| A254 | 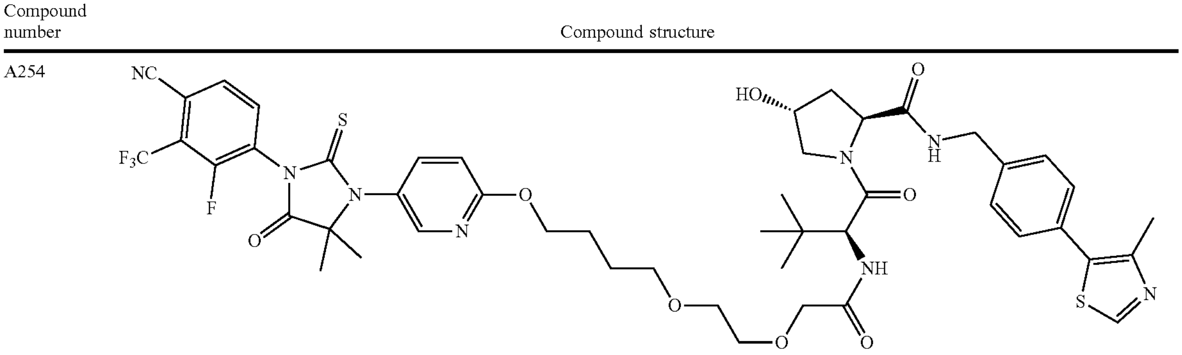 |
| A255 | 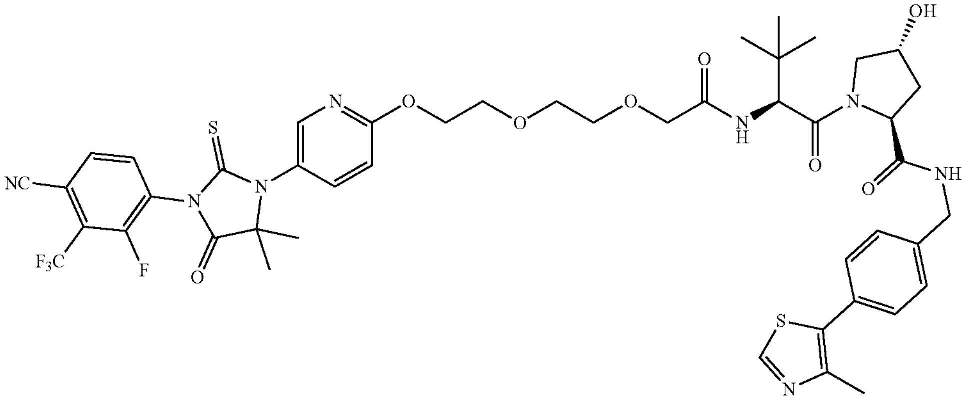 [SMILES: Cc1ncsc1-c1ccc(CNC(=O)[C@@H]2C[C@@H](O)CN2C(=O)[C@@H](NC(=O)COCCOCCOc2ccc(N3C(=S)N(c4ccc(C#N)c(C(F)(F)F)c4F)C(=O)C3(C)C)cn2)C(C)(C)C)cc1] |
| A256 | 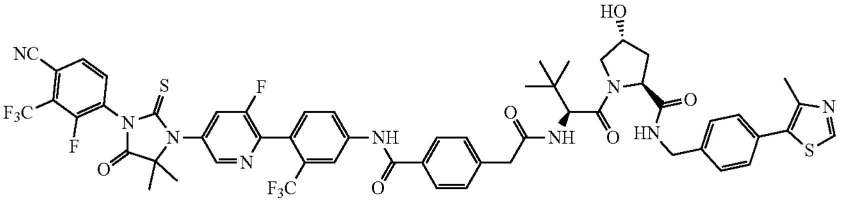 [SMILES: Cc1ncsc1-c1ccc(CNC(=O)[C@@H]2C[C@@H](O)CN2C(=O)[C@@H](NC(=O)Cc2ccc(C(=O)Nc3ccc(-c4ncc(N5C(=S)N(c6ccc(C#N)c(C(F)(F)F)c6F)C(=O)C5(C)C)cc4F)c(C(F)(F)F)c3)cc2)C(C)(C)C)cc1] |
| A257 | 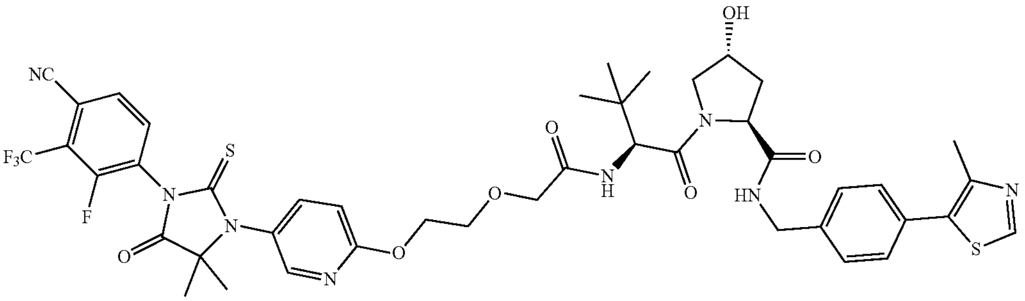 [SMILES: Cc1ncsc1-c1ccc(CNC(=O)[C@@H]2C[C@@H](O)CN2C(=O)[C@@H](NC(=O)COCCOc2ccc(N3C(=S)N(c4ccc(C#N)c(C(F)(F)F)c4F)C(=O)C3(C)C)cn2)C(C)(C)C)cc1] |
| A260 | 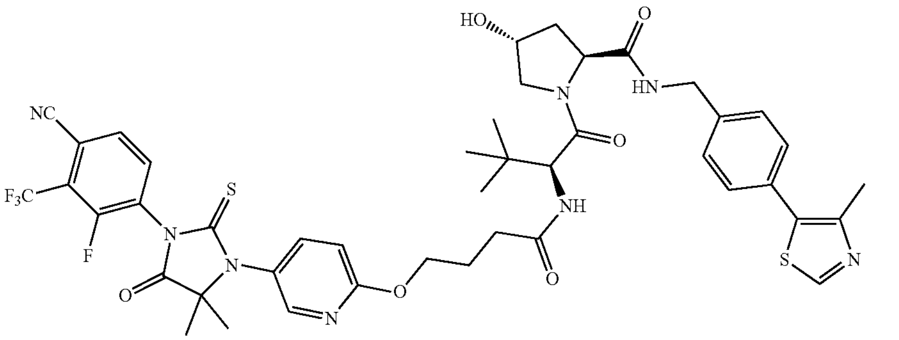 [SMILES: Cc1ncsc1-c1ccc(CNC(=O)[C@@H]2C[C@@H](O)CN2C(=O)[C@@H](NC(=O)CCCOc2ccc(N3C(=S)N(c4ccc(C#N)c(C(F)(F)F)c4F)C(=O)C3(C)C)cn2)C(C)(C)C)cc1] |

-continued
| Compound number | Compound structure |
| --- | --- |
| A262 | 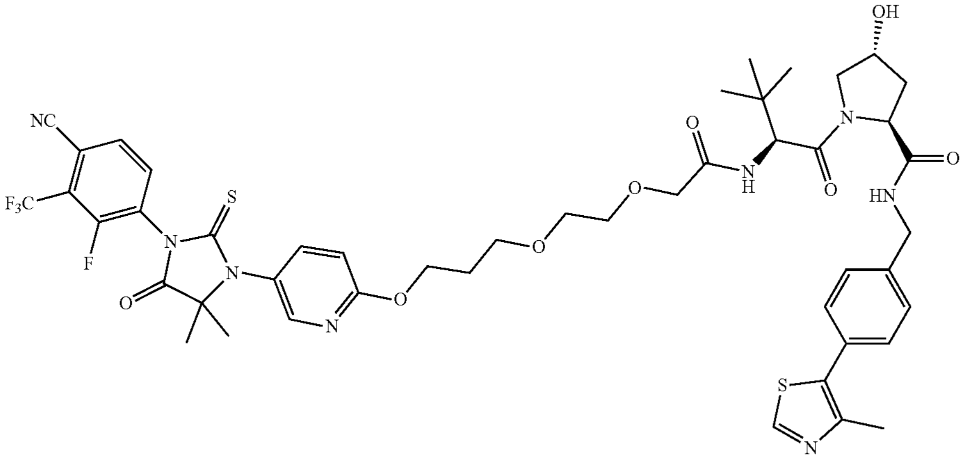 [SMILES: Cc1ncsc1-c1ccc(CNC(=O)[C@@H]2C[C@@H](O)CN2C(=O)[C@@H](NC(=O)COCCOCCCOc2ccc(N3C(=S)N(c4ccc(C#N)c(C(F)(F)F)c4F)C(=O)C3(C)C)cn2)C(C)(C)C)cc1] |
| A263 | 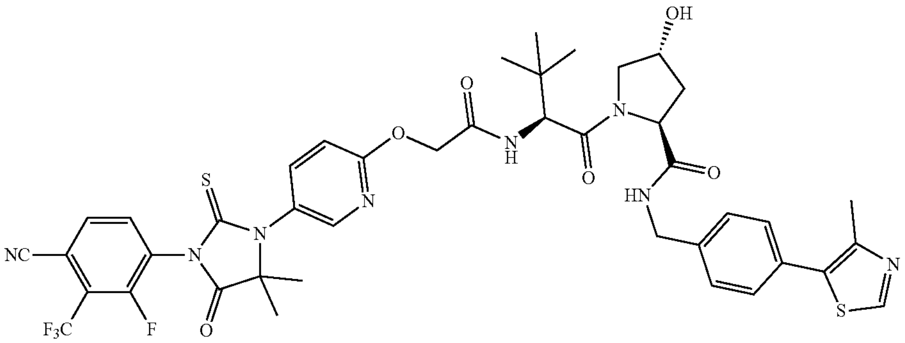 [SMILES: Cc1ncsc1-c1ccc(CNC(=O)[C@@H]2C[C@@H](O)CN2C(=O)[C@@H](NC(=O)COc2ccc(N3C(=S)N(c4ccc(C#N)c(C(F)(F)F)c4F)C(=O)C3(C)C)cn2)C(C)(C)C)cc1] |
| A264 | 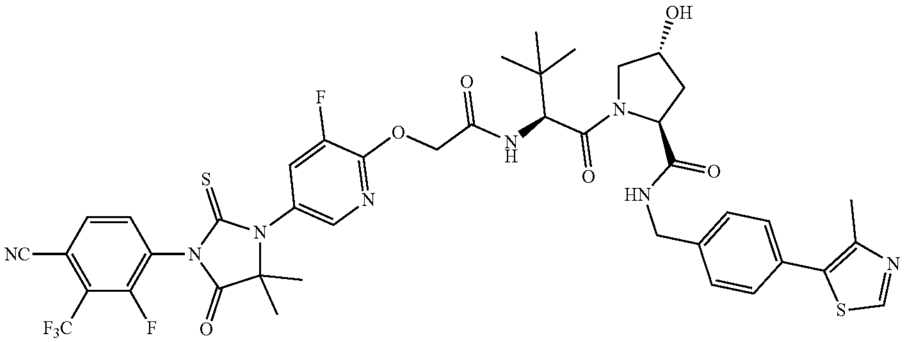 [SMILES: Cc1ncsc1-c1ccc(CNC(=O)[C@@H]2C[C@@H](O)CN2C(=O)[C@@H](NC(=O)COc2ncc(N3C(=S)N(c4ccc(C#N)c(C(F)(F)F)c4F)C(=O)C3(C)C)cc2F)C(C)(C)C)cc1] |
| A265 | 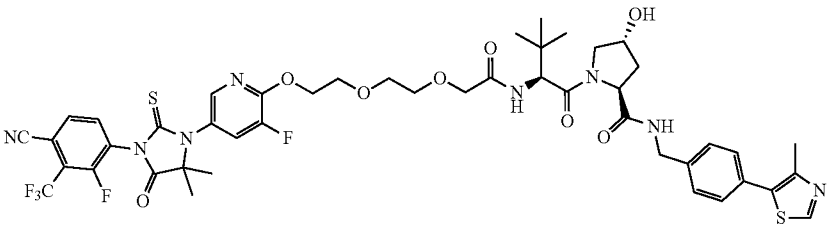 [SMILES: Cc1ncsc1-c1ccc(CNC(=O)[C@@H]2C[C@@H](O)CN2C(=O)[C@@H](NC(=O)COCCOCCOc2ncc(N3C(=S)N(c4ccc(C#N)c(C(F)(F)F)c4F)C(=O)C3(C)C)cc2F)C(C)(C)C)cc1] |

-continued
| Compound number | Compound structure |
|---|---|
| A266 | 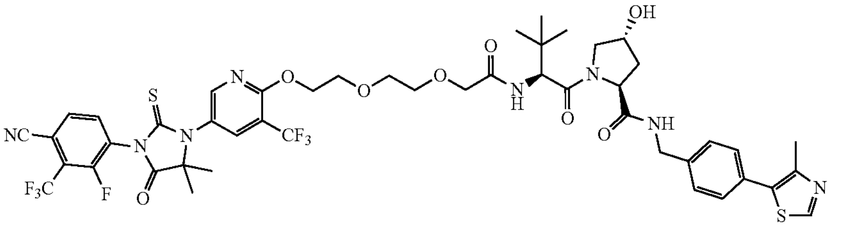 [SMILES: Cc1ncsc1-c1ccc(CNC(=O)[C@@H]2C[C@@H](O)CN2C(=O)[C@@H](NC(=O)COCCOCCOc2ncc(N3C(=S)N(c4ccc(C#N)c(C(F)(F)F)c4F)C(=O)C3(C)C)cc2C(F)(F)F)C(C)(C)C)cc1] |
| A267 | 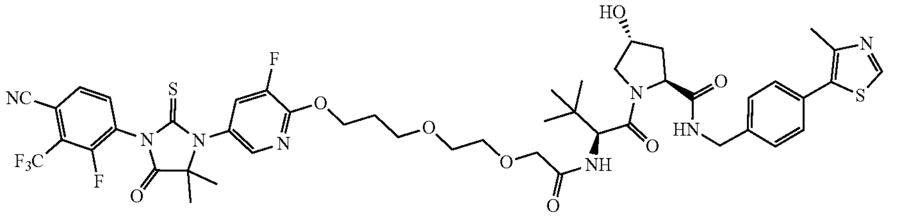 [SMILES: Cc1ncsc1-c1ccc(CNC(=O)[C@@H]2C[C@@H](O)CN2C(=O)[C@@H](NC(=O)COCCOCCCOc2ncc(N3C(=S)N(c4ccc(C#N)c(C(F)(F)F)c4F)C(=O)C3(C)C)cc2F)C(C)(C)C)cc1] |
| A268 | 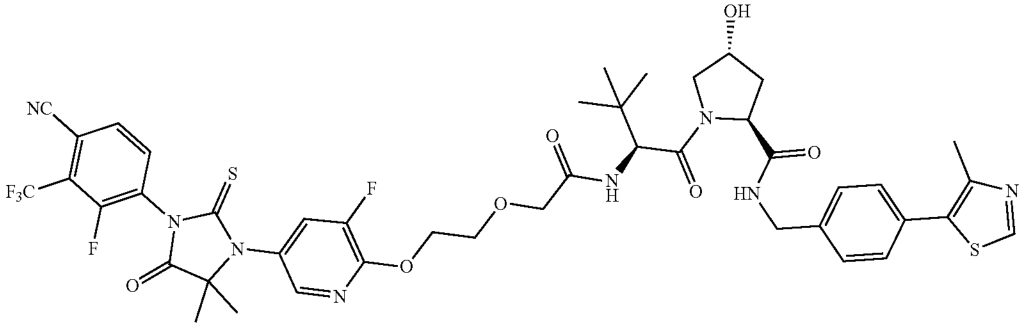 [SMILES: Cc1ncsc1-c1ccc(CNC(=O)[C@@H]2C[C@@H](O)CN2C(=O)[C@@H](NC(=O)COCCOc2ncc(N3C(=S)N(c4ccc(C#N)c(C(F)(F)F)c4F)C(=O)C3(C)C)cc2F)C(C)(C)C)cc1] |
| A269 | 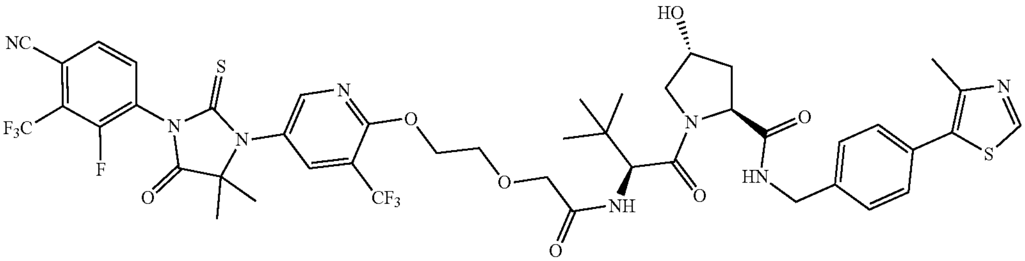 [SMILES: Cc1ncsc1-c1ccc(CNC(=O)[C@@H]2C[C@@H](O)CN2C(=O)[C@@H](NC(=O)COCCOc2ncc(N3C(=S)N(c4ccc(C#N)c(C(F)(F)F)c4F)C(=O)C3(C)C)cc2C(F)(F)F)C(C)(C)C)cc1] |
| A270 | 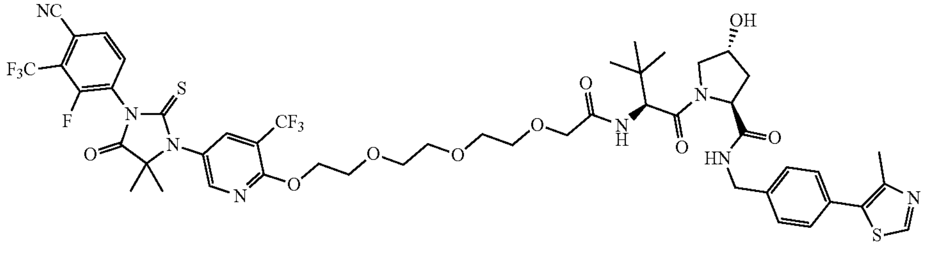 [SMILES: Cc1ncsc1-c1ccc(CNC(=O)[C@@H]2C[C@@H](O)CN2C(=O)[C@@H](NC(=O)COCCOCCOCCOc2ncc(N3C(=S)N(c4ccc(C#N)c(C(F)(F)F)c4F)C(=O)C3(C)C)cc2C(F)(F)F)C(C)(C)C)cc1] |
| A271 | 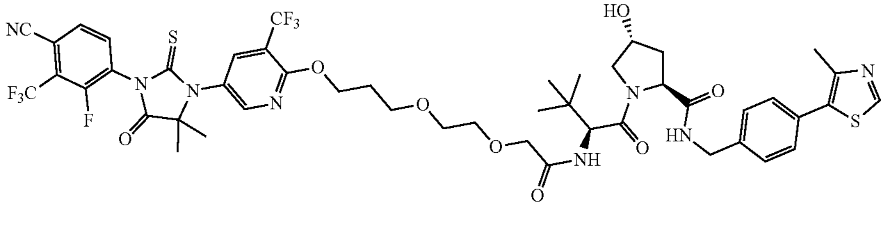 [SMILES: Cc1ncsc1-c1ccc(CNC(=O)[C@@H]2C[C@@H](O)CN2C(=O)[C@@H](NC(=O)COCCOCCCOc2ncc(N3C(=S)N(c4ccc(C#N)c(C(F)(F)F)c4F)C(=O)C3(C)C)cc2C(F)(F)F)C(C)(C)C)cc1] |

-continued
| Compound number | Compound structure |
|---|---|
| A272 | 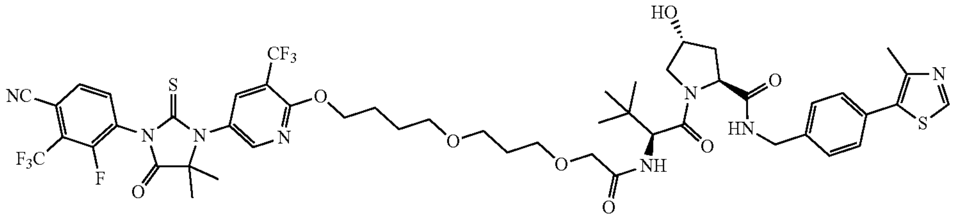 [SMILES: Cc1ncsc1-c1ccc(CNC(=O)[C@@H]2C[C@@H](O)CN2C(=O)[C@@H](NC(=O)COCCCOCCCCOc2ncc(N3C(=S)N(c4ccc(C#N)c(C(F)(F)F)c4F)C(=O)C3(C)C)cc2C(F)(F)F)C(C)(C)C)cc1] |
| A274 | 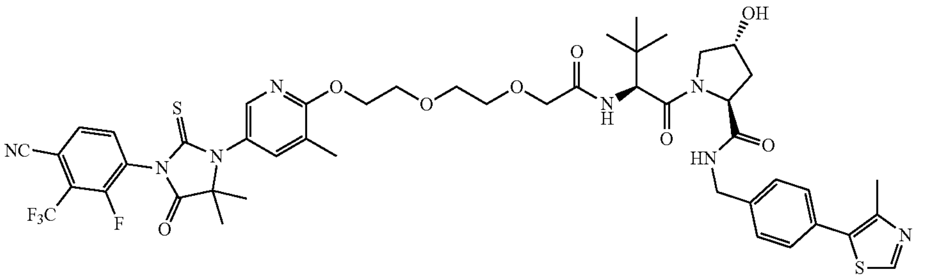 [SMILES: Cc1cc(N2C(=S)N(c3ccc(C#N)c(C(F)(F)F)c3F)C(=O)C2(C)C)cnc1OCCOCCOCC(=O)N[C@H](C(=O)N1C[C@H](O)C[C@H]1C(=O)NCc1ccc(-c2scnc2C)cc1)C(C)(C)C] |
| A275 | 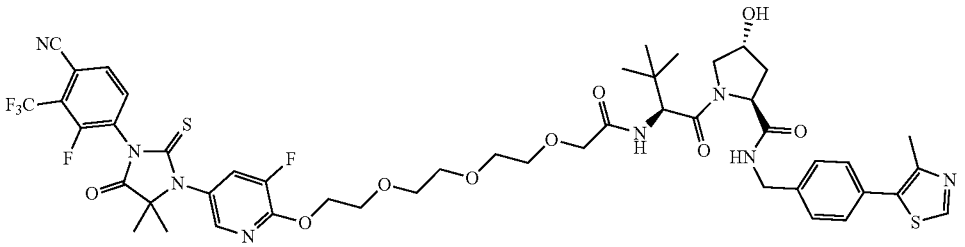 [SMILES: Cc1ncsc1-c1ccc(CNC(=O)[C@@H]2C[C@@H](O)CN2C(=O)[C@@H](NC(=O)COCCOCCOCCOc2ncc(N3C(=S)N(c4ccc(C#N)c(C(F)(F)F)c4F)C(=O)C3(C)C)cc2F)C(C)(C)C)cc1] |
| A276 | 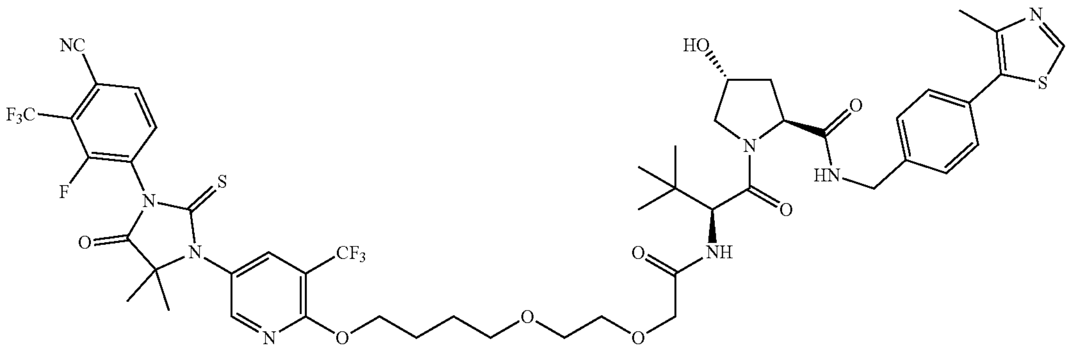 [SMILES: Cc1ncsc1-c1ccc(CNC(=O)[C@@H]2C[C@@H](O)CN2C(=O)[C@@H](NC(=O)COCCOCCCCOc2ncc(N3C(=S)N(c4ccc(C#N)c(C(F)(F)F)c4F)C(=O)C3(C)C)cc2C(F)(F)F)C(C)(C)C)cc1] |
| A277 | 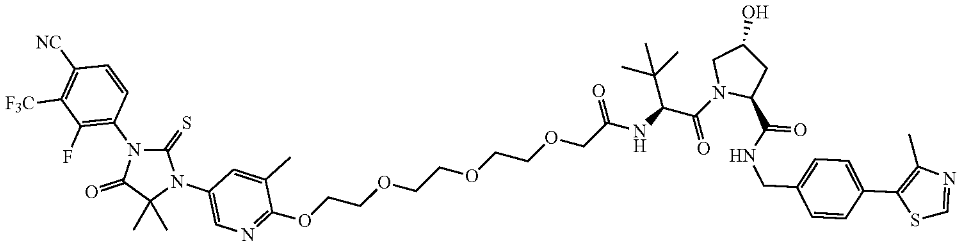 [SMILES: Cc1cc(N2C(=S)N(c3ccc(C#N)c(C(F)(F)F)c3F)C(=O)C2(C)C)cnc1OCCOCCOCCOCC(=O)N[C@H](C(=O)N1C[C@H](O)C[C@H]1C(=O)NCc1ccc(-c2scnc2C)cc1)C(C)(C)C] |

-continued
| Compound number | Compound structure |
| --- | --- |
| A278 | 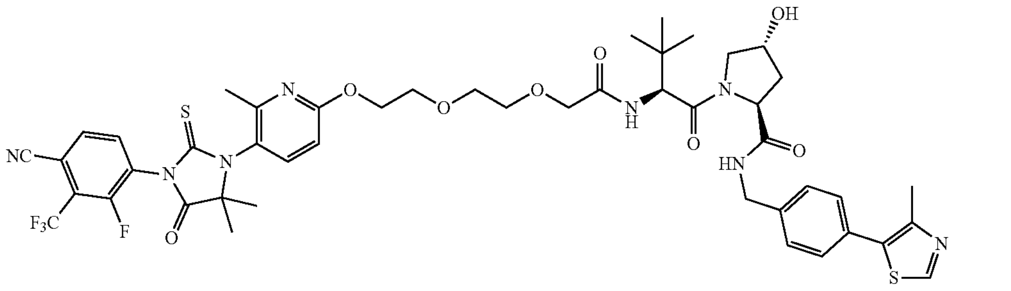 [SMILES: Cc1nc(OCCOCCOCC(=O)N[C@H](C(=O)N2C[C@H](O)C[C@H]2C(=O)NCc2ccc(-c3scnc3C)cc2)C(C)(C)C)ccc1N1C(=S)N(c2ccc(C#N)c(C(F)(F)F)c2F)C(=O)C1(C)C] |
| A279 | 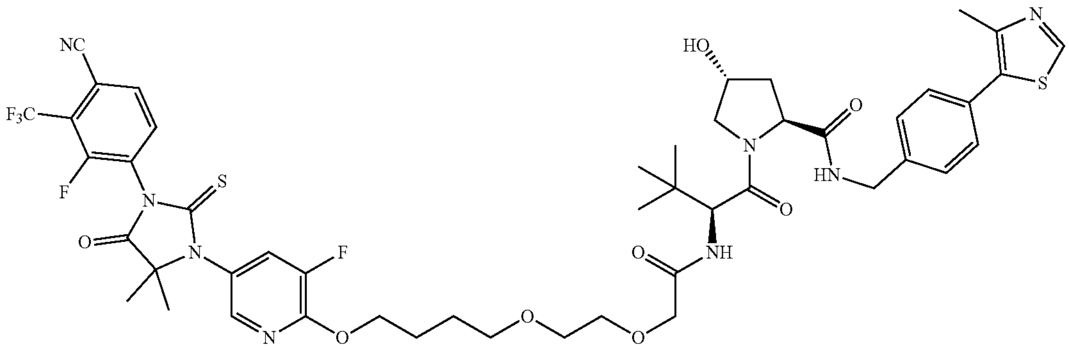 [SMILES: Cc1ncsc1-c1ccc(CNC(=O)[C@@H]2C[C@@H](O)CN2C(=O)[C@@H](NC(=O)COCCOCCCCOc2ncc(N3C(=S)N(c4ccc(C#N)c(C(F)(F)F)c4F)C(=O)C3(C)C)cc2F)C(C)(C)C)cc1] |
| A280 | 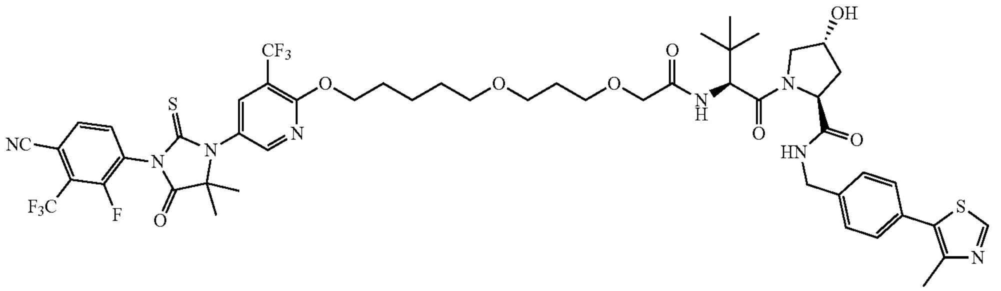 [SMILES: Cc1ncsc1-c1ccc(CNC(=O)[C@@H]2C[C@@H](O)CN2C(=O)[C@@H](NC(=O)COCCCOCCCCCOc2ncc(N3C(=S)N(c4ccc(C#N)c(C(F)(F)F)c4F)C(=O)C3(C)C)cc2C(F)(F)F)C(C)(C)C)cc1] |
| A281 | 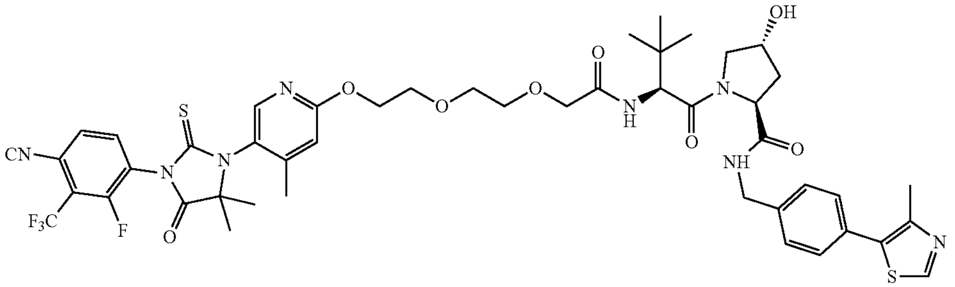 |
| A282 | 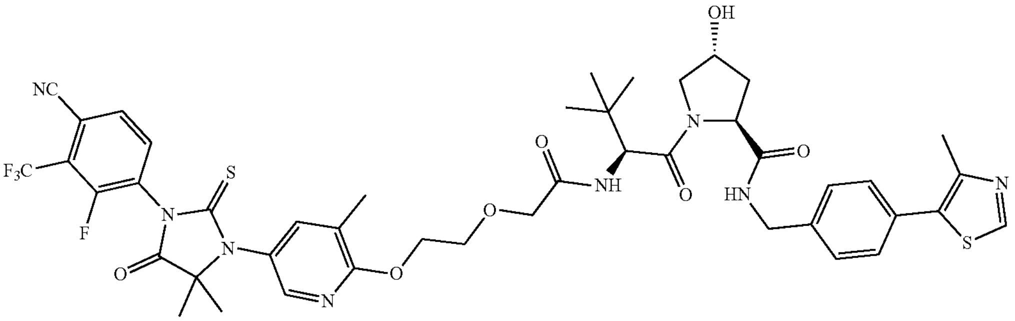 [SMILES: Cc1cc(N2C(=S)N(c3ccc(C#N)c(C(F)(F)F)c3F)C(=O)C2(C)C)cnc1OCCOCC(=O)N[C@H](C(=O)N1C[C@H](O)C[C@H]1C(=O)NCc1ccc(-c2scnc2C)cc1)C(C)(C)C] |

-continued
| Compound number | Compound structure |
|---|---|
| A283 | 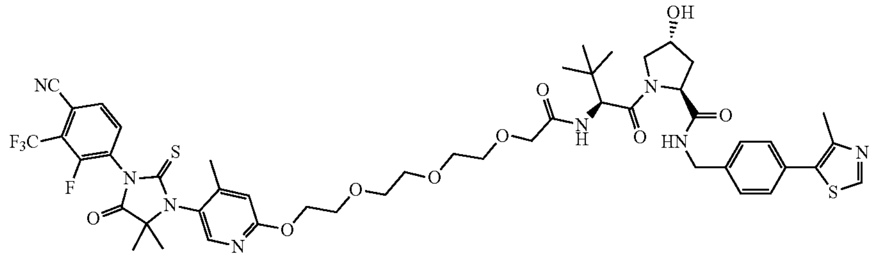 [SMILES: Cc1cc(OCCOCCOCCOCC(=O)N[C@H](C(=O)N2C[C@H](O)C[C@H]2C(=O)NCc2ccc(-c3scnc3C)cc2)C(C)(C)C)ncc1N1C(=S)N(c2ccc(C#N)c(C(F)(F)F)c2F)C(=O)C1(C)C] |
| A284 | 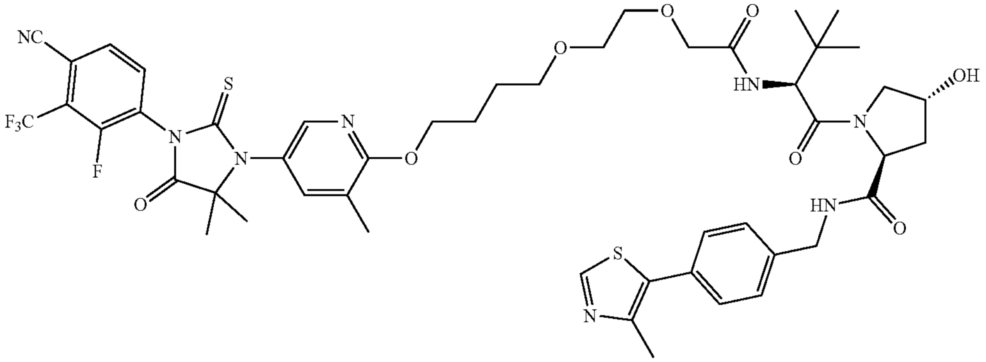 [SMILES: Cc1cc(N2C(=S)N(c3ccc(C#N)c(C(F)(F)F)c3F)C(=O)C2(C)C)cnc1OCCCCOCCOCC(=O)N[C@H](C(=O)N1C[C@H](O)C[C@H]1C(=O)NCc1ccc(-c2scnc2C)cc1)C(C)(C)C] |
| A285 | 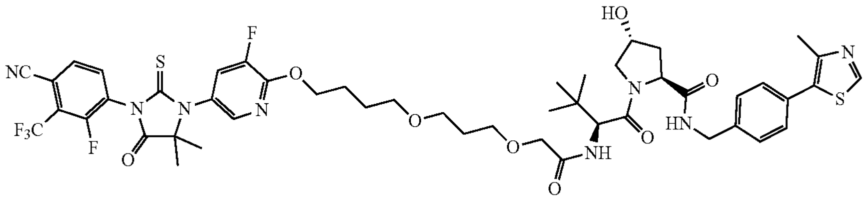 [SMILES: Cc1ncsc1-c1ccc(CNC(=O)[C@@H]2C[C@@H](O)CN2C(=O)[C@@H](NC(=O)COCCCOCCCCOc2ncc(N3C(=S)N(c4ccc(C#N)c(C(F)(F)F)c4F)C(=O)C3(C)C)cc2F)C(C)(C)C)cc1] |
| A286 | 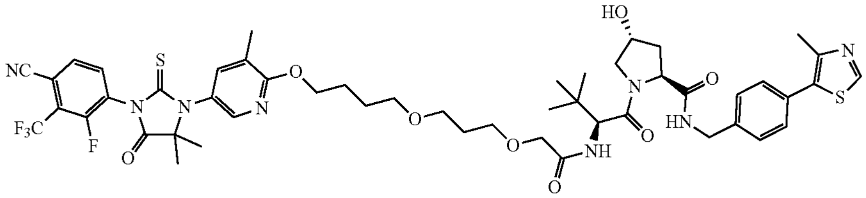 [SMILES: Cc1cc(N2C(=S)N(c3ccc(C#N)c(C(F)(F)F)c3F)C(=O)C2(C)C)cnc1OCCCCOCCCOCC(=O)N[C@H](C(=O)N1C[C@H](O)C[C@H]1C(=O)NCc1ccc(-c2scnc2C)cc1)C(C)(C)C] |
| A287 | 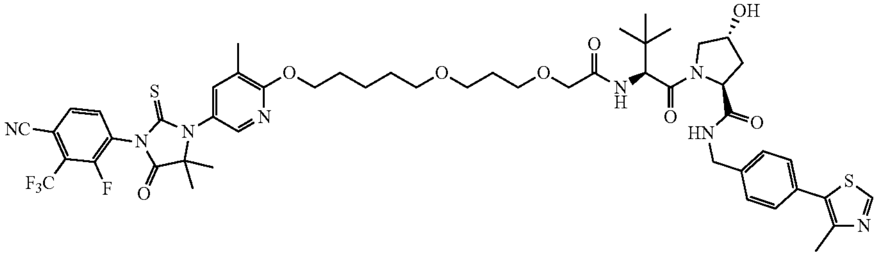 [SMILES: Cc1cc(N2C(=S)N(c3ccc(C#N)c(C(F)(F)F)c3F)C(=O)C2(C)C)cnc1OCCCCCOCCCOCC(=O)N[C@H](C(=O)N1C[C@H](O)C[C@H]1C(=O)NCc1ccc(-c2scnc2C)cc1)C(C)(C)C] |
| A288 | 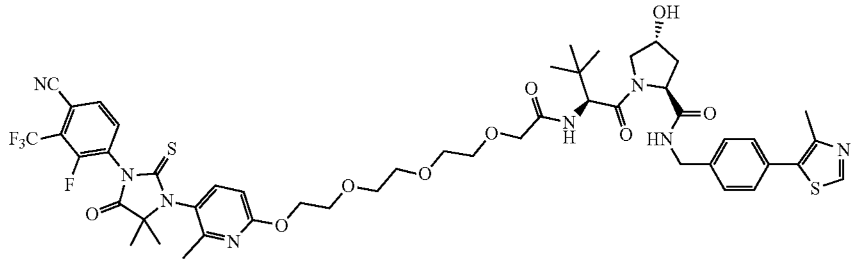 [SMILES: Cc1nc(OCCOCCOCCOCC(=O)N[C@H](C(=O)N2C[C@H](O)C[C@H]2C(=O)NCc2ccc(-c3scnc3C)cc2)C(C)(C)C)ccc1N1C(=S)N(c2ccc(C#N)c(C(F)(F)F)c2F)C(=O)C1(C)C] |

-continued
| Compound number | Compound structure |
| --- | --- |
| A289 | 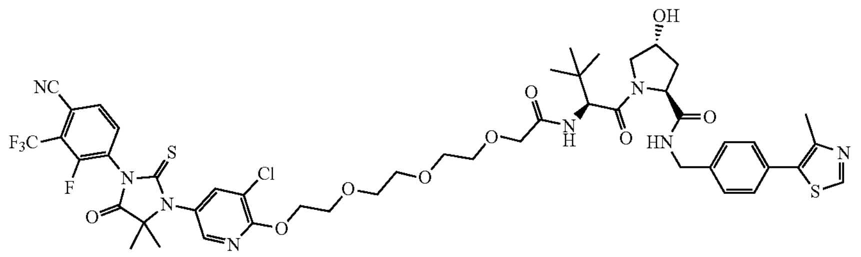 [SMILES: Cc1ncsc1-c1ccc(CNC(=O)[C@@H]2C[C@@H](O)CN2C(=O)[C@@H](NC(=O)COCCOCCOCCOc2ncc(N3C(=S)N(c4ccc(C#N)c(C(F)(F)F)c4F)C(=O)C3(C)C)cc2Cl)C(C)(C)C)cc1] |
| A290 | 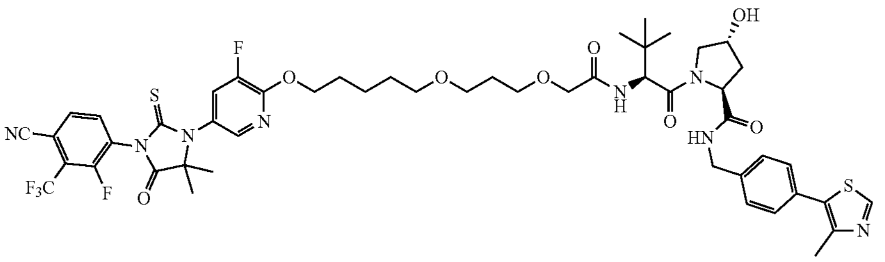 [SMILES: Cc1ncsc1-c1ccc(CNC(=O)[C@@H]2C[C@@H](O)CN2C(=O)[C@@H](NC(=O)COCCCOCCCCCOc2ncc(N3C(=S)N(c4ccc(C#N)c(C(F)(F)F)c4F)C(=O)C3(C)C)cc2F)C(C)(C)C)cc1] |
| A291 | 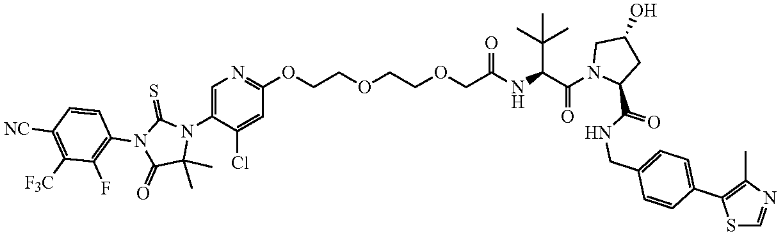 [SMILES: Cc1ncsc1-c1ccc(CNC(=O)[C@@H]2C[C@@H](O)CN2C(=O)[C@@H](NC(=O)COCCOCCOc2cc(Cl)c(N3C(=S)N(c4ccc(C#N)c(C(F)(F)F)c4F)C(=O)C3(C)C)cn2)C(C)(C)C)cc1] |
| A292 | 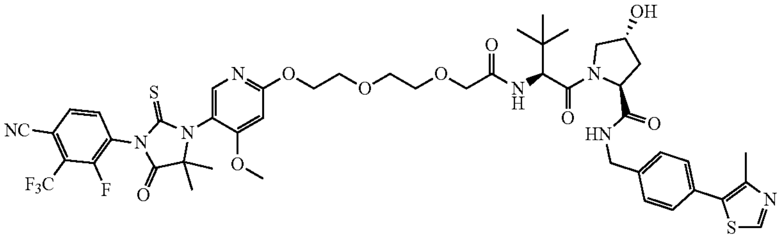 [SMILES: COc1cc(OCCOCCOCC(=O)N[C@H](C(=O)N2C[C@H](O)C[C@H]2C(=O)NCc2ccc(-c3scnc3C)cc2)C(C)(C)C)ncc1N1C(=S)N(c2ccc(C#N)c(C(F)(F)F)c2F)C(=O)C1(C)C] |
| A293 | 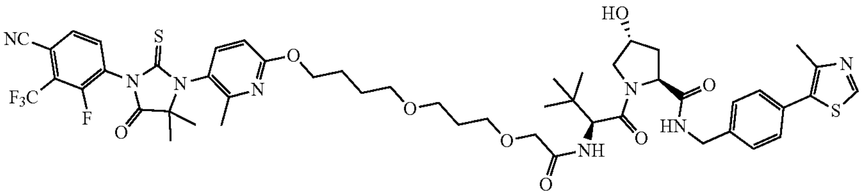 [SMILES: Cc1nc(OCCCCOCCCOCC(=O)N[C@H](C(=O)N2C[C@H](O)C[C@H]2C(=O)NCc2ccc(-c3scnc3C)cc2)C(C)(C)C)ccc1N1C(=S)N(c2ccc(C#N)c(C(F)(F)F)c2F)C(=O)C1(C)C] |
| A294 | 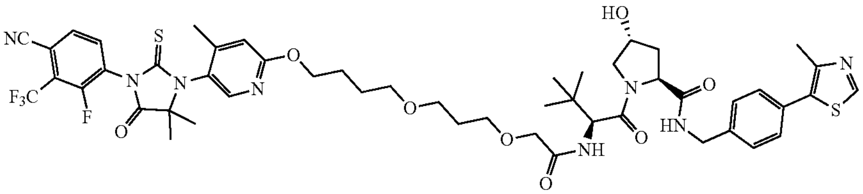 [SMILES: Cc1cc(OCCCCOCCCOCC(=O)N[C@H](C(=O)N2C[C@H](O)C[C@H]2C(=O)NCc2ccc(-c3scnc3C)cc2)C(C)(C)C)ncc1N1C(=S)N(c2ccc(C#N)c(C(F)(F)F)c2F)C(=O)C1(C)C] |

-continued
| Compound number | Compound structure |
| --- | --- |
| A295 | 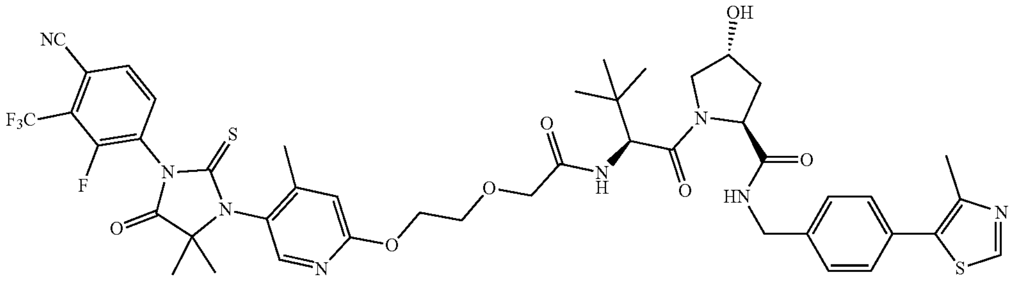 [SMILES: Cc1cc(OCCOCC(=O)N[C@H](C(=O)N2C[C@H](O)C[C@H]2C(=O)NCc2ccc(-c3scnc3C)cc2)C(C)(C)C)ncc1N1C(=S)N(c2ccc(C#N)c(C(F)(F)F)c2F)C(=O)C1(C)C] |
| A296 | 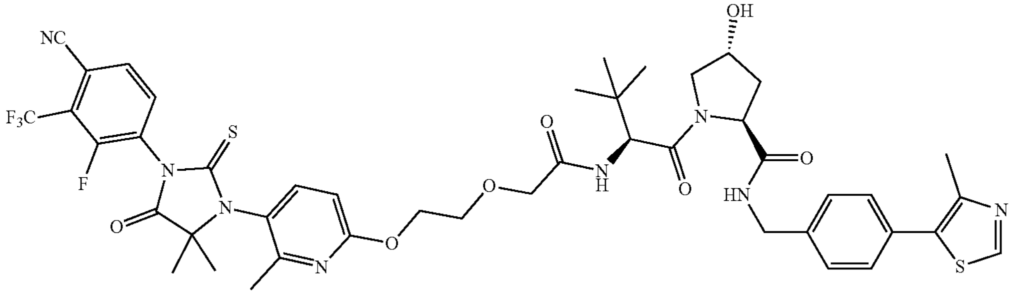 [SMILES: Cc1nc(OCCOCC(=O)N[C@H](C(=O)N2C[C@H](O)C[C@H]2C(=O)NCc2ccc(-c3scnc3C)cc2)C(C)(C)C)ccc1N1C(=S)N(c2ccc(C#N)c(C(F)(F)F)c2F)C(=O)C1(C)C] |
| A297 | 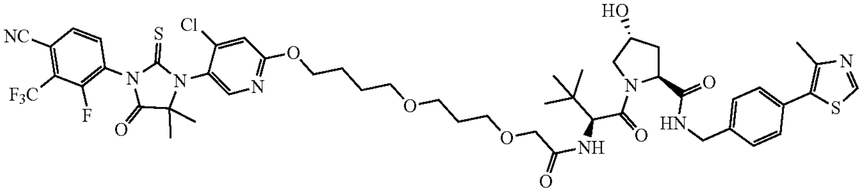 [SMILES: Cc1ncsc1-c1ccc(CNC(=O)[C@@H]2C[C@@H](O)CN2C(=O)[C@@H](NC(=O)COCCCOCCCCOc2cc(Cl)c(N3C(=S)N(c4ccc(C#N)c(C(F)(F)F)c4F)C(=O)C3(C)C)cn2)C(C)(C)C)cc1] |
| A298 | 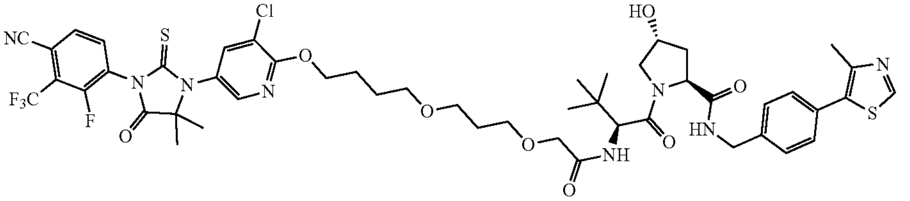 [SMILES: Cc1ncsc1-c1ccc(CNC(=O)[C@@H]2C[C@@H](O)CN2C(=O)[C@@H](NC(=O)COCCCOCCCCOc2ncc(N3C(=S)N(c4ccc(C#N)c(C(F)(F)F)c4F)C(=O)C3(C)C)cc2Cl)C(C)(C)C)cc1] |
| A299 | 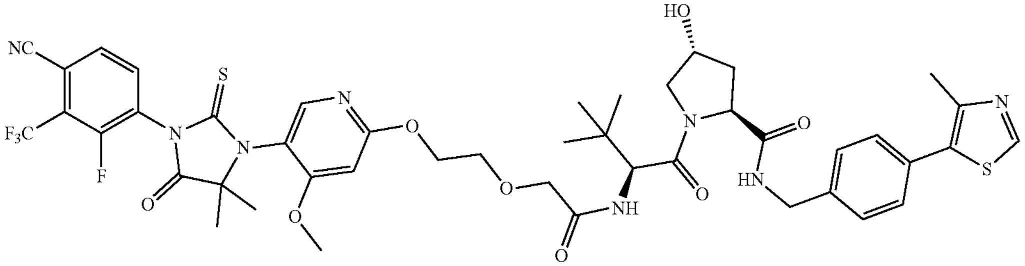 [SMILES: COc1cc(OCCOCC(=O)N[C@H](C(=O)N2C[C@H](O)C[C@H]2C(=O)NCc2ccc(-c3scnc3C)cc2)C(C)(C)C)ncc1N1C(=S)N(c2ccc(C#N)c(C(F)(F)F)c2F)C(=O)C1(C)C] |
| A300 | 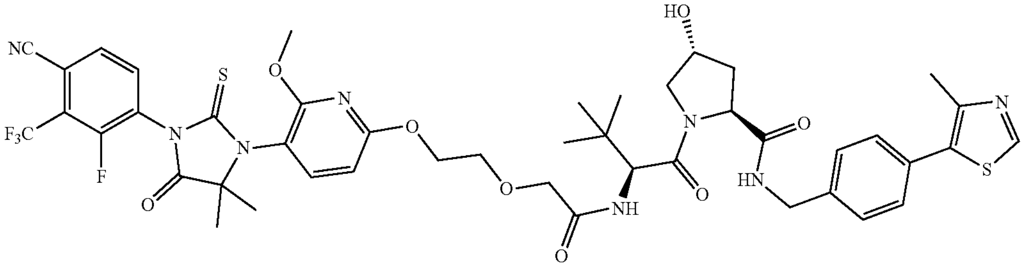 [SMILES: COc1nc(OCCOCC(=O)N[C@H](C(=O)N2C[C@H](O)C[C@H]2C(=O)NCc2ccc(-c3scnc3C)cc2)C(C)(C)C)ccc1N1C(=S)N(c2ccc(C#N)c(C(F)(F)F)c2F)C(=O)C1(C)C] |

-continued
| Compound number | Compound structure |
| --- | --- |
| A301 | 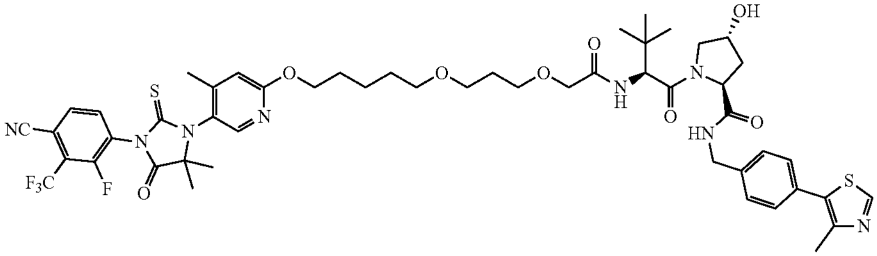 [SMILES: Cc1cc(OCCCCCOCCCOCC(=O)N[C@H](C(=O)N2C[C@H](O)C[C@H]2C(=O)NCc2ccc(-c3scnc3C)cc2)C(C)(C)C)ncc1N1C(=S)N(c2ccc(C#N)c(C(F)(F)F)c2F)C(=O)C1(C)C] |
| A302 | 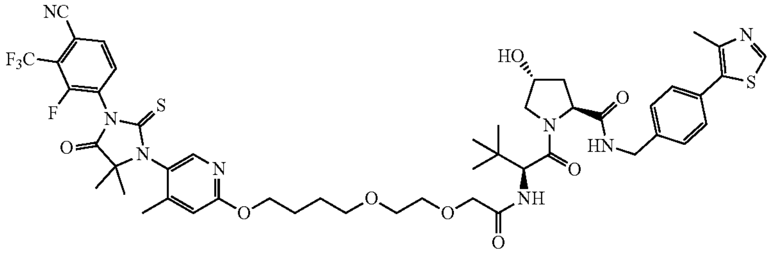 [SMILES: Cc1cc(OCCCCOCCOCC(=O)N[C@H](C(=O)N2C[C@H](O)C[C@H]2C(=O)NCc2ccc(-c3scnc3C)cc2)C(C)(C)C)ncc1N1C(=S)N(c2ccc(C#N)c(C(F)(F)F)c2F)C(=O)C1(C)C] |
| A303 | 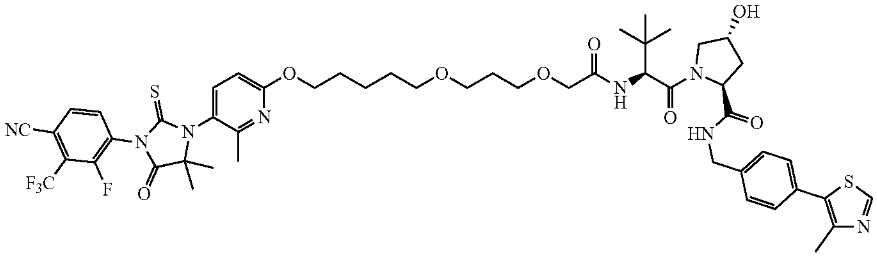 [SMILES: Cc1nc(OCCCCCOCCCOCC(=O)N[C@H](C(=O)N2C[C@H](O)C[C@H]2C(=O)NCc2ccc(-c3scnc3C)cc2)C(C)(C)C)ccc1N1C(=S)N(c2ccc(C#N)c(C(F)(F)F)c2F)C(=O)C1(C)C] |
| A304 | 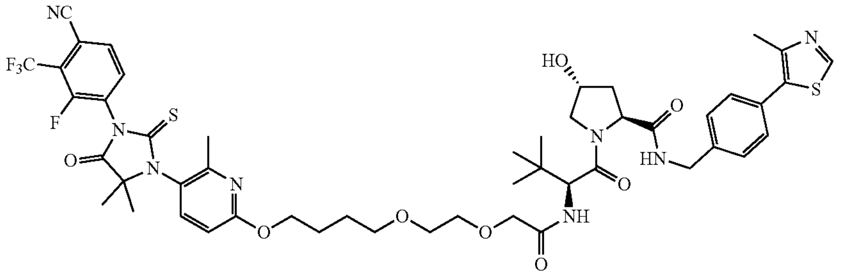 [SMILES: Cc1nc(OCCCCOCCOCC(=O)N[C@H](C(=O)N2C[C@H](O)C[C@H]2C(=O)NCc2ccc(-c3scnc3C)cc2)C(C)(C)C)ccc1N1C(=S)N(c2ccc(C#N)c(C(F)(F)F)c2F)C(=O)C1(C)C] |
| A305 | 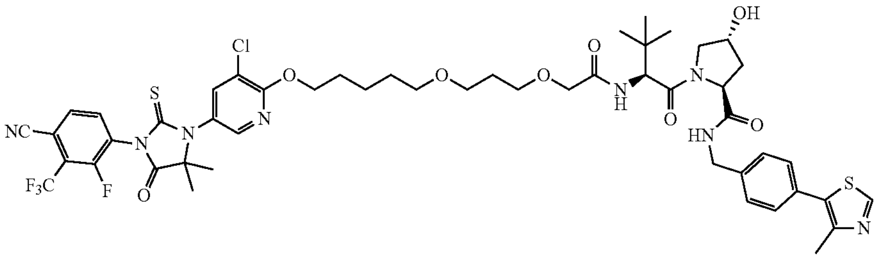 |
| A306 | 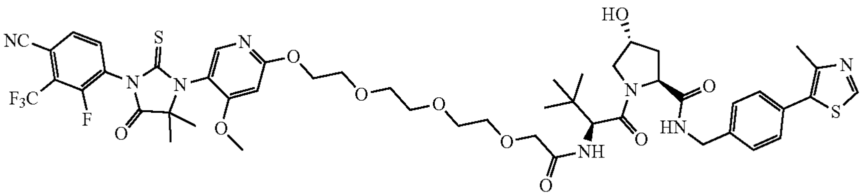 [SMILES: COc1cc(OCCOCCOCCOCC(=O)N[C@H](C(=O)N2C[C@H](O)C[C@H]2C(=O)NCc2ccc(-c3scnc3C)cc2)C(C)(C)C)ncc1N1C(=S)N(c2ccc(C#N)c(C(F)(F)F)c2F)C(=O)C1(C)C] |

-continued
| Compound number | Compound structure |
| --- | --- |
| A307 | 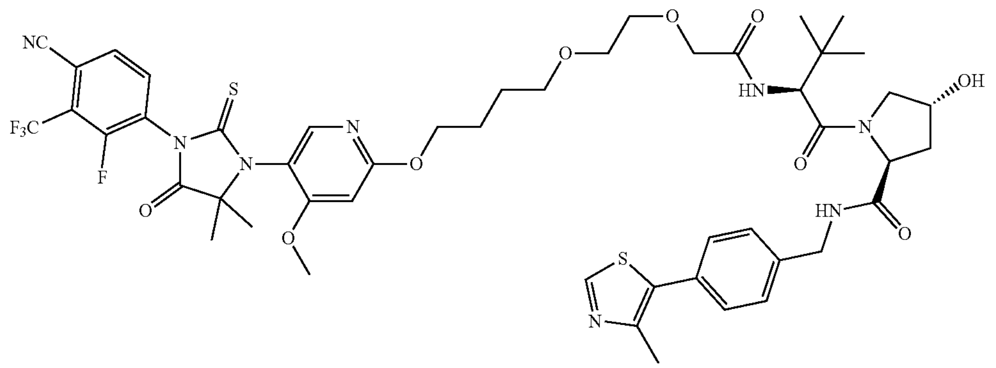 [SMILES: COc1cc(OCCCCOCCOCC(=O)N[C@H](C(=O)N2C[C@H](O)C[C@H]2C(=O)NCc2ccc(-c3scnc3C)cc2)C(C)(C)C)ncc1N1C(=S)N(c2ccc(C#N)c(C(F)(F)F)c2F)C(=O)C1(C)C] |
| A308 | 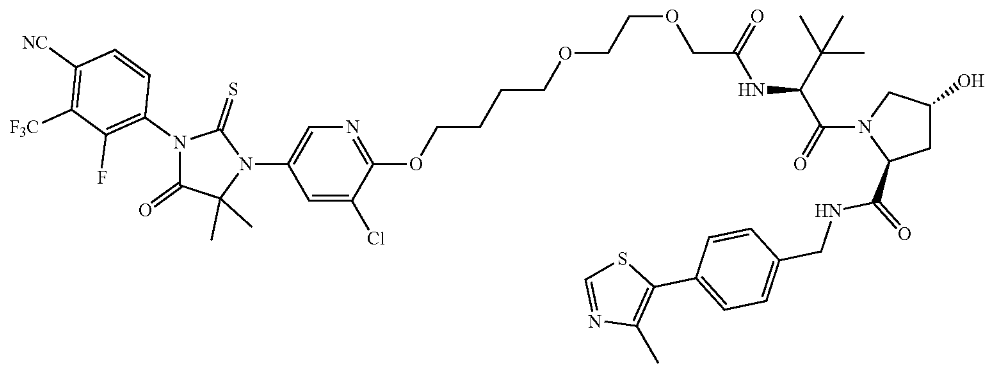 |
| A309 | 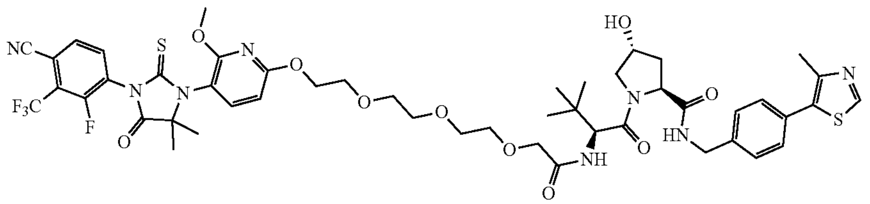 [SMILES: COc1nc(OCCOCCOCCOCC(=O)N[C@H](C(=O)N2C[C@H](O)C[C@H]2C(=O)NCc2ccc(-c3scnc3C)cc2)C(C)(C)C)ccc1N1C(=S)N(c2ccc(C#N)c(C(F)(F)F)c2F)C(=O)C1(C)C] |
| A310 | 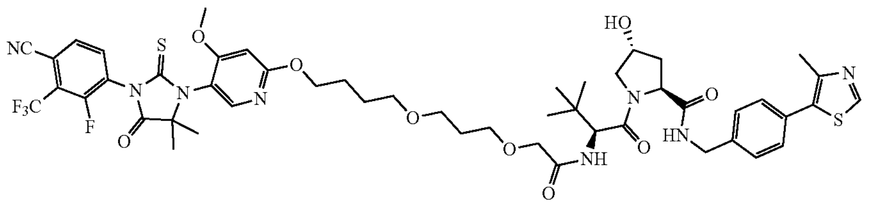 [SMILES: COc1cc(OCCCCOCCCOCC(=O)N[C@H](C(=O)N2C[C@H](O)C[C@H]2C(=O)NCc2ccc(-c3scnc3C)cc2)C(C)(C)C)ncc1N1C(=S)N(c2ccc(C#N)c(C(F)(F)F)c2F)C(=O)C1(C)C] |
| A311 | 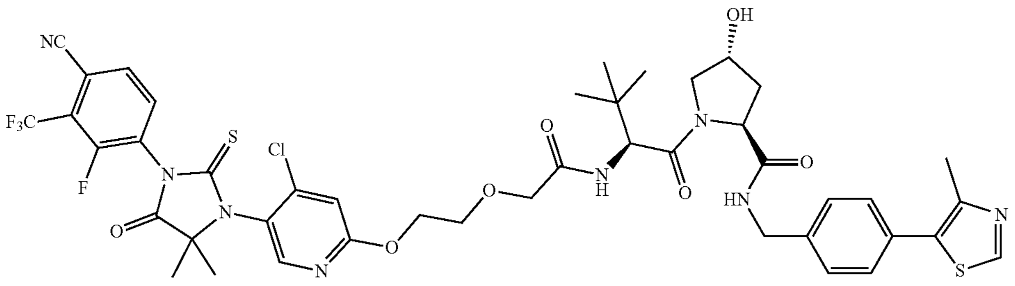 [SMILES: Cc1ncsc1-c1ccc(CNC(=O)[C@@H]2C[C@@H](O)CN2C(=O)[C@@H](NC(=O)COCCOc2cc(Cl)c(N3C(=S)N(c4ccc(C#N)c(C(F)(F)F)c4F)C(=O)C3(C)C)cn2)C(C)(C)C)cc1] |

-continued
| Compound number | Compound structure |
|---|---|
| A312 | 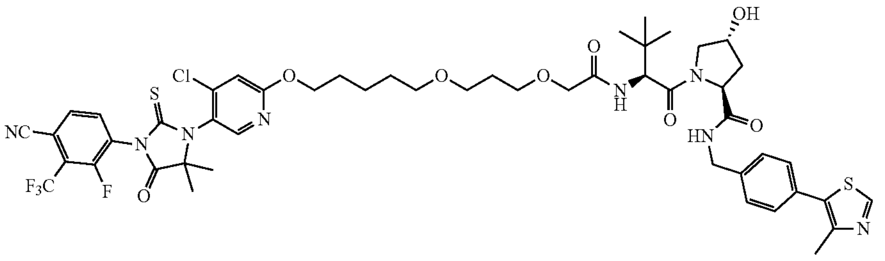 [SMILES: Cc1ncsc1-c1ccc(CNC(=O)[C@@H]2C[C@@H](O)CN2C(=O)[C@@H](NC(=O)COCCCOCCCCCOc2cc(Cl)c(N3C(=S)N(c4ccc(C#N)c(C(F)(F)F)c4F)C(=O)C3(C)C)cn2)C(C)(C)C)cc1] |
| A313 | 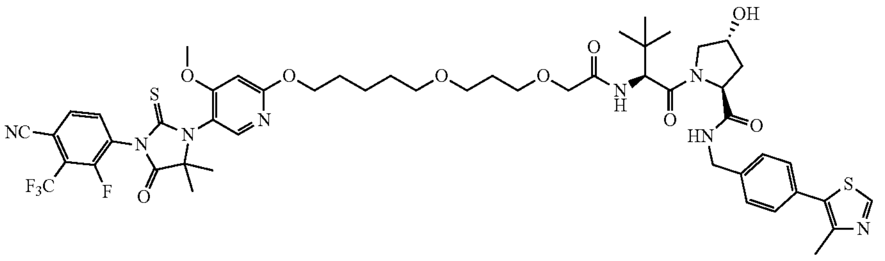 [SMILES: COc1cc(OCCCCCOCCCOCC(=O)N[C@H](C(=O)N2C[C@H](O)C[C@H]2C(=O)NCc2ccc(-c3scnc3C)cc2)C(C)(C)C)ncc1N1C(=S)N(c2ccc(C#N)c(C(F)(F)F)c2F)C(=O)C1(C)C] |
| A314 | 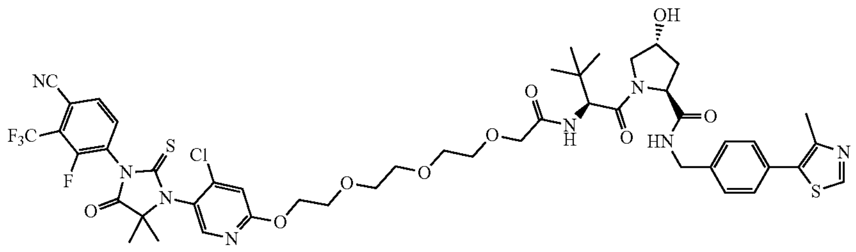 [SMILES: Cc1ncsc1-c1ccc(CNC(=O)[C@@H]2C[C@@H](O)CN2C(=O)[C@@H](NC(=O)COCCOCCOCCOc2cc(Cl)c(N3C(=S)N(c4ccc(C#N)c(C(F)(F)F)c4F)C(=O)C3(C)C)cn2)C(C)(C)C)cc1] |
| A315 | 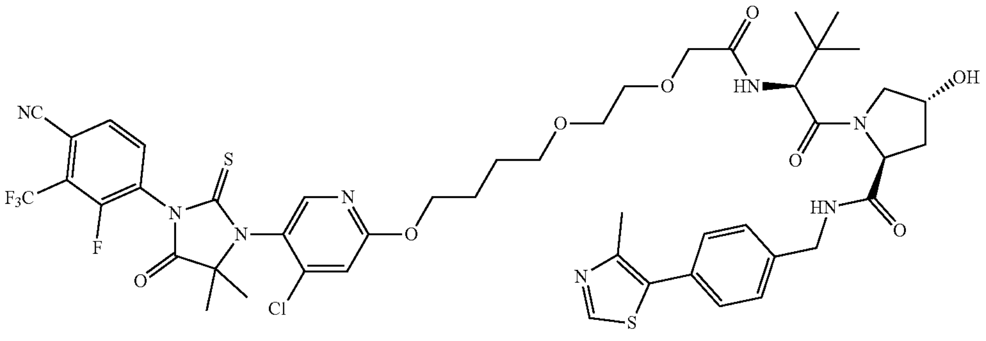 [SMILES: Cc1ncsc1-c1ccc(CNC(=O)[C@@H]2C[C@@H](O)CN2C(=O)[C@@H](NC(=O)COCCOCCCCOc2cc(Cl)c(N3C(=S)N(c4ccc(C#N)c(C(F)(F)F)c4F)C(=O)C3(C)C)cn2)C(C)(C)C)cc1] |
| A316 | 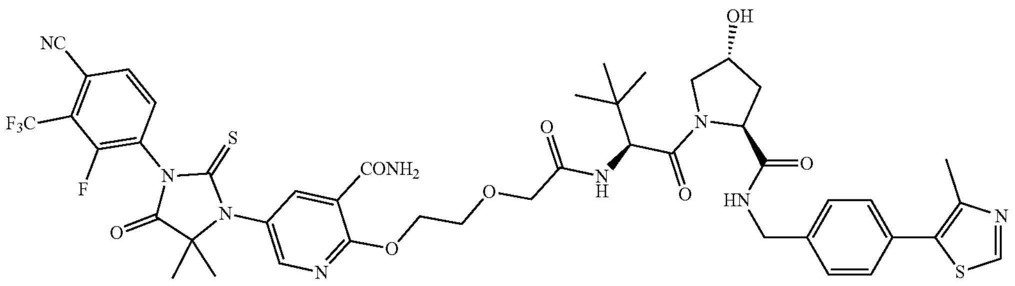 [SMILES: Cc1ncsc1-c1ccc(CNC(=O)[C@@H]2C[C@@H](O)CN2C(=O)[C@@H](NC(=O)COCCOc2ncc(N3C(=S)N(c4ccc(C#N)c(C(F)(F)F)c4F)C(=O)C3(C)C)cc2C(N)=O)C(C)(C)C)cc1] |

-continued
| Compound number | Compound structure |
|---|---|
| A317 | 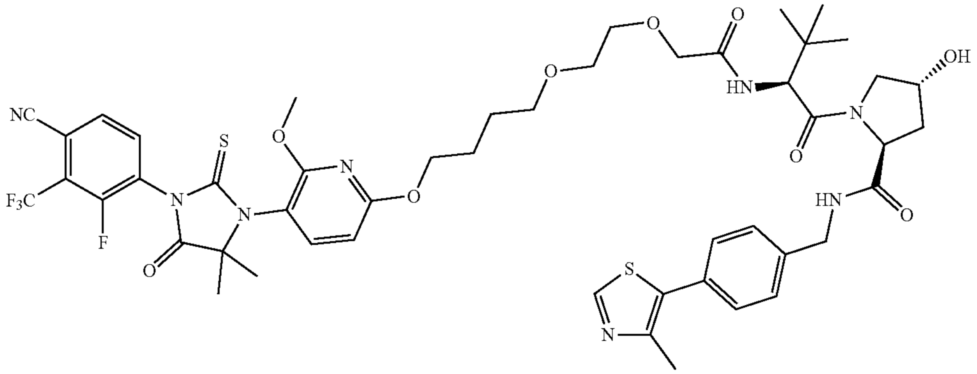 [SMILES: COc1nc(OCCCCOCCOCC(=O)N[C@H](C(=O)N2C[C@H](O)C[C@H]2C(=O)NCc2ccc(-c3scnc3C)cc2)C(C)(C)C)ccc1N1C(=S)N(c2ccc(C#N)c(C(F)(F)F)c2F)C(=O)C1(C)C] |
| A318 | 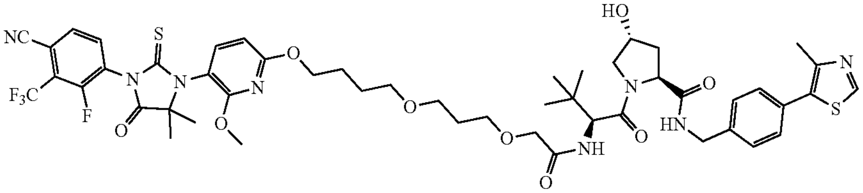 [SMILES: COc1nc(OCCCCOCCCOCC(=O)N[C@H](C(=O)N2C[C@H](O)C[C@H]2C(=O)NCc2ccc(-c3scnc3C)cc2)C(C)(C)C)ccc1N1C(=S)N(c2ccc(C#N)c(C(F)(F)F)c2F)C(=O)C1(C)C] |
| A319 | 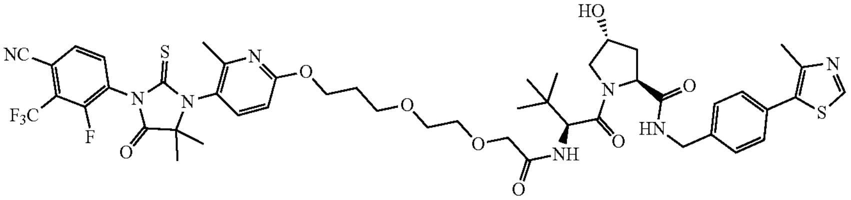 [SMILES: Cc1nc(OCCCOCCOCC(=O)N[C@H](C(=O)N2C[C@H](O)C[C@H]2C(=O)NCc2ccc(-c3scnc3C)cc2)C(C)(C)C)ccc1N1C(=S)N(c2ccc(C#N)c(C(F)(F)F)c2F)C(=O)C1(C)C] |
| A320 | 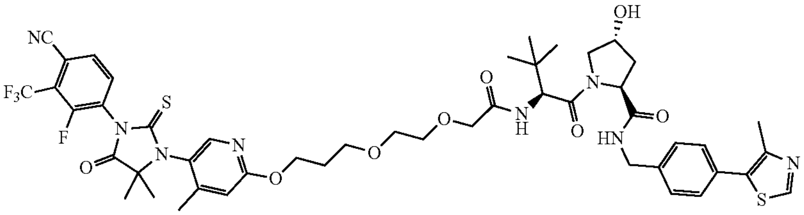 [SMILES: Cc1cc(OCCCOCCOCC(=O)N[C@H](C(=O)N2C[C@H](O)C[C@H]2C(=O)NCc2ccc(-c3scnc3C)cc2)C(C)(C)C)ncc1N1C(=S)N(c2ccc(C#N)c(C(F)(F)F)c2F)C(=O)C1(C)C] |
| A321 | 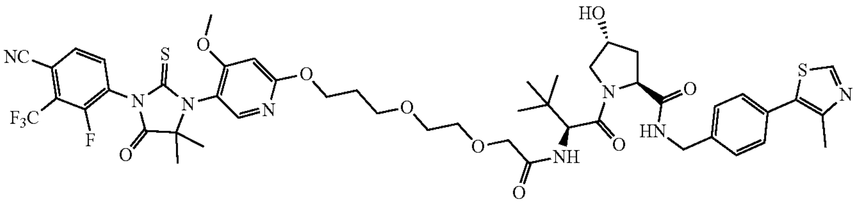 [SMILES: COc1cc(OCCCOCCOCC(=O)N[C@H](C(=O)N2C[C@H](O)C[C@H]2C(=O)NCc2ccc(-c3scnc3C)cc2)C(C)(C)C)ncc1N1C(=S)N(c2ccc(C#N)c(C(F)(F)F)c2F)C(=O)C1(C)C] |
| A322 | 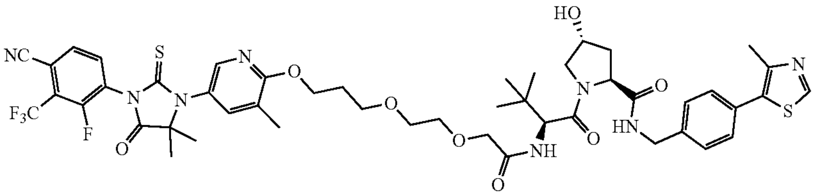 [SMILES: Cc1cc(N2C(=S)N(c3ccc(C#N)c(C(F)(F)F)c3F)C(=O)C2(C)C)cnc1OCCCOCCOCC(=O)N[C@H](C(=O)N1C[C@H](O)C[C@H]1C(=O)NCc1ccc(-c2scnc2C)cc1)C(C)(C)C] |

-continued
| Compound number | Compound structure |
|---|---|
| A323 | 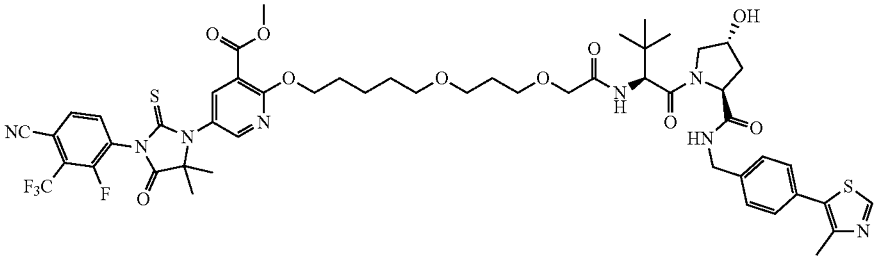 [SMILES: COC(=O)c1cc(N2C(=S)N(c3ccc(C#N)c(C(F)(F)F)c3F)C(=O)C2(C)C)cnc1OCCCCCOCCCOCC(=O)N[C@H](C(=O)N1C[C@H](O)C[C@H]1C(=O)NCc1ccc(-c2scnc2C)cc1)C(C)(C)C] |
| A324 | 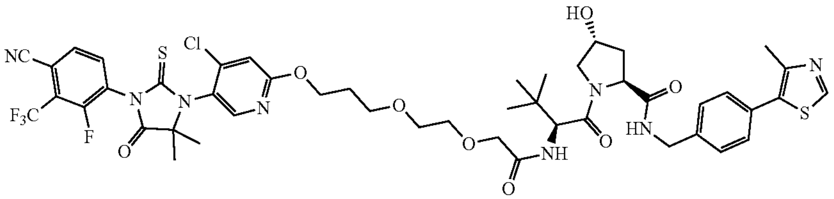 [SMILES: Cc1ncsc1-c1ccc(CNC(=O)[C@@H]2C[C@@H](O)CN2C(=O)[C@@H](NC(=O)COCCOCCCOc2cc(Cl)c(N3C(=S)N(c4ccc(C#N)c(C(F)(F)F)c4F)C(=O)C3(C)C)cn2)C(C)(C)C)cc1] |
| A325 | 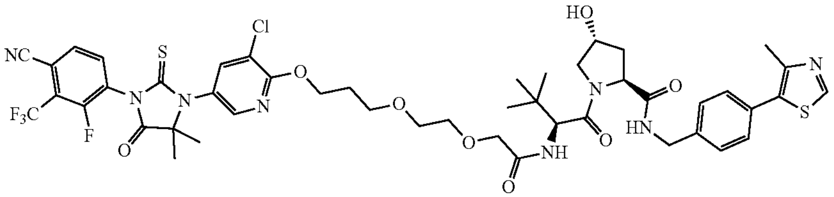 [SMILES: Cc1ncsc1-c1ccc(CNC(=O)[C@@H]2C[C@@H](O)CN2C(=O)[C@@H](NC(=O)COCCOCCCOc2ncc(N3C(=S)N(c4ccc(C#N)c(C(F)(F)F)c4F)C(=O)C3(C)C)cc2Cl)C(C)(C)C)cc1] |
| A326 | 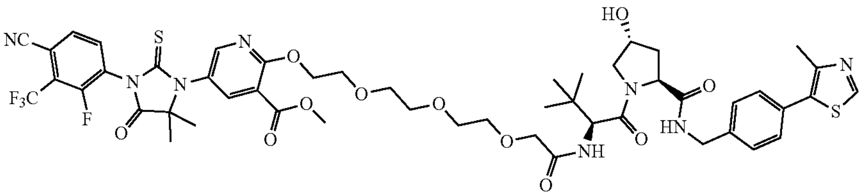 [SMILES: COC(=O)c1cc(N2C(=S)N(c3ccc(C#N)c(C(F)(F)F)c3F)C(=O)C2(C)C)cnc1OCCOCCOCCOCC(=O)N[C@H](C(=O)N1C[C@H](O)C[C@H]1C(=O)NCc1ccc(-c2scnc2C)cc1)C(C)(C)C] |
| A327 | 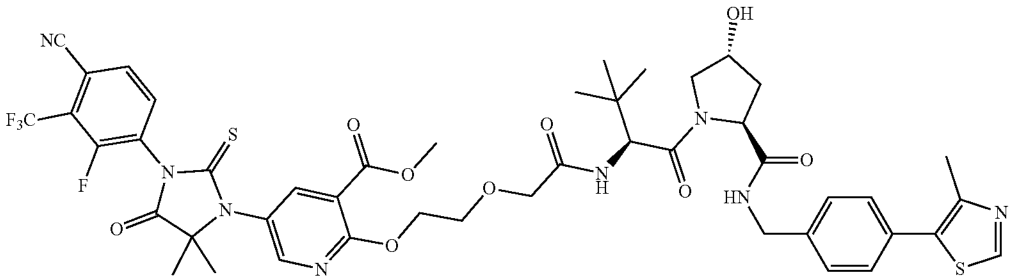 [SMILES: COC(=O)c1cc(N2C(=S)N(c3ccc(C#N)c(C(F)(F)F)c3F)C(=O)C2(C)C)cnc1OCCOCC(=O)N[C@H](C(=O)N1C[C@H](O)C[C@H]1C(=O)NCc1ccc(-c2scnc2C)cc1)C(C)(C)C] |
| A328 | 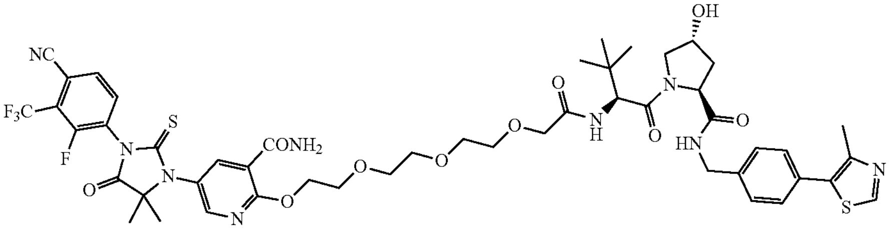 [SMILES: Cc1ncsc1-c1ccc(CNC(=O)[C@@H]2C[C@@H](O)CN2C(=O)[C@@H](NC(=O)COCCOCCOCCOc2ncc(N3C(=S)N(c4ccc(C#N)c(C(F)(F)F)c4F)C(=O)C3(C)C)cc2C(N)=O)C(C)(C)C)cc1] |

-continued
| Compound number | Compound structure |
| --- | --- |
| A329 | 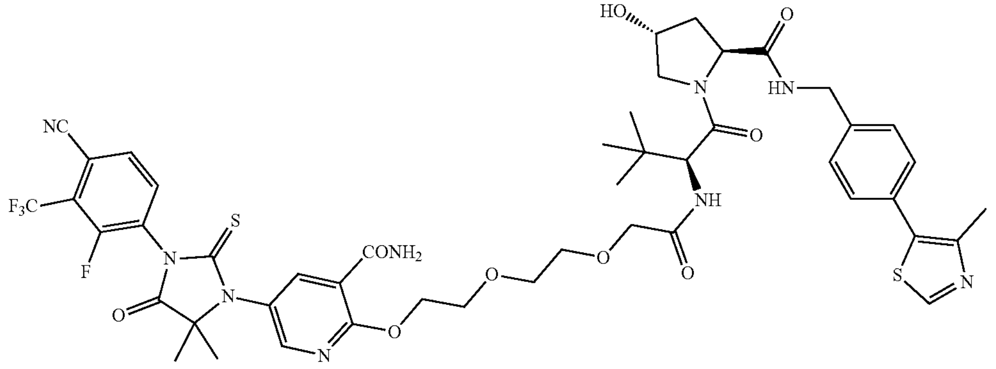 [SMILES: Cc1ncsc1-c1ccc(CNC(=O)[C@@H]2C[C@@H](O)CN2C(=O)[C@@H](NC(=O)COCCOCCOc2ncc(N3C(=S)N(c4ccc(C#N)c(C(F)(F)F)c4F)C(=O)C3(C)C)cc2C(N)=O)C(C)(C)C)cc1] |
| A330 | 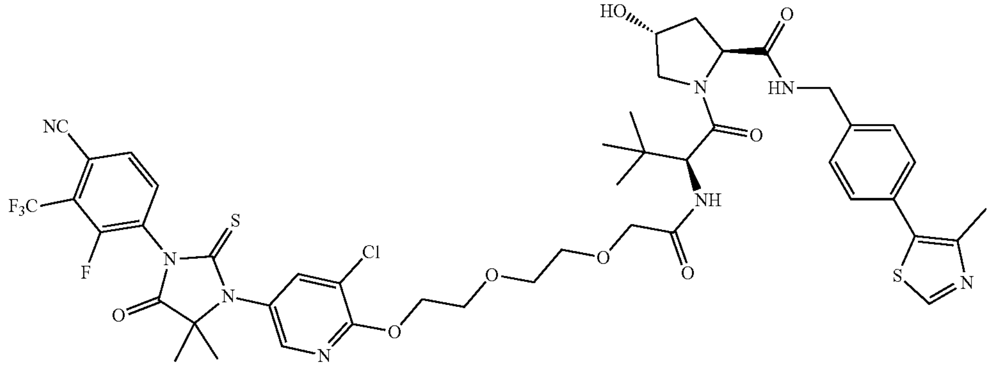 [SMILES: Cc1ncsc1-c1ccc(CNC(=O)[C@@H]2C[C@@H](O)CN2C(=O)[C@@H](NC(=O)COCCOCCOc2ncc(N3C(=S)N(c4ccc(C#N)c(C(F)(F)F)c4F)C(=O)C3(C)C)cc2Cl)C(C)(C)C)cc1] |
| A331 | 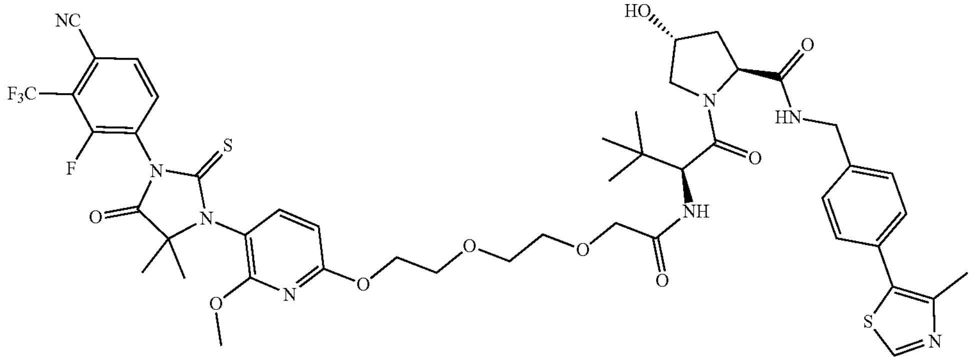 [SMILES: COc1nc(OCCOCCOCC(=O)N[C@H](C(=O)N2C[C@H](O)C[C@H]2C(=O)NCc2ccc(-c3scnc3C)cc2)C(C)(C)C)ccc1N1C(=S)N(c2ccc(C#N)c(C(F)(F)F)c2F)C(=O)C1(C)C] |
| A332 | 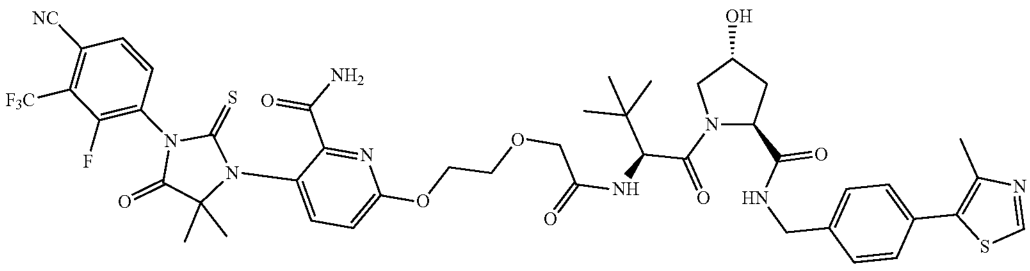 [SMILES: Cc1ncsc1-c1ccc(CNC(=O)[C@@H]2C[C@@H](O)CN2C(=O)[C@@H](NC(=O)COCCOc2ccc(N3C(=S)N(c4ccc(C#N)c(C(F)(F)F)c4F)C(=O)C3(C)C)c(C(N)=O)n2)C(C)(C)C)cc1] |

-continued
| Compound number | Compound structure |
| --- | --- |
| A333 | 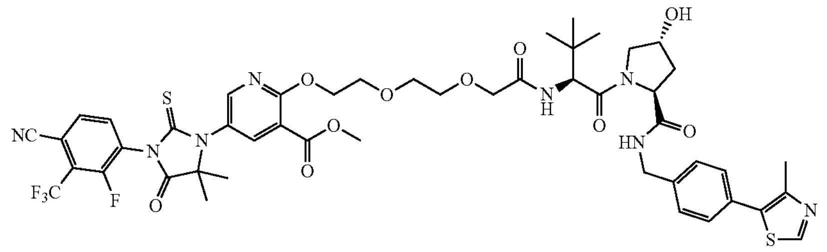 [SMILES: COC(=O)c1cc(N2C(=S)N(c3ccc(C#N)c(C(F)(F)F)c3F)C(=O)C2(C)C)cnc1OCCOCCOCC(=O)N[C@H](C(=O)N1C[C@H](O)C[C@H]1C(=O)NCc1ccc(-c2scnc2C)cc1)C(C)(C)C] |
| A334 | 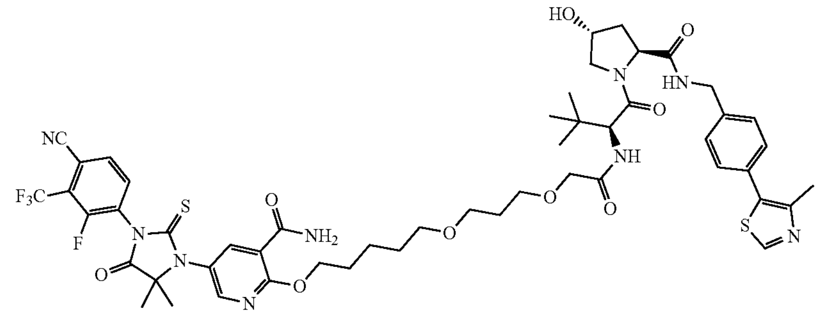 [SMILES: Cc1ncsc1-c1ccc(CNC(=O)[C@@H]2C[C@@H](O)CN2C(=O)[C@@H](NC(=O)COCCCOCCCCCOc2ncc(N3C(=S)N(c4ccc(C#N)c(C(F)(F)F)c4F)C(=O)C3(C)C)cc2C(N)=O)C(C)(C)C)cc1] |
| A335 | 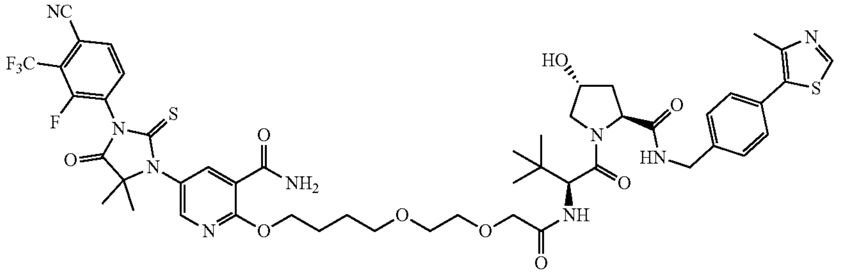 [SMILES: Cc1ncsc1-c1ccc(CNC(=O)[C@@H]2C[C@@H](O)CN2C(=O)[C@@H](NC(=O)COCCOCCCCOc2ncc(N3C(=S)N(c4ccc(C#N)c(C(F)(F)F)c4F)C(=O)C3(C)C)cc2C(N)=O)C(C)(C)C)cc1] |
| A336 | 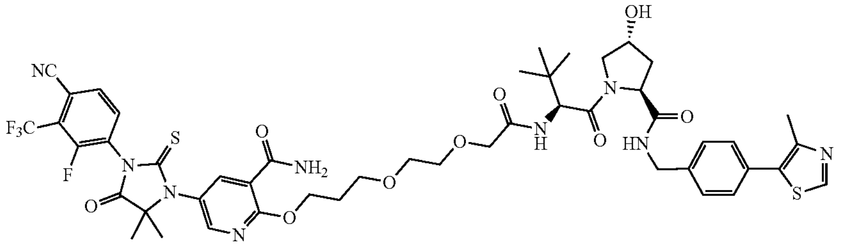 [SMILES: Cc1ncsc1-c1ccc(CNC(=O)[C@@H]2C[C@@H](O)CN2C(=O)[C@@H](NC(=O)COCCOCCCOc2ncc(N3C(=S)N(c4ccc(C#N)c(C(F)(F)F)c4F)C(=O)C3(C)C)cc2C(N)=O)C(C)(C)C)cc1] |
| A337 | 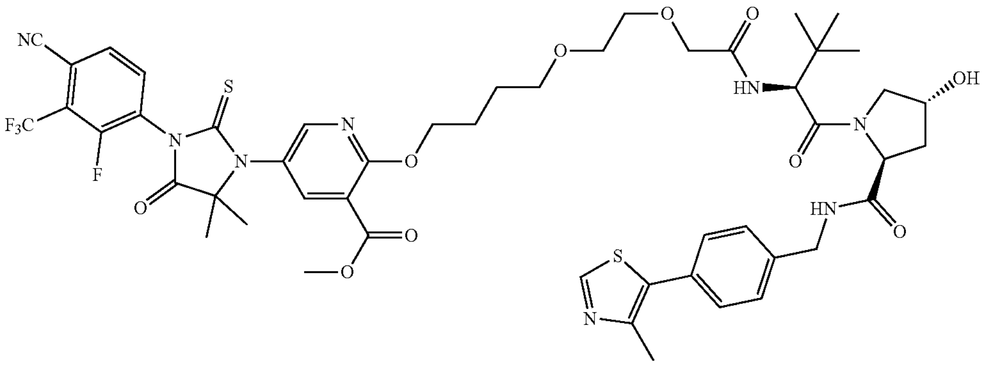 [SMILES: COC(=O)c1cc(N2C(=S)N(c3ccc(C#N)c(C(F)(F)F)c3F)C(=O)C2(C)C)cnc1OCCCCOCCOCC(=O)N[C@H](C(=O)N1C[C@H](O)C[C@H]1C(=O)NCc1ccc(-c2scnc2C)cc1)C(C)(C)C] |

-continued
| Compound number | Compound structure |
|---|---|
| A338 | 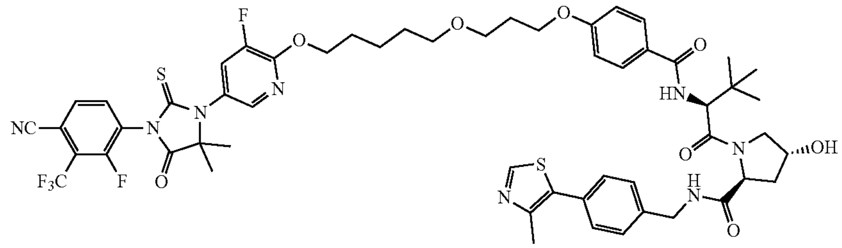 [SMILES: Cc1ncsc1-c1ccc(CNC(=O)[C@@H]2C[C@@H](O)CN2C(=O)[C@@H](NC(=O)c2ccc(OCCCOCCCCCOc3ncc(N4C(=S)N(c5ccc(C#N)c(C(F)(F)F)c5F)C(=O)C4(C)C)cc3F)cc2)C(C)(C)C)cc1] |
| A339 | 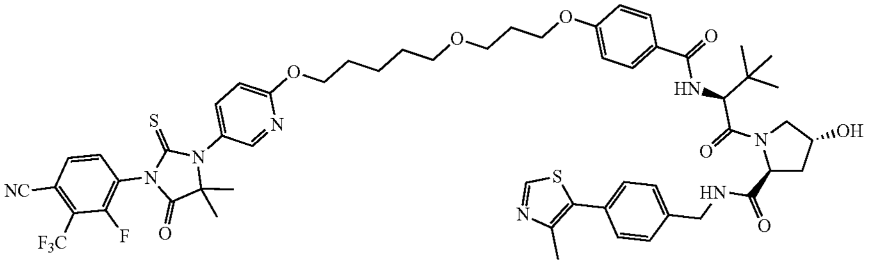 [SMILES: Cc1ncsc1-c1ccc(CNC(=O)[C@@H]2C[C@@H](O)CN2C(=O)[C@@H](NC(=O)c2ccc(OCCCOCCCCCOc3ccc(N4C(=S)N(c5ccc(C#N)c(C(F)(F)F)c5F)C(=O)C4(C)C)cn3)cc2)C(C)(C)C)cc1] |
| A340 | 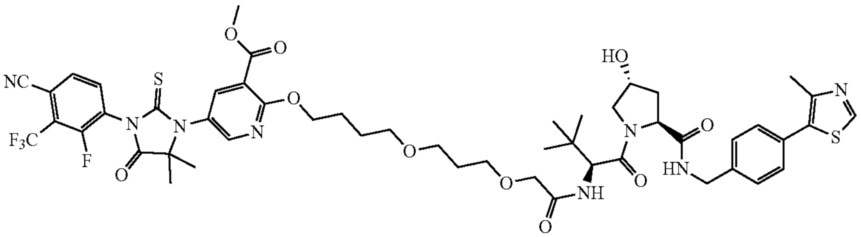 [SMILES: COC(=O)c1cc(N2C(=S)N(c3ccc(C#N)c(C(F)(F)F)c3F)C(=O)C2(C)C)cnc1OCCCCOCCCOCC(=O)N[C@H](C(=O)N1C[C@H](O)C[C@H]1C(=O)NCc1ccc(-c2scnc2C)cc1)C(C)(C)C] |
| A341 | 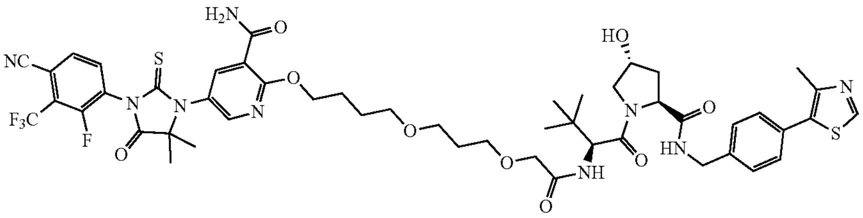 [SMILES: Cc1ncsc1-c1ccc(CNC(=O)[C@@H]2C[C@@H](O)CN2C(=O)[C@@H](NC(=O)COCCCOCCCCOc2ncc(N3C(=S)N(c4ccc(C#N)c(C(F)(F)F)c4F)C(=O)C3(C)C)cc2C(N)=O)C(C)(C)C)cc1] |
| A347 | 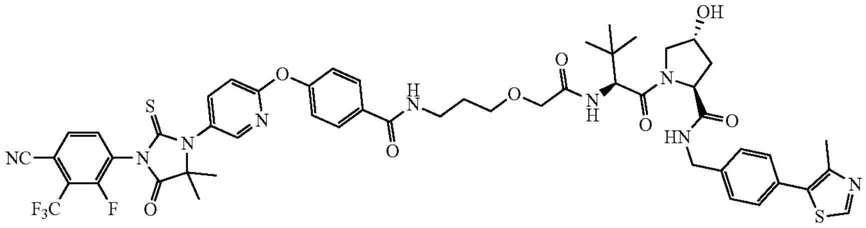 [SMILES: Cc1ncsc1-c1ccc(CNC(=O)[C@@H]2C[C@@H](O)CN2C(=O)[C@@H](NC(=O)COCCCNC(=O)c2ccc(Oc3ccc(N4C(=S)N(c5ccc(C#N)c(C(F)(F)F)c5F)C(=O)C4(C)C)cn3)cc2)C(C)(C)C)cc1] |
| A348 | 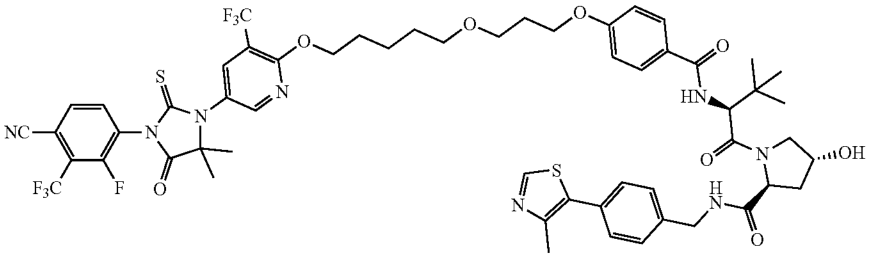 [SMILES: Cc1ncsc1-c1ccc(CNC(=O)[C@@H]2C[C@@H](O)CN2C(=O)[C@@H](NC(=O)c2ccc(OCCCOCCCCCOc3ncc(N4C(=S)N(c5ccc(C#N)c(C(F)(F)F)c5F)C(=O)C4(C)C)cc3C(F)(F)F)cc2)C(C)(C)C)cc1] |

-continued
| Compound number | Compound structure |
|---|---|
| A349 | 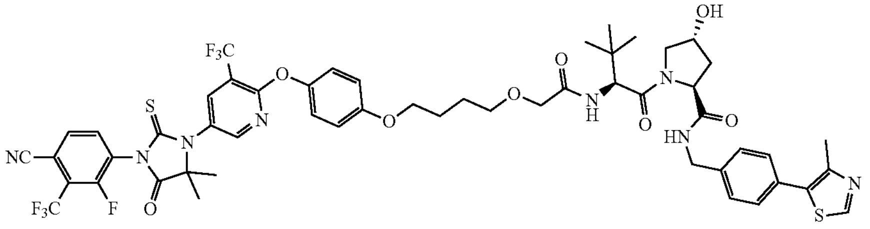 [SMILES: Cc1ncsc1-c1ccc(CNC(=O)[C@@H]2C[C@@H](O)CN2C(=O)[C@@H](NC(=O)COCCCCOc2ccc(Oc3ncc(N4C(=S)N(c5ccc(C#N)c(C(F)(F)F)c5F)C(=O)C4(C)C)cc3C(F)(F)F)cc2)C(C)(C)C)cc1] |
| A350 | 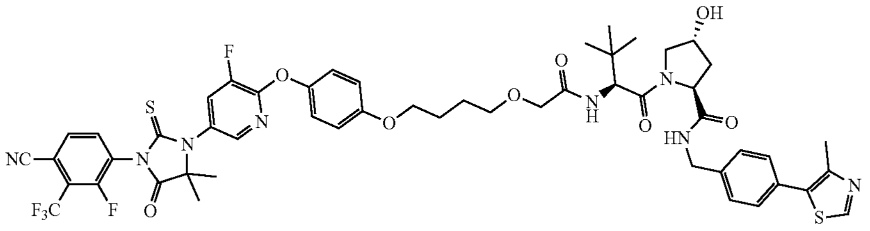 [SMILES: Cc1ncsc1-c1ccc(CNC(=O)[C@@H]2C[C@@H](O)CN2C(=O)[C@@H](NC(=O)COCCCCOc2ccc(Oc3ncc(N4C(=S)N(c5ccc(C#N)c(C(F)(F)F)c5F)C(=O)C4(C)C)cc3F)cc2)C(C)(C)C)cc1] |
| A351 | 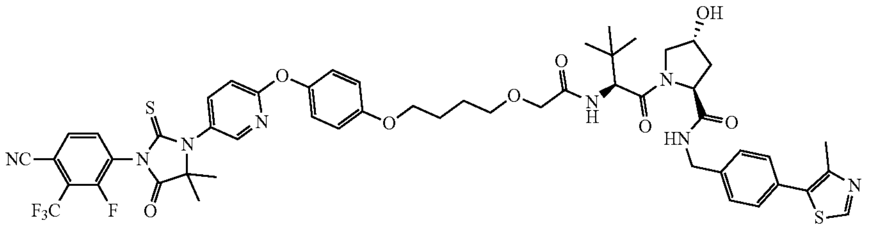 [SMILES: Cc1ncsc1-c1ccc(CNC(=O)[C@@H]2C[C@@H](O)CN2C(=O)[C@@H](NC(=O)COCCCCOc2ccc(Oc3ccc(N4C(=S)N(c5ccc(C#N)c(C(F)(F)F)c5F)C(=O)C4(C)C)cn3)cc2)C(C)(C)C)cc1] |
| A352 | 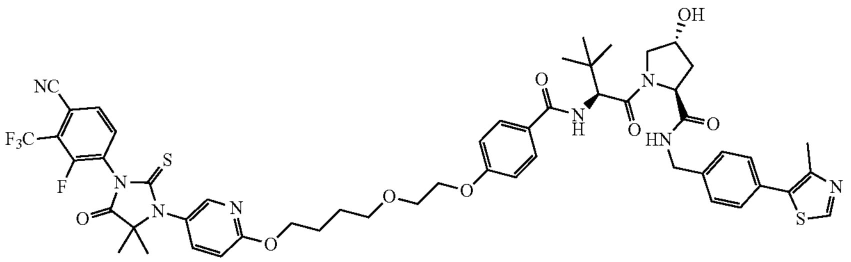 [SMILES: Cc1ncsc1-c1ccc(CNC(=O)[C@@H]2C[C@@H](O)CN2C(=O)[C@@H](NC(=O)c2ccc(OCCOCCCCOc3ccc(N4C(=S)N(c5ccc(C#N)c(C(F)(F)F)c5F)C(=O)C4(C)C)cn3)cc2)C(C)(C)C)cc1] |
| A353 | 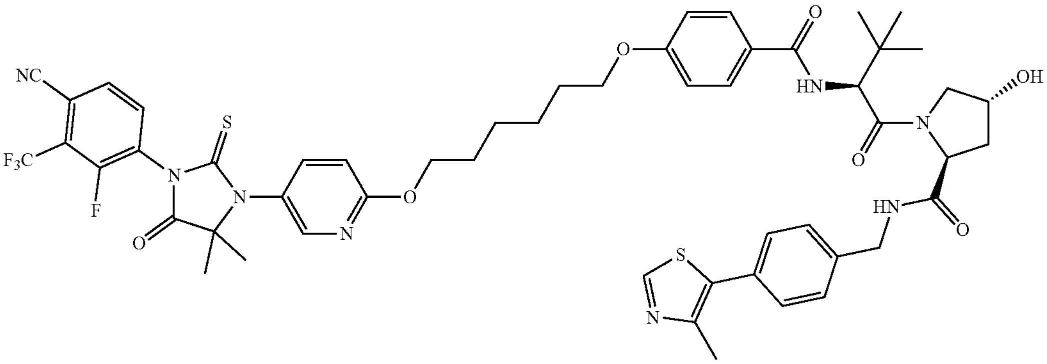 [SMILES: Cc1ncsc1-c1ccc(CNC(=O)[C@@H]2C[C@@H](O)CN2C(=O)[C@@H](NC(=O)c2ccc(OCCCCCCOc3ccc(N4C(=S)N(c5ccc(C#N)c(C(F)(F)F)c5F)C(=O)C4(C)C)cn3)cc2)C(C)(C)C)cc1] |
| A354 | 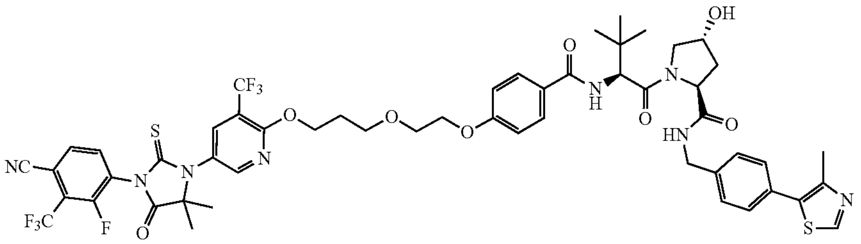 [SMILES: Cc1ncsc1-c1ccc(CNC(=O)[C@@H]2C[C@@H](O)CN2C(=O)[C@@H](NC(=O)c2ccc(OCCOCCCOc3ncc(N4C(=S)N(c5ccc(C#N)c(C(F)(F)F)c5F)C(=O)C4(C)C)cc3C(F)(F)F)cc2)C(C)(C)C)cc1] |

-continued
| Compound number | Compound structure |
| --- | --- |
| A355 | 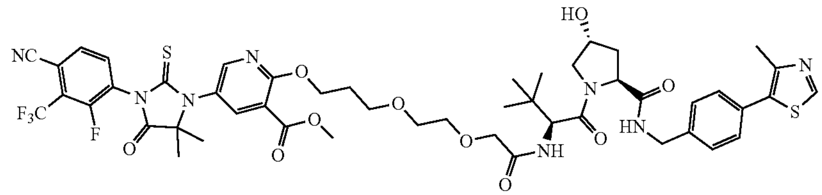 [SMILES: COC(=O)c1cc(N2C(=S)N(c3ccc(C#N)c(C(F)(F)F)c3F)C(=O)C2(C)C)cnc1OCCCOCCOCC(=O)N[C@H](C(=O)N1C[C@H](O)C[C@H]1C(=O)NCc1ccc(-c2scnc2C)cc1)C(C)(C)C] |
| A356 | 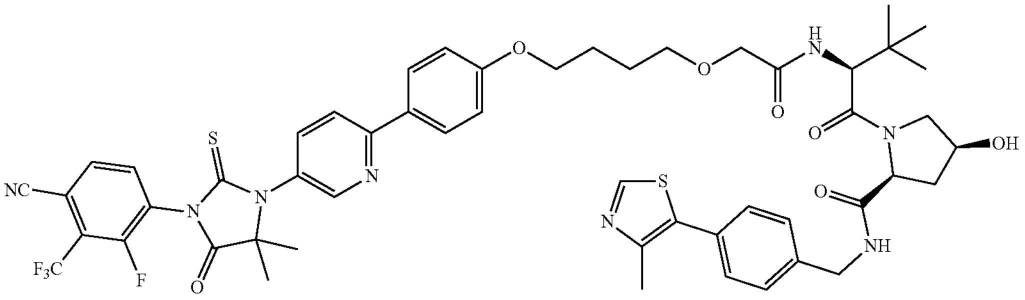 [SMILES: Cc1ncsc1-c1ccc(CNC(=O)[C@@H]2C[C@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2)C(C)(C)C)cc1] |
| A357 | 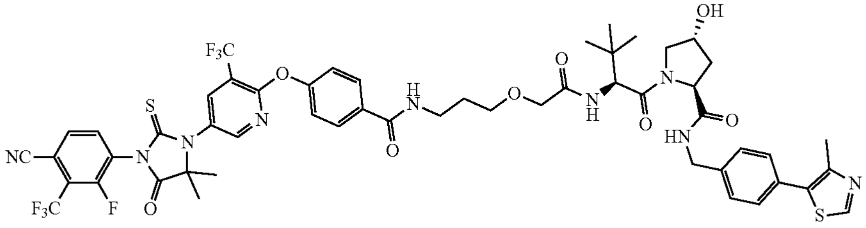 [SMILES: Cc1ncsc1-c1ccc(CNC(=O)[C@@H]2C[C@@H](O)CN2C(=O)[C@@H](NC(=O)COCCCNC(=O)c2ccc(Oc3ncc(N4C(=S)N(c5ccc(C#N)c(C(F)(F)F)c5F)C(=O)C4(C)C)cc3C(F)(F)F)cc2)C(C)(C)C)cc1] |
| A358 | 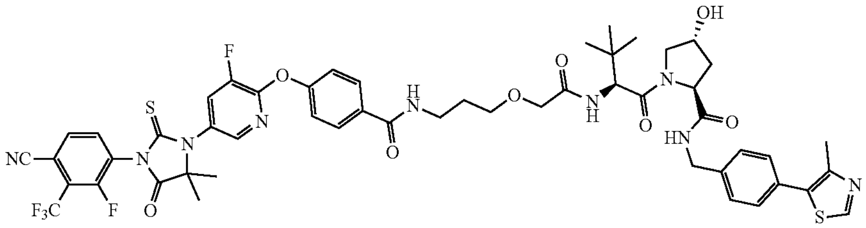 [SMILES: Cc1ncsc1-c1ccc(CNC(=O)[C@@H]2C[C@@H](O)CN2C(=O)[C@@H](NC(=O)COCCCNC(=O)c2ccc(Oc3ncc(N4C(=S)N(c5ccc(C#N)c(C(F)(F)F)c5F)C(=O)C4(C)C)cc3F)cc2)C(C)(C)C)cc1] |
| A359 | 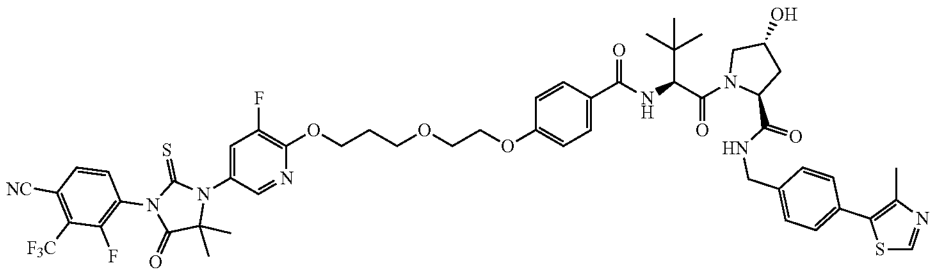 [SMILES: Cc1ncsc1-c1ccc(CNC(=O)[C@@H]2C[C@@H](O)CN2C(=O)[C@@H](NC(=O)c2ccc(OCCOCCCOc3ncc(N4C(=S)N(c5ccc(C#N)c(C(F)(F)F)c5F)C(=O)C4(C)C)cc3F)cc2)C(C)(C)C)cc1] |
| A360 | 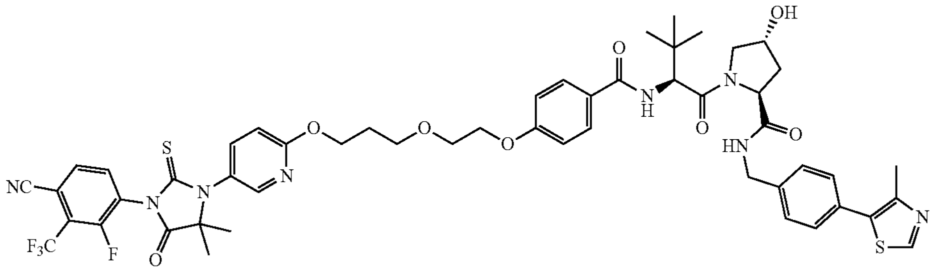 [SMILES: Cc1ncsc1-c1ccc(CNC(=O)[C@@H]2C[C@@H](O)CN2C(=O)[C@@H](NC(=O)c2ccc(OCCOCCCOc3ccc(N4C(=S)N(c5ccc(C#N)c(C(F)(F)F)c5F)C(=O)C4(C)C)cn3)cc2)C(C)(C)C)cc1] |

-continued

| Compound number | Compound structure |
| --- | --- |
| A361 | 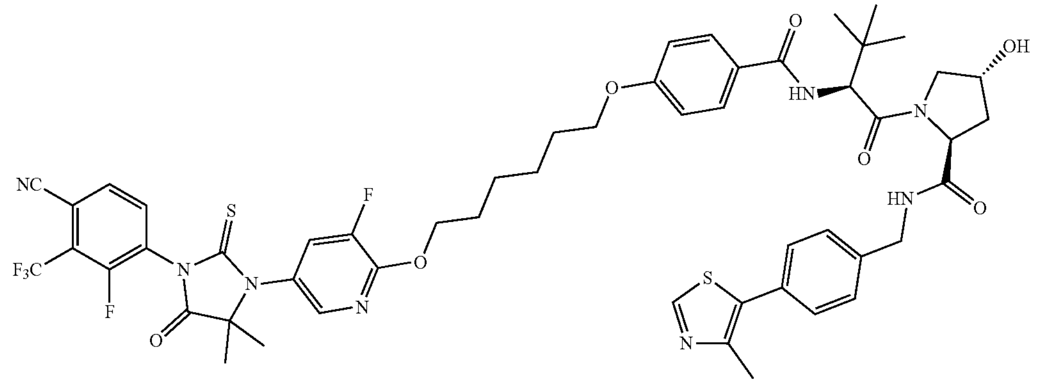 [SMILES: Cc1ncsc1-c1ccc(CNC(=O)[C@@H]2C[C@@H](O)CN2C(=O)[C@@H](NC(=O)c2ccc(OCCCCCCOc3ncc(N4C(=S)N(c5ccc(C#N)c(C(F)(F)F)c5F)C(=O)C4(C)C)cc3F)cc2)C(C)(C)C)cc1] |
| A362 | 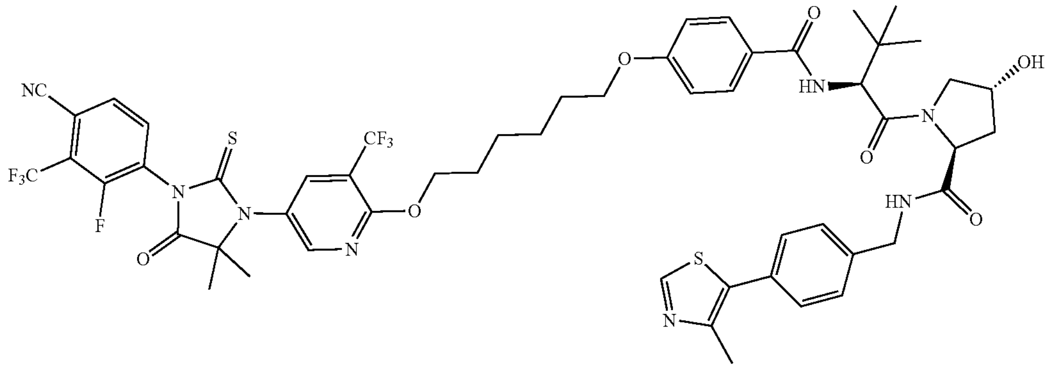 [SMILES: Cc1ncsc1-c1ccc(CNC(=O)[C@@H]2C[C@@H](O)CN2C(=O)[C@@H](NC(=O)c2ccc(OCCCCCCOc3ncc(N4C(=S)N(c5ccc(C#N)c(C(F)(F)F)c5F)C(=O)C4(C)C)cc3C(F)(F)F)cc2)C(C)(C)C)cc1] |

Another aspect of the present invention provides a composition comprising an effective amount of bifunctional compounds of the present invention and pharmaceutically acceptable carriers.

Pharmaceutically acceptable carriers of the present invention comprise ion exchangers, alumina, aluminum stearate, lecithin, serum proteins, buffer substances (e.g. phosphate, glycine, sorbic acid and potassium sorbate), partial glycerides mixture of saturated vegetable fatty acids, water, salt or electrolyte.

In one example, the active compound is prepared with carriers that protect the compounds from rapid elimination from the body, such as controlled release formulations, including implants and microencapsulated delivery systems. Biodegradable and biocompatible polymers can be used, such as ethylene vinyl acetate, polyanhydrides, polyglycolic acid, collagen, polyorthoesters, and polylactic acid. Methods for preparing such formulations are apparent to those skilled in the art.

Liposomal suspensions can also be pharmaceutically acceptable carriers, and liposomal formulations can be prepared as follows: appropriate lipid (e.g. stearoyl phosphatidyl ethanolamine, stearoyl phosphatidyl choline, arachidonoyl phosphatidyl choline and cholesterol) is dissolved in inorganic solvent and evaporated, leaving a film of dried lipid on the surface of the container. The aqueous solution of the active compound is then introduced into the container. Then the container is spun by hands to remove the lipid material from the sides of the container and to disperse the lipid aggregates, thereby forming liposomal suspension.

In the solution of the present invention, the composition further comprises at least one other biologically active agent.

In the solution of the present invention, the biologically active agent is an anticancer agent.

Another aspect of the present invention provides a therapeutic composition comprising an effective amount of at least two different compounds of the present invention.

Another aspect of the invention provides a method of recruiting endogenous proteins to E3 ubiquitin ligase for degradation in a subject in need thereof, the method comprising administering the compounds of the present invention.

Another aspect of the present invention provides a method of degrading or inhibiting androgen receptor in a subject in need thereof, the method comprising administering the compounds of the present invention.

Another aspect of the present invention provides a method of treating diseases or conditions in subjects, comprising the following steps: administrating a composition to a subject in need thereof, the composition comprising pharmaceutically acceptable carriers and an effective amount of the compounds of the present invention.

In some certain embodiments, the diseases or conditions are acne, hirsutism, sebaceous gland enlargement, alopecia, asthma, multiple sclerosis, cancer, Kenney's disease, ciliopathies, cleft palate, diabetes, heart disease, high blood pressure, inflammatory bowel disease, mental retardation, mood disorders, obesity, refractive errors, infertility, Angelman syndrome, Canavan disease, celiac disease, Charcot-Marie-Tooth disease, cystic fibrosis, Duchenne muscular dystrophy, hemochromatosis, hemophilia, Klinefelter's syndrome, neurofibromatosis, phenylketonuria, polycystic kidney disease (PKD1) or 4 (PKD2), Prader-Willi syndrome, sickle cell disease, Tay-Sachs disease, Turner syndrome. Among them, the cancers are squamous cell carcinoma, basal cell carcinoma, adenocarcinoma, hepatocellular carcinoma and renal cell carcinoma; cancers of bladder, bowel, breast, cervix, colon, esophagus, head, kidney, liver, lung, neck, ovary, pancreas, prostate and stomach; leukemia; benign and malignant lymphomas, especially Burkitt's lymphoma and Non-Hodgkin's lymphoma; benign and malignant melanoma; myeloproliferative diseases; sarcomas, including Ewing's sarcoma, hemangioendothelioma, Kaposi's sarcoma, liposarcoma, sarcoma, peripheral neuroepithelial tumor, synovial sarcoma, glioma, astrocytoma, oligodendroglioma, ependymoma, glioblastoma, neuroblastoma, ganglioglioma, medulloblastoma, pineal cell tumor, meningioma, meningiosarcoma, neurofibromas and Schwannomas; intestinal cancer, breast cancer, prostate cancer, cervix cancer, uterine cancer, lung cancer, ovarian cancer, testicular cancer, thyroid cancer, astrocytoma, esophageal cancer, pancreatic cancer, gastric cancer, liver cancer, colon cancer, melanoma; carcinosarcoma, Hodgkin's disease, Wilms tumor or teratoma.

In an embodiment of the present invention, the diseases or conditions are cancer, acne, hirsutism, sebaceous gland enlargement, alopecia, or Kennedy's disease.

In an embodiment of the present invention, the diseases or conditions are prostate cancer, acne, or alopecia.

In another aspect, the specification provides therapeutic compositions comprising an effective amount of the compounds of the present invention, or the salts form thereof, and pharmaceutically acceptable carriers. Therapeutic compositions modulate protein degradation in a patient or subject, and can be used to treat or ameliorate disease states or conditions modulated by the degradation of proteins. In some certain embodiments, the therapeutic compositions of the present invention can be used to achieve degradation and/or inhibition of proteins of interest in order to treat or ameliorate a disease such as cancer.

Definition

Unless otherwise defined, terms used herein have the same meaning as commonly understood by those of ordinary skill in the art. The terms used in the specification are only used to describe particular embodiments and are not intended to limit the present invention.

The term "hydrocarbyl" shall refer to compounds containing carbon and hydrogen, which may be fully saturated, partially unsaturated or aromatic and comprise aryl, alkyl, alkenyl and alkynyl.

The term "alkyl" in its context shall mean a straight-chain, branched-chain or cyclic fully saturated hydrocarbyl or alkyl which may be optionally substituted, preferably $C_1$-$C_{10}$, more preferably $C_1$-$C_6$, or $C_1$-$C_3$ alkyl. Examples of alkyl are methyl, ethyl, n-butyl, sec-butyl, n-hexyl, n-heptyl, n-octyl, n-nonyl, n-decyl, isopropyl, 2-methylpropyl, cyclopropyl cyclopropylmethyl, cyclobutyl, cyclopentyl, cyclopentylethyl, cyclohexylethyl, cyclohexyl, etc.

The term "alkenyl" refers to a straight-chain, branched-chain or cyclic $C_2$-$C_{10}$ (preferably $C_2$-$C_6$) hydrocarbyl containing at least one C═C bond.

The term "alkynyl" refers to a straight-chain, branched-chain or cyclic $C_2$-$C_{10}$ (preferably $C_2$-$C_6$) hydrocarbyl containing at least one C≡C bond.

The term "alkylene" as used refers to an optionally substituted $-(CH_2)_n-$ group (n is generally an integer 0-6). When substituted, alkylene is preferably substituted on one or more methylene with $C_1$-$C_6$ alkyl (including cyclopropyl or tert-butyl), and may be substituted with one or more halogen groups (preferably 1 to 3 halogen groups) or one or two hydroxyl or $C_{1-6}$ alkyloxy.

The term "unsubstituted" shall mean substitution with hydrogen atoms only.

The term "substituted" or "optionally substituted" refers to the presence of one or more substituents at any carbon (or nitrogen) position in the molecule, preferably 1-5 substituents, and most preferably 1-3 substituents. The substituents can be: hydroxyl, thiol, carboxyl, cyano, nitro, halogen (preferably, 1, 2 or 3 halogens, especially on alkyl, especially methyl, such as trifluoromethyl), alkyl (preferably $C_1$-$C_{10}$, more preferably $C_1$-$C_6$), haloalkyl, aryl (especially phenyl and substituted phenyl, such as benzyl or benzoyl), alkoxy (preferably $C_1$-$C_6$ alkyl or aryl, including phenyl and substituted phenyl), thioether ($C_1$-$C_6$ alkyl or aryl), acyl (preferably $C_1$-$C_6$ acyl), $C_1$-$C_6$ alkylamine, $C_1$-$C_6$ dialkylamine, amide groups substituted with one or two $C_1$-$C_6$ alkyl (including carboxamides optionally substituted with one or two $C_1$-$C_6$ alkyl), carboxyl, $C_1$-$C_6$ esters, etc.

The term "aryl" refers to a substituted or unsubstituted $C_6$-$C_{16}$ aromatic group, preferably $C_6$-$C_{10}$ aromatic group comprising a single ring (e.g. phenyl) or a fused ring (e.g. naphthyl, anthracenyl, phenanthrenyl, etc.).

The term "heteroaryl" refers to a 5-16 membered aromatic group comprising at least one heteroatom (e.g. N, O or S), preferably a 5-10 membered aromatic group, and can refer to an optionally substituted quinoline, optionally substituted indole, optionally substituted indolizine, optionally substituted azaindolizine, optionally substituted benzimidazole, benzodiazole, benzofuran, optionally substituted imidazole, optionally substituted isoxazole, optionally substituted oxazole (preferably substituted with methyl), optionally substituted diazole, optionally substituted triazole, tetrazole, optionally substituted benzofuran, optionally substituted thiophene, optionally substituted thiazole (preferably substituted with methyl and/or thiol), optionally substituted isothiazole, optionally substituted triazole, optionally substituted pyridine (2-pyridine, 3-pyridine or 4-pyridine).

The terms "aralkyl" and "heteroarylalkyl" refer to groups comprising aryl or heteroaryl, respectively, as well as alkyl and/or heteroalkyl and/or carbocyclic ring and/or heterocyclic alkyl ring system as defined above.

The term "heterocyclyl" refers to a 3-10 membered cyclic group containing at least one heteroatom (e.g. N, O, or S), preferably 3-6 membered cyclic group, and can be aromatic (heteroaryl) or non-aromatic. It comprises: azetidinyl, benzimidazolyl, 1,4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolane, 1,3-dioxane, 1,4-dioxane, furanyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyl, quinolyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane, etc.

The term "cycloalkyl" refers to a $C_3$-$C_{20}$ monocyclic or polycyclic alkyl group, preferably a $C_3$-$C_{15}$ monocyclic or polycyclic alkyl group, most preferably a $C_3$-$C_{10}$ monocyclic or polycyclic alkyl group, including cyclopropyl, cyclobutyl, cyclopentyl, cyclohexyl, cycloheptyl, etc.

"Heterocycloalkyl" refers to a 3-20 membered monocyclic or polycyclic alkyl group, preferably a 3-15 membered monocyclic or polycyclic alkyl group, and most preferably a 3-10 membered monocyclic or polycyclic alkyl group, wherein at least one ring carbon atom in its ring structure is replaced by a heteroatom selected from the group consisting of N, O, S or P.

"Halogen" refers to F, Cl, Br, I.

The term "pharmaceutically acceptable salt" is used to describe the salt form of one or more of the compounds described herein, which is provided to increase the solubility of the compounds in the gastric juices of the patient's gastrointestinal tract in order to facilitate dissolution and bioavailability of the compounds. Pharmaceutically acceptable salts comprise, where applicable, those derived from pharmaceutically acceptable inorganic or organic bases and acids. Suitable salts comprise those derived from alkaline metals (e.g. potassium and sodium), alkaline earth metals (e.g. calcium, magnesium, and ammonium salts), and many other acids and bases well known in the pharmaceutical arts.

The acids used to prepare the pharmaceutically acceptable acid addition salts suitable for use in the present invention are those that form non-toxic acid addition salts, i.e., salts containing pharmacologically acceptable anion, such as hydrochloride, hydrobromide, hydroiodide, nitrate, sulfate, bisulfate, phosphate, acid phosphate, acetate, lactate, citrate, acid citrate, tartrate, tartrate, bitartrate, succinate, maleate, fumarate, gluconate, glucarate, benzoate, methanesulfonate, ethanesulfonate, benzenesulfonate, p-toluenesulfonate, and pamoate, and various other salts.

The term "effective" can mean, but is not limited to the amount/dose of the active pharmaceutical ingredient. When it is used in the context of its intended use, it achieves or sufficiently prevents conditions, disorders or disease states in subjects who need or have received such treatment, and inhibits the occurrence thereof, and ameliorates, delays or treats the symptoms thereof (to a certain extent, preferably completely relieving symptoms).

The term "pharmaceutically acceptable carrier" can mean any and all solvents, dispersion media, coatings, antibacterial agents and the like, which are compatible with pharmaceutical administration.

Unless otherwise indicated, the term "compound" refers to any specific compound disclosed herein and comprises tautomers, regioisomers, geometric isomers, and, where applicable, stereoisomers, including optical isomers (enantiomers) and other stereoisomers (diastereomers), as well as pharmaceutically acceptable salts and derivatives thereof (including prodrug forms). When used in this context, the term compound generally not only refers to a single compound, but also may comprise other compounds, such as stereoisomers, regioisomers, and/or optical isomers (including racemic mixtures), as well as the specific enantiomers or enantiomerically enriched mixtures of the disclosed compounds. The term in this context also refers to prodrug forms of the compounds that have been modified to facilitate administration and delivery to the active site of the compounds.

BRIEF DESCRIPTION OF THE DRAWINGS

The drawings of the present invention illustrate several embodiments of the present invention, and together with the specification serve to explain the principles of the present invention. The drawings are only for purposes of illustrating examples of the present invention, and are not to be construed as limiting the present invention. In conjunction with the illustrative drawings showing embodiments of the present invention, other objects, features and advantages of the present invention will become apparent from the following detailed description, wherein.

DETAILED DESCRIPTION OF EMBODIMENTS

Figure 1:
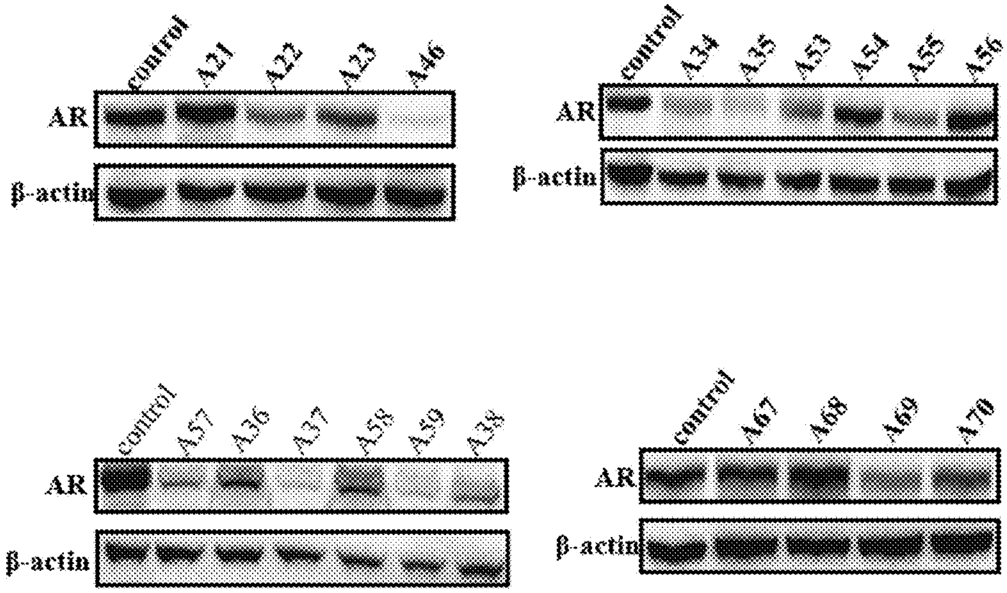
FIG. 1 is the result of the degradation experiment of the compounds of the present invention on AR protein in LNCaP cells.

The present invention will be exemplified below in conjunction with the drawings and further detailed description. It should be noted that the following descriptions are merely examples of the technical solutions claimed in the present invention, and are not intended to limit these technical solutions. The protection scope of the present invention is subjected to the contents described in the appended claims.

1. PREPARATION OF EXAMPLES

Synthesis of ABM-L-CLM

Example A1

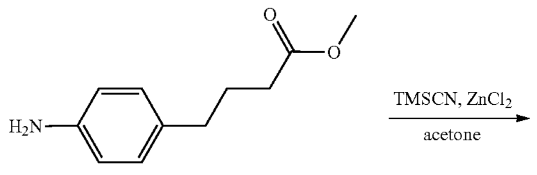

1-1

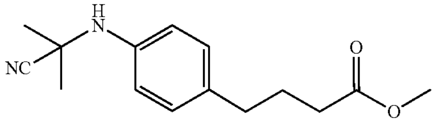

1-2

1-1 (2 g, 10 mmol), TMSCN (3 g, 30 mmol) and $ZnCl_2$ (136 mg, 1 mmol) were added to 50 ml of acetone successively, to react at room temperature for 1 h. After the reaction was completed, the obtained product was washed with 100 ml of water, extracted with 100 ml of EA, washed with 50 ml of saturated brine, dried over anhydrous sodium sulfate and rotating-dried to obtain 2.3 g of product 1-2 with a yield of 88%, and the product was directly used in the next step without purification.

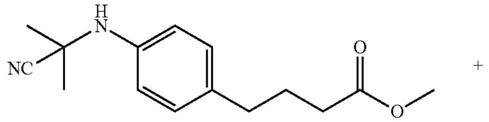

+

1-2

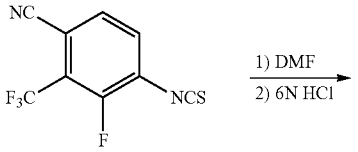

1-3

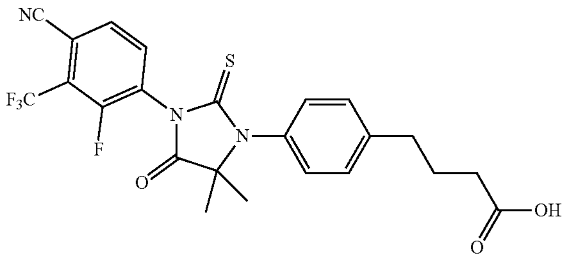

1-4

1-2 (2.3 g, 8.8 mmol) and 1-3 (4.3 g, 17.6 mmol) were added to 10 ml of DMF successively, to react at room temperature overnight. After the reaction was completed, 20 ml of methanol and 20 ml of 6N HCl were added, to react at 90° C. for 1 h. After the reaction was completed, the obtained product was washed with 50 ml of water, extracted with 50 ml of EA, washed with 20 ml of saturated brine, dried over anhydrous sodium sulfate, rotating-dried and loaded on the chromatographic column with PE:EA=5:1-2:1 to obtain 400 mg of product 1-4 with a yield of 9.2%.

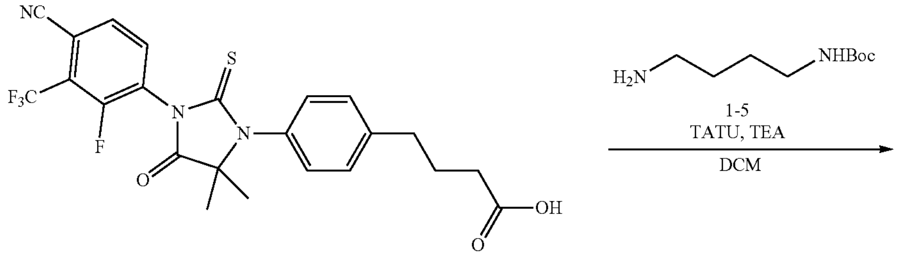

1-4

-continued

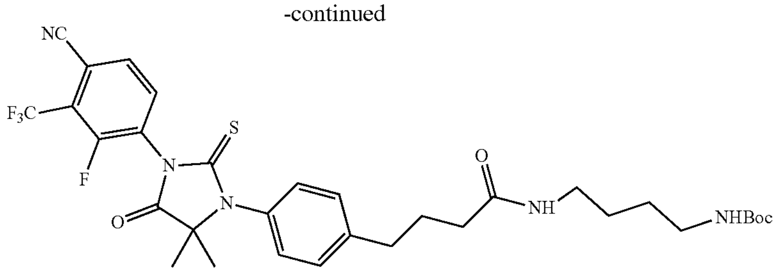

1-6

1-4 (300 mg, 0.6 mmol), 1-5 (112 mg, 0.6 mmol), HATU (456 mg, 1.2 mmol), and triethylamine (0.2 ml, 1.2 mmol) were successively added to 10 ml DCM, and stirred at room temperature for one hour. After the reaction was completed, the obtained product was washed with 50 ml of water, extracted with 50 ml of DCM, washed with 20 ml of saturated brine, dried over anhydrous sodium sulfate, and rotating-evaporated, and loaded on a thick preparative plate with DCM:MeOH=15:1 to obtain 150 mg of product 1-6 with a yield of 37%.

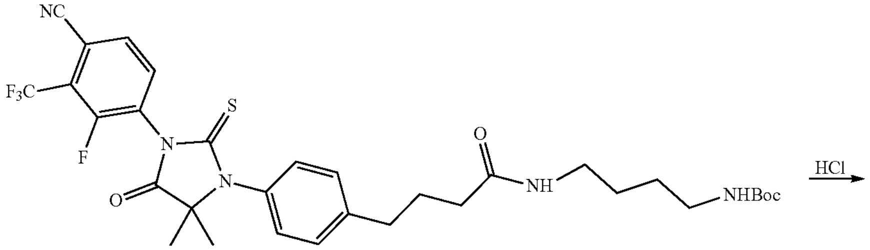

1-6

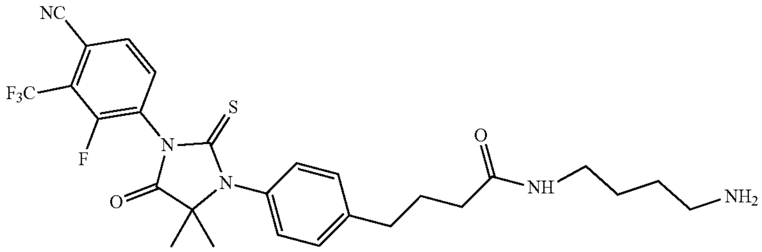

1-7

1-6 (150 mg) was added into 2 ml THF. The mixture was cooled to 0° C., provided with HCl gas, and reacted at 0° C. for 2 h. After the reaction was completed, the obtained product was adjusted at pH=8 with saturated sodium bicarbonate solution, extracted with 20 ml EA, washed with 10 ml saturated saline, dried over anhydrous sodium sulfate, and rotating-dried to obtain 80 mg of product 1-7 with a yield of 63%.

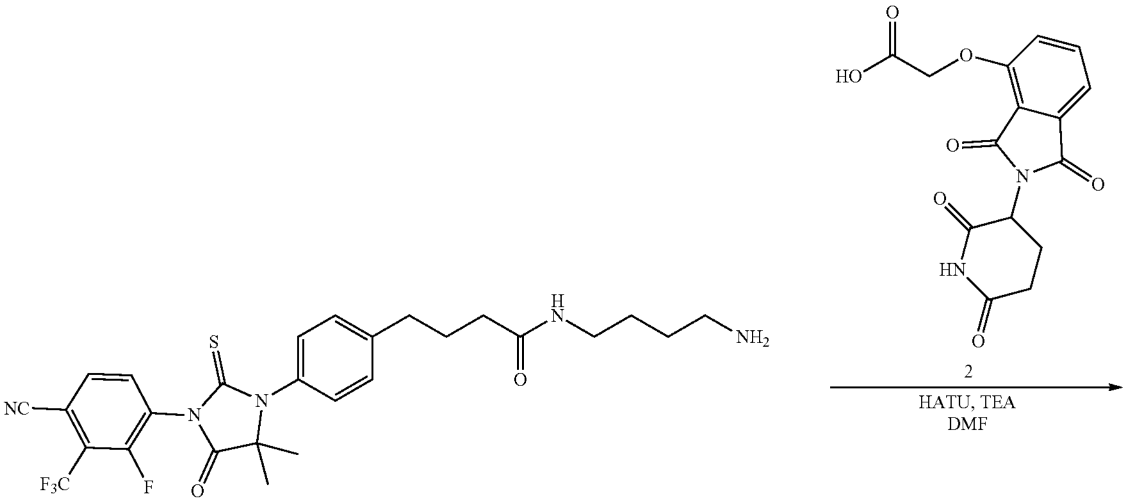

1-7

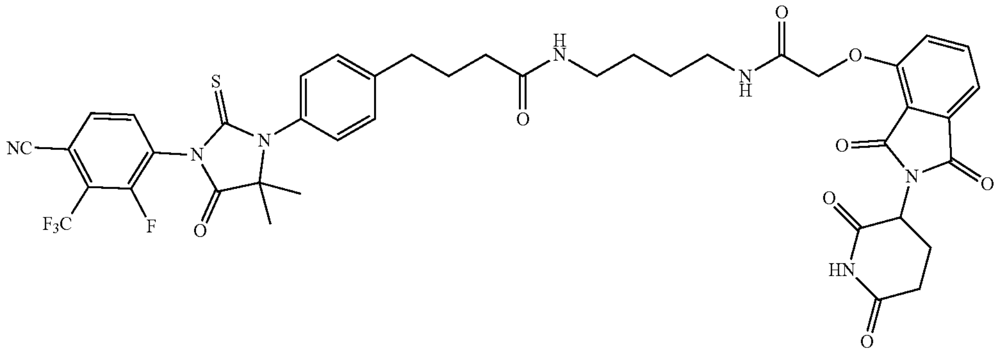

A1

1-7 (80 mg, 0.14 mmol), 2 (46 mg, 0.14 mmol), HATU (106 mg, 0.28 mmol), and triethylamine (28 mg, 0.28 mmol) were added to 5 ml of DMF successively, stirred at room temperature for one hour. After the reaction was completed, the obtained product was washed with 20 ml of water, extracted with 20 ml of EA, washed with 20 ml of saturated brine, dried over anhydrous sodium sulfate, rotating-evaporated, and loaded on a preparative plate with DCM: MeOH=10:1 to obtain 50 mg, and then on a preparative HPLC to obtain 25 mg of white solid A1 with a purity of 97.5% and a yield of 20%.

LCMS ($[M+H]^+$): 878.2

$^1$HNMR (400 MHz, DMSO-d6) δ11.13 (s, 1H), 8.39-8.21 (m, 2H), 7.99 (t, J=5.7 Hz, 1H), 7.82 (dd, J=13.9, 6.6 Hz, 2H), 7.50 (d, J=7.2 Hz, 1H), 7.37 (s, 3H), 7.32 (d, J=8.4 Hz, 2H), 5.13 (dd, J=12.9, 5.4 Hz, 1H), 4.77 (s, 2H), 3.15 (d, J=5.9 Hz, 2H), 3.05 (d, J=5.9 Hz, 2H), 3.01-2.83 (m, 1H), 2.62 (dd, J=18.9, 11.2 Hz, 3H), 2.13 (t, J=7.4 Hz, 2H), 2.03 (dd, J=25.3, 10.3 Hz, 2H), 1.85 (dd, J=15.2, 7.4 Hz, 2H), 1.50 (d, J=4.2 Hz, 6H), 1.43 (s, 4H).

Examples A2-A45 were synthesized with the corresponding reagents using similar procedures to Example A1.

Example A2

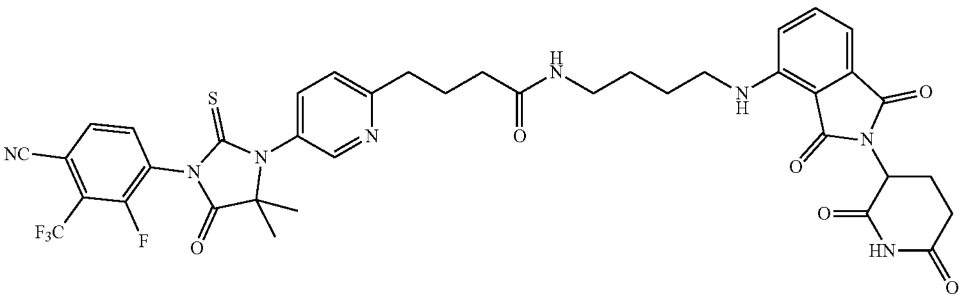 [SMILES: CC1(C)C(=O)N(c2ccc(C#N)c(C(F)(F)F)c2F)C(=S)N1c1ccc(CCCC(=O)NCCCCNc2cccc3c2C(=O)N(C2CCC(=O)NC2=O)C3=O)nc1]

LCMS ([M+H]+): 820.2
1HNMR (400 MHz, DMSO-d6) δ11.11 (s, 1H), 8.53 (d, J=2.4 Hz, 1H), 8.33-8.23 (m, 2H), 7.87 (t, J=5.6 Hz, 1H), 7.82 (dd, J=8.3, 2.5 Hz, 1H), 7.59-7.52 (m, 1H), 7.45 (t, J=9.8 Hz, 1H), 7.11 (d, J=8.6 Hz, 1H), 7.01 (d, J=7.0 Hz, 1H), 6.58 (t, J=5.9 Hz, 1H), 5.05 (dd, J=12.8, 5.4 Hz, 1H), 3.31 (s, 2H), 3.09 (dd, J=12.4, 6.3 Hz, 2H), 2.96-2.70 (m, 4H), 2.62-2.53 (m, 2H), 2.15 (t, J=7.4 Hz, 2H), 2.10-1.90 (m, 4H), 1.53 (s, 6H), 1.47 (d, J=7.3 Hz, 2H).
Example A3
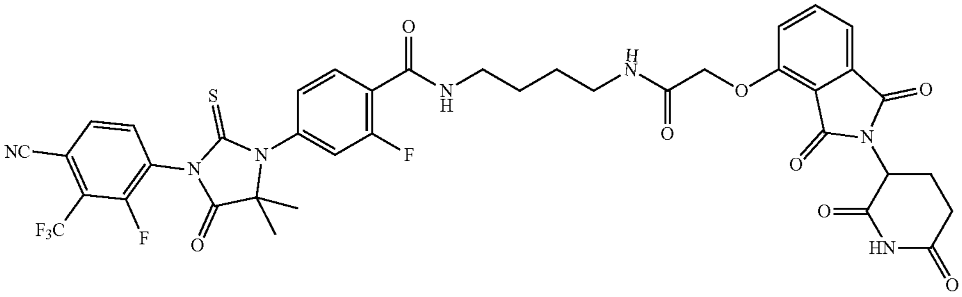 [SMILES: CC1(C)C(=O)N(c2ccc(C#N)c(C(F)(F)F)c2F)C(=S)N1c1ccc(C(=O)NCCCCNC(=O)COc2cccc3c2C(=O)N(C2CCC(=O)NC2=O)C3=O)c(F)c1]
LCMS ([M+H]+): 854.2
1HNMR (400 MHz, DMSO-d6) δ11.13 (s, 1H), 8.54 (t, J=5.4 Hz, 1H), 8.30-8.22 (m, 2H), 8.02 (t, J=5.7 Hz, 1H), 7.81 (dd, J=8.4, 7.4 Hz, 1H), 7.75 (t, J=8.0 Hz, 1H), 7.52 (dd, J=10.6, 1.8 Hz, 1H), 7.49 (d, J=7.2 Hz, 1H), 7.37 (m, 2H), 5.12 (dd, J=12.9, 5.4 Hz, 1H), 4.78 (s, 2H), 3.27 (d, J=5.5 Hz, 2H), 3.19 (d, J=5.7 Hz, 2H), 2.95-2.83 (m, 1H), 2.63-2.51 (m, 2H), 2.06-1.96 (m, 1H), 1.55 (d, J=1.7 Hz, 6H), 1.52 (m, 4H).
Example A4
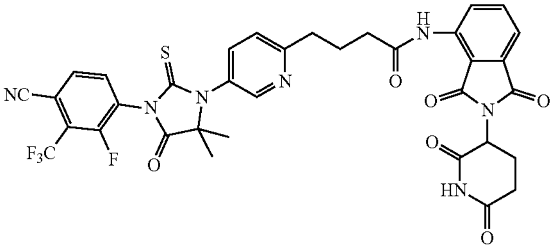 [SMILES: CC1(C)C(=O)N(c2ccc(C#N)c(C(F)(F)F)c2F)C(=S)N1c1ccc(CCCC(=O)Nc2cccc3c2C(=O)N(C2CCC(=O)NC2=O)C3=O)nc1]
LCMS ([M+H]+): 750.3
1HNMR (400 MHz, DMSO-d6) δ11.18 (s, 1H), 9.80 (s, 1H), 8.54 (d, J=2.4 Hz, 1H), 8.45 (d, J=8.4 Hz, 1H), 8.32-8.25 (m, 2H), 7.83 (m, 2H), 7.63 (d, J=7.3 Hz, 1H), 7.52 (d, J=8.2 Hz, 1H), 5.15 (dd, J=12.8, 5.3 Hz, 1H), 2.97-2.81 (m, 4H), 2.58 (m, 4H), 2.08 (m, 2H), 1.52 (s, 6H).
Example A5
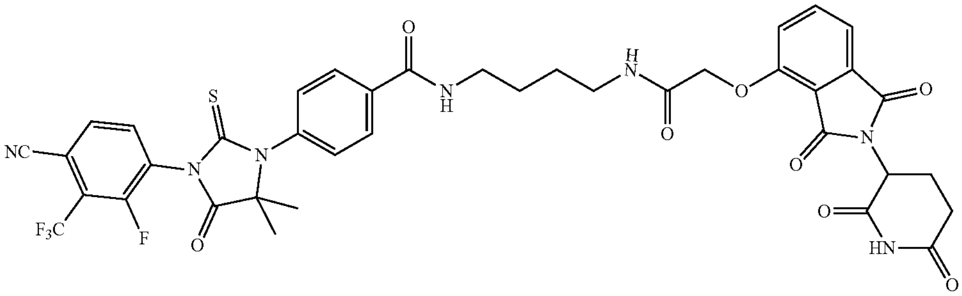 [SMILES: CC1(C)C(=O)N(c2ccc(C#N)c(C(F)(F)F)c2F)C(=S)N1c1ccc(C(=O)NCCCCNC(=O)COc2cccc3c2C(=O)N(C2CCC(=O)NC2=O)C3=O)cc1]

LCMS ([M+H]$^+$): 835.3
$^1$HNMR (400 MHz, DMSOd6) δ11.12 (s, 1H), 8.63 (t, J=5.6 Hz, 1H), 8.26 (s, 2H), 8.02 (d, J=5.8H z, 1H), 7.98 (d, J=8.4 Hz, 2H), 7.79 (t, J=7.9 Hz, 1H), 7.52 (d, J=8.2 Hz, 2H), 7.46 (d, J=7.2 Hz, 1H), 7.36 (d, J=8.5 Hz, 1H), 5.14-5.07 (m, 1H), 4.76 (s, 2H), 3.27 (d, J=6.0 Hz, 2H), 3.17 (t, J=6.4 Hz, 2H), 2.89-2.81 (m, 1H), 2.62-2.49 (m, 2H), 1.99 (t, J=7.6 Hz, 1H), 1.51 (d, J=2.3 Hz, 10H).
Example A6
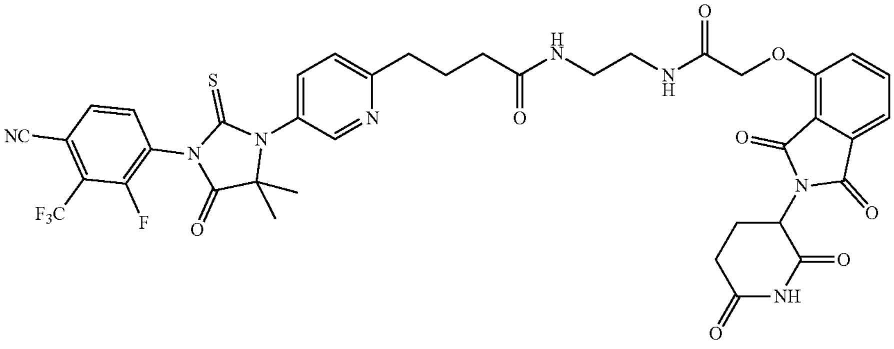 [SMILES: CC1(C)C(=O)N(c2ccc(C#N)c(C(F)(F)F)c2F)C(=S)N1c1ccc(CCCC(=O)NCCNC(=O)COc2cccc3c2C(=O)N(C2CCC(=O)NC2=O)C3=O)nc1]
LCMS ([M+H]$^+$): 851.2
$^1$HNMR (400 MHz, DMSO-d6) δ11.13 (s, 1H), 8.52 (d, J=2.4 Hz, 1H), 8.33-8.23 (m, 2H), 8.07 (t, J=5.6 Hz, 1H), 7.92 (t, J=5.4 Hz, 1H), 7.85-7.75 (m, 2H), 7.47 (dd, J=11.8, 7.8 Hz, 2H), 7.39 (d, J=8.5 Hz, 1H), 5.12 (dd, J=12.9, 5.3 Hz, 1H), 4.77 (s, 2H), 3.24-3.17 (m, 2H), 3.17-3.11 (m, 2H), 2.81-2.74 (m, 2H), 2.13 (t, J=7.4 Hz, 2H), 2.06-1.86 (m, 6H), 1.52 (s, 6H).
Example A7
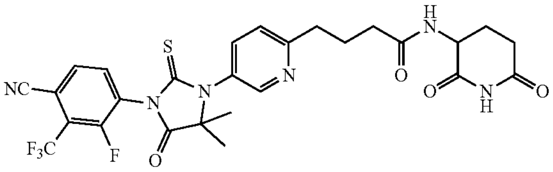 [SMILES: CC1(C)C(=O)N(c2ccc(C#N)c(C(F)(F)F)c2F)C(=S)N1c1ccc(CCCC(=O)NC2CCC(=O)NC2=O)nc1]
LCMS ([M+H]$^+$): 605.2
$^1$HNMR (400 MHz, DMSO-d6) δ10.81 (s, 1H), 8.53 (d, J=2.4 Hz, 1H), 8.32-8.20 (m, 3H), 7.82 (dd, J=8.3, 2.5 Hz, 1H), 7.49 (d, J=8.3 Hz, 1H), 4.56 (dd, J=18.0, 7.9 Hz, 1H), 2.88-2.80 (m, 2H), 2.77-2.68 (m, 1H), 2.47 (d, J=3.3 Hz, 1H), 2.23 (t, J=7.4 Hz, 2H), 2.00-1.89 (m, 4H), 1.53 (s, 6H).
Example A8
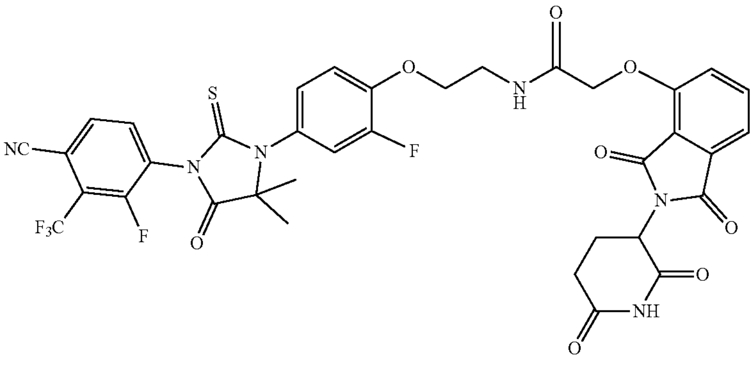 [SMILES: CC1(C)C(=O)N(c2ccc(C#N)c(C(F)(F)F)c2F)C(=S)N1c1ccc(OCCNC(=O)COc2cccc3c2C(=O)N(C2CCC(=O)NC2=O)C3=O)c(F)c1]

LCMS ($[M+H]^+$): 799.2

$^1$HNMR (400 MHz, DMSO-d6) δ11.14 (s, 1H), 8.33 (t, J=5.7 Hz, 1H), 8.29-8.22 (m, 2H), 7.74 (dd, J=8.4, 7.4 Hz, 1H), 7.47 (d, J=7.2 Hz, 1H), 7.42 (dd, J=11.7, 2.0 Hz, 1H), 7.39-7.32 (m, 2H), 7.21 (d, J=8.8 Hz, 1H), 5.12 (dd, J=12.8, 5.4 Hz, 1H), 4.84 (s, 2H), 4.20 (t, J=5.4 Hz, 2H), 3.60 (d, J=3.2 Hz, 2H), 2.95-2.84 (m, 1H), 2.60 (d, J=18.0 Hz, 1H), 2.08-1.92 (m, 2H), 1.52 (s, 6H).

Example A9

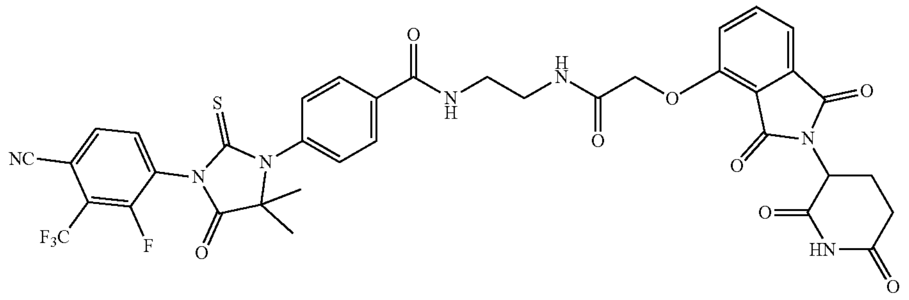 [SMILES: CC1(C)C(=O)N(c2ccc(C#N)c(C(F)(F)F)c2F)C(=S)N1c1ccc(C(=O)NCCNC(=O)COc2cccc3c2C(=O)N(C2CCC(=O)NC2=O)C3=O)cc1]

LCMS ($[M+H]^+$): 808.3

$^1$HNMR (400 MHz, DMSOd6) δ11.14 (s, 1H), 8.68 (t, J=5.3 Hz, 1H), 8.29 (d, J=5.2 Hz, 2H), 8.20 (t, J=5.6 Hz, 1H), 8.00-7.95 (m, 2H), 7.77-7.72 (m, 1H), 7.56-7.51 (m, 2H), 7.45 (dd, J=7.2, 2.7 Hz, 1H), 7.37 (d, J=8.6 Hz, 1H), 5.18-5.07 (m, 2H), 4.80 (s, 2H), 3.39 (d, J=7.8 Hz, 2H), 2.87 (d, J=17.1 Hz, 2H), 2.64-2.52 (m, 2H), 2.06-1.98 (m, 1H), 1.54 (d, J=2.0 Hz, 6H).

Example A10

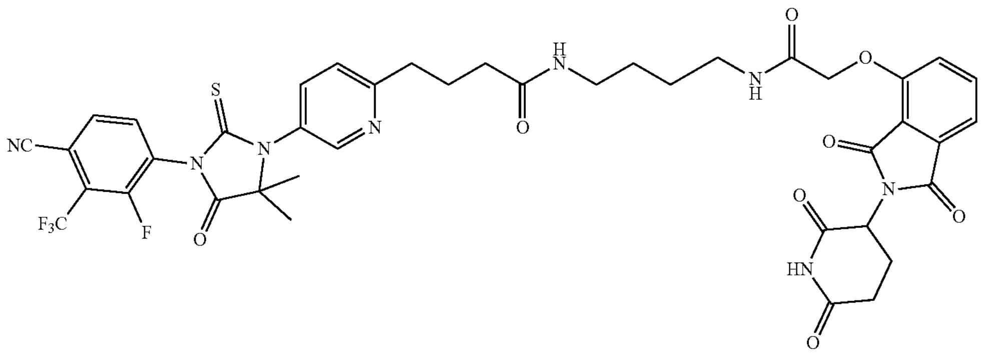 [SMILES: CC1(C)C(=O)N(c2ccc(C#N)c(C(F)(F)F)c2F)C(=S)N1c1ccc(CCCC(=O)NCCCCNC(=O)COc2cccc3c2C(=O)N(C2CCC(=O)NC2=O)C3=O)nc1]

LCMS ($[M+H]^+$): 879.3

$^1$HNMR (400 MHz, DMSO-d6) δ11.12 (s, 1H), 8.51 (d, J=2.3 Hz, 1H), 8.25 (s, 2H), 7.97 (t, J=5.6 Hz, 1H), 7.86-7.75 (m, 3H), 7.46 (t, J=7.7 Hz, 2H), 7.36 (d, J=8.5 Hz, 1H), 5.10 (dd, J=12.9, 5.4 Hz, 1H), 4.75 (s, 2H), 3.18-3.09 (m, 2H), 3.06-2.98 (m, 2H), 2.93-2.82 (m, 1H), 2.78 (s, 2H), 2.56 (t, J=13.3 Hz, 1H), 2.13 (s, 2H), 2.06 (s, 1H), 2.04-1.98 (m, 1H), 1.92 (dt, J=14.7, 7.5 Hz, 2H), 1.51 (s, 6H), 1.40 (s, 4H).

Example A11
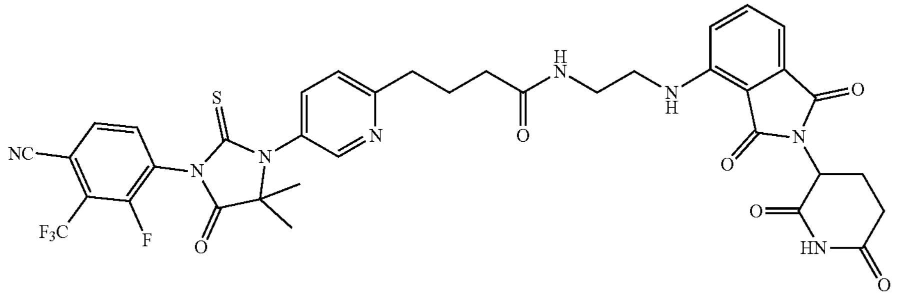 [SMILES: CC1(C)C(=O)N(c2ccc(C#N)c(C(F)(F)F)c2F)C(=S)N1c1ccc(CCCC(=O)NCCNc2cccc3c2C(=O)N(C2CCC(=O)NC2=O)C3=O)nc1]
LCMS ([M+H]+): 793.2
$^1$HNMR (400 MHz, DMSO-d6) δ11.10 (s, 1H), 8.52 (d, J=2.3 Hz, 1H), 8.33-8.24 (m, 2H), 8.13 (t, J=5.4 Hz, 1H), 7.80 (dd, J=8.2, 2.4 Hz, 1H), 7.61-7.53 (m, 1H), 7.44 (d, J=8.3 Hz, 1H), 7.19 (d, J=8.7 Hz, 1H), 7.02 (d, J=7.0 Hz, 1H), 6.75 (t, J=6.0 Hz, 1H), 5.05 (dd, J=12.8, 5.3 Hz, 1H), 3.40-3.38 (m, 2H), 3.26-3.25 (m, 2H), 2.92-2.74 (m, 3H), 2.59-2.55 (m, 2H), 2.15 (t, J=7.3 Hz, 2H), 2.01-1.88 (m, 3H), 1.53 (s, 6H).
Example A12
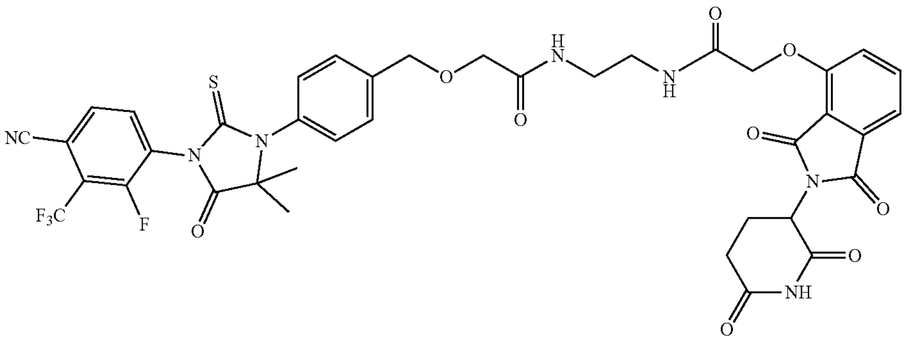 [SMILES: CC1(C)C(=O)N(c2ccc(C#N)c(C(F)(F)F)c2F)C(=S)N1c1ccc(COCC(=O)NCCNC(=O)COc2cccc3c2C(=O)N(C2CCC(=O)NC2=O)C3=O)cc1]
LCMS ([M+H]+): 852.2
$^1$HNMR (400 MHz, DMSO-d6) 11.17-11.10 (m, 1H), 8.36-8.23 (m, 2H), 8.17-8.05 (m, 1H), 8.05-7.90 (m, 1H), 7.86-7.75 (m, 1H), 7.64-7.54 (m, 2H), 7.53-7.47 (m, 1H), 7.41 (q, J=8.3 Hz, 3H), 5.20-5.05 (m, 1H), 4.86-4.69 (m, 2H), 4.65-4.50 (m, 2H), 4.04-3.90 (m, 2H), 3.30-3.17 (m, 4H), 2.59 (ddd, J=23.2, 12.6, 4.2 Hz, 2H), 2.06-1.94 (m, 2H), 1.57-1.47 (m, 6H).
Example A13
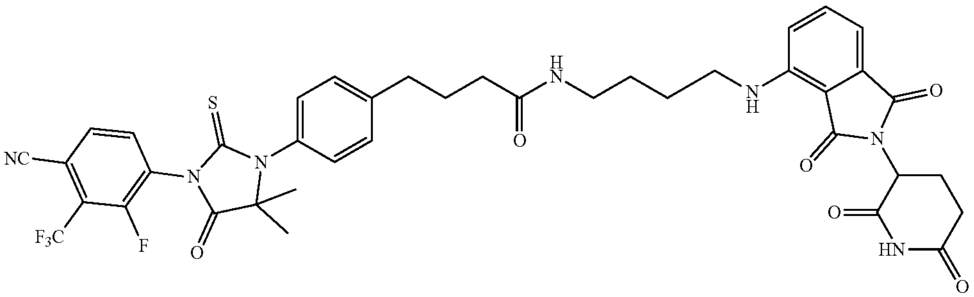 [SMILES: CC1(C)C(=O)N(c2ccc(C#N)c(C(F)(F)F)c2F)C(=S)N1c1ccc(CCCC(=O)NCCCCNc2cccc3c2C(=O)N(C2CCC(=O)NC2=O)C3=O)cc1]

LCMS ([M+H]$^+$): 820.2

$^1$HNMR (400 MHz, DMSO-d6) δ11.10 (s, 1H), 8.33-8.22 (m, 2H), 7.86 (d, J=5.4 Hz, 1H), 7.55 (t, J=7.8 Hz, 1H), 7.34 (dd, J=21.9, 8.2 Hz, 4H), 7.10 (d, J=8.6 Hz, 1H), 7.00 (d, J=7.0 Hz, 1H), 6.56 (d, J=6.0 Hz, 1H), 5.04 (dd, J=12.6, 5.2 Hz, 1H), 3.30 (s, 2H), 3.09 (d, J=5.8 Hz, 2H), 2.93-2.80 (m, 1H), 2.60 (dd, J=20.9, 12.9 Hz, 3H), 2.12 (t, J=7.2 Hz, 2H), 2.08-1.94 (m, 2H), 1.91-1.76 (m, 2H), 1.53 (dd, J=24.3, 5.8 Hz, 10H).

Example A14

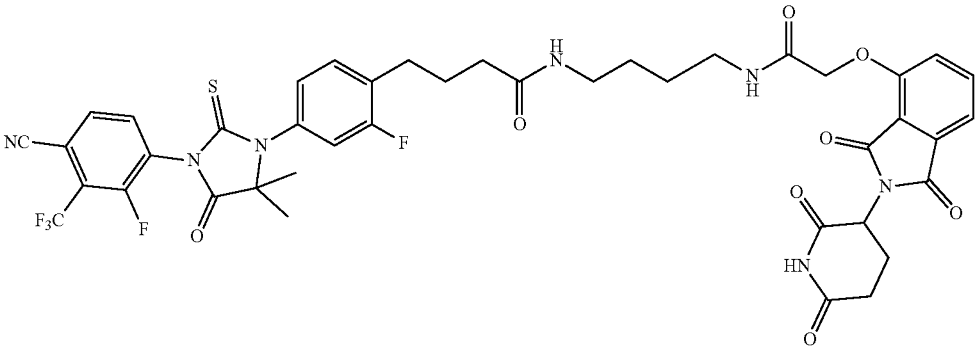 [SMILES: CC1(C)C(=O)N(c2ccc(C#N)c(C(F)(F)F)c2F)C(=S)N1c1ccc(CCCC(=O)NCCCCNC(=O)COc2cccc3c2C(=O)N(C2CCC(=O)NC2=O)C3=O)c(F)c1]

LCMS ([M+H]$^+$): 896.2

$^1$HNMR (400 MHz, DMSO-d6) δ11.15 (s, 1H), 8.27 (s, 2H), 8.00 (t, J=5.6 Hz, 1H), 7.86 (t, J=5.3 Hz, 1H), 7.81 (t, J=7.9 Hz, 1H), 7.50-7.46 (m, 2H), 7.40-7.30 (m, 2H), 7.21 (d, J=7.8 Hz, 1H), 5.12 (dd, J=12.9, 5.3 Hz, 1H), 4.77 (s, 2H), 3.14 (d, J=5.7 Hz, 2H), 3.03 (d, J=5.6 Hz, 2H), 2.92-2.86 (m, 1H), 2.68-2.55 (m, 3H), 2.13 (t, J=7.3 Hz, 2H), 2.07-1.93 (m, 2H), 1.87-1.76 (m, 2H), 1.52 (s, 6H), 1.41 (m, 4H).

Example A15

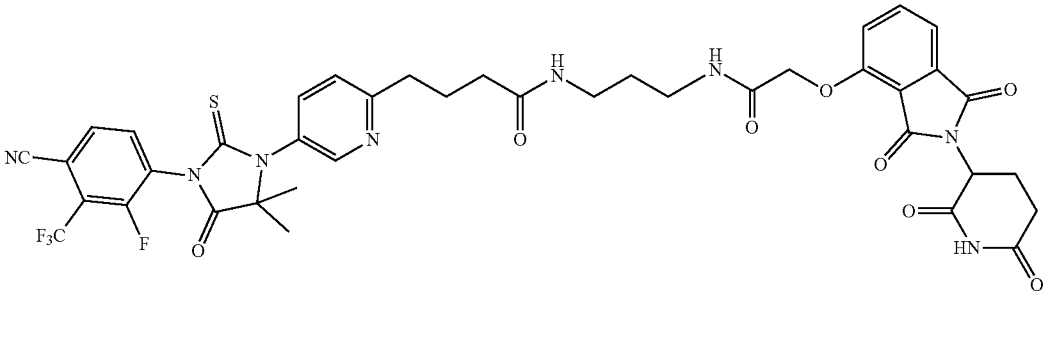 [SMILES: CC1(C)C(=O)N(c2ccc(C#N)c(C(F)(F)F)c2F)C(=S)N1c1ccc(CCCC(=O)NCCCNC(=O)COc2cccc3c2C(=O)N(C2CCC(=O)NC2=O)C3=O)nc1]

LCMS ([M+H]$^+$): 865.2

$^1$HNMR (400 MHz, DMSO-d6) δ11.13 (s, 1H), 8.53 (d, J=2.4 Hz, 1H), 8.36-8.20 (m, 2H), 8.11-7.96 (m, 1H), 7.91-7.74 (m, 3H), 7.49 (t, J=7.8 Hz, 2H), 7.40 (d, J=8.5 Hz, 1H), 5.12 (dd, J=12.9, 5.4 Hz, 1H), 4.79 (s, 2H), 3.16 (dd, J=12.9, 6.6 Hz, 2H), 3.07 (dd, J=12.2, 6.1 Hz, 2H), 2.96-2.73 (m, 4H), 2.66-2.52 (m, 2H), 2.15 (t, J=7.3 Hz, 2H), 2.10-1.90 (m, 4H), 1.67-1.44 (m, 6H).

Example A16
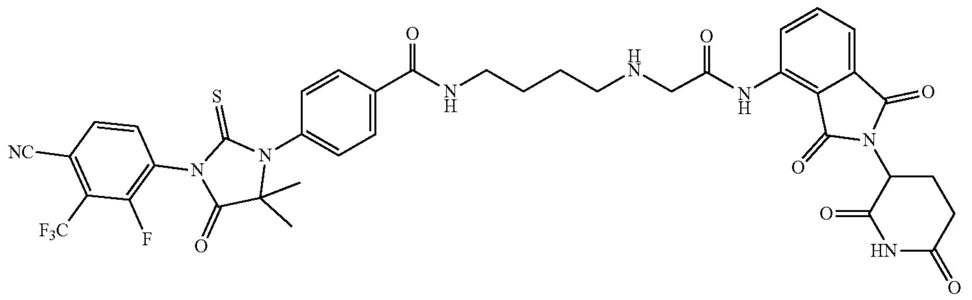 [SMILES: CC1(C)C(=O)N(c2ccc(C#N)c(C(F)(F)F)c2F)C(=S)N1c1ccc(C(=O)NCCCCNCC(=O)Nc2cccc3c2C(=O)N(C2CCC(=O)NC2=O)C3=O)cc1]
LCMS ([M+H]$^+$): 835.2
$^1$HNMR (400 MHz, DMSO-d6) δ11.15 (s, 1H), 8.81 (d, J=8.4 Hz, 1H), 8.61 (t, J=5.6 Hz, 1H), 8.28 (s, 2H), 7.99-7.94 (m, 2H), 7.85 (dd, J=8.5, 7.3 Hz, 1H), 7.60 (d, J=7.2 Hz, 1H), 7.55-7.50 (m, 2H), 5.16 (dd, J=13.0, 5.4 Hz, 1H), 3.41-3.36 (m, 2H), 3.28 (s, 2H), 2.89 (td, J=17.3, 16.0, 5.4 Hz, 1H), 2.67-2.53 (m, 4H), 2.10-1.95 (m, 2H), 1.59 (s, 4H), 1.54 (d, J=2.1 Hz, 6H).
Example A17
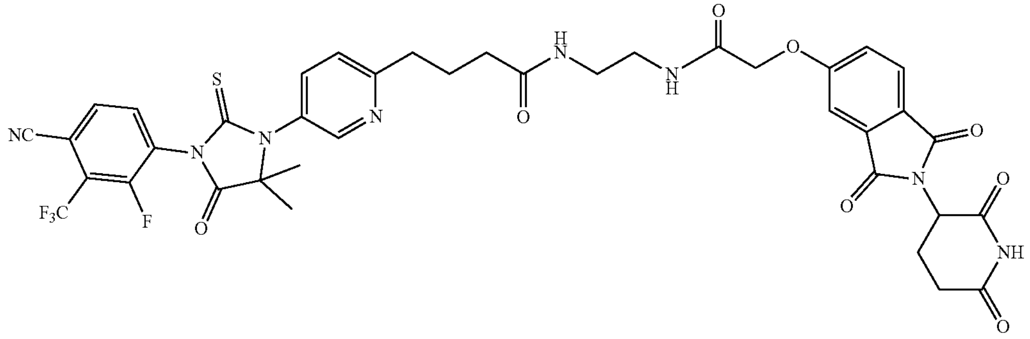 [SMILES: CC1(C)C(=O)N(c2ccc(C#N)c(C(F)(F)F)c2F)C(=S)N1c1ccc(CCCC(=O)NCCNC(=O)COc2ccc3c(c2)C(=O)N(C2CCC(=O)NC2=O)C3=O)nc1]
LCMS ([M+H]$^+$): 851.2
$^1$HNMR (400 MHz) δ11.13 (s, 1H), 8.52 (d, J=2.4 Hz, 1H), 8.28 (s, 3H), 8.10-7.71 (m, 3H), 7.43 (ddd, J=10.6, 7.1, 3.0 Hz, 3H), 5.13 (dd, J=12.9, 5.3 Hz, 1H), 4.72 (s, 2H), 3.19 (dt, J=11.2, 5.7 Hz, 4H), 2.96-2.72 (m, 4H), 2.70-2.53 (m, 2H), 2.16 (t, J=7.4 Hz, 2H), 2.08 (s, 4H), 1.53 (s, 6H).
Example A18
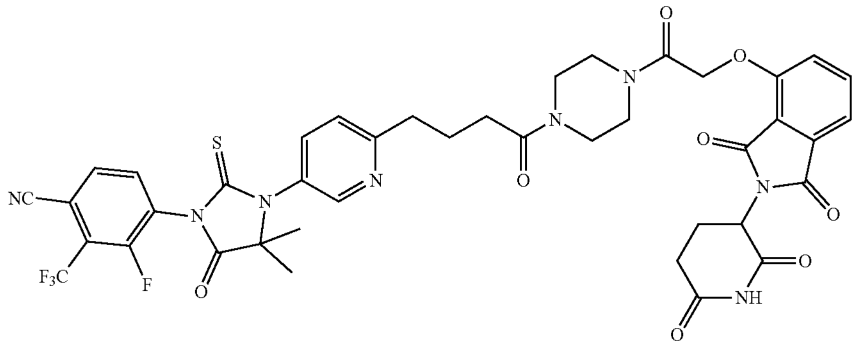 [SMILES: CC1(C)C(=O)N(c2ccc(C#N)c(C(F)(F)F)c2F)C(=S)N1c1ccc(CCCC(=O)N2CCN(C(=O)COc3cccc4c3C(=O)N(C3CCC(=O)NC3=O)C4=O)CC2)nc1]

LCMS ($[M+H]^+$): 877.2
$^1$HNMR (400 MHz, DMSO-d6) δ11.12 (s, 1H), 8.55 (s, 1H), 8.28 (d, J=5.1 Hz, 2H), 7.86-7.74 (m, 2H), 7.48 (dd, J=16.4, 7.7 Hz, 2H), 7.36 (d, J=8.5 Hz, 1H), 5.21 (s, 2H), 5.15-5.07 (m, 1H), 3.58 (s, 2H), 3.46 (d, J=12.7 Hz, 6H), 2.93-2.83 (m, 3H), 2.60 (d, J=17.2 Hz, 2H), 2.45 (s, 2H), 2.05-1.93 (m, 3H), 1.55 (s, 6H).
Example A19
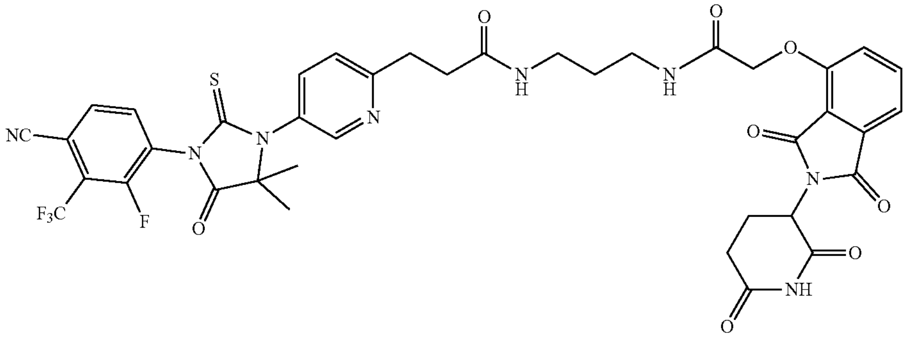 [SMILES: CC1(C)C(=O)N(c2ccc(C#N)c(C(F)(F)F)c2F)C(=S)N1c1ccc(CCC(=O)NCCCNC(=O)COc2cccc3c2C(=O)N(C2CCC(=O)NC2=O)C3=O)nc1]
LCMS ($[M+H]^+$): 851.2
$^1$HNMR (400 MHz, DMSO-d6) δ11.13 (s, 1H), 8.52 (d, J=2.4 Hz, 1H), 8.31-8.23 (m, 2H), 7.97 (t, J=5.7 Hz, 1H), 7.88 (t, J=5.6 Hz, 1H), 7.83-7.79 (m, 2H), 7.48 (t, J=8.1 Hz, 2H), 7.38 (d, J=8.5 Hz, 1H), 5.12 (dd, J=12.9, 5.3 Hz, 1H), 4.77 (s, 2H), 3.14 (dd, J=12.1, 6.1 Hz, 2H), 3.04 (dd, J=10.2, 4.9 Hz, 4H), 2.96-2.80 (m, 2H), 2.56-2.54 (m, 2H), 2.04-1.99 (m, 2H), 1.52 (s, 6H), 1.40-1.39 (m, 2H).
Example A20
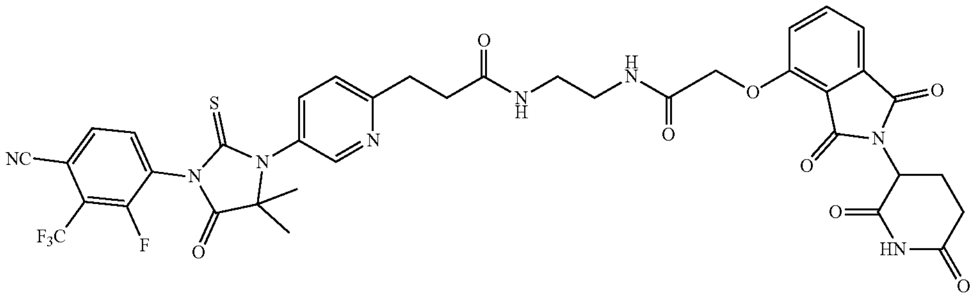 [SMILES: CC1(C)C(=O)N(c2ccc(C#N)c(C(F)(F)F)c2F)C(=S)N1c1ccc(CCC(=O)NCCNC(=O)COc2cccc3c2C(=O)N(C2CCC(=O)NC2=O)C3=O)nc1]
LCMS ($[M+H]^+$): 837.2
$^1$HNMR (400 MHz, DMSO-d6) δ11.12 (s, 1H), 8.52 (d, J=2.4 Hz, 1H), 8.31-8.24 (m, 2H), 8.06 (t, J=5.4 Hz, 1H), 7.98 (t, J=5.4 Hz, 1H), 7.84-7.76 (m, 2H), 7.51-7.43 (m, 2H), 7.39 (d, J=8.5 Hz, 1H), 5.12 (dd, J=12.9, 5.4 Hz, 1H), 4.77 (s, 2H), 3.22-3.10 (m, 4H), 3.06-2.99 (m, 2H), 2.94-2.81 (m, 2H), 2.56-2.54 (m, 3H), 2.03-1.99 (m, 3H), 1.52 (s, 6H).

Example A21
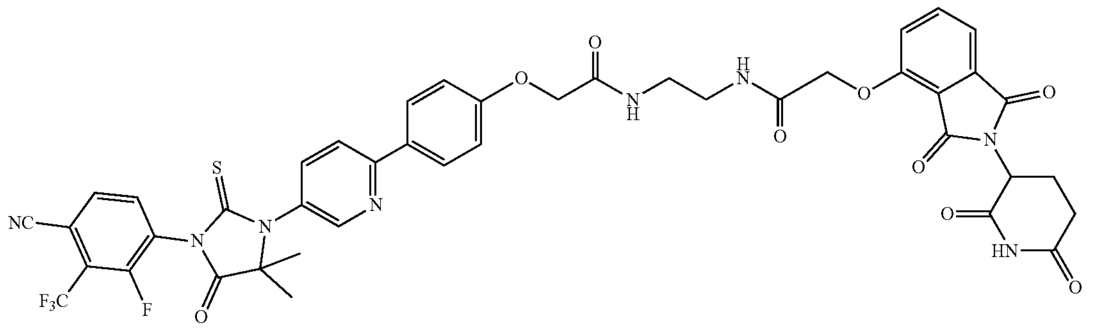 [SMILES: CC1(C)C(=O)N(c2ccc(C#N)c(C(F)(F)F)c2F)C(=S)N1c1ccc(-c2ccc(OCC(=O)NCCNC(=O)COc3cccc4c3C(=O)N(C3CCC(=O)NC3=O)C4=O)cc2)nc1]
LCMS ($[M+H]^+$): 915.2
$^1$HNMR (400 MHz, DMSO-d6) δ11.12 (s, 1H), 8.66 (d, J=2.4 Hz, 1H), 8.33-8.21 (m, 3H), 8.12 (d, J=8.8 Hz, 4H), 7.95 (dd, J=8.5, 2.5 Hz, 1H), 7.78 (dd, J=8.4, 7.4 Hz, 1H), 7.47 (d, J=7.2 Hz, 1H), 7.38 (d, J=8.5 Hz, 1H), 7.09 (d, J=8.9 Hz, 2H), 5.10 (dd, J=12.9, 5.4 Hz, 1H), 4.77 (s, 2H), 4.54 (s, 2H), 3.27 (m, 4H), 2.92-2.83 (m, 1H), 2.62-2.51 (m, 2H), 2.06-1.96 (m, 1H), 1.58 (s, 6H).
Example A22
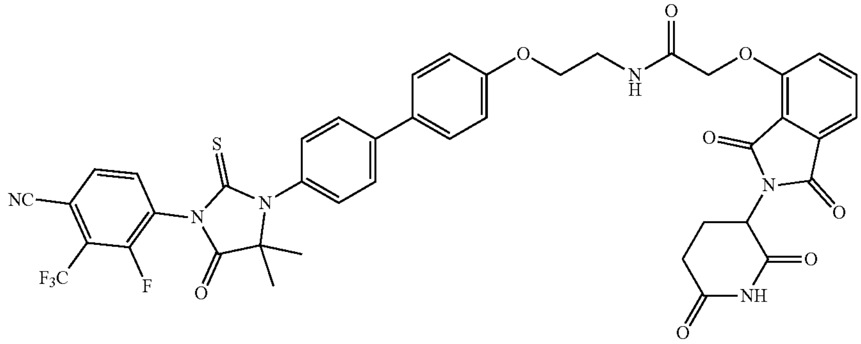 [SMILES: CC1(C)C(=O)N(c2ccc(C#N)c(C(F)(F)F)c2F)C(=S)N1c1ccc(-c2ccc(OCCNC(=O)COc3cccc4c3C(=O)N(C3CCC(=O)NC3=O)C4=O)cc2)cc1]
LCMS ($[M+H]^+$): 857.3
$^1$HNMR (400 MHz, DMSO-d6) δ11.15 (s, 1H), 8.33-8.19 (m, 3H), 7.84-7.74 (m, 3H), 7.69 (d, J=8.8 Hz, 2H), 7.51-7.44 (m, 3H), 7.41 (d, J=8.5 Hz, 1H), 7.07 (d, J=8.8 Hz, 2H), 5.12 (dd, J=12.8, 5.5 Hz, 1H), 4.83 (s, 2H), 4.11 (t, J=5.4 Hz, 2H), 3.60-3.58 (m, 2H), 2.95-287 (m, 1H), 2.62-2.54 (m, 2H), 2.10-1.94 (m, 2H), 1.56 (d, J=2.8 Hz, 6H).

Example A23
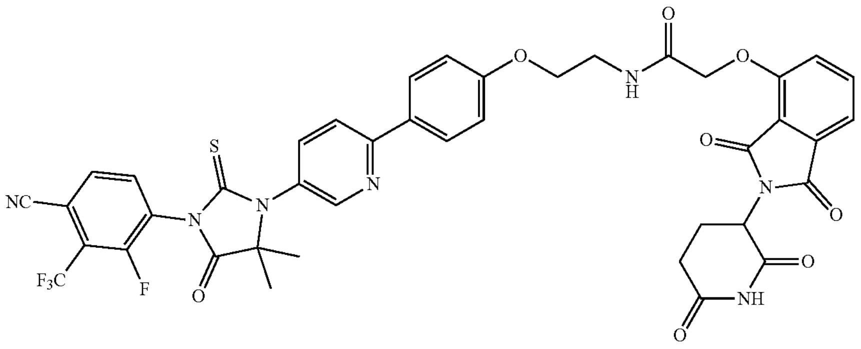 [SMILES: CC1(C)C(=O)N(c2ccc(C#N)c(C(F)(F)F)c2F)C(=S)N1c1ccc(-c2ccc(OCCNC(=O)COc3cccc4c3C(=O)N(C3CCC(=O)NC3=O)C4=O)cc2)nc1]
LCMS ($[M+H]^+$): 858.3
$^1$HNMR (400 MHz, DMSO-d6) δ11.14 (s, 1H), 8.66 (d, J=2.4 Hz, 1H), 8.34-8.20 (m, 3H), 8.14-8.07 (m, 3H), 7.95 (dd, J=8.5, 2.5 Hz, 1H), 7.77 (dd, J=8.3, 7.4 Hz, 1H), 7.47 (d, J=7.2 Hz, 1H), 7.41 (d, J=8.5 Hz, 1H), 7.09 (d, J=8.9 Hz, 2H), 5.11 (dd, J=12.8, 5.4 Hz, 1H), 4.83 (s, 2H), 4.1 4 (t, J=5.4 Hz, 2H), 3.64-3.55 (m, 2H), 2.90 (ddd, J=16.3, 13.8, 5.1 Hz, 1H), 2.66-2.51 (m, 2H), 2.03 (dd, J=10.2, 5.2 Hz, 1H), 1.59 (s, 6H).
Example A24
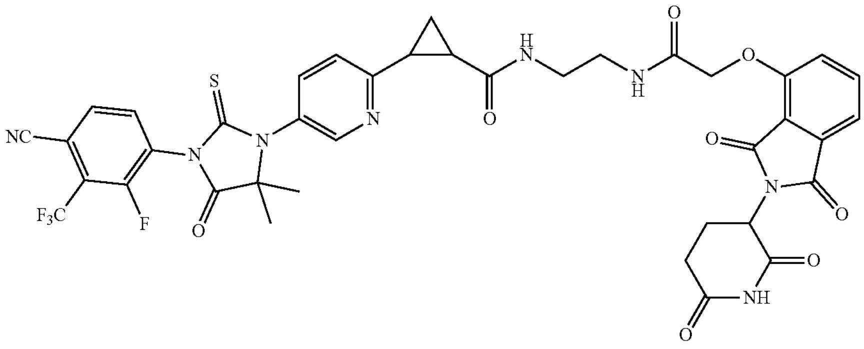 [SMILES: CC1(C)C(=O)N(c2ccc(C#N)c(C(F)(F)F)c2F)C(=S)N1c1ccc(C2CC2C(=O)NCCNC(=O)COc2cccc3c2C(=O)N(C2CCC(=O)NC2=O)C3=O)nc1]
LCMS ($[M+H]^+$): 849.3
$^1$HNMR (400 MHz, DMSO-d6) δ11.11 (s, 1H), 8.43 (d, J=2.4 Hz, 1H), 8.31-8.24 (m, 2H), 8.12 (m, 1H), 7.99 (m, 1H), 7.80-7.70 (m, 2H), 7.48 (d, J=7.3 Hz, 1H), 7.43 (d, J=8.4 Hz, 1H), 7.35 (d, J=8.6 Hz, 1H), 5.11 (dd, J=12.9, 5.4 Hz, 1H), 4.74 (s, 2H), 3.02-2.90 (m, 4H), 2.90-2.83 (m, 1H), 2.63-2.55 (m, 2H), 2.14-2.06 (m, 1H), 2.03-1.99 (m, 1H), 1.69-1.64 (m, 1H), 1.47 (s, 6H), 1.33-1.24 (m, 2H).

Example A25
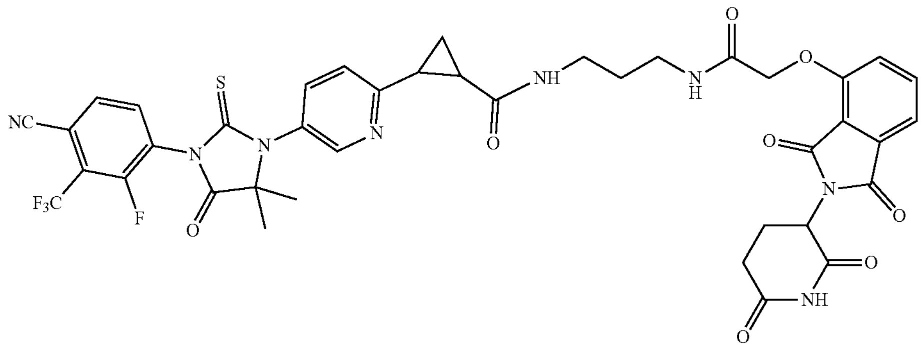 [SMILES: CC1(C)C(=O)N(c2ccc(C#N)c(C(F)(F)F)c2F)C(=S)N1c1ccc(C2CC2C(=O)NCCCNC(=O)COc2cccc3c2C(=O)N(C2CCC(=O)NC2=O)C3=O)nc1]
LCMS ([M+H]$^+$): 862.3
$^1$HNMR (400 MHz, DMSO-d6) δ11.12 (s, 1H), 8.43 (s, 1H), 8.30-8.22 (m, 2H), 8.04 (t, J=5.8 Hz, 1H), 7.87 (m, 1H), 7.81-7.75 (m, 1H), 7.72 (dt, J=8.4, 2.7 Hz, 1H), 7.49 (d, J=7.2 Hz, 1H), 7.41 (d, J=8.4 Hz, 1H), 7.36 (d, J=8.5 Hz, 1H), 5.11 (dd, J=12.9, 5.3 Hz, 1H), 4.74 (s, 2H), 3.0 6-2.82 (m, 5H), 2.58 (dd, J=16.6, 8.4 Hz, 3H), 2.13 (dd, J=15.3, 8.0 Hz, 1H), 2.03-1.99 (m, 1H), 1.67 (m, 1H), 1.47 (s, 6H), 1.39-1.27 (m, 3H).
Example A26
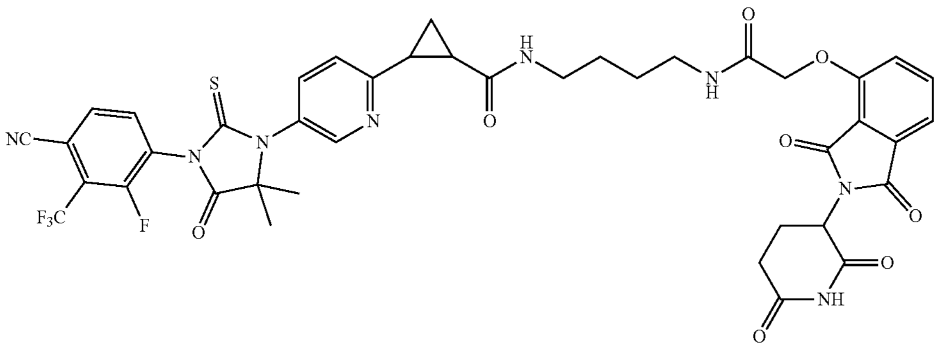 [SMILES: CC1(C)C(=O)N(c2ccc(C#N)c(C(F)(F)F)c2F)C(=S)N1c1ccc(C2CC2C(=O)NCCCCNC(=O)COc2cccc3c2C(=O)N(C2CCC(=O)NC2=O)C3=O)nc1]
LCMS ([M+H]$^+$): 877.3
$^1$HNMR (400 MHz, DMSO-d6) δ11.11 (s, 1H), 8.43 (d, J=2.3 Hz, 1H), 8.30-8.22 (m, 2H), 8.02 (t, J=5.7 Hz, 1H), 7.92 (t, J=5.6 Hz, 1H), 7.82-7.76 (m, 1H), 7.76-7.71 (m, 1H), 7.48 (d, J=7.2 Hz, 1H), 7.42 (d, J=8.4 Hz, 1H), 7.37 (d, J=8.5 Hz, 1H), 5.11 (dd, J=12.9, 5.4 Hz, 1H), 4.75 (s, 2H), 3.0 6 (dd, J=12.5, 6.3 Hz, 2H), 2.95-2.85 (m, 3H), 2.63-2.52 (m, 3H), 2.12 (dd, J=15.4, 8.1 Hz, 1H), 2.05-1.98 (m, 1H), 1.69-1.65 (m, 1H), 1.49 (s, 6H), 1.32-1.27 (m, 3H), 1.23-1.22 (m, 2H).

Example A27
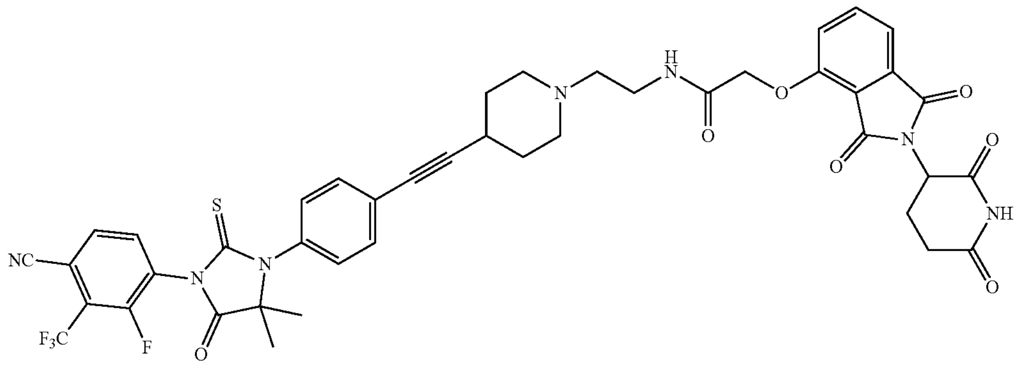 [SMILES: CC1(C)C(=O)N(c2ccc(C#N)c(C(F)(F)F)c2F)C(=S)N1c1ccc(C#CC2CCN(CCNC(=O)COc3cccc4c3C(=O)N(C3CCC(=O)NC3=O)C4=O)CC2)cc1]
LCMS ($[M+H]^+$): 872.3
$^1$HNMR (400 MHz, DMSO-d6) δ11.12 (s, 1H), 8.27 (d, J=4.6 Hz, 2H), 7.83 (q, J=8.1, 7.4 Hz, 2H), 7.57 (d, J=8.0 Hz, 2H), 7.51 (d, J=7.3 Hz, 1H), 7.42 (t, J=7.1 Hz, 3H), 5.11 (dd, J=12.6, 5.4 Hz, 1H), 4.78 (s, 2H), 3.2 8 (d, J=6.4 Hz, 3H), 2.87 (t, J=14.3 Hz, 1H), 2.74-2.62 (m, 3H), 2.40 (t, J=6.3 Hz, 2H), 2.24 (s, 2H), 2.09-2.00 (m, 1H), 1.92-1.80 (m, 2H), 1.60 (d, J=12.1 Hz, 2H), 1.52 (s, 6H).
Example A28
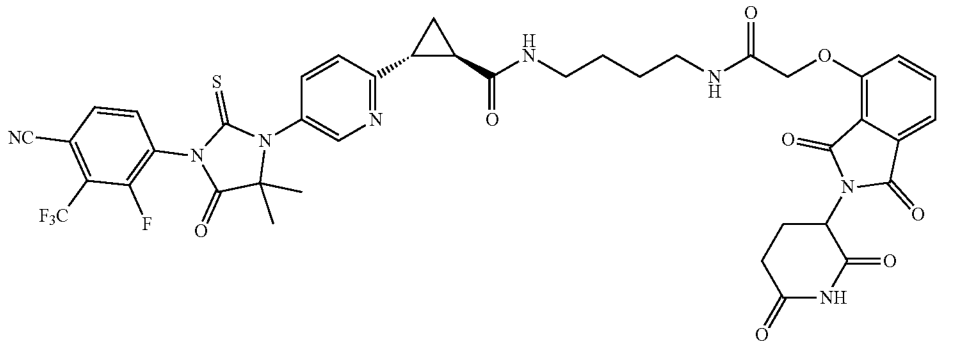 [SMILES: CC1(C)C(=O)N(c2ccc(C#N)c(C(F)(F)F)c2F)C(=S)N1c1ccc([C@@H]2C[C@H]2C(=O)NCCCCNC(=O)COc2cccc3c2C(=O)N(C2CCC(=O)NC2=O)C3=O)nc1]
LCMS ($[M+H]^+$): 877.2
$^1$HNMR (400 MHz, DMSO-d6) δ11.11 (s, 1H), 8.47 (s, 1H), 8.31-8.24 (m, 2H), 8.20 (t, J=5.1 Hz, 1H), 7.98 (t, J=5.7 Hz, 1H), 7.82-7.77 (m, 2H), 7.63 (d, J=8.3 Hz, 1H), 7.49 (d, J=7.2 Hz, 1H), 7.38 (d, J=8.5 Hz, 1H), 5.11 (dd, J=12.9, 5.3 Hz, 1H), 4.77 (s, 2H), 3.18-3.11 (m, 2H), 3.08 (d, J=5.8 Hz, 2H), 2.93-2.83 (m, 1H), 2.62-2.51 (m, 3H), 2.23-2.17 (m, 1H), 2.06-1.99 (m, 1H), 1.52 (s, 6H), 1.47-1.36 (m, 6H).

Example A29
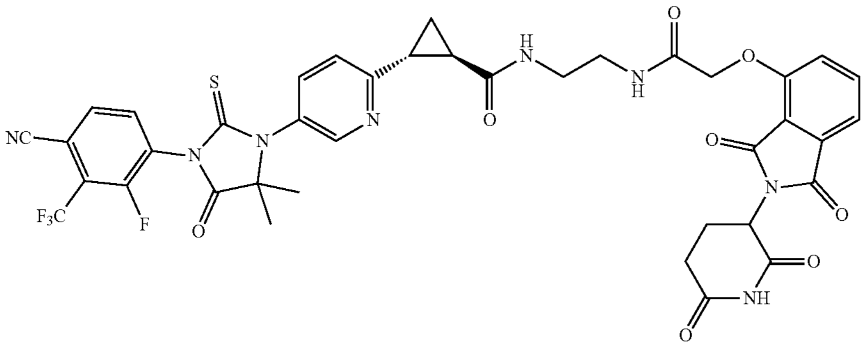 [SMILES: CC1(C)C(=O)N(c2ccc(C#N)c(C(F)(F)F)c2F)C(=S)N1c1ccc([C@@H]2C[C@H]2C(=O)NCCNC(=O)COc2cccc3c2C(=O)N(C2CCC(=O)NC2=O)C3=O)nc1]
LCMS ($[M+H]^+$): 849.2
$^1$HNMR (400 MHz, DMSO-d6) δ11.11 (s, 1H), 8.47 (s, 1H), 8.33-8.24 (m, 3H), 8.12 (m, 1H), 7.82-7.76 (m, 2H), 7.63 (d, J=8.3 Hz, 1H), 7.48 (d, J=7.2 Hz, 1H), 7.38 (d, J=8.5 Hz, 1H), 5.11 (dd, J=12.9, 5.5 Hz, 1H), 4.77 (s, 2H), 3.20 (s, 4H), 2.95-2.84 (m, 1H), 2.61-2.54 (m, 3H), 2.22-2.15 (m, 1H), 2.06-1.98 (m, 1H), 1.52 (s, 6H), 1.40-1.38 (m, 2H).
Example A30
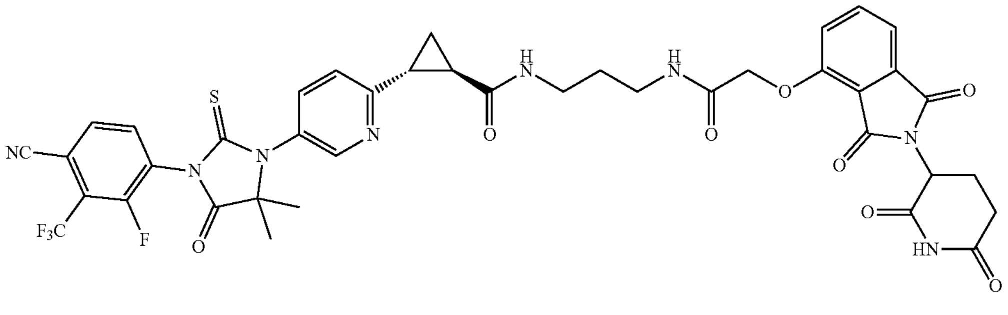 [SMILES: CC1(C)C(=O)N(c2ccc(C#N)c(C(F)(F)F)c2F)C(=S)N1c1ccc([C@@H]2C[C@H]2C(=O)NCCCNC(=O)COc2cccc3c2C(=O)N(C2CCC(=O)NC2=O)C3=O)nc1]
LCMS ($[M+H]^+$): 863.2
$^1$HNMR (400 MHz, DMSO-d6) δ11.10 (s, 1H), 8.47 (d, J=2.3 Hz, 1H), 8.31-8.25 (m, 2H), 8.27-8.23 (m, 1H), 8.01 (t, J=5.6 Hz, 1H), 7.84-7.76 (m, 2H), 7.63 (d, J=8.4 Hz, 1H), 7.49 (d, J=7.2 Hz, 1H), 7.39 (d, J=8.5 Hz, 1H), 5.12 (dd, J=12.9, 5.4 Hz, 1H), 4.77 (s, 2H), 3.20-3.06 (m, 4H), 2.94-2.82 (m, 1H), 2.63-2.52 (m, 3H), 2.23-2.16 (m, 1H), 2.05-1.99 (m, 1H), 1.62-1.55 (m, 2H), 1.52 (s, 6H), 1.43-1.38 (m, 2H).

Example A31
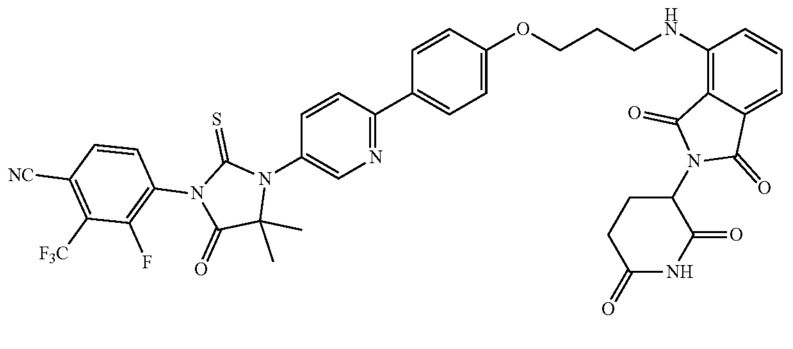 [SMILES: CC1(C)C(=O)N(c2ccc(C#N)c(C(F)(F)F)c2F)C(=S)N1c1ccc(-c2ccc(OCCCNc3cccc4c3C(=O)N(C3CCC(=O)NC3=O)C4=O)cc2)nc1]
LCMS ([M+H]+): 814.2
$^1$HNMR (400 MHz, DMSO-d6) δ11.10 (s, 1H), 8.65 (d, J=2.5 Hz, 1H), 8.29 (q, J=8.4 Hz, 2H), 8.1 2 (d, J=8.8 Hz, 3H), 7.95 (dd, J=8.5, 2.5 Hz, 1H), 7.60-7.54 (m, 1H), 7.14 (dd, J=13.8, 8.8 Hz, 3H), 7.03 (d, J=7.0 Hz, 1H), 6.78 (t, J=5.8 Hz, 1H), 5.06 (dd, J=12.9, 5.5 Hz, 1H), 4.17 (t, J=5.8 Hz, 2H), 3.53 (d, J=6.0 Hz, 2H), 2.88 (dd, J=22.5, 8.8 Hz, 1H), 2.63-2.52 (m, 3H), 2.13-2.05 (m, 2H), 1.58 (s, 6H).
Example A32
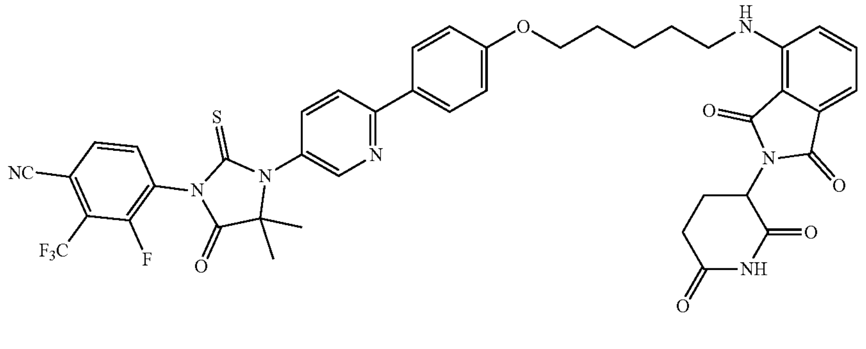 [SMILES: CC1(C)C(=O)N(c2ccc(C#N)c(C(F)(F)F)c2F)C(=S)N1c1ccc(-c2ccc(OCCCCCNc3cccc4c3C(=O)N(C3CCC(=O)NC3=O)C4=O)cc2)nc1]
LCMS ([M+H]+): 842.2
$^1$HNMR (400 MHz, DMSO-d6) δ11.10 (s, 1H), 8.66 (d, J=2.4 Hz, 1H), 8.30 (q, J=8.5 Hz, 2H), 8.1 2 (dd, J=8.8, 2.4 Hz, 3H), 7.95 (dd, J=8.5, 2.5 Hz, 1H), 7.62-7.56 (m, 1H), 7.15-7.00 (m, 4H), 6.59 (t, J=5.8 Hz, 1H), 5.06 (dd, J=12.8, 5.3 Hz, 1H), 4.08 (t, J=6.3 Hz, 2H), 2.95-2.83 (m, 1H), 2.64-2.51 (m, 3H), 2.21-1.95 (m, 2H), 1.86-1.76 (m, 2H), 1.67 (dd, J=14.4, 7.0 Hz, 2H), 1.59 (s, 6H), 1.54 (d, J=6.9 Hz, 2H).

Example A33
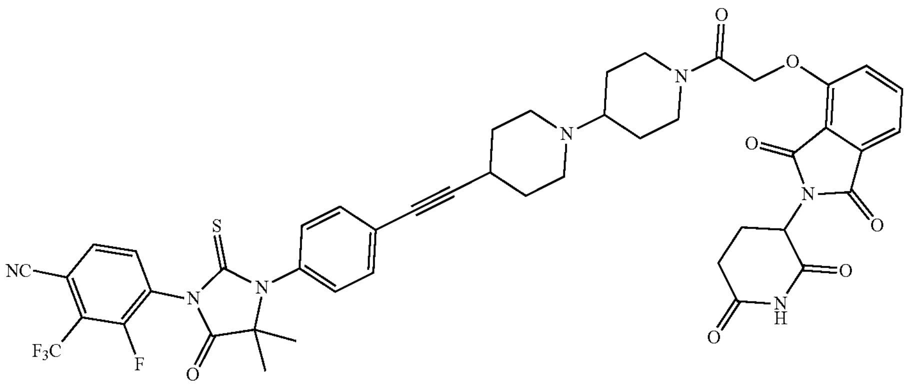 [SMILES: CC1(C)C(=O)N(c2ccc(C#N)c(C(F)(F)F)c2F)C(=S)N1c1ccc(C#CC2CCN(C3CCN(C(=O)COc4cccc5c4C(=O)N(C4CCC(=O)NC4=O)C5=O)CC3)CC2)cc1]
LCMS ([M+H]$^+$): 912.3
$^1$HNMR (400 MHz, DMSO-d6) δ11.11 (s, 1H), 8.27 (d, J=4.2 Hz, 2H), 7.77 (dd, J=8.5, 7.3 Hz, 1H), 7.57 (d, J=8.0 Hz, 2H), 7.47-7.39 (m, 3H), 7.32 (d, J=8.6 Hz, 1H), 5.21-5.06 (m, 3H), 4.34 (d, J=12.1 Hz, 1H), 3.84 (s, 1H), 3.04 (t, J=12.7 Hz, 2H), 2.96-2.82 (m, 2H), 2.78 (s, 1H), 2.68-2.52 (m, 4H), 2.39 (s, 1H), 2.14-1.56 (m, 9H), 1.51 (d, J=1.9 Hz, 7H).
Example A34
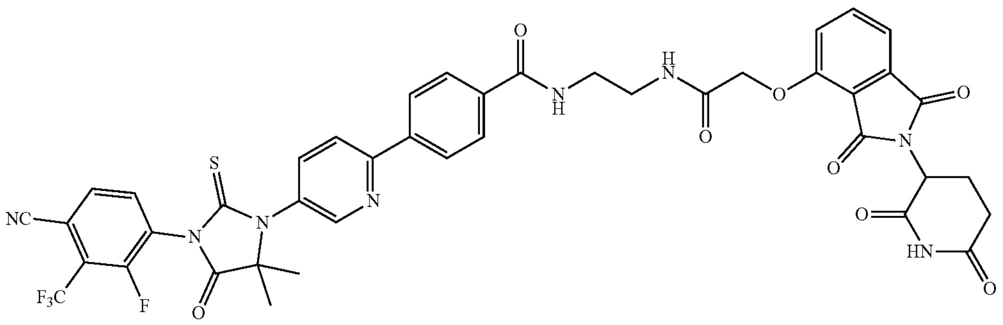 [SMILES: CC1(C)C(=O)N(c2ccc(C#N)c(C(F)(F)F)c2F)C(=S)N1c1ccc(-c2ccc(C(=O)NCCNC(=O)COc3cccc4c3C(=O)N(C3CCC(=O)NC3=O)C4=O)cc2)nc1]
LCMS ([M+H]$^+$): 885.3
$^1$HNMR (400 MHz, DMSO-d6) δ11.11 (s, 1H), 8.77 (d, J=2.0 Hz, 1H), 8.65 (m, 1H), 8.27 (m, 6H), 8.07 (dd, J=8.5, 2.4 Hz, 1H), 7.96 (d, J=8.4 Hz, 2H), 7.81-7.74 (m, 1H), 7.43 (dd, J=22.6, 7.9 Hz, 2H), 7.29-7.02 (m, 1H), 5.09 (m, 1H), 4.81 (m, 2H), 3.39 (m, 4H), 2.95-2.82 (m, 2H), 2.08-1.93 (m, 2H), 1.61 (s, 6H).

Example A35
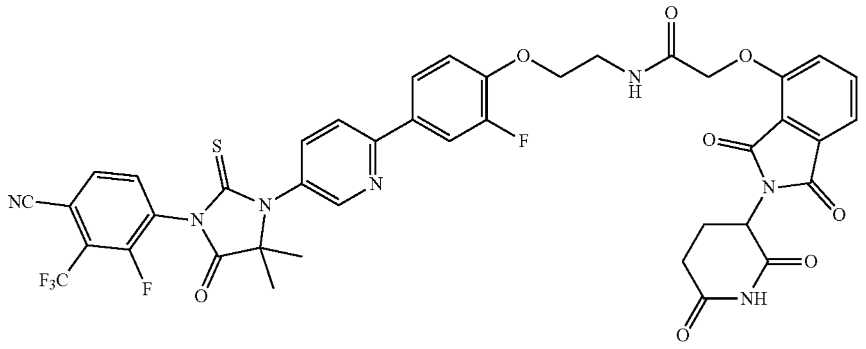 [SMILES: CC1(C)C(=O)N(c2ccc(C#N)c(C(F)(F)F)c2F)C(=S)N1c1ccc(-c2ccc(OCCNC(=O)COc3cccc4c3C(=O)N(C3CCC(=O)NC3=O)C4=O)c(F)c2)nc1]
LCMS ([M+H]+): 876.3
$^1$HNMR (400 MHz, DMSO-d6) δ11.11 (s, 1H), 8.67 (d, J=2.5 Hz, 1H), 8.34-8.23 (m, 3H), 8.17 (d, J=8.5 Hz, 1H), 8.06-7.92 (m, 3H), 7.75 (dd, J=8.5, 7.3 Hz, 1H), 7.47 (d, J=7.2 Hz, 1H), 7.39 (d, J=8.5 Hz, 1H), 7.33 (t, J=8.8 Hz, 1H), 5.09 (dd, J=12.9, 5.4 Hz, 1H), 4.83 (s, 2H), 4.22 (t, J=5.5 Hz, 2H), 3.61 (t, J=5.7 Hz, 2H), 2.88 (ddd, J=17.4, 14.0, 5.3 Hz, 1H), 2.57 (td, J=13.9, 3.9 Hz, 2H), 2.01 (ddd, J=14.8, 6.5, 2.3 Hz, 1H), 1.59 (s, 6H).
Example A36
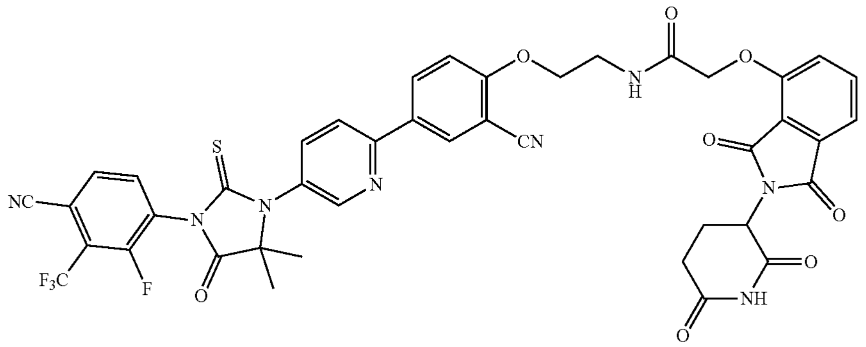 [SMILES: CC1(C)C(=O)N(c2ccc(C#N)c(C(F)(F)F)c2F)C(=S)N1c1ccc(-c2ccc(OCCNC(=O)COc3cccc4c3C(=O)N(C3CCC(=O)NC3=O)C4=O)c(C#N)c2)nc1]
LCMS ([M+H]+): 883.3
$^1$HNMR (400 MHz, DMSO-d6) δ11.10 (s, 1H), 8.71 (d, J=2.4 Hz, 1H), 8.51 (d, J=2.3 Hz, 1H), 8.4 5 (dd, J=8.9, 2.4 Hz, 1H), 8.32-8.23 (m, 4H), 8.03 (dd, J=8.5, 2.5 Hz, 1H), 7.76 (dd, J=8.5, 7.3 Hz, 1H), 7.48-7.38 (m, 3H), 5.08 (dd, J=12.9, 5.4 Hz, 1H), 4.83 (s, 2H), 4.33 (t, J=5.5 Hz, 2H), 3.63 (q, J=5.6 Hz, 2H), 2.87 (ddd, J=17.3, 14.0, 5.5 Hz, 1H), 2.63-2.51 (m, 2H), 1.59 (s, 6H).

Example A37
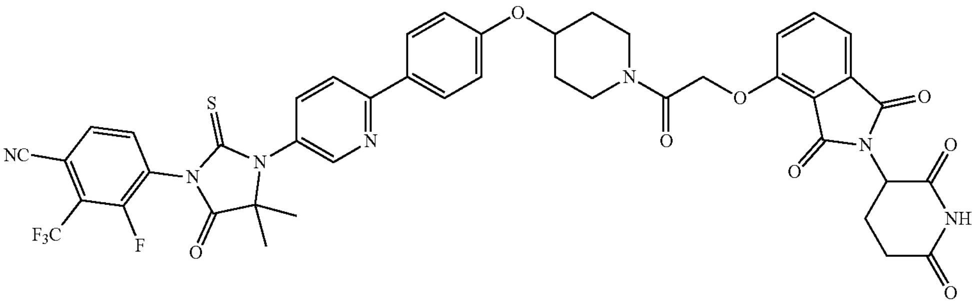 [SMILES: CC1(C)C(=O)N(c2ccc(C#N)c(C(F)(F)F)c2F)C(=S)N1c1ccc(-c2ccc(OC3CCN(C(=O)COc4cccc5c4C(=O)N(C4CCC(=O)NC4=O)C5=O)CC3)cc2)nc1]
LCMS ([M+H]+): 898.3
$^1$HNMR (400 MHz, DMSO-d6) δ11.11 (s, 1H), 8.67 (m, 1H), 8.29 (m, 2H), 8.13 (d, J=8.1 Hz, 3H), 7.96 (d, J=7.9 Hz, 1H), 7.79 (t, J=7.6 Hz, 1H), 7.47 (d, J=6.6 Hz, 1H), 7.37 (d, J=8.4 Hz, 1H), 7.16 (d, J=7.9 Hz, 2H), 5.23 (m, 2H), 5.11 (m, 1H), 4.79 (m, 1H), 3.79 (m, 3H), 2.88 (m, 1H), 2.66-2.51 (m, 4H), 2.05 (m, 3H), 1.78 (m, 1H), 1.59 (s, 6H).
Example A38
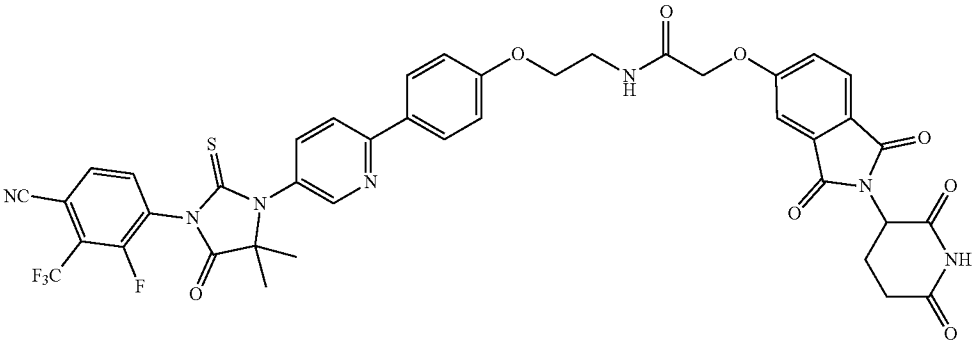 [SMILES: CC1(C)C(=O)N(c2ccc(C#N)c(C(F)(F)F)c2F)C(=S)N1c1ccc(-c2ccc(OCCNC(=O)COc3ccc4c(c3)C(=O)N(C3CCC(=O)NC3=O)C4=O)cc2)nc1]
LCMS ([M+H]+): 858.2
$^1$HNMR (400 MHz, DMSO-d6) δ11.10 (s, 1H), 8.65 (d, J=2.5 Hz, 1H), 8.48 (t, J=5.6 Hz, 1H), 8.29 (q, J=8.5 Hz, 2H), 8.11 (d, J=8.9 Hz, 3H), 7.95 (dd, J=8.5, 2.5 Hz, 1H), 7.84 (d, J=8.3 Hz, 1H), 7.46 (d, J=2.2 Hz, 1H), 7.39 (dd, J=8.3, 2.3 Hz, 1H), 7.07 (d, J=8.9 Hz, 2H), 5.11 (dd, J=12.8, 5.4 Hz, 1H), 4.78 (s, 2H), 4.13 (t, J=5.5 Hz, 2H), 3.61-3.52 (m, 2H), 2.93-2.80 (m, 1H), 2.57 (dd, J=21.7, 6.7 Hz, 2H), 2.08-1.97 (m, 1H), 1.58 (s, 6H).

Example A39
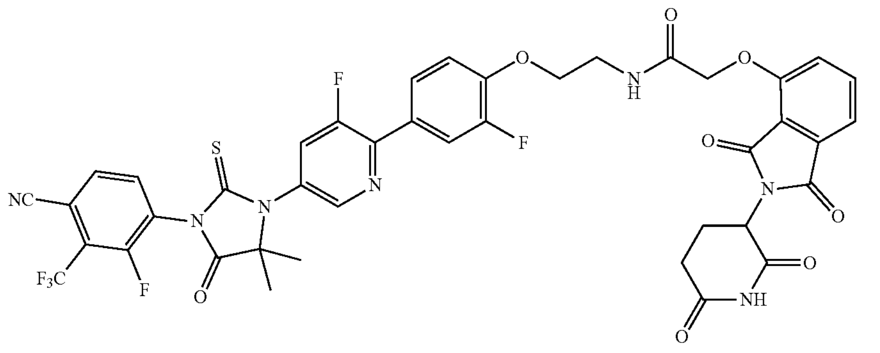
LCMS ([M+H]$^+$): 894.2
$^1$HNMR (400 MHz, DMSO-d6) δ11.10 (s, 1H), 8.63 (s, 1H), 8.32-8.25 (m, 3H), 8.16 (dd, J=11.9, 1.9 Hz, 1H), 7.84 (m, 2H), 7.75 (m, 1H), 7.47 (d, J=7.2 Hz, 1H), 7.38 (dd, J=16.1, 8.8 Hz, 2H), 5.08 (m, 1H), 4.83 (s, 2H), 4.24 (m, 2H), 3.62 (m, 2H), 2.88 (m, 1H), 2.62-2.51 (m, 2H), 2.03 (m, 1H), 1.61 (brs, 6H).
Example A40
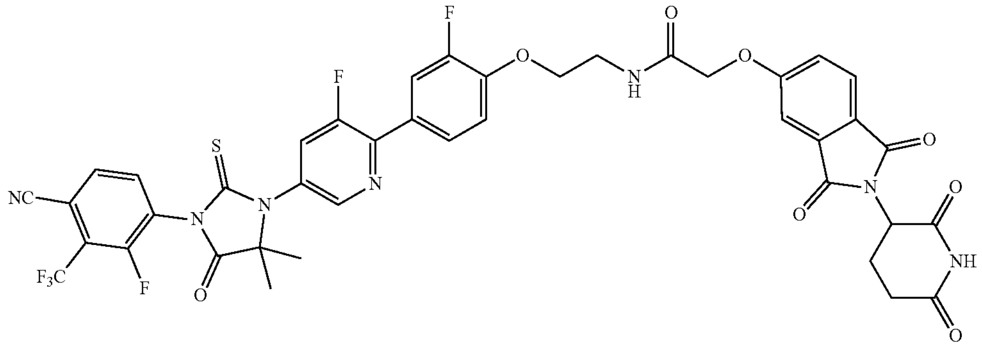 [SMILES: CC1(C)C(=O)N(c2ccc(C#N)c(C(F)(F)F)c2F)C(=S)N1c1cnc(-c2ccc(OCCNC(=O)COc3ccc4c(c3)C(=O)N(C3CCC(=O)NC3=O)C4=O)c(F)c2)c(F)c1]
LCMS ([M+H]$^+$): 894.2
$^1$HNMR (400 MHz, DMSO-d6) δ11.10 (s, 1H), 8.63 (s, 1H), 8.51 (t, J=5.7 Hz, 1H), 8.32-8.24 (m, 2H), 8.16 (dd, J=11.9, 1.9 Hz, 1H), 7.89-7.80 (m, 3H), 7.45 (d, J=2.2 Hz, 1H), 7.42-7.32 (m, 2H), 5.10 (m, J=12.9, 5.4 Hz, 1H), 4.78 (s, 2H), 4.23 (m, 2H), 3.59 (m, 2H), 2.88 (m, 1H), 2.63-2.51 (m, 2H), 2.06-1.97 (m, 1H), 1.61 (s, 6H).

Example A41
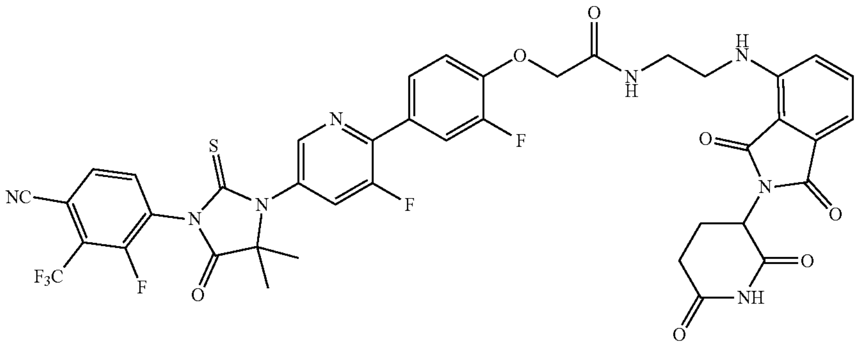 [SMILES: CC1(C)C(=O)N(c2ccc(C#N)c(C(F)(F)F)c2F)C(=S)N1c1cnc(-c2ccc(OCC(=O)NCCNc3cccc4c3C(=O)N(C3CCC(=O)NC3=O)C4=O)c(F)c2)c(F)c1]
LCMS ([M+H]$^+$): 893.2
$^1$HNMR (400 MHz, DMSO-d6) δ11.09 (s, 1H), 8.63 (s, 1H), 8.38 (t, J=5.8 Hz, 1H), 8.29 (s, 2H), 8.17 (d, J=11.9 Hz, 1H), 7.87 (d, J=13.8 Hz, 1H), 7.76 (d, J=8.0 Hz, 1H), 7.61-7.56 (m, 1H), 7.24-7.17 (m, 2H), 7.02 (d, J=6.9 Hz, 1H), 6.75 (s, 1H), 5.05 (dd, J=13.0, 5.4 Hz, 1H), 4.70 (s, 2H), 3.43 (s, 2H), 3.39 (d, J=4.8 Hz, 2H), 2.88 (s, 1H), 2.00 (d, J=7.6 Hz, 3H), 1.62 (s, 6H).
Example A42
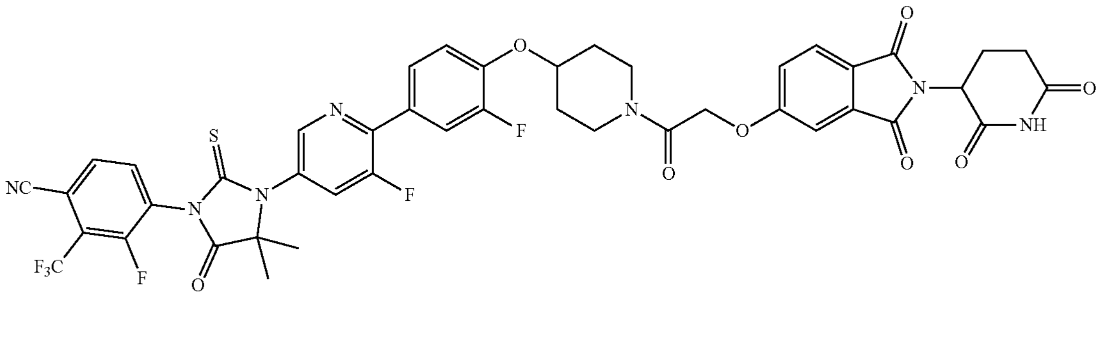 [SMILES: CC1(C)C(=O)N(c2ccc(C#N)c(C(F)(F)F)c2F)C(=S)N1c1cnc(-c2ccc(OC3CCN(C(=O)COc4ccc5c(c4)C(=O)N(C4CCC(=O)NC4=O)C5=O)CC3)c(F)c2)c(F)c1]
LCMS ([M+H]$^+$): 934.2
$^1$HNMR (400 MHz, DMSO-d6) δ11.10 (s, 1H), 8.64 (s, 1H), 8.28 (d, J=3.3 Hz, 2H), 8.17 (dd, J=1 1.8, 1.9 Hz, 1H), 7.86 (dd, J=12.4, 9.9 Hz, 3H), 7.48 (dd, J=16.3, 5.5 Hz, 2H), 7.36 (dd, J=8.3, 2.3 Hz, 1H), 5.18 (s, 2H), 5.12 (dd, J=12.9, 5.4 Hz, 1H), 4.83 (s, 1H), 3.78 (d, J=54.3 Hz, 2H), 3.41 (s, 2H), 2.87 (d, J=11.5 Hz, 1H), 2.61 (d d, J=31.3, 14.5 Hz, 2H), 2.12-1.94 (m, 4H), 1.81 (s, 1H), 1.61 (s, 6H).

Example A43
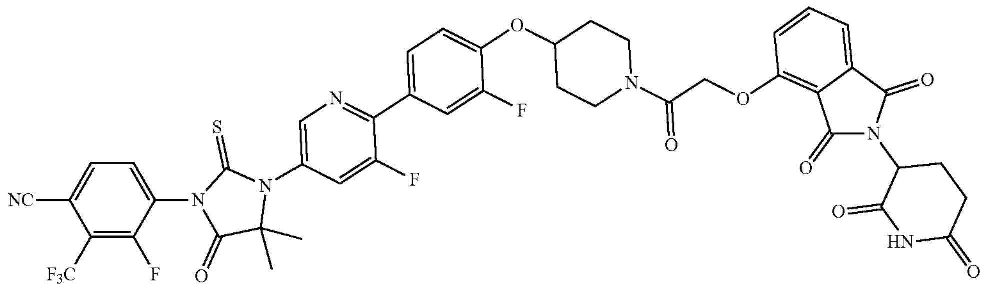 [SMILES: CC1(C)C(=O)N(c2ccc(C#N)c(C(F)(F)F)c2F)C(=S)N1c1cnc(-c2ccc(OC3CCN(C(=O)COc4cccc5c4C(=O)N(C4CCC(=O)NC4=O)C5=O)CC3)c(F)c2)c(F)c1]
LCMS ([M+H]+): 934.3
$^1$HNMR (400 MHz, DMSO-d6) δ11.10 (s, 1H), 8.64 (s, 1H), 8.28 (s, 2H), 8.17 (dd, J=11.8, 1.9 Hz, 1H), 7.86 (t, J=9.8 Hz, 2H), 7.82-7.76 (m, 1H), 7.48 (dd, J=17.1, 8.1 Hz, 2H), 7.37 (d, J=8.7 Hz, 1H), 5.23 (s, 2H), 5.10 (dd, J=12.8, 5.4 Hz, 1H), 4.83 (s, 1H), 3.86 (s, 2H), 3.40 (s, 2H), 2.88 (d, J=11.3 Hz, 1H), 2.70-2.56 (m, 2H), 2.06-1.91 (m, 4H), 1.81 (s, 1H), 1.61 (s, 6H).
Example A44
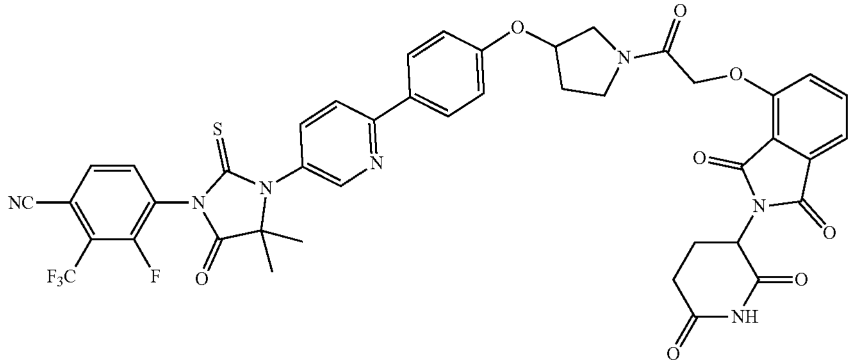 [SMILES: CC1(C)C(=O)N(c2ccc(C#N)c(C(F)(F)F)c2F)C(=S)N1c1ccc(-c2ccc(OC3CCN(C(=O)COc4cccc5c4C(=O)N(C4CCC(=O)NC4=O)C5=O)C3)cc2)nc1]
LCMS ([M+H]+): 884.3
$^1$HNMR (400 MHz, DMSO-d6) δ11.09 (s, 1H), 8.66 (s, 1H), 8.32-8.26 (m, 2H), 8.15-8.12 (m, 3H), 7.96 (d, J=8.3 Hz, 1H), 7.78 (t, J=7.9 Hz, 1H), 7.46 (d, J=7.3 Hz, 1H), 7.39 (d, J=8.5 Hz, 2H), 7.16-7.09 (m, 2H), 5.30-5.00 (m, 4H), 3.88-3.58 (m, 4H), 2.93-2.86 (m, 1H), 2.61-2.54 (m, 2H), 2.32-2.27 (m, 1H), 2.19-2.13 (m, 1H), 2.04-2.03 (m, 1H), 1.58 (s, 6H).

Example A45

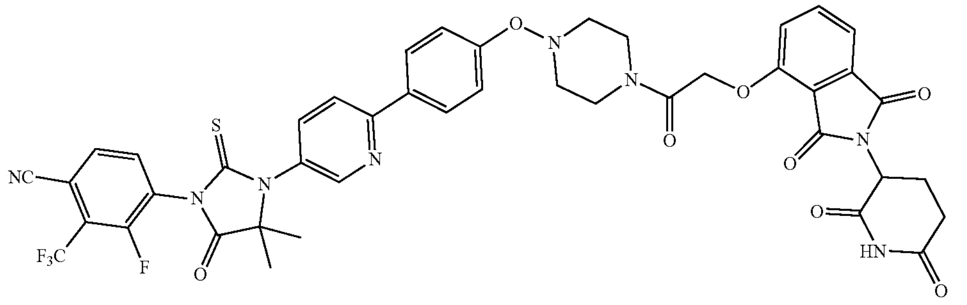 [SMILES: CC1(C)C(=O)N(c2ccc(C#N)c(C(F)(F)F)c2F)C(=S)N1c1ccc(-c2ccc(ON3CCN(C(=O)COc4cccc5c4C(=O)N(C4CCC(=O)NC4=O)C5=O)CC3)cc2)nc1]

LCMS ([M+H]$^+$): 911.2

$^1$HNMR (400 MHz, DMSO-d6) δ11.10 (s, 1H), 8.76 (d, J=2.4 Hz, 1H), 8.32-8.24 (m, 5H), 8.06 (dd, J=8.4, 2.4 Hz, 1H), 7.80-7.76 (m, 1H), 7.61 (d, J=8.3 Hz, 2H), 7.46 (d, J=7.2 Hz, 1H), 7.37 (d, J=8.7 Hz, 1H), 5.22 (s, 2H), 5.10 (dd, J=12.8, 5.4 Hz, 1H), 3.55 (m, 7H), 2.89 (t, J=12.8 Hz, 1H), 2.67-2.54 (m, 2H), 2.04-1.99 (m, 1H), 1.60 (s, 6H).

Example A46

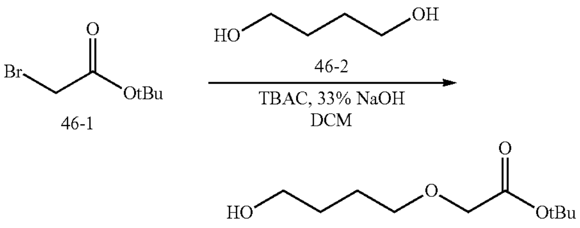

46-1

46-3

Intermediate 46-1 (5.85 g, 0.03 mol), compound 46-2 (5.4 g, 0.06 mol), and TBAC (4.17 g, 0.015 mol) were added to 120 ml of DCM successively and cooled to 0° C., to which 60 ml of 33% NaOH solution was added dropwise. The mixture was reacted at room temperature overnight. After the reaction was completed, the obtained product was washed with 200 ml of water, extracted with 200 ml of DCM, washed with 100 ml of saturated brine, dried over anhydrous sodium sulfate, and rotating-dried to obtain the crude product, which was subjected to column chromatography with PE:EA=2:1-1:1 to obtain 4.08 g of colorless oily intermediate 46-3 with a yield of 66.7%.

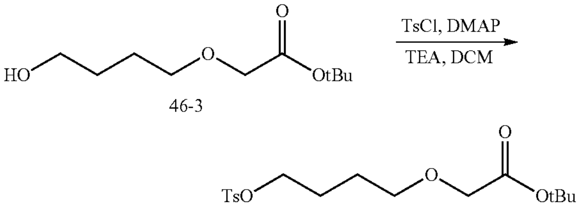

46-3

46-4

Intermediate 46-3 (4.08 g, 0.02 mmol), TsCl (5.72 g, 0.03 mol), triethylamine (4.04 g, 0.04 mol), and DMAP (244 mg, 0.002 mol) were successively added to 100 ml DCM, to react at room temperature for 1 hour. After the reaction was completed, the obtained product was washed with 100 ml of water, extracted with 100 ml of DCM, washed with 100 ml of saturated brine, dried over anhydrous sodium sulfate, rotating-dried and loaded on the chromatography column with PE:EA=20:1-10:1 to obtain 6 g of colorless liquid 46-4 with a yield of 83.7%.

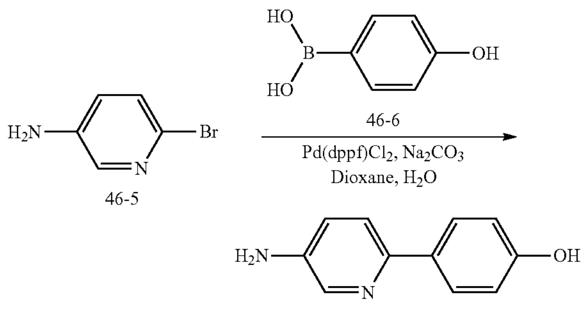

46-5

46-7

Intermediate 46-5 (5.02 g, 0.029 mol), compound 46-6 (4.83 g, 0.035 mol), Pd(dppf)$Cl_2$ (2.12 g, 0.0029 mol), and $Na_2CO_3$ (6.15 g, 0.058 mol) were added to 150 ml dioxane and 50 ml of water, and stirred at 90° C. overnight under the protection of $N_2$. After the reaction was completed, the obtained product was filtered, washed with 100 ml of water, extracted twice with 200 ml of EA, washed with 100 ml of saturated brine, dried over anhydrous sodium sulfate, rotating-dried and loaded on the chromatographic column with DCM:MeOH=100:1-50:1-20:1 to obtain 5.5 g of brown solid intermediate 46-7 with a yield of 92.6%.

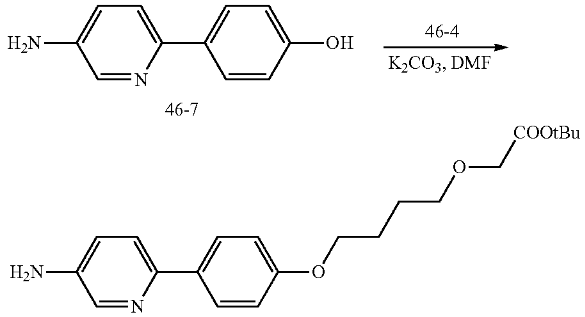

46-7

46-8

Intermediate 46-7 (1.19 g, 9.6 mmol), intermediate 46-4 (4.13 g, 11.52 mmol) and potassium carbonate (2.65 g, 19.2 mmol) were added to 20 ml of DMF, to react at 100° C. for 2 hours. After the reaction was completed, the obtained product was washed with 100 ml of water, extracted twice with 100 ml of EA, washed twice with 100 ml of saturated brine, dried over anhydrous sodium sulfate, rotating-dried and loaded on the chromatographic column with PE:EA=5:1-2:1 to obtain 2 g of light brown oily intermediate 46-8 with a yield of 56%.

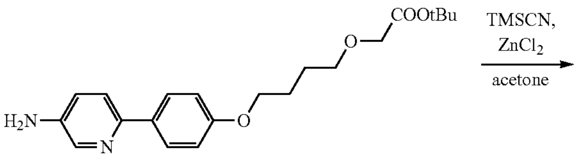

46-8

-continued

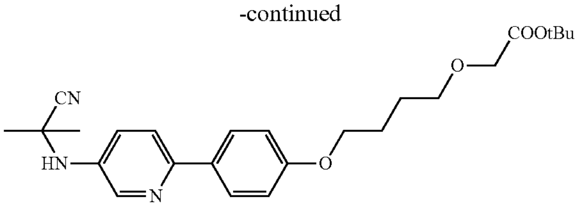

46-9

Intermediate 46-8 (2.01 g, 5.4 mmol), TMSCN (2.68 g, 27.0 mmol), and $ZnCl_2$ (147 mg, 1.08 mmol) were successively added to 20 ml of acetone, to react at room temperature for 1 hour. After the reaction was completed, the obtained product was washed with 100 ml of water, extracted with 100 ml of EA, washed with 100 ml of saturated brine, dried over anhydrous sodium sulfate, and rotating-dried to obtain 2.2 g of brown oily substance 46-9 with a yield of 92.8%.

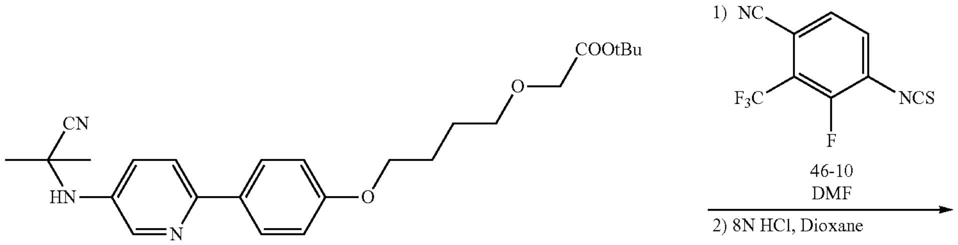

46-9

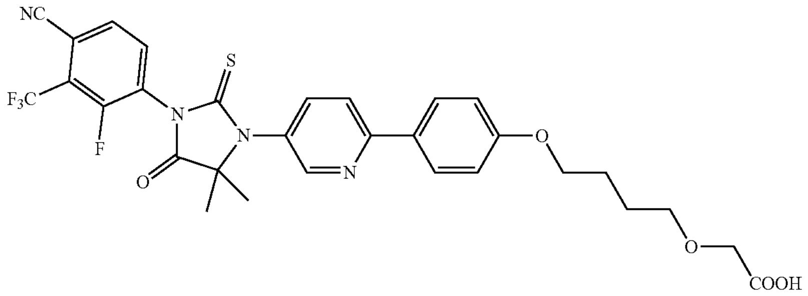

46-11

Intermediate 46-9 (2.2 g, 5 mmol) and compound 46-10 (2.46 g, 10 mmol) were added to 20 ml of DMF. The mixture was stirred at room temperature overnight, added with 20 ml of dioxane and 20 ml of 6N hydrochloric acid, and stirred at 90° C. for 1 hour. After the reaction was completed, the obtained product was washed with 100 ml of water, extracted twice with 100 ml of EA, washed with saturated brine, dried over anhydrous sodium sulfate, rotating-dried and loaded on the chromatographic column with PE:EA=5:1-2:1 to obtain 1.2 g of light brown intermediate 46-11 with a yield of 38%

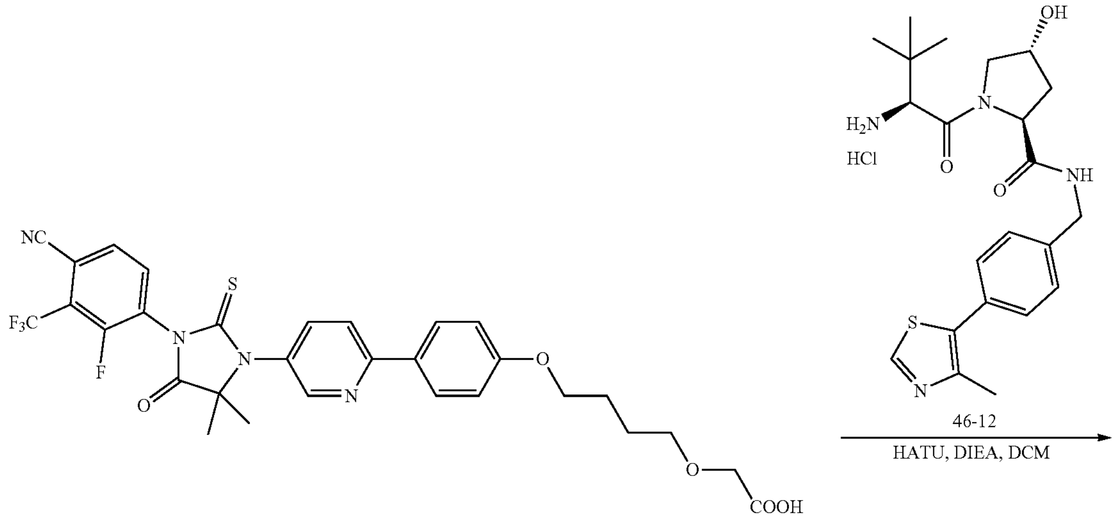

46-11

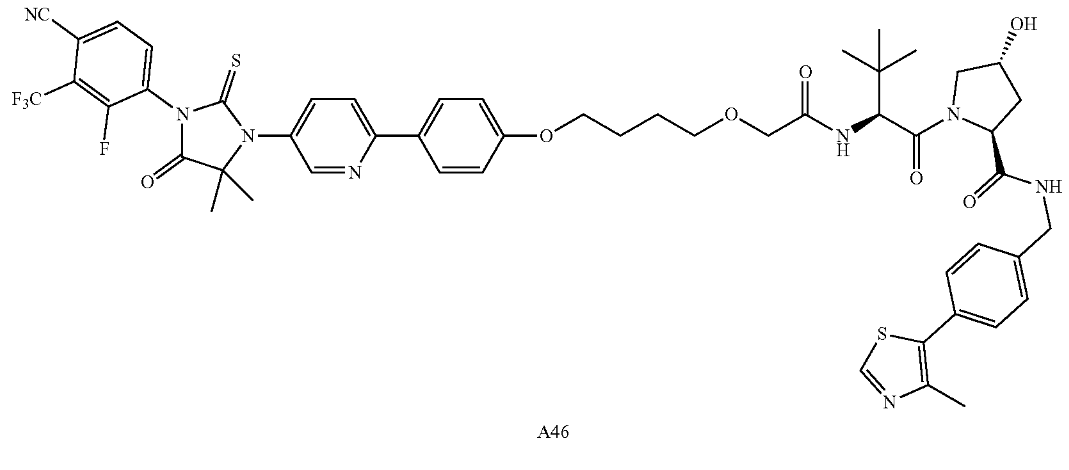

A46

46-11 (140 mg, 0.22 mmol), 46-12 (103 mg, 0.22 mmol), HATU (167 mg, 0.44 mmol), and triethylamine (66 mg, 0.66 mmol) were added to 10 ml of DCM successively. The mixture was stirred at room temperature for 1 hour. After the reaction was completed, the obtained product was washed with 20 ml of water, extracted with 20 ml of DCM, washed with 20 ml of saturated brine, dried over anhydrous sodium sulfate, rotating-evaporated, and loaded on a thick preparative plate with DCM:MeOH=10:1 to obtain 100 mg, and then on a preparative column to obtain 60 mg of white solid A46 with a purity of 98% and a yield of 26%.

LCMS ($[M+H]^+$): 1043.2

$^1$HNMR (400 MHz, DMSO-d6) δ8.97 (d, J=9.7 Hz, 1H), 8.68-8.57 (m, 2H), 8.30 (q, J=8.5 Hz, 2H), 8.10 (dd, J=8.7, 4.1 Hz, 3H), 7.95 (dd, J=8.5, 2.4 Hz, 1H), 7.477.36 (m, 5H), 7.06 (d, J=8.9 Hz, 2H), 5.17 (d, J=3.5 Hz, 1H), 4.58 (d, J=9.6 Hz, 1H), 4.504.33 (m, 3H), 4.27 (dd, J=15.8, 5.6 Hz, 1H), 4.09 (t, J=6.2 Hz, 2H), 3.96 (s, 2H), 3.70-3.54 (m, 4H), 2.44 (d, J=7.2 Hz, 3H), 2.07 (dd, J=12.4, 8.3 Hz, 1H), 1.95-1.80 (m, 3H), 1.75 (dd, J=13.9, 6.2 Hz, 2H), 1.59 (s, 6H), 0.94 (d, J=6.9 Hz, 9H).

Examples A47-A142 were synthesized with the corresponding reagents using a similar procedure to Example A46.

Example A47
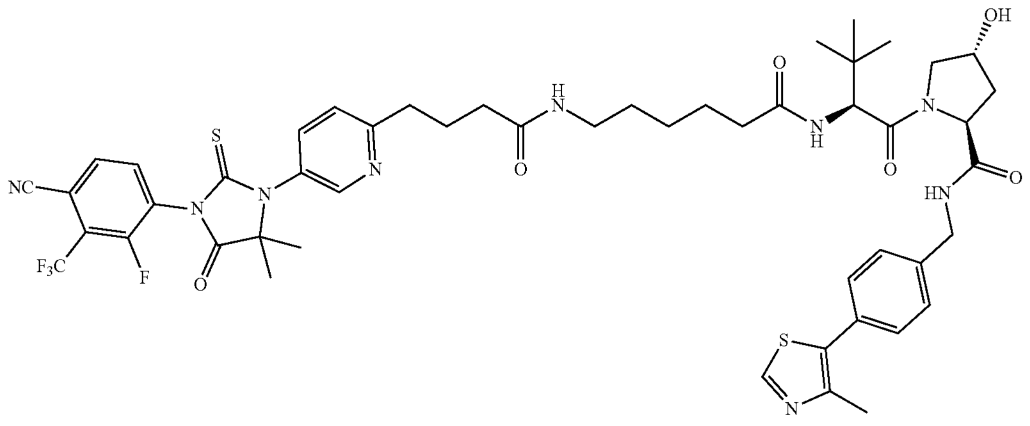 [SMILES: Cc1ncsc1-c1ccc(CNC(=O)[C@@H]2C[C@@H](O)CN2C(=O)[C@@H](NC(=O)CCCCCNC(=O)CCCc2ccc(N3C(=S)N(c4ccc(C#N)c(C(F)(F)F)c4F)C(=O)C3(C)C)cn2)C(C)(C)C)cc1]
LCMS ([M+H]$^+$): 1020.2
$^1$HNMR (400 MHz, DMSO-d6) δ8.98 (s, 1H), 8.59-8.50 (m, 2H), 8.32-8.24 (m, 2H), 7.82 (ddd, J=14.0, 13.5, 7.5 Hz, 3H), 7.42 (dt, J=16.1, 8.3 Hz, 5H), 5.13 (d, J=3.5 Hz, 1H), 4.54 (d, J=9.4 Hz, 1H), 4.43 (dd, J=15.7, 7.2 Hz, 2H), 4.34 (s, 1H), 4.21 (dd, J=15.9, 5.4 Hz, 1H), 3.71-3.59 (m, 2H), 3.01 (dd, J=13.1, 6.3 Hz, 2H), 2.83-2.74 (m, 2H), 2.44 (s, 3H), 2.29-2.20 (m, 1H), 2.13 (q, J=7.7 Hz, 3H), 1.92 (dd, J=14.8, 7.9 Hz, 3H), 1.53 (s, 6H), 1.51-1.34 (m, 4H), 1.28-1.17 (m, 3H), 0.92 (d, J=7.9 Hz, 9H).
Example A48
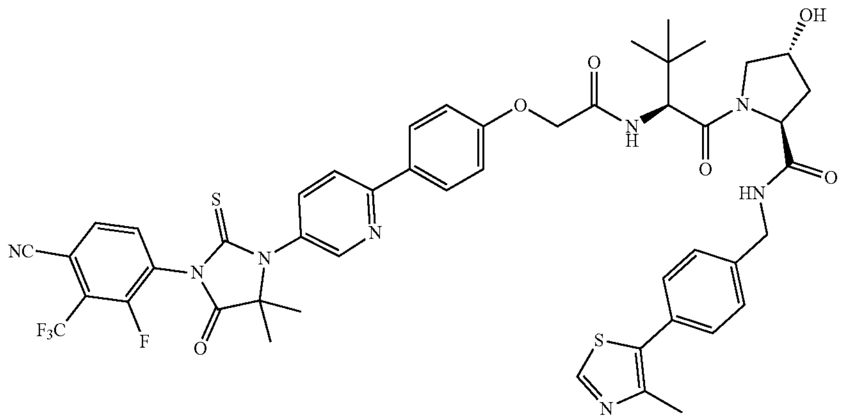 [SMILES: Cc1ncsc1-c1ccc(CNC(=O)[C@@H]2C[C@@H](O)CN2C(=O)[C@@H](NC(=O)COc2ccc(-c3ccc(N4C(=S)N(c5ccc(C#N)c(C(F)(F)F)c5F)C(=O)C4(C)C)cn3)cc2)C(C)(C)C)cc1]
LCMS ([M+H]$^+$): 971.2
$^1$HNMR (400 MHz, DMSO-d6) δ8.98 (d, J=5.3 Hz, 1H), 8.66 (d, J=2.3 Hz, 1H), 8.60 (t, J=6.1 Hz, 1H), 8.29 (q, J=8.7 Hz, 2H), 8.13 (d, J=8.9 Hz, 3H), 7.98-7.89 (m, 2H), 7.45-7.31 (m, 4H), 7.10 (d, J=8.9 Hz, 2H), 5.16 (d, J=3.5 Hz, 1H), 4.79-4.69 (m, 2H), 4.60 (d, J=9.4 Hz, 1H), 4.48-4.33 (m, 3H), 4.25 (dd, J=15.9, 5.4 Hz, 1H), 3.65 (dd, J=23.5, 8.8 Hz, 2H), 2.44 (d, J=6.2 Hz, 3H), 1.99 (ddd, J=31.9, 16.9, 10.7 Hz, 3H), 1.58 (s, 6H), 0.93 (d, J=10.6 Hz, 9H).

Example A49
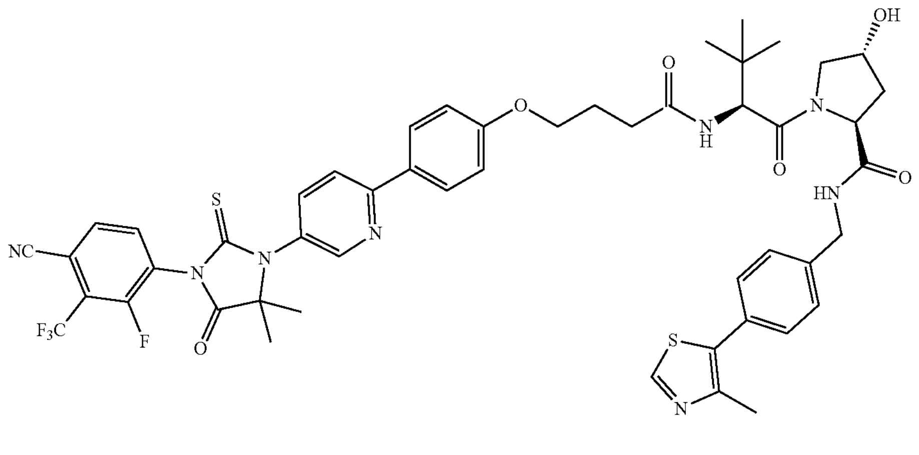 [SMILES: Cc1ncsc1-c1ccc(CNC(=O)[C@@H]2C[C@@H](O)CN2C(=O)[C@@H](NC(=O)CCCOc2ccc(-c3ccc(N4C(=S)N(c5ccc(C#N)c(C(F)(F)F)c5F)C(=O)C4(C)C)cn3)cc2)C(C)(C)C)cc1]
LCMS ([M+H]$^+$): 999.2
$^1$HNMR (400 MHz, DMSO-d6) δ8.97 (d, J=8.8 Hz, 1H), 8.65 (d, J=2.4 Hz, 1H), 8.56 (t, J=6.0 Hz, 1H), 8.29 (q, J=8.5 Hz, 2H), 8.09 (dd, J=17.2, 8.8 Hz, 3H), 7.99 (d, J=9.3 Hz, 1H), 7.94 (dd, J=8.5, 2.5 Hz, 1H), 7.40 (q, J=8.4 Hz, 4H), 7.07 (d, J=8.9 Hz, 2H), 5.14 (d, J=3.5 Hz, 1H), 4.57 (d, J=9.4 Hz, 1H), 4.47-4.39 (m, 2H), 4.36 (s, 1H), 4.21 (dd, J=15.9, 5.5 Hz, 1H), 4.05 (d, J=2.2 Hz, 2H), 3.67 (s, 2H), 2.47-2.31 (m, 5H), 2.07-1.87 (m, 4H), 1.58 (s, 6H), 0.93 (d, J=7.7 Hz, 9H).
Example A50
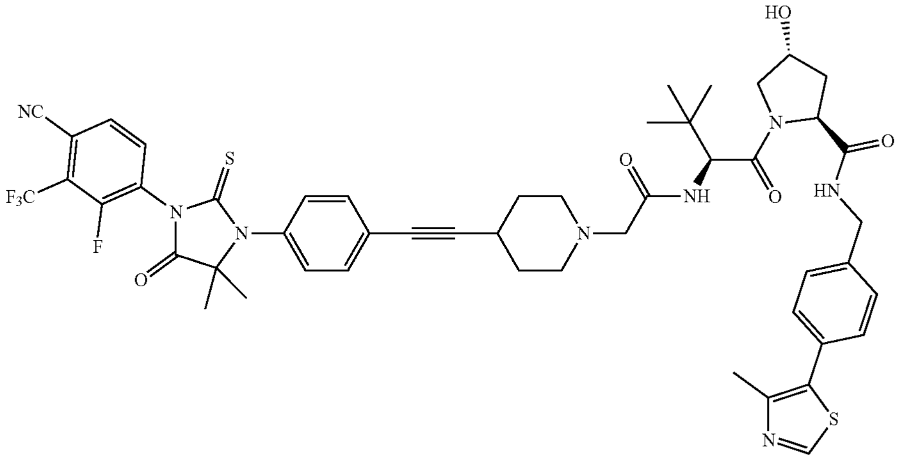 [SMILES: Cc1ncsc1-c1ccc(CNC(=O)[C@@H]2C[C@@H](O)CN2C(=O)[C@@H](NC(=O)CN2CCC(C#Cc3ccc(N4C(=S)N(c5ccc(C#N)c(C(F)(F)F)c5F)C(=O)C4(C)C)cc3)CC2)C(C)(C)C)cc1]
LCMS ([M+H]$^+$): 985.1
$^1$HNMR (400 MHz, DMSO-d6) δ8.94 (s, 1H), 8.60 (t, J=6.0 Hz, 1H), 8.27 (d, J=4.5 Hz, 2H), 7.80 (d, J=9.7 Hz, 1H), 7.55 (d, J=8.5 Hz, 2H), 7.41 (s, 5H), 5.15 (d, J=3.4 Hz, 1H), 4.51 (d, J=9.7 Hz, 1H), 4.44 (t, J=8.2 Hz, 1H), 4.35 (d, J=5.8 Hz, 2H), 4.30 (d, J=5.9 Hz, 1H), 3.70-3.57 (m, 2H), 3.04 (d, J=16.2 Hz, 1H), 2.95 (d, J=16.0 Hz, 1H), 2.74 (s, 3H), 2.44 (s, 3H), 2.35 (d, J=12.3 Hz, 2H), 2.06 (dd, J=13.7, 6.8 Hz, 1H), 1.90 (ddd, J=12.8, 8.9, 4.4 Hz, 3H), 1.51 (s, 7H), 0.95 (s, 9H).

Example A51
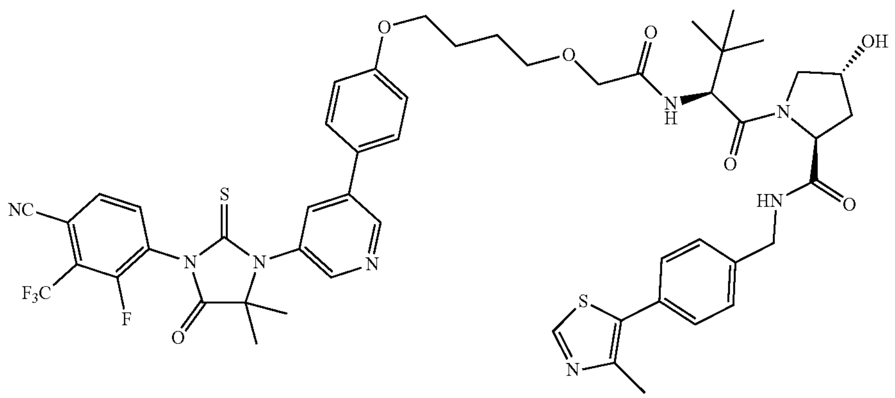 [SMILES: Cc1ncsc1-c1ccc(CNC(=O)[C@@H]2C[C@@H](O)CN2C(=O)[C@@H](NC(=O)COCCCCOc2ccc(-c3cncc(N4C(=S)N(c5ccc(C#N)c(C(F)(F)F)c5F)C(=O)C4(C)C)c3)cc2)C(C)(C)C)cc1]
LCMS ([M+H]$^+$): 1043.2
$^1$HNMR (400 MHz, DMSO-d6) δ9.01 (d, J=1.8 Hz, 1H), 8.98-8.95 (m, 1H), 8.63 (t, J=6.0 Hz, 1H), 8.57 (d, J=2.0 Hz, 1H), 8.33-8.25 (m, 2H), 8.19 (s, 1H), 7.72 (d, J=8.7 Hz, 2H), 7.46-7.34 (m, 5H), 7.07 (d, J=8.8 Hz, 2H), 5.20 (d, J=3.3 Hz, 1H), 4.56 (d, J=9.7 Hz, 1H), 4.45 (t, J=8.3 Hz, 1H), 4.41-4.35 (m, 2H), 4.27 (d, J=5.4 Hz, 1H), 4.07 (t, J=6.2 Hz, 2H), 3.93 (s, 2H), 3.66-3.62 (m, 2H), 3.57-3.54 (m, 2H), 2.42 (s, 3H), 2.11-2.03 (m, 1H), 2.00-1.99 (m, 1H), 1.94-1.87 (m, 1H), 1.83-1.81 (m, 2H), 1.77-1.69 (m, 2H), 1.60 (d, J=2.6 Hz, 6H), 0.94 (s, 9H).
Example A52
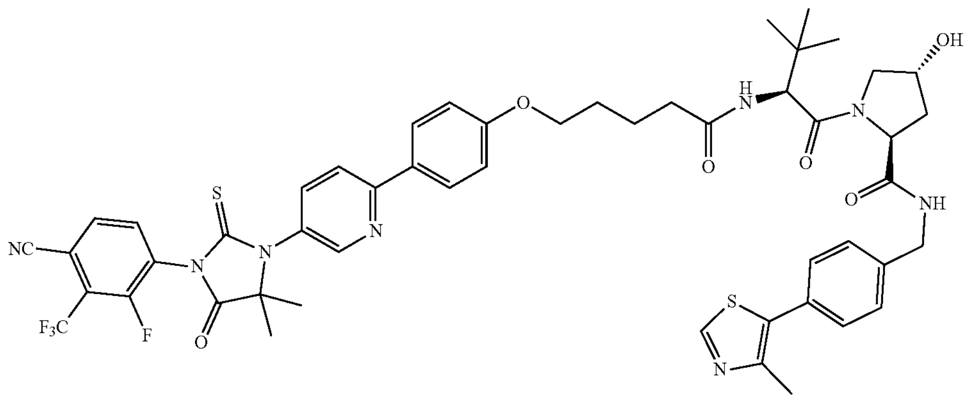 [SMILES: Cc1ncsc1-c1ccc(CNC(=O)[C@@H]2C[C@@H](O)CN2C(=O)[C@@H](NC(=O)CCCCOc2ccc(-c3ccc(N4C(=S)N(c5ccc(C#N)c(C(F)(F)F)c5F)C(=O)C4(C)C)cn3)cc2)C(C)(C)C)cc1]
LCMS ([M+H]$^+$): 1013.3
$^1$HNMR (400 MHz, DMSO-d6) δ8.97 (d, J=6.8 Hz, 1H), 8.65 (d, J=2.4 Hz, 1H), 8.56 (t, J=5.8 Hz, 1H), 8.29 (q, J=8.5 Hz, 2H), 8.11 (d, J=8.8 Hz, 3H), 7.96-7.89 (m, 2H), 7.40 (q, J=8.4 Hz, 4H), 7.07 (d, J=8.9 Hz, 2H), 5.13 (d, J=3.5 Hz, 1H), 4.57 (d, J=9.3 Hz, 1H), 4.48-4.39 (m, 2H), 4.36 (s, 1H), 4.21 (dd, J=15.9, 5.5 Hz, 1H), 4.06 (t, J=5.7 Hz, 2H), 3.73-3.62 (m, 2H), 2.44 (d, J=3.5 Hz, 3H), 2.41-2.32 (m, 1H), 2.23 (dd, J=14.0, 6.9 Hz, 1H), 2.04 (dd, J=19.1, 6.1 Hz, 1H), 1.95-1.86 (m, 1H), 1.78-1.63 (m, 4H), 1.58 (s, 6H), 0.95 (s, 9H).

Example A53
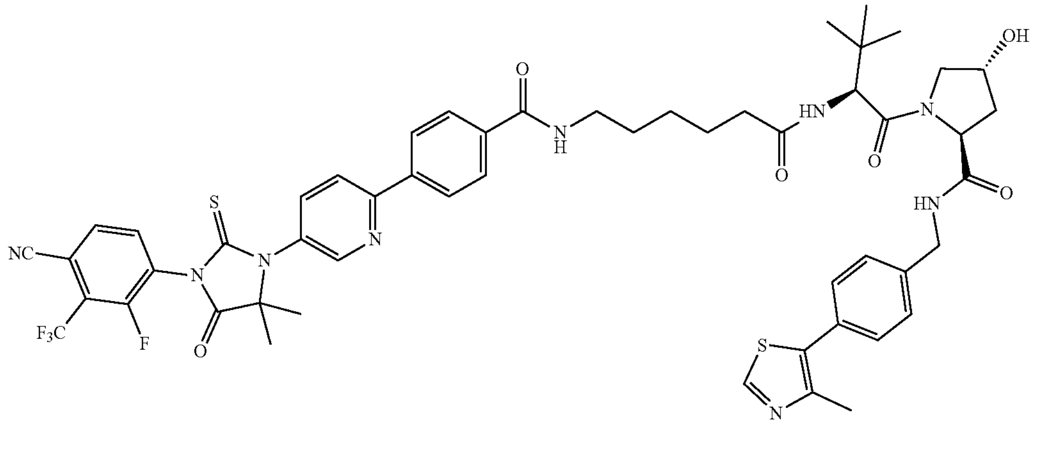 [SMILES: Cc1ncsc1-c1ccc(CNC(=O)[C@@H]2C[C@@H](O)CN2C(=O)[C@@H](NC(=O)CCCCCNC(=O)c2ccc(-c3ccc(N4C(=S)N(c5ccc(C#N)c(C(F)(F)F)c5F)C(=O)C4(C)C)cn3)cc2)C(C)(C)C)cc1]
LCMS ([M+H]$^+$): 1054.3
$^1$HNMR (400 MHz, DMSO-d6):8.91 (s, 1H), 8.69 (s, 1H), 8.10 (d, J=12 Hz 2H), 7.96-7.87 (m, 4H), 7.83 (d, J=8 Hz 2H), 7.44-7.41 (t, 1H), 7.34-7.36 (t, 4H), 6.81 (s, 1H), 6.37-6.39 (d, J=8 Hz 1H), 4.72-4.76 (t, 1H), 4.55-4.61 (t, 3H), 4.33-4.38 (m, 1H), 4.08-4.13 (m, 1H), 3.62-3.65 (m, 1H), 3.45-3.49 (m, 2H), 2.42-2.49 (m, 5H), 2.15-2.33 (m, 4H), 1.61-1.67 (m, 10H), 1.38-1.44 (m, 2H), 0.97 (s, 9H).
Example A54
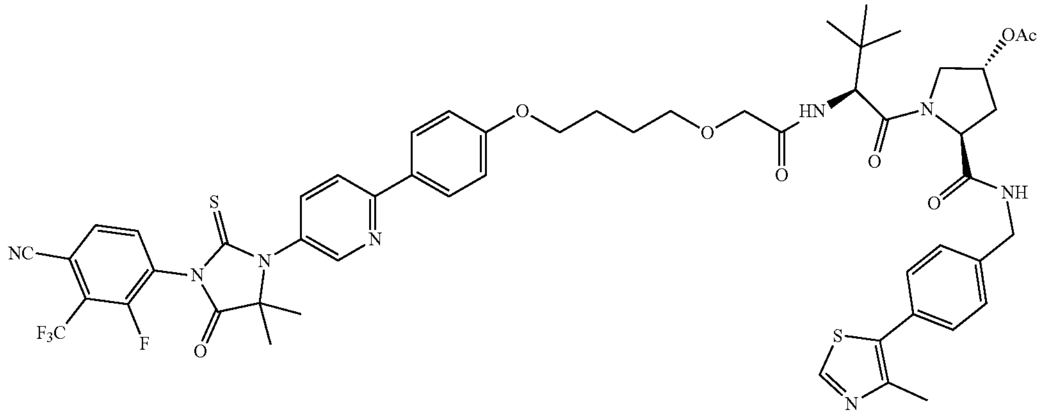 [SMILES: CC(=O)O[C@@H]1C[C@@H](C(=O)NCc2ccc(-c3scnc3C)cc2)N(C(=O)[C@@H](NC(=O)COCCCCOc2ccc(-c3ccc(N4C(=S)N(c5ccc(C#N)c(C(F)(F)F)c5F)C(=O)C4(C)C)cn3)cc2)C(C)(C)C)C1]
LCMS ([M+H]$^+$): 1085.3
$^1$HNMR (400 MHz, DMSO-d6) δ8.97 (d, J=6.7 Hz, 1H), 8.66-8.58 (m, 2H), 8.29 (q, J=8.5 Hz, 2H), 8.10 (dd, J=8.7, 1.9 Hz, 3H), 7.94 (dd, J=8.5, 2.5 Hz, 1H), 7.46-7.37 (m, 5H), 7.06 (d, J=8.9 Hz, 2H), 5.27 (s, 1H), 4.44 (ddd, J=32.8, 16.1, 7.3 Hz, 3H), 4.28 (dd, J=15.7, 5.8 Hz, 1H), 4.09 (t, J=6.2 Hz, 2H), 3.94 (t, J=7.4 Hz, 3H), 3.84 (dd, J=11.7, 4.1 Hz, 1H), 3.55 (t, J=6.2 Hz, 2H), 2.44 (d, J=5.8 Hz, 3H), 2.26 (dd, J=13.6, 7.8 Hz, 1H), 2.12 (ddd, J=13.7, 9.0, 4.9 Hz, 1H), 1.98 (d, J=13.4 Hz, 3H), 1.82 (dd, J=14.0, 6.2 Hz, 2H), 1.78-1.69 (m, 2H), 1.58 (s, 6H), 1.35 (s, 1H), 0.94 (d, J=8.2
Hz, 9H).

Example A55
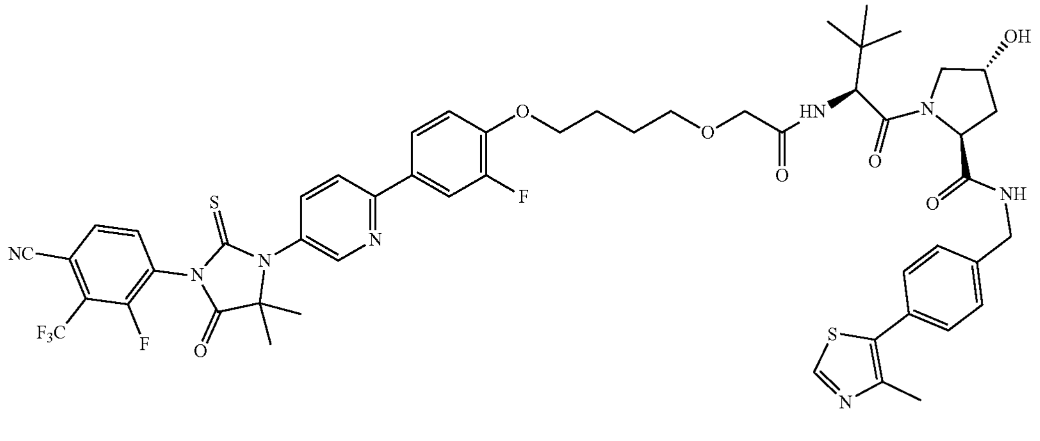 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2F)C(C)(C)C)cc1]
LCMS ([M+H]$^+$): 1061.3
$^1$HNMR (400 MHz, DMSO-d6) δ8.97-(m, 1H), 8.67 (d, J=2.3 Hz, 1H), 8.60 (t, J=6.0 Hz, 1H), 8.34-8.24 (m, 2H), 8.17 (d, J=8.5 Hz, 1H), 8.03-7.93 (m, 3H), 7.45-7.35 (m, 5H), 7.29 (t, J=8.6 Hz, 1H), 5.16 (d, J=3.5 Hz, 1H), 4.56 (d, J=9.5 Hz, 1H), 4.49-4.34 (m, 3H), 4.28-4.23 (m, 1H), 4.17 (t, J=6.2 Hz, 2H), 3.96 (d, J=1.7 Hz, 2H), 3.70-3.53 (m, 5H), 2.44-2.42 (m, 3H), 2.09-2.04 (m, 1H), 1.93-1.83 (m, 3H), 1.77-1.72 (m, 2H), 1.58 (s, 6H), 0.94-0.92 (m, 9H)
Example A56
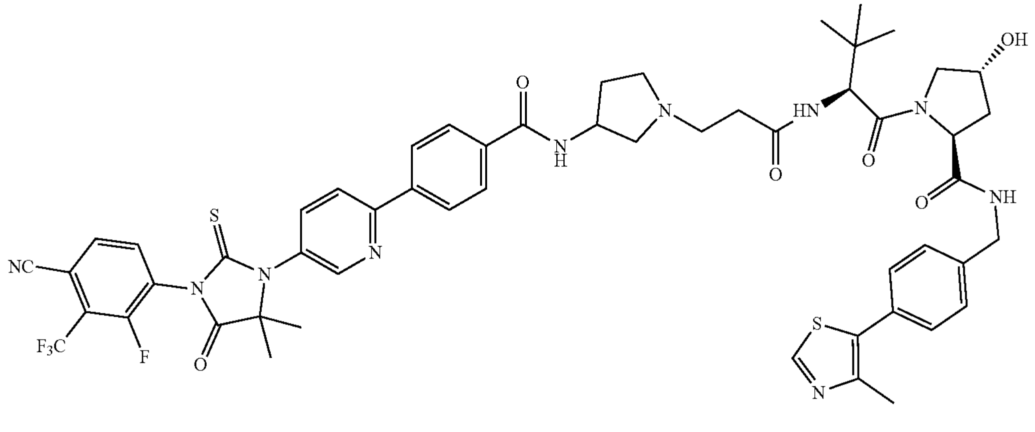 [SMILES: Cc1ncsc1-c1ccc(CNC(=O)[C@@H]2C[C@@H](O)CN2C(=O)[C@@H](NC(=O)CCN2CCC(NC(=O)c3ccc(-c4ccc(N5C(=S)N(c6ccc(C#N)c(C(F)(F)F)c6F)C(=O)C5(C)C)cn4)cc3)C2)C(C)(C)C)cc1]
LCMS ([M+H]$^+$): 1081.3
$^1$HNMR (400 MHz, DMSO-d6) δ8.97-8.95 (m, 1H), 8.75 (d, J=2.4 Hz, 1H), 8.62-8.43 (m, 3H), 8.33-8.20 (m, 5H), 8.4-8.00 (m, 3H), 7.45-7.35 (m, 4H), 5.19-5.12 (m, 1H), 4.54 (dd, J=9.3, 2.6 Hz, 1H), 4.50-4.33 (m, 4H), 4.29-4.20 (m, 1H), 3.70-3.63 (m, 2H), 2.89 (m, 1H), 2.79-2.57 (m, 4H), 2.43 (s, 3H), 2.34-2.18 (m, 3H), 2.04 (m, 1H), 1.99-1.86 (m, 2H), 1.82 (m, 1H), 1.59 (s, 6H), 0.94 (d, J=4.8 Hz, 9H).

Example A57

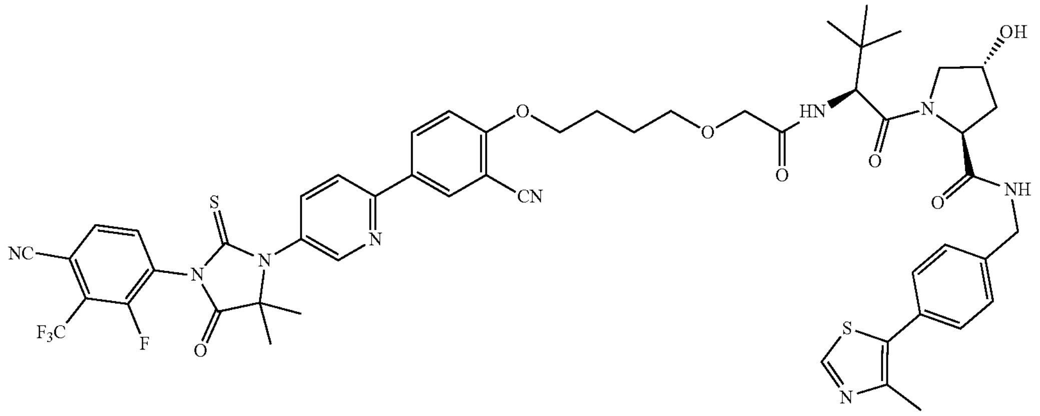 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2C#N)C(C)(C)C)cc1]

LCMS ([M+H]$^+$): 1068.2

$^1$HNMR (400 MHz, DMSO-d6) δ8.96 (d, J=8.2 Hz, 1H), 8.70 (d, J=2.0 Hz, 1H), 8.59 (t, J=6.1 Hz, 1H), 8.50 (d, J=2.2 Hz, 1H), 8.46 (d, J=8.9 Hz, 1H), 8.27 (dd, J=17.1, 7.1 Hz, 3H), 8.02 (dd, J=8.5, 2.3 Hz, 1H), 7.44-7.35 (m, 6H), 5.15 (d, J=3.4 Hz, 1H), 4.56 (d, J=9.6 Hz, 1H), 4.48-4.38 (m, 2H), 4.36 (d, J=6.0 Hz, 4H), 4.27 (t, J=6.1 Hz, 3H), 3.96 (d, J=3.2 Hz, 2H), 3.69-3.62 (m, 2H), 3.59 (t, J=6.2 Hz, 5H), 2.43 (d, J=6.7 Hz, 3H), 2.03 (dd, J=22.7, 10.5 Hz, 2H), 1.88 (d, J=8.0 Hz, 6H), 1.80-1.73 (m, 2H), 1.58 (s, 6H), 0.93 (d, J=7.9 Hz, 9H).

Example A58

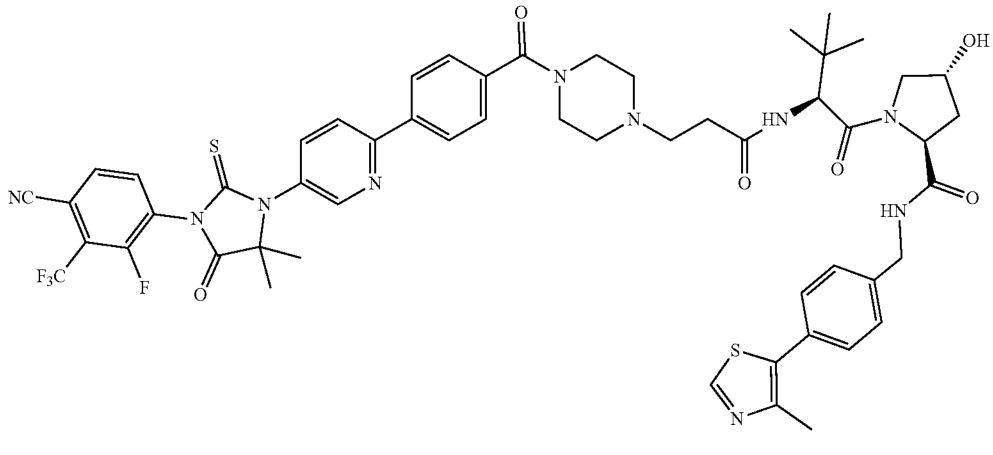 [SMILES: Cc1ncsc1-c1ccc(CNC(=O)[C@@H]2C[C@@H](O)CN2C(=O)[C@@H](NC(=O)CCN2CCN(C(=O)c3ccc(-c4ccc(N5C(=S)N(c6ccc(C#N)c(C(F)(F)F)c6F)C(=O)C5(C)C)cn4)cc3)CC2)C(C)(C)C)cc1]

LCMS ([M+H]$^+$): 1081.3

$^1$HNMR (400 MHz, DMSO-d6) δ8.97 (d, J=8.2 Hz, 1H), 8.75 (d, J=2.5 Hz, 1H), 8.59 (t, J=6.2 Hz, 1H), 8.47 (d, J=9.5 Hz, 1H), 8.30 (q, J=8.5 Hz, 2H), 8.21 (dd, J=18.2, 8.4 Hz, 3H), 8.05 (dd, J=8.4, 2.5 Hz, 1H), 7.49 (d, J=8.2 Hz, 2H), 7.44 (d, J=8.2 Hz, 2H), 7.37 (d, J=8.3 Hz, 2H), 5.32 (t, J=4.7 Hz, 1H), 5.14 (d, J=3.4 Hz, 1H), 4.56 (d, J=9.5 Hz, 1H), 4.44 (dd, J=16.8, 8.7 Hz, 2H), 4.35 (s, 1H), 4.21 (dd, J=15.9, 5.5 Hz, 1H), 3.64 (dd, J=23.6, 8.3 Hz, 4H), 2.65 (d, J=12.2 Hz, 3H), 2.44 (d, J=8.5 Hz, 5H), 2.28 (d, J=15.5 Hz, 1H), 2.00 (dd, J=14.8, 7.2 Hz, 3H), 1.91 (dd, J=17.3, 8.6 Hz, 1H), 1.60 (s, 6H), 1.45 (s, 1H), 0.95 (s, 8H).

Example A59
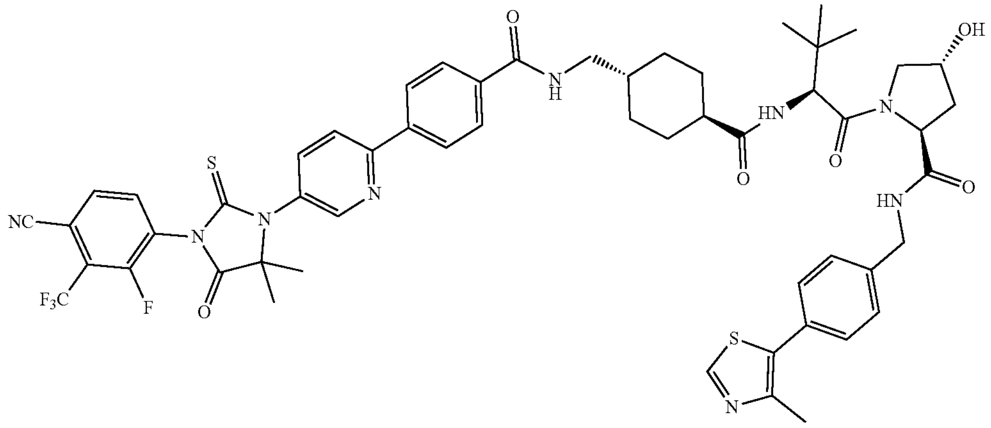 [SMILES: Cc1ncsc1-c1ccc(CNC(=O)[C@@H]2C[C@@H](O)CN2C(=O)[C@@H](NC(=O)[C@H]2CC[C@H](CNC(=O)c3ccc(-c4ccc(N5C(=S)N(c6ccc(C#N)c(C(F)(F)F)c6F)C(=O)C5(C)C)cn4)cc3)CC2)C(C)(C)C)cc1]
LCMS ([M+H]$^+$): 1080.3
$^1$HNMR (400 MHz, DMSO-d6) δ8.99 (s, 1H), 8.76 (d, J=2.3 Hz, 1H), 8.60-8.54 (m, 2H), 8.34-8.23 (m, 5H), 8.06 (dd, J=8.5, 2.4 Hz, 1H), 8.01 (d, J=8.5 Hz, 2H), 7.72 (d, J=9.3 Hz, 1H), 7.41 (q, J=8.4 Hz, 4H), 5.14 (m, 1H), 4.52 (m, 1H), 4.44 (m, 2H), 4.36 (m, 1H), 4.22 (m, 1H), 3.69-3.61 (m, 2H), 3.16 (m, 2H), 2.45 (s, 3H), 2.36 (m, 1H), 2.07-1.99 (m, 1H), 1.90 (m, 1H), 1.80 (m, 3H), 1.69 (m, 1H), 1.61 (s, 6H), 1.31 (m, 4H), 0.93 (m, 9H).
Example A60
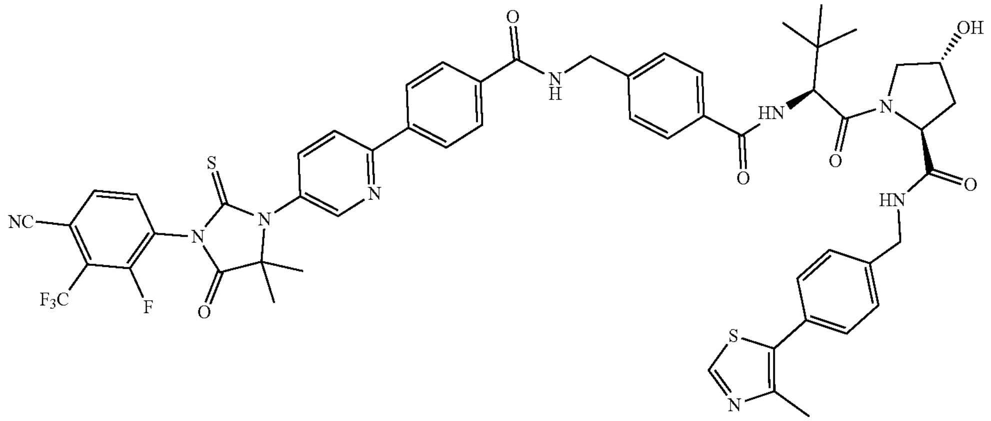 [SMILES: Cc1ncsc1-c1ccc(CNC(=O)[C@@H]2C[C@@H](O)CN2C(=O)[C@@H](NC(=O)c2ccc(CNC(=O)c3ccc(-c4ccc(N5C(=S)N(c6ccc(C#N)c(C(F)(F)F)c6F)C(=O)C5(C)C)cn4)cc3)cc2)C(C)(C)C)cc1]
LCMS ([M+H]$^+$): 1074.3
$^1$HNMR (400 MHz, DMSO-d6) δ9.25 (t, J=6.0 Hz, 1H), 8.98 (s, 1H), 8.76 (d, J=2.4 Hz, 1H), 8.58 (t, J=6.0 Hz, 1H), 8.31-8.26 (m, 5H), 8.06 (dd, J=8.5, 2.6 Hz, 3H), 7.91 (d, J=9.1 Hz, 1H), 7.85 (d, J=8.2 Hz, 2H), 7.45-7.39 (m, 6H), 5.15 (d, J=3.6 Hz, 1H), 4.77 (d, J=9.1 Hz, 1H), 4.56 (d, J=5.8 Hz, 2H), 4.49-4.35 (m, 3H), 4.24 (dd, J=15.9, 5.5 Hz, 1H), 3.73 (d, J=3.1 Hz, 2H), 2.44 (s, 3H), 2.06-1.88 (m, 2H), 1.60 (s, 6H), 1.03 (s, 9H).

Example A61
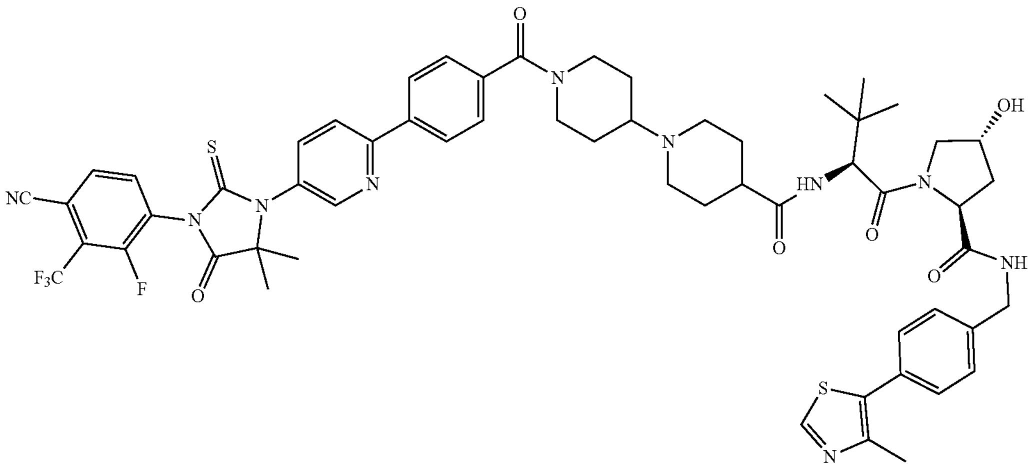 [SMILES: Cc1ncsc1-c1ccc(CNC(=O)[C@@H]2C[C@@H](O)CN2C(=O)[C@@H](NC(=O)C2CCN(C3CCN(C(=O)c4ccc(-c5ccc(N6C(=S)N(c7ccc(C#N)c(C(F)(F)F)c7F)C(=O)C6(C)C)cn5)cc4)CC3)CC2)C(C)(C)C)cc1]
LCMS ([M+H]$^+$): 1135.3
$^1$HNMR (400 MHz, DMSO-d6):8.99 (s, 1H), 8.76 (s, 1H), 8.56 (s, 1H), 8.21-8.31 (m, 5H), 8.05 (d, J=8 Hz 1H), 7.73-7.76 (d, J=12 Hz 1H), 7.55 (d, J=8 Hz 2H), 7.38-7.43 (m, 4H), 5.14 (s, 1H), 4.36-4.54 (m, 5H), 4.2 1-4.24 (m, 1H), 3.64 (m, 3H), 3.06 (s, 2H), 2.86 (s, 2H), 2.45 (s, 3H), 2.35 (s, 1H), 2.02-2.14 (m, 4H), 1.68-1.90 (m, 5H), 1.58-1.60 (m, 6H), 1.44-1.48 (m, 4H), 0.94 (s, 9H).
Example A62
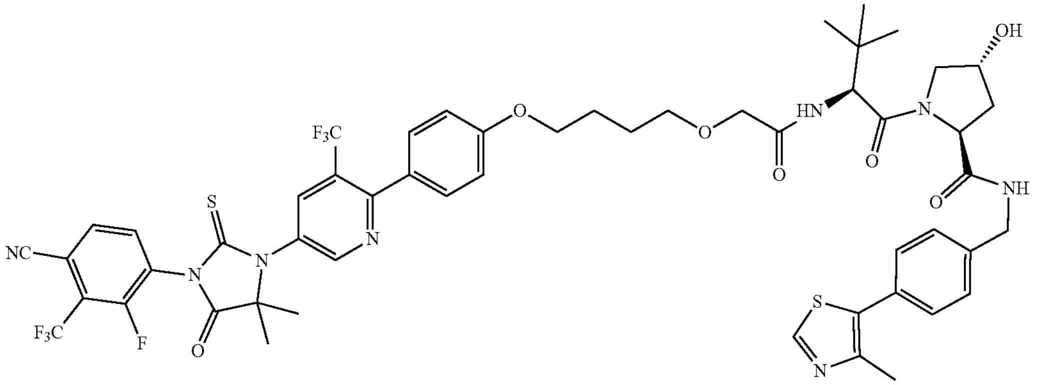 [SMILES: Cc1ncsc1-c1ccc(CNC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3C(F)(F)F)cc2)C(C)(C)C)cc1]
LCMS ([M+H]$^+$): 1111.3
$^1$HNMR (400 MHz, DMSO-d6) δ8.96 (d, J=9.9 Hz, 2H), 8.60 (t, J=5.8 Hz, 1H), 8.49 (d, J=1.8 Hz, 1H), 8.27 (d, J=12.3 Hz, 2H), 7.50 (d, J=8.5 Hz, 2H), 7.46-7.35 (m, 5H), 7.05 (d, J=8.7 Hz, 2H), 5.17 (s, 1H), 4.57 (d, J=9.6 Hz, 1H), 4.50-4.33 (m, 3H), 4.26 (m, 1H), 4.09 (m, 2H), 3.95 (m, 2H), 3.69-3.54 (m, 5H), 2.44 (m, 3H), 2.00 (m, 3H), 1.89-1.79 (m, 2H), 1.80-1.70 (m, 2H), 1.64 (d, J=7.1 Hz, 6H), 1.24 (m, 2H), 0.95 (s, 9H).

Example A63
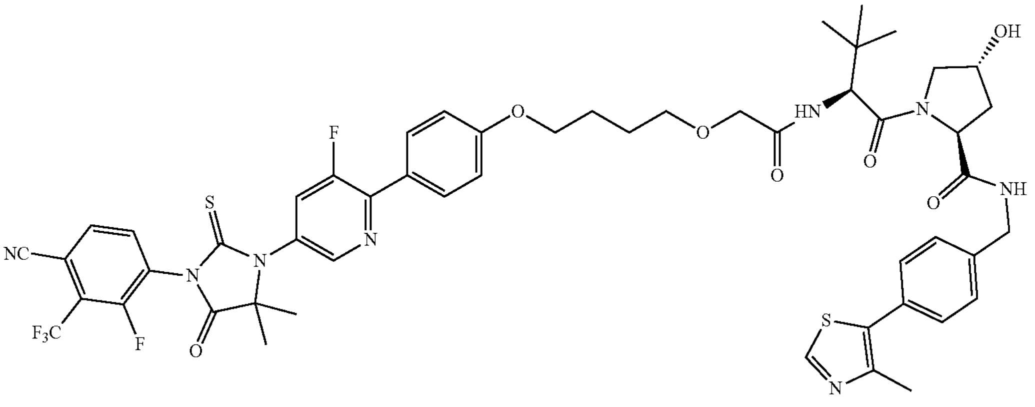 [SMILES: Cc1ncsc1-c1ccc(CNC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)cc2)C(C)(C)C)cc1]
LCMS ($[M+H]^+$): 1061.3
$^1$HNMR (400 MHz, DMSO-d6) δ8.96 (d, J=10.8 Hz, 1H), 8.60 (s, 2H), 8.29 (d, J=12.7 Hz, 2H), 8.11 (d, J=11.7 Hz, 1H), 7.96 (d, J=7.9 Hz, 2H), 7.40 (d, J=7.7 Hz, 5H), 7.09 (d, J=8.7 Hz, 2H), 5.17 (d, J=3.1 Hz, 1H), 4 0.57 (d, J=9.5 Hz, 1H), 4.50-4.32 (m, 3H), 4.26 (dd, J=15.7, 5.4 Hz, 1H), 4.09 (t, J=5.9 Hz, 2H), 3.96 (s, 2H), 3.70-3.51 (m, 4H), 2.43 (d, J=7.2 Hz, 3H), 2.07 (t, J=9.8 Hz, 1H), 1.96-1.79 (m, 3H), 1.79-1.69 (m, 2H), 1.61 (s, 6H), 0.94 (s, 9H).
Example A64
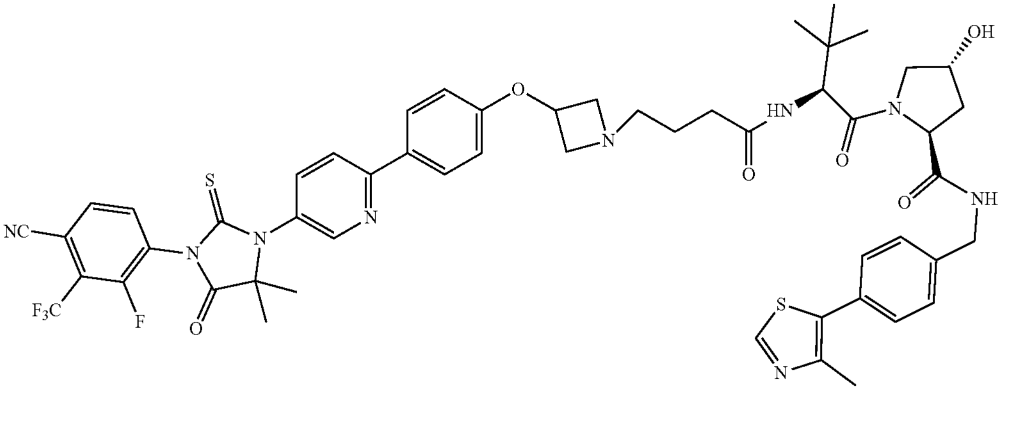 [SMILES: Cc1ncsc1-c1ccc(CNC(=O)[C@@H]2C[C@@H](O)CN2C(=O)[C@@H](NC(=O)CCCN2CC(Oc3ccc(-c4ccc(N5C(=S)N(c6ccc(C#N)c(C(F)(F)F)c6F)C(=O)C5(C)C)cn4)cc3)C2)C(C)(C)C)cc1]
LCMS ($[M+H]^+$): 1054.3
$^1$HNMR (400 MHz, DMSO-d6) δ8.96 (d, J=7.5 Hz, 1H), 8.67 (d, J=2.4 Hz, 1H), 8.55 (t, J=6.0 Hz, 1H), 8.29 (q, J=8.5 Hz, 2H), 8.16-8.05 (m, 3H), 8.01-7.93 (m, 2H), 7.39 (q, J=8.3 Hz, 4H), 6.99 (dd, J=30.6, 8.8 Hz, 2H), 5.17-5.09 (m, 1H), 4.55 (d, J=9.4 Hz, 1H), 4.47-4.38 (m, 2H), 4.34 (s, 1H), 4.31-4.16 (m, 3H), 4.07-3.96 (m, 2H), 3.66 (dt, J=16.6, 7.2 Hz, 2H), 3.13-2.99 (m, 2H), 2.43 (d, J=6.5 Hz, 3H), 2.36-2.26 (m, 1H), 2.25-2.14 (m, 1H), 2.02 (d, J=7.7 Hz, 1H), 1.89 (ddd, J=40.5, 20.4, 16.0 Hz, 4H), 1.58 (s, 6H), 0.93 (d, J=9.0 Hz, 9H).

Example A65
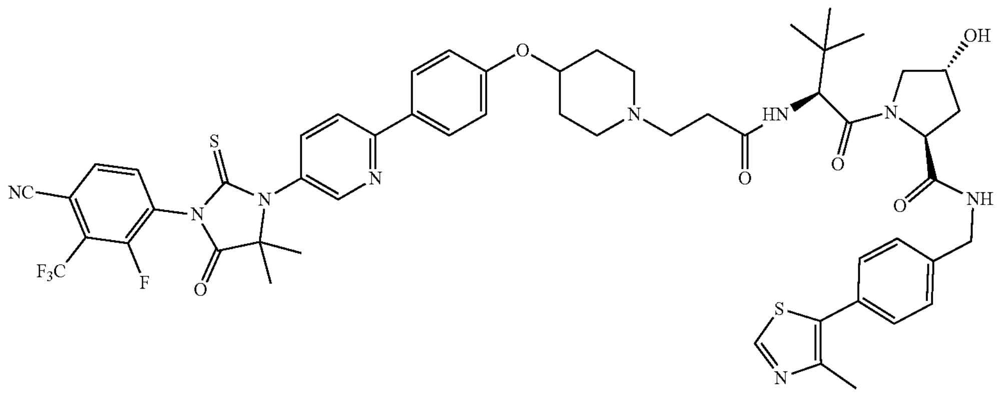 [SMILES: Cc1ncsc1-c1ccc(CNC(=O)[C@@H]2C[C@@H](O)CN2C(=O)[C@@H](NC(=O)CCN2CCC(Oc3ccc(-c4ccc(N5C(=S)N(c6ccc(C#N)c(C(F)(F)F)c6F)C(=O)C5(C)C)cn4)cc3)CC2)C(C)(C)C)cc1]
LCMS ([M+H]$^+$): 1068.4
$^1$HNMR (400 MHz, DMSO-d6):8.95 (s, 1H), 8.74-8.77 (d, J=12 Hz 1H), 8.62-8.66 (m, 2H), 8.26-8.33 (m, 2H), 8.04-8.10 (m, 3H), 7.96-7.94 (d, J=8 Hz 1H), 7.39-7.47 (m, 4H), 6.99-7.01 (d, J=8 Hz 2H), 5.16 (s, 1H), 4.19-4.59 (m, 6H), 3.62-3.68 (m, 2H), 2.76-2.82 (m, 2H), 2.61 (s, 1H), 2.44 (m, 4H), 2.27-2.35 (m, 3H), 1.92-2.05 (m, 4H), 2.02-2.14 (m, 4H), 1.74-1.80 (m, 2H), 1.59 (s, 6H), 1.23 (s, 1H), 0.97 (s, 9H).
Example A66
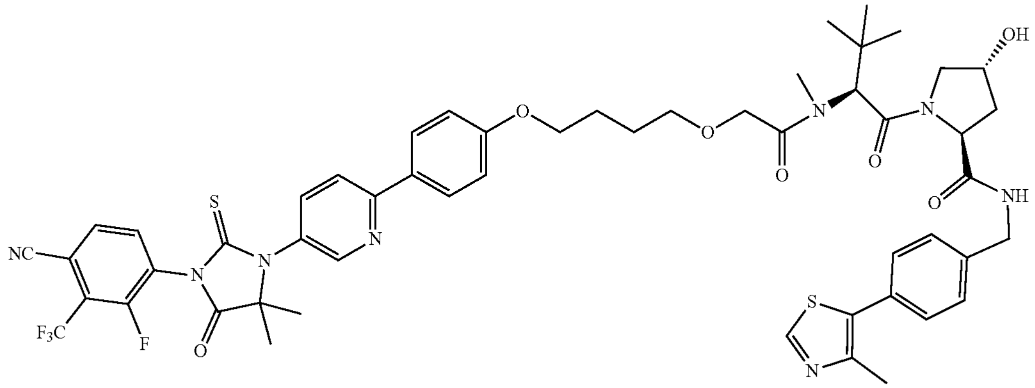 [SMILES: Cc1ncsc1-c1ccc(CNC(=O)[C@@H]2C[C@@H](O)CN2C(=O)[C@@H](N(C)C(=O)COCCCCOc2ccc(-c3ccc(N4C(=S)N(c5ccc(C#N)c(C(F)(F)F)c5F)C(=O)C4(C)C)cn3)cc2)C(C)(C)C)cc1]
LCMS ([M+H]$^+$): 1057.3
$^1$HNMR (400 MHz, DMSO-d6) δ8.96 (d, J=10.1 Hz, 1H), 8.65 (d, J=2.3 Hz, 1H), 8.47 (t, J=5.9 Hz, 1H), 8.33-8.24 (m, 2H), 8.10 (t, J=9.1 Hz, 3H), 7.94 (dd, J=8.5, 2.4 Hz, 1H), 7.39 (s, 4H), 7.06 (t, J=9.9 Hz, 2H), 5.15 (dd, J=11.0, 3.5 Hz, 1H), 5.06 (s, 1H), 4.33 (dt, J=14.5, 8.1 Hz, 4H), 4.23 (d, J=12.2 Hz, 1H), 4.09 (t, J=6.2 Hz, 2H), 3.62 (dd, J=10.6, 4.3 Hz, 1H), 3.53 (dt, J=12.1, 6.0 Hz, 2H), 3.03-2.92 (m, 3H), 2.43 (d, J=5.8 Hz, 3H), 2.07-1.98 (m, 1H), 1.94-1.78 (m, 3H), 1.71 (dd, J=14.2, 6.3 Hz, 2H), 1.58 (s, 6H), 1.08-0.88 (m, 9H).

Example A67
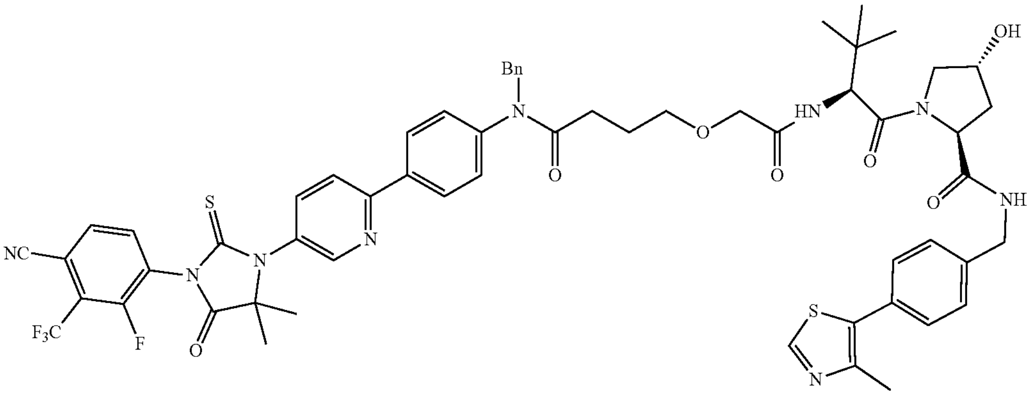 [SMILES: Cc1ncsc1-c1ccc(CNC(=O)[C@@H]2C[C@@H](O)CN2C(=O)[C@@H](NC(=O)COCCCC(=O)N(Cc2ccccc2)c2ccc(-c3ccc(N4C(=S)N(c5ccc(C#N)c(C(F)(F)F)c5F)C(=O)C4(C)C)cn3)cc2)C(C)(C)C)cc1]
LCMS ($[M+H]^+$): 1146.3
$^1$HNMR (400 MHz, DMSO-d6) δ8.97-8.96 (m, 1H), 8.69 (d, J=2.4, 1H), 8.59 (t, J=5.9 Hz, 1H), 8.32-8.24 (m, 2H), 8.17-8.12 (m, 3H), 8.00 (dd, J=8.5, 2.5 Hz, 1H), 7.39-7.18 (m, 12H), 5.15 (d, J=3.5 Hz, 1H), 4.92 (s, 2H), 4.51 (d, J=9.6 Hz, 1H), 4.44 (t, J=8.2 Hz, 1H), 4.40-4.34 (m, 2H), 4.26 (dd, J=15.9, 5.7 Hz, 1H), 3.85 (s, 2H), 3.65-3.57 (m, 2H), 3.42 (m, 2H), 2.41 (s, 3H), 2.25 (m, 2H), 2.08-2.02 (m, 1H), 1.92-1.87 (m, 1H), 1.84-1.78 (m, 2H), 1.56 (s, 6H), 0.86 (s, 9H).
Example A68
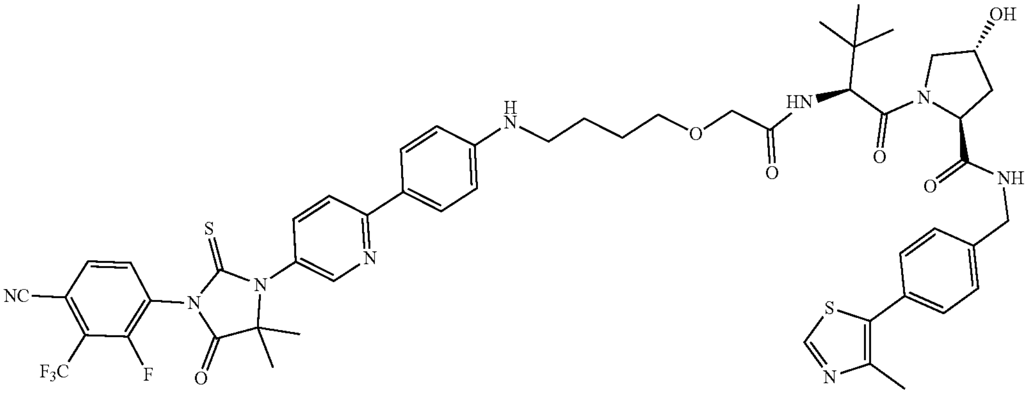 [SMILES: Cc1ncsc1-c1ccc(CNC(=O)[C@@H]2C[C@@H](O)CN2C(=O)[C@@H](NC(=O)COCCCCNc2ccc(-c3ccc(N4C(=S)N(c5ccc(C#N)c(C(F)(F)F)c5F)C(=O)C4(C)C)cn3)cc2)C(C)(C)C)cc1]
LCMS ($[M+H]^+$): 1042.3
$^1$HNMR (400 MHz, DMSO-d6) δ8.99 (s, 1H), 8.58 (d, J=2.6 Hz, 2H), 8.30 (q, J=8.6 Hz, 2H), 8.04-7.95 (m, 3H), 7.85 (t, J=7.8 Hz, 2H), 7.40 (d, J=2.7 Hz, 4H), 6.77 (d, J=8.9 Hz, 2H), 5.33 (m, 1H), 5.16 (m, 1H), 4.57 (m, 1H), 4.45 (m, 3H), 4.41-4.34 (m, 2H), 4.26 (m, 2H), 4.244.04 (m, 2H), 3.66 (m, 2H), 3.60 (m, 2H), 2.45 (s, 3H), 2.04-1.99 (m, 2H), 1.58 (s, 6H), 1.53-1.43 (m, 4H), 0.91 (d, J=11.8 Hz, 9H).

Example A69
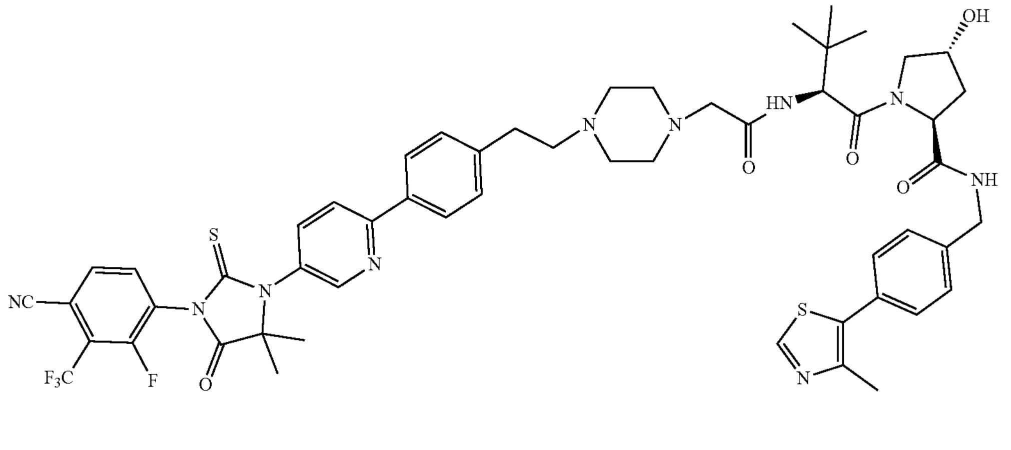 [SMILES: Cc1ncsc1-c1ccc(CNC(=O)[C@@H]2C[C@@H](O)CN2C(=O)[C@@H](NC(=O)CN2CCN(CCc3ccc(-c4ccc(N5C(=S)N(c6ccc(C#N)c(C(F)(F)F)c6F)C(=O)C5(C)C)cn4)cc3)CC2)C(C)(C)C)cc1]
LCMS ([M+H]$^+$): 1067.4
$^1$HNMR (400 MHz, DMSO-d6) δ8.99-8.94 (m, 1H), 8.70 (d, J=2.4 Hz, 1H), 8.59 (t, J=5.6 Hz, 1H), 8.32-8.26 (m, 2H), 8.17 (d, J=8.3 Hz, 1H), 8.08 (d, J=7.2 Hz, 2H), 7.99 (d, J=8.2 Hz, 1H), 7.78 (d, J=9.2 Hz, 1H), 7.41-7.38 (m, 6H), 5.15 (d, J=3.4 Hz, 1H), 4.51 (d, J=9.6 Hz, 1H), 4.45-4.36 (m, 3H), 4.30-4.25 (m, 1H), 3.66 (m, 2H), 3.60 (m, 2H), 2.82 (m, 6H), 2.54 (m, 4H), 2.45 (m, 3H), 2.09-1.83 (m, 4H), 1.59 (s, 6H), 0.94 (m, 9H).
Example A70
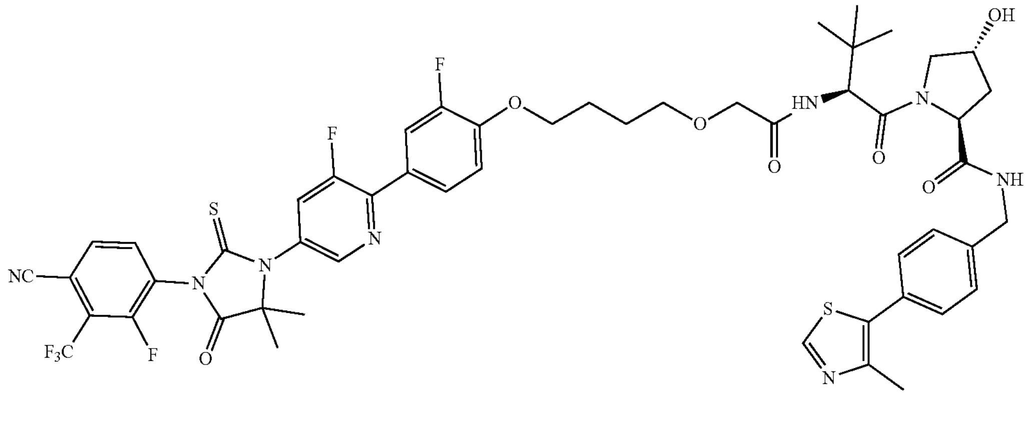 [SMILES: Cc1ncsc1-c1ccc(CNC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)cc2F)C(C)(C)C)cc1]
LCMS ([M+H]$^+$): 1079.3
$^1$HNMR (400 MHz, DMSO-d6) δ8.97 (d, J=10.8 Hz, 1H), 8.66-8.57 (m, 2H), 8.33-8.26 (m, 2H), 8.16 (dd, J=11.9, 1.8 Hz, 1H), 7.83 (d, J=10.6 Hz, 2H), 7.46-7.31 (m, 6H), 5.17 (d, J=3.5 Hz, 1H), 4.57 (d, J=9.6 Hz, 1H), 4.49-4.33 (m, 3H), 4.32-4.16 (m, 3H), 4.01-3.90 (m, 2H), 3.63 (ddd, J=27.9, 11.5, 4.8 Hz, 4H), 2.44 (d, J=7.4 Hz, 3H), 2.07 (dd, J=12.5, 7.3 Hz, 1H), 1.95-1.83 (m, 3H), 1.76 (dd, J=14.0, 6.1 Hz, 2H), 1.61 (s, 6H), 0.94 (d, J=7.0 Hz, 9H).

Example A71
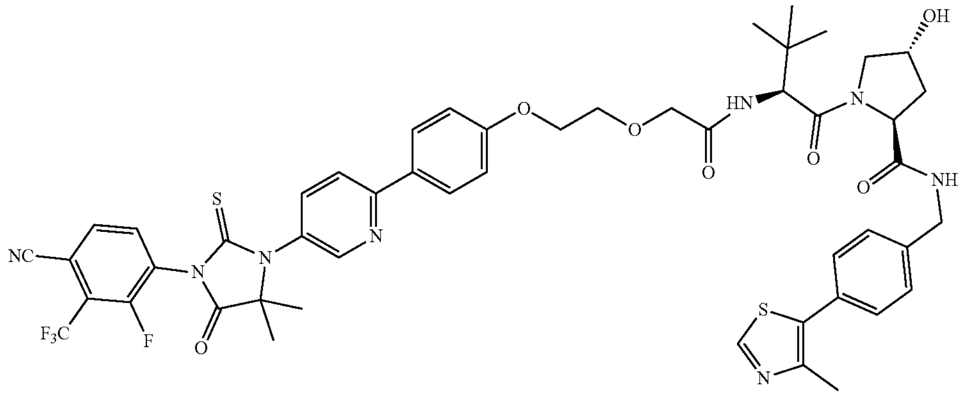 [SMILES: Cc1ncsc1-c1ccc(CNC(=O)[C@@H]2C[C@@H](O)CN2C(=O)[C@@H](NC(=O)COCCOc2ccc(-c3ccc(N4C(=S)N(c5ccc(C#N)c(C(F)(F)F)c5F)C(=O)C4(C)C)cn3)cc2)C(C)(C)C)cc1]
LCMS ([M+H]$^+$): 1015.3
$^1$HNMR (400 MHz, DMSO-d6) δ8.98-8.92 (m, 1H), 8.63-8.60 (m, 2H), 8.32-8.26 (m, 2H), 8.13-8.03 (m, 3H), 7.93 (dd, J=8.5, 2.5 Hz, 1H), 7.51 (d, J=9.5 Hz, 1H), 7.40 (dd, J=19.6, 8.4 Hz, 4H), 7.15 (d, J=8.9 Hz, 2H), 5.17 (d, J=3.6 Hz, 1H), 4.61 (d, J=9.6 Hz, 1H), 4.48-4.39 (m, 2H), 4.36 (m, 1H), 4.29-4.21 (m, 3H), 4.07 (s, 2H), 3.89-3.88 (m, 2H), 3.71-3.66 (m, 1H), 3.63-3.60 (m, 1H), 2.39 (s, 3H), 2.10-1.87 (m, 2H), 1.57 (s, 6H), 0.96 (s, 9H).
Example A72
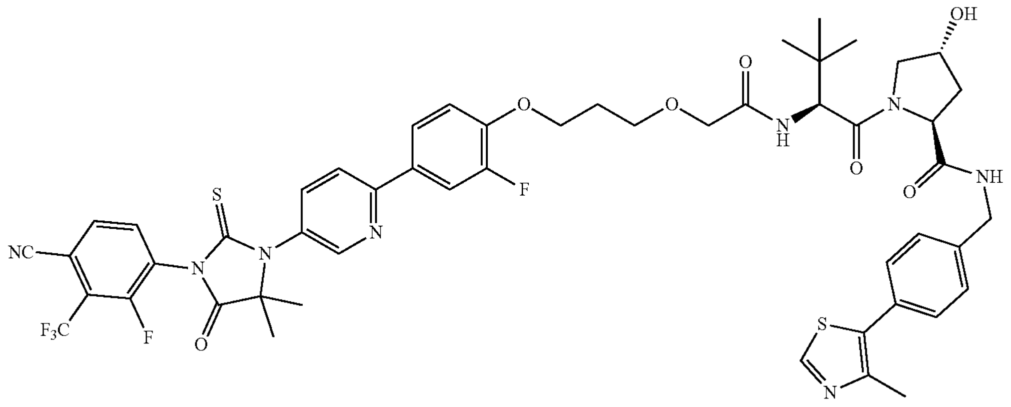 [SMILES: Cc1ncsc1-c1ccc(CNC(=O)[C@@H]2C[C@@H](O)CN2C(=O)[C@@H](NC(=O)COCCCOc2ccc(-c3ccc(N4C(=S)N(c5ccc(C#N)c(C(F)(F)F)c5F)C(=O)C4(C)C)cn3)cc2F)C(C)(C)C)cc1]
LCMS ([M+H]$^+$): 1047.3
$^1$HNMR (400 MHz, DMSO-d6) δ8.95 (s, 1H), 8.67 (d, J=2.5 Hz, 1H), 8.59 (t, J=6.0 Hz, 1H), 8.32-8.25 (m, 2H), 8.15 (d, J=8.5 Hz, 1H), 7.97 (dt, J=8.5, 2.3 Hz, 3H), 7.45 (d, J=9.5 Hz, 1H), 7.38 (d, J=1.7 Hz, 4H), 7.36-7.31 (m, 1H), 5.16 (d, J=3.5 Hz, 1H), 4.57 (d, J=9.5 Hz, 1H), 4.46 (t, J=8.2 Hz, 1H), 4.38 (dd, J=15.8, 6.0 Hz, 2H), 4.29 (d, J=5.7 Hz, 1H), 4.24 (t, J=6.4 Hz, 2H), 3.98 (d, J=1.5 Hz, 2H), 3.70-3.59 (m, 4H), 2.42 (s, 3H), 2.11-2.03 (m, 3H), 1.90 (ddd, J=13.0, 8.9, 4.5 Hz, 1H), 1.58 (s, 6H), 0.94 (s, 9H).

Example A73
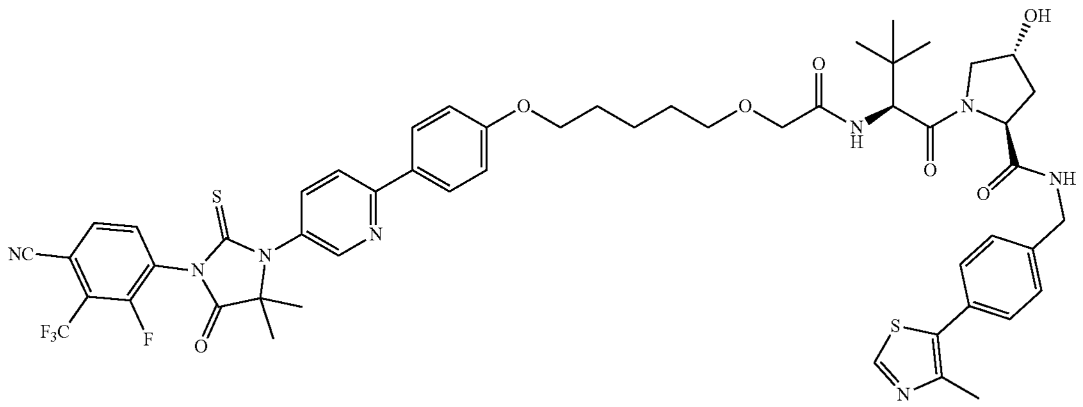 [SMILES: Cc1ncsc1-c1ccc(CNC(=O)[C@@H]2C[C@@H](O)CN2C(=O)[C@@H](NC(=O)COCCCCCOc2ccc(-c3ccc(N4C(=S)N(c5ccc(C#N)c(C(F)(F)F)c5F)C(=O)C4(C)C)cn3)cc2)C(C)(C)C)cc1]
LCMS ([M+H]$^+$): 1058.3
$^1$HNMR (400 MHz, DMSO-d6):8.96 (s, 1H), 8.65-8.66 (d, J=4 Hz 1H), 8.60-8.61 (m, 1H), 8.27-8.31 (m, 2H), 8.09-8.11 (m, 3H), 7.93-7.96 (m, 1H), 7.37-7.44 (m, 5H), 7.04-7.06 (d, J=8 Hz 2H), 5.16-5.17 (d, J=4 Hz 1H), 4.56-4.58 (d, J=8 Hz 2H), 4.36-4.44 (m, 5H), 4.24-4.28 (m, 2H), 4.04-4.07 (m, 2H), 3.94 (s, 2H), 3.60-3.68 (m, 3H), 3.51-3.54 (m, 3H), 2.45 (s, 3H), 2.0-2.07 (m, 6H), 1.77-1.79 (m, 3H), 1.63-1.65 (m, 3H), 1.53-1.58 (m, 3H), 1.24 (s, 6), 0.95 (s, 9H).
Example A74
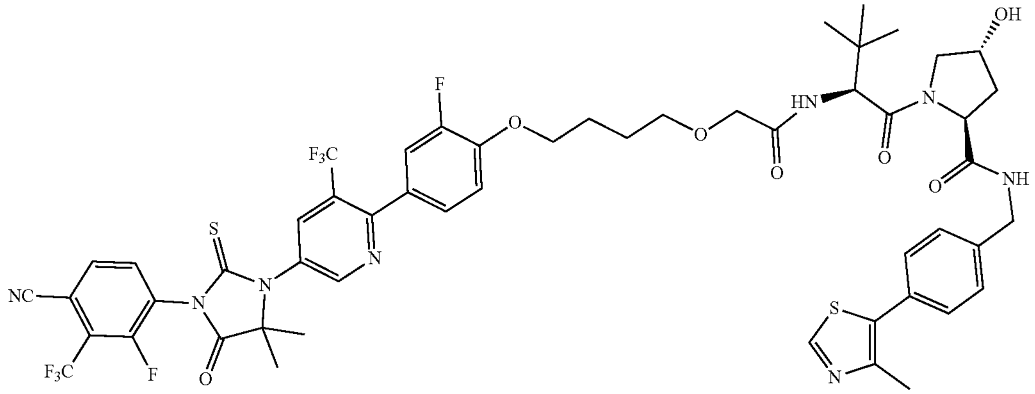 [SMILES: Cc1ncsc1-c1ccc(CNC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3C(F)(F)F)cc2F)C(C)(C)C)cc1]
LCMS ([M+H]$^+$): 1129.2
$^1$HNMR (400 MHz, DMSO-d6) δ8.99 (t, J=3.0 Hz, 1H), 8.95 (m, 1H), 8.60 (t, J=6.0 Hz, 1H), 8.53 (d, J=2.1 Hz, 1H), 8.32-8.24 (m, 2H), 7.40 (m, 6H), 7.32 (m, 2H), 5.16 (m, 1H), 4.57 (m, 1H), 4.46 (m, 1H), 4.39 (m, 2H), 4.26 (m, 1H), 4.18 (m, 2H), 3.97 (m, 2H), 3.71-3.62 (m, 2H), 3.58 (m, 2H), 2.44 (s, 3H), 2.10-1.93 (m, 2H), 1.92-1.84 (m, 2H), 1.76 (m, 2H), 1.64 (d, J=7.1 Hz, 6H), 0.95 (s, 9H).

Example A75
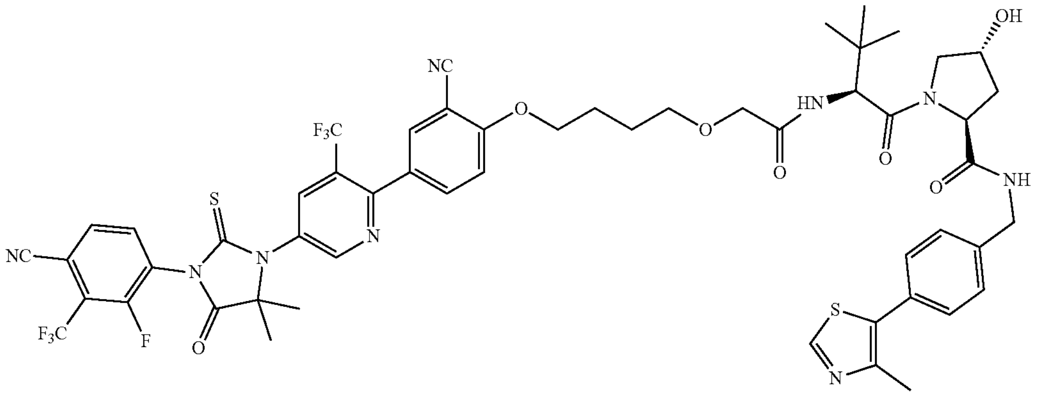 [SMILES: Cc1ncsc1-c1ccc(CNC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3C(F)(F)F)cc2C#N)C(C)(C)C)cc1]
LCMS ([M+H]+): 1136.3
$^1$HNMR (400 MHz, DMSO-d6) δ9.02 (d, J=1.9 Hz, 1H), 8.95 (m, 1H), 8.60 (t, J=6.0 Hz, 1H), 8.56 (d, J=2.1 Hz, 1H), 8.31-8.24 (m, 2H), 7.91 (d, J=2.2 Hz, 1H), 7.88-7.81 (m, 1H), 7.46-7.37 (m, 6H), 5.17 (d, J=3.5 Hz, 1H), 4.57 (m, 1H), 4.46 (m, 1H), 4.39 (m, 2H), 4.32-4.24 (m, 3H), 3.97 (m, 2H), 3.71-3.63 (m, 2H), 3.60 (m, 2H), 2.44 (m, 3H), 2.11-2.03 (m, 1H), 1.91 (m, 3H), 1.79 (m, 2H), 1.64 (d, J=7.7 Hz, 6H), 0.94 (d, J=7.0 Hz, 9H).
Example A76
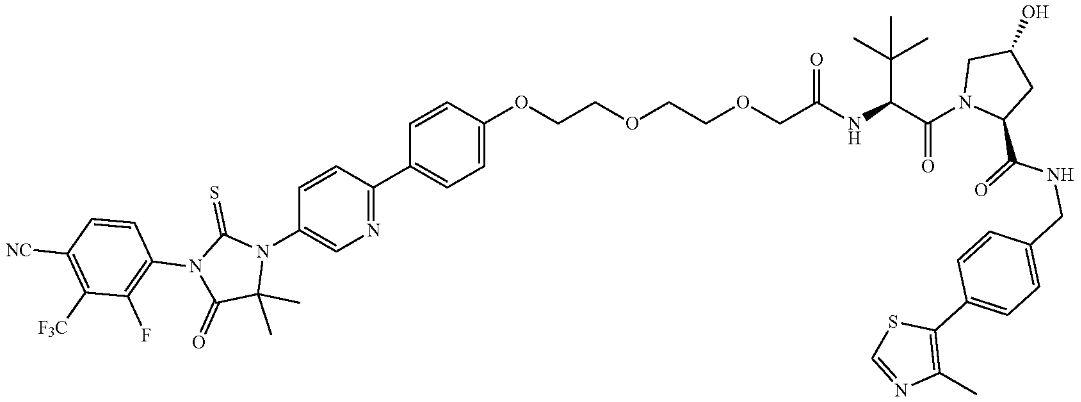 [SMILES: Cc1ncsc1-c1ccc(CNC(=O)[C@@H]2C[C@@H](O)CN2C(=O)[C@@H](NC(=O)COCCOCCOc2ccc(-c3ccc(N4C(=S)N(c5ccc(C#N)c(C(F)(F)F)c5F)C(=O)C4(C)C)cn3)cc2)C(C)(C)C)cc1]
LCMS ([M+H]+): 1059.3
$^1$HNMR (400 MHz, DMSO-d6) δ8.96 (d, J=8.3 Hz, 1H), 8.65 (d, J=2.4 Hz, 1H), 8.58 (t, J=6.0 Hz, 1H), 8.29 (q, J=8.5 Hz, 2H), 8.09 (dd, J=8.8, 2.3 Hz, 3H), 7.94 (dd, J=8.5, 2.5 Hz, 1H), 7.48-7.35 (m, 5H), 7.08 (t, J=10.5 Hz, 2H), 5.15 (d, J=3.5 Hz, 1H), 4.57 (d, J=9.6 Hz, 1H), 4.45 (t, J=8.2 Hz, 1H), 4.38 (dd, J=15.9, 6.3 Hz, 2H), 4.31-4.16 (m, 3H), 3.97 (d, J=15.2 Hz, 2H), 3.82 (dd, J=8.8, 4.3 Hz, 2H), 3.72-3.58 (m, 6H), 2.43 (d, J=8.5 Hz, 3H), 2.11-1.85 (m, 3H), 1.58 (s, 6H), 0.93 (d, J=8.2 Hz, 9H).

Example A77
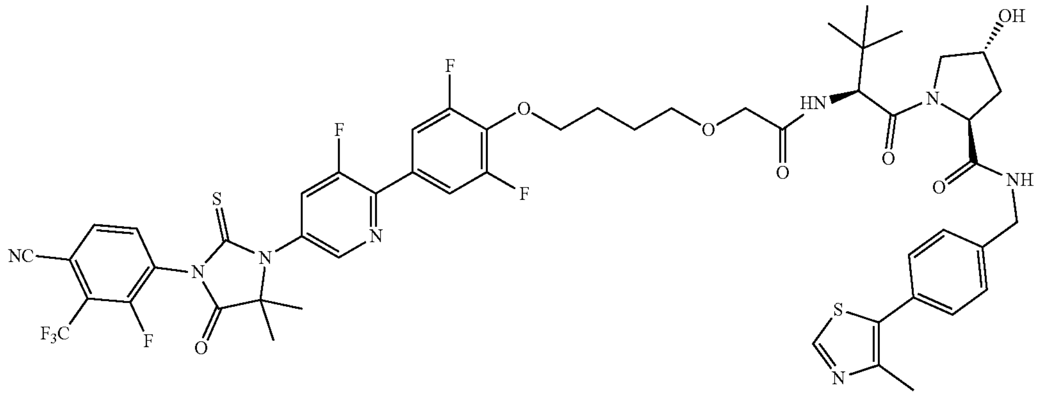 [SMILES: Cc1ncsc1-c1ccc(CNC(=O)[C@@H]2C[C@@H](O)CN2C(=O)[C@@H](NC(=O)COCCCCOc2c(F)cc(-c3ncc(N4C(=S)N(c5ccc(C#N)c(C(F)(F)F)c5F)C(=O)C4(C)C)cc3F)cc2F)C(C)(C)C)cc1]
LCMS ($[M+H]^+$): 1097.3
$^1$HNMR (400 MHz, DMSO-d6) δ8.95 (d, J=15.1 Hz, 1H), 8.66 (s, 1H), 8.60 (t, J=5.9 Hz, 1H), 8.27 (s, 2H), 8.22 (dd, J=11.8, 1.9 Hz, 1H), 7.78-7.70 (m, 2H), 7.45-7.34 (m, 5H), 5.15 (d, J=3.5 Hz, 1H), 4.56 (d, J=9.6 Hz, 1H), 4.48-4.32 (m, 4H), 4.25 (dd, J=12.5, 6.3 Hz, 2H), 3.94 (s, 2H), 3.65 (dd, J=12.9, 9.3 Hz, 2H), 3.55 (t, J=6.3 Hz, 2H), 2.43 (d, J=10.2 Hz, 3H), 2.10-1.86 (m, 4H), 1.78 (ddd, J=19.5, 13.8, 7.0 Hz, 4H), 1.61 (s, 6H), 0.92 (d, J=8.4 Hz, 9H).
Example A78
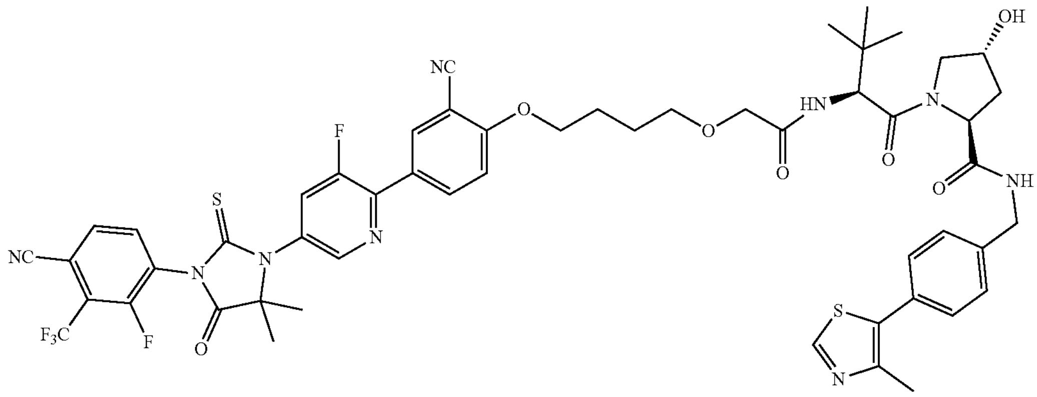 [SMILES: Cc1ncsc1-c1ccc(CNC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)cc2C#N)C(C)(C)C)cc1]
LCMS ($[M+H]^+$): 1086.3
$^1$HNMR (400 MHz, DMSO-d6):8.95 (s, 1H), 8.66 (s, 1H), 8.59-8.62 (m, 1H), 8.29-8.30 (m, 5H), 8.20-8.23 (m, 1H), 7.40-7.43 (m, 6H), 5.16-5.17 (d, J=4 Hz 1H), 4.56-4.57 (d, J=8 Hz 1H), 4.36-4.44 (m, 2H), 4.29-4.31 (m, 2H), 4.24-4.28 (m, 3H), 3.97 (s, 2H), 3.58-3.67 (m, 5H), 2.43 (s, 3H), 1.99-2.06 (m, 2H), 1.89-1.92 (m, 4H), 1.77-1.79 (m, 2H), 1.62 (s, 6H), 0.94 (s, 9H).

Example A79
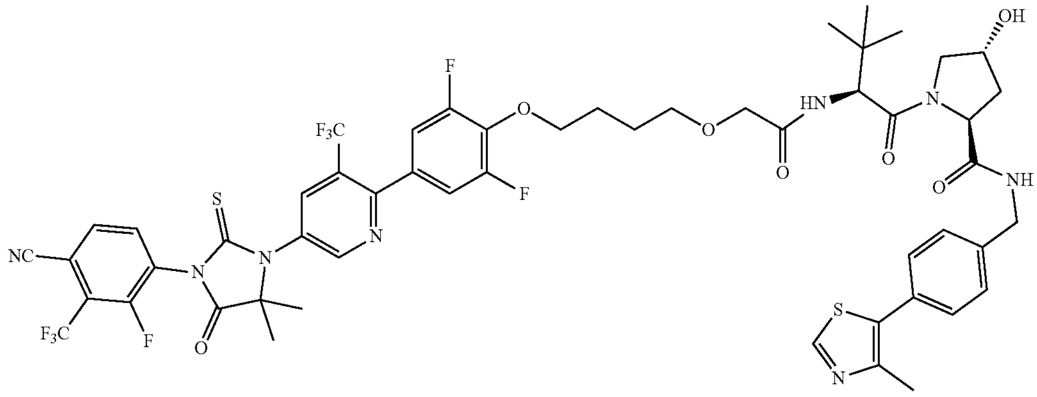 [SMILES: Cc1ncsc1-c1ccc(CNC(=O)[C@@H]2C[C@@H](O)CN2C(=O)[C@@H](NC(=O)COCCCCOc2c(F)cc(-c3ncc(N4C(=S)N(c5ccc(C#N)c(C(F)(F)F)c5F)C(=O)C4(C)C)cc3C(F)(F)F)cc2F)C(C)(C)C)cc1]
LCMS ([M+H]$^+$): 1147.3
$^1$HNMR (400 MHz, DMSO-d6) δ9.01 (d, J=2.1 Hz, 1H), 8.94 (s, 1H), 8.60 (t, J=6.0 Hz, 1H), 8.57 (d, J=2.2 Hz, 1H), 8.28 (s, 2H), 7.46-7.31 (m, 7H), 5.15 (d, J=3.6 Hz, 1H), 4.56 (d, J=9.6 Hz, 1H), 4.49-4.32 (m, 3H), 4.29-4.21 (m, 3H), 3.95 (s, 2H), 3.70-3.59 (m, 2H), 3.56 (t, J=6.3 Hz, 2H), 2.42 (s, 3H), 2.06 (dd, J=13.1, 7.7 Hz, 1H), 1.90 (ddd, J=13.1, 8.8, 4.5 Hz, 1H), 1.85-1.72 (m, 4H), 1.63 (d, J=7.5 Hz, 6H), 0.94 (s, 9H).
Example A80
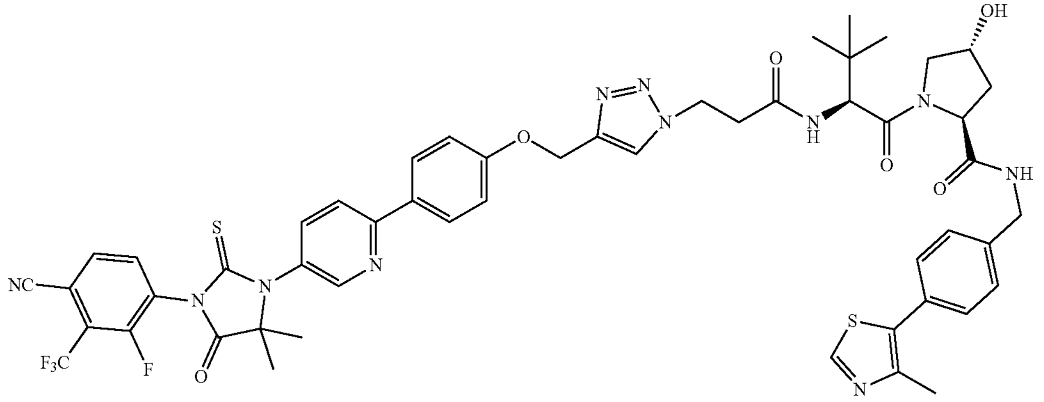 [SMILES: Cc1ncsc1-c1ccc(CNC(=O)[C@@H]2C[C@@H](O)CN2C(=O)[C@@H](NC(=O)CCn2cc(COc3ccc(-c4ccc(N5C(=S)N(c6ccc(C#N)c(C(F)(F)F)c6F)C(=O)C5(C)C)cn4)cc3)nn2)C(C)(C)C)cc1]
LCMS ([M+H]$^+$): 1066.3
$^1$HNMR (400 MHz, DMSO-d6) δ8.97-8.95 (m, 1H), 8.66 (d, J=2.5 Hz, 1H), 8.56 (t, J=6.0 Hz, 1H), 8.34-8.24 (m, 2H), 8.22-8.06 (m, 5H), 7.95 (dd, J=8.5, 2.5 Hz, 1H), 7.39 (q, J=8.4 Hz, 4H), 7.18 (d, J=8.9 Hz, 2H), 5.21 (s, 2H), 5.17 (d, J=3.5 Hz, 1H), 4.67-4.50 (m, 3H), 4.47-4.39 (m, 2H), 4.36 (s, 1H), 4.21 (dd, J=15.8, 5.5 Hz, 1H), 3.66-3.65 (m, 2H), 2.98-2.92 (m, 1H), 2.83-2.73 (m, 1H), 2.43 (s, 3H), 2.08-2.00 (m, 1H), 1.90-1.87 (m, 1H), 1.58 (s, 6H), 0.87 (s, 9H).

Example A81
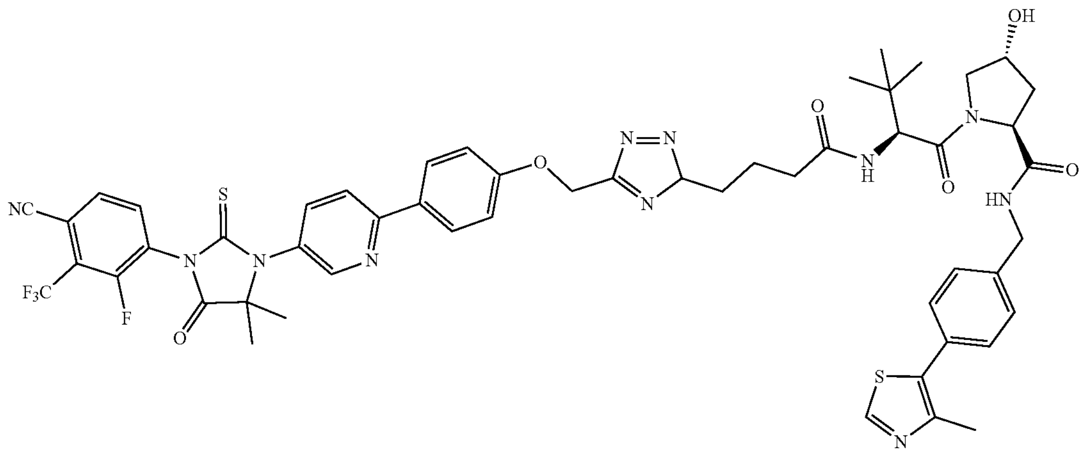 [SMILES: Cc1ncsc1-c1ccc(CNC(=O)[C@@H]2C[C@@H](O)CN2C(=O)[C@@H](NC(=O)CCCC2N=NC(COc3ccc(-c4ccc(N5C(=S)N(c6ccc(C#N)c(C(F)(F)F)c6F)C(=O)C5(C)C)cn4)cc3)=N2)C(C)(C)C)cc1]
LCMS ([M+H]$^+$): 1080.1
$^1$HNMR (400 MHz, DMSO-d6) δ8.97-8.96 (m, 1H), 8.66 (d, J=2.5 Hz, 1H), 8.56 (t, J=6.0 Hz, 1H), 8.34-8.23 (m, 3H), 8.13 (d, J=9.0 Hz, 3H), 8.03-7.92 (m, 2H), 7.40 (q, J=8.4 Hz, 4H), 7.19 (d, J=9.0 Hz, 2H), 5.23 (m, 2H), 5.14 (d, J=3.6 Hz, 1H), 4.54 (d, J=9.3 Hz, 1H), 4.45-4.36 (m, 5H), 4.21 (dd, J=15.9, 5.5 Hz, 1H), 3.70-3.61 (m, 2H), 2.44-2.43 (m, 3H), 2.33-2.17 (m, 2H), 2.07-2.04 (m, 3H), 1.93-1.87 (m, 1H), 1.58 (s, 6H), 0.93 (s, 9H).
Example A82
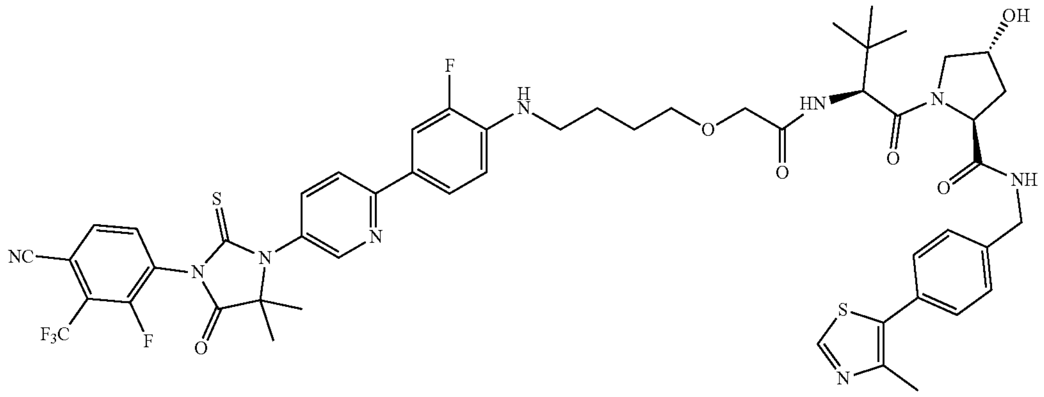 [SMILES: Cc1ncsc1-c1ccc(CNC(=O)[C@@H]2C[C@@H](O)CN2C(=O)[C@@H](NC(=O)COCCCCNc2ccc(-c3ccc(N4C(=S)N(c5ccc(C#N)c(C(F)(F)F)c5F)C(=O)C4(C)C)cn3)cc2F)C(C)(C)C)cc1]
LCMS ([M+H]$^+$): 1033.3
$^1$HNMR (400 MHz, DMSO-d6):8.95 (s, 1H), 8.68 (s, 1H), 8.57-8.60 (m, 1H), 8.26-8.32 (m, 2H), 8.15-8.17 (d, J=8 Hz 1H), 7.97-8.02 (m, 3H), 7.34-7.40 (m, 6H), 5.16 (s, 1H), 4.57-4.60 (d, J=12 Hz 1H), 4.22-4.35 (m, 6H), 4.05-4.09 (m, 1H), 3.9-3.92 (m, 2H), 3.61-3.70 (m, 3H), 2.43 (s, 3H), 1.88-2.06 (m, 4H), 1.6 (s, 6H), 1.77-1.79 (m, 2H), 1.62 (s, 6H), 0.94 (s, 9H).

Example A83
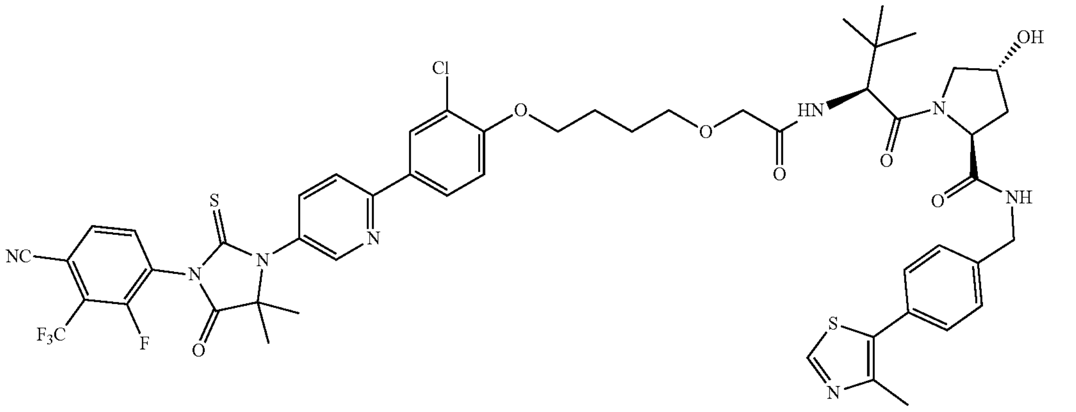 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2Cl)C(C)(C)C)cc1]
LCMS ([M+H]$^+$): 1077.3
$^1$HNMR (400 MHz, DMSO-d6) δ9.00-8.97 (m, 1H), 8.71 (d, J=2.3 Hz, 1H), 8.61 (t, J=6.0 Hz, 1H), 8.35-8.29 (m, 2H), 8.25 (d, J=2.2 Hz, 1H), 8.21 (d, J=8.5 Hz, 1H), 8.13 (dd, J=8.7, 2.2 Hz, 1H), 8.01 (dd, J=8.5, 2.5 Hz, 1H), 7.48-7.38 (m, 5H), 7.30 (d, J=8.9 Hz, 1H), 5.18 (d, J=3.5 Hz, 1H), 4.60 (d, J=9.6 Hz, 1H), 4.52-4.36 (m, 3H), 4.29 (dd, J=15.8, 5.8 Hz, 1H), 4.22 (t, J=6.2 Hz, 2H), 4.04-3.92 (m, 2H), 3.72-3.60 (m, 4H), 2.47-2.45 (m, 3H), 2.14-1.98 (m, 1H), 1.97-1.87 (m, 3H), 1.83-1.78 (m, 2H), 1.61 (s, 6H), 0.97 (s, 9H).
Example A84
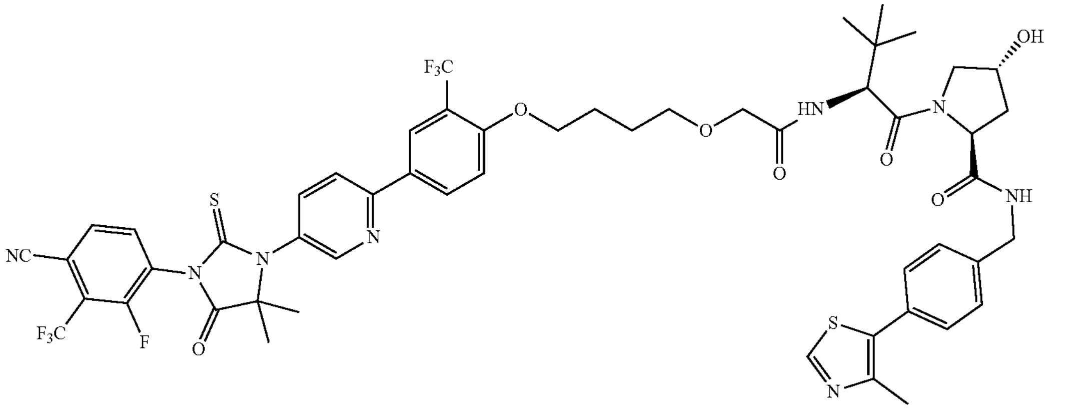 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2C(F)(F)F)C(C)(C)C)cc1]
LCMS ([M+H]$^+$): 1111.3
$^1$HNMR (400 MHz, DMSO-d6): δ8.94 (s, 1H), 8.73-8.68 (m, 1H), 8.58 (t, J=6.0 Hz, 1H), 8.39 (d, J=5.9 Hz, 2H), 8.34-8.20 (m, 3H), 8.01 (dd, J=8.5, 2.5 Hz, 1H), 7.46-7.33 (m, 6H), 5.15 (d, J=3.5 Hz, 1H), 4.56 (d, J=9.6 Hz, 1H), 4.51-4.20 (m, 6H), 3.95 (d, J=1.7 Hz, 2H), 3.72-3.59 (m, 2H), 3.57 (t, J=6.3 Hz, 2H), 2.42 (s, 3H), 2.14-1.67 (m, 6H), 1.59 (s, 6), 0.94 (s, 9H).

Example A85
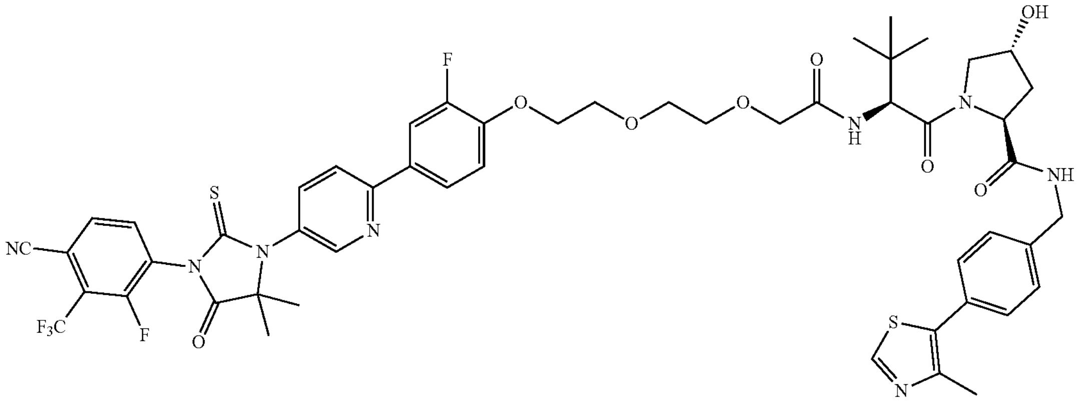 [SMILES: Cc1ncsc1-c1ccc(CNC(=O)[C@@H]2C[C@@H](O)CN2C(=O)[C@@H](NC(=O)COCCOCCOc2ccc(-c3ccc(N4C(=S)N(c5ccc(C#N)c(C(F)(F)F)c5F)C(=O)C4(C)C)cn3)cc2F)C(C)(C)C)cc1]
LCMS ([M+H]+): 1077.3
$^1$HNMR (400 MHz, DMSO-d6) δ8.97 (s, 1H), 8.69 (t, J=7.4 Hz, 1H), 8.63-8.56 (m, 1H), 8.30 (s, 2H), 8.17 (t, J=8.4 Hz, 1H), 8.08-7.93 (m, 3H), 7.47 (d, J=9.6 Hz, 1H), 7.41 (s, 4H), 7.33 (q, J=8.3 Hz, 1H), 5.17 (t, J=10.1 Hz, 1H), 4.59 (t, J=9.3 Hz, 1H), 4.48 (q, J=8.1 Hz, 1H), 4.44-4.35 (m, 2H), 4.31 (s, 3H), 4.02 (s, 2H), 3.92-3.79 (m, 2H), 3.70 (s, 6H), 2.45 (s, 3H), 2.14-2.04 (m, 1H), 1.93 (tt, J=15.1, 7.6 Hz, 1H), 1.61 (s, 6H), 0.96 (d, J=7.7 Hz, 9H).
Example A86
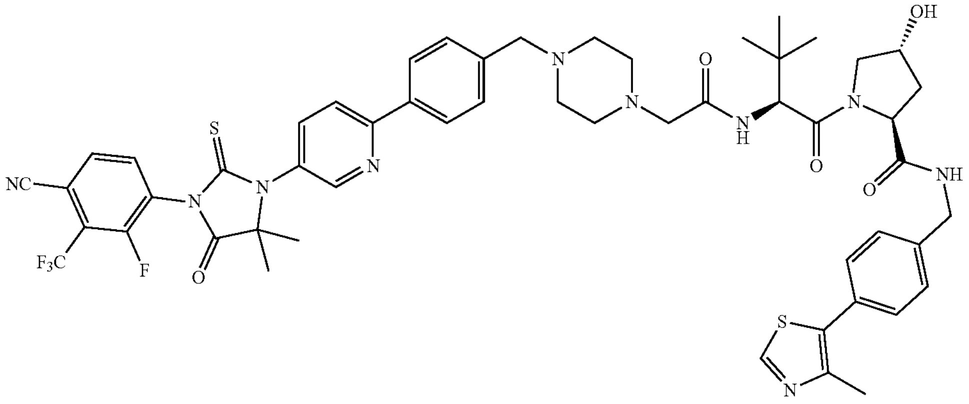 [SMILES: Cc1ncsc1-c1ccc(CNC(=O)[C@@H]2C[C@@H](O)CN2C(=O)[C@@H](NC(=O)CN2CCN(Cc3ccc(-c4ccc(N5C(=S)N(c6ccc(C#N)c(C(F)(F)F)c6F)C(=O)C5(C)C)cn4)cc3)CC2)C(C)(C)C)cc1]
LCMS ([M+H]+): 1053.3
$^1$HNMR (400 MHz, DMSO-d6) δ8.99-8.98 (m, 1H), 8.70 (d, J=2.5 Hz, 1H), 8.59 (t, J=6.1 Hz, 1H), 8.34-8.24 (m, 2H), 8.16 (d, J=8.5 Hz, 1H), 8.10 (d, J=8.3 Hz, 2H), 7.99 (dd, J=8.5, 2.5 Hz, 1H), 7.78 (d, J=9.6 Hz, 1H), 7.49-7.37 (m, 6H), 5.14 (d, J=3.4 Hz, 1H), 4.49 (d, J=9.7 Hz, 1H), 4.46-4.33 (m, 3H), 4.27 (dd, J=15.7, 5.7 Hz, 1H), 3.69-3.52 (m, 6H), 2.99 (dd, J=41.9, 16.1 Hz, 2H), 2.52 (m, 3H), 2.46-2.44 (m, 6H), 2.06-1.85 (m, 2H), 1.59 (s, 6H), 0.94 (s, 9H).

Example A87
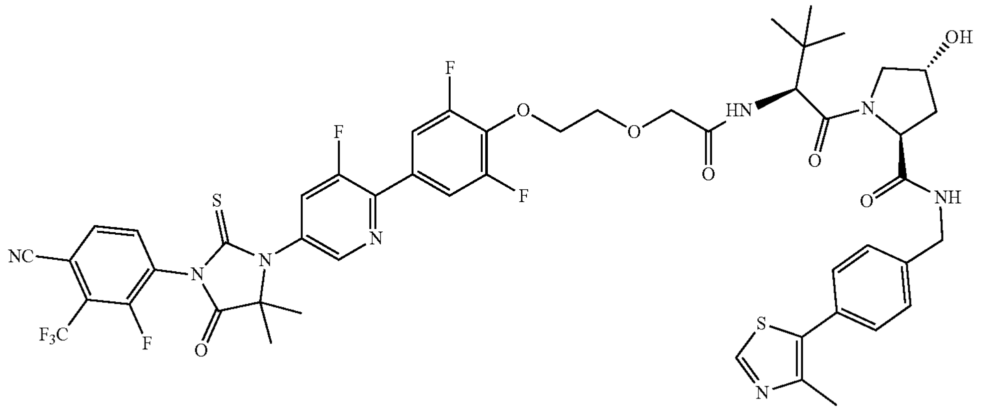 [SMILES: Cc1ncsc1-c1ccc(CNC(=O)[C@@H]2C[C@@H](O)CN2C(=O)[C@@H](NC(=O)COCCOc2c(F)cc(-c3ncc(N4C(=S)N(c5ccc(C#N)c(C(F)(F)F)c5F)C(=O)C4(C)C)cc3F)cc2F)C(C)(C)C)cc1]
LCMS ([M+H]+): 1070.3
$^1$HNMR (400 MHz, DMSO-d6) δ8.92 (s, 1H), 8.66 (s, 1H), 8.59 (t, J=6.2 Hz, 1H), 8.28 (s, 2H), 8.2 2 (d, J=11.7 Hz, 1H), 7.73 (d, J=9.3 Hz, 2H), 7.45-7.33 (m, 5H), 4.57 (d, J=9.6 Hz, 1H), 4.40 (t, J=17.8 Hz, 5H), 4.24-4.19 (m, 1H), 4.04 (s, 2H), 3.85 (s, 2H), 3.66 (s, 2H), 2.42 (d, J=16.6 Hz, 4H), 2.08-1.96 (m, 3H), 1.61 (s, 6H), 0.91 (d, J=8.9 Hz, 8H).
Example A88
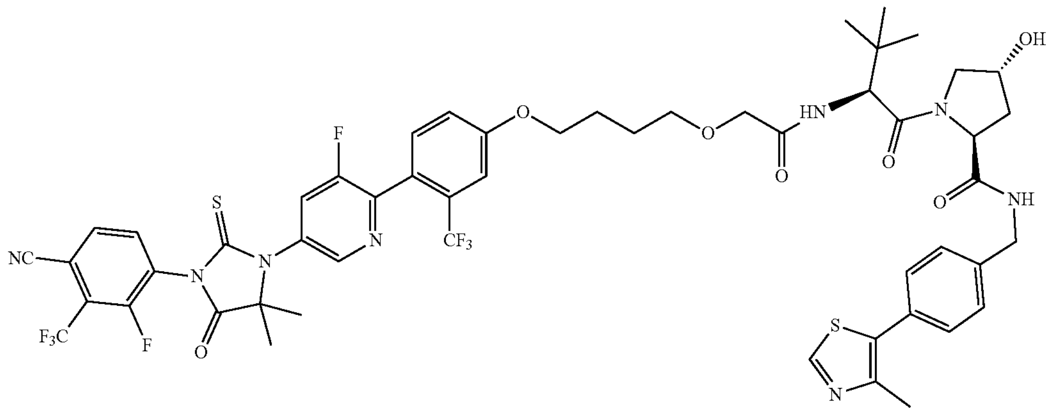 [SMILES: Cc1ncsc1-c1ccc(CNC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)c(C(F)(F)F)c2)C(C)(C)C)cc1]
LCMS ([M+H]+): 1028.3
$^1$HNMR (400 MHz, DMSO-d6) δ8.89 (s, 1H), 8.54 (dd, J=11.8, 5.8 Hz, 2H), 8.22 (s, 2H), 8.13 (dd, J=9.7, 1.9 Hz, 1H), 7.48 (d, J=9.0 Hz, 1H), 7.32 (d, J=10.3 Hz, 7H), 5.09 (d, J=3.5 Hz, 1H), 4.51 (d, J=9.6 Hz, 1H), 4.39 (t, J=8.2 Hz, 1H), 4.32 (dd, J=15.8, 6.2 Hz, 2H), 4.20 (dd, J=15.7, 5.7 Hz, 1H), 4.11 (t, J=6.2 Hz, 2H), 3.93-3.83 (m, 2H), 3.57 (ddd, J=26.4, 11.6, 4.9 Hz, 4H), 2.37 (s, 3H), 2.04-1.95 (m, 1H), 1.88-1.74 (m, 3H), 1.70 (dd, J=13.9, 6.1 Hz, 2H), 1.54 (s, 6H), 0.88 (s, 9H).

Example A89
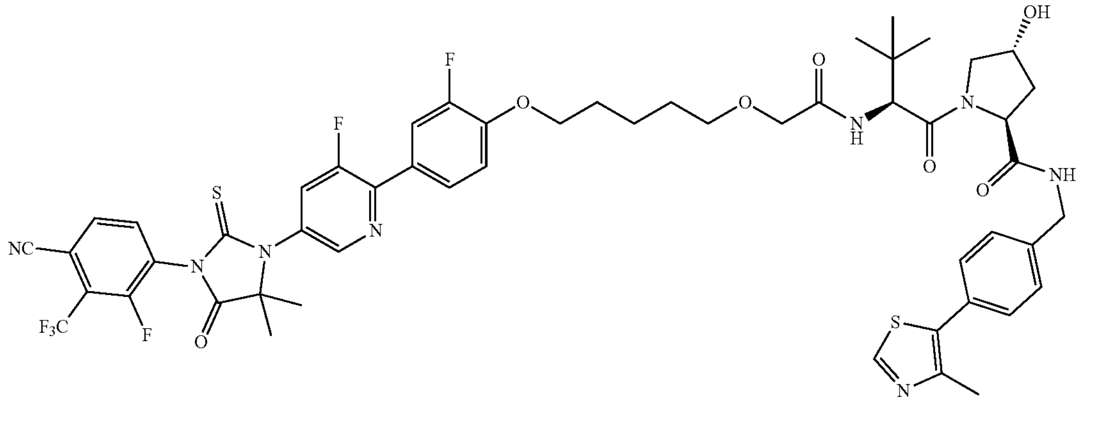 [SMILES: Cc1ncsc1-c1ccc(CNC(=O)[C@@H]2C[C@@H](O)CN2C(=O)[C@@H](NC(=O)COCCCCCOc2ccc(-c3ncc(N4C(=S)N(c5ccc(C#N)c(C(F)(F)F)c5F)C(=O)C4(C)C)cc3F)cc2F)C(C)(C)C)cc1]
LCMS ([M+H]$^+$): 1093.3
$^1$HNMR (400 MHz, DMSO-d6) δ8.96 (s, 1H), 8.63 (s, 1H), 8.60 (t, J=6.0 Hz, 1H), 8.28 (s, 2H), 8.1 6 (dd, J=11.9, 1.9 Hz, 1H), 7.86-7.80 (m, 2H), 7.39 (s, 6H), 5.16 (d, J=3.5 Hz, 1H), 4.57 (d, J=9.6 Hz, 1H), 4.49-4.39 (m, 1H), 4.37 (d, J=6.1 Hz, 2H), 4.26 (dd, J=15.8, 5.7 Hz, 1H), 4.15 (t, J=6.4 Hz, 2H), 3.95 (d, J=1.7 Hz, 2H), 3.66 (dt, J=21.8, 7.3 Hz, 2H), 3.53 (t, J=6.3 Hz, 2H), 2.43 (s, 3H), 2.09-2.03 (m, 1H), 1.90 (ddd, J=19.8, 10.0, 5.6 Hz, 1H), 1.86 (s, 2H), 1.69-1.63 (m, 2H), 1.61 (s, 6H), 1.54 (dd, J=15.0, 8.0 Hz, 2H), 0.95 (s, 9H).
Example A90
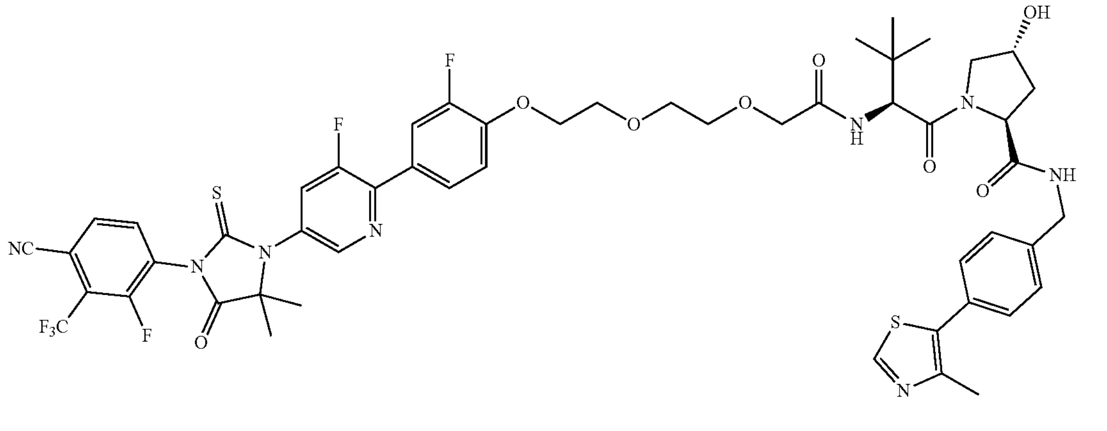 [SMILES: Cc1ncsc1-c1ccc(CNC(=O)[C@@H]2C[C@@H](O)CN2C(=O)[C@@H](NC(=O)COCCOCCOc2ccc(-c3ncc(N4C(=S)N(c5ccc(C#N)c(C(F)(F)F)c5F)C(=O)C4(C)C)cc3F)cc2F)C(C)(C)C)cc1]
LCMS ([M+H]$^+$): 1095.3
$^1$HNMR (400 MHz, DMSO-d6) δ8.97-8.95 (m, 1H), 8.62 (s, 1H), 8.58 (t, J=6.0 Hz, 1H), 8.31-8.26 (m, 2H), 8.15 (dd, J=11.9, 1.9 Hz, 1H), 7.85-7.81 (m, 2H), 7.46-7.30 (m, 6H), 5.15 (d, J=3.6 Hz, 1H), 4.57 (d, J=9.6 Hz, 1H), 4.47-4.36 (m, 3H), 4.32-4.23 (m, 3H), 4.03-3.95 (m, 2H), 3.87-3.82 (m, 2H), 3.69-3.63 (m, 6H), 2.44-2.42 (m, 3H), 2.09-2.04 (m, 1H), 1.90 (ddd, J=12.9, 8.8, 4.5 Hz, 1H), 1.61-1.55 (m, 6H), 0.94-0.92 (m, 9H).

Example A91
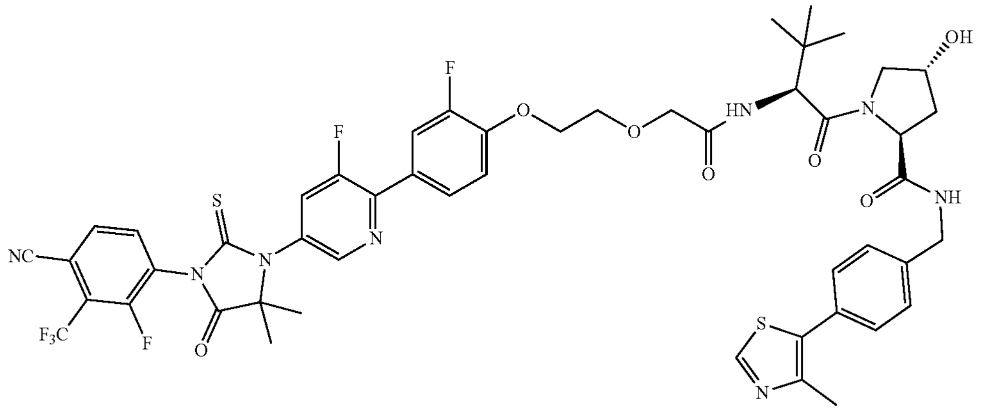 [SMILES: Cc1ncsc1-c1ccc(CNC(=O)[C@@H]2C[C@@H](O)CN2C(=O)[C@@H](NC(=O)COCCOc2ccc(-c3ncc(N4C(=S)N(c5ccc(C#N)c(C(F)(F)F)c5F)C(=O)C4(C)C)cc3F)cc2F)C(C)(C)C)cc1]
LCMS ($[M+H]^+$): 1051.3
$^1$HNMR (400 MHz, DMSO-d6) δ8.95 (s, 1H), 8.63 (s, 1H), 8.59 (t, J=6.0 Hz, 1H), 8.29 (s, 2H), 8.1 6 (dd, J=11.9, 1.9 Hz, 1H), 7.87-7.79 (m, 2H), 7.47 (t, J=6.9 Hz, 1H), 7.40 (d, J=4.2 Hz, 5H), 5.16 (s, 1H), 4.59 (d, J=9.6 Hz, 1H), 4.49-4.39 (m, 2H), 4.38-4.33 (m, 3H), 4.24 (dd, J=15.9, 5.5 Hz, 1H), 4.10 (s, 2H), 3.96-3.88 (m, 2H), 3.69 (dd, J=10.6, 3.8 Hz, 1H), 3.63 (d, J=10.9 Hz, 1H), 2.43 (s, 3H), 2.10-2.02 (m, 1H), 1.92 (ddd, J=12.9, 8.8, 4.5 Hz, 1H), 1.62 (s, 6H), 0.94 (s, 9H).
Example A92
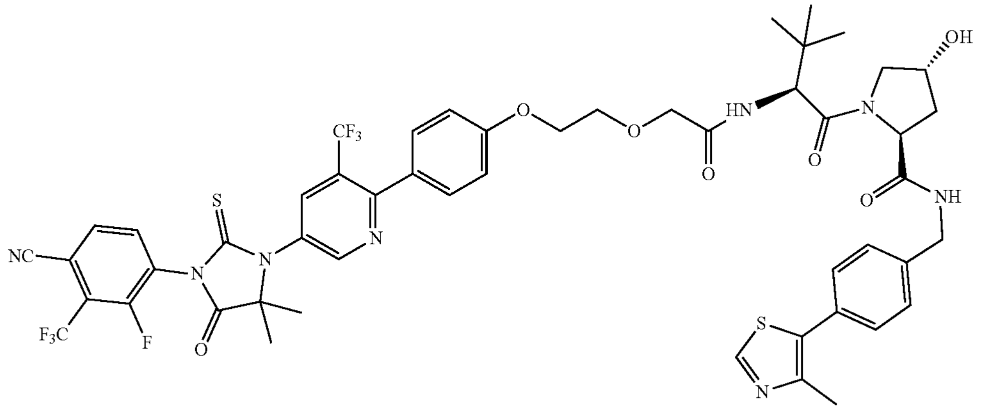 [SMILES: Cc1ncsc1-c1ccc(CNC(=O)[C@@H]2C[C@@H](O)CN2C(=O)[C@@H](NC(=O)COCCOc2ccc(-c3ncc(N4C(=S)N(c5ccc(C#N)c(C(F)(F)F)c5F)C(=O)C4(C)C)cc3C(F)(F)F)cc2)C(C)(C)C)cc1]
LCMS ($[M+H]^+$): 1083.2
$^1$HNMR (400 MHz, DMSO-d6) δ8.95 (m, 2H), 8.61 (t, J=6.0 Hz, 1H), 8.48 (d, J=2.2 Hz, 1H), 8.30-8.24 (m, 2H), 7.49 (m, 3H), 7.39 (m, 4H), 7.14 (d, J=8.8 Hz, 2H), 5.16 (m, 1H), 4.61 (m, 1H), 4.45 (m, 2H), 4.41-4.34 (m, 2H), 4.26-4.22 (m, 2H), 4.08 (m, 2H), 3.88 (m, 2H), 3.71-3.67 (m, 1H), 3.63 (m, 1H), 2.39 (s, 3H), 2.04 (m, 1H), 1.94-1.88 (m, 1H), 1.63 (d, J=7.0 Hz, 6H), 0.95 (d, J=7.6 Hz, 9H).

Example A93
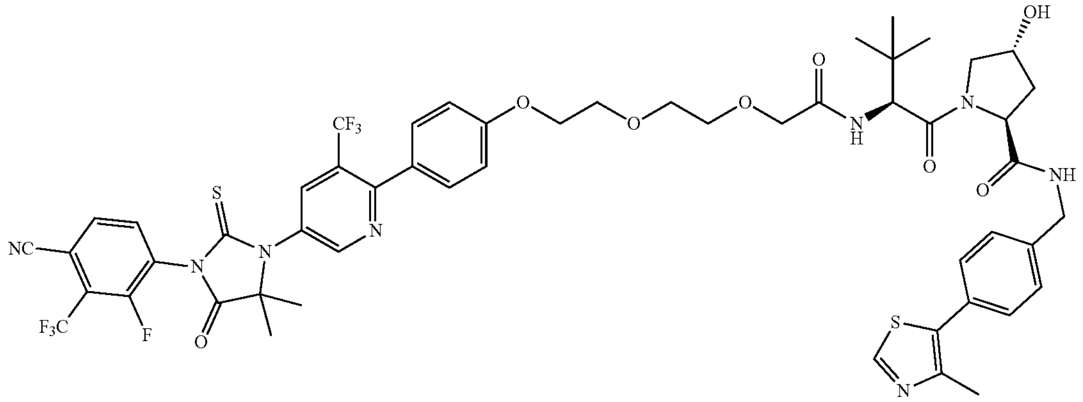 [SMILES: Cc1ncsc1-c1ccc(CNC(=O)[C@@H]2C[C@@H](O)CN2C(=O)[C@@H](NC(=O)COCCOCCOc2ccc(-c3ncc(N4C(=S)N(c5ccc(C#N)c(C(F)(F)F)c5F)C(=O)C4(C)C)cc3C(F)(F)F)cc2)C(C)(C)C)cc1]
LCMS ([M+H]$^+$): 1127.2
$^1$HNMR (400 MHz, DMSO-d6) δ8.99-8.93 (m, 2H), 8.58 (t, J=5.9 Hz, 1H), 8.49 (d, J=2.2 Hz, 1H), 8.31-8.23 (m, 2H), 7.50 (d, J=8.6 Hz, 2H), 7.45 (d, J=9.6 Hz, 1H), 7.47-7.36 (m, 5H), 7.07 (t, J=10.6 Hz, 2H), 5.15 (d, J=3.6 Hz, 1H), 4.57 (d, J=9.6 Hz, 1H), 4.45 (t, J=8.1 Hz, 1H), 4.38 (dd, J=15.8, 6.2 Hz, 2H), 4.25 (dd, J=15.7, 5.7 Hz, 1H), 4.20 (dd, J=9.9, 5.2 Hz, 2H), 3.98 (d, J=15.7 Hz, 2H), 3.87-3.79 (m, 2H), 3.71-3.58 (m, 6H), 2.43 (d, J=7.2 Hz, 3H), 2.06 (dd, J=13.5, 7.1 Hz, 1H), 1.90 (ddd, J=12.9, 8.8, 4.4 Hz, 1H), 1.63 (d, J=7.0 Hz, 6H), 0.93 (d, J=7.0 Hz, 9H).
Example A94
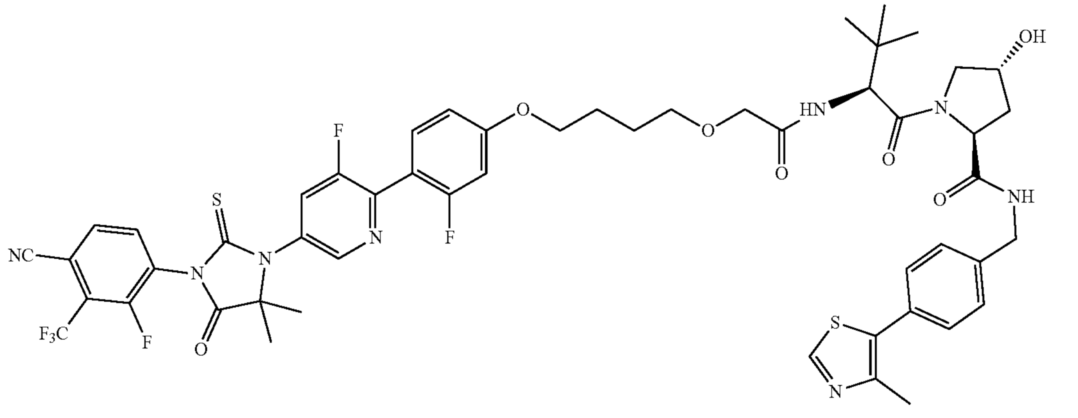 [SMILES: Cc1ncsc1-c1ccc(CNC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)c(F)c2)C(C)(C)C)cc1]
LCMS ([M+H]$^+$): 1079.3
$^1$HNMR (400 MHz, DMSO-d6) δ8.98-8.95 (m, 1H), 8.66 (s, 1H), 8.59 (t, J=6.0 Hz, 1H), 8.31-8.26 (m, 2H), 8.17 (dd, J=10.2, 1.8 Hz, 1H), 7.59 (t, J=8.5 Hz, 1H), 7.43-7.37 (m, 5H), 7.01-6.94 (m, 2H), 5.16 (d, J=3.5 Hz, 1H), 4.57 (d, J=9.6 Hz, 1H), 4.45 (t, J=8.3 Hz, 1H), 4.41-4.36 (m, 2H), 4.26 (dd, J=15.7, 5.6 Hz, 1H), 4.11 (t, J=6.2 Hz, 2H), 4.00-3.90 (m, 2H), 3.69-3.60 (m, 2H), 3.56 (t, J=6.2 Hz, 2H), 2.45-2.43 (m, 3H), 2.09-2.04 (m, 1H), 1.94-1.88 (m, 1H), 1.87-1.81 (m, 2H), 1.76-1.71 (m, 2H), 1.62 (s, 6H), 0.94-0.92 (d, J=6.4 Hz, 9H).

Example A95
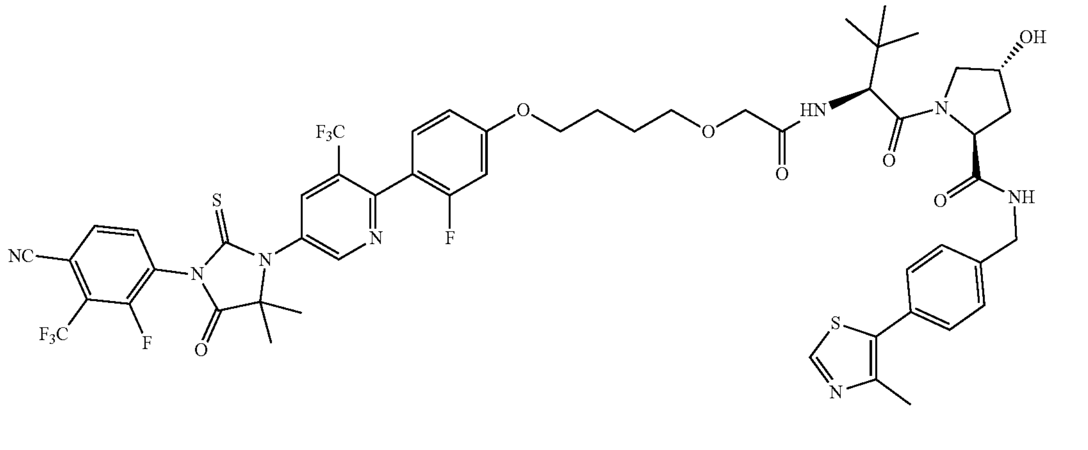 [SMILES: Cc1ncsc1-c1ccc(CNC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3C(F)(F)F)c(F)c2)C(C)(C)C)cc1]
LCMS ([M+H]+): 1129.2
$^1$HNMR (400 MHz, DMSO-d6) δ9.02 (s, 1H), 8.95 (s, 1H), 8.60 (s, 1H), 8.55 (s, 2H), 8.28 (s, 2H), 7.45-7.32 (m, 6H), 6.92 (dd, J=25.4, 10.3 Hz, 2H), 4.56 (d, J=9.5 Hz, 1H), 4.48-4.34 (m, 3H), 4.26 (dd, J=15.6, 5.3 Hz, 1H), 4.09 (d, J=6.2 Hz, 2H), 3.96 (s, 2H), 3.64 (d, J=13.8 Hz, 2H), 3.56 (d, J=6.1 Hz, 2H), 2.44 (d, J=6.4 Hz, 3H), 2.02 (dd, J=20.8, 7.9 Hz, 2H), 1.83 (d, J=7.6 Hz, 2H), 1.74 (d, J=7.0 Hz, 2H), 1.63 (d, J=7.9 Hz, 6H), 0.94 (s, 9H).
Example A96
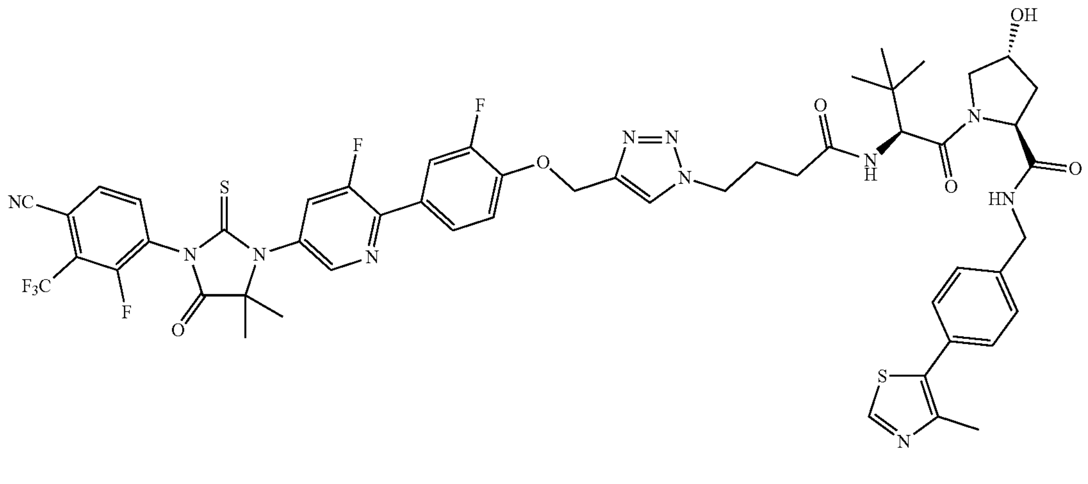 [SMILES: Cc1ncsc1-c1ccc(CNC(=O)[C@@H]2C[C@@H](O)CN2C(=O)[C@@H](NC(=O)CCCn2cc(COc3ccc(-c4ncc(N5C(=S)N(c6ccc(C#N)c(C(F)(F)F)c6F)C(=O)C5(C)C)cc4F)cc3F)nn2)C(C)(C)C)cc1]
LCMS ([M+H]+): 1116.2
$^1$HNMR (400 MHz, DMSO-d6) δ8.97-8.95 (m, 1H), 8.63 (s, 1H), 8.56 (t, J=6.0 Hz, 1H), 8.30-8.2 6 (m, 3H), 8.16 (dd, J=11.8, 1.9 Hz, 1H), 8.00 (d, J=9.3 Hz, 1H), 7.90-7.81 (m, 2H), 7.57 (t, J=8.8 Hz, 1H), 7.39 (q, J=8.4 Hz, 4H), 5.32-5.30 (m, 2H), 4.54 (d, J=9.3 Hz, 1H), 4.40-4.35 (m, 5H), 4.24-4.18 (m, 1H), 3.65 (d, J=10.2 Hz, 2H), 2.43 (d, J=3.7 Hz, 3H), 2.33-2.16 (m, 2H), 2.09-2.00 (m, 3H), 1.90 (ddd, J=12.9, 8.6, 4.6 Hz, 1H), 1.61-1.55 (m, 6H), 0.930.92 (m, 9H).

Example A97
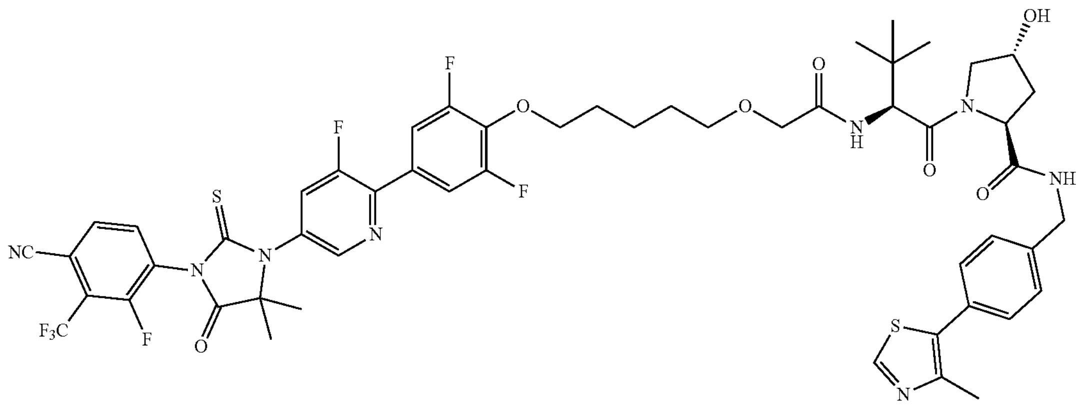 [SMILES: Cc1ncsc1-c1ccc(CNC(=O)[C@@H]2C[C@@H](O)CN2C(=O)[C@@H](NC(=O)COCCCCCOc2c(F)cc(-c3ncc(N4C(=S)N(c5ccc(C#N)c(C(F)(F)F)c5F)C(=O)C4(C)C)cc3F)cc2F)C(C)(C)C)cc1]
LCMS ([M+H]+): 1111.3
$^1$HNMR (400 MHz, DMSO-d6) δ8.95 (d, J=11.5 Hz, 1H), 8.66 (s, 1H), 8.59 (t, J=5.7 Hz, 1H), 8.27 (s, 2H), 8.22 (dd, J=11.8, 1.9 Hz, 1H), 7.74 (d, J=9.3 Hz, 3H), 7.44-7.33 (m, 5H), 5.16 (d, J=3.5 Hz, 1H), 4.55 (d, J=9.7 Hz, 1H), 4.43 (dd, J=16.8, 8.4 Hz, 2H), 4.37 (d, J=6.6 Hz, 2H), 4.22 (t, J=6.2 Hz, 2H), 3.93 (s, 2H), 3.6 5 (d, J=3.3 Hz, 2H), 3.51 (d, J=2.6 Hz, 2H), 2.43 (d, J=9.7 Hz, 3H), 2.09-1.97 (m, 2H), 1.78-1.71 (m, 2H), 1.67-1.50 (m, 10H), 0.92 (d, J=7.5 Hz, 9H).
Example A98
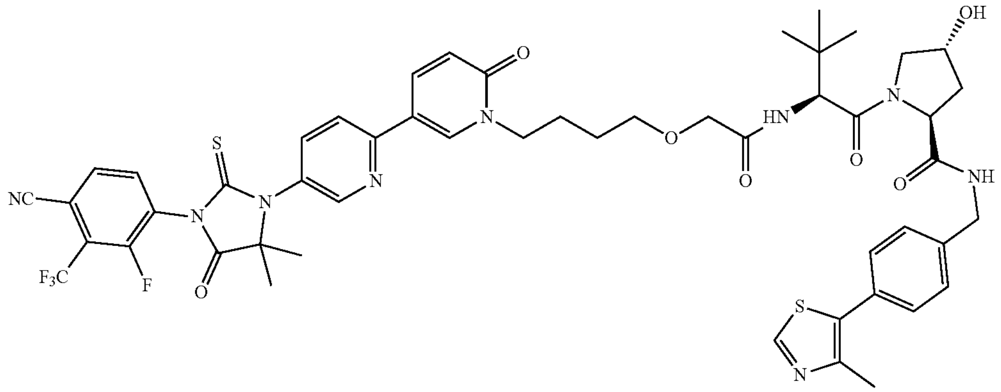 [SMILES: Cc1ncsc1-c1ccc(CNC(=O)[C@@H]2C[C@@H](O)CN2C(=O)[C@@H](NC(=O)COCCCCn2cc(-c3ccc(N4C(=S)N(c5ccc(C#N)c(C(F)(F)F)c5F)C(=O)C4(C)C)cn3)ccc2=O)C(C)(C)C)cc1]
LCMS ([M+H]+): 1044.3
$^1$HNMR (400 MHz, DMSO-d6) δ8.96 (s, 1H), 8.65-8.55 (m, 3H), 8.32-8.23 (m, 2H), 8.19 (dd, J=9.5, 2.4 Hz, 1H), 8.02 (d, J=8.5 Hz, 1H), 7.95 (dd, J=8.5, 2.2 Hz, 1H), 7.39 (d, J=9.9 Hz, 5H), 6.51 (d, J=9.5 Hz, 1H), 5.16 (d, J=3.4 Hz, 1H), 4.55 (d, J=9.5 Hz, 1H), 4.43 (dd, J=15.3, 7.2 Hz, 1H), 4.36 (dd, J=15.4, 6.2 Hz, 2H), 4.25 (dd, J=15.7, 5.6 Hz, 1H), 4.04 (t, J=6.8 Hz, 2H), 3.99-3.86 (m, 2H), 3.64 (dt, J=20.6, 7.2 Hz, 2H), 3.51 (t, J=6.2 Hz, 2H), 2.43 (s, 3H), 2.06 (dd, J=13.1, 7.1 Hz, 1H), 1.94-1.85 (m, 1H), 1.83-1.71 (m, 2H), 1.58 (d, J=16.3 Hz, 8H), 0.90 (d, J=7.9 Hz, 9H).

Example A99
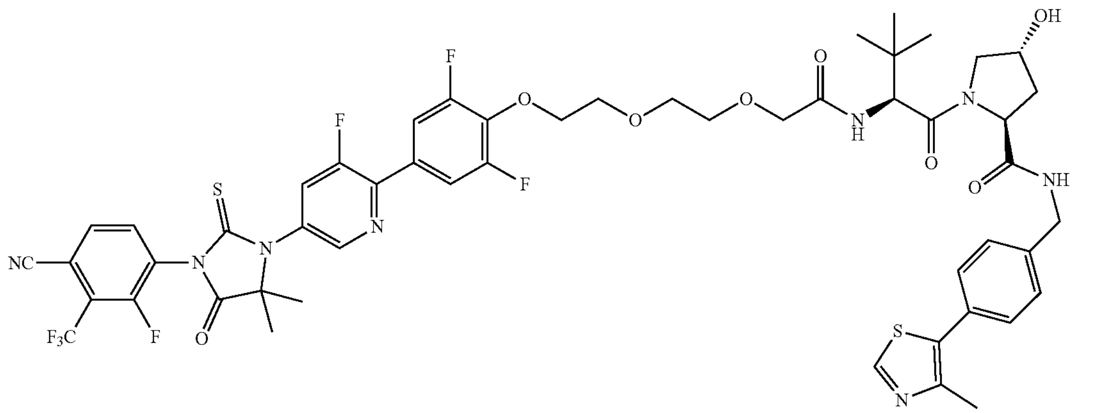 [SMILES: Cc1ncsc1-c1ccc(CNC(=O)[C@@H]2C[C@@H](O)CN2C(=O)[C@@H](NC(=O)COCCOCCOc2c(F)cc(-c3ncc(N4C(=S)N(c5ccc(C#N)c(C(F)(F)F)c5F)C(=O)C4(C)C)cc3F)cc2F)C(C)(C)C)cc1]
LCMS ([M+H]$^+$): 1113.3
$^1$HNMR (400 MHz, DMSO-d6) δ8.95 (d, J=12.2 Hz, 1H), 8.66 (s, 1H), 8.59 (t, J=5.9 Hz, 1H), 8.29 (d, J=11.9 Hz, 2H), 8.21 (dd, J=11.8, 1.7 Hz, 1H), 7.74 (t, J=7.6 Hz, 2H), 7.45-7.33 (m, 5H), 5.16 (m, 1H), 4.56 (m, 1H), 4.41 (m, 5H), 4.24 (m, 1H), 3.94 (m, 2H), 3.83-3.74 (m, 2H), 3.71-3.57 (m, 6H), 2.43 (m, 3H), 2.06 (m, 1H), 1.95-1.86 (m, 1H), 1.60 (s, 6H), 0.92 (d, J=8.3 Hz, 9H).
Example A100
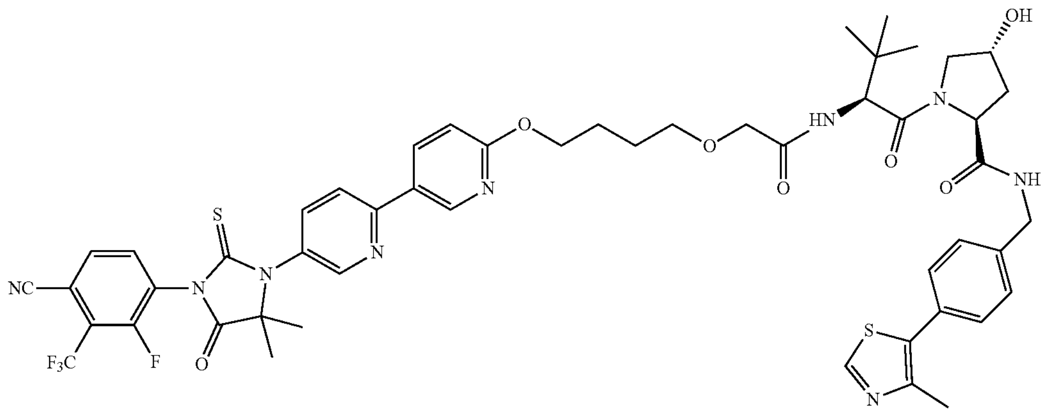 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cn2)C(C)(C)C)cc1]
LCMS ([M+H]$^+$): 1044.3
$^1$HNMR (400 MHz, DMSO-d6) δ8.96 (d, J=11.6 Hz, 1H), 8.92 (d, J=2.4 Hz, 1H), 8.70 (d, J=2.4H z, 1H), 8.60 (t, J=6.0 Hz, 1H), 8.41 (dd, J=8.7, 2.5 Hz, 1H), 8.33-8.25 (m, 2H), 8.19-8.15 (m, 1H), 8.00 (dd, J=8.5, 2.5 Hz, 1H), 7.44-7.35 (m, 5H), 6.92 (d, J=8.7 Hz, 1H), 5.16 (d, J=3.5 Hz, 1H), 4.56 (d, J=9.6 Hz, 1H), 4.48-4.32 (m, 5H), 4.25 (dd, J=15.8, 5.6 Hz, 1H), 4.00-3.89 (m, 2H), 3.65 (dt, J=21.3, 7.3 Hz, 2H), 3.56 (t, J=6.4 Hz, 2H), 2.43 (d, J=8.5 Hz, 3H), 2.11-2.02 (m, 1H), 1.91 (ddd, J=12.9, 8.9, 4.3 Hz, 1H), 1.83 (dd, J=14.5, 6.3 Hz, 2H), 1.76-1.67 (m, 2H), 1.58 (s, 6H), 0.92 (d, J=7.0 Hz, 9H).

Example A101
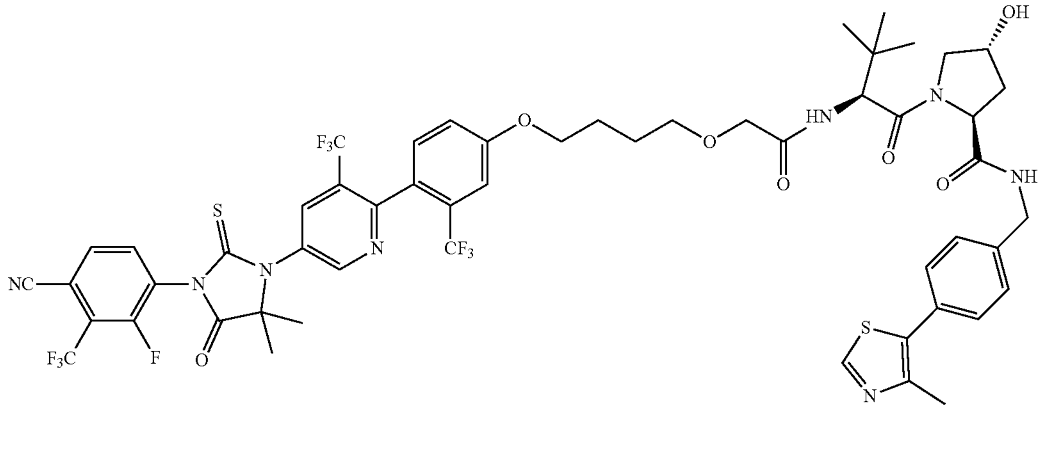 [SMILES: Cc1ncsc1-c1ccc(CNC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3C(F)(F)F)c(C(F)(F)F)c2)C(C)(C)C)cc1]
LCMS ($[M+H]^+$): 1178.3
$^1$HNMR (400 MHz, DMSO-d6) δ9.00 (d, J=9.1 Hz, 1H), 8.96 (s, 1H), 8.59 (dd, J=15.5, 9.3 Hz, 2H), 8.31-8.25 (m, 2H), 7.40 (s, 9H), 5.16 (d, J=3.5 Hz, 1H), 4.58 (d, J=9.6 Hz, 1H), 4.46 (t, J=8.2 Hz, 1H), 4.39 (dd, J=15.7, 6.0 Hz, 2H), 4.27 (dd, J=15.7, 5.7 Hz, 1H), 4.17 (t, J=6.2 Hz, 2H), 4.00-3.92 (m, 2H), 3.64 (ddd, J=26.2, 11.7, 5.0 Hz, 4H), 2.44 (s, 3H), 1.95-1.83 (m, 3H), 1.80-1.72 (m, 2H), 1.63 (d, J=9.8 Hz, 6H), 0.95 (s, 9H).
Example A102
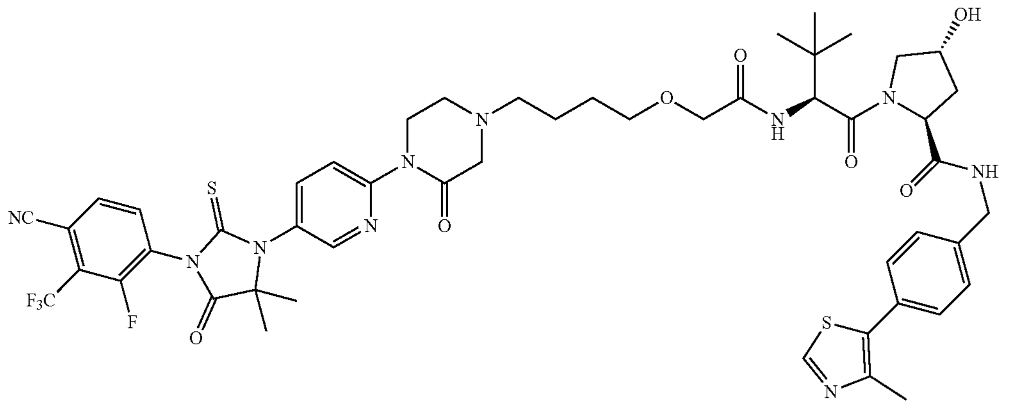 [SMILES: Cc1ncsc1-c1ccc(CNC(=O)[C@@H]2C[C@@H](O)CN2C(=O)[C@@H](NC(=O)COCCCCN2CCN(c3ccc(N4C(=S)N(c5ccc(C#N)c(C(F)(F)F)c5F)C(=O)C4(C)C)cn3)C(=O)C2)C(C)(C)C)cc1]
LCMS ($[M+H]^+$): 1049.4
$^1$HNMR (400 MHz, DMSO-d6) δ10.81 (s, 1H), 8.62 (s, 1H), 8.31-8.24 (m, 2H), 8.15 (dd, J=11.9, 1.9 Hz, 1H), 8.01 (d, J=8.3 Hz, 1H), 7.85 (d, J=10.8 Hz, 2H), 7.36 (t, J=8.7 Hz, 1H), 4.67-4.55 (m, 1H), 4.19 (t, J=6.3 Hz, 2H), 3.93 (s, 2H), 3.56 (td, J=9.3, 3.1 Hz, 2H), 2.74 (ddd, J=18.8, 13.5, 5.5 Hz, 1H), 2.11-1.91 (m, 2H), 1.90-1.83 (m, 2H), 1.76 (dd, J=14.2, 6.3 Hz, 2H), 1.61 (s, 6H).

Example A103
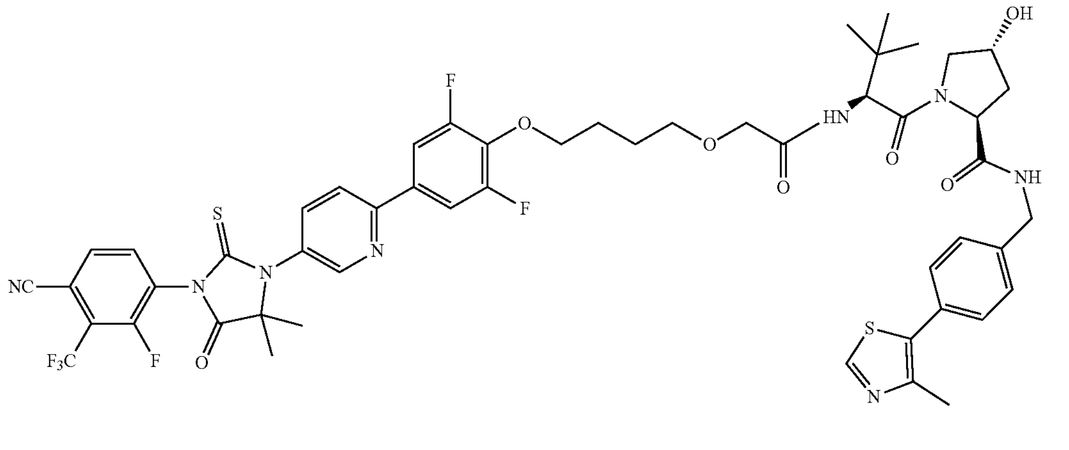 [SMILES: Cc1ncsc1-c1ccc(CNC(=O)[C@@H]2C[C@@H](O)CN2C(=O)[C@@H](NC(=O)COCCCCOc2c(F)cc(-c3ccc(N4C(=S)N(c5ccc(C#N)c(C(F)(F)F)c5F)C(=O)C4(C)C)cn3)cc2F)C(C)(C)C)cc1]
LCMS ([M+H]$^+$): 1178.2
$^1$HNMR (400 MHz, DMSO-d6) δ9.00 (s, 1H), 8.77 (d, J=2.3 Hz, 1H), 8.65 (t, J=6.0 Hz, 1H), 8.34 (s, 3H), 8.10 (dd, J=8.5, 2.5 Hz, 1H), 8.03-7.95 (m, 2H), 7.45 (d, J=2.3 Hz, 5H), 5.20 (d, J=3.5 Hz, 1H), 4.61 (d, J=9.6 Hz, 1H), 4.54-4.39 (m, 3H), 4.35-4.24 (m, 3H), 4.04-3.93 (m, 2H), 3.76-3.55 (m, 4H), 2.48 (s, 3H), 2.15-2.07 (m, 1H), 1.95 (ddd, J=22.9, 11.6, 7.2 Hz, 1H), 1.90-1.76 (m, 4H), 1.64 (s, 6H), 1.29 (s, 2H), 0.99 (s, 9H).
Example A104
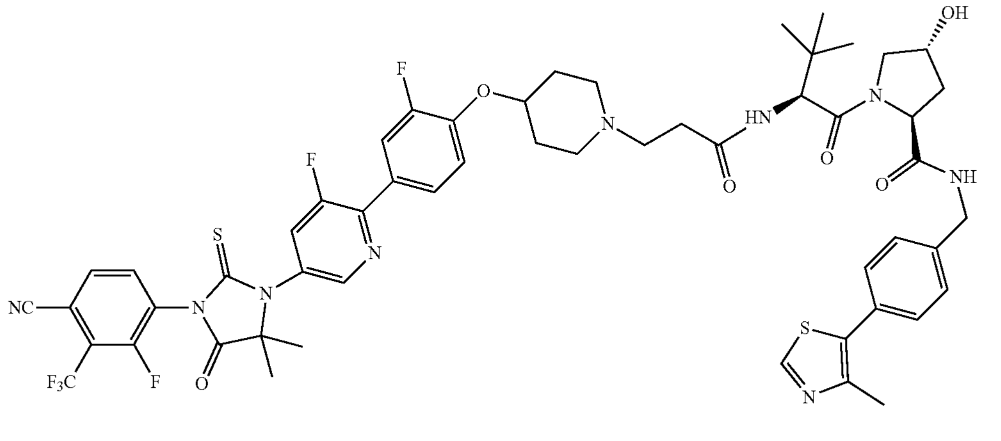 [SMILES: Cc1ncsc1-c1ccc(CNC(=O)[C@@H]2C[C@@H](O)CN2C(=O)[C@@H](NC(=O)CCN2CCC(Oc3ccc(-c4ncc(N5C(=S)N(c6ccc(C#N)c(C(F)(F)F)c6F)C(=O)C5(C)C)cc4F)cc3F)CC2)C(C)(C)C)cc1]
LCMS ([M+H]$^+$): 1104.3
1HNMR (400 MHz, DMSO-d6) δ8.96 (d, J=21.9 Hz, 1H), 8.62 (dt, J=12.1, 6.9 Hz, 3H), 8.32-8.25 (m, 2H), 8.16 (dd, J=11.8, 1.9 Hz, 1H), 7.86-7.78 (m, 2H), 7.44 (d, J=8.3 Hz, 2H), 7.37 (dd, J=11.7, 8.8 Hz, 3H), 5.15 (s, 1H), 4.57 (d, J=9.5 Hz, 2H), 4.50-4.41 (m, 2H), 4.37 (s, 1H), 4.22 (dd, J=15.9, 5.3 Hz, 1H), 3.67 (dt, J=21.4, 7.5 Hz, 2H), 2.76 (d, J=32.2 Hz, 2H), 2.61 (dd, J=11.8, 6.0 Hz, 1H), 2.43 (s, 3H), 2.41-2.24 (m, 4H), 2.02 (dd, J=12.9, 5.6 Hz, 4H), 1.94-1.88 (m, 1H), 1.78 (dd, J=21.9, 9.1 Hz, 2H), 1.62 (s, 6H), 0.96 (d, J=6.4 Hz, 9H).

Example A105
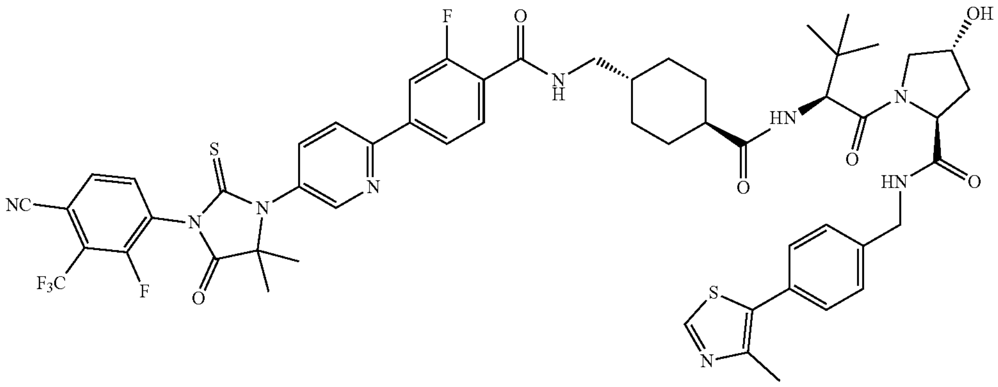 [SMILES: Cc1ncsc1-c1ccc(CNC(=O)[C@@H]2C[C@@H](O)CN2C(=O)[C@@H](NC(=O)[C@H]2CC[C@H](CNC(=O)c3ccc(-c4ccc(N5C(=S)N(c6ccc(C#N)c(C(F)(F)F)c6F)C(=O)C5(C)C)cn4)cc3F)CC2)C(C)(C)C)cc1]
LCMS ([M+H]+): 1098.3
$^1$HNMR (400 MHz, DMSO-d6) δ8.97-8.97 (m, 1H), 8.77 (d, J=2.4 Hz, 1H), 8.55 (t, J=6.0 Hz, 1H), 8.42 (s, 1H), 8.33-8.26 (m, 3H), 8091-8.04 (m, 3H), 7.75-7.71 (m, 2H), 7.40 (q, J=8.4 Hz, 4H), 5.13 (d, J=3.5 Hz, 1H), 4.51 (d, J=9.3 Hz, 1H), 4.46-4.39 (m, 2H), 4.35 (s, 1H), 4.22 (dd, J=15.8, 5.4 Hz, 1H), 3.69-3.61 (m, 2H), 3.14 (t, J=6.1 Hz, 2H), 2.44 (s, 3H), 2.38-2.33 (m, 1H), 2.07-2.00 (m, 1H), 1.94-1.86 (m, 1H), 1.80 (d, J=11.2 Hz, 3H), 1.69 (d, J=10.8 Hz, 1H), 1.60-1.58 (m, 6H), 1.51 (s, 1H), 1.38-1.28 (m, 2H), 1.05-0.88 (m, 11H).
Example A106
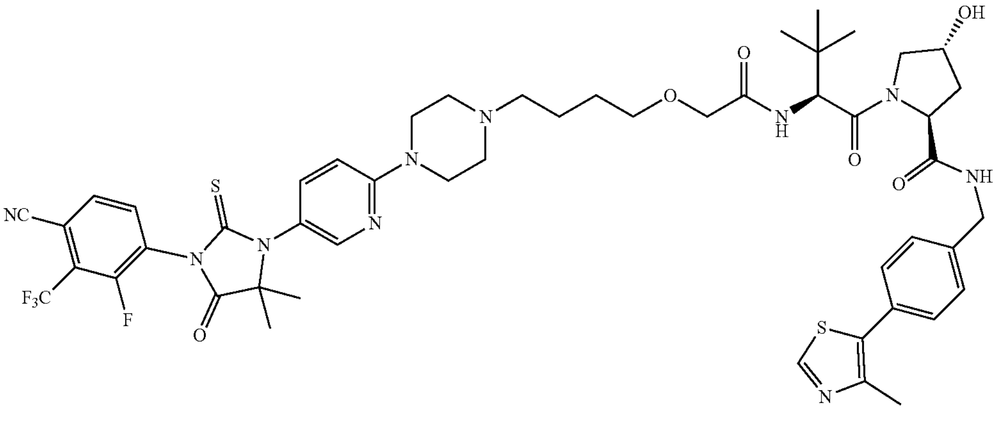 [SMILES: Cc1ncsc1-c1ccc(CNC(=O)[C@@H]2C[C@@H](O)CN2C(=O)[C@@H](NC(=O)COCCCCN2CCN(c3ccc(N4C(=S)N(c5ccc(C#N)c(C(F)(F)F)c5F)C(=O)C4(C)C)cn3)CC2)C(C)(C)C)cc1]
LCMS ([M+H]+): 1035.3
$^1$HNMR (400 MHz, MeOD) δ8.87 (s, 1H), 8.13-8.05 (m, 2H), 8.01 (d, J=8.4 Hz, 1H), 7.54 (dd, J=9.1, 2.7 Hz, 1H), 7.50-7.39 (m, 4H), 6.90 (m, 1H), 4.72 (s, 1H), 4.64-4.50 (m, 3H), 4.37 (m, 1H), 4.08-3.94 (m, 2H), 3.89 (m, 1H), 3.82 (m, 1H), 3.63 (m, 6H), 2.66-2.58 (m, 4H), 2.53-2.45 (m, 5H), 2.30-2.22 (m, 1H), 2.11 (m, 1H), 1.72 (m, 4H), 1.56 (dd, J=5.6, 4.9 Hz, 6H), 1.05 (d, J=9.6 Hz, 9H).

Example A107
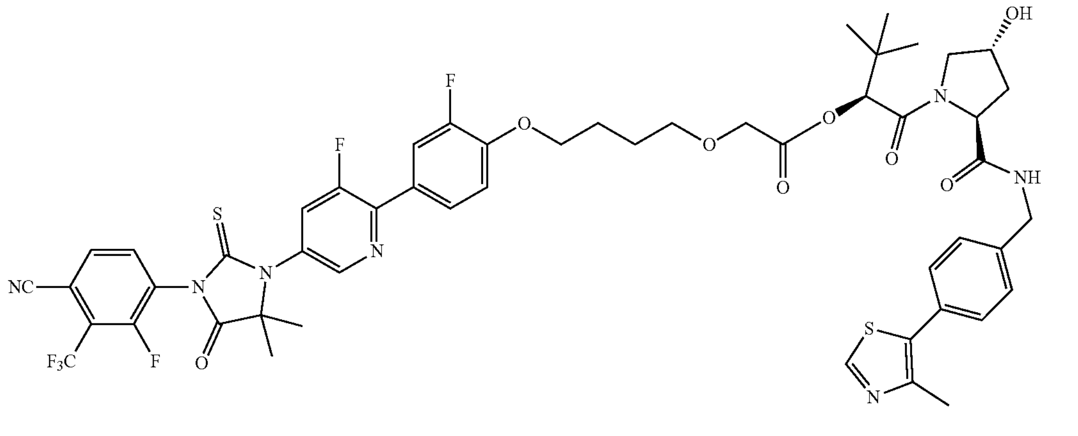 [SMILES: Cc1ncsc1-c1ccc(CNC(=O)[C@@H]2C[C@@H](O)CN2C(=O)[C@@H](OC(=O)COCCCCOc2ccc(-c3ncc(N4C(=S)N(c5ccc(C#N)c(C(F)(F)F)c5F)C(=O)C4(C)C)cc3F)cc2F)C(C)(C)C)cc1]
LCMS ([M+H]+): 1080.3
$^1$HNMR (400 MHz, DMSO-d6) δ8.98 (d, J=3.3 Hz, 1H), 8.62 (s, 1H), 8.58 (t, J=6.2 Hz, 1H), 8.28 (d, J=3.2 Hz, 2H), 8.16 (dd, J=11.9, 1.9 Hz, 1H), 7.85 (d, J=10.9 Hz, 2H), 7.46-7.33 (m, 5H), 5.38 (s, 1H), 4.68 (d, J=7.9 Hz, 1H), 4.51 (t, J=8.3 Hz, 1H), 4.40 (dd, J=15.8, 6.3 Hz, 1H), 4.27 (dd, J=15.8, 5.7 Hz, 1H), 4.19 (t, J=6.3 Hz, 2H), 4.12 (s, 2H), 3.96 (d, J=12.1 Hz, 1H), 3.90 (d, J=7.9 Hz, 1H), 3.75 (dd, J=12.2, 4.0 Hz, 1H), 3.54 (t, J=6.3 Hz, 2H), 2.44 (s, 3H), 2.27 (d, J=7.6 Hz, 1H), 2.16-2.08 (m, 1H), 2.04-1.95 (m, 1H), 1.89-1.79 (m, 2H), 1.74-1.66 (m, 2H), 1.61 (s, 6H), 0.89 (d, J=10.4 Hz, 9H).
Example A108
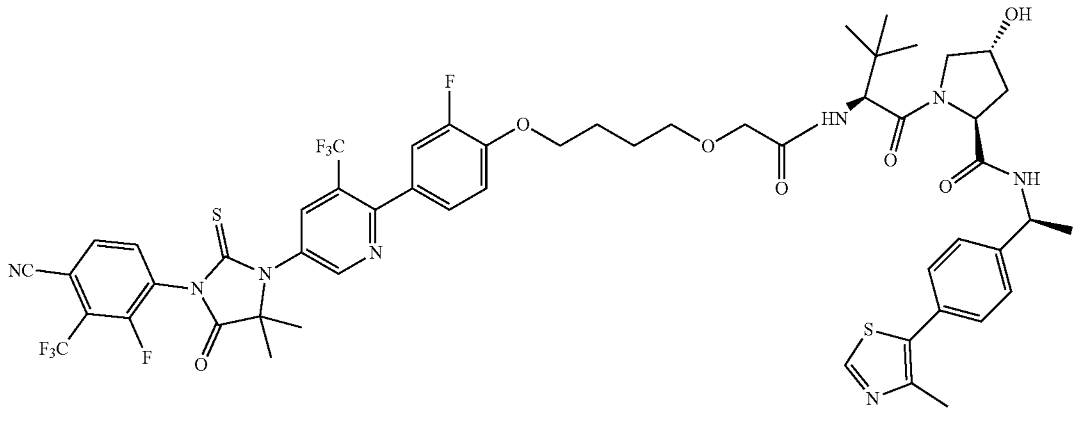 [SMILES: Cc1ncsc1-c1ccc([C@H](C)NC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3C(F)(F)F)cc2F)C(C)(C)C)cc1]
LCMS ([M+H]+): 1143.3
$^1$HNMR (400 MHz, DMSO-d6) δ8.99 (d, J=2.0 Hz, 1H), 8.97 (s, 1H), 8.52 (d, J=2.1 Hz, 1H), 8.44 (d, J=7.7 Hz, 1H), 8.30-8.24 (m, 2H), 7.48-7.30 (m, 8H), 5.14 (m, 1H), 4.90 (m, 1H), 4.56 (m, 1H), 4.47 (m, 1H), 4.29 (m, 1H), 4.19 (m, 2H), 4.01-3.88 (m, 2H), 3.65-3.53 (m, 4H), 2.45 (s, 3H), 2.11-2.03 (m, 1H), 1.93-1.83 (m, 2H), 1.82-1.71 (m, 3H), 1.63 (d, J=7.2 Hz, 6H), 1.36 (d, J=7.0 Hz, 3H), 0.94 (s, 9H).

Example A109
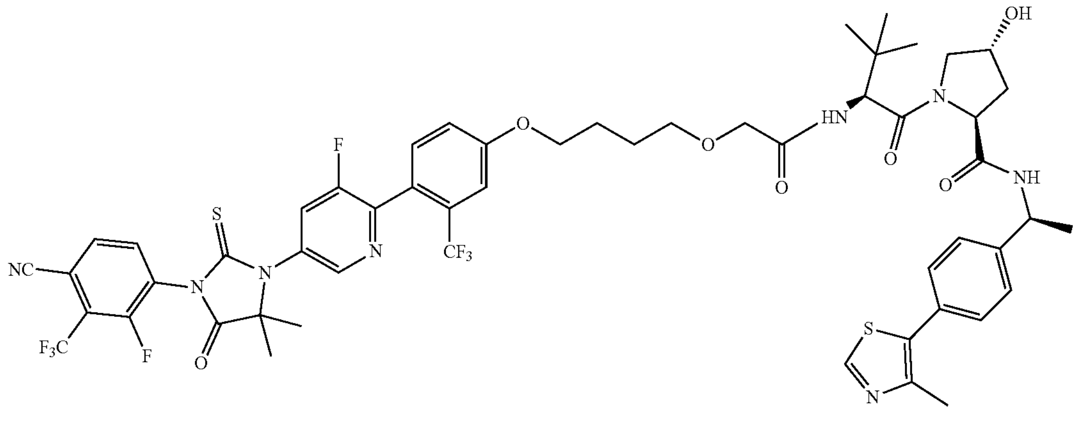 [SMILES: Cc1ncsc1-c1ccc([C@H](C)NC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)c(C(F)(F)F)c2)C(C)(C)C)cc1]
LCMS ([M+H]$^+$): 1143.3
$^1$HNMR (400 MHz, DMSO-d6) δ8.98 (s, 1H), 8.63 (s, 1H), 8.44 (d, J=7.7 Hz, 1H), 8.28 (s, 2H), 8.20 (dd, J=9.7, 1.9 Hz, 1H), 7.57 (d, J=9.3 Hz, 1H), 7.40 (dt, J=16.2, 8.3 Hz, 8H), 5.13 (d, J=3.5 Hz, 1H), 4.89 (dd, J=1 4.3, 7.2 Hz, 1H), 4.56 (d, J=9.6 Hz, 1H), 4.45 (dd, J=15.3, 7.1 Hz, 1H), 4.27 (d, J=17.5 Hz, 1H), 4.19 (s, 2H), 3.96 (d, J=1.3 Hz, 2H), 3.59 (d, J=6.1 Hz, 4H), 2.45 (s, 3H), 2.05 (dd, J=20.1, 11.5 Hz, 1H), 1.86 (dd, J=13.7, 6.2 Hz, 2H), 1.7 7 (dd, J=13.1, 7.7 Hz, 3H), 1.61 (s, 6H), 1.37 (d, J=7.0 Hz, 2H), 0.94 (s, 9H).
Example A110
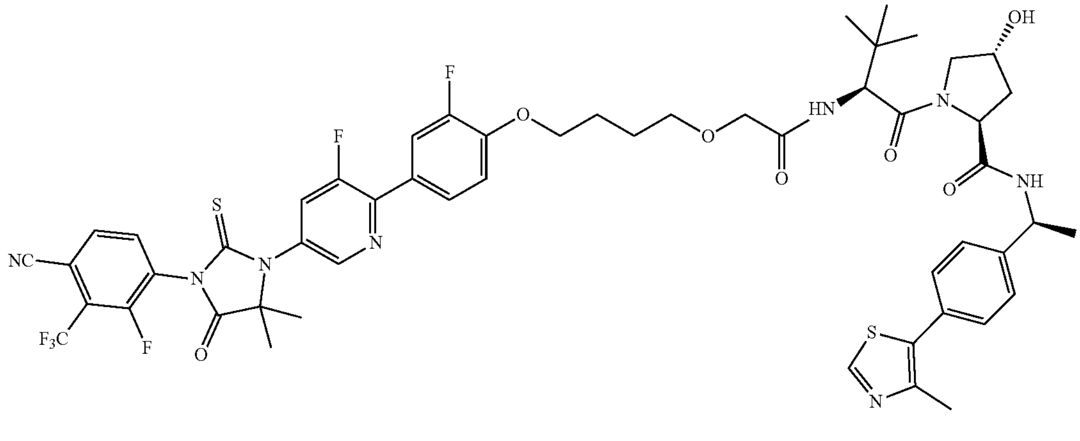 [SMILES: Cc1ncsc1-c1ccc([C@H](C)NC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)cc2F)C(C)(C)C)cc1]
LCMS ([M+H]$^+$): 1093.3
$^1$HNMR (400 MHz, DMSO-d6) δ8.97 (s, 1H), 8.62 (s, 1H), 8.43 (d, J=7.7 Hz, 1H), 8.31-8.24 (m, 2H), 8.16 (dd, J=11.9, 1.9 Hz, 1H), 7.85 (d, J=11.0 Hz, 2H), 7.38 (dt, J=23.4, 6.5 Hz, 6H), 5.13 (d, J=3.5 Hz, 1H), 4.93-4.87 (m, 1H), 4.54 (d, J=9.6 Hz, 1H), 4.45 (t, J=8.1 Hz, 1H), 4.28 (s, 1H), 4.20 (t, J=6.3 Hz, 2H), 3.96 (t, J=8.8 Hz, 2H), 3.57 (t, J=6.2 Hz, 4H), 2.45 (s, 3H), 2.10-1.95 (m, 3H), 1.91-1.83 (m, 2H), 1.81-1.71 (m, 3H), 1.61 (s, 6H), 1.36 (d, J=7.0 Hz, 3H), 0.93 (s, 9H).

Example A111
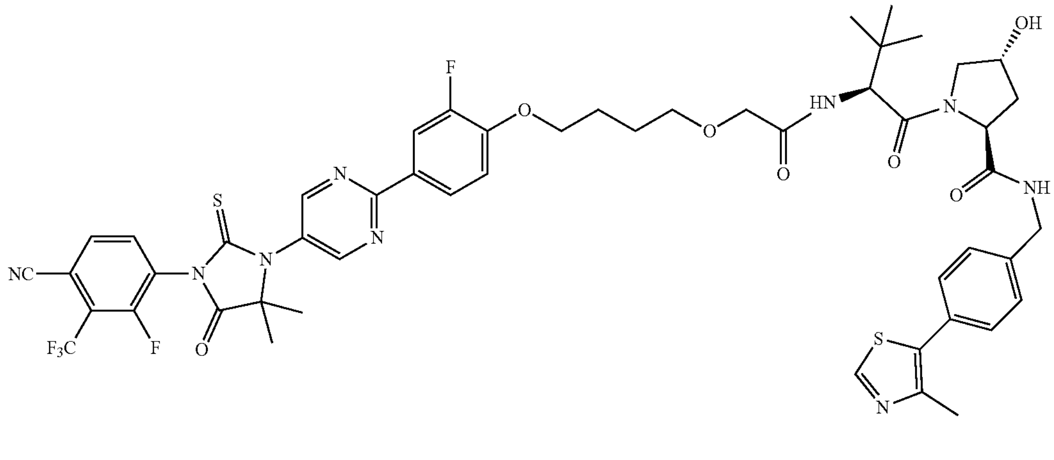 [SMILES: Cc1ncsc1-c1ccc(CNC(=O)[C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cn3)cc2F)C(C)(C)C)cc1]
LCMS ($[M+H]^+$): 1062.3
$^1$HNMR (400 MHz, DMSO-d6) δ8.99 (s, 2H), 8.97-8.95 (m, 1H), 8.59 (t, J=5.9 Hz, 1H), 8.31-8.23 (m, 3H), 8.14 (dd, J=12.6, 1.9 Hz, 1H), 7.42-7.32 (m, 6H), 5.16 (d, J=3.5 Hz, 1H), 4.56 (d, J=9.6 Hz, 1H), 4.45 (t, J=8.2 Hz, 1H), 4.41-4.36 (m, 2H), 4.26 (dd, J=15.9, 5.6 Hz, 1H), 4.20 (t, J=6.2 Hz, 2H), 4.00-3.90 (m, 2H), 3.66-3.55 (m, 4H), 2.44-2.42 (m, 3H), 2.11-2.02 (m, 1H), 2.00-1.83 (m, 4H), 1.76-1.72 (m, 2H), 1.62 (s, 6H), 0.93-0.92 (m, 9H).
Example A112
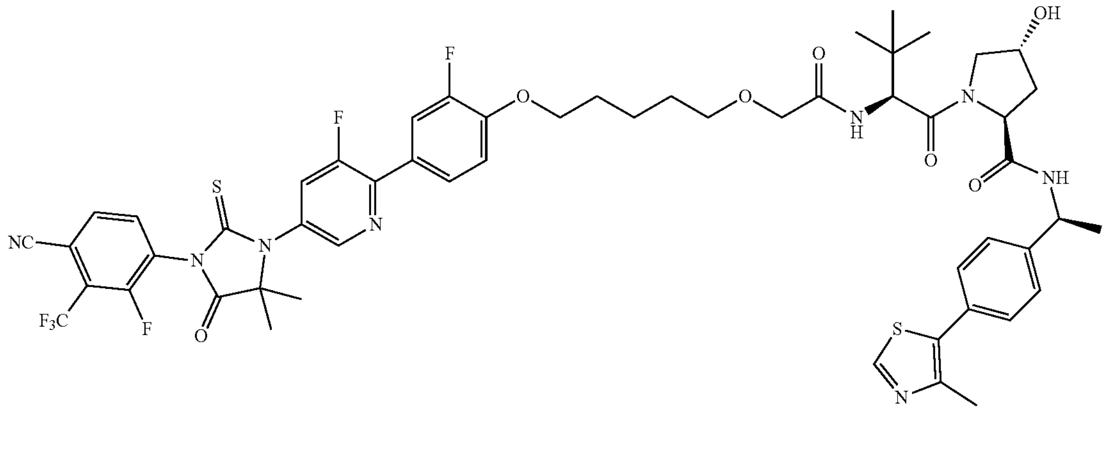 [SMILES: Cc1ncsc1-c1ccc([C@H](C)NC(=O)[C@@H]2C[C@@H](O)CN2C(=O)[C@@H](NC(=O)COCCCCCOc2ccc(-c3ncc(N4C(=S)N(c5ccc(C#N)c(C(F)(F)F)c5F)C(=O)C4(C)C)cc3F)cc2F)C(C)(C)C)cc1]
LCMS ($[M+H]^+$): 1107.3
$^1$HNMR (400 MHz, DMSO-d6) δ8.97 (s, 1H), 8.62 (s, 1H), 8.42 (d, J=7.7 Hz, 1H), 8.28 (d, J=3.3H z, 2H), 8.15 (dd, J=11.9, 1.9 Hz, 1H), 7.85 (d, J=10.5 Hz, 2H), 7.42 (d, J=8.3 Hz, 2H), 7.39-7.30 (m, 4H), 5.13 (s, 1H), 4.94-4.84 (m, 1H), 4.54 (d, J=9.6 Hz, 1H), 4.45 (t, J=8.2 Hz, 1H), 4.28 (s, 1H), 4.17 (t, J=6.4 Hz, 2H), 3.98-3.86 (m, 2H), 3.64-3.48 (m, 4H), 2.44 (s, 3H), 2.10-2.02 (m, 1H), 1.81 (ddd, J=17.4, 11.1, 5.4 Hz, 3H), 1.66 (dd, J=14.1, 7.2 Hz, 2H), 1.60 (s, 6H), 1.57-1.50 (m, 2H), 1.35 (d, J=7.0 Hz, 3H), 0.93 (s, 9H).

Example A113
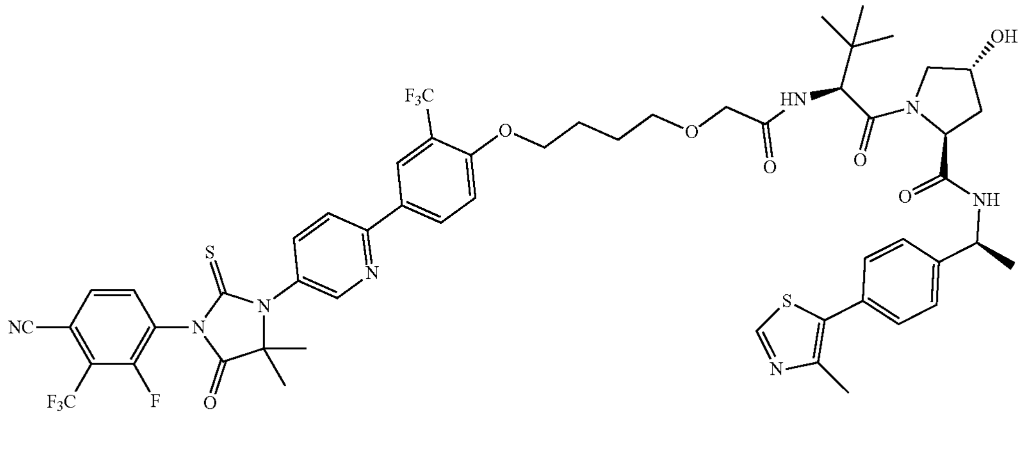 [SMILES: Cc1ncsc1-c1ccc([C@H](C)NC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2C(F)(F)F)C(C)(C)C)cc1]
LCMS ([M+H]+): 1125.2
$^1$HNMR (400 MHz, DMSO-d6) δ8.97 (s, 1H), 8.71 (d, J=2.4 Hz, 1H), 8.47-8.40 (m, 3H), 8.34-8.23 (m, 3H), 8.01 (dd, J=8.5, 2.5 Hz, 1H), 7.45-7.41 (m, 3H), 7.37-7.33 (m, 3H), 5.14 (d, J=3.5 Hz, 1H), 4.95-4.86 (m, 1H), 4.54 (d, J=9.6 Hz, 1H), 4.45 (t, J=8.2 Hz, 1H), 4.28-4.24 (m, 3H), 3.98-3.88 (m, 2H), 3.59-3.55 (m, 4H), 2.45 (s, 3H), 2.10-2.02 (m, 1H), 1.88-1.83 (m, 2H), 1.77-1.74 (m, 3H), 1.58 (s, 6H), 1.36 (d, J=7.0 Hz, 3H), 0.93 (s, 9H).
Example A114
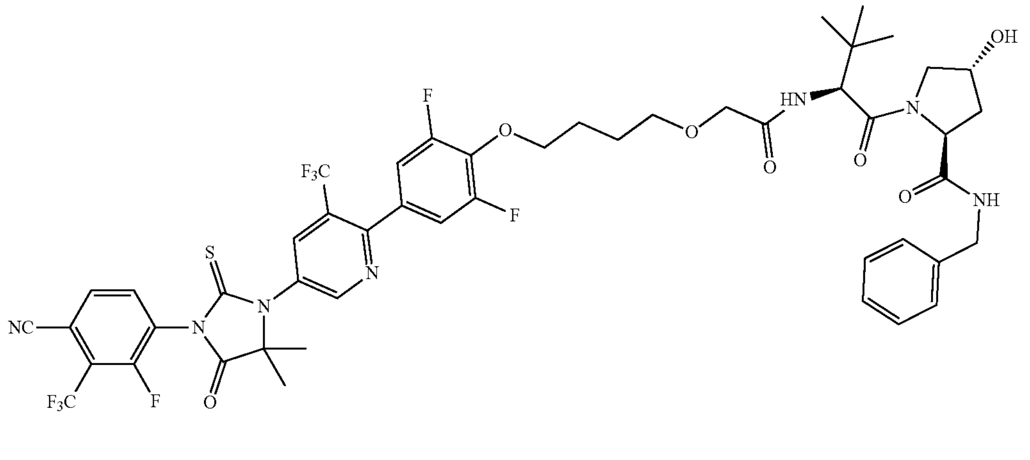 [SMILES: CC(C)(C)[C@H](NC(=O)COCCCCOc1c(F)cc(-c2ncc(N3C(=S)N(c4ccc(C#N)c(C(F)(F)F)c4F)C(=O)C3(C)C)cc2C(F)(F)F)cc1F)C(=O)N1C[C@H](O)C[C@H]1C(=O)NCc1ccccc1]
LCMS ([M+H]+): 1050.3
$^1$HNMR (400 MHz, DMSO-d6) δ9.01 (d, J=2.0 Hz, 1H), 8.57 (d, J=2.1 Hz, 1H), 8.52 (t, J=6.0 Hz, 1H), 8.31-8.23 (m, 2H), 7.43-7.33 (m, 3H), 7.32-7.22 (m, 4H), 7.17 (dd, J=11.1, 4.3 Hz, 1H), 5.14 (m, 1H), 4.56 (m, 1H), 4.43 (m, 1H), 4.35 (m, 2H), 4.30-4.17 (m, 3H), 3.98-3.87 (m, 2H), 3.69-3.53 (m, 4H), 2.01 (m, 1H), 1.83 (m, 5H), 1.63 (d, J=7.6 Hz, 6H), 0.93 (d, J=11.3 Hz, 9H).

Example A115
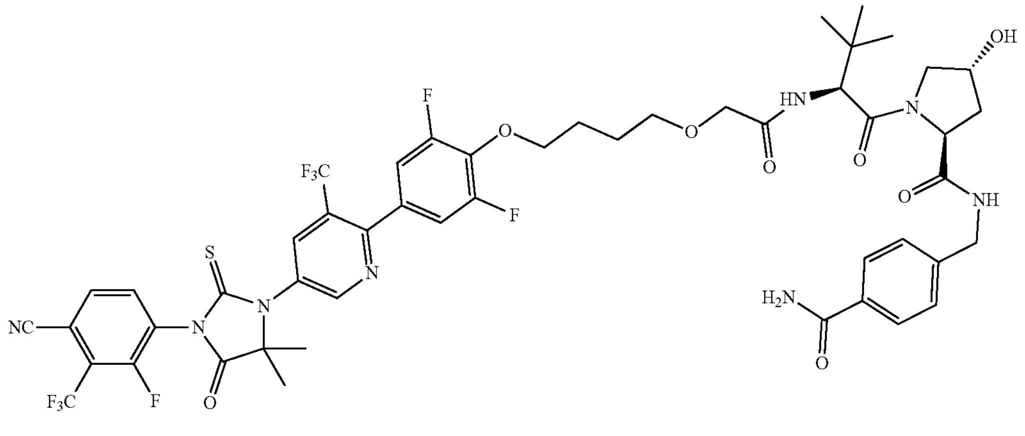
LCMS ([M+H]$^+$): 1161.2
$^1$HNMR (400 MHz, DMSO-d6) δ9.01 (d, J=2.0 Hz, 1H), 8.97 (s, 1H), 8.57 (d, J=2.1 Hz, 1H), 8.43 (d, J=7.7 Hz, 1H), 8.31-8.23 (m, 2H), 7.47-7.41 (m, 2H), 7.36 (m, 5H), 5.13 (m, 1H), 4.90 (m, 1H), 4.54 (d, J=9.6 Hz, 1H), 4.45 (m, 1H), 4.26 (m, 3H), 3.99-3.87 (m, 2H), 3.57 (m, 4H), 2.45 (s, 3H), 2.09-2.00 (m, 1H), 1.78 (m, 5H), 1.63 (d, J=7.6 Hz, 6H), 1.37 (d, J=7.0 Hz, 3H), 0.93 (s, 9H).
Example A116
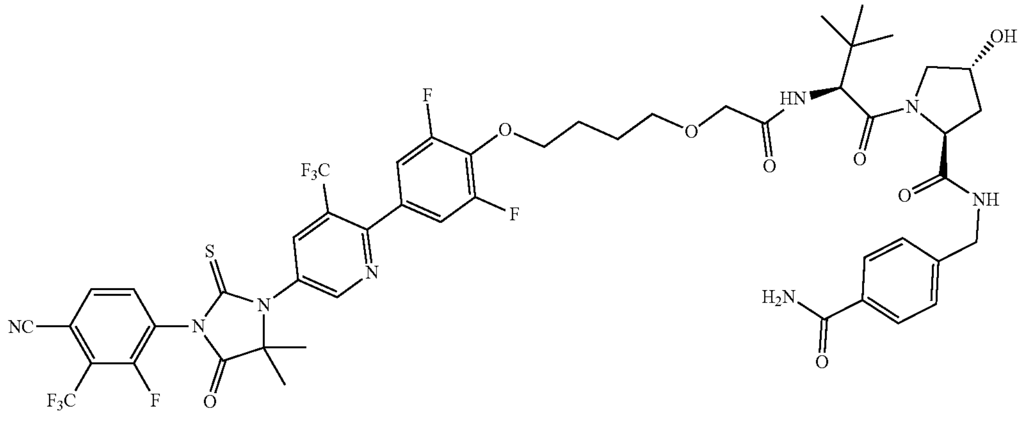 [SMILES: CC(C)(C)[C@H](NC(=O)COCCCCOc1c(F)cc(-c2ncc(N3C(=S)N(c4ccc(C#N)c(C(F)(F)F)c4F)C(=O)C3(C)C)cc2C(F)(F)F)cc1F)C(=O)N1C[C@H](O)C[C@H]1C(=O)NCc1ccc(C(N)=O)cc1]
LCMS ([M+H]$^+$): 1093.3
$^1$HNMR (400 MHz, DMSO-d6) δ9.01 (d, J=1.9 Hz, 1H), 8.58 (m, 2H), 8.31-8.23 (m, 2H), 7.90 (s, 1H), 7.80 (m, 2H), 7.42-7.32 (m, 5H), 7.27 (s, 1H), 5.15 (d, J=3.5 Hz, 1H), 4.56 (d, J=9.6 Hz, 1H), 4.47-4.32 (m, 3H), 4.27 (m, 3H), 3.99-3.88 (m, 2H), 3.70-3.53 (m, 4H), 2.07-1.99 (m, 1H), 1.93-1.70 (m, 5H), 1.63 (d, J=7.7 Hz, 6H), 0.93 (d, J=11.4 Hz, 9H).

Example A117
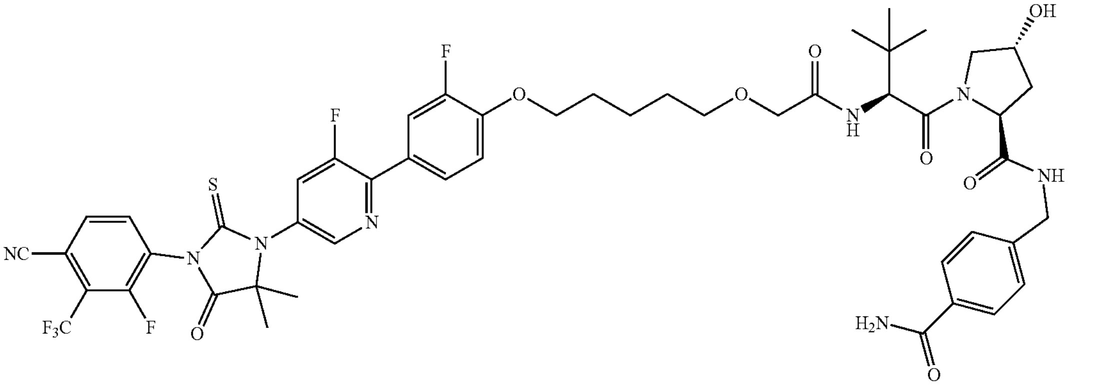 [SMILES: CC(C)(C)[C@H](NC(=O)COCCCCCOc1ccc(-c2ncc(N3C(=S)N(c4ccc(C#N)c(C(F)(F)F)c4F)C(=O)C3(C)C)cc2F)cc1F)C(=O)N1C[C@H](O)C[C@H]1C(=O)NCc1ccc(C(N)=O)cc1]
LCMS ([M+H]$^+$): 1039.3
$^1$HNMR (400 MHz, DMSO-d6) δ8.59 (dd, J=13.7, 7.7 Hz, 2H), 8.32-8.25 (m, 2H), 8.15 (dd, J=11.9, 1.9 Hz, 1H), 7.91 (s, 1H), 7.88-7.81 (m, 2H), 7.79 (t, J=6.4 Hz, 2H), 7.40-7.31 (m, 4H), 7.28 (s, 1H), 5.15 (s, 1H), 4.56 (d, J=9.6 Hz, 1H), 4.46-4.32 (m, 3H), 4.25 (dd, J=15.7, 5.6 Hz, 1H), 4.16 (t, J=6.4 Hz, 2H), 3.99-3.89 (m, 2H), 3.68-3.58 (m, 2H), 3.52 (t, J=6.3 Hz, 2H), 2.06-1.95 (m, 2H), 1.92-1.78 (m, 3H), 1.69-1.58 (m, 7H), 1.53 (dd, J=15.1, 8.0 Hz, 2H), 0.93 (d, J=10.3 Hz, 9H).
Example A118
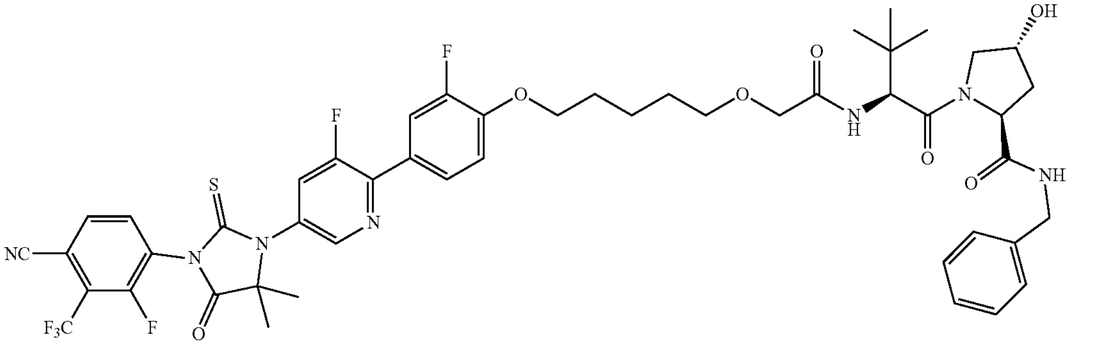 [SMILES: CC(C)(C)[C@H](NC(=O)COCCCCCOc1ccc(-c2ncc(N3C(=S)N(c4ccc(C#N)c(C(F)(F)F)c4F)C(=O)C3(C)C)cc2F)cc1F)C(=O)N1C[C@H](O)C[C@H]1C(=O)NCc1ccccc1]
LCMS ([M+H]$^+$): 996.3
$^1$HNMR (400 MHz, DMSO-d6) δ8.62 (s, 1H), 8.51 (t, J=6.0 Hz, 1H), 8.32-8.24 (m, 2H), 8.16 (dd, J=11.9, 1.9 Hz, 1H), 7.88-7.81 (m, 2H), 7.39-7.23 (m, 6H), 7.22-7.15 (m, 1H), 5.14 (s, 1H), 4.56 (d, J=9.6 Hz, 1H), 4.43 (t, J=8.2 Hz, 1H), 4.33 (dd, J=15.2, 6.2 Hz, 2H), 4.19 (dt, J=13.2, 6.1 Hz, 3H), 3.98-3.87 (m, 2H), 3.69-3.57 (m, 2H), 3.52 (t, J=6.3 Hz, 2H), 2.07-1.95 (m, 2H), 1.92-1.80 (m, 3H), 1.70-1.49 (m, 10H), 0.93 (d, J=10.6 Hz, 9H).

Example A119
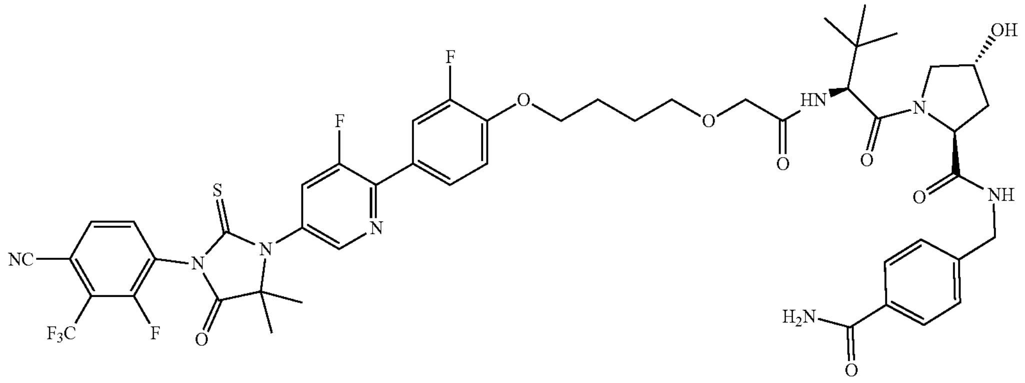 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)cc1F)C(=O)N1C[C@H](O)C[C@H]1C(=O)NCc1ccc(C(N)=O)cc1]
LCMS ([M+H]+): 1025.3
$^1$HNMR (400 MHz, DMSO-d6) δ8.62 (s, 1H), 8.59 (t, J=6.0 Hz, 1H), 8.32-8.25 (m, 2H), 8.16 (dd, J=11.9, 1.9 Hz, 1H), 7.91 (s, 1H), 7.88-7.82 (m, 2H), 7.79 (d, J=8.3 Hz, 2H), 7.37 (dd, J=18.8, 9.2 Hz, 4H), 7.28 (s, 1H), 5.15 (s, 1H), 4.56 (d, J=9.6 Hz, 1H), 4.47-4.32 (m, 3H), 4.30-4.17 (m, 3H), 4.02-3.89 (m, 2H), 3.70-3.61 (m, 2H), 3.57 (t, J=6.3 Hz, 2H), 2.02 (dt, J=14.4, 9.8 Hz, 2H), 1.92-1.82 (m, 3H), 1.75 (dd, J=14.4, 6.3 Hz, 2H), 1.61 (s, 6H), 0.93 (d, J=11.2 Hz, 9H).
Example A120
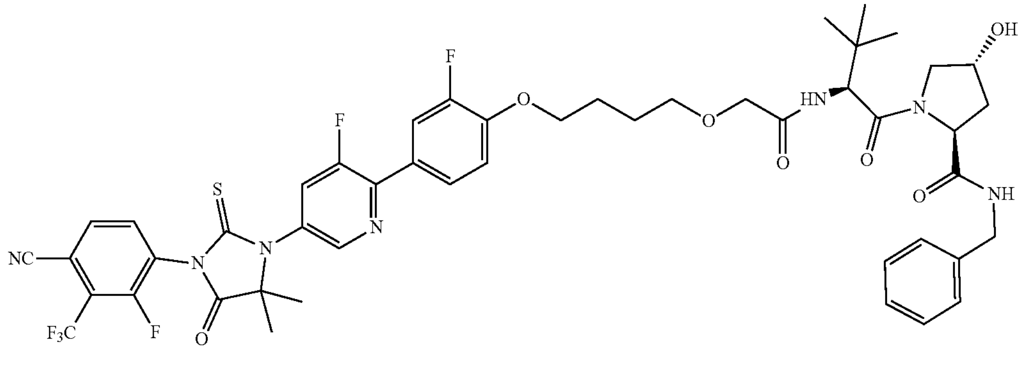 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)cc1F)C(=O)N1C[C@H](O)C[C@H]1C(=O)NCc1ccccc1]
LCMS ([M+H]+): 982.4
$^1$HNMR (400 MHz, DMSO-d6) δ8.63 (s, 1H), 8.51 (t, J=6.0 Hz, 1H), 8.31-8.25 (m, 2H), 8.16 (dd, J=11.9, 1.9 Hz, 1H), 7.89-7.81 (m, 2H), 7.37 (dd, J=16.6, 9.1 Hz, 2H), 7.32-7.23 (m, 4H), 7.21-7.15 (m, 1H), 5.14 (d, J=3.2 Hz, 1H), 4.56 (d, J=9.6 Hz, 1H), 4.43 (t, J=8.3 Hz, 1H), 4.34 (dd, J=15.3, 6.4 Hz, 2H), 4.25-4.17 (m, 3H), 4.00-3.91 (m, 2H), 3.62 (ddd, J=23.4, 11.7, 5.1 Hz, 4H), 2.03 (dd, J=15.2, 10.1 Hz, 1H), 1.92-1.82 (m, 3H), 1.75 (dd, J=14.2, 6.4 Hz, 2H), 1.61 (s, 6H), 0.93 (d, J=10.8 Hz, 9H).

Example A121
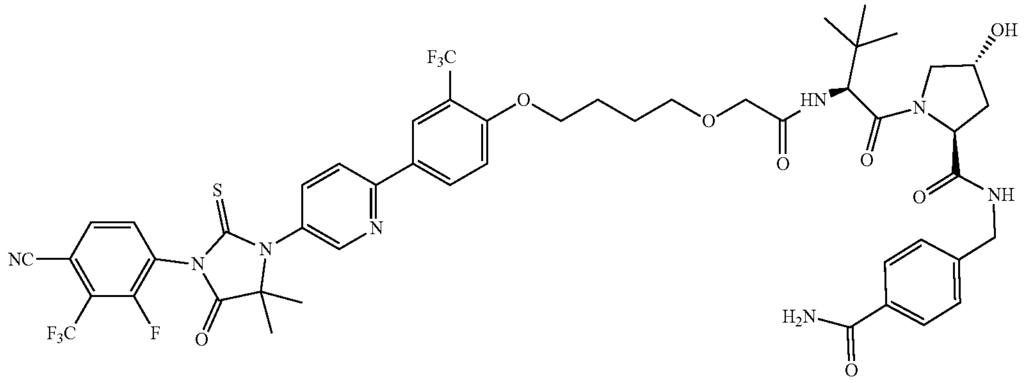 [SMILES: CC(C)(C)[C@H](NC(=O)COCCCCOc1ccc(-c2ccc(N3C(=S)N(c4ccc(C#N)c(C(F)(F)F)c4F)C(=O)C3(C)C)cn2)cc1C(F)(F)F)C(=O)N1C[C@H](O)C[C@H]1C(=O)NCc1ccc(C(N)=O)cc1]
LCMS ([M+H]$^+$): 1014.3
$^1$HNMR (400 MHz, DMSO-d6) δ8.71 (d, J=2.4 Hz, 1H), 8.53 (t, J=6.0 Hz, 1H), 8.45-8.38 (m, 2H), 8.33-8.24 (m, 3H), 8.01 (dd, J=8.5, 2.5 Hz, 1H), 7.40 (dd, J=17.2, 9.6 Hz, 2H), 7.33-7.23 (m, 4H), 7.19-7.15 (m, 1H), 5.16 (d, J=3.5 Hz, 1H), 4.56 (d, J=9.6 Hz, 1H), 4.43 (t, J=8.2 Hz, 1H), 4.35-4.31 (m, 2H), 4.27-4.18 (m, 3H), 4.00-3.88 (m, 2H), 3.68-3.55 (m, 4H), 2.07-2.01 (m, 1H), 1.93-1.82 (m, 3H), 1.78-1.73 (m, 2H), 1.58 (s, 6H), 0.94-0.91 (m, 9H).
Example A122
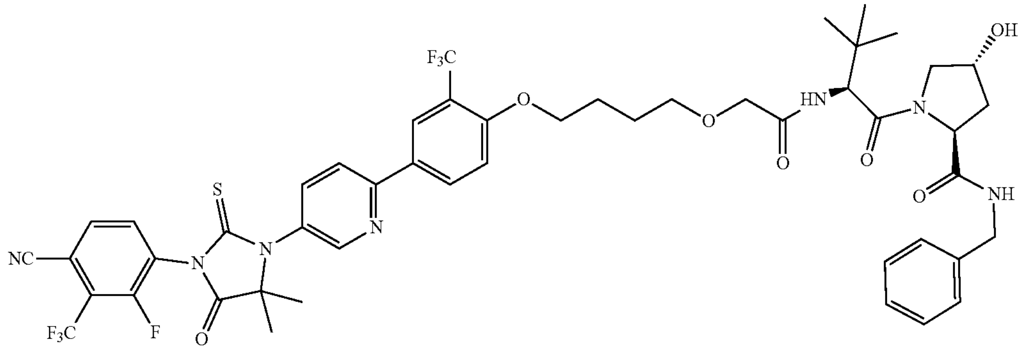 [SMILES: CC(C)(C)[C@H](NC(=O)COCCCCOc1ccc(-c2ccc(N3C(=S)N(c4ccc(C#N)c(C(F)(F)F)c4F)C(=O)C3(C)C)cn2)cc1C(F)(F)F)C(=O)N1C[C@H](O)C[C@H]1C(=O)NCc1ccccc1]
LCMS ([M+H]$^+$): 1057.3
$^1$HNMR (400 MHz, DMSO-d6) δ8.70 (d, J=2.4 Hz, 1H), 8.59 (t, J=6.0 Hz, 1H), 8.41 (m, 2H), 8.34-8.22 (m, 3H), 8.01 (dd, J=8.5, 2.4 Hz, 1H), 7.91 (s, 1H), 7.83-7.78 (m, 2H), 7.45-7.32 (m, 4H), 7.28 (s, 1H), 5.16 (d, J=3.5 Hz, 1H), 4.56 (d, J=9.6 Hz, 1H), 4.47-4.32 (m, 3H), 4.30-4.22 (m, 3H), 4.00-3.90 (m, 2H), 3.69-3.54 (m, 4H), 2.07-1.99 (m, 1H), 1.93-1.81 (m, 3H), 1.80-1.70 (m, 2H), 1.58 (s, 6H), 0.93 (d, J=11.2 Hz, 9H).

Example A123
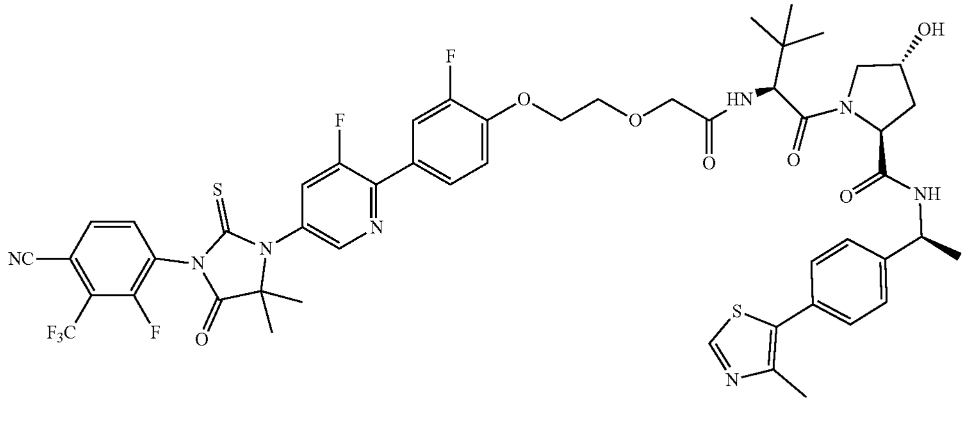 [SMILES: Cc1ncsc1-c1ccc([C@H](C)NC(=O)[C@@H]2C[C@@H](O)CN2C(=O)[C@@H](NC(=O)COCCOc2ccc(-c3ncc(N4C(=S)N(c5ccc(C#N)c(C(F)(F)F)c5F)C(=O)C4(C)C)cc3F)cc2F)C(C)(C)C)cc1]
LCMS ([M+H]$^+$): 1065.3
$^1$HNMR (400 MHz, DMSO-d6) δ8.98 (s, 1H), 8.64 (s, 1H), 8.43 (d, J=7.7 Hz, 1H), 8.29 (d, J=3.5H z, 2H), 8.17 (dd, J=11.9, 1.8 Hz, 1H), 7.88 (d, J=4.2 Hz, 2H), 7.86 (s, 1H), 7.50-7.22 (m, 7H), 5.14 (d, J=3.5 Hz, 1H), 4.95-4.86 (m, 1H), 4.56 (d, J=9.5 Hz, 1H), 4.45 (t, J=8.1 Hz, 1H), 4.40-4.33 (m, 2H), 4.29 (s, 1H), 4.07 (d, J=17.5 Hz, 2H), 3.93 (d, J=4.0 Hz, 2H), 3.66-3.56 (m, 2H), 2.45 (s, 3H), 2.14-1.96 (m, 1H), 1.78 (ddd, J=13.0, 8.8, 4.4 Hz, 1H), 1.62 (s, 6H), 1.37 (d, J=7.0 Hz, 1H), 1.24 (s, 1H), 0.94 (s, 9H).
Example A124
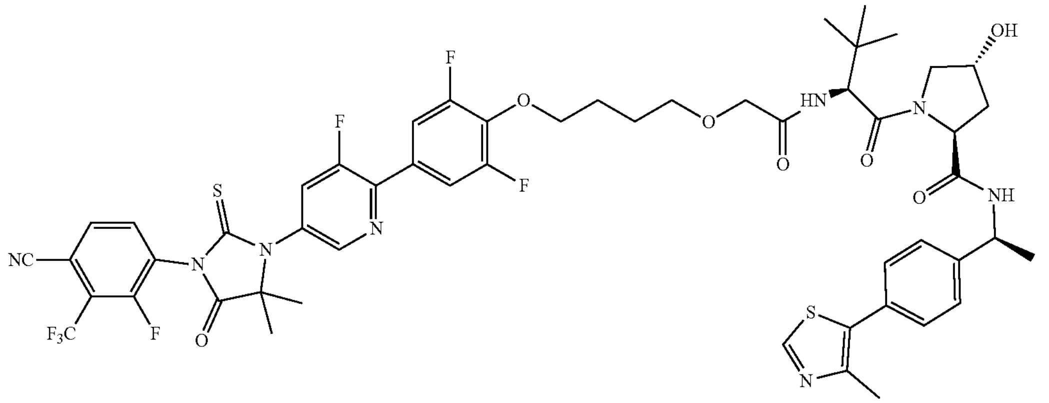 [SMILES: Cc1ncsc1-c1ccc([C@H](C)NC(=O)[C@@H]2C[C@@H](O)CN2C(=O)[C@@H](NC(=O)COCCCCOc2c(F)cc(-c3ncc(N4C(=S)N(c5ccc(C#N)c(C(F)(F)F)c5F)C(=O)C4(C)C)cc3F)cc2F)C(C)(C)C)cc1]
LCMS ([M+H]$^+$): 1111.3
$^1$HNMR (400 MHz, DMSO-d6) δ8.98 (s, 1H), 8.67 (s, 1H), 8.44 (d, J=7.7 Hz, 1H), 8.28-8.22 (m, 3H), 7.80-7.76 (m, 2H), 7.43 (d, J=8.2 Hz, 2H), 7.37-7.33 (m, 3H), 5.14 (d, J=3.4 Hz, 1H), 4.90 (t, J=7.2 Hz, 1H), 4.54 (d, J=9.6 Hz, 1H), 4.44 (t, J=8.2 Hz, 1H), 4.28 (t, J=5.9 Hz, 3H), 3.94-3.87 (m, 2H), 3.62-3.54 (m, 4H), 2.45 (s, 3H), 2.08-2.03 (m, 1H), 1.83-1.73 (m, 5H), 1.61 (s, 6H), 1.37 (d, J=7.0 Hz, 3H), 0.92 (s, 9H).

Example A125
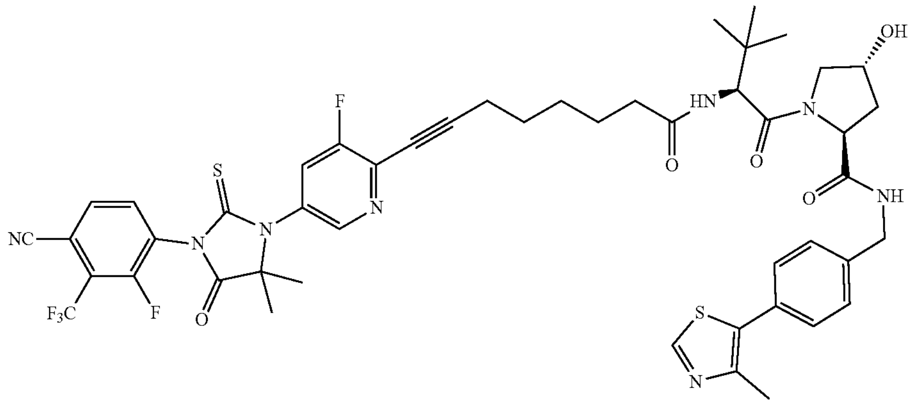 [SMILES: Cc1ncsc1-c1ccc(CNC(=O)[C@@H]2C[C@@H](O)CN2C(=O)[C@@H](NC(=O)CCCCCC#Cc2ncc(N3C(=S)N(c4ccc(C#N)c(C(F)(F)F)c4F)C(=O)C3(C)C)cc2F)C(C)(C)C)cc1]
LCMS ([M+H]$^+$): 977.3
$^1$HNMR (400 MHz, DMSO-d6) δ8.97 (s, 1H), 8.55 (t, J=6.1 Hz, 1H), 8.50 (d, J=1.1 Hz, 1H), 8.30-8.21 (m, 2H), 8.12 (dd, J=9.5, 1.9 Hz, 1H), 7.90 (d, J=9.4 Hz, 1H), 7.40 (q, J=8.4 Hz, 4H), 5.12 (d, J=3.6 Hz, 1H), 4.55 (d, J=9.4 Hz, 1H), 4.47-4.38 (m, 2H), 4.35 (s, 1H), 4.21 (dd, J=15.9, 5.5 Hz, 1H), 3.66 (d, J=4.1 Hz, 2H), 3.39 (s, 2H), 2.58 (t, J=6.5 Hz, 2H), 2.44 (s, 3H), 2.35 (dt, J=14.1, 7.1 Hz, 1H), 2.19 (dt, J=14.0, 7.0 Hz, 1H), 2.02 (dd, J=17.4, 9.7 Hz, 1H), 1.94-1.86 (m, 1H), 1.67 (dd, J=14.4, 7.4 Hz, 2H), 1.60 (d, J=6.7 Hz, 8H), 0.93 (d, J=8.7 Hz, 9H).
Example A126
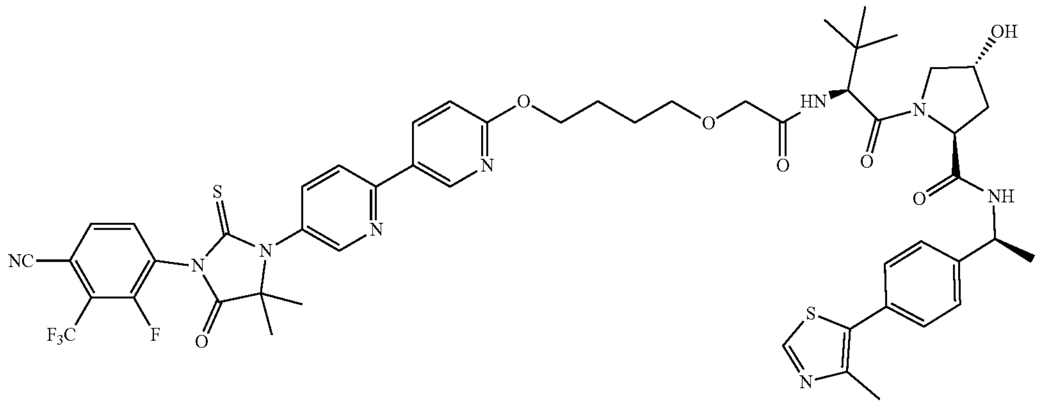 [SMILES: Cc1ncsc1-c1ccc([C@H](C)NC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cn2)C(C)(C)C)cc1]
LCMS ([M+H]$^+$): 1058.3
$^1$HNMR (400 MHz, DMSO-d6) δ8.98 (s, 1H), 8.95 (d, J=2.2 Hz, 1H), 8.70 (d, J=2.1 Hz, 1H), 8.49-8.40 (m, 2H), 8.29 (q, J=8.5 Hz, 2H), 8.19 (d, J=8.5 Hz, 1H), 8.01 (dd, J=8.5, 2.5 Hz, 1H), 7.38 (dt, J=19.1, 9.5 Hz, 5H), 6.97 (d, J=8.8 Hz, 1H), 5.13 (d, J=3.5 Hz, 1H), 4.95-4.85 (m, 1H), 4.54 (d, J=9.6 Hz, 1H), 4.45 (t, J=8.2 Hz, 1H), 4.38 (t, J=6.5 Hz, 2H), 4.28 (s, 1H), 4.00-3.87 (m, 2H), 3.64-3.51 (m, 4H), 2.45 (s, 3H), 2.11-1.94 (m, 2H), 1.87-1.69 (m, 5H), 1.59 (s, 6H), 1.37 (d, J=7.0 Hz, 3H), 0.93 (s, 9H).

Example A127

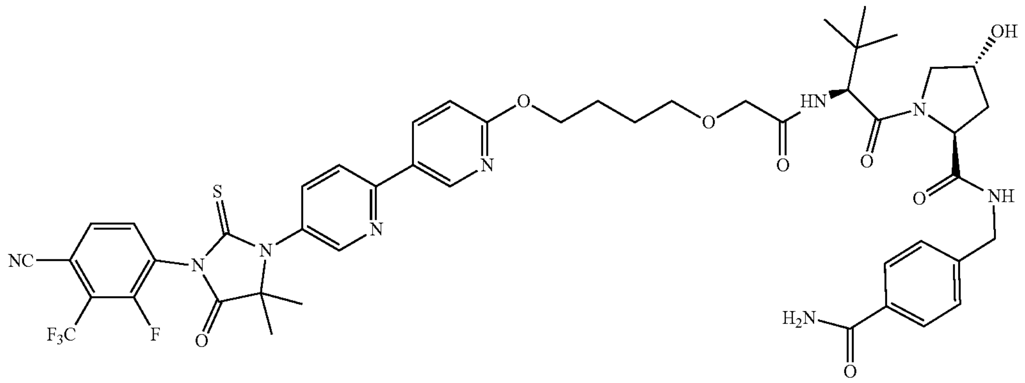 [SMILES: CC(C)(C)[C@H](NC(=O)COCCCCOc1ccc(-c2ccc(N3C(=S)N(c4ccc(C#N)c(C(F)(F)F)c4F)C(=O)C3(C)C)cn2)cn1)C(=O)N1C[C@H](O)C[C@H]1C(=O)NCc1ccc(C(N)=O)cc1]

LCMS ([M+H]$^+$): 990.3

$^1$HNMR (400 MHz, DMSO-d6) δ8.94 (d, J=2.4 Hz, 1H), 8.70 (d, J=2.3 Hz, 1H), 8.59 (t, J=6.0 Hz, 1H), 8.44 (dd, J=8.7, 2.5 Hz, 1H), 8.29 (q, J=8.5 Hz, 2H), 8.18 (d, J=8.5 Hz, 1H), 8.00 (dd, J=8.5, 2.5 Hz, 1H), 7.91 (s, 1H), 7.80 (t, J=9.7 Hz, 2H), 7.37 (dd, J=12.0, 9.0 Hz, 3H), 7.28 (s, 1H), 6.96 (d, J=8.8 Hz, 1H), 5.15 (d, J=3.5 Hz, 1H), 4.56 (d, J=9.6 Hz, 1H), 4.47-4.32 (m, 5H), 4.26 (dd, J=16.1, 5.7 Hz, 1H), 4.01-3.89 (m, 2H), 3.70-3.51 (m, 4H), 2.09-2.01 (m, 1H), 1.93-1.79 (m, 3H), 1.73 (dd, J=14.4, 6.3 Hz, 2H), 1.58 (s, 6H), 0.92 (d, J=10.7 Hz, 9H).

Example A128

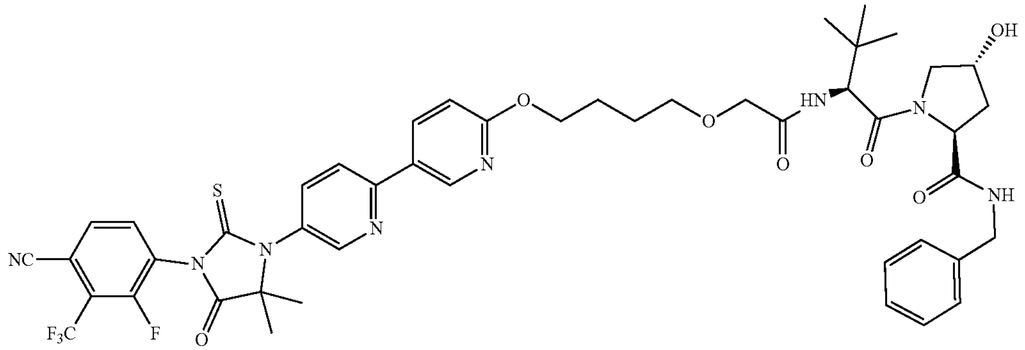 [SMILES: CC(C)(C)[C@H](NC(=O)COCCCCOc1ccc(-c2ccc(N3C(=S)N(c4ccc(C#N)c(C(F)(F)F)c4F)C(=O)C3(C)C)cn2)cn1)C(=O)N1C[C@H](O)C[C@H]1C(=O)NCc1ccccc1]

LCMS ([M+H]$^+$): 947.3

$^1$HNMR (400 MHz, DMSO-d6) δ8.94 (d, J=2.3 Hz, 1H), 8.70 (d, J=2.4 Hz, 1H), 8.52 (t, J=6.0 Hz, 1H), 8.44 (dd, J=8.7, 2.5 Hz, 1H), 8.29 (q, J=8.5 Hz, 2H), 8.19 (d, J=8.6 Hz, 1H), 8.00 (dd, J=8.5, 2.5 Hz, 1H), 7.38 (d, J=9.6 Hz, 1H), 7.33-7.23 (m, 4H), 7.18 (t, J=6.7 Hz, 1H), 6.96 (d, J=8.7 Hz, 1H), 5.14 (d, J=3.5 Hz, 1H), 4.56 (d, J=9.6 Hz, 1H), 4.43 (t, J=8.3 Hz, 1H), 4.40-4.31 (m, 4H), 4.21 (dd, J=15.5, 5.6 Hz, 1H), 4.00-3.87 (m, 2H), 3.62 (ddd, J=27.3, 11.7, 5.1 Hz, 4H), 2.03 (dd, J=20.1, 12.9 Hz, 1H), 1.92-1.79 (m, 3H), 1.73 (dd, J=14.4, 6.2 Hz, 2H), 1.59 (s, 6H), 0.92 (d, J=11.0 Hz, 9H).

Example A129
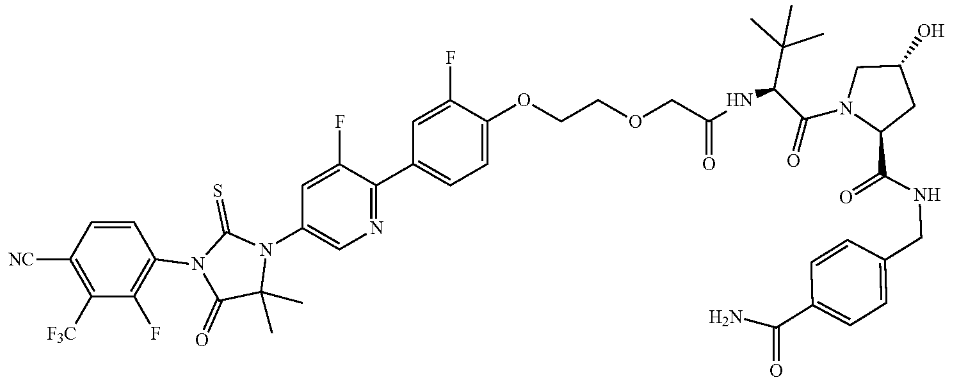 [SMILES: CC(C)(C)[C@H](NC(=O)COCCOc1ccc(-c2ncc(N3C(=S)N(c4ccc(C#N)c(C(F)(F)F)c4F)C(=O)C3(C)C)cc2F)cc1F)C(=O)N1C[C@H](O)C[C@H]1C(=O)NCc1ccc(C(N)=O)cc1]
LCMS ([M+H]+): 997.3
$^1$HNMR (400 MHz, DMSO-d6) δ8.63 (s, 1H), 8.57 (t, J=6.0 Hz, 1H), 8.32-8.24 (m, 2H), 8.16 (dd, J=11.9, 1.9 Hz, 1H), 7.91-7.82 (m, 3H), 7.79 (t, J=6.5 Hz, 2H), 7.47 (d, J=9.5 Hz, 1H), 7.43-7.33 (m, 3H), 7.27 (s, 1H), 5.15 (d, J=3.6 Hz, 1H), 4.57 (d, J=9.5 Hz, 1H), 4.46-4.37 (m, 2H), 4.37-4.31 (m, 3H), 4.25 (dd, J=15.9, 5.5 Hz, 1H), 4.07 (d, J=19.9 Hz, 2H), 3.95-3.87 (m, 2H), 3.65 (dt, J=22.5, 7.3 Hz, 2H), 2.06-1.99 (m, 1H), 1.88 (ddd, J=13.0, 8.8, 4.5 Hz, 1H), 1.61 (s, 6H), 0.93 (d, J=12.7 Hz, 9H).
Example A130
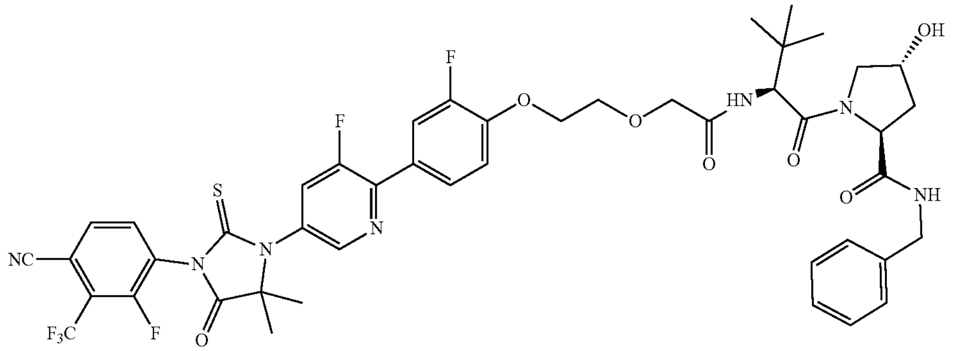 [SMILES: CC(C)(C)[C@H](NC(=O)COCCOc1ccc(-c2ncc(N3C(=S)N(c4ccc(C#N)c(C(F)(F)F)c4F)C(=O)C3(C)C)cc2F)cc1F)C(=O)N1C[C@H](O)C[C@H]1C(=O)NCc1ccccc1]
LCMS ([M+H]+): 954.3
$^1$HNMR (400 MHz, DMSO-d6) δ8.66-8.60 (m, 1H), 8.51 (t, J=6.0 Hz, 1H), 8.33-8.24 (m, 2H), 8.16 (dd, J=11.9, 1.9 Hz, 1H), 7.92-7.81 (m, 2H), 7.47 (d, J=9.5 Hz, 1H), 7.40 (t, J=9.0 Hz, 1H), 7.34-7.14 (m, 5H), 5.15 (d, J=3.5 Hz, 1H), 4.57 (d, J=9.6 Hz, 1H), 4.44 (dd, J=13.9, 5.7 Hz, 1H), 4.39-4.31 (m, 4H), 4.19 (dd, J=15.6, 5.6 Hz, 1H), 4.11-4.02 (m, 2H), 3.95-3.87 (m, 2H), 3.65 (dt, J=23.5, 7.4 Hz, 2H), 2.09-1.99 (m, 1H), 1.88 (ddd, J=12.9, 8.7, 4.5 Hz, 1H), 1.61 (s, 6H), 0.92 (d, J=11.6 Hz, 9H).

Example A131
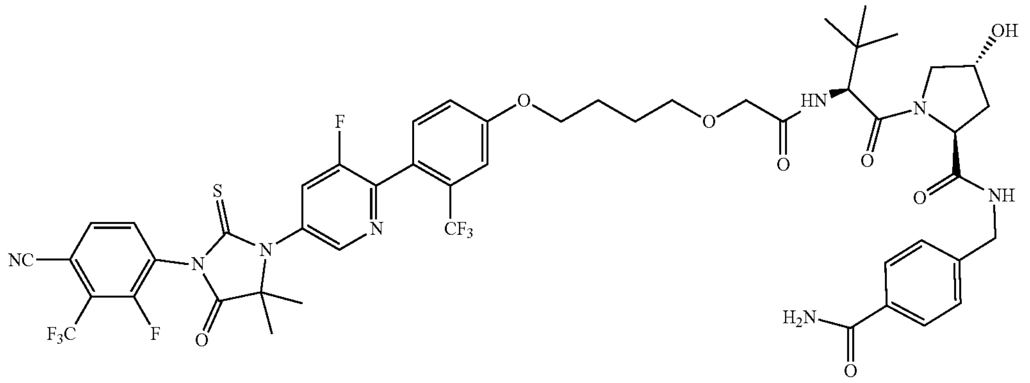 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)c(C(F)(F)F)c1)C(=O)N1C[C@H](O)C[C@H]1C(=O)NCc1ccc(C(N)=O)cc1]
LCMS ([M+H]$^+$): 1075.3
$^1$HNMR (400 MHz, DMSO-d6) δ8.62 (d, J=0.9 Hz, 1H), 8.59 (t, J=6.0 Hz, 1H), 8.32-8.24 (m, 2H), 8.19 (dd, J=9.7, 1.9 Hz, 1H), 7.91 (s, 1H), 7.80 (dd, J=12.8, 8.3 Hz, 2H), 7.59-7.53 (m, 1H), 7.44-7.32 (m, 5H), 7.28 (s, 1H), 5.15 (d, J=3.5 Hz, 1H), 4.57 (d, J=9.6 Hz, 1H), 4.47-4.32 (m, 3H), 4.26 (dd, J=15.9, 5.6 Hz, 1H), 4.18 (t, J=6.2 Hz, 2H), 4.01-3.89 (m, 2H), 3.67 (dd, J=10.7, 3.7 Hz, 1H), 3.59 (dd, J=15.2, 8.9 Hz, 3H), 2.06 (dd, J=15.0, 6.3 Hz, 1H), 1.92-1.81 (m, 3H), 1.80-1.71 (m, 2H), 1.60 (s, 6H), 0.93 (d, J=10.4 Hz, 9H).
Example A132
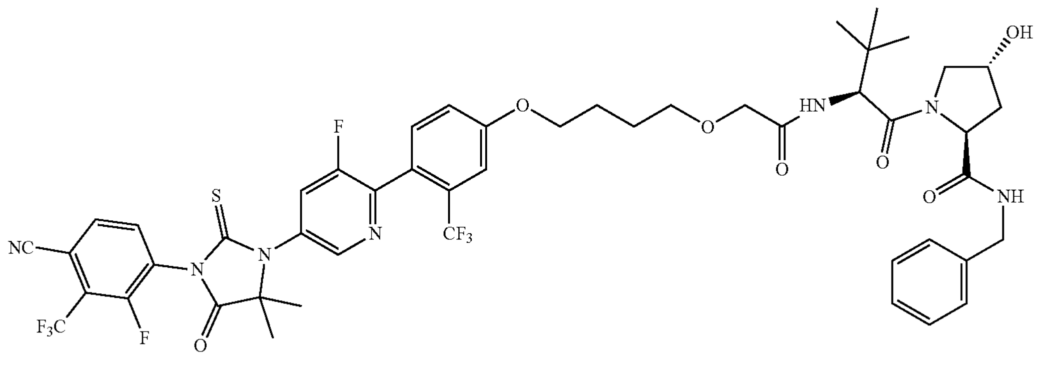 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)c(C(F)(F)F)c1)C(=O)N1C[C@H](O)C[C@H]1C(=O)NCc1ccccc1]
LCMS ([M+H]$^+$): 1032.3
$^1$HNMR (400 MHz, DMSO-d6) δ8.64-8.60 (m, 1H), 8.52 (t, J=6.0 Hz, 1H), 8.32-8.25 (m, 2H), 8.19 (dd, J=9.7, 1.9 Hz, 1H), 7.58-7.53 (m, 1H), 7.39 (dd, J=6.5, 3.8 Hz, 3H), 7.32-7.23 (m, 4H), 7.20-7.13 (m, 1H), 5.15 (d, J=3.5 Hz, 1H), 4.57 (d, J=9.6 Hz, 1H), 4.44 (t, J=8.2 Hz, 1H), 4.34 (dd, J=15.4, 6.3 Hz, 2H), 4.24-4.14 (m, 3H), 4.03-3.87 (m, 2H), 3.62 (ddd, J=22.7, 11.6, 5.1 Hz, 4H), 2.09-2.00 (m, 1H), 1.88 (tt, J=12.2, 5.9 Hz, 3H), 1.76 (dd, J=14.2, 6.2 Hz, 2H), 1.61 (s, 6H), 0.93 (d, J=10.7 Hz, 9H).

Example A133
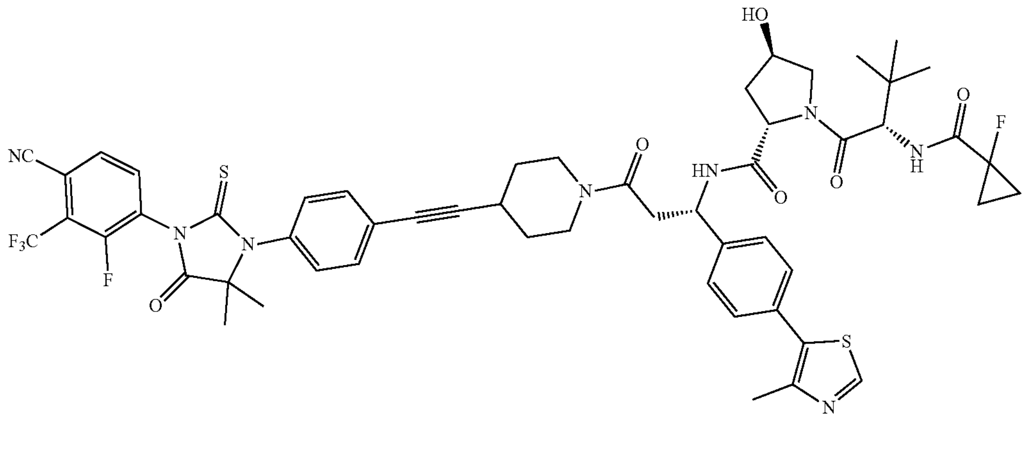 [SMILES: Cc1ncsc1-c1ccc([C@H](CC(=O)N2CCC(C#Cc3ccc(N4C(=S)N(c5ccc(C#N)c(C(F)(F)F)c5F)C(=O)C4(C)C)cc3)CC2)NC(=O)[C@@H]2C[C@@H](O)CN2C(=O)[C@@H](NC(=O)C2(F)CC2)C(C)(C)C)cc1]
LCMS ([M+H]+): 1071.3
$^1$HNMR (400 MHz, DMSO-d6) δ8.99-8.90 (m, 1H), 8.52 (t, J=8.4 Hz, 1H), 8.31-8.24 (m, 2H), 7.55 (d, J=8.4 Hz, 1H), 7.42 (dq, J=10.9, 8.4 Hz, 7H), 7.27 (d, J=7.8 Hz, 1H), 5.26-5.11 (m, 2H), 4.57 (d, J=9.2 Hz, 1H), 4.46 (t, J=8.3 Hz, 1H), 4.28 (s, 1H), 3.84 (d, J=46.3 Hz, 1H), 3.58 (dd, J=22.1, 1 0.4 Hz, 3H), 3.24 (d, J=10.2 Hz, 1H), 3.06 (d, J=9.7 Hz, 1H), 2.97-2.76 (m, 3H), 2.44 (d, J=5.4 Hz, 3H), 2.02 (dd, J=15.9, 8.5 Hz, 1H), 1.76 (s, 3H), 1.52 (s, 6H), 1.49-1.41 (m, 1H), 1.36 (d, J=12.3 Hz, 3H), 1.17 (d, J=27.1 Hz, 2H), 0.96 (d, J=5.8 Hz, 9H).
Example A134
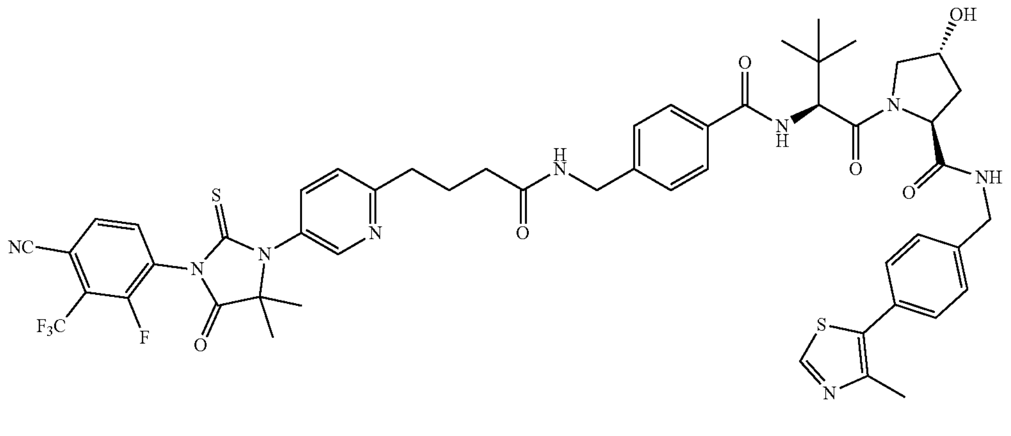 [SMILES: Cc1ncsc1-c1ccc(CNC(=O)[C@@H]2C[C@@H](O)CN2C(=O)[C@@H](NC(=O)c2ccc(CNC(=O)CCCc3ccc(N4C(=S)N(c5ccc(C#N)c(C(F)(F)F)c5F)C(=O)C4(C)C)cn3)cc2)C(C)(C)C)cc1]
LCMS ([M+H]+): 1040.3
$^1$HNMR (400 MHz, DMSO-d6) δ8.97 (s, 1H), 8.58 (t, J=6.0 Hz, 1H), 8.54 (d, J=2.4 Hz, 1H), 8.44 (t, J=5.9 Hz, 1H), 8.33-8.23 (m, 2H), 7.91 (d, J=9.1 Hz, 1H), 7.87-7.77 (m, 3H), 7.48 (d, J=8.3 Hz, 1H), 7.44-7.36 (m, 4H), 7.33 (d, J=8.2 Hz, 2H), 5.15 (d, J=3.5 Hz, 1H), 4.76 (d, J=9.1 Hz, 1H), 4.48-4.17 (m, 6H), 3.73 (s, 2H), 2.85 (dd, J=19.4, 11.8 Hz, 2H), 2.44 (d, J=4.5 Hz, 3H), 2.26 (t, J=7.3 Hz, 2H), 2.11-1.91 (m, 4H), 1.53 (s, 6H), 1.01 (d, J=11.4 Hz, 9H).

Example A135
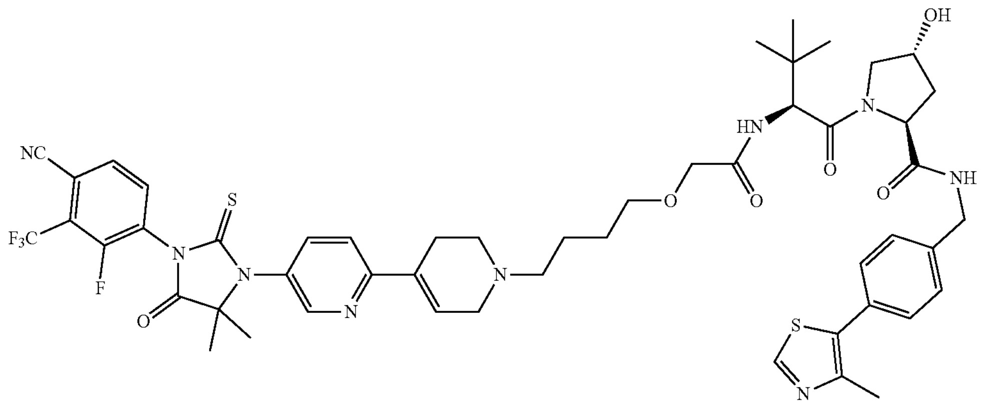 [SMILES: Cc1ncsc1-c1ccc(CNC(=O)[C@@H]2C[C@@H](O)CN2C(=O)[C@@H](NC(=O)COCCCCN2CC=C(c3ccc(N4C(=S)N(c5ccc(C#N)c(C(F)(F)F)c5F)C(=O)C4(C)C)cn3)CC2)C(C)(C)C)cc1]
LCMS ([M+H]+): 1032.3
$^1$HNMR (400 MHz, DMSO-d6) δ8.99-8.97 (m, 1H), 8.65-8.58 (m, 2H), 8.33-8.22 (m, 2H), 7.89 (s, 1H), 7.77 (s, 1H), 7.45-7.34 (m, 6H), 6.80 (s, 1H), 5.20 (d, J=3.2 Hz, 1H), 4.56 (d, J=9.5 Hz, 1H), 4.51-4.32 (m, 4H), 4.30-4.19 (m, 2H), 3.99-3.90 (m, 2H), 3.69-3.58 (m, 2H), 3.55-3.47 (m, 3H), 2.90-2.67 (m, 5H), 2.45-2.41 (m, 4H), 2.10-2.05 (m, 1H), 1.90 (td, J=8.6, 4.2 Hz, 1H), 1.62 (s, 2H), 1.54 (s, 6H), 0.95-0.93 (m, 9H).
Example A136
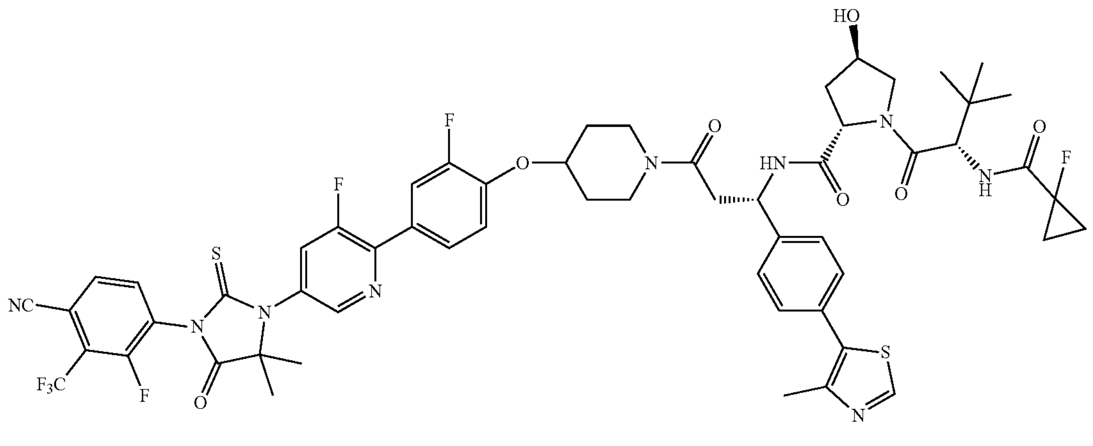 [SMILES: Cc1ncsc1-c1ccc([C@H](CC(=O)N2CCC(Oc3ccc(-c4ncc(N5C(=S)N(c6ccc(C#N)c(C(F)(F)F)c6F)C(=O)C5(C)C)cc4F)cc3F)CC2)NC(=O)[C@@H]2C[C@@H](O)CN2C(=O)[C@@H](NC(=O)C2(F)CC2)C(C)(C)C)cc1]
LCMS ([M+H]+): 1176.3
$^1$HNMR (400 MHz, DMSO-d6) δ8.98 (d, J=1.8 Hz, 1H), 8.63 (brs, 1H), 8.51 (m, 1H), 8.32-8.24 (m, 2H), 8.16 (dd, J=11.9, 1.8 Hz, 1H), 7.84 (m, 2H), 7.48-7.37 (m, 5H), 7.27 (dd, J=9.2, 2.5 Hz, 1H), 5.26-5.17 (m, 1H), 5.14 (m, 1H), 4.72 (m, 1H), 4.58 (m, 1H), 4.46 (m, 1H), 4.29 (m, 1H), 3.83 (m, 1H), 3.74-3.41 (m, 3H), 3.22 (m, 2H), 2.96-2.83 (m, 2H), 2.45 (d, J=5.5 Hz, 3H), 2.04 (m, 1H), 2.00-1.88 (m, 2H), 1.83-1.73 (m, 1H), 1.61 (s, 6H), 1.53-1.43 (m, 1H), 1.40-1.31 (m, 2H), 1.21 (m, 2H), 0.96 (d, J=6.5 Hz, 9H).

Example A137
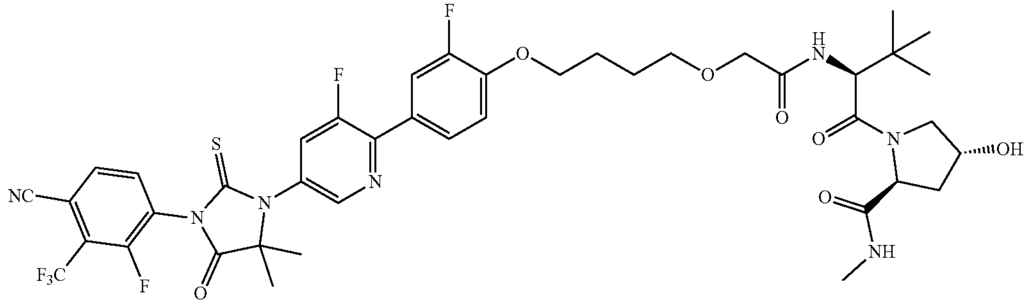 [SMILES: CNC(=O)[C@@H]1C[C@@H](O)CN1C(=O)[C@@H](NC(=O)COCCCCOc1ccc(-c2ncc(N3C(=S)N(c4ccc(C#N)c(C(F)(F)F)c4F)C(=O)C3(C)C)cc2F)cc1F)C(C)(C)C]
LCMS ([M+H]$^+$): 906.4
$^1$HNMR (400 MHz, DMSO-d6) δ8.63 (brs, 1H), 8.31-8.25 (m, 2H), 8.16 (dd, J=11.9, 1.8 Hz, 1H), 7.90-7.81 (m, 3H), 7.41-7.28 (m, 2H), 5.12 (d, J=3.5 Hz, 1H), 4.54 (d, J=9.6 Hz, 1H), 4.32 (m, 2H), 4.19 (m, 2H), 3.92 (m, 2H), 3.63 (m, 1H), 3.60-3.52 (m, 3H), 2.55 (d, J=8.0 Hz, 3H), 1.97 (m, 1H), 1.83 (m, 3H), 1.79-1.70 (m, 2H), 1.61 (s, 6H), 0.91 (d, J=15.4 Hz, 9H).
Example A138
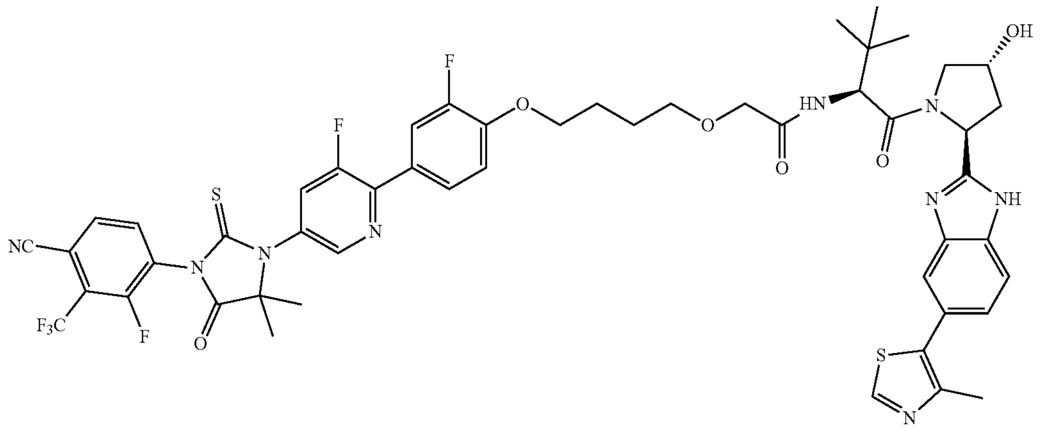 [SMILES: Cc1ncsc1-c1ccc2[nH]c([C@@H]3C[C@@H](O)CN3C(=O)[C@@H](NC(=O)COCCCCOc3ccc(-c4ncc(N5C(=S)N(c6ccc(C#N)c(C(F)(F)F)c6F)C(=O)C5(C)C)cc4F)cc3F)C(C)(C)C)nc2c1]
LCMS ([M+H]$^+$): 1062.2
$^1$HNMR (400 MHz, DMSO-d6) δ12.45 (s, 1H), 8.94 (d, J=7.6 Hz, 1H), 8.62 (s, 1H), 8.34-8.23 (m, 2H), 8.15 (dd, J=11.9, 1.8 Hz, 1H), 7.84 (d, J=10.8 Hz, 2H), 7.55 (s, 2H), 7.39-7.29 (m, 2H), 7.23 (brs, 1H), 5.28 (d, J=3.7 Hz, 1H), 5.21 (t, J=7.8 Hz, 1H), 4.60 (d, J=9.6 Hz, 1H), 4.53 (brs, 1H), 4.17 (m, 2H), 4.0 4-3.86 (m, 3H), 3.76-3.68 (m, 1H), 3.55 (m, 2H), 2.45 (s, 3H), 2.24 (m, 2H), 1.84 (m, 2H), 1.78-1.67 (m, 2H), 1.60 (s, 6H), 0.89 (d, J=27.7 Hz, 9H).

Example A139
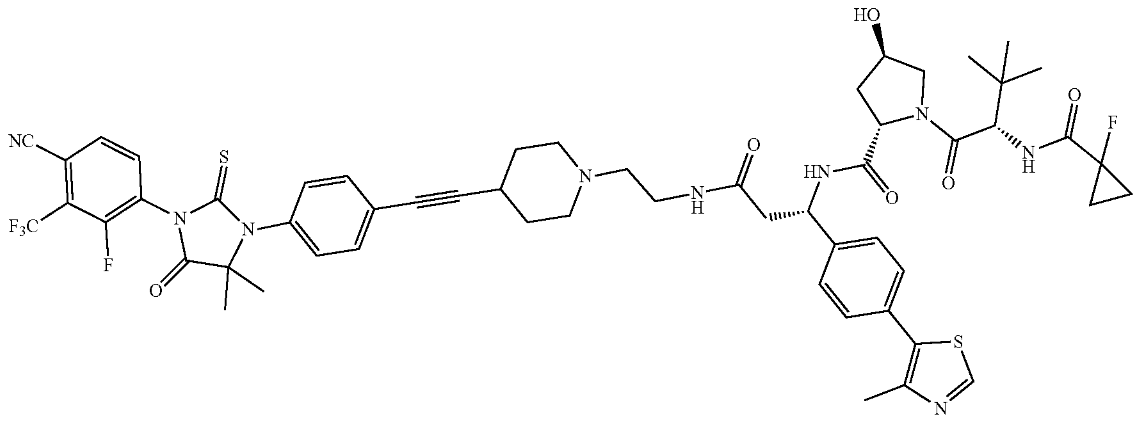 [SMILES: Cc1ncsc1-c1ccc([C@H](CC(=O)NCCN2CCC(C#Cc3ccc(N4C(=S)N(c5ccc(C#N)c(C(F)(F)F)c5F)C(=O)C4(C)C)cc3)CC2)NC(=O)[C@@H]2C[C@@H](O)CN2C(=O)[C@@H](NC(=O)C2(F)CC2)C(C)(C)C)cc1]
LCMS ([M+H]+): 1114.3
$^1$HNMR (400 MHz, DMSO-d6) δ9.12 (s, 1H), 8.98 (s, 1H), 8.57 (d, J=7.9 Hz, 1H), 8.26 (s, 2H), 8.21 (s, 1H), 7.63 (s, 1H), 7.58 (d, J=8.0 Hz, 1H), 7.44 (d, J=6.8 Hz, 3H), 7.37 (d, J=7.7 Hz, 2H), 7.20 (s, 1H), 5.23 (s, 2H), 5.16 (d, J=3.4 Hz, 1H), 4.57 (d, J=9.2 Hz, 1H), 4.44 (t, J=8.2 Hz, 1H), 4.28 (s, 1H), 3.58 (s, 2H), 3.23-2.93 (m, 6H), 2.66 (s, 2H), 2.45 (d, J=6.9 Hz, 3H), 2.19-1.93 (m, 6H), 1.72 (s, 3H), 1.52 (s, 6H), 1.37 (d, J=10.2 Hz, 2H), 0.97 (d, J=5.3 Hz, 9H).
Example A140
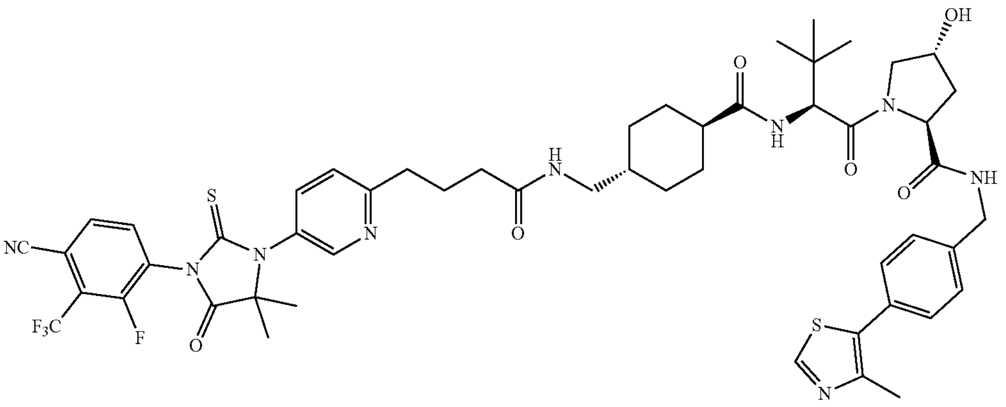 [SMILES: Cc1ncsc1-c1ccc(CNC(=O)[C@@H]2C[C@@H](O)CN2C(=O)[C@@H](NC(=O)[C@H]2CC[C@H](CNC(=O)CCCc3ccc(N4C(=S)N(c5ccc(C#N)c(C(F)(F)F)c5F)C(=O)C4(C)C)cn3)CC2)C(C)(C)C)cc1]
LCMS ([M+H]+): 1046.3
$^1$HNMR (400 MHz, DMSO-d6) δ8.98 (s, 1H), 8.59-8.50 (m, 2H), 8.33-8.22 (m, 2H), 7.84-7.75 (m, 2H), 7.70 (d, J=9.3 Hz, 1H), 7.47 (d, J=8.3 Hz, 1H), 7.40 (q, J=8.4 Hz, 4H), 5.12 (d, J=3.4 Hz, 1H), 4.50 (d, J=9.3 Hz, 1H), 4.43 (dd, J=15.3, 7.0 Hz, 2H), 4.34 (s, 1H), 4.21 (dd, J=15.9, 5.4 Hz, 1H), 3.64 (dt, J=18.7, 7.4 Hz, 2H), 2.90 (t, J=6.1 Hz, 2H), 2.84-2.75 (m, 2H), 2.44 (s, 3H), 2.31 (t, J=11.9 Hz, 1H), 2.16 (t, J=7.3 Hz, 2H), 2.06-1.85 (m, 4H), 1.81-1.61 (m, 5H), 1.53 (s, 6H), 1.31 (dd, J=23.9, 11.4 Hz, 4H), 0.91 (d, J=9.5 Hz, 9H).

Example A141

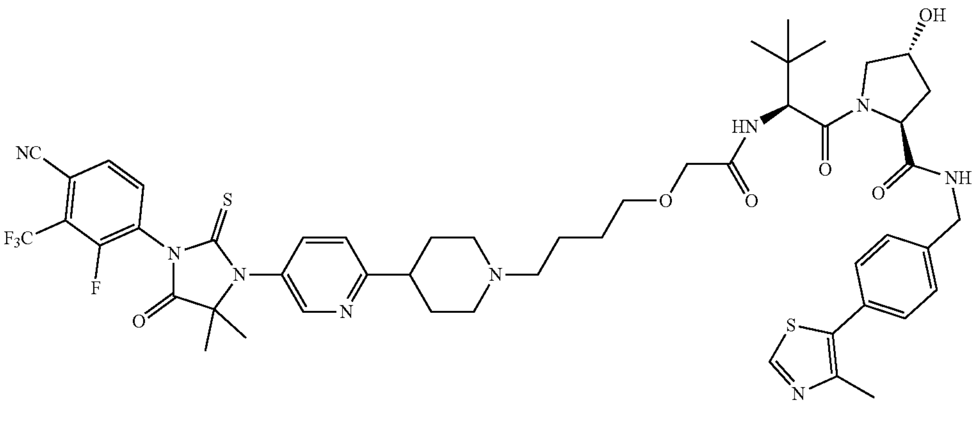 [SMILES: Cc1ncsc1-c1ccc(CNC(=O)[C@@H]2C[C@@H](O)CN2C(=O)[C@@H](NC(=O)COCCCCN2CCC(c3ccc(N4C(=S)N(c5ccc(C#N)c(C(F)(F)F)c5F)C(=O)C4(C)C)cn3)CC2)C(C)(C)C)cc1]

LCMS ($[M+H]^+$): 1034.3

$^1$HNMR (400 MHz, DMSO-d6) δ8.99-8.97 (m, 1H), 8.60 (t, J=5.9 Hz, 1H), 8.56 (s, 1H), 8.32-8.24 (m, 2H), 7.85 (d, J=8.0 Hz, 1H), 7.50 (d, J=8.2 Hz, 1H), 7.42-7.39 (m, 5H), 5.17 (d, J=3.3 Hz, 1H), 4.56 (d, J=9.5 Hz, 1H), 4.44 (t, J=8.4 Hz, 1H), 4.35 (m, 2H), 4.25 (dd, J=15.5, 5.7 Hz, 1H), 3.94 (s, 2H), 3.67-3.59 (m, 2H), 3.51 (m, 2H), 2.49-2.43 (m, 3H), 2.06-1.87 (m, 9H), 1.61 (s, 5H), 1.52 (s, 6H), 1.23 (s, 3H), 0.95-0.93 (m, 9H).

Example A142

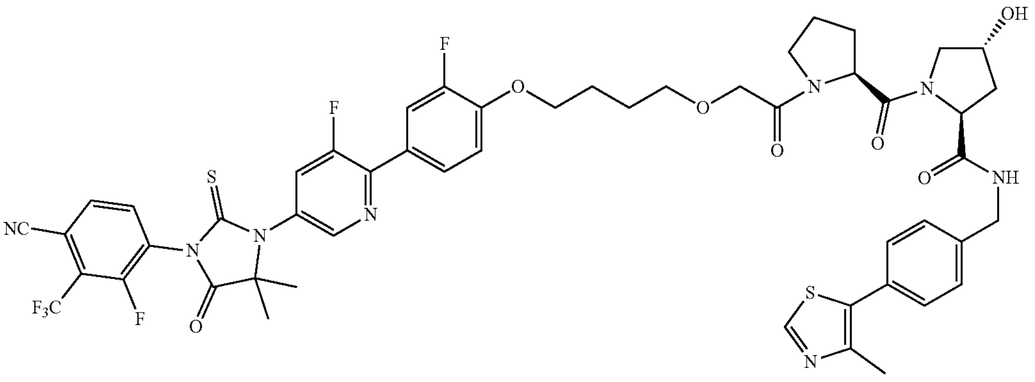 [SMILES: Cc1ncsc1-c1ccc(CNC(=O)[C@@H]2C[C@@H](O)CN2C(=O)[C@@H]2CCCN2C(=O)COCCCCOc2ccc(-c3ncc(N4C(=S)N(c5ccc(C#N)c(C(F)(F)F)c5F)C(=O)C4(C)C)cc3F)cc2F)cc1]

LCMS ($[M+H]^+$): 1063.3

$^1$HNMR (400 MHz, DMSO-d6) δ8.98-8.95 (m, 1H), 8.62 (s, 1H), 8.45-8.39 (m, 1H), 8.31-8.28 (m, 2H), 8.16 (d, J=11.9H-z, 1H), 7.867.81 (m, 2H), 7.42-7.33 (m, 5H), 5.19-5.05 (m, 1H), 4.78-4.41 (m, 1H), 4.48-4.23 (m, 4H), 4.19-3.64 (m, 4H), 3.67-3.41 (m, 6H), 2.44-2.41 (m, 3H), 2.04-2.01 (m, 2H), 1.93-1.81 (m, 5H), 1.73-1.61 (m, 9H).

In the following Examples A143-A362, A155, A156, A179, A180, A181, A182, A187-A195, A197, A199, and A200 were synthesized with the corresponding reagents using a similar operation to Example A1; others were synthesized with the corresponding reagents using a similar operation to Example A46.

Example A143
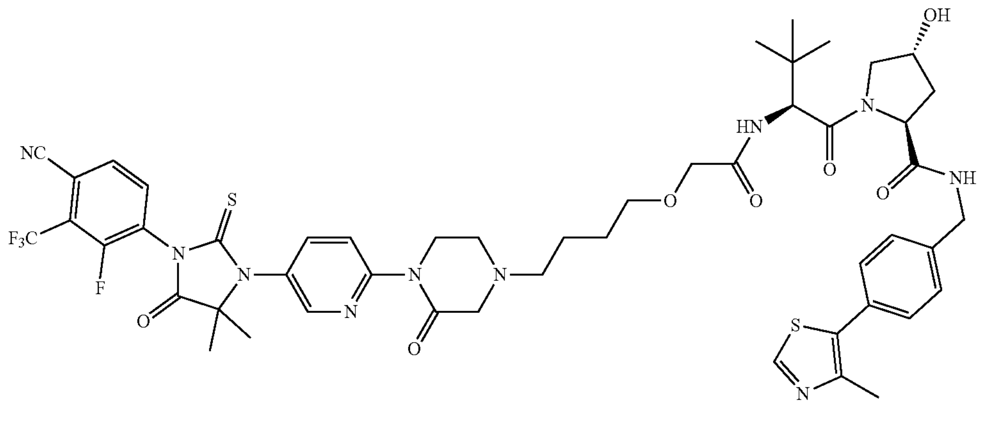 [SMILES: Cc1ncsc1-c1ccc(CNC(=O)[C@@H]2C[C@@H](O)CN2C(=O)[C@@H](NC(=O)COCCCCN2CCN(c3ccc(N4C(=S)N(c5ccc(C#N)c(C(F)(F)F)c5F)C(=O)C4(C)C)cn3)C(=O)C2)C(C)(C)C)cc1]
LCMS ([M+H]$^+$): 1149.4
$^1$HNMR (400 MHz, DMSO-d6) δ8.98 (d, J=7.4 Hz, 1H), 8.60 (t, J=5.9 Hz, 1H), 8.50 (d, J=2.5 Hz, 1H), 8.32-8.24 (m, 2H), 8.15 (d, J=8.9 Hz, 1H), 7.93 (dd, J=8.9, 2.6 Hz, 1H), 7.46-7.32 (m, 5H), 5.18 (d, J=2.6 Hz, 1H), 4.57 (d, J=9.6 Hz, 1H), 4.50-4.32 (m, 3H), 4.25 (dd, J=15.8, 5.6 Hz, 1H), 3.98-3.87 (m, 4H), 3.65 (dt, J=22.0, 7.2 Hz, 2H), 3.52 (t, J=5.5 Hz, 2H), 3.28 (d, J=8.2 Hz, 2H), 2.86-2.75 (m, 2H), 2.47-2.39 (m, 5H), 2.10-2.01 (m, 1H), 1.98-1.85 (m, 1H), 1.56 (t, J=10.2 Hz, 10H), 0.94 (d, J=7.6 Hz, 9H).
Example A144
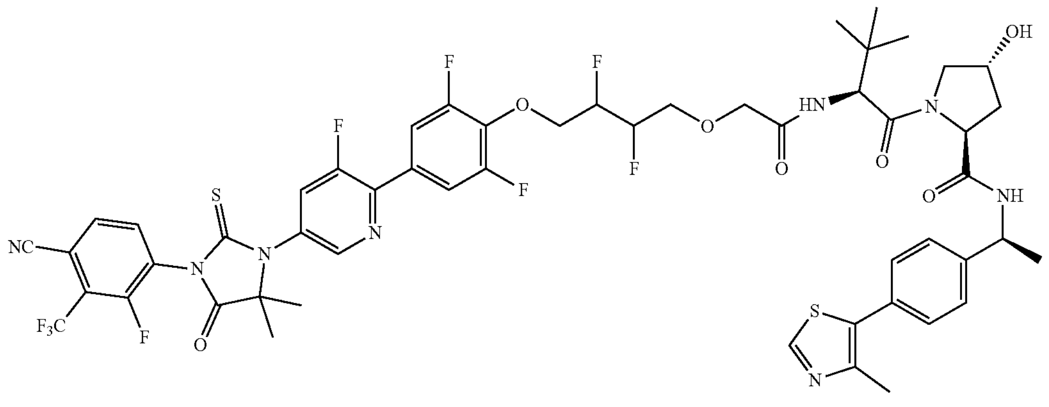 [SMILES: Cc1ncsc1-c1ccc([C@H](C)NC(=O)[C@@H]2C[C@@H](O)CN2C(=O)[C@@H](NC(=O)COCC(F)C(F)COc2c(F)cc(-c3ncc(N4C(=S)N(c5ccc(C#N)c(C(F)(F)F)c5F)C(=O)C4(C)C)cc3F)cc2F)C(C)(C)C)cc1]
LCMS ([M+H]$^+$): 1147.3
$^1$HNMR (400 MHz, DMSO-d6) δ8.99 (s, 1H), 8.69 (s, 1H), 8.45 (d, J=7.6 Hz, 1H), 8.29 (s, 3H), 7.80 (d, J=9.2 Hz, 2H), 7.44 (d, J=8.3 Hz, 3H), 7.37 (d, J=8.3 Hz, 2H), 5.15 (d, J=3.5 Hz, 3H), 4.91 (p, J=6.9 Hz, 1H), 4.71-4.42 (m, 4H), 4.26 (d, J=19.1 Hz, 1H), 4.07 (s, 4H), 3.65-3.42 (m, 2H), 2.46 (s, 3H), 2.09-1.99 (m, 1H), 1.82-1.72 (m, 1H), 1.62 (s, 6H), 1.37 (d, J=7.0 Hz, 3H), 0.94 (s, 9H).

Example A145
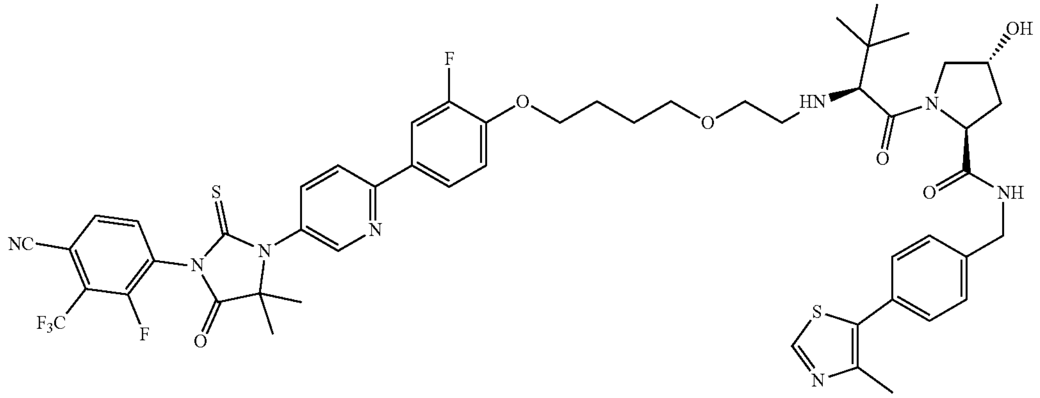 [SMILES: Cc1ncsc1-c1ccc(CNC(=O)[C@@H]2C[C@@H](O)CN2C(=O)[C@@H](NCCOCCCCOc2ccc(-c3ccc(N4C(=S)N(c5ccc(C#N)c(C(F)(F)F)c5F)C(=O)C4(C)C)cn3)cc2F)C(C)(C)C)cc1]
LCMS ([M+H]+): 1047.4
$^1$HNMR (400 MHz, DMSO-d6) δ8.97 (m, 1H), 8.67 (d, J=2.4 Hz, 1H), 8.57 (s, 1H), 8.33-8.26 (m, 2H), 8.17 (d, J=8.5 Hz, 1H), 8.05-7.94 (m, 3H), 7.46-7.34 (m, 4H), 7.30 (t, J=8.7 Hz, 1H), 5.08-4.96 (m, 1H), 4.55-4.51 (m, 1H), 4.43-4.32 (m, 2H), 4.25 (dd, J=15.8, 5.6 Hz, 1H), 4.19-4.11 (m, 2H), 3.64 (d, J=10.4 Hz, 1H), 3.58-3.52 (m, 1H), 3.44 (dd, J=14.8, 6.2 Hz, 4H), 3.19-3.09 (m, 1H), 2.64 (m, 1H), 2.43 (d, J=6.4 Hz, 4H), 2.10-1.74 (m, 5H), 1.67 (dt, J=13.9, 6.8 Hz, 2H), 1.58 (s, 6H), 0.90 (d, J=5.8 Hz, 9H).
Example A146
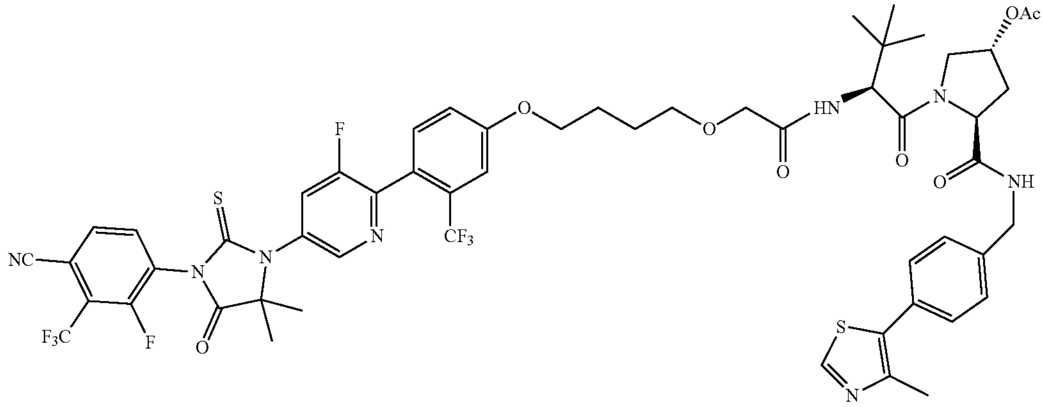 [SMILES: CC(=O)O[C@@H]1C[C@@H](C(=O)NCc2ccc(-c3scnc3C)cc2)N(C(=O)[C@@H](NC(=O)COCCCCOc2ccc(-c3ncc(N4C(=S)N(c5ccc(C#N)c(C(F)(F)F)c5F)C(=O)C4(C)C)cc3F)c(C(F)(F)F)c2)C(C)(C)C)C1]
LCMS ([M+H]+): 1171.3
$^1$HNMR (400 MHz, DMSO-d6) δ8.97 (s, 1H), 8.64 (s, 2H), 8.29 (s, 2H), 8.21 (dd, J=9.7, 1.8 Hz, 1H), 7.56 (d, J=9.1 Hz, 1H), 7.39 (d, J=8.1 Hz, 7H), 5.30 (d, J=18.9 Hz, 1H), 4.58-4.34 (m, 3H), 4.34-4.24 (m, 1H), 4.18 (s, 2H), 3.97 (s, 3H), 3.89-3.79 (m, 1H), 3.57 (s, 2H), 2.44 (s, 3H), 2.27 (dd, J=13.7, 7.6 Hz, 1H), 2.12 (ddd, J=13.8, 9.3, 4.9 Hz, 1H), 2.01 (s, 3H), 1.85 (dd, J=14.0, 6.4 Hz, 2H), 1.79-1.70 (m, 2H), 1.61 (s, 6H), 0.95 (d, J=8.5 Hz, 9H).

Example A147
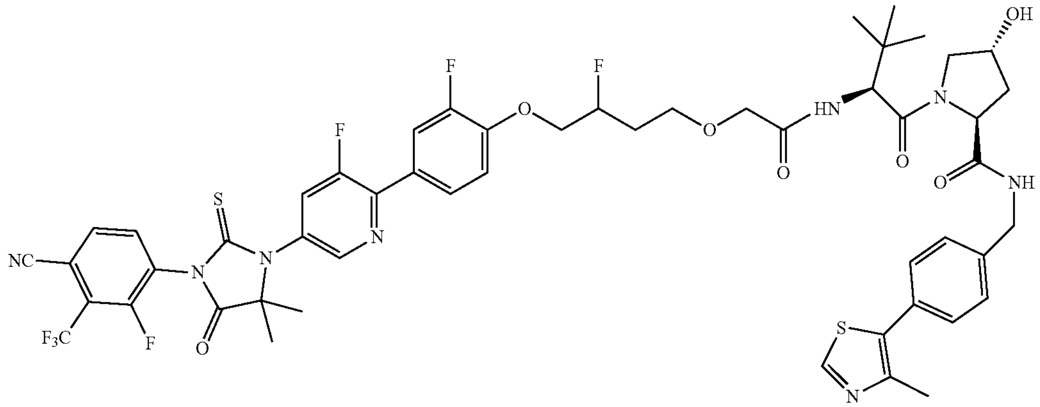 [SMILES: Cc1ncsc1-c1ccc(CNC(=O)[C@@H]2C[C@@H](O)CN2C(=O)[C@@H](NC(=O)COCCC(F)COc2ccc(-c3ncc(N4C(=S)N(c5ccc(C#N)c(C(F)(F)F)c5F)C(=O)C4(C)C)cc3F)cc2F)C(C)(C)C)cc1]
LCMS ([M+H]+): 1097.3
$^1$HNMR (400 MHz, DMSO-d6) δ8.96 (s, 1H), 8.64 (s, 2H), 8.29 (s, 2H), 8.18 (dd, J=11.8, 1.5 Hz, 1H), 7.84 (s, 2H), 7.51 (d, J=9.5 Hz, 1H), 7.40 (s, 5H), 5.20-4.97 (m, 2H), 4.58 (d, J=9.5 Hz, 1H), 4.41 (d, J=36.4 Hz, 7H), 4.01 (s, 2H), 3.67 (d, J=4.9 Hz, 4H), 2.43 (s, 3H), 2.11-2.00 (m, 3H), 1.91 (ddd, J=12.9, 8.8, 4.4 Hz, 1H), 1.61 (s, 6H), 0.94 (d, J=7.1 Hz, 9H).
Example A148
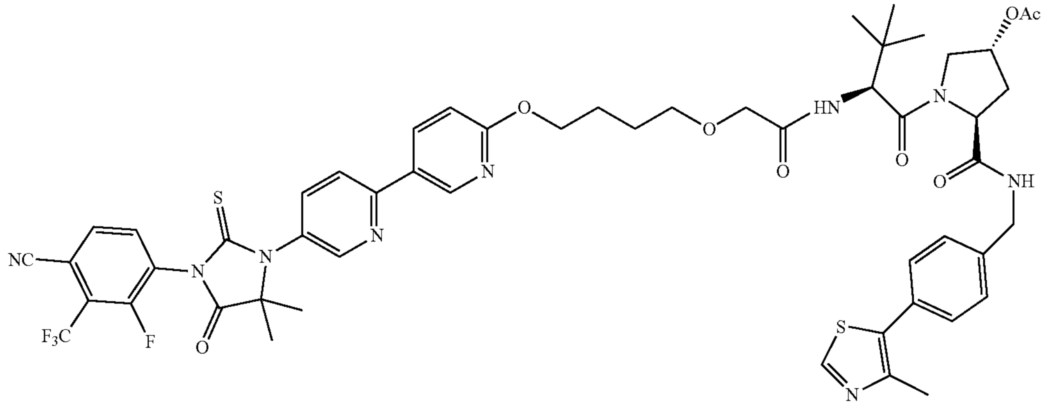 [SMILES: CC(=O)O[C@@H]1C[C@@H](C(=O)NCc2ccc(-c3scnc3C)cc2)N(C(=O)[C@@H](NC(=O)COCCCCOc2ccc(-c3ccc(N4C(=S)N(c5ccc(C#N)c(C(F)(F)F)c5F)C(=O)C4(C)C)cn3)cn2)C(C)(C)C)C1]
LCMS ([M+H]+): 1086.4
$^1$HNMR (400 MHz, DMSO-d6) δ8.95 (d, J=12.0 Hz, 2H), 8.71 (s, 1H), 8.64 (s, 1H), 8.43 (d, J=8.5 Hz, 1H), 8.30 (d, J=6.2 Hz, 2H), 8.19 (d, J=8.5 Hz, 1H), 8.01 (d, J=7.8 Hz, 1H), 7.47-7.36 (m, 5H), 6.94 (d, J=8.6 Hz, 1H), 5.28 (s, 1H), 4.40 (ddd, J=32.5, 21.3, 6.8 Hz, 6H), 3.94 (d, J=12.2 Hz, 3H), 3.85 (s, 1H), 3.55 (s, 2H), 2.43 (s, 3H), 2.32-2.19 (m, 1H), 2.13 (s, 1H), 1.99 (d, J=15.0 Hz, 3H), 1.83 (d, J=7.0 Hz, 2H), 1.72 (s, 2H), 1.59 (s, 6H), 0.95 (s, 9H).

Example A149
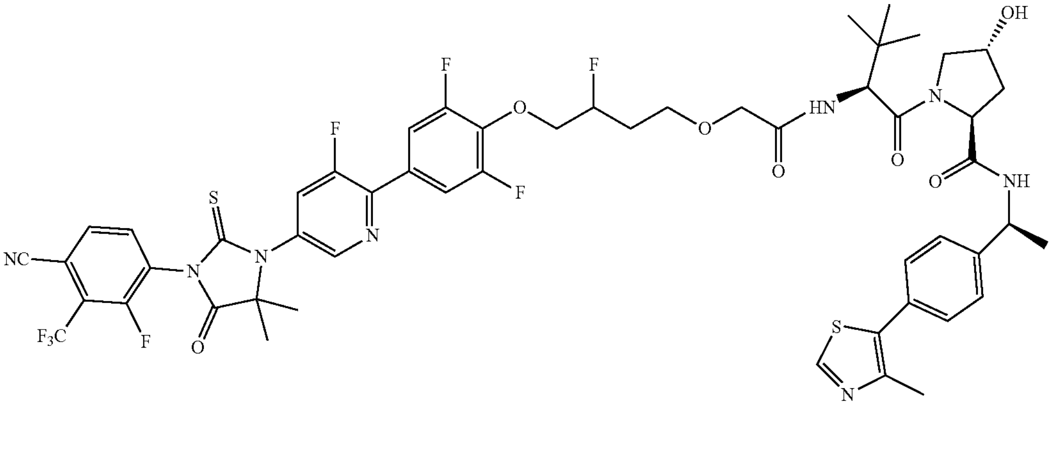 [SMILES: Cc1ncsc1-c1ccc([C@H](C)NC(=O)[C@@H]2C[C@@H](O)CN2C(=O)[C@@H](NC(=O)COCCC(F)COc2c(F)cc(-c3ncc(N4C(=S)N(c5ccc(C#N)c(C(F)(F)F)c5F)C(=O)C4(C)C)cc3F)cc2F)C(C)(C)C)cc1]
LCMS ([M+H]$^+$): 1128.3
$^1$HNMR (400 MHz, DMSO-d6) δ8.97 (s, 1H), 8.67 (s, 1H), 8.45 (d, J=7.7 Hz, 1H), 8.32-8.20 (m, 3H), 7.83-7.73 (m, 2H), 7.39 (dt, J=27.3, 8.6 Hz, 5H), 5.18-4.85 (m, 3H), 4.59-4.34 (m, 4H), 4.26 (d, J=17.8 Hz, 1H), 4.04-3.90 (m, 2H), 3.57 (ddd, J=60.5, 30.4, 8.4 Hz, 4H), 2.45 (s, 3H), 2.08-1.96 (m, 3H), 1.81-1.72 (m, 1H), 1.61 (s, 6H), 1.42 (dd, J=41.5, 7.0 Hz, 3H), 0.93 (s, 9H).
Example A150
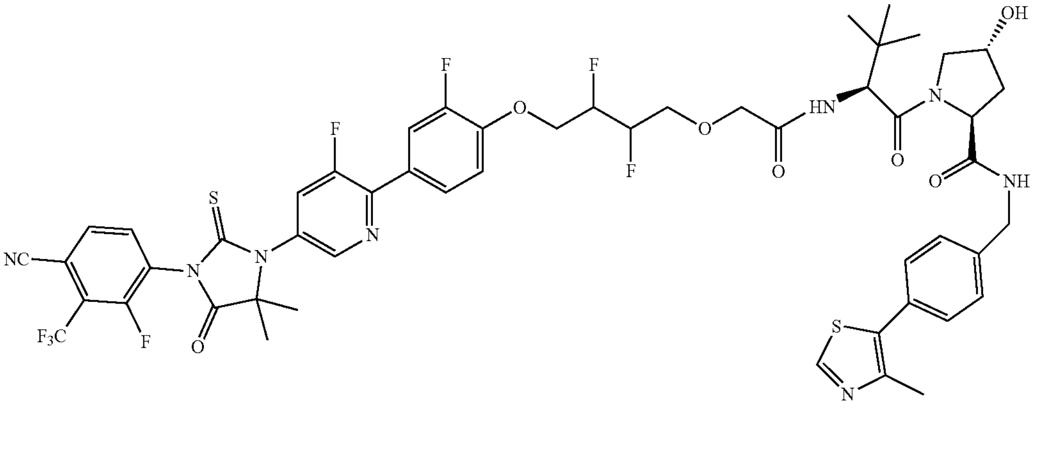 [SMILES: Cc1ncsc1-c1ccc(CNC(=O)[C@@H]2C[C@@H](O)CN2C(=O)[C@@H](NC(=O)COCC(F)C(F)COc2ccc(-c3ncc(N4C(=S)N(c5ccc(C#N)c(C(F)(F)F)c5F)C(=O)C4(C)C)cc3F)cc2F)C(C)(C)C)cc1]
LCMS ([M+H]$^+$): 1115.3
$^1$HNMR (400 MHz, DMSO-d6) δ8.97 (s, 1H), 8.64 (m, 2H), 8.29 (s, 2H), 8.19 (dd, J=11.8, 1.8 Hz, 1H), 7.87 (t, J=8.6 Hz, 2H), 7.57 (d, J=8.2 Hz, 1H), 7.41 (m, 6H), 5.17 (m, 2H), 4.59 (m, 1H), 4.49-4.42 (m, 2H), 4.38 (m, 2H), 4.30-4.24 (m, 1H), 4.10 (m, 2H), 4.03-3.86 (m, 2H), 3.66 (m, 2H), 2.44 (s, 3H), 2.05 (m, 1H), 1.96-1.85 (m, 1H), 1.62 (s, 6H), 0.94 (d, J=7.5 Hz, 9H).

Example A151
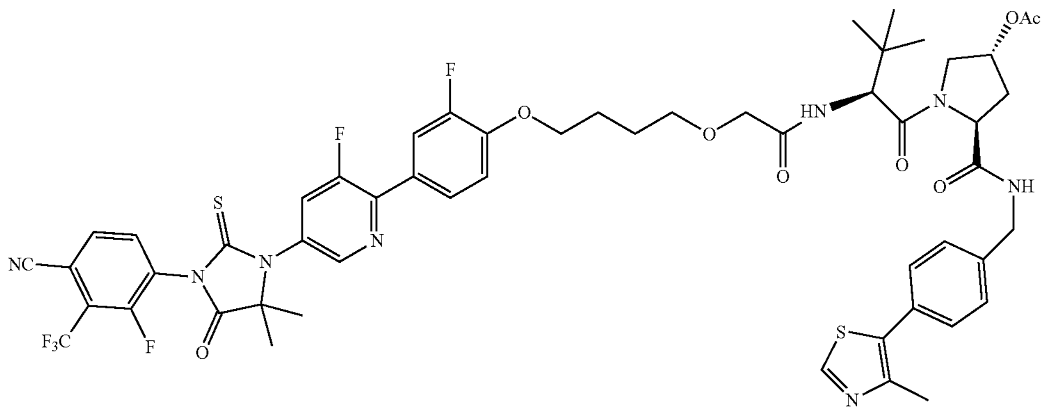 [SMILES: CC(=O)O[C@@H]1C[C@@H](C(=O)NCc2ccc(-c3scnc3C)cc2)N(C(=O)[C@@H](NC(=O)COCCCCOc2ccc(-c3ncc(N4C(=S)N(c5ccc(C#N)c(C(F)(F)F)c5F)C(=O)C4(C)C)cc3F)cc2F)C(C)(C)C)C1]
LCMS ([M+H]$^+$): 1121.3
$^1$HNMR (400 MHz, DMSO-d6) δ8.98 (d, J=7.2 Hz, 1H), 8.63 (s, 2H), 8.30 (d, J=11.6 Hz, 2H), 8.17 (d, J=11.9 Hz, 1H), 7.84 (d, J=10.4 Hz, 2H), 7.50-7.30 (m, 6H), 5.28 (m, 1H), 4.45 (m, 3H), 4.28 (m, 1H), 4.19 (m, 2H), 4.01-3.90 (m, 3H), 3.84 (m, 1H), 3.56 (m, 2H), 2.44 (d, J=5.5 Hz, 3H), 2.27 (m, 1H), 2.12 (m, 1H), 1.99 (d, J=14.4 Hz, 3H), 1.93-1.82 (m, 2H), 1.75 (m, 2H), 1.61 (s, 6H), 0.95 (d, J=8.7 Hz, 9H).
Example A152
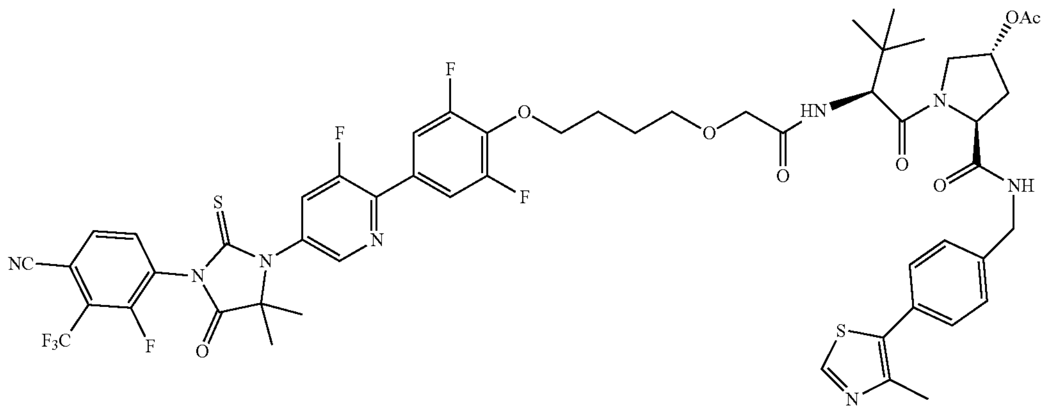 [SMILES: CC(=O)O[C@@H]1C[C@@H](C(=O)NCc2ccc(-c3scnc3C)cc2)N(C(=O)[C@@H](NC(=O)COCCCCOc2c(F)cc(-c3ncc(N4C(=S)N(c5ccc(C#N)c(C(F)(F)F)c5F)C(=O)C4(C)C)cc3F)cc2F)C(C)(C)C)C1]
LCMS ([M+H]$^+$): 1139.3
$^1$HNMR (400 MHz, DMSO-d6) δ8.96 (d, J=10.2 Hz, 1H), 8.62 (dd, J=17.8, 11.9 Hz, 2H), 8.32-8.19 (m, 3H), 7.74 (t, J=7.5 Hz, 2H), 7.47-7.31 (m, 5H), 5.27 (s, 1H), 4.44 (ddd, J=22.0, 16.5, 7.4 Hz, 3H), 4.27 (dd, J=11.4, 5.7 Hz, 3H), 3.99-3.89 (m, 3H), 3.83 (dd, J=11.7, 4.1 Hz, 1H), 3.54 (t, J=5.5 Hz, 2H), 2.43 (d, J=7.7 Hz, 3H), 2.26 (dd, J=13.7, 7.9 Hz, 1H), 2.12 (ddd, J=13.6, 8.9, 4.8 Hz, 1H), 2.00 (s, 3H), 1.77 (ddd, J=19.6, 14.0, 7.1 Hz, 4H), 1.61 (s, 6H), 0.93 (d, J=9.9 Hz, 9H).

Example A153
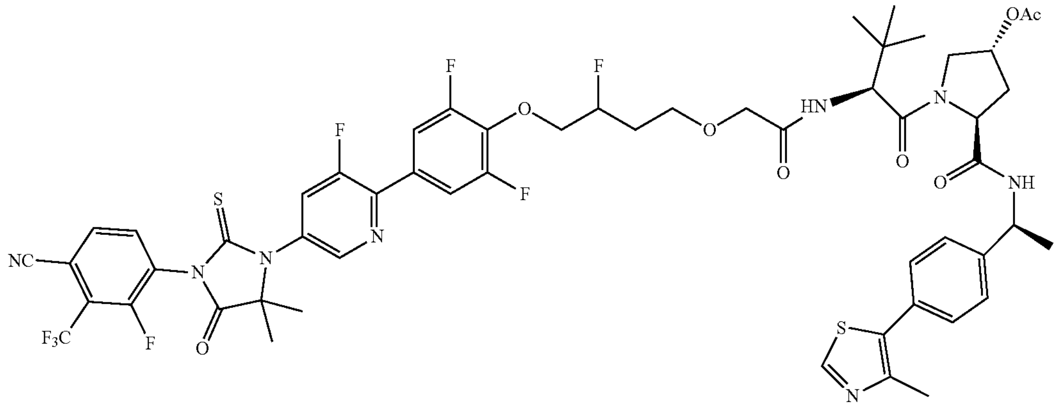 [SMILES: CC(=O)O[C@@H]1C[C@@H](C(=O)N[C@@H](C)c2ccc(-c3scnc3C)cc2)N(C(=O)[C@@H](NC(=O)COCCC(F)COc2c(F)cc(-c3ncc(N4C(=S)N(c5ccc(C#N)c(C(F)(F)F)c5F)C(=O)C4(C)C)cc3F)cc2F)C(C)(C)C)C1]
LCMS ([M+H]+): 1152.3
$^1$HNMR (400 MHz, DMSO-d6) δ8.97 (s, 1H), 8.67 (s, 1H), 8.47 (d, J=7.6 Hz, 1H), 8.33-8.18 (m, 3H), 7.78 (t, J=7.5 Hz, 2H), 7.39 (dt, J=14.2, 7.2 Hz, 5H), 5.17 (d, J=22.5 Hz, 1H), 4.96-4.84 (m, 1H), 4.53-4.39 (m, 2H), 4.27 (t, J=6.0 Hz, 2H), 4.00-3.85 (m, 3H), 3.76 (dd, J=11.7, 3.8 Hz, 1H), 3.54 (t, J=5.1 Hz, 2H), 2.45 (s, 3H), 2.26 (dd, J=13.4, 7.5 Hz, 1H), 2.05-1.92 (m, 4H), 1.77 (ddd, J=19.4, 13.5, 6.9 Hz, 4H), 1.61 (s, 6H), 1.42 (dd, J=38.8, 6.9 Hz, 3H), 0.94 (s, 9H).
Example A154
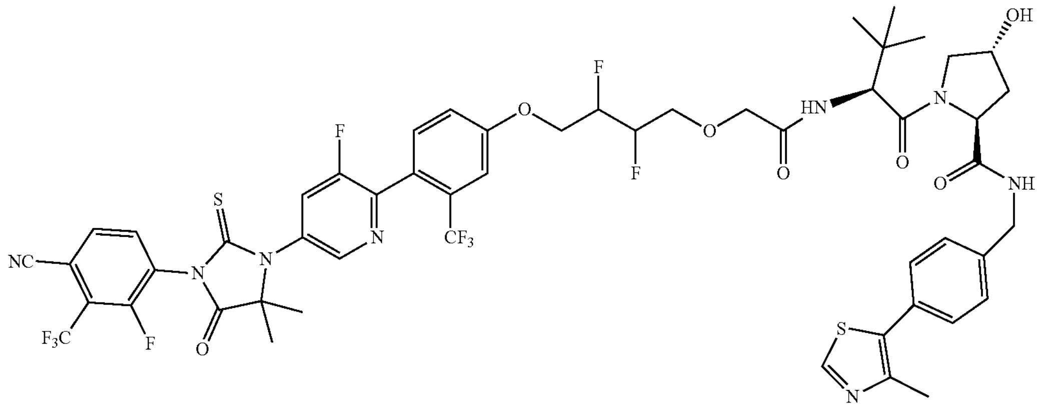 [SMILES: Cc1ncsc1-c1ccc(CNC(=O)[C@@H]2C[C@@H](O)CN2C(=O)[C@@H](NC(=O)COCC(F)C(F)COc2ccc(-c3ncc(N4C(=S)N(c5ccc(C#N)c(C(F)(F)F)c5F)C(=O)C4(C)C)cc3F)c(C(F)(F)F)c2)C(C)(C)C)cc1]
LCMS ([M+H]+): 1165.3
$^1$HNMR (400 MHz, DMSO-d6) δ8.97 (d, J=6.6 Hz, 1H), 8.6 3-8.58 (m, 2H), 8.34-8.25 (m, 2H), 8.20 (dd, J=9.7, 1.8 Hz, 1H), 7.57 (dd, J=18.1, 9.0 Hz, 2H), 7.50-7.36 (m, 6H), 5.33-5.01 (m, 3H), 4.64-4.32 (m, 6H), 4.25 (dd, J=15.7, 5.5 Hz, 1H), 4.15-4.04 (m, 2H), 4.04-3.81 (m, 2H), 3.69-3060 (m 2H), 2.44 (d, J=3.2 Hz, 3H), 2.10-2.03 (m, 1H), 1.90 (ddd, J=12.9, 8.7, 4.4 Hz, 1H), 1.61 (s, 6H), 0.93 (d, J=7.0 Hz, 9H).

Example A155
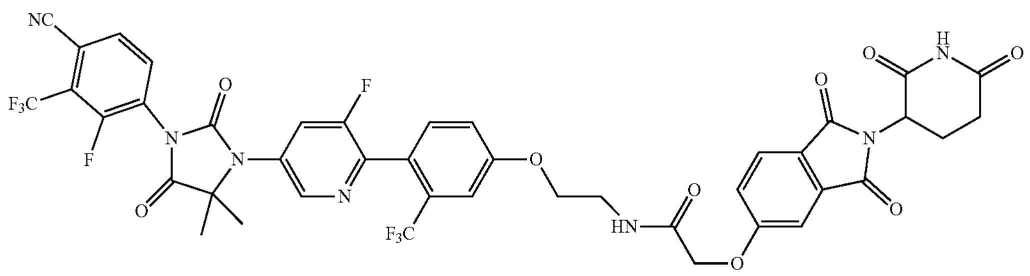 [SMILES: CC1(C)C(=O)N(c2ccc(C#N)c(C(F)(F)F)c2F)C(=O)N1c1cnc(-c2ccc(OCCNC(=O)COc3ccc4c(c3)C(=O)N(C3CCC(=O)NC3=O)C4=O)cc2C(F)(F)F)c(F)c1]
LCMS ($[M+H]^+$): 944.2
$^1$HNMR (400 MHz, DMSO-d6) δ11.10 (s, 1H), 8.63 (d, J=0.9 Hz, 1H), 8.49 (t, J=5.6 Hz, 1H), 8.29 (d, J=3.2 Hz, 2H), 8.20 (dd, J=9.7, 1.9 Hz, 1H), 7.86 (d, J=8.3 Hz, 1H), 7.58 (d, J=9.2 Hz, 1H), 7.47 (d, J=2.2 Hz, 1H), 7.43-7.34 (m, 3H), 5.11 (dd, J=12.9, 5.4 Hz, 1H), 4.78 (s, 2H), 4.24 (t, J=5.5 Hz, 2H), 3.59 (dd, J=11.0, 5.5 Hz, 2H), 2.88 (ddd, J=17.3, 14.0, 5.3 Hz, 1H), 2.70-2.51 (m, 2H), 2.10-1.97 (m, 1H), 1.61 (s, 6H).
Example A156
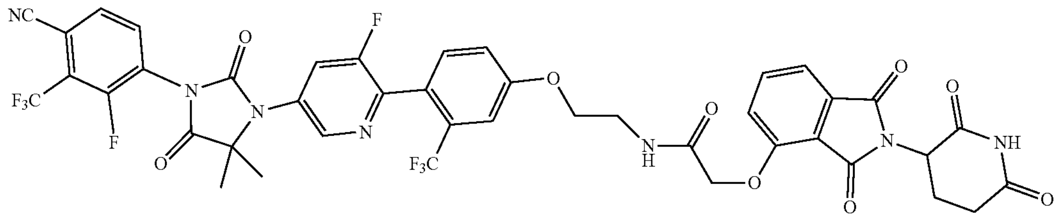 [SMILES: CC1(C)C(=O)N(c2ccc(C#N)c(C(F)(F)F)c2F)C(=O)N1c1cnc(-c2ccc(OCCNC(=O)COc3cccc4c3C(=O)N(C3CCC(=O)NC3=O)C4=O)cc2C(F)(F)F)c(F)c1]
LCMS ($[M+H]^+$): 944.2
$^1$HNMR (400 MHz, DMSO-d6) δ11.10 (s, 1H), 8.63 (d, J=0.9 Hz, 1H), 8.49 (t, J=5.6 Hz, 1H), 8.29 (d, J=3.2 Hz, 2H), 8.20 (dd, J=9.7, 1.9 Hz, 1H), 7.86 (d, J=8.3 Hz, 1H), 7.58 (d, J=9.2 Hz, 1H), 7.47 (d, J=2.2 Hz, 1H), 7.43-7.34 (m, 3H), 5.11 (dd, J=12.9, 5.4 Hz, 1H), 4.78 (s, 2H), 4.24 (t, J=5.5 Hz, 2H), 3.59 (dd, J=11.0, 5.5 Hz, 2H), 2.88 (ddd, J=17.3, 14.0, 5.3 Hz, 1H), 2.70-2.51 (m, 2H), 2.10-1.97 (m, 1H), 1.61 (s, 6H).

Example A157
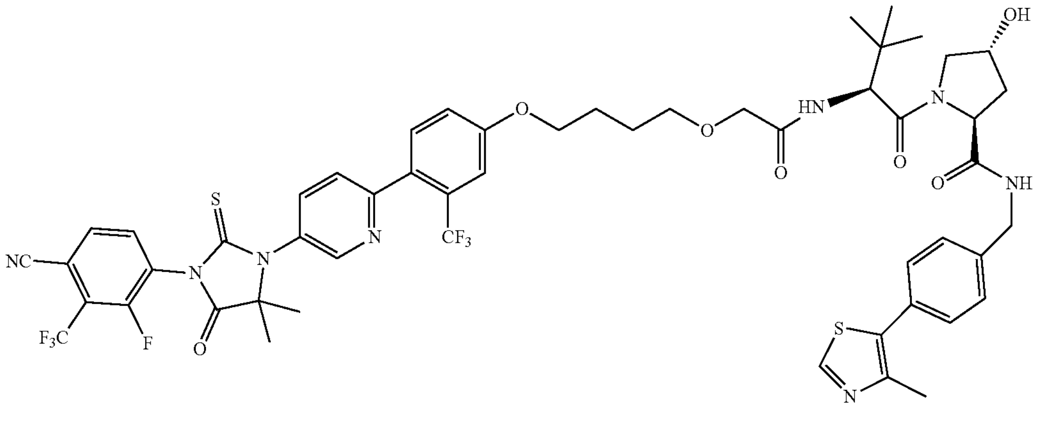 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)c(C(F)(F)F)c2)C(C)(C)C)cc1]
LCMS ([M+H]$^+$): 1111.3
$^1$HNMR (400 MHz, DMSO-d6) δ8.96 (s, 1H), 8.71 (s, 1H), 8.61 (s, 1H), 8.29 (t, J=7.9 Hz, 2H), 8.03 (d, J=7.4 Hz, 1H), 7.69 (d, J=8.2 Hz, 1H), 7.56 (d, J=8.6 Hz, 1H), 7.37 (d, J=25.5 Hz, 7H), 5.17 (s, 1H), 4.58 (d, J=9.4 Hz, 1H), 4.51-4.32 (m, 3H), 4.29 (d, J=4.8 Hz, 1H), 4.17 (s, 2H), 3.97 (s, 2H), 3.75-3.50 (m, 4H), 2.43 (s, 3H), 2.08 (s, 2H), 1.98-1.68 (m, 5H), 1.59 (s, 6H), 0.95 (s, 9H).
Example A158
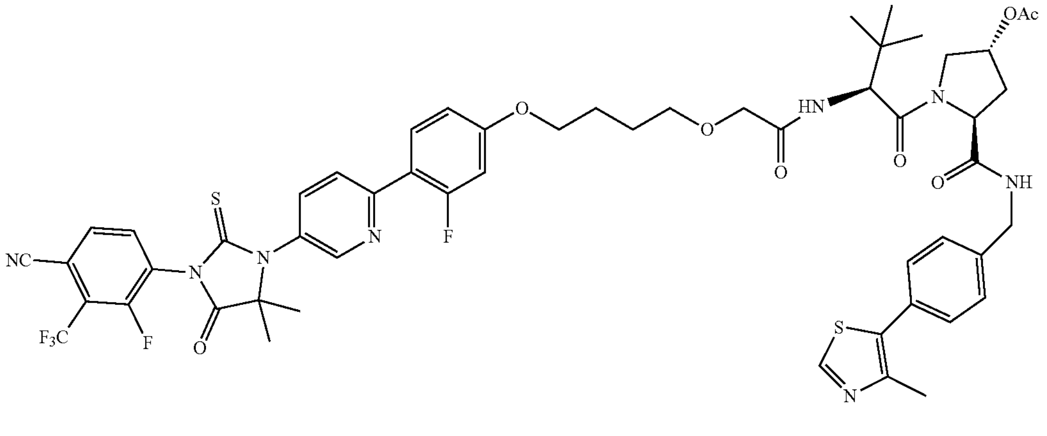 [SMILES: CC(=O)O[C@@H]1C[C@@H](C(=O)NCc2ccc(-c3scnc3C)cc2)N(C(=O)[C@@H](NC(=O)COCCCCOc2ccc(-c3ccc(N4C(=S)N(c5ccc(C#N)c(C(F)(F)F)c5F)C(=O)C4(C)C)cn3)c(F)c2)C(C)(C)C)C1]
LCMS ([M+H]$^+$): 1061.3
$^1$HNMR (400 MHz, DMSO-d6) δ8.96 (d, J=10.0 Hz, 1H), 8.73 (d, J=2.1 Hz, 1H), 8.60 (t, J=5.9 Hz, 1H), 8.34-8.25 (m, 2H), 7.97 (dd, J=18.2, 8.8 Hz, 3H), 7.47-7.34 (m, 5H), 7.00-6.90 (m, 2H), 5.15 (d, J=3.5 Hz, 1H), 4.57 (d, J=9.5 Hz, 1H), 4.49-4.32 (m, 3H), 4.26 (dd, J=15.7, 5.6 Hz, 1H), 4.10 (t, J=6.3 Hz, 2H), 4.01-3.89 (m, 2H), 3.71-3.52 (m, 4H), 2.43 (d, J=7.2 Hz, 3H), 2.07 (dd, J=12.2, 7.9 Hz, 1H), 2.01-1.89 (m, 1H), 1.88-1.79 (m, 2H), 1.74 (dd, J=14.1, 6.3 Hz, 2H), 1.59 (s, 6H), 0.93 (s, 9H).

Example A159
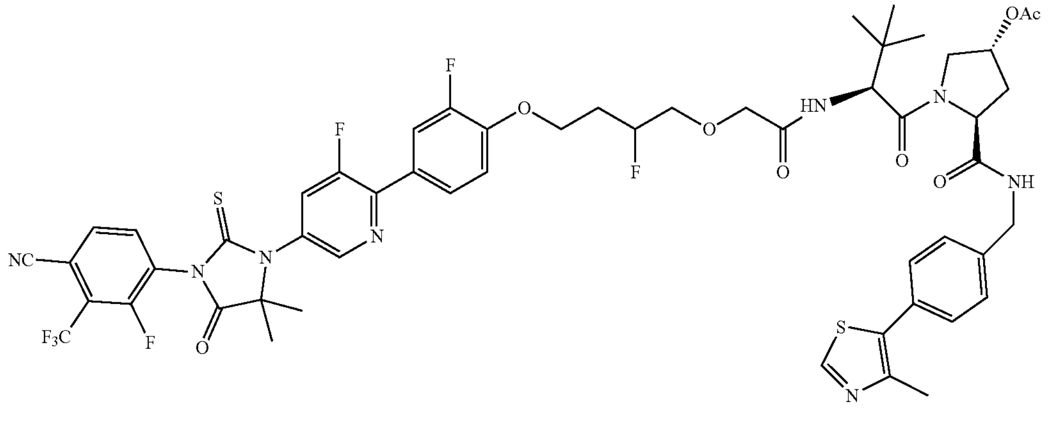 [SMILES: CC(=O)O[C@@H]1C[C@@H](C(=O)NCc2ccc(-c3scnc3C)cc2)N(C(=O)[C@@H](NC(=O)COCC(F)CCOc2ccc(-c3ncc(N4C(=S)N(c5ccc(C#N)c(C(F)(F)F)c5F)C(=O)C4(C)C)cc3F)cc2F)C(C)(C)C)C1]
LCMS ([M+H]$^+$): 1097.3
$^1$HNMR (400 MHz, DMSO-d6) δ8.96 (s, 1H), 8.64 (s, 2H), 8.28 (s, 2H), 8.17 (dd, J=11.9, 1.8 Hz, 1H), 7.84 (s, 2H), 7.48 (t, J=9.0 Hz, 1H), 7.40 (d, J=1.4 Hz, 5H), 5.16 (d, J=3.5 Hz, 1H), 5.08-4.84 (m, 1H), 4.58 (d, J=8.2 Hz, 1H), 4.50-4.33 (m, 3H), 4.29 (s, 3H), 4.06 (s, 2H), 3.88-3.59 (m, 4H), 2.44 (s, 3H), 2.24-2.10 (m, 2H), 2.10 (s, 1H), 1.91 (ddd, J=12.9, 8.8, 4.4 Hz, 1H), 1.62 (s, 6H), 0.95 (s, 9H).
Example A160
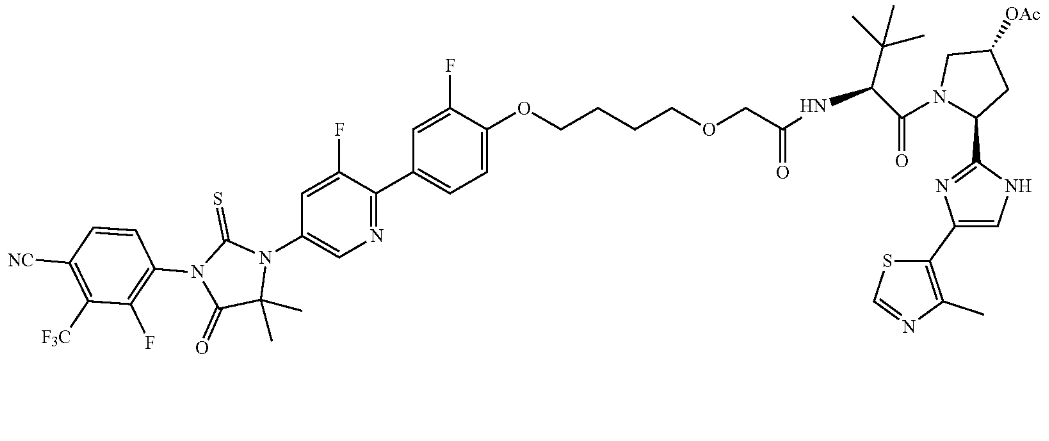 [SMILES: CC(=O)O[C@@H]1C[C@@H](c2nc(-c3scnc3C)c[nH]2)N(C(=O)[C@@H](NC(=O)COCCCCOc2ccc(-c3ncc(N4C(=S)N(c5ccc(C#N)c(C(F)(F)F)c5F)C(=O)C4(C)C)cc3F)cc2F)C(C)(C)C)C1]
LCMS ([M+H]$^+$): 1012.3
$^1$HNMR (400 MHz, DMSO-d6) δ12.19 (d, J=61.4 Hz, 1H), 8.73 (s, 1H), 8.63 (s, 1H), 8.29 (s, 2H), 8.16 (d, J=10.5 Hz, 1H), 7.93-7.77 (m, 2H), 7.35 (dd, J=18.8, 9.2 Hz, 2H), 7.25 (s, 1H), 5.20 (d, J=3.6 Hz, 1H), 5.06 (t, J=7.8 Hz, 1H), 4.57 (d, J=9.5 Hz, 1H), 4.43 (d, J=31.3 Hz, 1H), 4.19 (t, J=6.2 Hz, 2H), 3.96 (s, 2H), 3.85 (d, J=6.4 Hz, 1H), 3.68-3.51 (m, 4H), 2.47 (s, 3H), 2.15 (d, J=4.4 Hz, 2H), 1.85 (d, J=7.7 Hz, 2H), 1.79-1.69 (m, 2H), 1.62 (s, 6H), 0.89 (s, 9H).

Example A161
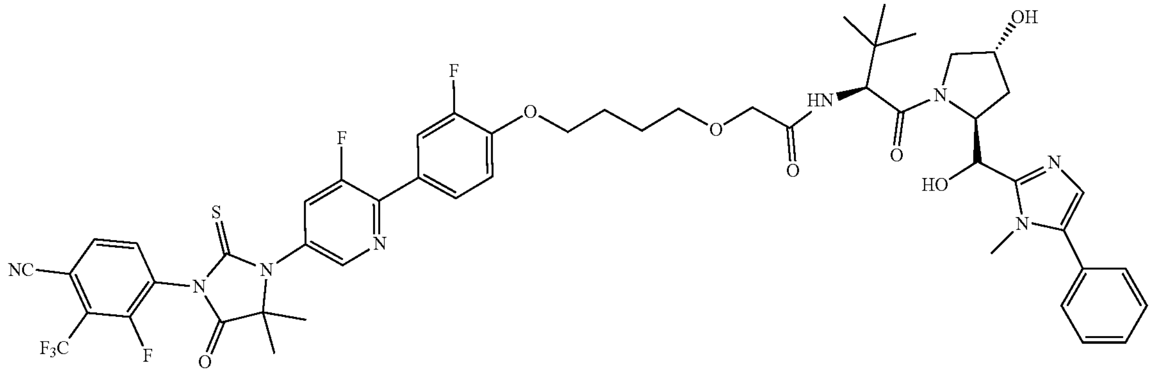 [SMILES: Cn1c(-c2ccccc2)cnc1C(O)[C@@H]1C[C@@H](O)CN1C(=O)[C@@H](NC(=O)COCCCCOc1ccc(-c2ncc(N3C(=S)N(c4ccc(C#N)c(C(F)(F)F)c4F)C(=O)C3(C)C)cc2F)cc1F)C(C)(C)C]
LCMS ([M+H]$^+$): 1035.3
$^1$HNMR (400 MHz, DMSO-d6) δ8.63 (s, 1H), 8.28 (s, 2H), 8.16 (dd, J=11.9, 1.9 Hz, 1H), 7.85 (d, J=10.6 Hz, 2H), 7.41 (dd, J=37.5, 4.4 Hz, 7H), 6.90 (s, 1H), 5.61 (dd, J=27.6, 5.7 Hz, 1H), 5.42-5.30 (m, 1H), 5.00-4.83 (m, 1H), 4.64 (dt, J=15.2, 6.8 Hz, 1H), 4.51 (d, J=9.5 Hz, 1H), 4.26 (d, J=29.6 Hz, 1H), 4.23 (s, 2H), 3.95 (s, 2H), 3.58 (d, J=6.8 Hz, 6H), 2.87 (ddd, J=13.2, 8.4, 4.9 Hz, 1H), 1.95-1.80 (m, 3H), 1.76 (dd, J=14.0, 6.1 Hz, 2H), 1.61 (s, 6H), 0.97 (s, 3H), 0.68 (s, 6H).
Example A162
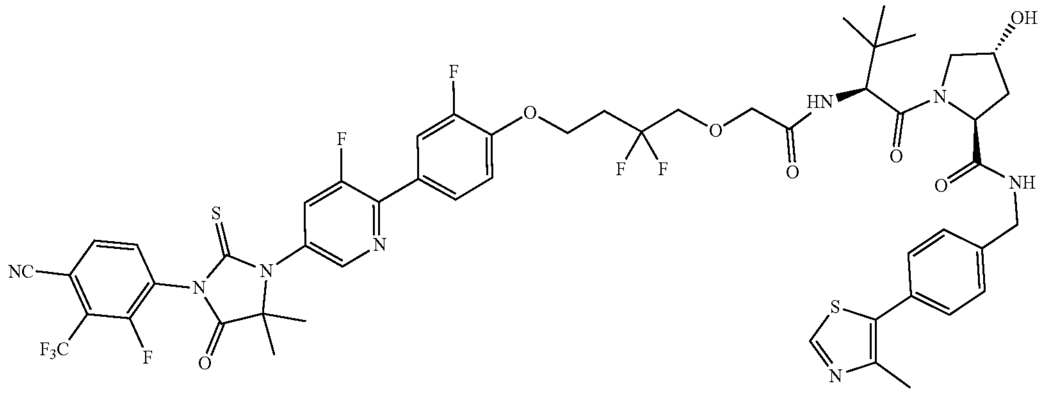 [SMILES: Cc1ncsc1-c1ccc(CNC(=O)[C@@H]2C[C@@H](O)CN2C(=O)[C@@H](NC(=O)COCC(F)(F)CCOc2ccc(-c3ncc(N4C(=S)N(c5ccc(C#N)c(C(F)(F)F)c5F)C(=O)C4(C)C)cc3F)cc2F)C(C)(C)C)cc1]
LCMS ([M+H]$^+$): 1115.3
$^1$HNMR (400 MHz, DMSO-d6) δ8.97 (s, 1H), 8.64 (s, 2H), 8.28 (s, 2H), 8.17 (dd, J=11.9, 1.8 Hz, 1H), 7.86 (d, J=10.5 Hz, 2H), 7.59 (d, J=9.4 Hz, 1H), 7.40 (d, J=2.9 Hz, 5H), 5.16 (d, J=3.5 Hz, 1H), 4.58 (d, J=9.5 Hz, 1H), 4.44 (dt, J=14.1, 7.1 Hz, 2H), 4.39 (d, J=11.9 Hz, 4H), 4.25 (dd, J=15.7, 5.5 Hz, 1H), 4.14 (s, 2H), 3.93 (t, J=13.5 Hz, 2H), 3.66 (dt, J=20.8, 7.3 Hz, 2H), 2.44 (s, 3H), 2.08 (s, 2H), 1.96-1.86 (m, 1H), 1.62 (s, 6H), 0.93 (d, J=7.3 Hz, 9H).

Example A163
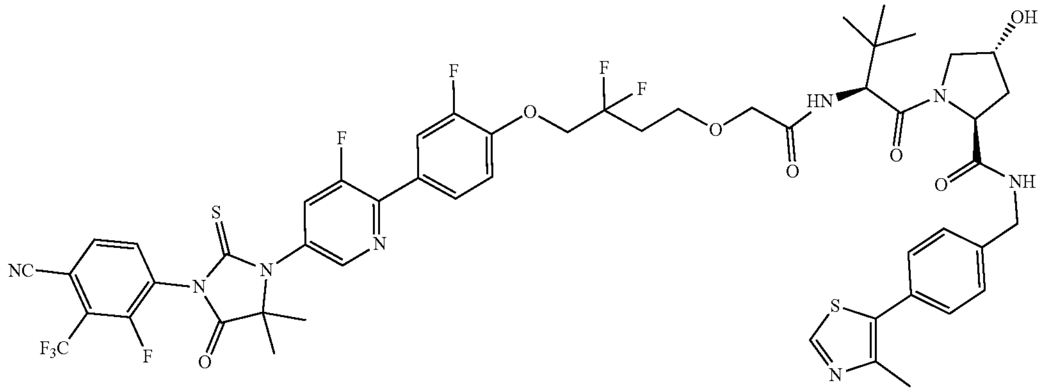 [SMILES: Cc1ncsc1-c1ccc(CNC(=O)[C@@H]2C[C@@H](O)CN2C(=O)[C@@H](NC(=O)COCCC(F)(F)COc2ccc(-c3ncc(N4C(=S)N(c5ccc(C#N)c(C(F)(F)F)c5F)C(=O)C4(C)C)cc3F)cc2F)C(C)(C)C)cc1]
LCMS ([M+H]+): 1115.3
$^1$HNMR (400 MHz, DMSO-d6) δ8.97 (d, J=5.7 Hz, 1H), 8.64 (s, 1H), 8.58 (t, J=5.9 Hz, 1H), 8.28 (m, 2H), 8.18 (dd, J=11.8, 1.8 Hz, 1H), 7.86 (t, J=9.1 Hz, 2H), 7.51 (d, J=9.5 Hz, 1H), 7.46 (d, J=8.6 Hz, 1H), 7.41 (d, J=9.3 Hz, 4H), 5.15 (m, 1H), 4.59 (m, 2H), 4.47-4.41 (m, 2H), 4.37 (m, 2H), 4.25 (m, 2H), 4.00 (m, 2H), 3.75 (m, 2H), 3.70-3.62 (m, 2H), 2.43 (s, 3H), 2.05 (m, 2H), 2.02-1.97 (m, 2H), 1.62 (s, 6H), 0.93 (s, 9H).
Example A164
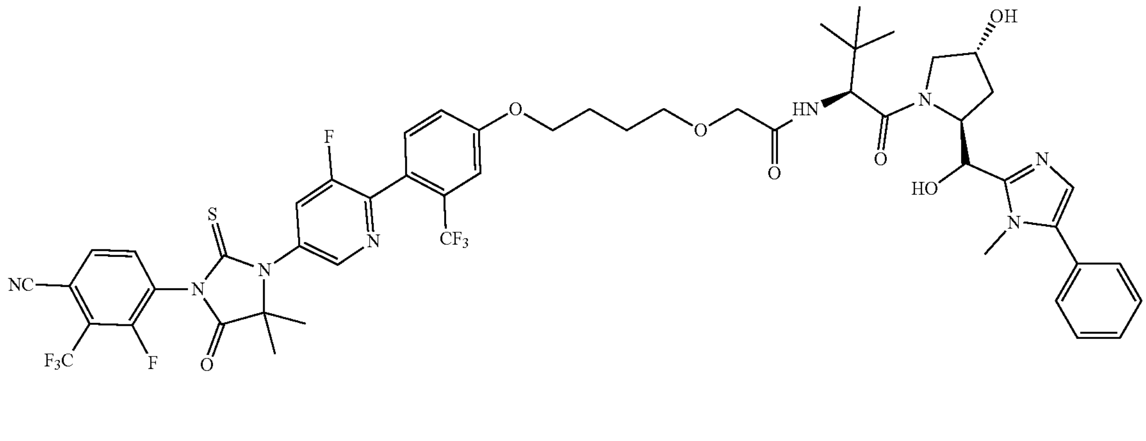 [SMILES: Cn1c(-c2ccccc2)cnc1C(O)[C@@H]1C[C@@H](O)CN1C(=O)[C@@H](NC(=O)COCCCCOc1ccc(-c2ncc(N3C(=S)N(c4ccc(C#N)c(C(F)(F)F)c4F)C(=O)C3(C)C)cc2F)c(C(F)(F)F)c1)C(C)(C)C]
LCMS ([M+H]+): 1085.4
$^1$HNMR (400 MHz, DMSO-d6) δ8.63 (s, 1H), 8.34-8.26 (m, 2H), 8.20 (dd, J=9.7, 1.9 Hz, 1H), 7.62-7.54 (m, 1H), 7.51-7.30 (m, 8H), 6.94 (d, J=32.8 Hz, 1H), 5.61 (dd, J=28.0, 5.7 Hz, 1H), 5.40-5.31 (m, 1H), 4.97 (dd, J=23.3, 6.4 Hz, 1H), 4.64 (dt, J=15.1, 6.9 Hz, 1H), 4.52 (d, J=9.5 Hz, 1H), 4.30 (s, 1H), 4.19 (t, J=6.0 Hz, 2H), 4.00-3.84 (m, 2H), 3.64-3.49 (m, 7H), 2.87 (ddd, J=13.2, 8.4, 5.0 Hz, 1H), 1.95-1.69 (m, 5H), 1.61 (s, 6H), 0.97 (s, 2H), 0.68 (s, 7H).

Example A165
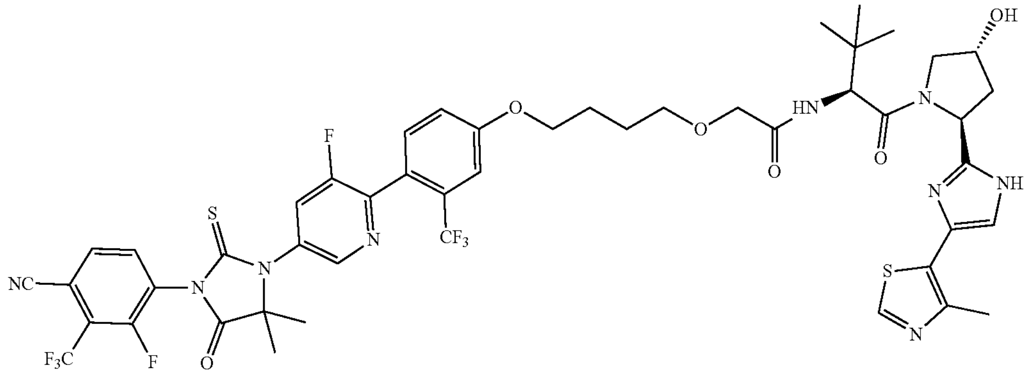 [SMILES: Cc1ncsc1-c1c[nH]c([C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)c(C(F)(F)F)c2)C(C)(C)C)n1]
LCMS ($[M+H]^+$): 1062.3
$^1$HNMR (400 MHz, DMSO-d6) δ12.31-12.05 (m, 1H), 8.73 (d, J=10.2 Hz, 1H), 8.62 (s, 1H), 8.34-8.24 (m, 2H), 8.19 (dd, J=9.7, 1.7 Hz, 1H), 7.55 (d, J=9.1 Hz, 1H), 7.43-7.29 (m, 3H), 7.25 (d, J=5.5 Hz, 1H), 5.20 (d, J=3.7 Hz, 1H), 5.06 (t, J=7.7 Hz, 1H), 4.57 (d, J=9.5 Hz, 1H), 4.49-4.33 (m, 1H), 4.17 (t, J=6.1 Hz, 2H), 4.01-3.90 (m, 2H), 3.82 (dt, J=34.8, 17.4 Hz, 1H), 3.68-3.52 (m, 3H), 2.48-2.39 (m, 3H), 2.25-2.10 (m, 2H), 1.83 (dd, J=13.7, 6.3 Hz, 2H), 1.78-1.68 (m, 2H), 1.61 (s, 6H), 0.95-0.80 (m, 9H).
Example A166
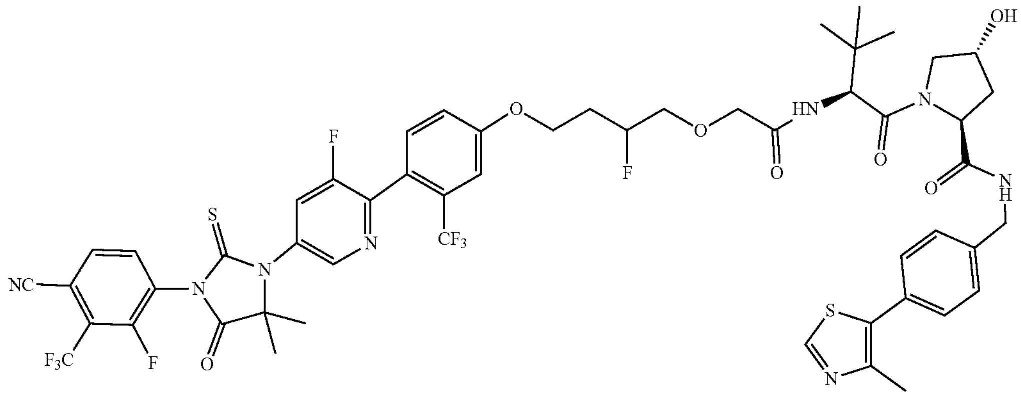 [SMILES: Cc1ncsc1-c1ccc(CNC(=O)[C@@H]2C[C@@H](O)CN2C(=O)[C@@H](NC(=O)COCC(F)CCOc2ccc(-c3ncc(N4C(=S)N(c5ccc(C#N)c(C(F)(F)F)c5F)C(=O)C4(C)C)cc3F)c(C(F)(F)F)c2)C(C)(C)C)cc1]
LCMS ($[M+H]^+$): 1147.3
$^1$HNMR (400 MHz, DMSO-d6) δ8.97 (d, J=8.0 Hz, 1H), 8.66-8.56 (m, 2H), 8.28 (s, 2H), 8.20 (d, J=9.7 Hz, 1H), 7.57 (d, J=8.2 Hz, 1H), 7.49 (d, J=9.5 Hz, 1H), 7.40 (d, J=4.2 Hz, 5H), 5.15 (d, J=3.4 Hz, 1H), 5.03 (s, 1H), 4.92 (s, 1H), 4.57 (d, J=9.5 Hz, 1H), 4.49-4.33 (m, 3H), 4.25 (dd, J=15.6, 5.7 Hz, 3H), 4.05 (d, J=9.5 Hz, 2H), 3.88-3.58 (m, 5H), 2.44 (d, J=4.7 Hz, 3H), 2.22-1.86 (m, 6H), 1.61 (s, 6H), 0.94 (s, 9H).

Example A167
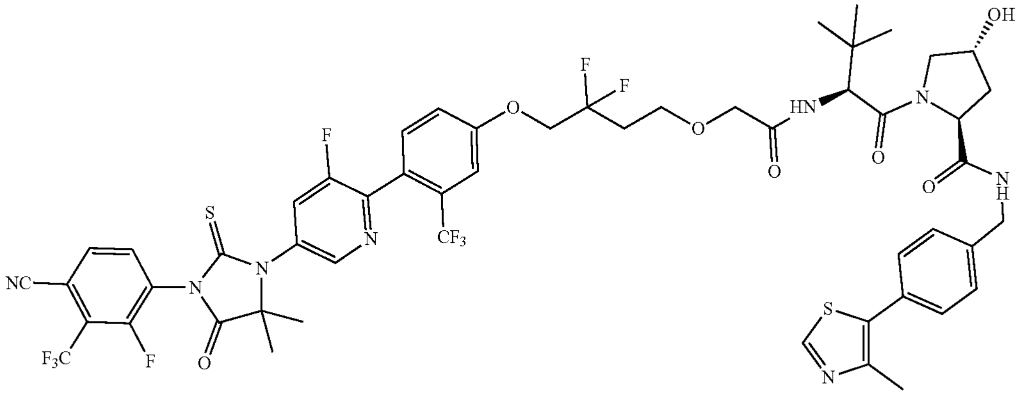 [SMILES: Cc1ncsc1-c1ccc(CNC(=O)[C@@H]2C[C@@H](O)CN2C(=O)[C@@H](NC(=O)COCCC(F)(F)COc2ccc(-c3ncc(N4C(=S)N(c5ccc(C#N)c(C(F)(F)F)c5F)C(=O)C4(C)C)cc3F)c(C(F)(F)F)c2)C(C)(C)C)cc1]
LCMS ([M+H]$^+$): 1165.3
$^1$HNMR (400 MHz, DMSO-d6) δ8.96 (s, 1H), 8.63 (s, 1H), 8.58 (t, J=6.0 Hz, 1H), 8.28 (s, 2H), 8.20 (dd, J=9.7, 1.8 Hz, 1H), 7.59 (d, J=8.6 Hz, 1H), 7.55-7.44 (m, 3H), 7.39 (s, 4H), 5.14 (d, J=2.5 Hz, 1H), 4.59 (dd, J=16.1, 11.3 Hz, 3H), 4.49-4.31 (m, 3H), 4.25 (dd, J=15.8, 5.6 Hz, 1H), 4.01 (s, 2H), 3.75 (t, J=6.2 Hz, 2H), 3.70-3.57 (m, 2H), 2.44 (d, J=4.1 Hz, 5H), 2.07-2.00 (m, 1H), 1.90 (ddd, J=13.0, 8.8, 4.5 Hz, 1H), 1.61 (s, 6H), 0.91 (d, J=6.4 Hz, 9H).
Example A168
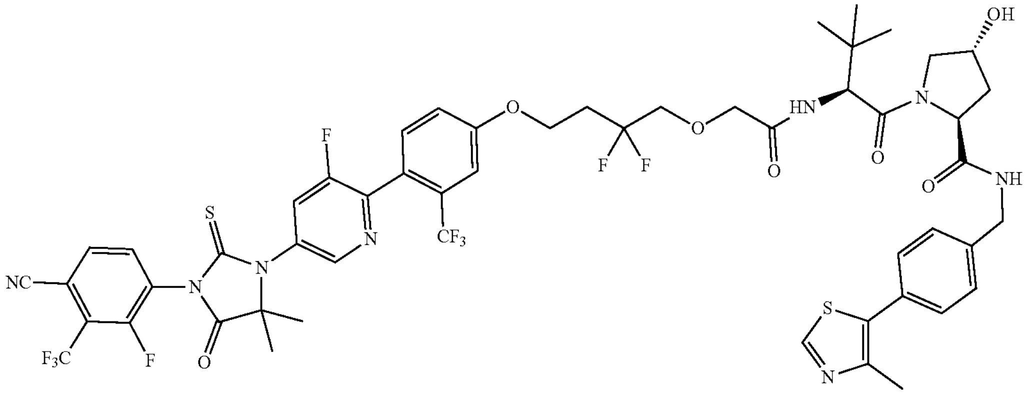 [SMILES: Cc1ncsc1-c1ccc(CNC(=O)[C@@H]2C[C@@H](O)CN2C(=O)[C@@H](NC(=O)COCC(F)(F)CCOc2ccc(-c3ncc(N4C(=S)N(c5ccc(C#N)c(C(F)(F)F)c5F)C(=O)C4(C)C)cc3F)c(C(F)(F)F)c2)C(C)(C)C)cc1]
LCMS ([M+H]$^+$): 1165.3
$^1$HNMR (400 MHz, DMSO-d6) δ8.96 (s, 1H), 8.66-8.56 (m, 2H), 8.29 (d, J=3.4 Hz, 2H), 8.20 (dd, J=9.7, 1.8 Hz, 1H), 7.59 (dd, J=13.2, 9.3 Hz, 2H), 7.46-7.33 (m, 6H), 5.15 (d, J=3.4 Hz, 1H), 4.58 (d, J=9.5 Hz, 1H), 4.50-4.32 (m, 5H), 4.25 (dd, J=15.8, 5.6 Hz, 1H), 4.15 (s, 2H), 3.93 (t, J=13.7 Hz, 2H), 3.71-3.57 (m, 2H), 2.60-2.52 (m, 1H), 2.43 (s, 5H), 2.05 (d, J=8.6 Hz, 1H), 1.91 (ddd, J=13.0, 8.9, 4.5 Hz, 1H), 1.61 (s, 6H), 0.93 (d, J=6.1 Hz, 9H).

Example A169
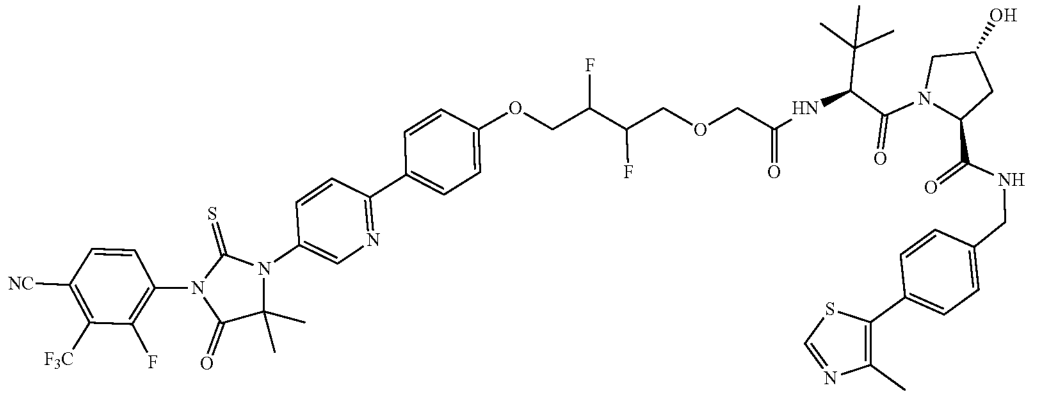 [SMILES: Cc1ncsc1-c1ccc(CNC(=O)[C@@H]2C[C@@H](O)CN2C(=O)[C@@H](NC(=O)COCC(F)C(F)COc2ccc(-c3ccc(N4C(=S)N(c5ccc(C#N)c(C(F)(F)F)c5F)C(=O)C4(C)C)cn3)cc2)C(C)(C)C)cc1]
LCMS ([M+H]$^+$): 1079.3
$^1$HNMR (400 MHz, DMSO-d6) δ8.97-8.96 (m, 1H), 8.66 (d, J=2.2 Hz, 1H), 8.59 (t, J=5.9 Hz, 1H), 8.32-8.26 (m, 2H), 8.13 (d, J=8.7 Hz, 3H), 7.96 (dd, J=8.5, 2.4 Hz, 1H), 7.54 (d, J=8.8 Hz, 1H), 7.45-7.35 (m, 4H), 7.14 (d, J=8.8 Hz, 2H), 5.32-4.96 (m, 3H), 4.58 (d, J=9.4 Hz, 1H), 4.48-4.32 (m, 5H), 4.25 (dd, J=15.8, 5.6 Hz, 1H), 4.15-4.04 (m, 2H), 4.02-3.87 (m, 2H), 3.70-3.61 (m, 2H), 2.43 (s, 3H), 2.07-2.04 (m, 1H), 1.96-1.86 (m, 1H), 1.58 (s, 6H), 0.94 (d, J=6.9 Hz, 9H).
Example A170
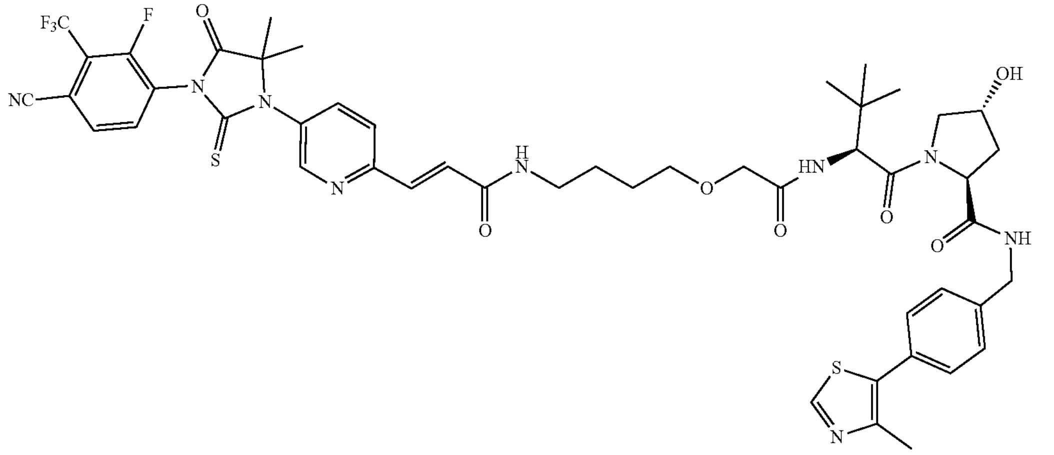 [SMILES: Cc1ncsc1-c1ccc(CNC(=O)[C@@H]2C[C@@H](O)CN2C(=O)[C@@H](NC(=O)COCCCCNC(=O)/C=C/c2ccc(N3C(=S)N(c4ccc(C#N)c(C(F)(F)F)c4F)C(=O)C3(C)C)cn2)C(C)(C)C)cc1]
LCMS ([M+H]$^+$): 1020.3
$^1$HNMR (400 MHz, DMSO-d6) δ8.98-8.97 (m, 1H), 8.66 (d, J=2.3 Hz, 1H), 8.59 (t, J=5.9 Hz, 1H), 8.36 (t, J=5.5 Hz, 1H), 8.33-8.23 (m, 2H), 7.96 (dd, J=8.3, 2.4 Hz, 1H), 7.79 (d, J=8.3 Hz, 1H), 7.51 (d, J=15.4 Hz, 1H), 7.46-7.35 (m, 5H), 7.14 (d, J=15.4 Hz, 1H), 5.15 (d, J=3.5 Hz, 1H), 4.56 (d, J=9.6 Hz, 1H), 4.45 (t, J=8.2 Hz, 1H), 4.40-4.34 (m, 2H), 4.29-4.24 (m, 1H), 3.98-3.86 (m, 2H), 3.68-3.59 (m, 2H), 3.50 (t, J=6.0 Hz, 2H), 3.26-3.18 (m, 2H), 2.44 (s, 3H), 2.06-2.01 (m, 1H), 1.95-1.86 (m, 1H), 1.59-1.56 (m, 10H), 0.93 (d, J=6.8 Hz, 9H).

Example A171
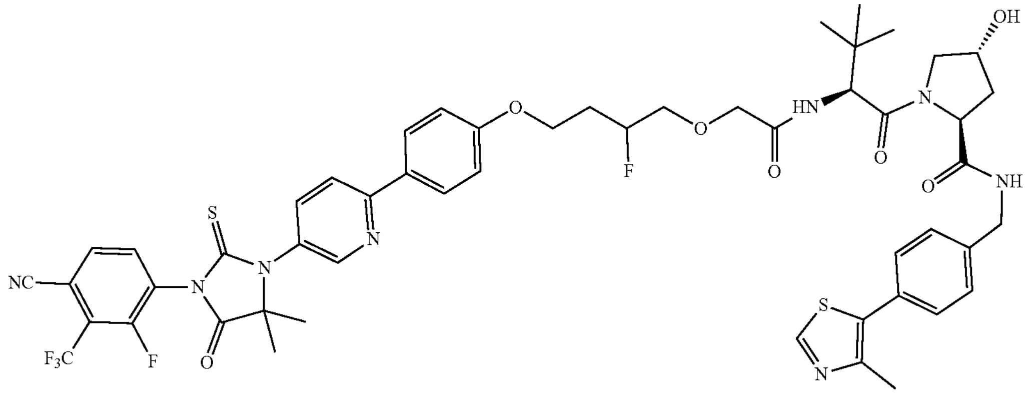 [SMILES: Cc1ncsc1-c1ccc(CNC(=O)[C@@H]2C[C@@H](O)CN2C(=O)[C@@H](NC(=O)COCC(F)CCOc2ccc(-c3ccc(N4C(=S)N(c5ccc(C#N)c(C(F)(F)F)c5F)C(=O)C4(C)C)cn3)cc2)C(C)(C)C)cc1]
LCMS ([M+H]+): 1061.3
$^1$HNMR (400 MHz, DMSO-d6) δ8.96 (d, J=6.8 Hz, 1H), 8.66 (d, J=2.3 Hz, 1H), 8.59 (t, J=5.9 Hz, 1H), 8.29 (q, J=8.5 Hz, 2H), 8.11 (d, J=8.7 Hz, 3H), 7.95 (dd, J=8.5, 2.3 Hz, 1H), 7.48 (d, J=9.5 Hz, 1H), 7.45-7.36 (m, 4H), 7.09 (d, J=8.8 Hz, 2H), 5.16 (d, J=3.4 Hz, 1H), 4.95 (dd, J=47.5, 6.7 Hz, 1H), 4.57 (d, J=9.5 Hz, 1H), 4.50-4.33 (m, 3H), 4.25 (dd, J=15.8, 5.6 Hz, 1H), 4.18 (t, J=6.1 Hz, 2H), 4.11-3.99 (m, 2H), 3.88-3.58 (m, 4H), 2.44 (d, J=4.4 Hz, 3H), 2.15 (d, J=6.1 Hz, 1H), 2.10 (d, J=7.6 Hz, 2H), 1.91 (ddd, J=13.0, 8.9, 4.4 Hz, 1H), 1.58 (s, 6H), 0.94 (s, 9H).
Example A172
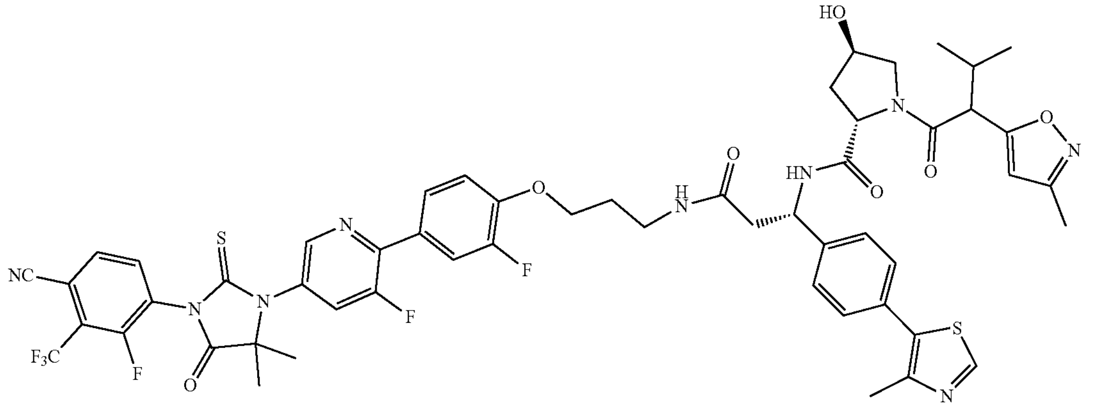 [SMILES: Cc1cc(C(C(=O)N2C[C@H](O)C[C@H]2C(=O)N[C@@H](CC(=O)NCCCOc2ccc(-c3ncc(N4C(=S)N(c5ccc(C#N)c(C(F)(F)F)c5F)C(=O)C4(C)C)cc3F)cc2F)c2ccc(-c3scnc3C)cc2)C(C)C)on1]
LCMS ([M+H]+): 1116.3
$^1$HNMR (400 MHz, DMSO-d6) δ8.97-8.88 (m, 1H), 8.63 (s, 1H), 8.44 (dd, J=51.5, 8.1 Hz, 1H), 8.33-8.23 (m, 2H), 8.16 (d, J=11.9 Hz, 1H), 8.07-7.93 (m, 1H), 7.81 (dt, J=12.1, 10.3 Hz, 2H), 7.49-7.28 (m, 4H), 7.26-7.14 (m, 1H), 6.22 (d, J=9.7 Hz, 1H), 5.36-4.89 (m, 2H), 4.50-3.39 (m, 7H), 3.20 (m, 2H), 2.69-2.54 (m, 2H), 2.46-2.36 (m, 3H), 2.34-2.11 (m, 4H), 2.05-1.73 (m, 4H), 1.62 (s, 7H), 0.96 (dd, J=6.5, 2.9 Hz, 3H), 0.78 (dd, J=12.0, 6.7 Hz, 3H).

Example A173
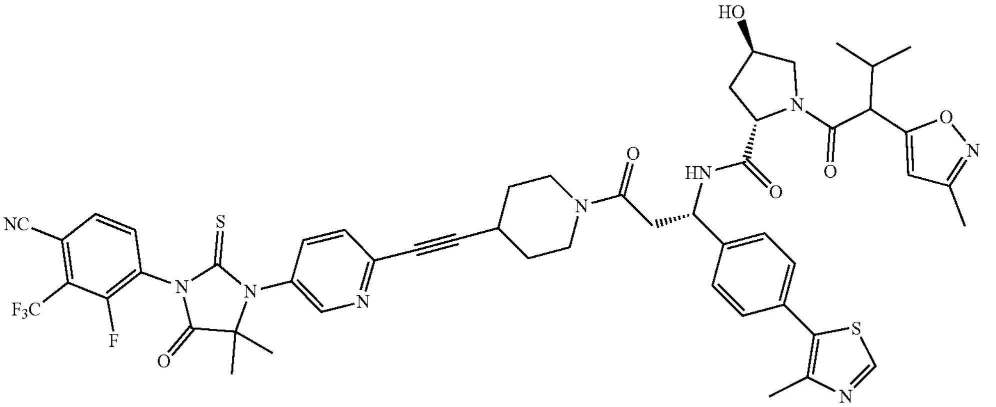 [SMILES: Cc1cc(C(C(=O)N2C[C@H](O)C[C@H]2C(=O)N[C@@H](CC(=O)N2CCC(C#Cc3ccc(N4C(=S)N(c5ccc(C#N)c(C(F)(F)F)c5F)C(=O)C4(C)C)cn3)CC2)c2ccc(-c3scnc3C)cc2)C(C)C)on1]
LCMS ($[M+H]^+$): 1038.3
$^1$HNMR (400 MHz, DMSO-d6) δ9.00-8.86 (m, 1H), 8.59 (m, 1H), 8.46 (m, 1H), 8.30-8.27 (m, 2H), 7.91-7.87 (m, 1H), 7.69-7.54 (m, 1H), 7.49-7.33 (m, 4H), 6.25-6.16 (m, 1H), 5.32-5.09 (m, 2H), 4.40-4.20 (m, 2H), 3.94-3.49 (m, 5H), 3.05-2.81 (m, 5H), 2.46-2.43 (m, 3H), 2.27-2.18 (m, 4H), 1.99 (m, 1H), 1.79 (m, 3H), 1.55-1.45 (m, 8H), 0.97-0.73 (m, 6H).
Example A174
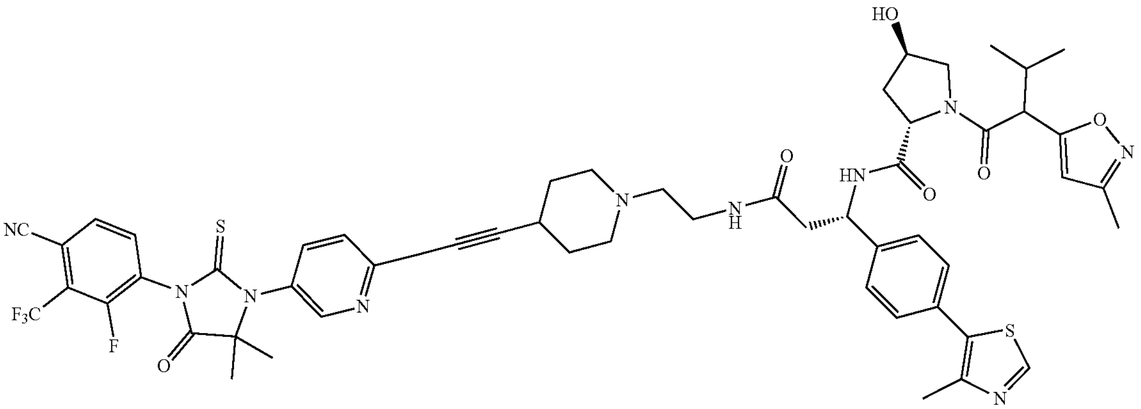 [SMILES: Cc1cc(C(C(=O)N2C[C@H](O)C[C@H]2C(=O)N[C@@H](CC(=O)NCCN2CCC(C#CCc3ccc(N4C(=S)N(c5ccc(C#N)c(C(F)(F)F)c5F)C(=O)C4(C)C)cn3)CC2)c2ccc(-c3scnc3C)cc2)C(C)C)on1]
LCMS ($[M+H]^+$): 1081.4
$^1$HNMR (400 MHz, DMSO-d6) δ8.97-8.59 (m, 3H), 7.41-7.29 (m, 8H), 6.25-6.21 (m, 2H), 5.11-5.07 (m, 3H), 4.39-4.20 (m, 5H), 3.85-3.73 (m, 4H), 2.67-2.56 (m, 5H), 2.43 (s, 6H), 2.29-2.23 (m, 3H), 2.19-2.16 (m, 7H), 2.00-1.97 (m, 3H), 1.81-1.78 (m, 2H), 0.97-0.93 (m, 6H), 0.78 (dd, J=14.2, 6.8 Hz, 6H).

Example A175
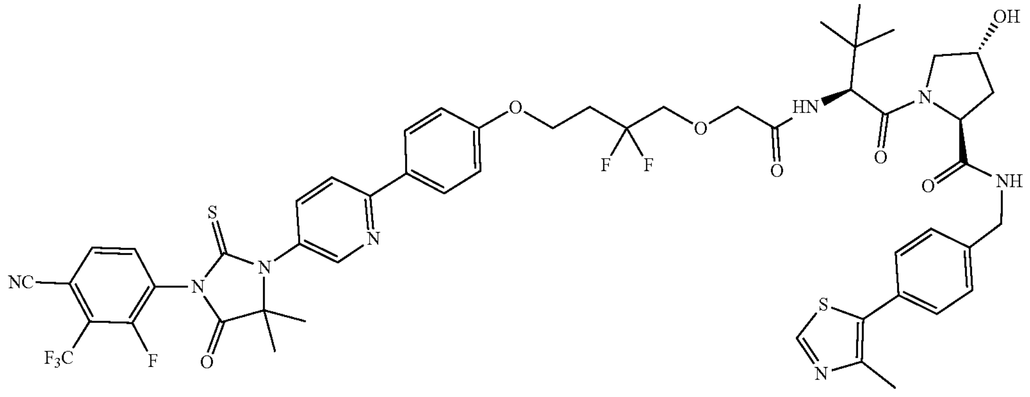 [SMILES: Cc1ncsc1-c1ccc(CNC(=O)[C@@H]2C[C@@H](O)CN2C(=O)[C@@H](NC(=O)COCC(F)(F)CCOc2ccc(-c3ccc(N4C(=S)N(c5ccc(C#N)c(C(F)(F)F)c5F)C(=O)C4(C)C)cn3)cc2)C(C)(C)C)cc1]
LCMS ([M+H]$^+$): 1079.3
$^1$HNMR (400 MHz, DMSO-d6) δ8.96 (s, 1H), 8.66 (d, J=2.2 Hz, 1H), 8.59 (t, J=5.9 Hz, 1H), 8.29 (q, J=8.5 Hz, 2H), 8.12 (d, J=8.8 Hz, 3H), 7.95 (dd, J=8.5, 2.4 Hz, 1H), 7.59 (d, J=9.5 Hz, 1H), 7.39 (q, J=8.3 Hz, 4H), 7.10 (d, J=8.8 Hz, 2H), 5.16 (d, J=3.4 Hz, 1H), 4.57 (d, J=9.5 Hz, 1H), 4.49-4.33 (m, 3H), 4.31-4.20 (m, 3H), 4.12 (d, J=16.6 Hz, 2H), 3.91 (t, J=13.3 Hz, 2H), 3.66 (dt, J=21.0, 7.1 Hz, 2H), 2.52 (d, J=7.6 Hz, 1H), 2.43 (s, 4H), 2.06 (dd, J=12.9, 6.9 Hz, 1H), 1.96-1.86 (m, 1H), 1.58 (s, 6H), 0.93 (d, J=7.0 Hz, 9H).
Example A176
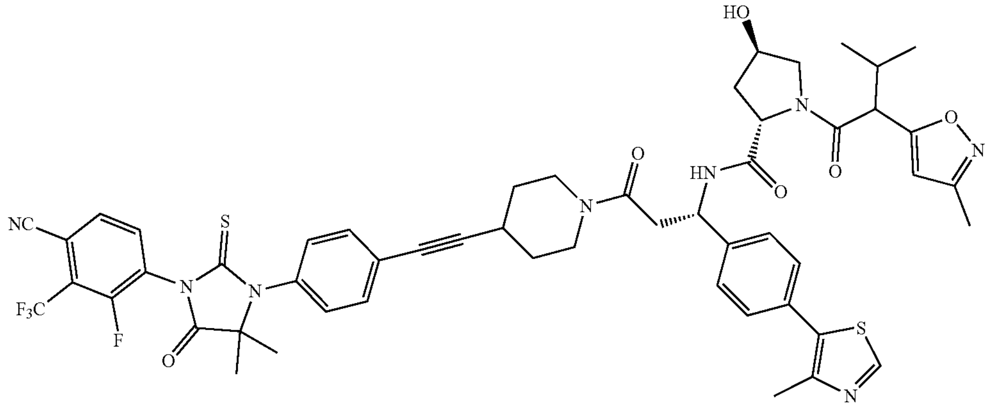 [SMILES: Cc1cc(C(C(=O)N2C[C@H](O)C[C@H]2C(=O)N[C@@H](CC(=O)N2CCC(C#Cc3ccc(N4C(=S)N(c5ccc(C#N)c(C(F)(F)F)c5F)C(=O)C4(C)C)cc3)CC2)c2ccc(-c3scnc3C)cc2)C(C)C)on1]
LCMS ([M+H]$^+$): 1037.1
$^1$HNMR (400 MHz, DMSO-d6) δ9.02-8.87 (m, 1H), 8.61 (d, J=133.7 Hz, 1H), 8.32-8.22 (m, 2H), 7.66-7.25 (m, 8H), 6.28-6.14 (m, 1H), 5.38-4.87 (m, 2H), 4.33 (ddd, J=58.1, 32.8, 20.0 Hz, 2H), 3.96-3.49 (m, 4H), 3.24-2.65 (m, 6H), 2.47-2.41 (m, 3H), 2.33-2.09 (m, 4H), 2.00 (d, J=7.5 Hz, 1H), 1.78 (s, 3H), 1.52 (s, 8H), 0.84 (ddd, J=32.0, 22.1, 6.4 Hz, 6H).

Example A177
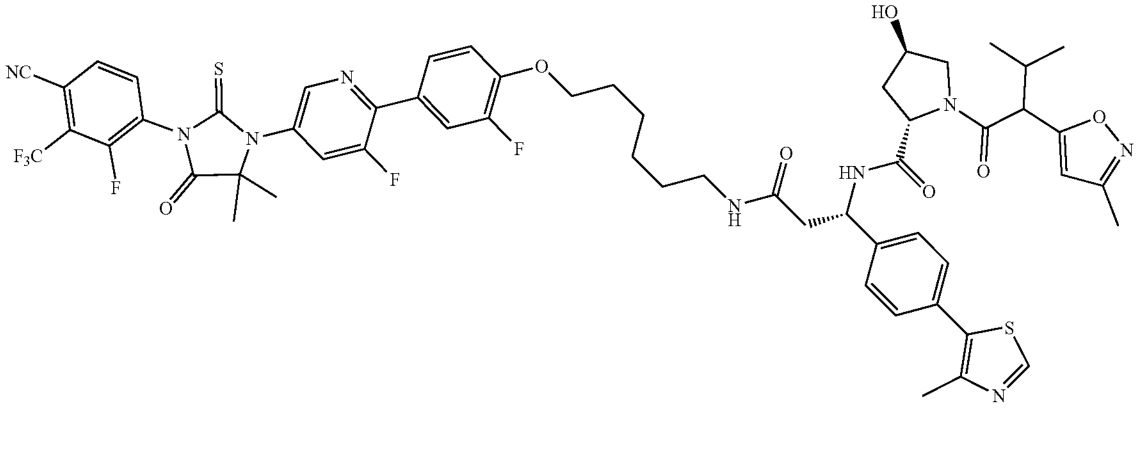 [SMILES: Cc1cc(C(C(=O)N2C[C@H](O)C[C@H]2C(=O)N[C@@H](CC(=O)NCCCCCCOc2ccc(-c3ncc(N4C(=S)N(c5ccc(C#N)c(C(F)(F)F)c5F)C(=O)C4(C)C)cc3F)cc2F)c2ccc(-c3scnc3C)cc2)C(C)C)on1]
LCMS ([M+H]+): 1158.4
$^1$HNMR (400 MHz, DMSO-d6) δ9.00-8.84 (m, 1H), 8.63 (s, 1H), 8.41 (dd, J=59.3, 8.0 Hz, 1H), 8.29 (d, J=11.9 Hz, 2H), 8.20-8.12 (m, 1H), 7.83 (t, J=10.7 Hz, 3H), 7.50-7.25 (m, 5H), 6.22 (d, J=9.8 Hz, 1H), 5.37-5.03 (m, 2H), 4.50-4.23 (m, 2H), 4.14-4.02 (m, 2H), 3.88-3.69 (m, 1H), 3.49 (m, 2H), 3.10-2.87 (m, 2H), 2.68-2.52 (m, 2H), 2.45 (d, J=3.3 Hz, 3H), 2.35-2.13 (m, 4H), 2.00 (m, 1H), 1.89-1.65 (m, 3H), 1.61 (s, 6H), 1.41-1.25 (m, 4H), 1.20 (m, 1H), 1.00-0.94 (m, 2H), 0.78 (dd, J=12.6, 6.7 Hz, 3H).
Example A178
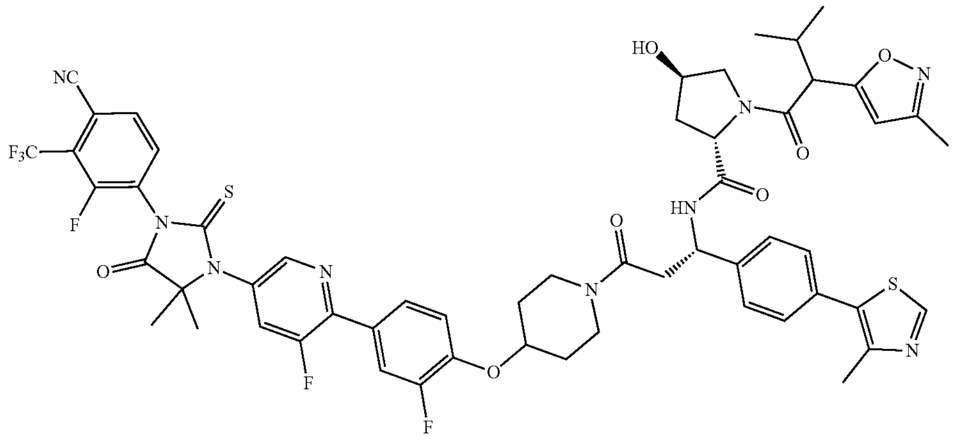 [SMILES: Cc1cc(C(C(=O)N2C[C@H](O)C[C@H]2C(=O)N[C@@H](CC(=O)N2CCC(Oc3ccc(-c4ncc(N5C(=S)N(c6ccc(C#N)c(C(F)(F)F)c6F)C(=O)C5(C)C)cc4F)cc3F)CC2)c2ccc(-c3scnc3C)cc2)C(C)C)on1]
LCMS ([M+H]+): 1142.3
$^1$HNMR (400 MHz, DMSO-d6) δ8.98 (s, 1H), 8.77 (m, 0.5H), 8.63 (s, 1H), 8.44 (m, 0.5H), 8.30-8.28 (m, 2H), 8.17 (d, J=11.7 Hz, 1H), 7.87-7.83 (m, 2H), 7.51-7.32 (m, 5H), 6.25-6.16 (m, 1H), 5.33-4.72 (m, 4H), 4.48-4.16 (m, 2H), 4.01-3.38 (m, 6H), 2.95-2.84 (m, 2H), 2.45-2.44 (m, 3H), 2.28-2.17 (m, 4H), 2.05-1.75 (m, 4H), 1.61 (s, 7H), 1.03-0.69 (m, 6H).

Example A179
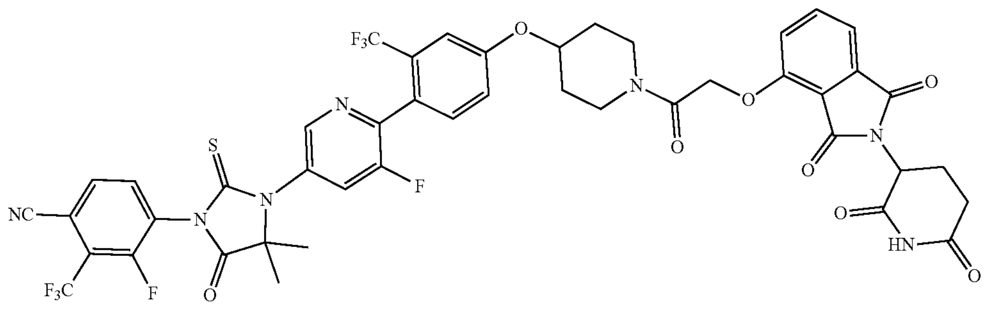 [SMILES: CC1(C)C(=O)N(c2ccc(C#N)c(C(F)(F)F)c2F)C(=S)N1c1cnc(-c2ccc(OC3CCN(C(=O)COc4cccc5c4C(=O)N(C4CCC(=O)NC4=O)C5=O)CC3)cc2C(F)(F)F)c(F)c1]
LCMS ([M+H]$^+$): 984.2
$^1$HNMR (400 MHz, DMSO-d6) δ11.10 (s, 1H), 8.63 (s, 1H), 8.31-8.27 (m, 2H), 8.20 (dd, J=9.7, 1.8 Hz, 1H), 7.81-7.77 (m, 1H), 7.60-7.58 (m, 1H), 7.49-7.45 (m, 3H), 7.37 (d, J=8.7 Hz, 1H), 5.23 (s, 2H), 5.11 (dd, J=12.9, 5.4 Hz, 1H), 4.91 (m, 1H), 3.85 (s, 1H), 3.72 (s, 1H), 3.43-3.38 (m, 2H), 2.94-2.85 (m, 1H), 2.62-2.54 (m, 2H), 2.08 (m, 1H), 2.02-1.99 (m, 2H), 1.81 (m, 1H), 1.61 (s, 7H).
Example A180
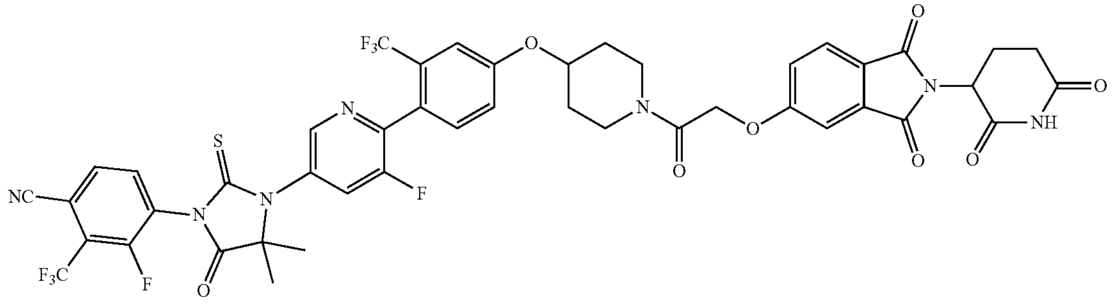 [SMILES: CC1(C)C(=O)N(c2ccc(C#N)c(C(F)(F)F)c2F)C(=S)N1c1cnc(-c2ccc(OC3CCN(C(=O)COc4ccc5c(c4)C(=O)N(C4CCC(=O)NC4=O)C5=O)CC3)cc2C(F)(F)F)c(F)c1]
LCMS ([M+H]$^+$): 984.2
$^1$HNMR (400 MHz, DMSO-d6) δ11.11 (s, 1H), 8.64 (s, 1H), 8.32-8.29 (m, 2H), 8.21 (dd, J=9.7, 1.7 Hz, 1H), 7.85 (d, J=8.3 Hz, 1H), 7.60 (d, J=8.5 Hz, 1H), 7.50-7.46 (m, 3H), 7.37 (dd, J=8.3, 2.2 Hz, 1H), 5.19 (s, 2H), 5.13 (dd, J=12.9, 5.3 Hz, 1H), 4.92 (m, 1H), 3.87 (s, 1H), 3.73 (s, 1H), 3.43-3.39 (m, 2H), 2.97-2.84 (m, 1H), 2.63-2.56 (m, 2H), 2.08 (s, 1H), 2.04-2.00 (m, 2H), 1.78 (m, 1H), 1.62 (s, 7H).

Example A181
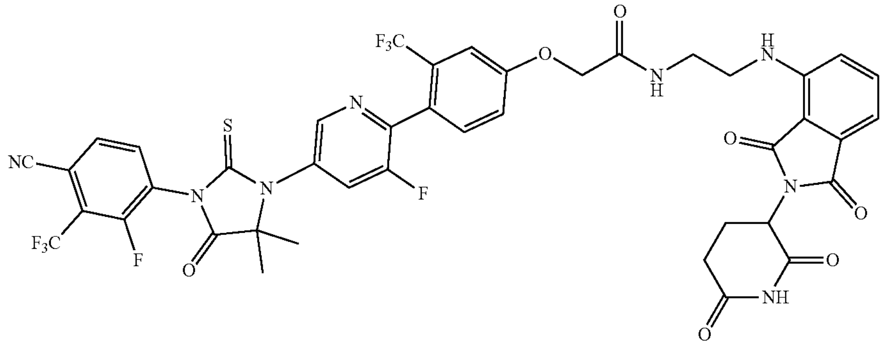 [SMILES: CC1(C)C(=O)N(c2ccc(C#N)c(C(F)(F)F)c2F)C(=S)N1c1cnc(-c2ccc(OCC(=O)NCCNc3cccc4c3C(=O)N(C3CCC(=O)NC3=O)C4=O)cc2C(F)(F)F)c(F)c1]
LCMS ([M+H]$^+$): 943.2
$^1$HNMR (400 MHz, DMSO-d6) δ11.08 (s, 1H), 8.63 (s, 1H), 8.47 (t, J=5.5 Hz, 1H), 8.32-8.26 (m, 2H), 8.20 (dd, J=9.7, 1.9 Hz, 1H), 7.62-7.55 (m, 2H), 7.47 (d, J=2.4 Hz, 1H), 7.38 (dd, J=8.6, 2.3 Hz, 1H), 7.21 (d, J=8.6 Hz, 1H), 7.03 (d, J=7.0 Hz, 1H), 6.79 (t, J=5.9 Hz, 1H), 5.05 (m, 1H), 4.69 (m, 2H), 3.49-3.37 (m, 4H), 2.88 (m, 1H), 2.64-2.51 (m, 2H), 2.00 (m 1H), 1.61 (s, 6H).
Example A182
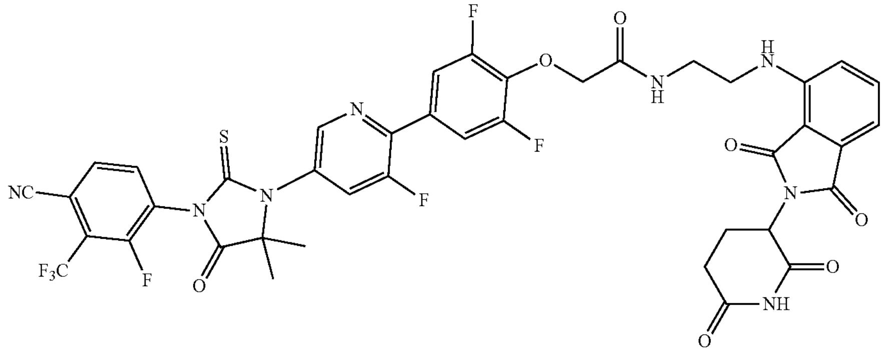 [SMILES: CC1(C)C(=O)N(c2ccc(C#N)c(C(F)(F)F)c2F)C(=S)N1c1cnc(-c2cc(F)c(OCC(=O)NCCNc3cccc4c3C(=O)N(C3CCC(=O)NC3=O)C4=O)c(F)c2)c(F)c1]
LCMS ([M+H]$^+$): 911.2
$^1$HNMR (400 MHz, DMSO-d6) δ11.09 (s, 1H), 8.67 (s, 1H), 8.41 (s, 1H), 8.29 (s, 2H), 8.23 (dd, J=11.8, 1.8 Hz, 1H), 7.76 (d, J=9.5 Hz, 2H), 7.64-7.54 (m, 1H), 7.20 (d, J=8.6 Hz, 1H), 7.03 (d, J=7.0 Hz, 1H), 6.77 (s, 1H), 5.05 (s, 1H), 4.71 (s, 2H), 3.54-3.35 (m, 4H), 2.98-2.80 (m, 1H), 2.57 (s, 2H), 2.07-1.94 (m, 1H), 1.62 (s, 6H).

Example A183
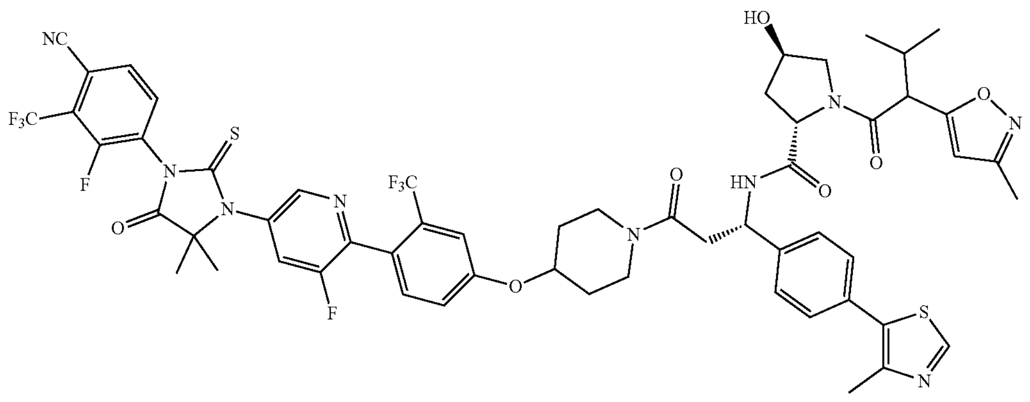 [SMILES: Cc1cc(C(C(=O)N2C[C@H](O)C[C@H]2C(=O)N[C@@H](CC(=O)N2CCC(Oc3ccc(-c4ncc(N5C(=S)N(c6ccc(C#N)c(C(F)(F)F)c6F)C(=O)C5(C)C)cc4F)c(C(F)(F)F)c3)CC2)c2ccc(-c3scnc3C)cc2)C(C)C)on1]
LCMS ([M+H]+): 1192.3
$^1$HNMR (400 MHz, DMSO-d6) δ8.99 (d, J=4.1 Hz, 1H), 8.79 (s, 1H), 8.62 (s, 1H), 8.45 (d, J=5.1 Hz, 1H), 8.28 (s, 2H), 8.23-8.16 (m, 1H), 7.62-7.29 (m, 7H), 6.28-6.16 (m, 1H), 5.41-4.74 (m, 5H), 4.47-4.24 (m, 2H), 4.01-3.64 (m, 4H), 3.62-3.35 (m, 4H), 2.89 (d, J=22.1 Hz, 3H), 2.46 (d, J=3.8 Hz, 3H), 2.38-2.11 (m, 5H), 2.05-1.75 (m, 5H), 1.61 (s, 8H), 1.02-0.67 (m, 7H).
Example A184
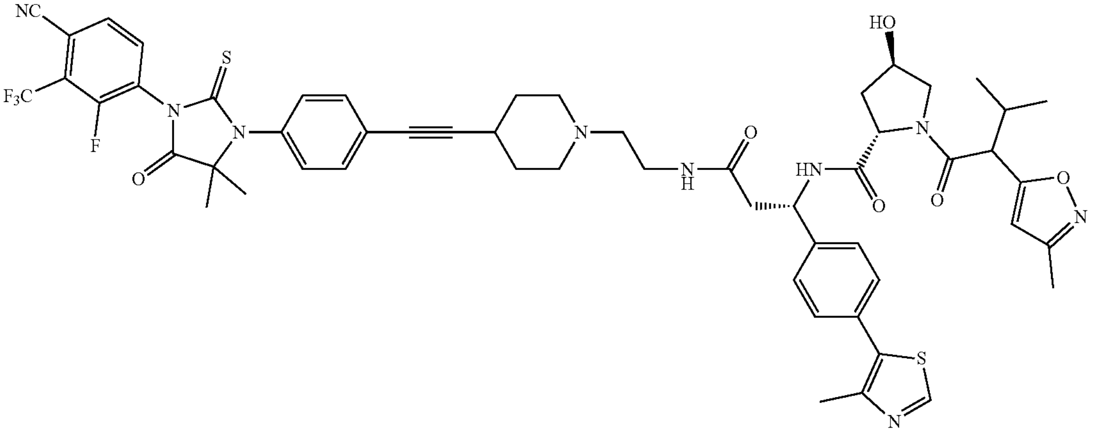 [SMILES: Cc1cc(C(C(=O)N2C[C@H](O)C[C@H]2C(=O)N[C@@H](CC(=O)NCCN2CCC(C#Cc3ccc(N4C(=S)N(c5ccc(C#N)c(C(F)(F)F)c5F)C(=O)C4(C)C)cc3)CC2)c2ccc(-c3scnc3C)cc2)C(C)C)on1]
LCMS ([M+H]+): 1080.2
$^1$HNMR (400 MHz, DMSO-d6) δ8.97 (d, J=6.2 Hz, 1H), 8.28 (d, J=4.8 Hz, 2H), 7.85 (s, 2H), 7.55 (d, J=8.2 Hz, 2H), 7.41 (dt, J=17.3, 11.0 Hz, 6H), 6.23 (d, J=10.8 Hz, 1H), 5.24-5.10 (m, 2H), 4.34 (dd, J=28.4, 19.6 Hz, 3H), 3.80 (dd, J=40.6, 9.2 Hz, 3H), 3.14 (s, 4H), 2.64 (s, 5H), 2.46 (s, 4H), 2.19 (d, J=8.8 Hz, 9H), 2.06-1.95 (m, 3H), 1.80 (s, 4H), 1.61 (s, 3H), 1.52 (s, 6H), 1.02-0.71 (m, 9H).

Example A185
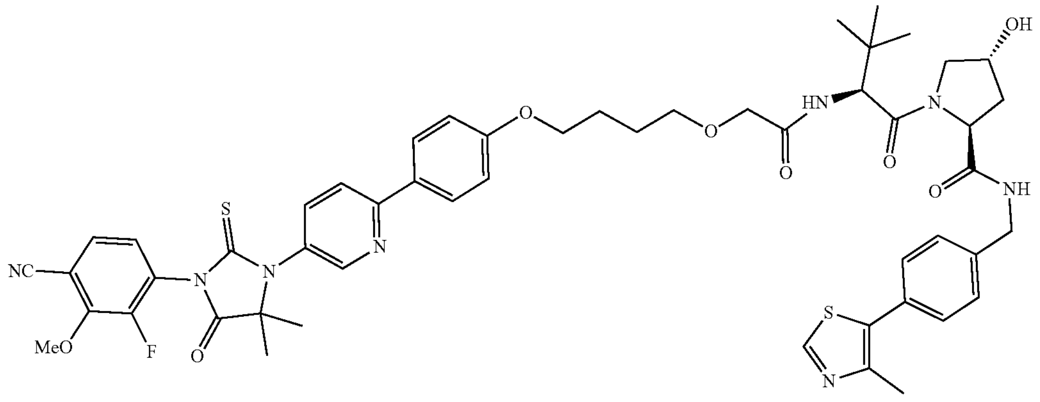 [SMILES: COc1c(C#N)ccc(N2C(=O)C(C)(C)N(c3ccc(-c4ccc(OCCCCOCC(=O)N[C@H](C(=O)N5C[C@H](O)C[C@H]5C(=O)NCc5ccc(-c6scnc6C)cc5)C(C)(C)C)cc4)nc3)C2=S)c1F]
LCMS ([M+H]$^+$): 1005.4
$^1$HNMR (400 MHz, DMSO-d6) δ8.96 (d, J=9.6 Hz, 1H), 8.68-8.56 (m, 2H), 8.09 (d, J=8.8 Hz, 3H), 7.94 (dd, J=8.5, 2.5 Hz, 1H), 7.84 (dd, J=8.4, 1.6 Hz, 1H), 7.53 (dd, J=8.4, 6.4 Hz, 1H), 7.46-7.36 (m, 5H), 7.05 (d, J=8.9 Hz, 2H), 5.16 (s, 1H), 4.57 (m, 1H), 4.49-4.33 (m, 3H), 4.26 (m, 1H), 4.13 (m, 3H), 4.08 (m, 2H), 4.01-3.89 (m, 2H), 3.70-3.53 (m, 4H), 2.43 (d, J=7.2 Hz, 3H), 2.11-2.03 (m, 1H), 1.95-1.79 (m, 3H), 1.74 (m, 2H), 1.56 (s, 6H), 0.93 (d, J=6.9 Hz, 9H).
Example A186
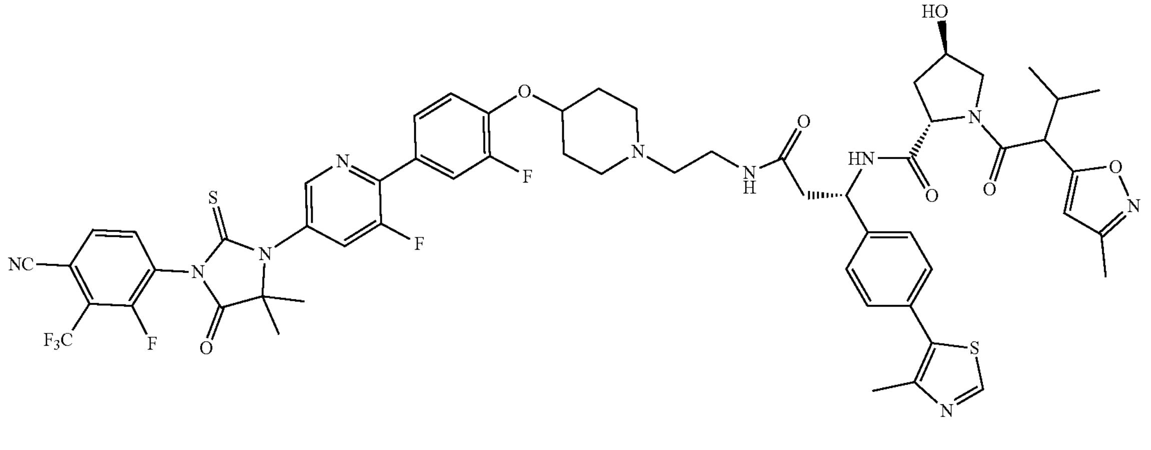 [SMILES: Cc1cc(C(C(=O)N2C[C@H](O)C[C@H]2C(=O)N[C@@H](CC(=O)NCCN2CCC(Oc3ccc(-c4ncc(N5C(=S)N(c6ccc(C#N)c(C(F)(F)F)c6F)C(=O)C5(C)C)cc4F)cc3F)CC2)c2ccc(-c3scnc3C)cc2)C(C)C)on1]
LCMS ([M+H]$^+$): 1185.4
$^1$HNMR (400 MHz, DMSO-d6) δ9.00-8.93 (m, 1H), 8.64 (s, 1H), 8.29 (d, J=3.6 Hz, 2H), 8.17 (dd, J=11.8, 1.8 Hz, 1H), 7.85 (t, J=11.1 Hz, 2H), 7.49-7.27 (m, 5H), 6.23 (d, J=12.4 Hz, 1H), 5.21 (d, J=7.4 Hz, 1H), 5.10 (s, 1H), 4.65 (d, J=36.0 Hz, 1H), 4.36 (s, 1H), 4.28 (s, 1H), 3.76 (d, J=9.7 Hz, 1H), 3.59-3.43 (m, 2H), 3.34-3.12 (m, 10H), 2.70-2.54 (m, 3H), 2.46 (s, 3H), 2.20 (d, J=10.2 Hz, 3H), 2.13-1.96 (m, 3H), 1.92-1.68 (m, 3H), 1.62 (s, 6H), 1.24 (s, 1H), 0.97 (t, J=6.2 Hz, 2H), 0.82-0.71 (m, 3H).

Example A187
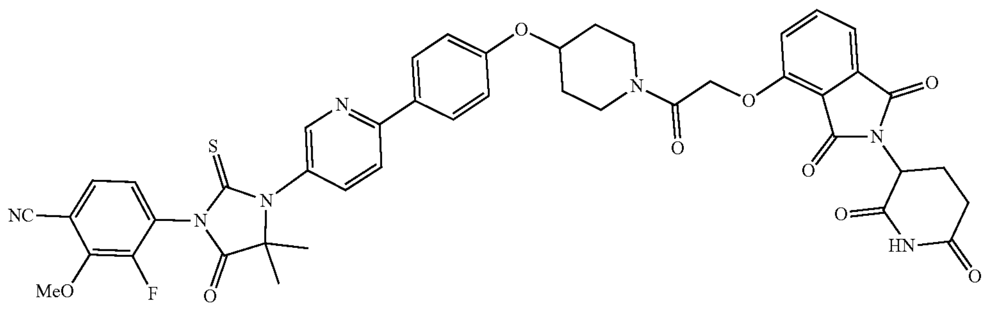 [SMILES: COc1c(C#N)ccc(N2C(=O)C(C)(C)N(c3ccc(-c4ccc(OC5CCN(C(=O)COc6cccc7c6C(=O)N(C6CCC(=O)NC6=O)C7=O)CC5)cc4)nc3)C2=S)c1F]
LCMS ([M+H]$^+$): 860.2
$^1$HNMR (400 MHz, DMSO-d6) δ11.12 (s, 1H), 8.22 (d, J=2.8 Hz, 1H), 7.92-7.70 (m, 5H), 7.47 (dd, J=25.9, 7.8 Hz, 2H), 7.29 (dd, J=8.7, 2.8 Hz, 1H), 7.05 (d, J=7.3 Hz, 2H), 6.43 (s, 1H), 5.40-5.09 (m, 4H), 4.77 (1H), 4.10-3.89 (m, 5H), 2.94-2.86 (m, 2H), 2.67-2.57 (m, 2H), 2.03 (m, 2H), 1.68 (s, 6H).
Example A188
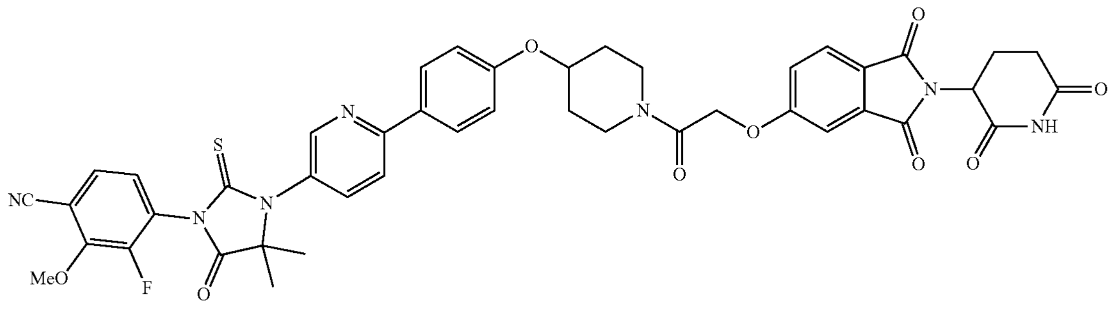 [SMILES: COc1c(C#N)ccc(N2C(=O)C(C)(C)N(c3ccc(-c4ccc(OC5CCN(C(=O)COc6ccc7c(c6)C(=O)N(C6CCC(=O)NC6=O)C7=O)CC5)cc4)nc3)C2=S)c1F]
LCMS ([M+H]$^+$): 860.2
$^1$HNMR (400 MHz, DMSO-d6) δ11.11 (s, 1H), 8.23 (d, J=2.7 Hz, 1H), 7.92-7.86 (m, 3H), 7.75 (d, J=8.7 Hz, 2H), 7.49 (s, 1H), 7.37 (m, 1H), 7.29 (dd, J=8.7, 2.9 Hz, 1H), 7.05 (d, J=8.6 Hz, 2H), 6.45 (s, 1H), 5.55-4.99 (m, 4H), 4.77 (s, 1H), 4.20-4.03 (m, 4H), 3.89-3.73 (m, 4H), 2.88 (m, 1H), 2.61 (m, 2H), 2.03-1.99 (m, 2H), 1.69 (s, 6H).

Example A189
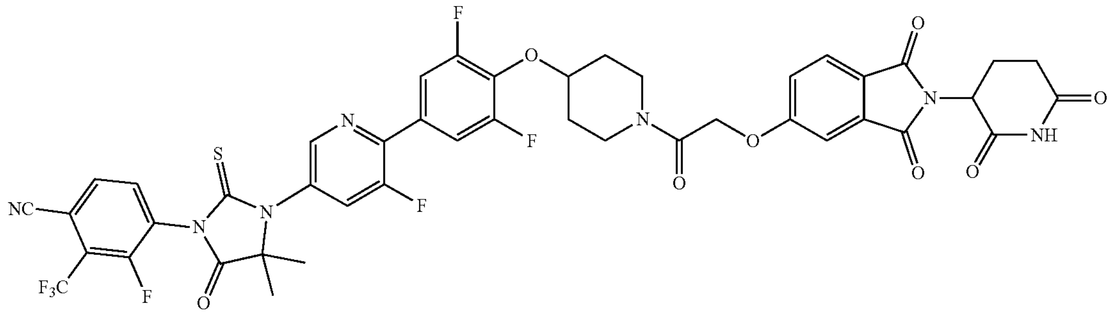 [SMILES: CC1(C)C(=O)N(c2ccc(C#N)c(C(F)(F)F)c2F)C(=S)N1c1cnc(-c2cc(F)c(OC3CCN(C(=O)COc4ccc5c(c4)C(=O)N(C4CCC(=O)NC4=O)C5=O)CC3)c(F)c2)c(F)c1]
LCMS ([M+H]+): 951.8
$^1$HNMR (400 MHz, DMSO-d6) δ11.10 (s, 1H), 8.68 (s, 1H), 8.32-8.20 (m, 3H), 7.82 (dd, J=11.7, 8.7 Hz, 3H), 7.46 (d, J=2.2 Hz, 1H), 7.36 (dd, J=8.3, 2.3 Hz, 1H), 5.23-5.06 (m, 3H), 4.57 (s, 1H), 3.84 (s, 1H), 3.72 (s, 1H), 3.35 (s, 2H), 2.97-2.82 (m, 1H), 2.57 (dd, J=19.9, 10.6 Hz, 2H), 2.03 (d, J=5.7 Hz, 2H), 1.95 (s, 1H), 1.83 (s, 1H), 1.61 (s, 6H).
Example A190
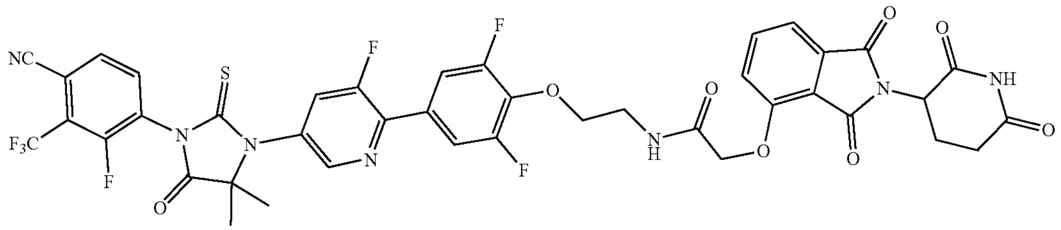 [SMILES: CC1(C)C(=O)N(c2ccc(C#N)c(C(F)(F)F)c2F)C(=S)N1c1cnc(-c2cc(F)c(OCCNC(=O)COc3cccc4c3C(=O)N(C3CCC(=O)NC3=O)C4=O)c(F)c2)c(F)c1]
LCMS ([M+H]+): 912.2
$^1$HNMR (400 MHz, DMSO-d6) δ11.10 (s, 1H), 8.66 (s, 1H), 8.28 (s, 2H), 8.25-8.17 (m, 2H), 7.77 (dd, J=16.9, 8.6 Hz, 3H), 7.47 (d, J=7.2 Hz, 1H), 7.40 (d, J=8.5 Hz, 1H), 5.10 (dd, J=12.9, 5.4 Hz, 1H), 4.81 (s, 2H), 4.31 (t, J=5.3 Hz, 2H), 3.57 (d, J=3.9 Hz, 2H), 2.96-2.79 (m, 1H), 2.55 (dd, J=20.2, 10.7 Hz, 2H), 2.03 (dd, J=14.8, 9.7 Hz, 1H), 1.61 (s, 6H).

Example A191
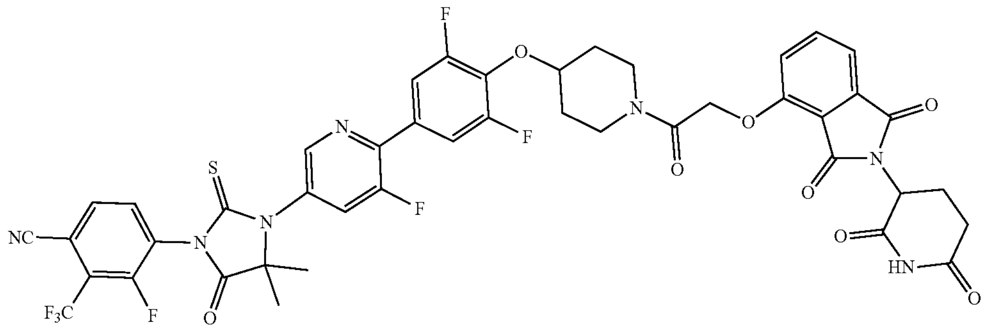 [SMILES: CC1(C)C(=O)N(c2ccc(C#N)c(C(F)(F)F)c2F)C(=S)N1c1cnc(-c2cc(F)c(OC3CCN(C(=O)COc4cccc5c4C(=O)N(C4CCC(=O)NC4=O)C5=O)CC3)c(F)c2)c(F)c1]
LCMS ([M+H]$^+$): 951.8
$^1$HNMR (400 MHz, DMSO-d6) δ11.10 (s, 1H), 8.68 (s, 1H), 8.31-8.21 (m, 3H), 7.79 (dd, J=14.1, 8.7 Hz, 3H), 7.45 (d, J=7.2 Hz, 1H), 7.36 (d, J=8.6 Hz, 1H), 5.23 (s, 2H), 5.11 (dd, J=12.9, 5.4 Hz, 1H), 4.57 (s, 1H), 3.77 (d, J=48.3 Hz, 2H), 3.34 (s, 2H), 2.88 (dd, J=17.4, 5.6 Hz, 1H), 2.57 (dd, J=19.5, 10.4 Hz, 2H), 2.07-2.01 (m, 2H), 1.95 (s, 1H), 1.86 (s, 1H), 1.68 (d, J=8.4 Hz, 1H), 1.61 (s, 6H).
Example A192
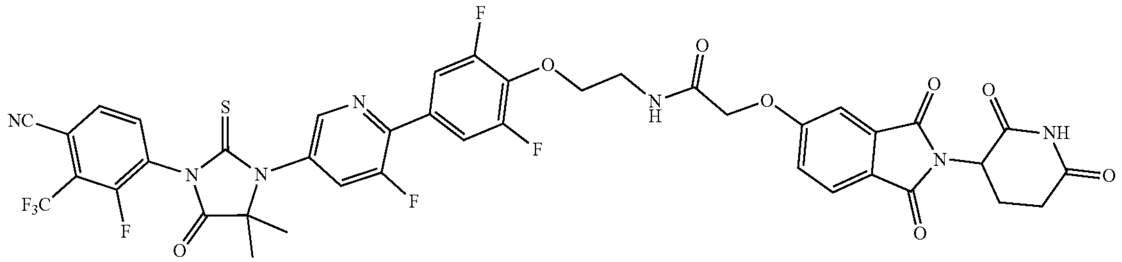 [SMILES: CC1(C)C(=O)N(c2ccc(C#N)c(C(F)(F)F)c2F)C(=S)N1c1cnc(-c2cc(F)c(OCCNC(=O)COc3ccc4c(c3)C(=O)N(C3CCC(=O)NC3=O)C4=O)c(F)c2)c(F)c1]
LCMS ([M+H]$^+$): 912.2
$^1$HNMR (400 MHz, DMSO-d6) δ11.10 (s, 1H), 8.66 (s, 1H), 8.44 (t, J=5.6 Hz, 1H), 8.29 (d, J=11.3 Hz, 2H), 8.25-8.19 (m, 1H), 7.85 (d, J=8.3 Hz, 1H), 7.81-7.71 (m, 2H), 7.46 (d, J=2.2 Hz, 1H), 7.39 (dd, J=8.3, 2.3 Hz, 1H), 5.11 (dd, J=12.9, 5.4 Hz, 1H), 4.76 (s, 2H), 4.30 (t, J=5.5 Hz, 2H), 3.55 (q, J=5.5 Hz, 2H), 2.88 (ddd, J=17.5, 14.3, 5.5 Hz, 1H), 2.64-2.51 (m, 2H), 2.04 (dd, J=9.0, 3.7 Hz, 1H), 1.61 (s, 6H).

Example A193
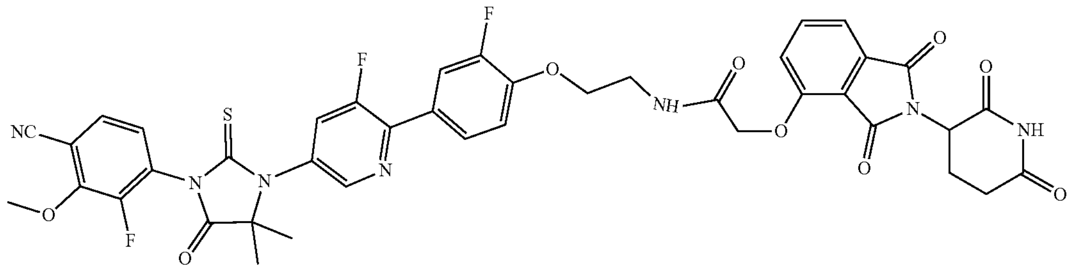 [SMILES: COc1c(C#N)ccc(N2C(=O)C(C)(C)N(c3cnc(-c4ccc(OCCNC(=O)COc5cccc6c5C(=O)N(C5CCC(=O)NC5=O)C6=O)c(F)c4)c(F)c3)C2=S)c1F]
LCMS ([M+H]$^+$): 856.2
$^1$HNMR (400 MHz, DMSO-d6) δ11.16 (s, 1H), 8.69 (s, 1H), 8.35 (t, J=5.6 Hz, 1H), 8.23 (dd, J=11.9, 1.9 Hz, 1H), 7.91 (t, J=8.7 Hz, 3H), 7.86-7.78 (m, 1H), 7.61-7.51 (m, 2H), 7.44 (m, 2H), 5.14 (m, 1H), 4.90 (m, 2H), 4.30 (m, 2H), 4.20 (d, J=2.5 Hz, 3H), 3.75-3.62 (m, 2H), 3.00-2.89 (m, 1H), 2.69-2.58 (m, 2H), 2.13-2.04 (m, 1H), 1.66 (d, J=2.9 Hz, 6H).
Example A194
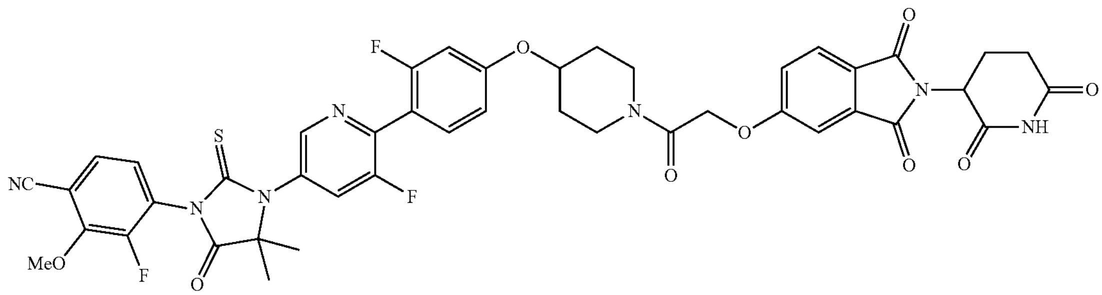 [SMILES: COc1c(C#N)ccc(N2C(=O)C(C)(C)N(c3cnc(-c4ccc(OC5CCN(C(=O)COc6ccc7c(c6)C(=O)N(C6CCC(=O)NC6=O)C7=O)CC5)cc4F)c(F)c3)C2=S)c1F]
LCMS ([M+H]$^+$): 896.2
$^1$HNMR (400 MHz, DMSO-d6) δ11.11 (s, 1H), 8.64 (s, 1H), 8.17 (dd, J=11.9, 1.8 Hz, 1H), 7.94-7.74 (m, 4H), 7.50 (ddd, J=13.8, 9.0, 4.2 Hz, 3H), 7.36 (dd, J=8.3, 2.3 Hz, 1H), 5.25-5.07 (m, 3H), 4.89-4.74 (m, 1H), 4.14 (d, J=2.6 Hz, 3H), 3.92-3.81 (m, 1H), 3.73 (d, J=12.7 Hz, 1H), 3.40 (dd, J=21.0, 6.7 Hz, 2H), 2.89 (ddd, J=17.4, 14.5, 5.4 Hz, 1H), 2.65-2.51 (m, 2H), 2.08 (s, 1H), 2.07-1.95 (m, 2H), 1.81 (d, J=8.2 Hz, 1H), 1.61 (t, J=11.2 Hz, 7H).

Example A195
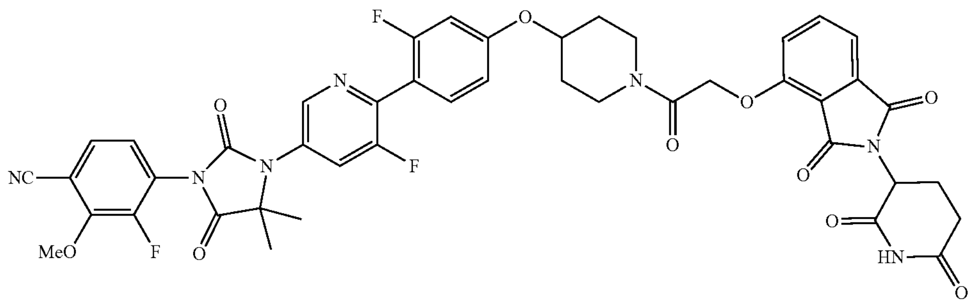 [SMILES: COc1c(C#N)ccc(N2C(=O)N(c3cnc(-c4ccc(OC5CCN(C(=O)COc6cccc7c6C(=O)N(C6CCC(=O)NC6=O)C7=O)CC5)cc4F)c(F)c3)C(C)(C)C2=O)c1F]
LCMS ([M+H]$^+$): 896.2
$^1$HNMR (400 MHz, DMSO-d6) δ11.16 (s, 1H), 8.69 (s, 1H), 8.23 (dd, J=11.9, 1.8 Hz, 1H), 7.87 (dt, J=15.8, 9.5 Hz, 4H), 7.55 (ddd, J=19.1, 11.5, 6.8 Hz, 3H), 7.42 (d, J=8.6 Hz, 1H), 5.28 (s, 2H), 5.16 (dd, J=12.9, 5.4 Hz, 1H), 4.88 (d, J=3.4 Hz, 1H), 4.19 (d, J=2.5 Hz, 3H), 3.92 (d, J=13.0 Hz, 1H), 3.78 (d, J=13.7 Hz, 1H), 3.52-3.38 (m, 2H), 2.95 (ddd, J=17.4, 13.9, 5.4 Hz, 1H), 2.69-2.56 (m, 2H), 2.11 (dt, J=11.1, 9.1 Hz, 3H), 1.88 (d, J=7.9 Hz, 1H), 1.68 (dd, J=22.4, 6.0 Hz, 7H).
Example A196
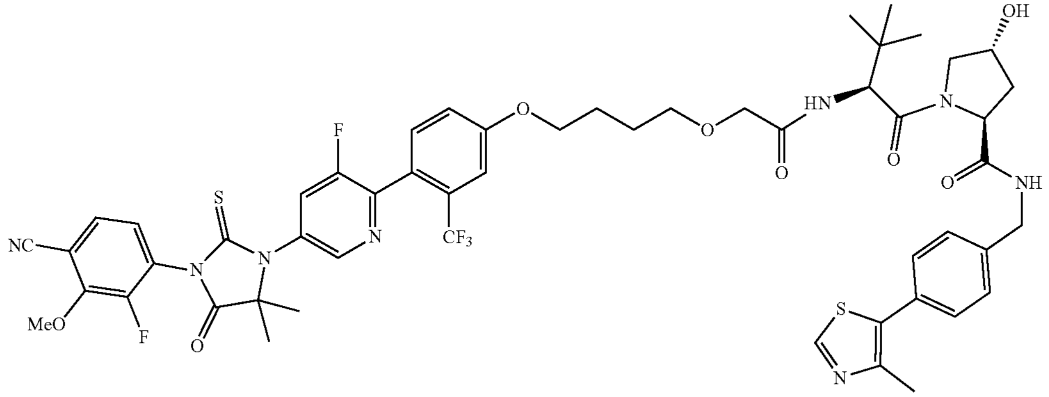 [SMILES: COc1c(C#N)ccc(N2C(=O)C(C)(C)N(c3cnc(-c4ccc(OCCCCOCC(=O)N[C@H](C(=O)N5C[C@H](O)C[C@H]5C(=O)NCc5ccc(-c6scnc6C)cc5)C(C)(C)C)cc4C(F)(F)F)c(F)c3)C2=S)c1F]
LCMS ([M+H]$^+$): 1091.4
$^1$HNMR (400 MHz, DMSO-d6) δ8.97 (d, J=10.7 Hz, 1H), 8.66-8.57 (m, 2H), 8.20 (dd, J=9.7, 1.9 Hz, 1H), 7.86 (dd, J=8.4, 1.6 Hz, 1H), 7.57-7.48 (m, 2H), 7.45-7.33 (m, 7H), 5.16 (d, J=3.5 Hz, 1H), 4.57 (d, J=9.6 Hz, 1H), 4.49-4.32 (m, 3H), 4.26 (dd, J=15.7, 5.6 Hz, 1H), 4.17 (t, J=6.2 Hz, 2H), 4.14 (d, J=2.6 Hz, 3H), 4.01-3.89 (m, 2H), 3.63 (ddd, J=27.0, 11.6, 5.0 Hz, 4H), 2.44 (d, J=7.1 Hz, 3H), 2.11-2.03 (m, 1H), 1.89 (tdd, J=17.0, 11.5, 5.2 Hz, 3H), 1.79-1.71 (m, 2H), 1.59 (d, J=5.6 Hz, 6H), 0.93 (d, J=6.5 Hz, 9H).

Example A197
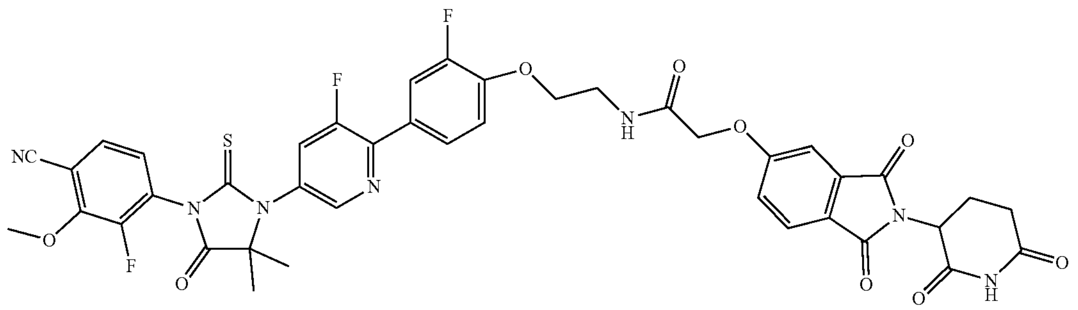 [SMILES: COc1c(C#N)ccc(N2C(=O)C(C)(C)N(c3cnc(-c4ccc(OCCNC(=O)COc5ccc6c(c5)C(=O)N(C5CCC(=O)NC5=O)C6=O)c(F)c4)c(F)c3)C2=S)c1F]
LCMS ([M+H]$^+$): 856.2
$^1$HNMR (400 MHz, DMSO-d6) δ11.10 (s, 1H), 8.63 (s, 1H), 8.51 (s, 1H), 8.16 (dd, J=11.9, 1.9 Hz, 1H), 7.89-7.80 (m, 4H), 7.51 (dd, J=8.4, 6.4 Hz, 1H), 7.46 (d, J=2.2 Hz, 1H), 7.42-7.33 (m, 2H), 5.11 (m, 1H), 4.78 (m, 2H), 4.23 (m, 2H), 4.14 (d, J=2.6 Hz, 3H), 3.60 (m, 2H), 2.88 (m, 1H), 2.64-2.51 (m, 2H), 2.04 (m, 1H), 1.59 (d, J=3.2 Hz, 6H).
Example A198
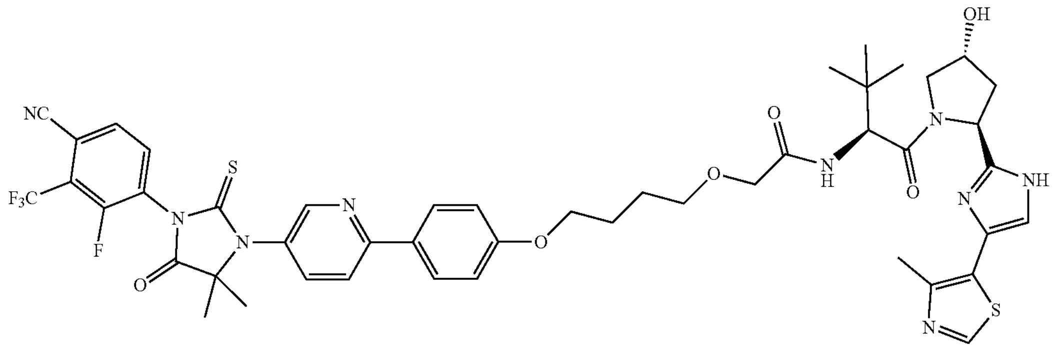 [SMILES: Cc1ncsc1-c1c[nH]c([C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2)C(C)(C)C)n1]
LCMS ([M+H]$^+$): 976.3
$^1$HNMR (400 MHz, DMSO-d6) δ12.13 (s, 1H), 8.72 (s, 1H), 8.65 (d, J=2.3 Hz, 1H), 8.29 (d, J=7.1 Hz, 2H), 8.10 (d, J=8.7 Hz, 3H), 7.94 (dd, J=8.5, 2.5 Hz, 1H), 7.32 (d, J=9.6 Hz, 1H), 7.25 (s, 1H), 7.07 (d, J=8.9 Hz, 2H), 5.21 (d, J=3.6 Hz, 1H), 5.05 (t, J=7.8 Hz, 1H), 4.57 (d, J=9.6 Hz, 1H), 4.45 (s, 1H), 4.08 (t, J=6.2 Hz, 2H), 3.95 (d, J=2.1 Hz, 2H), 3.84 (dd, J=10.7, 4.3 Hz, 1H), 3.63 (d, J=9.2 Hz, 1H), 3.55 (t, J=6.3 Hz, 2H), 2.46 (s, 3H), 2.26-2.11 (m, 2H), 1.86-1.77 (m, 2H), 1.77-1.68 (m, 2H), 1.58 (s, 6H), 0.88 (s, 9H).

Example A199
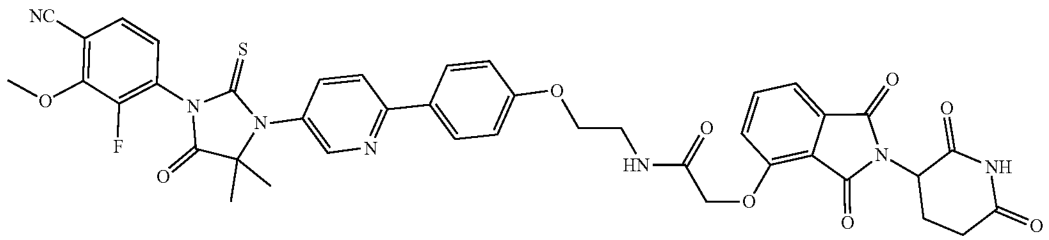 [SMILES: COc1c(C#N)ccc(N2C(=O)C(C)(C)N(c3ccc(-c4ccc(OCCNC(=O)COc5cccc6c5C(=O)N(C5CCC(=O)NC5=O)C6=O)cc4)nc3)C2=S)c1F]
LCMS ([M+H]$^+$): 820.2
$^1$HNMR (400 MHz, DMSO-d6) δ11.15 (s, 1H), 8.65 (s, 1H), 8.24 (s, 1H), 8.11 (d, J=8.4 Hz, 3H), 7.95 (d, J=7.8 Hz, 1H), 7.85 (d, J=8.2 Hz, 1H), 7.76 (t, J=7.8 Hz, 1H), 7.59-7.36 (m, 3H), 7.09 (d, J=8.4 Hz, 2H), 5.11 (dd, J=12.6, 5.1 Hz, 1H), 4.83 (s, 2H), 4.14 (s, 5H), 3.60 (d, J=4.4 Hz, 2H), 2.90 (t, J=13.2 Hz, 1H), 2.60 (d, J=18.5 Hz, 2H), 2.04 (dd, J=14.0, 7.3 Hz, 1H), 1.57 (s, 6H).
Example A200
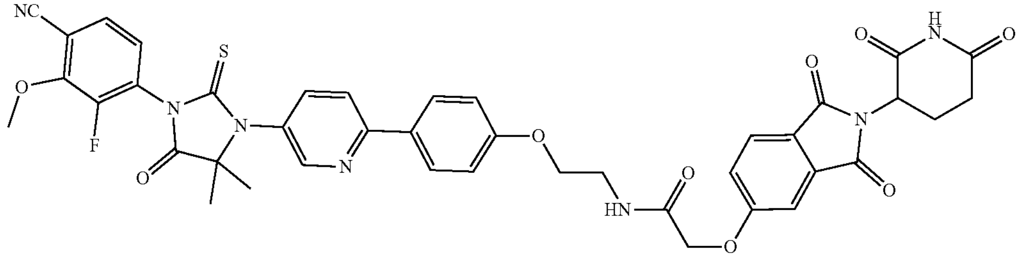 [SMILES: COc1c(C#N)ccc(N2C(=O)C(C)(C)N(c3ccc(-c4ccc(OCCNC(=O)COc5ccc6c(c5)C(=O)N(C5CCC(=O)NC5=O)C6=O)cc4)nc3)C2=S)c1F]
LCMS ([M+H]$^+$): 820.2
$^1$HNMR (400 MHz, DMSO-d6) δ11.13 (s, 1H), 8.66 (d, J=2.4 Hz, 1H), 8.50 (t, J=5.6 Hz, 1H), 8.12 (d, J=8.8 Hz, 3H), 7.96 (dd, J=8.5, 2.5 Hz, 1H), 7.86 (d, J=8.3 Hz, 2H), 7.54 (dd, J=8.4, 6.4 Hz, 1H), 7.47 (d, J=2.2 Hz, 1H), 7.40 (dd, J=8.3, 2.3 Hz, 1H), 7.08 (d, J=8.9 Hz, 2H), 5.12 (dd, J=12.9, 5.4 Hz, 1H), 4.79 (s, 2H), 4.13 (t, J=4.6 Hz, 5H), 3.57 (dd, J=11.0, 5.5 Hz, 2H), 2.88 (ddd, J=17.0, 13.9, 5.2 Hz, 1H), 2.58 (dd, J=21.5, 6.6 Hz, 2H), 2.04 (dd, J=10.6, 5.3 Hz, 1H), 1.57 (s, 6H).

Example A201
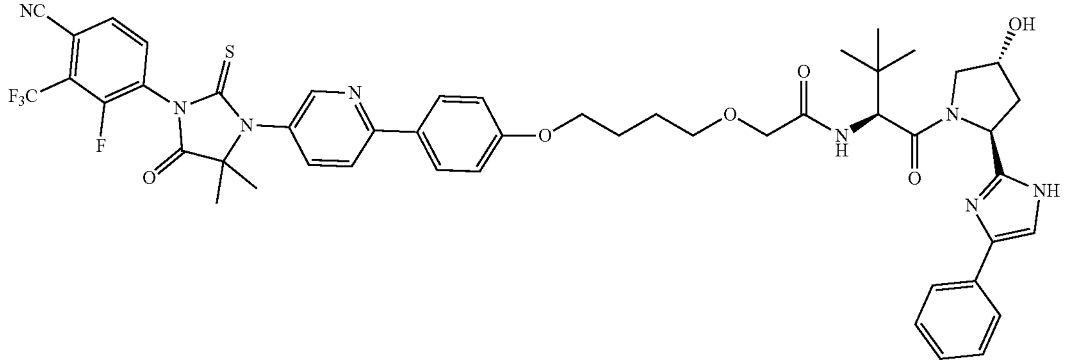 [SMILES: CC(C)(C)[C@H](NC(=O)COCCCCOc1ccc(-c2ccc(N3C(=S)N(c4ccc(C#N)c(C(F)(F)F)c4F)C(=O)C3(C)C)cn2)cc1)C(=O)N1C[C@H](O)C[C@H]1c1nc(-c2ccccc2)c[nH]1]
LCMS ([M+H]$^+$): 955.3
$^1$HNMR (400 MHz, DMSO-d6) δ11.89 (s, 1H), 8.65 (d, J=2.3 Hz, 1H), 8.29 (d, J=6.9 Hz, 2H), 8.10 (d, J=8.7 Hz, 3H), 7.93 (dd, J=8.4, 2.4 Hz, 1H), 7.69 (d, J=6.8 Hz, 2H), 7.45 (s, 1H), 7.34 (d, J=9.6 Hz, 3H), 7.18-7.02 (m, 3H), 5.22 (s, 1H), 5.08 (s, 1H), 4.57 (d, J=9.4 Hz, 1H), 4.48 (s, 1H), 4.08 (t, J=6.0 Hz, 2H), 3.95 (s, 2H), 3.86 (d, J=7.6 Hz, 1H), 3.64 (d, J=10.9 Hz, 1H), 3.55 (s, 1H), 2.20 (d, J=27.5 Hz, 2H), 2.04-1.93 (m, 1H), 1.81 (d, J=7.6 Hz, 2H), 1.76-1.68 (m, 2H), 1.58 (s, 6H), 0.90 (d, J=27.2 Hz, 9H).
Example A202
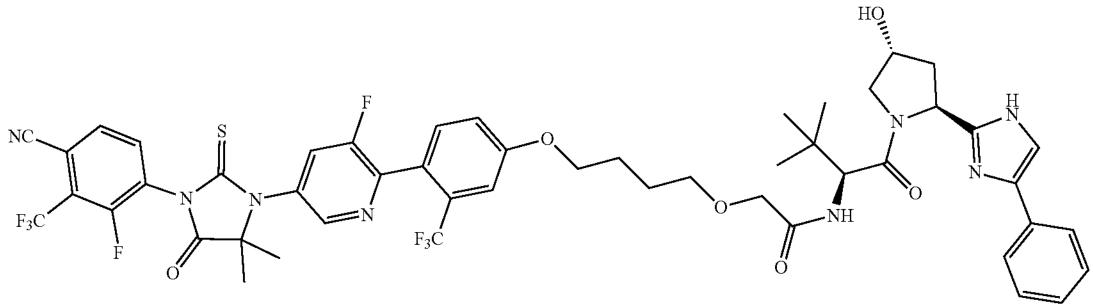 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)c(C(F)(F)F)c1)C(=O)N1C[C@H](O)C[C@H]1c1nc(-c2ccccc2)c[nH]1]
LCMS ([M+H]$^+$): 1041.3
$^1$HNMR (400 MHz, DMSO-d6) δ12.07 (d, J=149.8 Hz, 1H), 8.63 (s, 1H), 8.28 (s, 2H), 8.23-8.16 (m, 1H), 7.65 (dd, J=35.7, 7.4 Hz, 2H), 7.54 (t, J=7.2 Hz, 1H), 7.48-7.22 (m, 6H), 7.15 (dt, J=25.3, 7.4 Hz, 1H), 5.21 (d, J=3.5 Hz, 1H), 5.13-5.02 (m, 1H), 4.58 (d, J=9.5 Hz, 1H), 4.48 (s, 1H), 4.17 (t, J=6.0 Hz, 2H), 4.02-3.82 (m, 3H), 3.64 (d, J=9.6 Hz, 1H), 3.56 (t, J=6.2 Hz, 2H), 2.28-2.19 (m, 1H), 2.18-2.10 (m, 1H), 1.89-1.79 (m, 2H), 1.79-1.69 (m, 2H), 1.60 (s, 6H), 0.96-0.81 (m, 9H).

Example A203
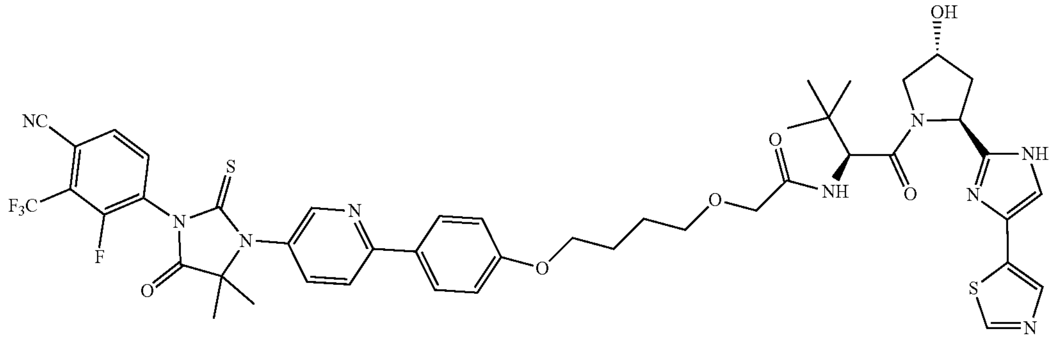 [SMILES: CC(C)(C)[C@H](NC(=O)COCCCCOc1ccc(-c2ccc(N3C(=S)N(c4ccc(C#N)c(C(F)(F)F)c4F)C(=O)C3(C)C)cn2)cc1)C(=O)N1C[C@H](O)C[C@H]1c1nc(-c2cncs2)c[nH]1]
LCMS ([M+H]$^+$): 962.3
$^1$HNMR (400 MHz, DMSO-d6) δ12.60-12.02 (m, 1H), 8.96-8.81 (m, 1H), 8.65 (d, J=2.2 Hz, 1H), 8.29 (q, J=8.5 Hz, 2H), 8.08 (t, J=12.4 Hz, 3H), 8.01-7.91 (m, 2H), 7.45 (d, J=1.8 Hz, 1H), 7.33 (d, J=9.5 Hz, 1H), 7.08 (t, J=13.6 Hz, 2H), 5.22 (m, 1H), 5.04 (m, 1H), 4.57 (m, 1H), 4.45 (m, 1H), 4.07 (m, 2H), 4.01-3.88 (m, 2H), 3.84 (m, 1H), 3.63 (m, 1H), 3.55 (m, 2H), 2.26-2.10 (m, 2H), 1.80 (m, 2H), 1.72 (m, 2H), 1.58 (m, 6H), 0.98-0.81 (m, 9H).
Example A204
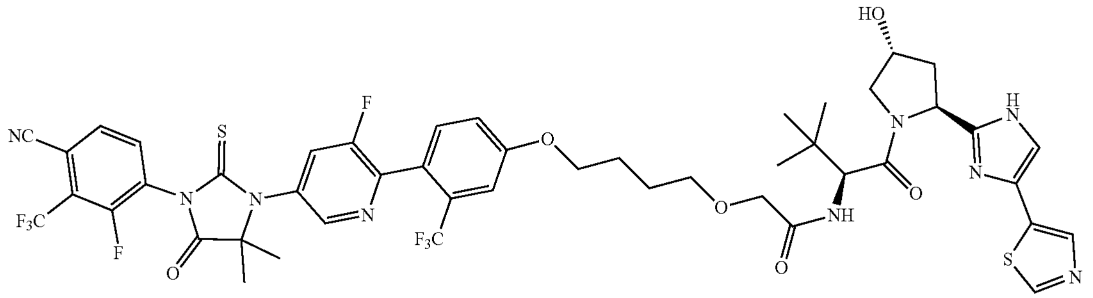 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)c(C(F)(F)F)c1)C(=O)N1C[C@H](O)C[C@H]1c1nc(-c2cncs2)c[nH]1]
LCMS ([M+H]$^+$): 1048.3
$^1$HNMR (400 MHz, DMSO-d6) δ12.17 (d, J=70.6 Hz, 1H), 8.99-8.80 (m, 1H), 8.63 (s, 1H), 8.30 (d, J=11.6 Hz, 2H), 8.20 (dd, J=9.7, 1.7 Hz, 1H), 8.01 (d, J=28.8 Hz, 1H), 7.55 (d, J=9.2 Hz, 1H), 7.44 (t, J=4.8 Hz, 1H), 7.37 (d, J=6.7 Hz, 2H), 7.33 (d, J=9.6 Hz, 1H), 5.21 (m, 1H), 5.04 (m, 1H), 4.57 (m, 1H), 4.44 (s, 1H), 4.17 (m, 2H), 4.03-3.90 (m, 2H), 3.84 (m, 1H), 3.63 (m, 1H), 3.56 (m, 2H), 2.26-2.09 (m, 2H), 1.83 (m, 2H), 1.74 (m, 2H), 1.60 (m, 6H), 0.97-0.81 (m, 9H).

6Example A205
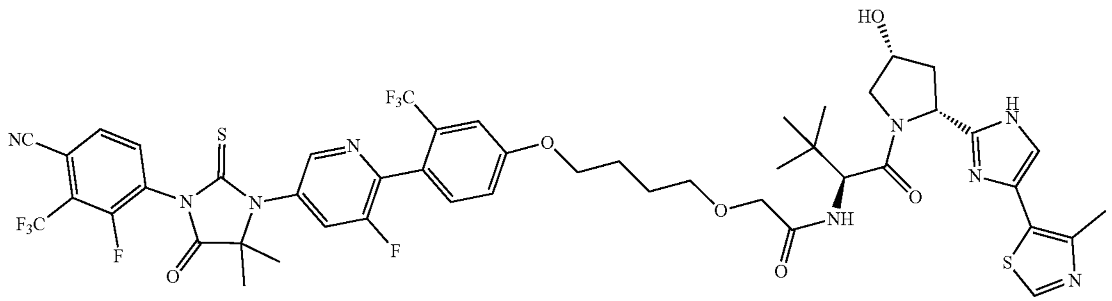 [SMILES: Cc1ncsc1-c1c[nH]c([C@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)c(C(F)(F)F)c2)C(C)(C)C)n1]
LCMS ([M+H]+): 1062.1
$^1$HNMR (400 MHz, DMSO-d6) δ12.22 (s, 1H), 8.77 (d, J=10.0 Hz, 1H), 8.62 (s, 1H), 8.29 (s, 2H), 8.20 (d, J=9.8 Hz, 1H), 7.56 (d, J=8.5 Hz, 1H), 7.37 (t, J=10.7 Hz, 3H), 7.22 (s, 1H), 6.37 (d, J=7.9 Hz, 1H), 5.38-5.29 (m, 1H), 5.06 (d, J=7.3 Hz, 1H), 4.57 (d, J=9.5 Hz, 1H), 4.38 (s, 2H), 4.20-4.08 (m, 3H), 4.00-3.82 (m, 4H), 3.75-3.64 (m, 2H), 3.57 (s, 2H), 3.43 (s, 2H), 2.45 (s, 3H), 1.99 (dd, J=14.4, 7.0 Hz, 3H), 1.75 (s, 2H), 1.63 (d, J=18.2 Hz, 6H), 1.45 (s, 1H), 0.89 (d, J=35.1 Hz, 7H), 0.59 (s, 2H).
Example A206
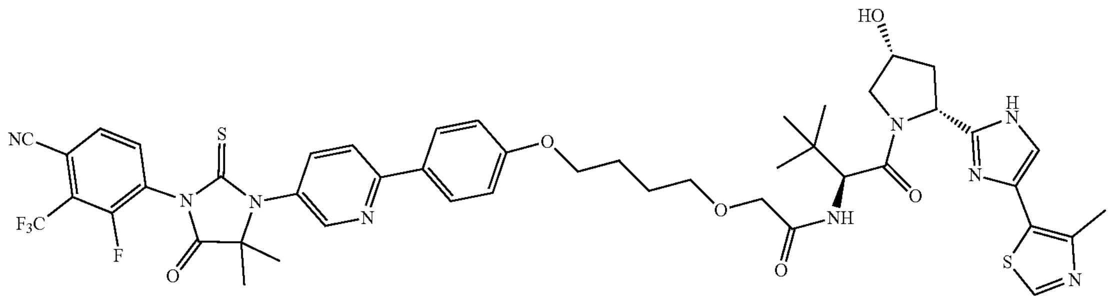 [SMILES: Cc1ncsc1-c1c[nH]c([C@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2)C(C)(C)C)n1]
LCMS ([M+H]+): 976.1
$^1$HNMR (400 MHz, DMSO-d6) δ12.13 (d, J=72.7 Hz, 1H), 8.77 (d, J=7.7 Hz, 1H), 8.65 (s, 1H), 8.29 (q, J=8.6 Hz, 2H), 8.11 (dd, J=8.4, 4.7 Hz, 3H), 7.95 (dd, J=8.4, 2.5 Hz, 1H), 7.41-7.19 (m, 2H), 7.06 (dd, J=15.5, 8.9 Hz, 2H), 6.32 (dd, J=40.6, 6.2 Hz, 1H), 5.67 (d, J=9.3 Hz, OH), 5.07 (d, J=7.6 Hz, 1H), 4.76 (d, J=8.9 Hz, OH), 4.56 (d, J=9.4 Hz, 1H), 4.38 (s, 1H), 4.13-3.83 (m, 5H), 3.69 (dd, J=22.9, 8.1 Hz, 1H), 3.56 (s, 1H), 3.41 (d, J=8.3 Hz, 2H), 2.46 (d, J=12.6 Hz, 3H), 2.09-1.97 (m, 1H), 1.76 (dd, J=39.5, 6.4 Hz, 3H), 1.66-1.52 (m, 7H), 0.94 (s, 6H), 0.59 (s, 3H).

Example A207
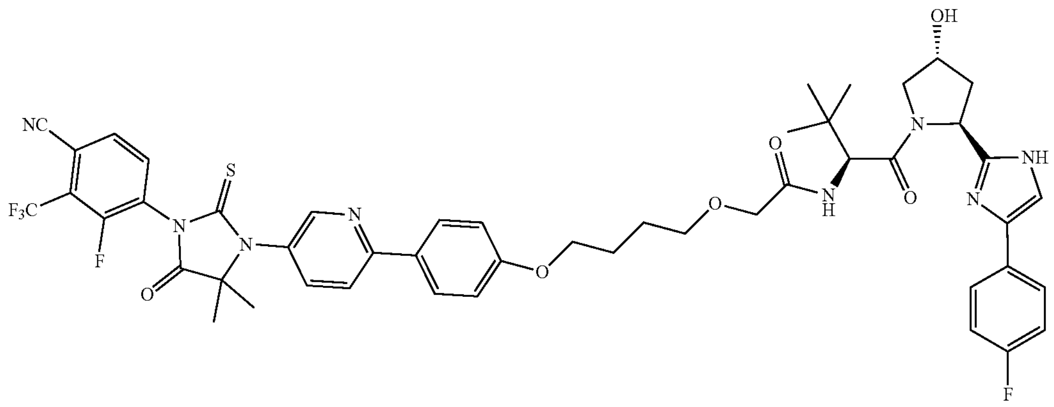 [SMILES: CC(C)(C)[C@H](NC(=O)COCCCCOc1ccc(-c2ccc(N3C(=S)N(c4ccc(C#N)c(C(F)(F)F)c4F)C(=O)C3(C)C)cn2)cc1)C(=O)N1C[C@H](O)C[C@H]1c1nc(-c2ccc(F)cc2)c[nH]1]
LCMS ([M+H]$^+$): 973.3
$^1$HNMR (400 MHz, DMSO-d6) δ12.31-11.85 (m, 1H), 8.65 (d, J=2.3 Hz, 1H), 8.35-8.24 (m, 2H), 8.11 (t, J=6.9 Hz, 3H), 7.93 (dd, J=8.5, 2.4 Hz, 1H), 7.68 (ddd, J=30.2, 8.7, 5.5 Hz, 2H), 7.48-7.18 (m, 2H), 7.17-7.03 (m, 4H), 5.37-5.19 (m, 1H), 5.14-5.04 (m, 1H), 4.57 (m, 1H), 4.47 (m, 1H), 4.08 (m, 2H), 4.01-3.90 (m, 2H), 3.86 (m, 1H), 3.64 (m, 1H), 3.56 (m, 2H), 2.30-2.09 (m, 2H), 1.89-1.77 (m, 2H), 1.77-1.67 (m, 2H), 1.58 (s, 6H), 0.98-0.79 (m, 9H).
Example A208
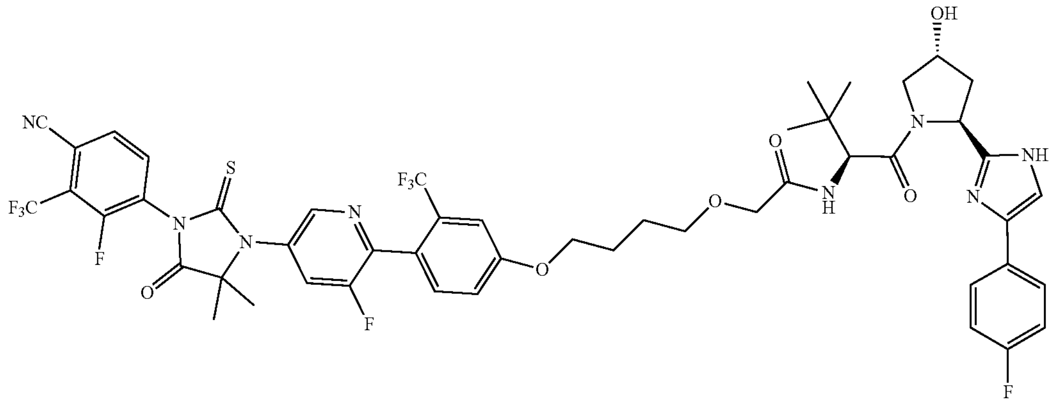 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)c(C(F)(F)F)c1)C(=O)N1C[C@H](O)C[C@H]1c1nc(-c2ccc(F)cc2)c[nH]1]
LCMS ([M+H]$^+$): 973.3
$^1$HNMR (400 MHz, DMSO-d6) δ12.32-11.83 (m, 1H), 8.63 (s, 1H), 8.34-8.25 (m, 2H), 8.20 (dd, J=9.7, 1.8 Hz, 1H), 7.67 (m, 2H), 7.55 (d, J=9.1 Hz, 1H), 7.48-7.08 (m, 6H), 5.20 (d, J=3.7 Hz, 1H), 5.06 (t, J=7.8 Hz, 1H), 4.58 (d, J=9.6 Hz, 1H), 4.47 (m, 1H), 4.17 (m, 2H), 3.96 (m, 2H), 3.85 (m, 1H), 3.69-3.52 (m, 3H), 2.27-2.06 (m, 2H), 1.92-1.80 (m, 2H), 1.74 (m, 2H), 1.60 (s, 6H), 0.99-0.78 (m, 9H).

Example A209
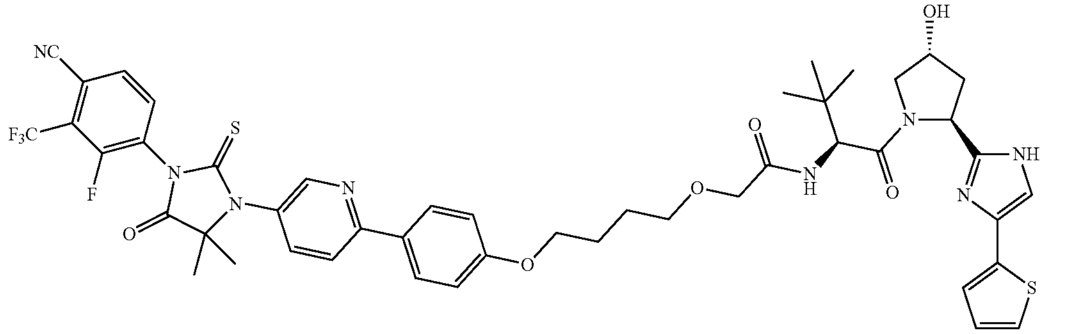 [SMILES: CC(C)(C)[C@H](NC(=O)COCCCCOc1ccc(-c2ccc(N3C(=S)N(c4ccc(C#N)c(C(F)(F)F)c4F)C(=O)C3(C)C)cn2)cc1)C(=O)N1C[C@H](O)C[C@H]1c1nc(-c2cccs2)c[nH]1]
LCMS ([M+H]$^+$): 961.3
$^1$HNMR (400 MHz, DMSO-d6) δ12.40-11.86 (m, 1H), 8.65 (d, J=2.4 Hz, 1H), 8.32-8.26 (m, 2H), 8.10 (d, J=8.7 Hz, 3H), 7.94 (dd, J=8.5, 2.5 Hz, 1H), 7.41-7.28 (m, 2H), 7.28-7.22 (m, 1H), 7.20-7.11 (m, 1H), 7.07 (d, J=8.9 Hz, 2H), 7.03-6.95 (m, 1H), 5.21 (d, J=3.7 Hz, 1H), 5.13-4.98 (m, 1H), 4.57 (d, J=9.6 Hz, 1H), 4.46-4.44 (m, 1H), 4.08 (t, J=6.2 Hz, 2H), 4.01-3.89 (m, 2H), 3.84 (dd, J=10.6, 4.3 Hz, 1H), 3.67-3.62 (m, 1H), 3.60-3.54 (m, 2H), 2.23-2.11 (m, 2H), 1.83-1.78 (m, 2H), 1.75-1.70 (m, 2H), 1.58 (s, 6H), 0.93-0.85 (m, 9H).
Example A210
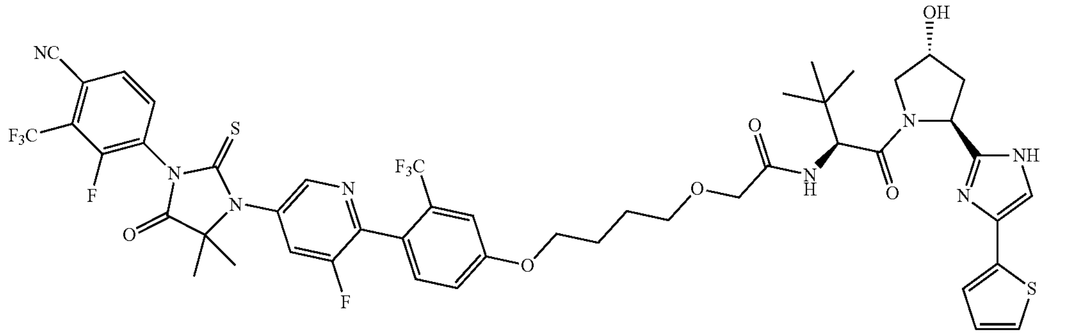 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)c(C(F)(F)F)c1)C(=O)N1C[C@H](O)C[C@H]1c1nc(-c2cccs2)c[nH]1]
LCMS ([M+H]$^+$): 1047.3
$^1$HNMR (400 MHz, DMSO-d6) δ12.35-11.92 (m, 1H), 8.63 (s, 1H), 8.32-8.27 (m, 2H), 8.20 (dd, J=9.7, 1.8 Hz, 1H), 7.55 (d, J=9.2 Hz, 1H), 7.39-7.30 (m, 4H), 7.27-7.23 (m, 1H), 7.16 (d, J=2.5 Hz, 1H), 7.00-6.96 (m, 1H), 5.20 (d, J=3.7 Hz, 1H), 5.09-5.02 (m, 1H), 4.57 (d, J=9.6 Hz, 1H), 4.46-4.43 (m, 1H), 4.17 (t, J=6.1 Hz, 2H), 4.00-3.92 (m, 2H), 3.84 (dd, J=10.6, 4.3 Hz, 1H), 3.64-3.55 (m, 3H), 2.22-2.10 (m, 2H), 1.86-1.82 (m, 2H), 1.77-1.72 (m, 2H), 1.60 (s, 6H), 0.93-0.84 (m, 9H).

Example A211
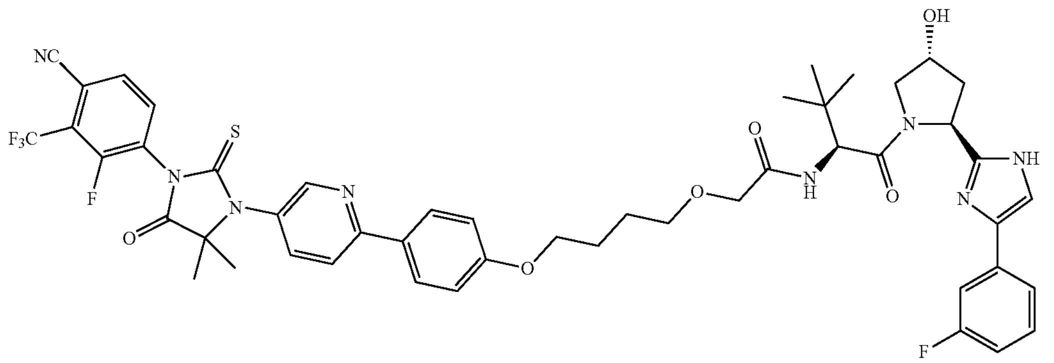 [SMILES: CC(C)(C)[C@H](NC(=O)COCCCCOc1ccc(-c2ccc(N3C(=S)N(c4ccc(C#N)c(C(F)(F)F)c4F)C(=O)C3(C)C)cn2)cc1)C(=O)N1C[C@H](O)C[C@H]1c1nc(-c2cccc(F)c2)c[nH]1]
LCMS ([M+H]$^+$): 973.3
$^1$HNMR (400 MHz, DMSO-d6) δ12.04 (s, 1H), 8.65 (d, J=2.4 Hz, 1H), 8.34-8.25 (m, 2H), 8.10 (d, J=8.8 Hz, 3H), 7.93 (dd, J=8.5, 2.5 Hz, 1H), 7.65-7.44 (m, 3H), 7.34 (d, J=9.5 Hz, 2H), 7.06 (d, J=8.9 Hz, 2H), 6.96 (s, 1H), 5.24 (s, 1H), 5.09 (t, J=7.8 Hz, 1H), 4.58 (d, J=9.6 Hz, 1H), 4.47 (d, J=9.5 Hz, 1H), 4.07 (t, J=6.1 Hz, 2H), 4.01-3.73 (m, 3H), 3.64 (dd, J=14.4, 7.8 Hz, 1H), 3.55 (t, J=6.3 Hz, 2H), 2.31-2.11 (m, 2H), 1.81 (dt, J=13.7, 6.3 Hz, 2H), 1.71 (dq, J=15.4, 8.3, 7.0 Hz, 2H), 1.58 (s, 6H), 0.91 (d, J=23.4 Hz, 9H).
Example A212
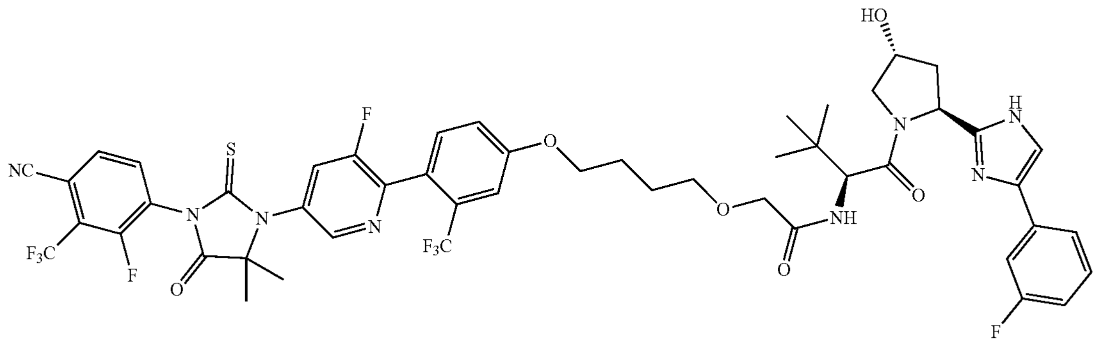 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)c(C(F)(F)F)c1)C(=O)N1C[C@H](O)C[C@H]1c1nc(-c2cccc(F)c2)c[nH]1]
LCMS ([M+H]$^+$): 1059.3
$^1$HNMR (400 MHz, DMSO-d6) δ12.17 (d, J=148.3 Hz, 1H), 8.63 (s, 1H), 8.28 (s, 2H), 8.19 (dd, J=9.7, 1.6 Hz, 1H), 7.61-7.42 (m, 4H), 7.42-7.27 (m, 4H), 6.93 (td, J=8.6, 2.3 Hz, 1H), 5.21 (d, J=3.6 Hz, 1H), 5.07 (t, J=7.7 Hz, 1H), 4.59 (d, J=9.5 Hz, 1H), 4.46 (d, J=13.4 Hz, 1H), 4.17 (t, J=5.9 Hz, 2H), 3.96 (s, 2H), 3.87 (dd, J=10.4, 4.1 Hz, 1H), 3.69-3.60 (m, 1H), 3.56 (t, J=6.2 Hz, 2H), 2.32-2.10 (m, 2H), 1.92-1.79 (m, 2H), 1.74 (dt, J=13.3, 6.4 Hz, 2H), 1.60 (s, 6H), 0.96-0.80 (m, 9H).

Example A213
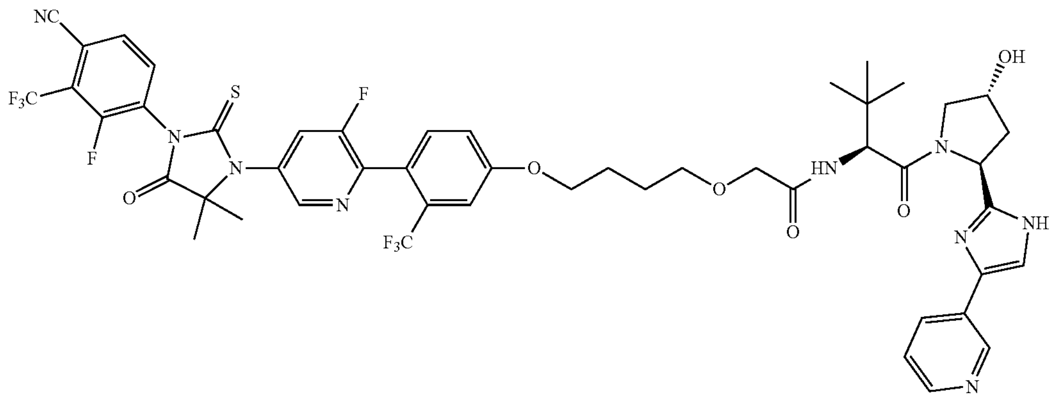 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)c(C(F)(F)F)c1)C(=O)N1C[C@H](O)C[C@H]1c1nc(-c2cccnc2)c[nH]1]
LCMS ([M+H]$^+$): 1042.3
$^1$HNMR (400 MHz, DMSO-d6) δ12.51-12.00 (m, 1H), 8.89 (dd, J=19.1, 1.9 Hz, 1H), 8.63 (s, 1H), 8.41-8.32 (m, 1H), 8.32-8.25 (m, 2H), 8.19 (dd, J=9.7, 1.9 Hz, 1H), 8.00 (ddd, J=13.9, 7.9, 6.0 Hz, 1H), 7.61 (dd, J=12.5, 2.0 Hz, 1H), 7.55 (d, J=9.2 Hz, 1H), 7.43-7.28 (m, 4H), 5.25 (t, J=23.5 Hz, 1H), 5.09 (d, J=7.9 Hz, 1H), 4.57 (t, J=8.1 Hz, 1H), 4.52-4.32 (m, 1H), 4.17 (t, J=6.1 Hz, 2H), 4.05-3.91 (m, 2H), 3.87 (dd, J=10.5, 4.1 Hz, 1H), 3.60 (dt, J=12.4, 8.3 Hz, 3H), 2.29-2.11 (m, 2H), 1.93-1.68 (m, 4H), 1.60 (s, 6H), 1.00-0.77 (m, 9H).
Example A214
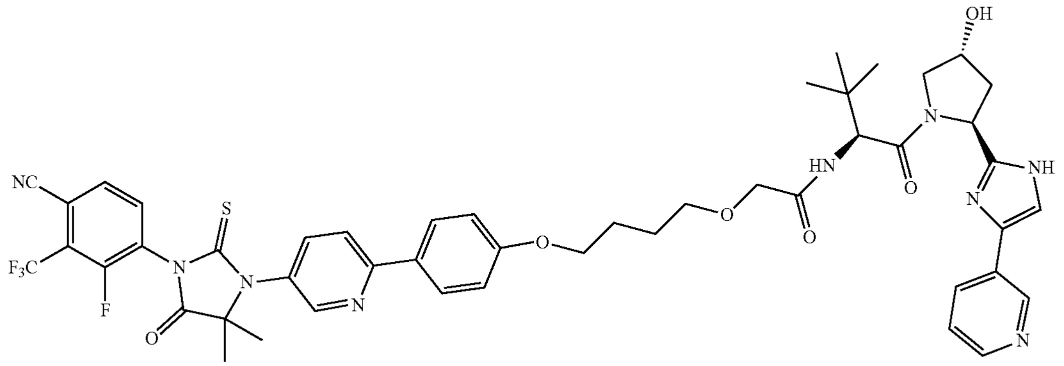 [SMILES: CC(C)(C)[C@H](NC(=O)COCCCCOc1ccc(-c2ccc(N3C(=S)N(c4ccc(C#N)c(C(F)(F)F)c4F)C(=O)C3(C)C)cn2)cc1)C(=O)N1C[C@H](O)C[C@H]1c1nc(-c2cccnc2)c[nH]1]
LCMS ([M+H]$^+$): 956.4
$^1$HNMR (400 MHz, DMSO-d6) δ12.17 (s, 1H), 8.92 (dd, J=7.7, 1.9 Hz, 1H), 8.66 (d, J=2.4 Hz, 1H), 8.36 (dd, J=4.7, 1.4 Hz, 1H), 8.34-8.24 (m, 2H), 8.11 (t, J=7.4 Hz, 3H), 8.03 (dt, J=7.9, 1.8 Hz, 1H), 7.94 (dd, J=8.5, 2.5 Hz, 1H), 7.62 (s, 1H), 7.41-7.30 (m, 2H), 7.07 (d, J=8.9 Hz, 2H), 5.24 (d, J=3.0 Hz, 1H), 5.10 (t, J=7.8 Hz, 1H), 4.59 (d, J=9.6 Hz, 1H), 4.54-4.41 (m, 1H), 4.08 (t, J=6.2 Hz, 2H), 4.02-3.83 (m, 3H), 3.71 (dd, J=38.2, 12.9 Hz, 1H), 3.56 (t, J=6.2 Hz, 2H), 2.36-2.10 (m, 2H), 1.92-1.67 (m, 4H), 1.59 (s, 6H), 0.92 (d, J=22.6 Hz, 9H).

Example A215
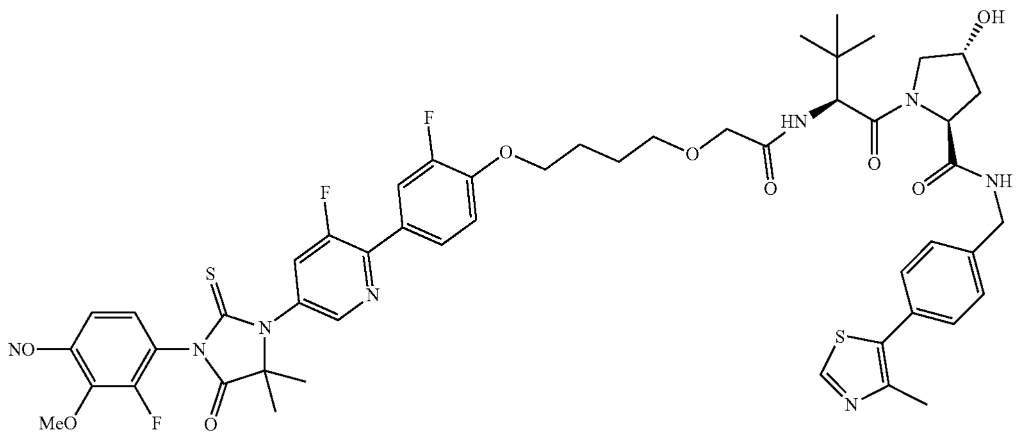
LCMS ([M+H]$^+$): 1041.3
$^1$HNMR (400 MHz, DMSO-d6) δ8.96 (d, J=10.6 Hz, 1H), 8.60 (dd, J=11.6, 5.6 Hz, 2H), 8.16 (dd, J=11.9, 1.9 Hz, 1H), 7.84 (dd, J=13.0, 6.2 Hz, 3H), 7.51 (dd, J=8.4, 6.4 Hz, 1H), 7.47-7.29 (m, 6H), 5.16 (m, 1H), 4.57 (m, 1H), 4.50-4.33 (m, 3H), 4.31-4.15 (m, 3H), 4.13 (d, J=2.6 Hz, 3H), 4.02-3.89 (m, 2H), 3.71-3.52 (m, 4H), 2.43 (d, J=7.3 Hz, 3H), 2.07 (m, 1H), 1.89 (m, 3H), 1.80-1.69 (m, 2H), 1.59 (d, J=3.2 Hz, 6H), 0.93 (d, J=7.1 Hz, 9H).
Example A216
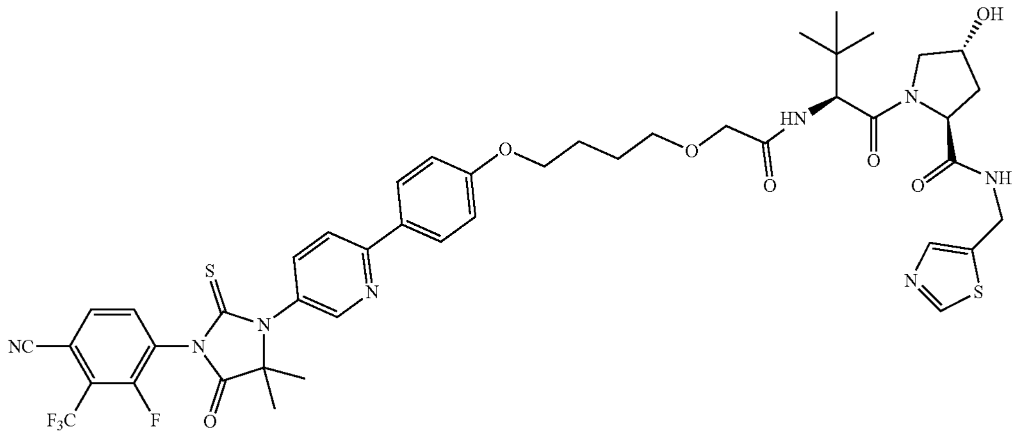 [SMILES: CC(C)(C)[C@H](NC(=O)COCCCCOc1ccc(-c2ccc(N3C(=S)N(c4ccc(C#N)c(C(F)(F)F)c4F)C(=O)C3(C)C)cn2)cc1)C(=O)N1C[C@H](O)C[C@H]1C(=O)NCc1cncs1]
LCMS ([M+H]$^+$): 953.3
$^1$HNMR (400 MHz, DMSO-d6) δ8.96-8.93 (m, 1H), 8.70 (t, J=6.0 Hz, 1H), 8.65 (d, J=2.4 Hz, 1H), 8.32-8.26 (m, 2H), 8.11 (d, J=8.9 Hz, 3H), 7.94 (dd, J=8.5, 2.5 Hz, 1H), 7.78 (d, J=0.7 Hz, 1H), 7.36 (d, J=9.6 Hz, 1H), 7.08 (d, J=8.9 Hz, 2H), 5.16 (d, J=3.5 Hz, 1H), 4.55 (d, J=9.6 Hz, 1H), 4.47 (d, J=6.0 Hz, 2H), 4.39-4.33 (m, 2H), 4.09 (t, J=6.2 Hz, 2H), 3.99-3.90 (m, 2H), 3.68-3.60 (m, 2H), 3.55 (t, J=6.3 Hz, 2H), 2.03-1.98 (m, 1H), 1.86-1.81 (m, 3H), 1.76-1.71 (m, 2H), 1.58 (s, 6H), 0.92 (d, J=14.3 Hz, 9H).

Example A217
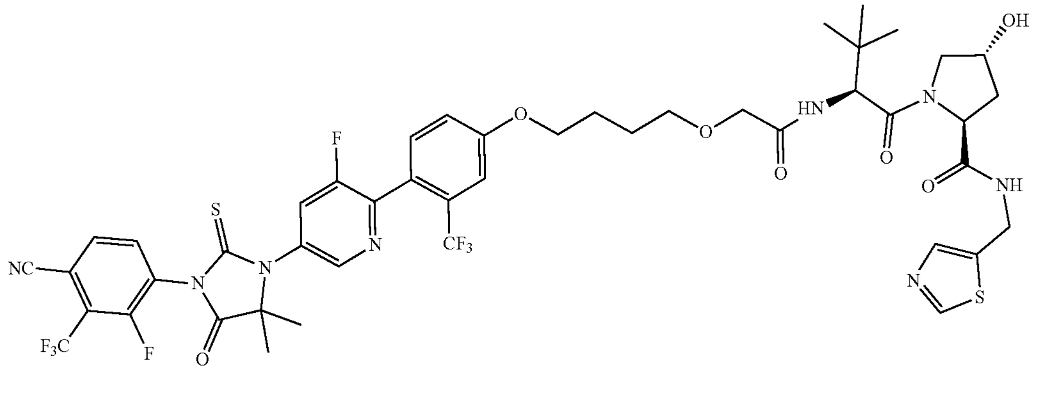 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)c(C(F)(F)F)c1)C(=O)N1C[C@H](O)C[C@H]1C(=O)NCc1cncs1]
LCMS ([M+H]+): 1038.3
$^1$HNMR (400 MHz, DMSO-d6) δ8.96-8.93 (m, 1H), 8.70 (t, J=5.9 Hz, 1H), 8.63 (d, J=0.9 Hz, 1H), 8.31-8.27 (m, 2H), 8.20 (dd, J=9.7, 1.9 Hz, 1H), 7.79 (d, J=0.6 Hz, 1H), 7.58-7.55 (m, 1H), 7.39-7.35 (m, 3H), 5.15 (d, J=3.5 Hz, 1H), 4.55 (d, J=9.6 Hz, 1H), 4.47 (d, J=6.0 Hz, 2H), 4.39-4.33 (m, 2H), 4.18 (t, J=6.2 Hz, 2H), 3.99-3.90 (m, 2H), 3.68-3.55 (m, 4H), 2.03-1.98 (m, 1H), 1.86-1.80 (m, 3H), 1.78-1.72 (m, 2H), 1.61 (s, 6H), 0.94-0.90 (m, 9H).
Example A218
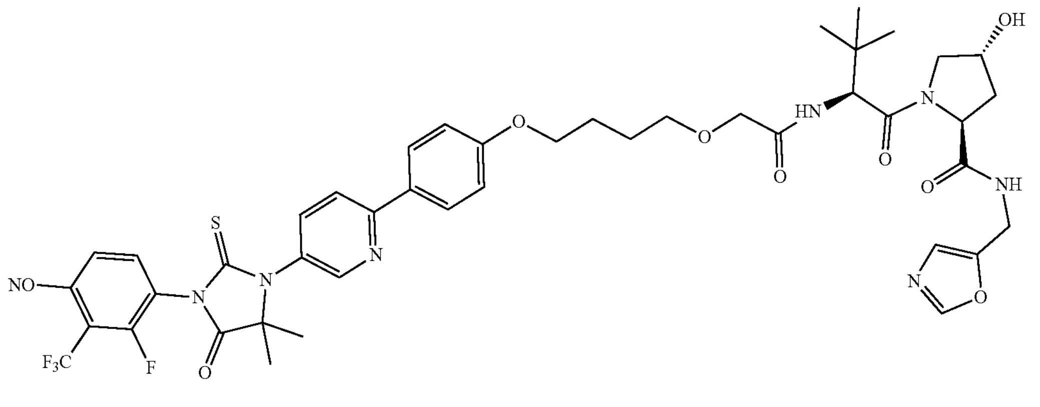
LCMS ([M+H]+): 937.3
$^1$HNMR (400 MHz, DMSO-d6) δ8.65 (d, J=2.5 Hz, 1H), 8.56 (t, J=5.7 Hz, 1H), 8.34-8.21 (m, 3H), 8.11 (d, J=8.9 Hz, 3H), 7.94 (dd, J=8.5, 2.5 Hz, 1H), 7.36 (d, J=9.5 Hz, 1H), 7.08 (d, J=8.9 Hz, 2H), 7.03 (d, J=6.5 Hz, 1H), 5.15 (m, 1H), 4.55 (m, 1H), 4.42-4.29 (m, 4H), 4.09 (m, 2H), 4.01-3.87 (m, 2H), 3.61 (m, 4H), 2.02 (m, 1H), 1.91-1.79 (m, 3H), 1.78-1.69 (m, 2H), 1.58 (s, 6H), 0.91 (d, J=10.5 Hz, 9H).

Example A219
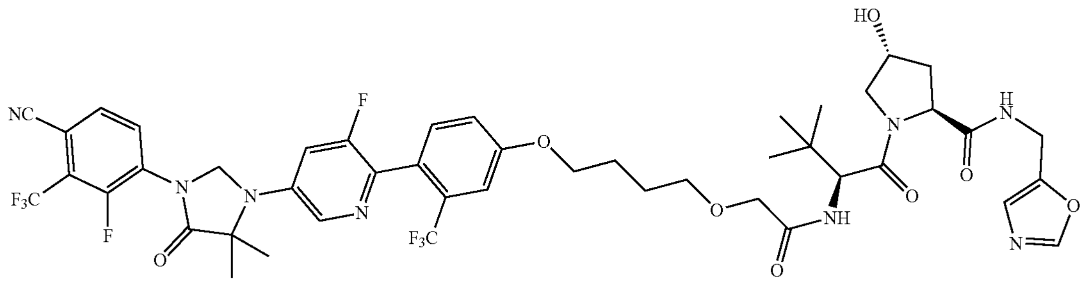 [SMILES: CC(C)(C)[C@H](NC(=O)COCCCCOc1ccc(-c2ncc(N3CN(c4ccc(C#N)c(C(F)(F)F)c4F)C(=O)C3(C)C)cc2F)c(C(F)(F)F)c1)C(=O)N1C[C@H](O)C[C@H]1C(=O)NCc1cnco1]
LCMS ([M+H]$^+$): 1023.3
$^1$HNMR (400 MHz, DMSO-d6) δ8.62 (d, J=0.9 Hz, 1H), 8.56 (t, J=5.7 Hz, 1H), 8.34-8.23 (m, 3H), 8.19 (dd, J=9.7, 1.9 Hz, 1H), 7.59-7.53 (m, 1H), 7.38 (dd, J=8.7, 6.0 Hz, 3H), 7.03 (d, J=6.7 Hz, 1H), 5.15 (m, 1H), 4.56 (m, 1H), 4.43-4.24 (m, 4H), 4.19 (m, 2H), 4.02-3.86 (m, 2H), 3.61 (m, 4H), 2.02 (m, 1H), 1.91-1.79 (m, 3H), 1.79-1.70 (m, 2H), 1.60 (s, 6H), 0.91 (d, J=10.6 Hz, 9H).
Example A220
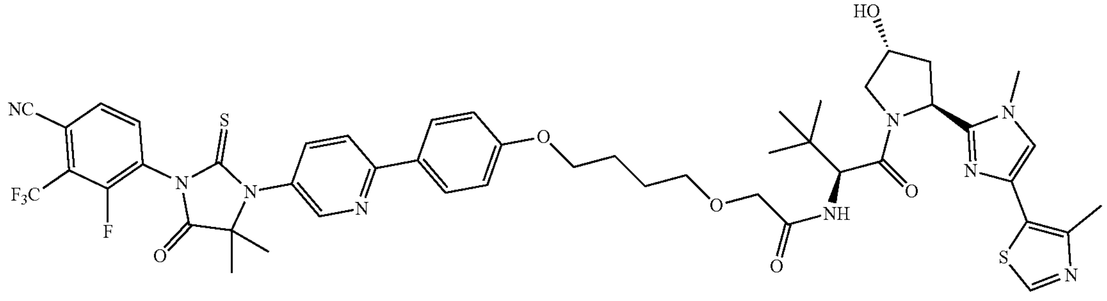 [SMILES: Cc1ncsc1-c1cn(C)c([C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2)C(C)(C)C)n1]
LCMS ([M+H]$^+$): 990.3
$^1$HNMR (400 MHz, DMSO-d6) δ8.72 (s, 1H), 8.65 (d, J=2.4 Hz, 1H), 8.35-8.24 (m, 2H), 8.11 (t, J=8.5 Hz, 3H), 7.93 (dd, J=8.5, 2.5 Hz, 1H), 7.36-7.27 (m, 2H), 7.06 (d, J=8.9 Hz, 2H), 5.23 (m, 1H), 5.07 (m, 1H), 4.55 (m, 2H), 4.08 (m, 2H), 3.94 (s, 2H), 3.86 (m, 1H), 3.78-3.62 (m, 4H), 3.55 (m, 2H), 2.45 (s, 3H), 2.21-2.13 (m, 1H), 1.81 (m, 2H), 1.72 (m, 2H), 1.58 (m, 6H), 0.92-0.75 (m, 9H).

Example A221
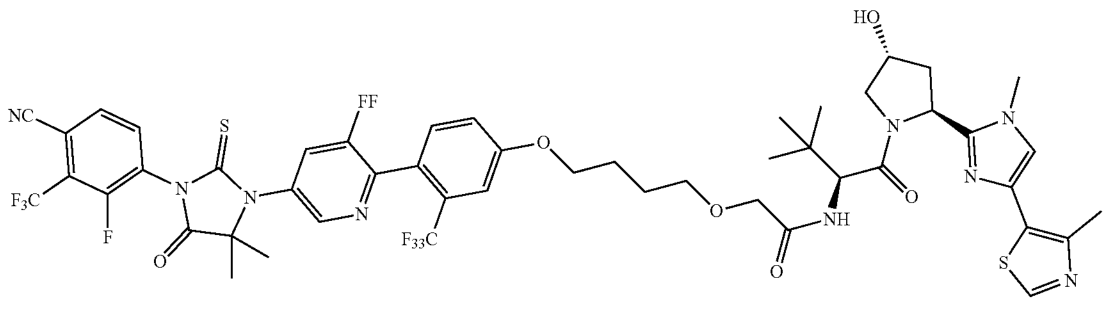
LCMS ([M+H]+): 1076.3
$^1$HNMR (400 MHz, DMSO-d6) δ8.72 (d, J=4.1 Hz, 1H), 8.63 (s, 1H), 8.33-8.25 (m, 2H), 8.19 (dd, J=9.7, 1.8 Hz, 1H), 7.55 (d, J=8.5 Hz, 1H), 7.41-7.25 (m, 4H), 5.22 (d, J=3.8 Hz, 1H), 5.06 (t, J=7.9 Hz, 1H), 4.61-4.47 (m, 2H), 4.17 (m, 2H), 3.95 (m, 2H), 3.86 (m, 1H), 3.73 (d, J=11.7 Hz, 3H), 3.66 (m, 1H), 3.56 (m, 2H), 2.44 (s, 3H), 2.17 (m, 1H), 1.83 (m, 2H), 1.74 (m, 2H), 1.61 (s, 6H), 0.82 (d, J=19.6 Hz, 9H).
Example A222
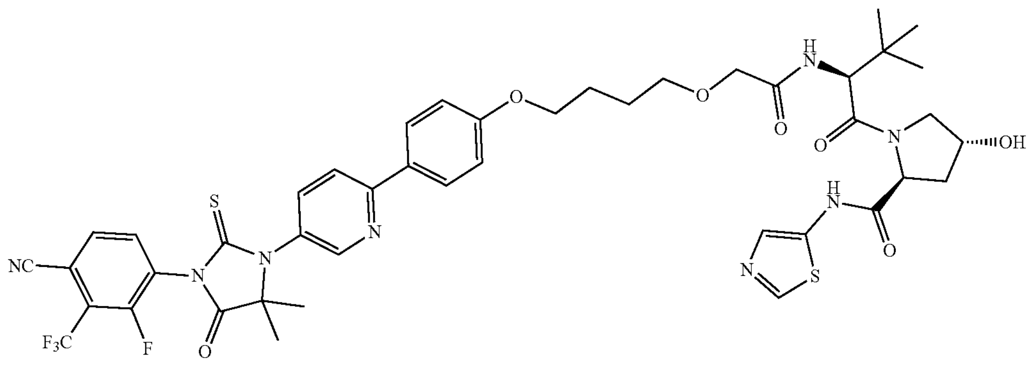 [SMILES: CC(C)(C)[C@H](NC(=O)COCCCCOc1ccc(-c2ccc(N3C(=S)N(c4ccc(C#N)c(C(F)(F)F)c4F)C(=O)C3(C)C)cn2)cc1)C(=O)N1C[C@H](O)C[C@H]1C(=O)Nc1cncs1]
LCMS ([M+H]+): 939.3
$^1$HNMR (400 MHz, DMSO-d6) δ11.59 (s, 1H), 8.65 (d, J=2.4 Hz, 1H), 8.55 (d, J=0.6 Hz, 1H), 8.32-8.26 (m, 2H), 8.11-8.08 (m, 3H), 7.95-7.93 (m, 1H), 7.64-7.59 (m, 1H), 7.33 (d, J=9.5 Hz, 1H), 7.09-7.05 (m, 2H), 5.27 (d, J=3.5 Hz, 1H), 4.58-4.52 (m, 2H), 4.38 (s, 1H), 4.07 (t, J=6.2 Hz, 2H), 3.99-3.91 (m, 2H), 3.73-3.64 (m, 2H), 3.55 (t, J=6.2 Hz, 2H), 2.16-2.11 (m, 1H), 1.94-1.88 (m, 1H), 1.80 (dd, J=14.0, 6.2 Hz, 2H), 1.72 (dd, J=13.8, 6.1 Hz, 2H), 1.58 (s, 6H), 0.94-0.91 (m, 9H).

Example A223
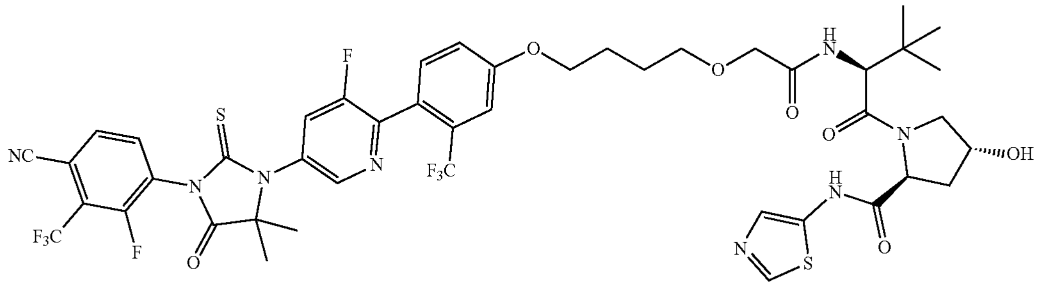 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)c(C(F)(F)F)c1)C(=O)N1C[C@H](O)C[C@H]1C(=O)Nc1cncs1]
LCMS ([M+H]$^+$): 1025.3
$^1$HNMR (400 MHz, DMSO-d6) δ11.58 (s, 1H), 8.62 (d, J=1.0 Hz, 1H), 8.56-8.54 (m, 1H), 8.31-8.26 (m, 2H), 8.19 (dd, J=9.7, 1.9 Hz, 1H), 7.58 (d, J=0.7 Hz, 1H), 7.54-7.52 (m, 1H), 7.38-7.33 (m, 3H), 5.26 (d, J=3.5 Hz, 1H), 4.58-4.51 (m, 2H), 4.38 (s, 1H), 4.16 (t, J=6.2 Hz, 2H), 3.99-3.91 (m, 2H), 3.73-3.64 (m, 2H), 3.56 (t, J=6.2 Hz, 2H), 2.16-2.10 (m, 1H), 1.94-1.80 (m, 3H), 1.76-1.71 (m, 2H), 1.61 (s, 6H), 0.94-0.91 (m, 9H).
Example A224
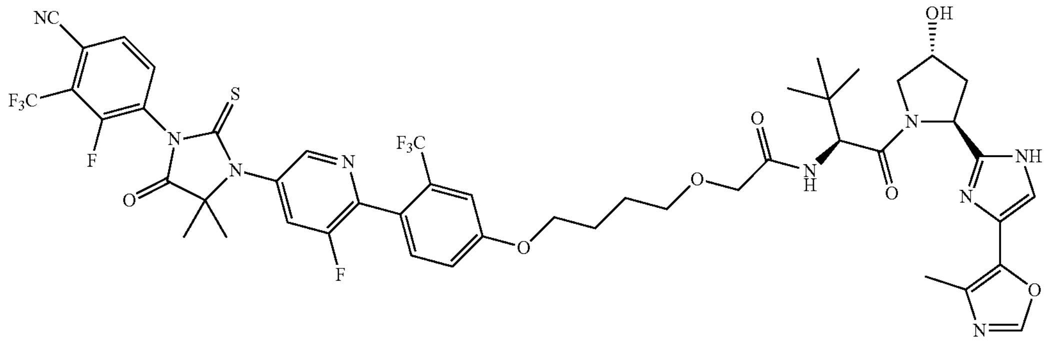 [SMILES: Cc1ncoc1-c1c[nH]c([C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)c(C(F)(F)F)c2)C(C)(C)C)n1]
LCMS ([M+H]$^+$): 1046.2
$^1$HNMR (400 MHz, DMSO-d6) δ12.11 (s, 1H), 8.30 (d, J=11.4 Hz, 2H), 8.19 (dd, J=9.7, 1.8 Hz, 1H), 8.12 (d, J=6.3 Hz, 1H), 7.55 (d, J=9.2 Hz, 1H), 7.37 (d, J=6.6 Hz, 2H), 7.32 (d, J=9.6 Hz, 1H), 7.24 (t, J=6.8 Hz, 1H), 5.20 (d, J=3.7 Hz, 1H), 5.07 (t, J=7.7 Hz, 1H), 4.56 (d, J=9.5 Hz, 1H), 4.48 (s, 1H), 4.17 (t, J=6.2 Hz, 2H), 4.02-3.90 (m, 2H), 3.84 (dd, J=10.6, 4.3 Hz, 1H), 3.63 (d, J=10.3 Hz, 1H), 3.56 (t, J=6.2 Hz, 2H), 2.31 (d, J=14.1 Hz, 3H), 2.24-2.09 (m, 2H), 1.90-1.79 (m, 2H), 1.74 (dd, J=13.8, 6.4 Hz, 2H), 1.61 (s, 6H), 0.88 (d, J=30.2 Hz, 9H).

Example A225
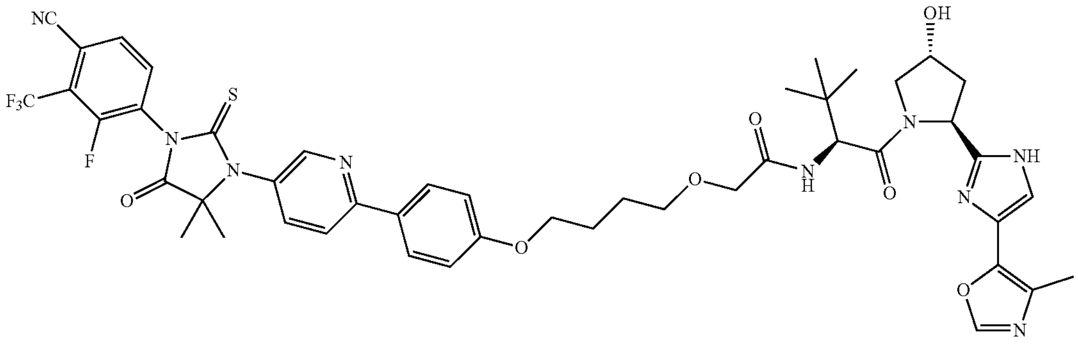 [SMILES: Cc1ncoc1-c1c[nH]c([C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2)C(C)(C)C)n1]
LCMS ([M+H]+): 960.0
$^1$HNMR (400 MHz, DMSO-d6) δ12.19 (d, J=61.7 Hz, 1H), 8.65 (d, J=2.3 Hz, 1H), 8.33-8.26 (m, 2H), 8.10 (d, J=8.7 Hz, 4H), 7.94 (dd, J=8.5, 2.4 Hz, 1H), 7.32 (d, J=9.5 Hz, 1H), 7.25 (t, J=4.1 Hz, 1H), 7.07 (d, J=8.9 Hz, 2H), 5.21 (d, J=3.7 Hz, 1H), 5.08 (t, J=7.6 Hz, 1H), 4.56 (d, J=9.5 Hz, 1H), 4.49 (s, 1H), 4.08 (t, J=6.2 Hz, 2H), 4.01-3.89 (m, 2H), 3.84 (dd, J=10.5, 4.3 Hz, 1H), 3.63 (d, J=10.3 Hz, 1H), 3.60-3.49 (m, 2H), 2.35 (d, J=43.7 Hz, 3H), 2.26-2.09 (m, 2H), 1.81 (dd, J=13.9, 6.2 Hz, 2H), 1.76-1.66 (m, 2H), 1.58 (s, 6H), 0.89 (d, J=30.6 Hz, 9H).
Example A226
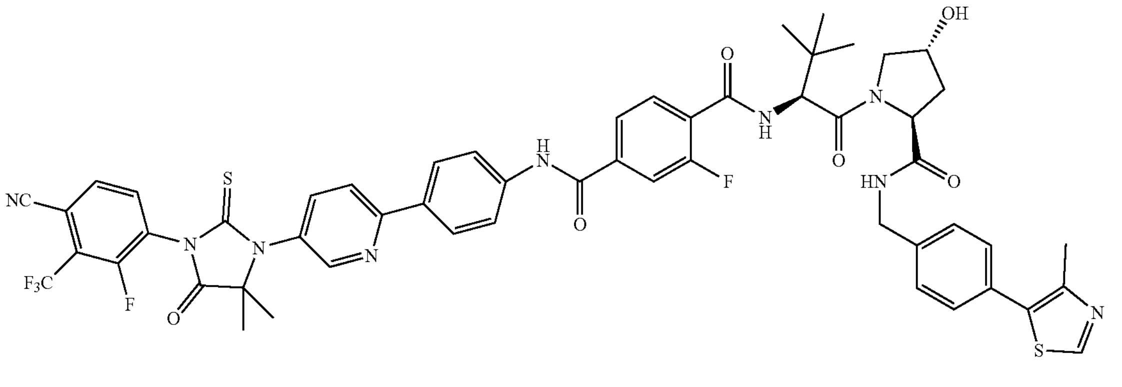 [SMILES: Cc1ncsc1-c1ccc(CNC(=O)[C@@H]2C[C@@H](O)CN2C(=O)[C@@H](NC(=O)c2ccc(C(=O)Nc3ccc(-c4ccc(N5C(=S)N(c6ccc(C#N)c(C(F)(F)F)c6F)C(=O)C5(C)C)cn4)cc3)cc2F)C(C)(C)C)cc1]
LCMS ([M+H]+): 1078.3
$^1$HNMR (400 MHz, DMSO-d6) δ10.64 (s, 1H), 8.96 (s, 1H), 8.69 (d, J=2.3 Hz, 1H), 8.63 (t, J=6.1 Hz, 1H), 8.39-8.17 (m, 8H), 8.00-7.96 (m, 2H), 7.91-7.88 (m, 2H), 7.79-7.75 (m, 1H), 7.40 (q, J=8.4 Hz, 3H), 5.32-5.26 (m, 2H), 4.76 (d, J=9.1 Hz, 1H), 4.49 (d, J=7.9 Hz, 1H), 4.43-4.39 (m, 2H), 4.27 (d, J=5.3 Hz, 1H), 2.43 (s, 2H), 2.11-2.08 (m, 1H), 2.02-1.90 (m, 2H), 1.59 (s, 6H), 1.03-1.01 (m, 7H).

Example A227
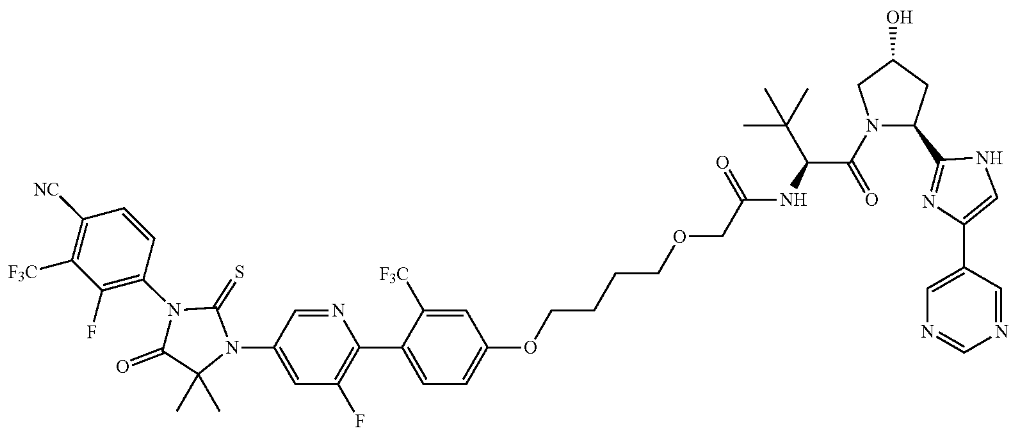 [SMILES: CC(C)(C)[C@H](NC(=O)COCCCCOc1ccc(-c2ncc(N3C(=S)N(c4ccc(C#N)c(C(F)(F)F)c4F)C(=O)C3(C)C)cc2F)c(C(F)(F)F)c1)C(=O)N1C[C@H](O)C[C@H]1c1nc(-c2cncnc2)c[nH]1]
LCMS ([M+H]$^+$): 1043.0
$^1$HNMR (400 MHz, DMSO-d6) δ12.22 (s, 1H), 9.10-8.93 (m, 3H), 8.61 (s, 1H), 8.31-8.24 (m, 2H), 8.17 (dd, J=9.6, 1.9 Hz, 1H), 7.73 (t, J=5.0 Hz, 1H), 7.54 (dd, J=11.0, 6.2 Hz, 1H), 7.42-7.28 (m, 3H), 5.25 (d, J=3.6 Hz, 1H), 5.07 (t, J=7.9 Hz, 1H), 4.58 (d, J=9.6 Hz, 1H), 4.46 (s, 1H), 4.16 (t, J=6.1 Hz, 2H), 3.95 (s, 2H), 3.89-3.85 (m, 1H), 2.18 (dd, J=7.5, 4.0 Hz, 2H), 2.04-1.91 (m, 1H), 1.88-1.78 (m, 2H), 1.73 (dd, J=13.7, 6.2 Hz, 2H), 1.60 (d, J=3.6 Hz, 6H), 0.98-0.79 (m, 9H).
Example A228
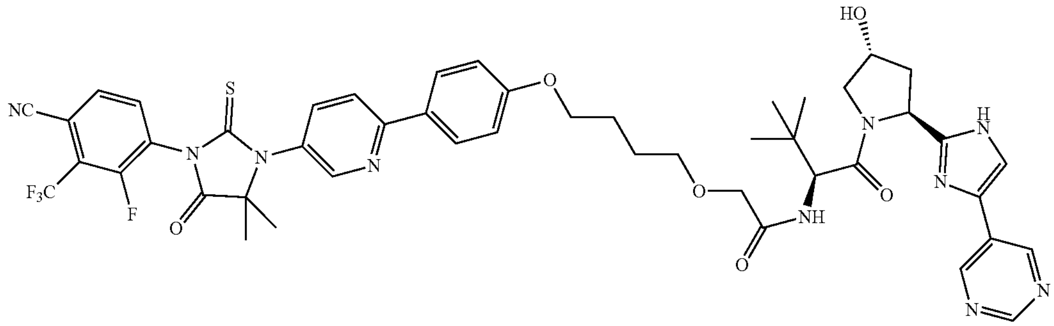 [SMILES: CC(C)(C)[C@H](NC(=O)COCCCCOc1ccc(-c2ccc(N3C(=S)N(c4ccc(C#N)c(C(F)(F)F)c4F)C(=O)C3(C)C)cn2)cc1)C(=O)N1C[C@H](O)C[C@H]1c1nc(-c2cncnc2)c[nH]1]
LCMS ([M+H]$^+$): 957.1
$^1$HNMR (400 MHz, DMSO-d6) δ12.26 (s, 1H), 9.05 (s, 1H), 9.05-8.94 (m, 1H), 8.64 (d, J=2.2 Hz, 1H), 8.33-8.23 (m, 2H), 8.09 (t, J=7.3 Hz, 3H), 7.93 (dd, J=8.5, 2.4 Hz, 1H), 7.73 (s, 1H), 7.32 (d, J=9.5 Hz, 1H), 7.07 (t, J=7.2 Hz, 2H), 5.33-5.21 (m, 1H), 5.08 (t, J=7.9 Hz, 1H), 4.57 (d, J=9.6 Hz, 1H), 4.47 (s, 1H), 4.07 (t, J=6.2 Hz, 2H), 4.00-3.83 (m, 3H), 3.67 (s, 1H), 2.18 (dd, J=7.5, 4.1 Hz, 1H), 1.80 (dd, J=14.0, 6.3 Hz, 2H), 1.70 (dd, J=13.7, 7.0 Hz, 2H), 1.57 (s, 6H), 0.97-0.79 (m, 9H).

Example A229
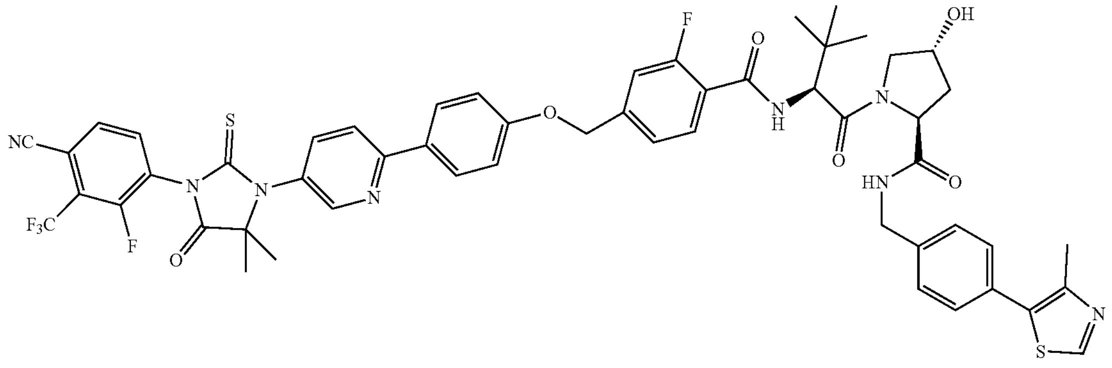 [SMILES: Cc1ncsc1-c1ccc(CNC(=O)[C@@H]2C[C@@H](O)CN2C(=O)[C@@H](NC(=O)c2ccc(COc3ccc(-c4ccc(N5C(=S)N(c6ccc(C#N)c(C(F)(F)F)c6F)C(=O)C5(C)C)cn4)cc3)cc2F)C(C)(C)C)cc1]
LCMS ([M+H]$^+$): 1065.3
$^1$HNMR (400 MHz, DMSO-d6) δ8.97 (s, 1H), 8.66 (d, J=2.2 Hz, 1H), 8.61 (t, J=5.9 Hz, 1H), 8.34-8.24 (m, 2H), 8.13 (dd, J=8.5, 4.7 Hz, 3H), 8.07 (dd, J=8.8, 5.6 Hz, 1H), 7.95 (dd, J=8.5, 2.2 Hz, 1H), 7.72 (t, J=7.8 Hz, 1H), 7.40 (q, J=7.9 Hz, 6H), 7.18 (d, J=8.8 Hz, 2H), 5.28 (s, 2H), 5.18 (d, J=3.4 Hz, 1H), 4.75 (m, 1H), 4.53-4.35 (m, 3H), 4.26 (m, 1H), 3.73 (m, 2H), 2.44 (s, 3H), 2.07 (m, 1H), 1.93 (m, 1H), 1.58 (s, 6H), 1.01 (d, J=9.1 Hz, 9H).
Example A230
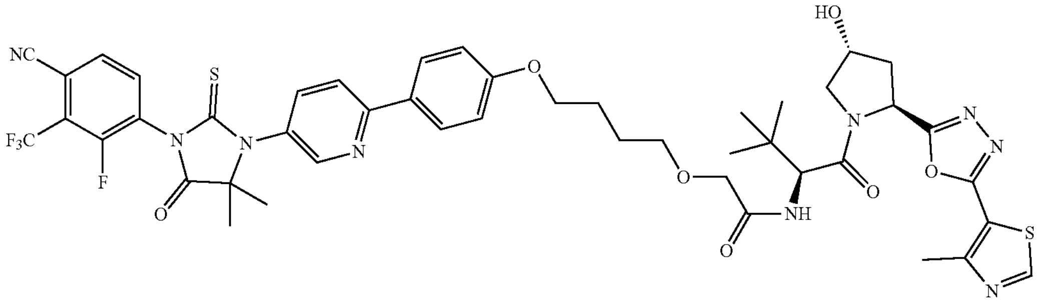 [SMILES: Cc1ncsc1-c1nnc([C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2)C(C)(C)C)o1]
LCMS ([M+H]$^+$): 978.3
$^1$HNMR (400 MHz, DMSO-d6) δ9.23 (d, J=4.7 Hz, 1H), 8.65 (d, J=2.4 Hz, 1H), 8.34-8.24 (m, 2H), 8.10 (dd, J=8.8, 2.4 Hz, 3H), 7.94 (dd, J=8.5, 2.5 Hz, 1H), 7.39 (d, J=9.5 Hz, 1H), 7.06 (d, J=8.9 Hz, 2H), 5.41-5.34 (m, 1H), 5.26 (m, 1H), 4.62 (m, 1H), 4.46 (m, 1H), 4.07 (m, 2H), 4.01-3.84 (m, 3H), 3.73 (m, 1H), 3.54 (m, 2H), 2.69 (m, 3H), 2.33-2.18 (m, 2H), 1.80 (m, 2H), 1.72 (m, 2H), 1.58 (s, 6H), 0.93 (d, J=5.2 Hz, 9H).

Example A231
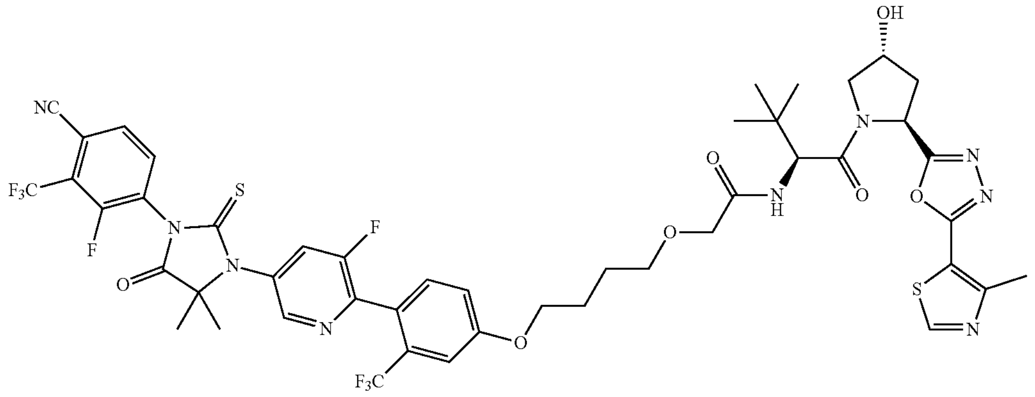 [SMILES: Cc1ncsc1-c1nnc([C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)c(C(F)(F)F)c2)C(C)(C)C)o1]
LCMS ([M+H]+): 1064.2
$^1$HNMR (400 MHz, DMSO-d6) δ9.24 (s, 1H), 8.62 (s, 1H), 8.29 (d, J=3.1 Hz, 2H), 8.19 (dd, J=9.7, 1.9 Hz, 1H), 7.54 (d, J=9.2 Hz, 1H), 7.38 (dd, J=11.7, 8.1 Hz, 3H), 5.37 (d, J=3.9 Hz, 1H), 5.25 (t, J=8.1 Hz, 1H), 4.62 (m, 1H), 4.45 (m, 1H), 4.16 (m, 2H), 3.98 (m, 2H), 3.89 (m, 1H), 3.72 (m, 1H), 3.55 (m, 2H), 2.69 (d, J=14.7 Hz, 3H), 2.34-2.18 (m, 2H), 1.82 (m, 2H), 1.73 (m, 2H), 1.61 (s, 6H), 0.91 (s, 9H).
Example A232
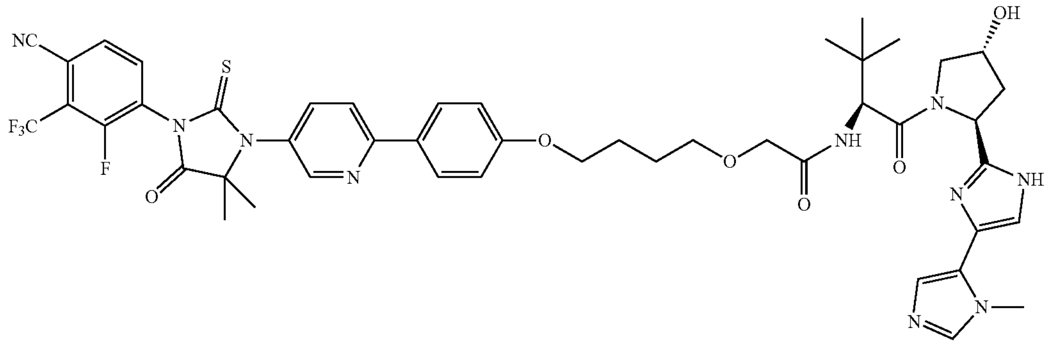 [SMILES: Cn1cncc1-c1c[nH]c([C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2)C(C)(C)C)n1]
LCMS ([M+H]+): 959.4
$^1$HNMR (400 MHz, DMSO-d6) δ9.09 (s, 1H), 8.71 (d, J=2.3 Hz, 1H), 8.36 (d, J=6.3 Hz, 2H), 8.24-8.11 (m, 3H), 8.01 (dd, J=8.5, 2.4 Hz, 1H), 7.72 (d, J=45.5 Hz, 2H), 7.40 (d, J=9.5 Hz, 1H), 7.13 (d, J=8.9 Hz, 2H), 5.18 (t, J=7.9 Hz, 1H), 4.64 (d, J=9.5 Hz, 1H), 4.15 (t, J=6.2 Hz, 2H), 4.02 (dd, J=10.5, 8.9 Hz, 5H), 3.91 (s, 1H), 3.73 (d, J=10.6 Hz, 2H), 3.62 (t, J=6.3 Hz, 3H), 2.26 (d, J=7.2 Hz, 3H), 1.93-1.73 (m, 4H), 1.65 (s, 6H), 0.95 (d, J=28.8 Hz, 9H).

Example A233
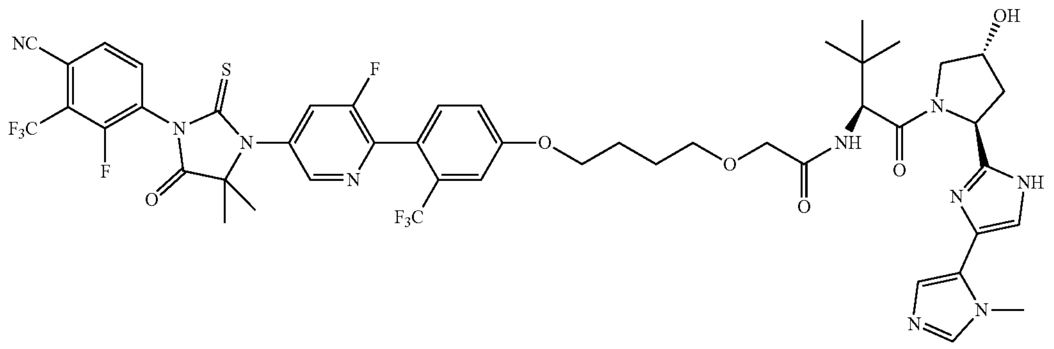 [SMILES: Cn1cncc1-c1c[nH]c([C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)c(C(F)(F)F)c2)C(C)(C)C)n1]
LCMS ([M+H]+): 1045.3
$^1$HNMR (400 MHz, DMSO-d6) δ8.81 (s, 1H), 8.62 (s, 1H), 8.34-8.23 (m, 2H), 8.18 (dd, J=9.7, 1.7 Hz, 1H), 7.64-7.52 (m, 2H), 7.49 (d, J=4.2 Hz, 1H), 7.42-7.26 (m, 3H), 5.29 (d, J=7.2 Hz, 1H), 5.09 (t, J=7.8 Hz, 1H), 4.57 (d, J=9.6 Hz, 1H), 4.47 (s, 1H), 4.16 (t, J=6.1 Hz, 2H), 3.98-3.82 (m, 7H), 2.25-2.13 (m, 3H), 1.89-1.78 (m, 2H), 1.74 (dd, J=14.0, 6.3 Hz, 2H), 1.60 (d, J=2.7 Hz, 6H), 1.26 (td, J=7.3, 3.9 Hz, 2H), 0.87 (d, J=25.8 Hz, 9H).
Example A234
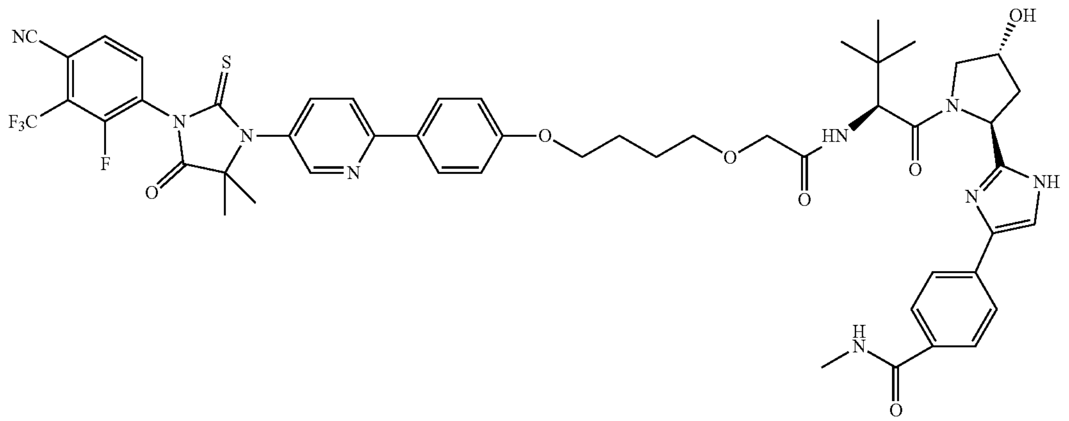 [SMILES: CNC(=O)c1ccc(-c2c[nH]c([C@@H]3C[C@@H](O)CN3C(=O)[C@@H](NC(=O)COCCCCOc3ccc(-c4ccc(N5C(=S)N(c6ccc(C#N)c(C(F)(F)F)c6F)C(=O)C5(C)C)cn4)cc3)C(C)(C)C)n2)cc1]
LCMS ([M+H]+): 1012.3
$^1$HNMR (400 MHz, DMSO-d6) δ11.98 (s, 1H), 8.64 (d, J=2.4 Hz, 1H), 8.36-8.24 (m, 4H), 8.09 (d, J=8.8 Hz, 3H), 7.95-7.90 (m, 1H), 7.77 (s, 4H), 7.57 (s, 1H), 7.32 (d, J=9.4 Hz, 1H), 7.06 (d, J=8.8 Hz, 2H), 5.21 (s, 1H), 5.08 (t, J=7.6 Hz, 1H), 4.58 (d, J=9.4 Hz, 1H), 4.49 (s, 1H), 4.08 (t, J=6.2 Hz, 2H), 4.00-3.91 (m, 2H), 3.86 (d, J=6.2 Hz, 1H), 3.64 (d, J=10.4 Hz, 1H), 3.56 (t, J=6.3 Hz, 2H), 2.77 (d, J=4.4 Hz, 3H), 2.04-1.93 (m, 1H), 1.87-1.67 (m, 4H), 1.58 (s, 6H), 1.51-1.41 (m, 1H), 0.97-0.85 (m, 9H).

Example A235
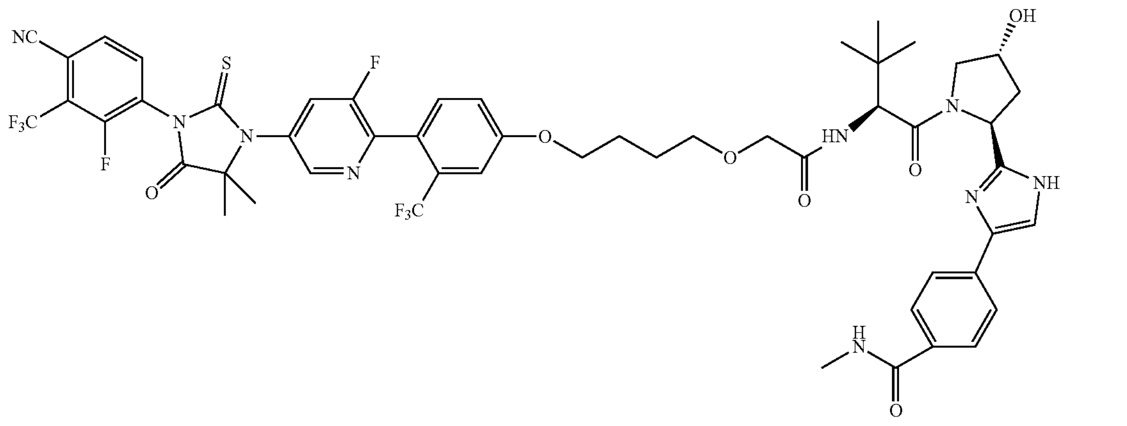 [SMILES: CNC(=O)c1ccc(-c2c[nH]c([C@@H]3C[C@@H](O)CN3C(=O)[C@@H](NC(=O)COCCCCOc3ccc(-c4ncc(N5C(=S)N(c6ccc(C#N)c(C(F)(F)F)c6F)C(=O)C5(C)C)cc4F)c(C(F)(F)F)c3)C(C)(C)C)n2)cc1]
LCMS ([M+H]$^+$): 1098.3
$^1$HNMR (400 MHz, DMSO-d6) δ8.95 (s, 1H), 8.63 (s, 1H), 8.59 (t, J=6.0 Hz, 1H), 8.29 (s, 2H), 8.16 (dd, J=11.9, 1.9 Hz, 1H), 7.87-7.79 (m, 2H), 7.47 (t, J=6.9 Hz, 1H), 7.40 (d, J=4.2 Hz, 5H), 5.16 (s, 1H), 4.59 (d, J=9.6 Hz, 1H), 4.49-4.39 (m, 2H), 4.38-4.33 (m, 3H), 4.24 (dd, J=15.9, 5.5 Hz, 1H), 4.10 (s, 2H), 3.96-3.88 (m, 2H), 3.69 (dd, J=10.6, 3.8 Hz, 1H), 3.63 (d, J=10.9 Hz, 1H), 2.43 (s, 3H), 2.10-2.02 (m, 1H), 1.92 (ddd, J=12.9, 8.8, 4.5 Hz, 1H), 1.62 (s, 6H), 0.94 (s, 9H).
Example A236
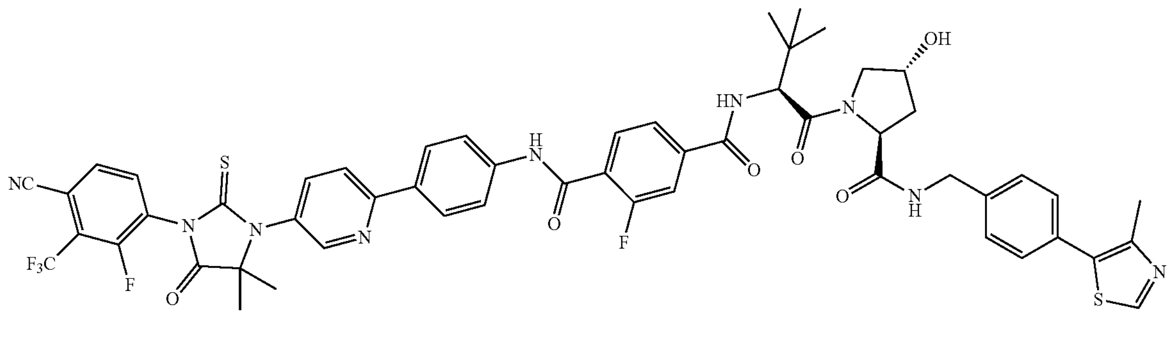 [SMILES: Cc1ncsc1-c1ccc(CNC(=O)[C@@H]2C[C@@H](O)CN2C(=O)[C@@H](NC(=O)c2ccc(C(=O)Nc3ccc(-c4ccc(N5C(=S)N(c6ccc(C#N)c(C(F)(F)F)c6F)C(=O)C5(C)C)cn4)cc3)c(F)c2)C(C)(C)C)cc1]
LCMS ([M+H]$^+$): 1078.3
$^1$HNMR (400 MHz, DMSO-d6) δ10.75 (s, 1H), 8.98 (s, 1H), 8.70 (d, J=2.5 Hz, 1H), 8.60 (t, J=6.1 Hz, 1H), 8.41 (d, J=9.0 Hz, 1H), 8.33-8.26 (m, 2H), 8.21-8.17 (m, 3H), 7.91-7.86 (m, 1H), 7.88 (dd, J=14.7, 7.1 Hz, 4H), 7.82-7.75 (m, 1H), 7.44-7.39 (m, 4H), 5.18 (d, J=3.6 Hz, 1H), 4.81 (d, J=9.0 Hz, 1H), 4.50-4.40 (m, 3H), 4.25 (dd, J=15.9, 5.6 Hz, 1H), 3.74 (s, 2H), 2.45 (s, 3H), 2.09-2.05 (m, 1H), 1.97-1.90 (m, 1H), 1.60 (s, 6H), 1.05-1.02 (m, 9H).

Example A237
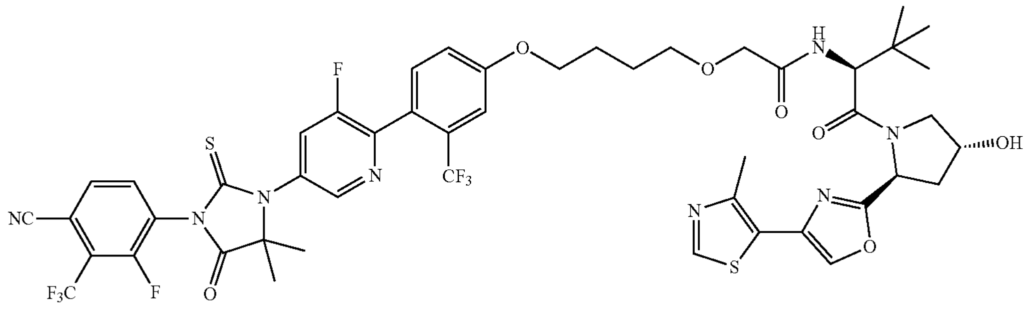 [SMILES: Cc1ncsc1-c1coc([C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)c(C(F)(F)F)c2)C(C)(C)C)n1]
LCMS ([M+H]$^+$): 1063.3
$^1$HNMR (400 MHz, DMSO-d6) δ8.94 (s, 1H), 8.62 (s, 1H), 8.37 (s, 1H), 8.29-8.28 (m, 2H), 8.19 (dd, J=9.7, 1.9 Hz, 1H), 7.54 (d, J=9.3 Hz, 1H), 7.38-7.34 (m, 3H), 5.32 (d, J=3.8 Hz, 1H), 5.07 (t, J=8.2 Hz, 1H), 4.61 (d, J=9.6 Hz, 1H), 4.43 (s, 1H), 4.16 (t, J=6.2 Hz, 2H), 3.96 (s, 2H), 3.86 (dd, J=10.6, 4.1 Hz, 1H), 3.70 (d, J=11.0 Hz, 1H), 3.56 (t, J=6.3 Hz, 2H), 2.48 (s, 3H), 2.30-2.23 (m, 1H), 2.10-2.06 (m, 1H), 1.84-1.82 (m, 2H), 1.75-1.71 (m, 2H), 1.61 (s, 6H), 0.94-0.91 (m, 9H).
Example A238
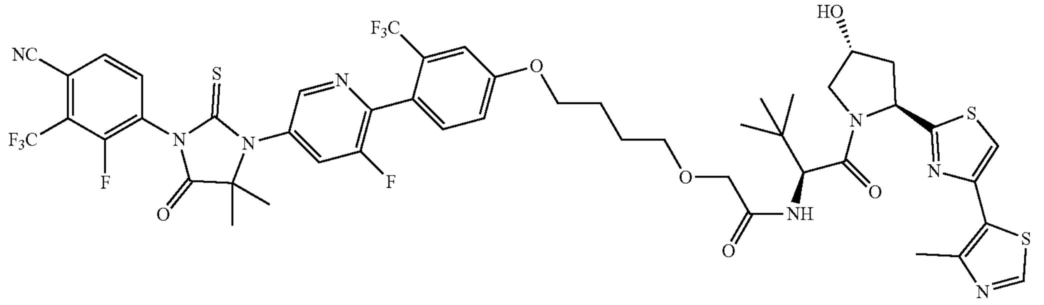 [SMILES: Cc1ncsc1-c1csc([C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)c(C(F)(F)F)c2)C(C)(C)C)n1]
LCMS ([M+H]$^+$): 1079.1
$^1$HNMR (400 MHz, DMSO-d6) δ8.92 (d, J=3.6 Hz, 1H), 8.62 (s, 1H), 8.33-8.25 (m, 2H), 8.19 (dd, J=9.7, 1.8 Hz, 1H), 7.73 (d, J=5.5 Hz, 1H), 7.55 (d, J=9.2 Hz, 1H), 7.40 (dd, J=17.2, 7.9 Hz, 3H), 5.36 (t, J=7.4 Hz, 1H), 5.29 (s, 1H), 4.63 (d, J=9.5 Hz, 1H), 4.44 (s, 1H), 4.17 (t, J=6.2 Hz, 2H), 4.04-3.90 (m, 2H), 3.85 (dd, J=10.7, 4.6 Hz, 1H), 3.69 (dd, J=10.7, 2.9 Hz, 1H), 3.57 (t, J=6.2 Hz, 2H), 2.58 (s, 3H), 2.26 (dd, J=7.2, 4.8 Hz, 2H), 1.84 (dd, J=13.8, 6.3 Hz, 2H), 1.79-1.68 (m, 2H), 1.60 (s, 6H), 0.93 (s, 9H).

Example A239
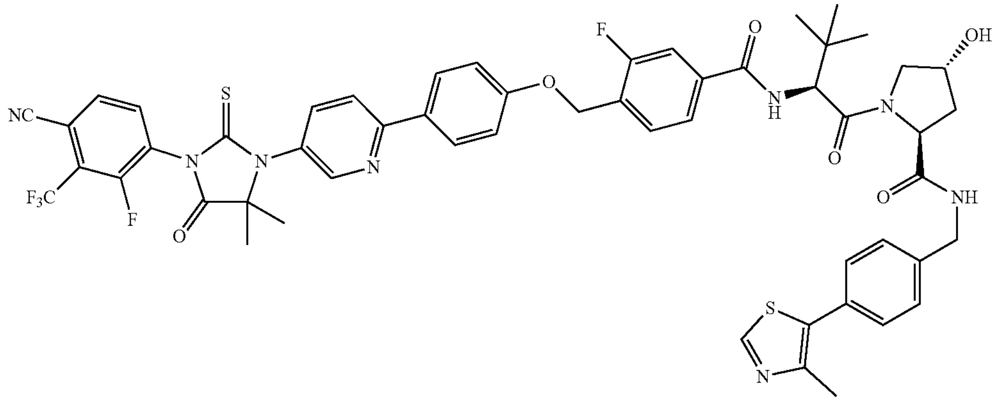 [SMILES: Cc1ncsc1-c1ccc(CNC(=O)[C@@H]2C[C@@H](O)CN2C(=O)[C@@H](NC(=O)c2ccc(COc3ccc(-c4ccc(N5C(=S)N(c6ccc(C#N)c(C(F)(F)F)c6F)C(=O)C5(C)C)cn4)cc3)c(F)c2)C(C)(C)C)cc1]
LCMS ([M+H]$^+$): 1065.3
$^1$HNMR (400 MHz, DMSO-d6) δ8.95 (d, J=23.2 Hz, 1H), 8.65 (dd, J=6.7, 2.4 Hz, 1H), 8.58 (t, J=6.0 Hz, 1H), 8.34-8.22 (m, 3H), 8.18-8.07 (m, 3H), 7.95 (dd, J=8.5, 2.5 Hz, 1H), 7.81-7.64 (m, 3H), 7.46-7.37 (m, 3H), 7.13 (dd, J=51.5, 8.9 Hz, 3H), 5.17 (d, J=3.5 Hz, 1H), 4.77 (d, J=9.1 Hz, 1H), 4.45 (dd, J=16.8, 8.9 Hz, 2H), 4.39 (d, J=6.4 Hz, 1H), 4.24 (dd, J=15.8, 5.4 Hz, 1H), 4.13-4.05 (m, 1H), 3.73 (s, 2H), 2.58 (s, 1H), 2.44 (s, 3H), 2.10-2.02 (m, 1H), 1.96-1.89 (m, 1H), 1.58 (s, 6H), 1.09-0.89 (m, 9H).
Example A240
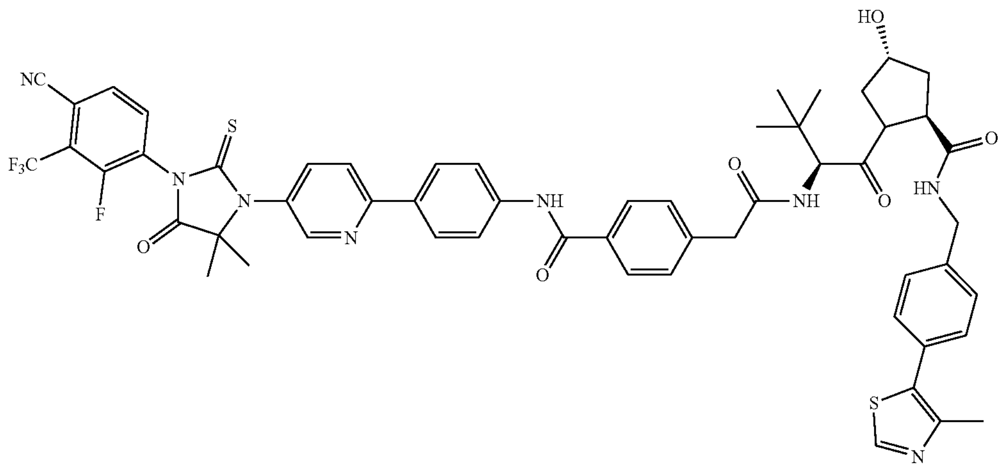 [SMILES: Cc1ncsc1-c1ccc(CNC(=O)[C@@H]2C[C@@H](O)CC2C(=O)[C@@H](NC(=O)Cc2ccc(C(=O)Nc3ccc(-c4ccc(N5C(=S)N(c6ccc(C#N)c(C(F)(F)F)c6F)C(=O)C5(C)C)cn4)cc3)cc2)C(C)(C)C)cc1]
LCMS ([M+H]$^+$): 1074.3
$^1$HNMR (400 MHz, DMSO-d6) δ10.40-10.38 (m, 1H), 8.97 (d, J=10.0 Hz, 1H), 8.69 (d, J=2.6 Hz, 1H), 8.59 (t, J=6.0 Hz, 1H), 8.33-8.28 (m, 2H), 8.27-8.15 (m, 4H), 8.02-7.89 (m, 5H), 7.48-7.37 (m, 6H), 5.14 (d, J=3.5 Hz, 1H), 4.55 (d, J=9.4 Hz, 1H), 4.47-4.41 (m, 2H), 4.35 (s, 1H), 4.22 (dd, J=15.8, 5.4 Hz, 1H), 3.77 (d, J=14.0 Hz, 1H), 3.68-3.62 (m, 2H), 3.57 (d, J=13.9 Hz, 1H), 2.45-2.43 (m, 3H), 2.08-1.99 (m, 1H), 1.95-1.87 (m, 1H), 1.59 (s, 6H), 0.93-0.90 (m, 9H).

Example A241
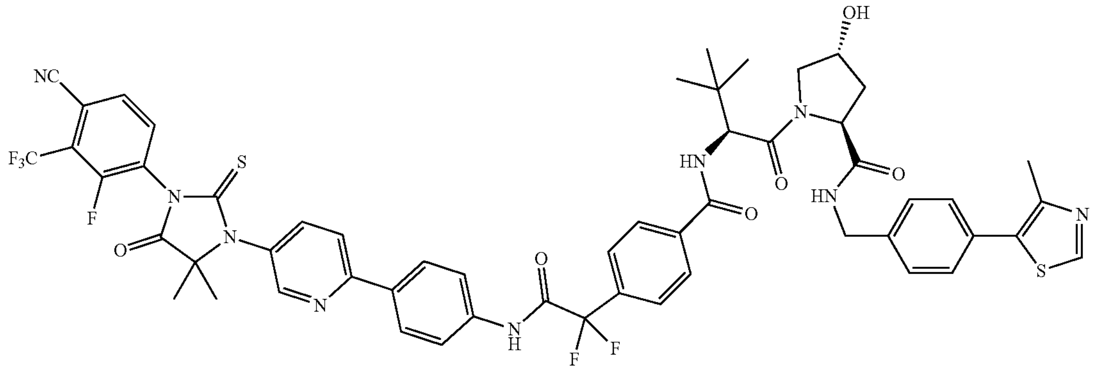 [SMILES: Cc1ncsc1-c1ccc(CNC(=O)[C@@H]2C[C@@H](O)CN2C(=O)[C@@H](NC(=O)c2ccc(C(F)(F)C(=O)Nc3ccc(-c4ccc(N5C(=S)N(c6ccc(C#N)c(C(F)(F)F)c6F)C(=O)C5(C)C)cn4)cc3)cc2)C(C)(C)C)cc1]
LCMS ([M+H]$^+$): 1110.3
$^1$HNMR (400 MHz, DMSO-d6) δ11.98 (s, 1H), 8.62 (s, 1H), 8.36-8.27 (m, 4H), 8.19 (d, J=9.7 Hz, 1H), 7.85-7.74 (m, 5H), 7.59-7.53 (m, 2H), 7.41-7.31 (m, 4H), 5.32 (t, J=4.7 Hz, 2H), 5.20 (d, J=3.7 Hz, 1H), 5.08 (t, J=7.8 Hz, 2H), 4.58 (d, J=9.4 Hz, 1H), 4.48 (s, 1H), 4.16 (d, J=6.5 Hz, 2H), 3.96 (s, 2H), 3.86 (s, 2H), 3.66 (s, 1H), 3.57 (d, J=6.2 Hz, 3H), 2.77 (d, J=4.4 Hz, 3H), 2.03-1.94 (m, 4H), 1.84 (s, 2H), 1.73 (s, 2H), 1.60 (s, 6H), 1.45 (s, 2H), 0.95-0.85 (m, 8H).
Example A242
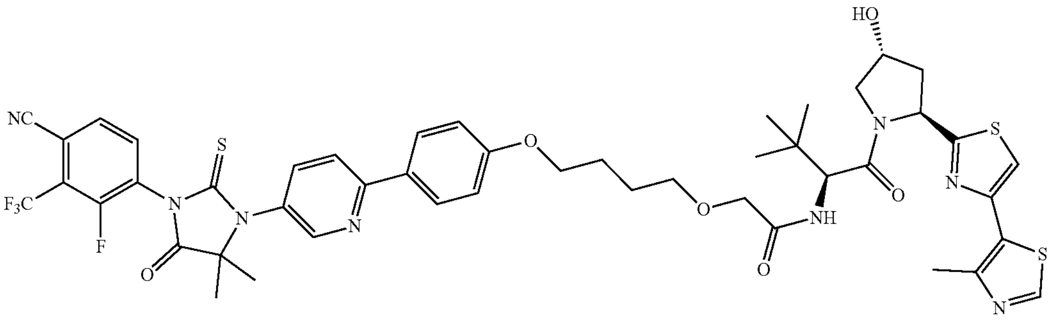 [SMILES: Cc1ncsc1-c1csc([C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2)C(C)(C)C)n1]
LCMS ([M+H]$^+$): 993.1
$^1$HNMR (400 MHz, DMSO-d6) δ8.92 (s, 1H), 8.65 (d, J=2.4 Hz, 1H), 8.29 (q, J=8.4 Hz, 2H), 8.10 (d, J=8.8 Hz, 3H), 7.93 (dd, J=8.5, 2.5 Hz, 1H), 7.74 (d, J=11.5 Hz, 1H), 7.41 (d, J=9.5 Hz, 1H), 7.07 (d, J=8.9 Hz, 2H), 5.36 (t, J=7.5 Hz, 1H), 5.29 (d, J=4.1 Hz, 1H), 4.63 (d, J=9.4 Hz, 1H), 4.44 (d, J=3.8 Hz, 1H), 4.08 (t, J=6.2 Hz, 2H), 4.02-3.91 (m, 2H), 3.85 (dd, J=10.6, 4.6 Hz, 1H), 3.69 (dd, J=10.9, 2.9 Hz, 1H), 3.56 (t, J=6.2 Hz, 2H), 2.57 (d, J=4.9 Hz, 3H), 2.26 (dd, J=7.4, 4.6 Hz, 2H), 1.81 (dd, J=14.0, 6.5 Hz, 2H), 1.77-1.68 (m, 2H), 1.58 (s, 6H), 0.92 (d, J=6.1 Hz, 9H).

Example A243
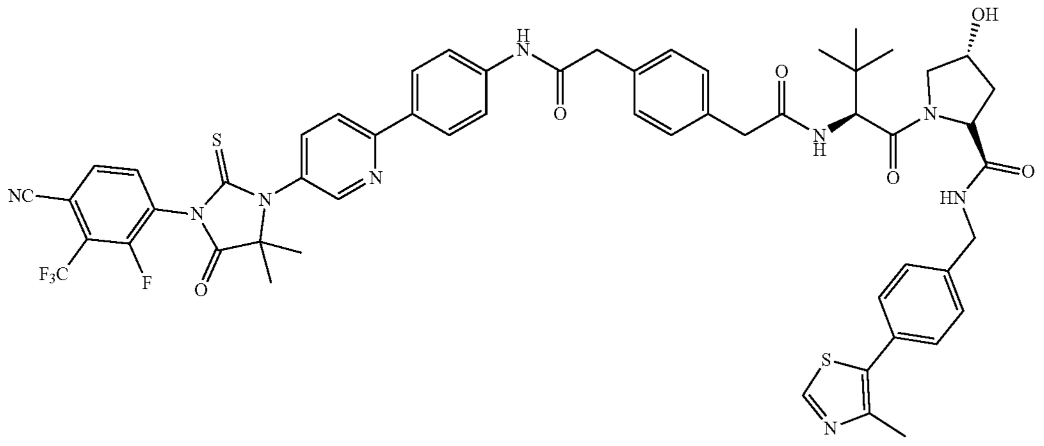
LCMS ([M+H]$^+$): 1088.4
$^1$HNMR (400 MHz, DMSO-d6) δ10.41 (s, 1H), 8.98 (s, 1H), 8.66 (d, J=2.4 Hz, 1H), 8.57 (t, J=6.0 Hz, 1H), 8.34-8.24 (m, 2H), 8.14-8.09 (m, 4H), 7.96 (dd, J=8.5, 2.4 Hz, 1H), 7.76 (d, J=8.8 Hz, 2H), 7.40 (q, J=8.3 Hz, 4H), 7.24 (q, J=8.2 Hz, 4H), 5.12 (d, J=3.5 Hz, 1H), 4.51 (d, J=9.3 Hz, 1H), 4.43 (dd, J=15.5, 7.1 Hz, 2H), 4.33 (s, 1H), 4.21 (dd, J=15.9, 5.3 Hz, 1H), 3.65-3.61 (m, 4H), 3.45 (s, 2H), 2.44-2.43 (m, 3H), 2.06-1.97 (m, 1H), 1.93-1.85 (m, 1H), 1.58 (s, 6H), 0.92-0.89 (m, 9H).
Example A244
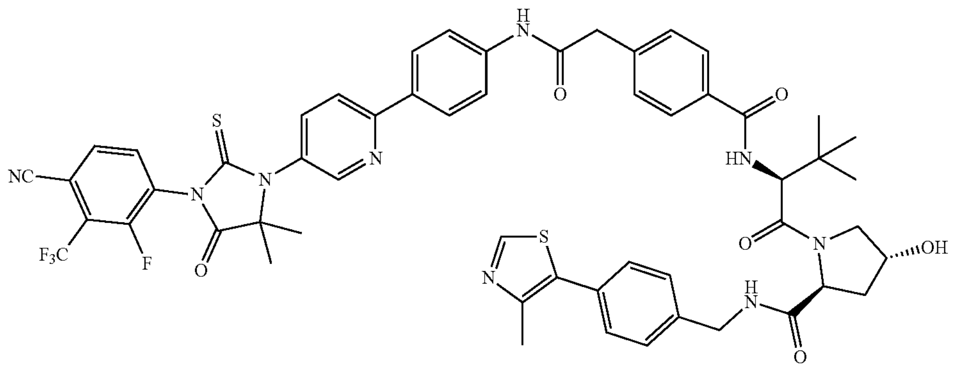 [SMILES: Cc1ncsc1-c1ccc(CNC(=O)[C@@H]2C[C@@H](O)CN2C(=O)[C@@H](NC(=O)c2ccc(CC(=O)Nc3ccc(-c4ccc(N5C(=S)N(c6ccc(C#N)c(C(F)(F)F)c6F)C(=O)C5(C)C)cn4)cc3)cc2)C(C)(C)C)cc1]
LCMS ([M+H]$^+$): 1074.3
$^1$HNMR (400 MHz, DMSO-d6) δ10.43 (s, 1H), 8.97 (d, J=6.1 Hz, 1H), 8.67 (d, J=2.2 Hz, 1H), 8.58 (t, J=6.0 Hz, 1H), 8.29 (q, J=8.6 Hz, 2H), 8.13 (dd, J=8.6, 3.1 Hz, 3H), 7.99-7.91 (m, 2H), 7.85 (d, J=8.2 Hz, 2H), 7.76 (d, J=8.7 Hz, 2H), 7.54-7.35 (m, 6H), 5.16 (m, 1H), 4.77 (m, 1H), 4.50-4.35 (m, 3H), 4.24 (m, 1H), 3.74 (m, 4H), 2.43 (d, J=5.9 Hz, 3H), 2.06-1.89 (m, 2H), 1.58 (s, 6H), 1.01 (d, J=10.8 Hz, 9H).

Example A245
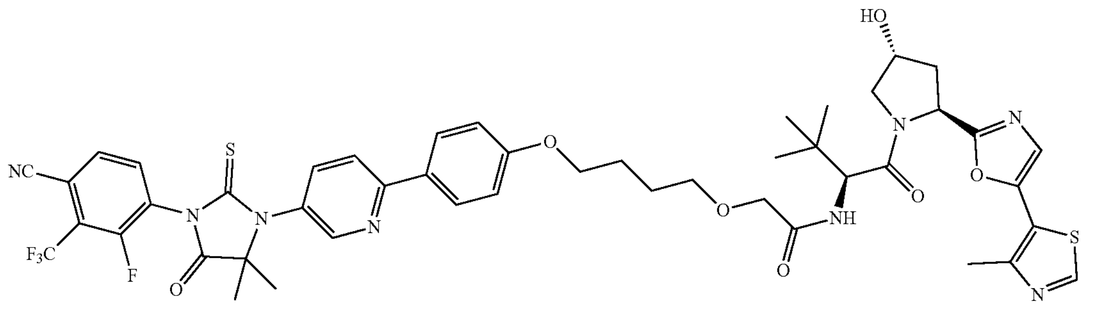 [SMILES: Cc1ncsc1-c1cnc([C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2)C(C)(C)C)o1]
LCMS ([M+H]+): 997.1
$^1$HNMR (400 MHz, DMSO-d6) δ9.03 (s, 1H), 8.65 (d, J=2.3 Hz, 1H), 8.29 (q, J=8.6 Hz, 2H), 8.16-8.05 (m, 3H), 7.94 (dd, J=8.5, 2.4 Hz, 1H), 7.41 (s, 1H), 7.36 (d, J=9.6 Hz, 1H), 7.06 (d, J=8.8 Hz, 2H), 5.32 (d, J=3.8 Hz, 1H), 5.10 (t, J=8.0 Hz, 1H), 4.61 (d, J=9.5 Hz, 1H), 4.43 (s, 1H), 4.07 (t, J=6.2 Hz, 2H), 4.01-3.90 (m, 2H), 3.86 (dd, J=10.6, 4.2 Hz, 1H), 3.70 (d, J=10.3 Hz, 1H), 3.55 (t, J=6.2 Hz, 2H), 2.49-2.48 (m, 3H), 2.28-2.20 (m, 1H), 2.15-2.05 (m, 1H), 1.86-1.76 (m, 2H), 1.76-1.66 (m, 2H), 1.58 (s, 6H), 0.92 (s, 9H).
Example A246
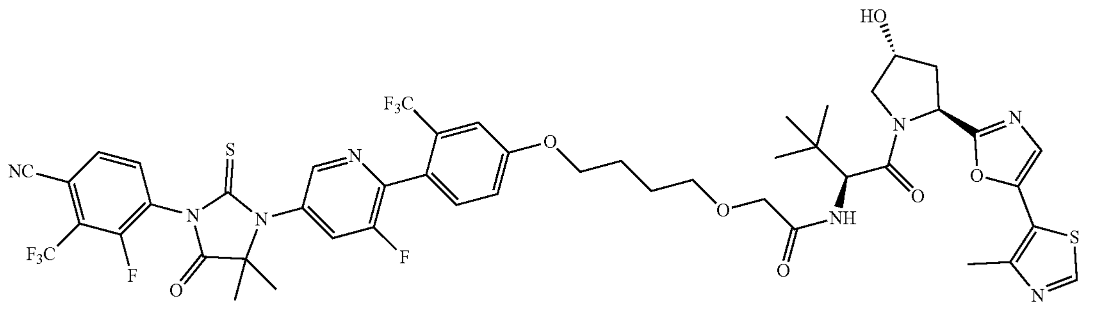 [SMILES: Cc1ncsc1-c1cnc([C@@H]2C[C@@H](O)CN2C(=O)[C@@H](NC(=O)COCCCCOc2ccc(-c3ncc(N4C(=S)N(c5ccc(C#N)c(C(F)(F)F)c5F)C(=O)C4(C)C)cc3F)c(C(F)(F)F)c2)C(C)(C)C)o1]
LCMS ([M+H]+): 1063.1
$^1$HNMR (400 MHz, DMSO-d6) δ9.04 (d, J=4.8 Hz, 1H), 8.62 (s, 1H), 8.32-8.25 (m, 2H), 8.19 (dd, J=9.7, 1.8 Hz, 1H), 7.54 (d, J=9.2 Hz, 1H), 7.37 (dd, J=12.6, 6.5 Hz, 4H), 5.32 (d, J=3.9 Hz, 1H), 5.09 (t, J=8.1 Hz, 1H), 4.61 (d, J=9.5 Hz, 1H), 4.43 (s, 1H), 4.16 (t, J=6.1 Hz, 2H), 3.96 (s, 2H), 3.86 (dd, J=10.6, 4.1 Hz, 1H), 3.70 (d, J=10.8 Hz, 1H), 3.56 (t, J=6.2 Hz, 2H), 2.28-2.20 (m, 1H), 2.15-2.08 (m, 1H), 1.88-1.79 (m, 2H), 1.74 (dd, J=13.9, 6.2 Hz, 2H), 1.61 (s, 6H), 0.92 (s, 9H).

Example A247
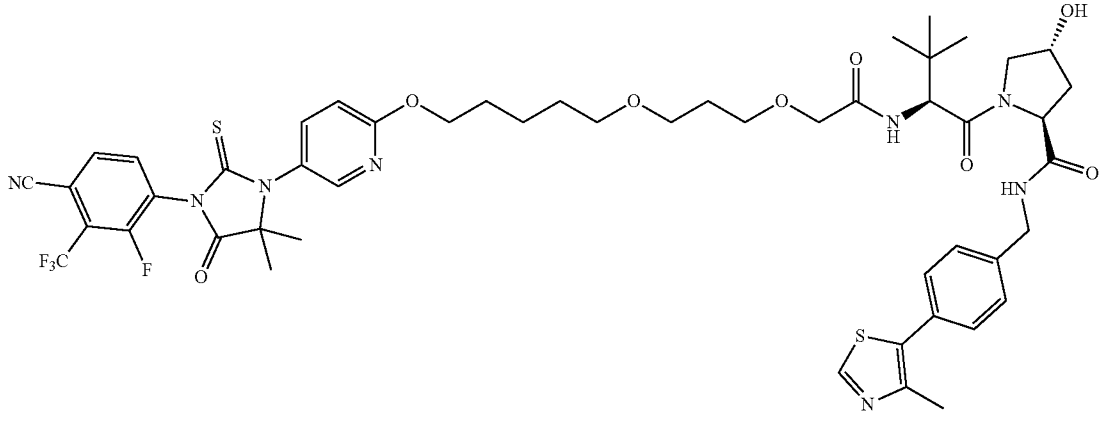 [SMILES: Cc1ncsc1-c1ccc(CNC(=O)[C@@H]2C[C@@H](O)CN2C(=O)[C@@H](NC(=O)COCCCOCCCCCOc2ccc(N3C(=S)N(c4ccc(C#N)c(C(F)(F)F)c4F)C(=O)C3(C)C)cn2)C(C)(C)C)cc1]
LCMS ([M+H]+): 1039.3
$^1$HNMR (400 MHz, DMSO-d6) δ8.96 (d, J=3.8 Hz, 1H), 8.60 (t, J=6.0 Hz, 1H), 8.29-8.21 (m, 2H), 8.19 (d, J=2.6 Hz, 1H), 7.76 (dd, J=8.8, 2.7 Hz, 1H), 7.45-7.33 (m, 5H), 6.96 (d, J=8.8 Hz, 1H), 5.18 (d, J=3.5 Hz, 1H), 4.55 (m, 1H), 4.49-4.32 (m, 3H), 4.30-4.20 (m, 3H), 3.95-3.86 (m, 2H), 3.64 (m, 2H), 3.53 (m, 2H), 3.36 (m, 2H), 2.43 (d, J=4.8 Hz, 3H), 2.06 (m, 1H), 1.90 (m, 1H), 1.81-1.66 (m, 4H), 1.53 (m, 8H), 1.46-1.36 (m, 2H), 0.92 (d, J=6.9 Hz, 9H).
Example A248
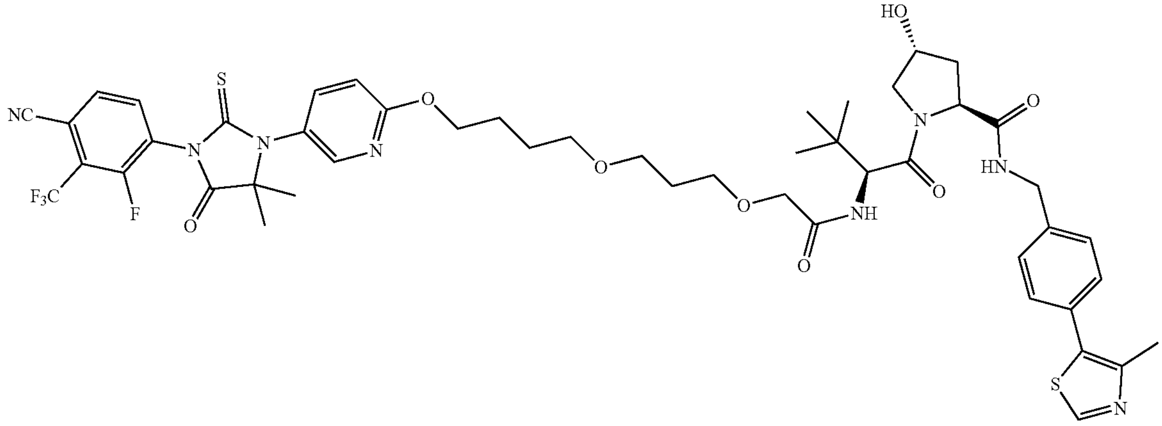 [SMILES: Cc1ncsc1-c1ccc(CNC(=O)[C@@H]2C[C@@H](O)CN2C(=O)[C@@H](NC(=O)COCCCOCCCCOc2ccc(N3C(=S)N(c4ccc(C#N)c(C(F)(F)F)c4F)C(=O)C3(C)C)cn2)C(C)(C)C)cc1]
LCMS ([M+H]+): 1025.1
$^1$HNMR (400 MHz, DMSO-d6) δ8.96 (d, J=4.6 Hz, 1H), 8.60 (t, J=6.0 Hz, 1H), 8.29-8.22 (m, 2H), 8.19 (d, J=2.5 Hz, 1H), 7.77 (dd, J=8.8, 2.7 Hz, 1H), 7.46-7.32 (m, 5H), 7.01-6.94 (m, 1H), 5.18 (d, J=2.7 Hz, 1H), 4.55 (d, J=9.6 Hz, 1H), 4.48-4.33 (m, 3H), 4.26 (dt, J=15.9, 6.0 Hz, 3H), 3.94-3.85 (m, 2H), 3.70-3.46 (m, 8H), 2.43 (d, J=4.6 Hz, 3H), 2.06 (t, J=10.3 Hz, 1H), 1.95-1.85 (m, 1H), 1.83-1.69 (m, 4H), 1.61 (dt, J=13.0, 6.4 Hz, 2H), 1.51 (s, 6H), 0.92 (d, J=7.2 Hz, 9H).

Example A252
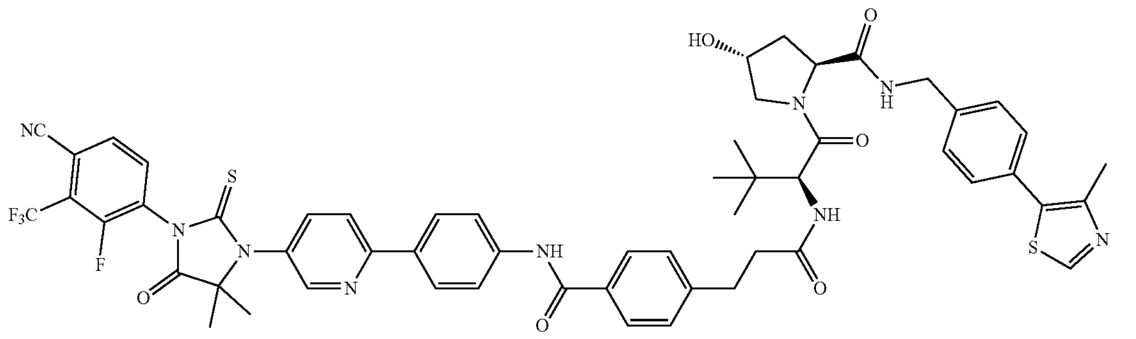 [SMILES: Cc1ncsc1-c1ccc(CNC(=O)[C@@H]2C[C@@H](O)CN2C(=O)[C@@H](NC(=O)CCc2ccc(C(=O)Nc3ccc(-c4ccc(N5C(=S)N(c6ccc(C#N)c(C(F)(F)F)c6F)C(=O)C5(C)C)cn4)cc3)cc2)C(C)(C)C)cc1]
LCMS ([M+H]$^+$): 1088.4
$^1$HNMR (400 MHz, DMSO-d6) δ10.36 (s, 1H), 8.98 (s, 1H), 8.69 (d, J=2.5 Hz, 1H), 8.56 (t, J=6.0 Hz, 1H), 8.34-8.25 (m, 2H), 8.17 (d, J=8.8 Hz, 3H), 7.99-7.95 (m, 4H), 7.91 (d, J=8.2 Hz, 2H), 7.40 (q, J=8.4 Hz, 6H), 5.16 (d, J=3.5 Hz, 1H), 4.56 (d, J=9.4 Hz, 1H), 4.46-4.41 (m, 2H), 4.36 (s, 1H), 4.22 (dd, J=15.8, 5.5 Hz, 1H), 3.67-3.64 (m, 2H), 2.96-2.87 (m, 2H), 2.69-2.62 (m, 1H), 2.44 (s, 3H), 2.09-2.00 (m, 1H), 1.96-1.86 (m, 1H), 1.59 (s, 6H), 0.91-0.89 (m, 9H).
Example A254
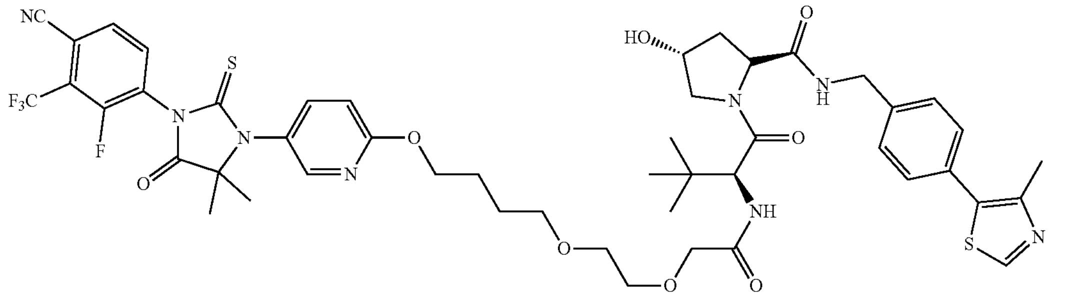
LCMS ([M+H]$^+$): 1011.1
$^1$HNMR (400 MHz, DMSO-d6) δ8.96 (d, J=8.0 Hz, 1H), 8.58 (t, J=6.0 Hz, 1H), 8.30-8.22 (m, 2H), 8.18 (d, J=2.5 Hz, 1H), 7.76 (dd, J=8.8, 2.7 Hz, 1H), 7.49-7.34 (m, 5H), 6.95 (d, J=8.8 Hz, 1H), 5.16 (d, J=3.5 Hz, 1H), 4.56 (d, J=9.6 Hz, 1H), 4.47-4.32 (m, 3H), 4.25 (dt, J=15.8, 5.9 Hz, 3H), 3.94 (d, J=16.8 Hz, 2H), 3.68-3.49 (m, 8H), 2.43 (d, J=6.8 Hz, 3H), 2.04 (dd, J=18.4, 10.1 Hz, 1H), 1.95-1.85 (m, 1H), 1.76 (dd, J=14.2, 6.5 Hz, 2H), 1.66 (dd, J=14.1, 6.5 Hz, 2H), 1.51 (s, 6H), 0.92 (d, J=8.6 Hz, 9H).

Example A255
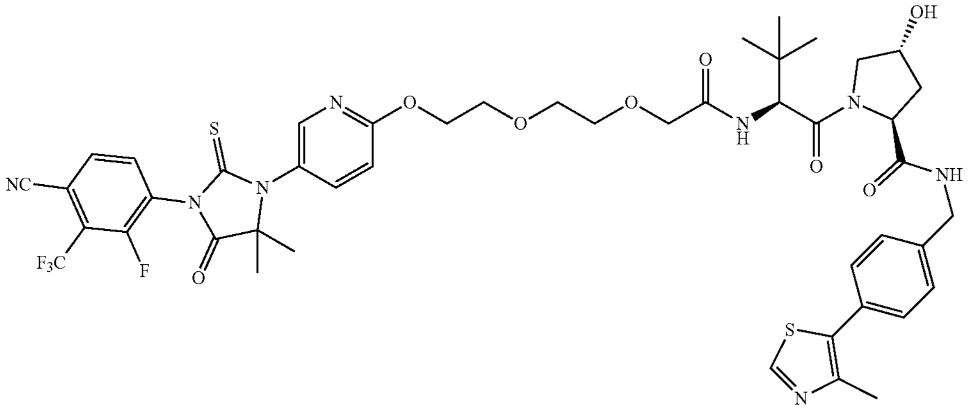 [SMILES: Cc1ncsc1-c1ccc(CNC(=O)[C@@H]2C[C@@H](O)CN2C(=O)[C@@H](NC(=O)COCCOCCOc2ccc(N3C(=S)N(c4ccc(C#N)c(C(F)(F)F)c4F)C(=O)C3(C)C)cn2)C(C)(C)C)cc1]
LCMS ($[M+H]^+$): 983.3
$^1$HNMR (400 MHz, DMSO-d6) δ8.96 (d, J=8.5 Hz, 1H), 8.63 (dt, J=40.5, 5.8 Hz, 1H), 8.31-8.23 (m, 2H), 8.21-8.16 (m, 1H), 7.77 (dd, J=8.8, 2.1 Hz, 1H), 7.48-7.35 (m, 5H), 7.02 (t, J=9.6 Hz, 1H), 5.15 (d, J=3.5 Hz, 1H), 4.56 (d, J=9.6 Hz, 1H), 4.49-4.33 (m, 5H), 4.25 (dd, J=15.8, 5.6 Hz, 1H), 3.97 (d, J=15.4 Hz, 2H), 3.88-3.76 (m, 2H), 3.71-3.58 (m, 6H), 2.44 (d, J=6.2 Hz, 3H), 2.12-2.01 (m, 1H), 1.96-1.85 (m, 1H), 1.51 (d, J=3.5 Hz, 6H), 0.92 (d, J=7.4 Hz, 9H).
Example A256
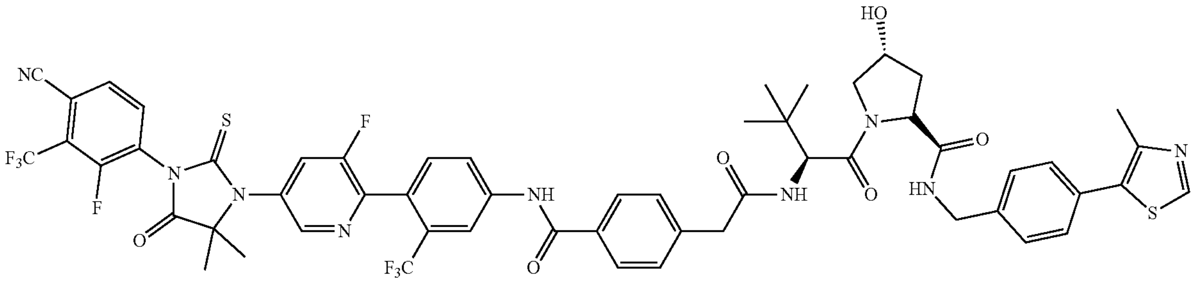
LCMS ($[M+H]^+$): 1160.3
$^1$HNMR (400 MHz, DMSO-d6) δ10.68 (s, 1H), 8.97 (s, 1H), 8.65 (s, 1H), 8.58 (t, J=5.7 Hz, 1H), 8.41 (s, 1H), 8.34-8.18 (m, 5H), 7.94 (d, J=8.0 Hz, 2H), 7.65 (d, J=8.4 Hz, 1H), 7.47 (d, J=8.1 Hz, 2H), 7.41 (q, J=8.2 Hz, 4H), 5.16 (d, J=3.3 Hz, 1H), 4.54 (d, J=9.3 Hz, 1H), 4.48-4.40 (m, 2H), 4.35 (s, 1H), 4.22 (dd, J=15.9, 5.4 Hz, 1H), 3.78 (d, J=13.8 Hz, 1H), 3.65 (d, J=5.2 Hz, 2H), 3.59 (s, 1H), 2.45 (s, 3H), 2.03 (d, J=7.0 Hz, 1H), 1.92 (d, J=12.9 Hz, 1H), 1.68-1.55 (m, 6H), 0.93 (s, 9H).

Example A257
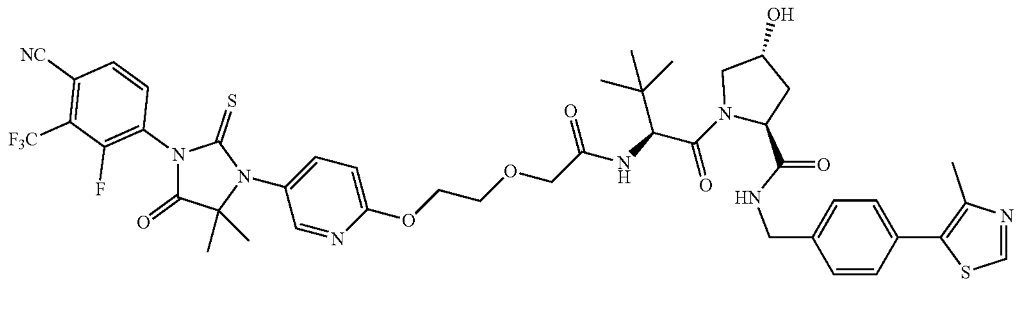 [SMILES: Cc1ncsc1-c1ccc(CNC(=O)[C@@H]2C[C@@H](O)CN2C(=O)[C@@H](NC(=O)COCCOc2ccc(N3C(=S)N(c4ccc(C#N)c(C(F)(F)F)c4F)C(=O)C3(C)C)cn2)C(C)(C)C)cc1]
LCMS ([M+H]$^+$): 939.3
$^1$HNMR (400 MHz, DMSO-d6) δ8.98-8.96 (m, 1H), 8.59 (t, J=5.9 Hz, 1H), 8.32-8.24 (m, 2H), 8.21 (d, J=2.6 Hz, 1H), 7.74 (d, J=8.8 Hz, 1H), 7.50 (d, J=9.5 Hz, 1H), 7.46-7.35 (m, 4H), 7.18-7.10 (m, 1H), 5.16 (d, J=3.5 Hz, 1H), 4.59 (d, J=9.6 Hz, 1H), 4.54-4.42 (m, 3H), 4.39-4.25 (m, 3H), 4.06-4.01 (m, 2H), 3.88 (t, J=4.3 Hz, 2H), 3.72-3.57 (m, 2H), 2.45-2.42 (m, 3H), 2.11-2.02 (m, 1H), 1.97-1.88 (m, 1H), 1.57-1.42 (m, 6H), 0.95 (s, 9H).
Example A260
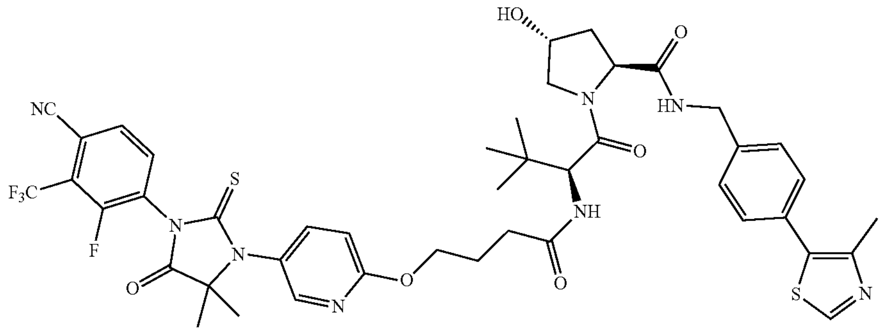 [SMILES: Cc1ncsc1-c1ccc(CNC(=O)[C@@H]2C[C@@H](O)CN2C(=O)[C@@H](NC(=O)CCCOc2ccc(N3C(=S)N(c4ccc(C#N)c(C(F)(F)F)c4F)C(=O)C3(C)C)cn2)C(C)(C)C)cc1]
LCMS ([M+H]$^+$): 923.3
$^1$HNMR (400 MHz, DMSO-d6) δ8.98 (s, 1H), 8.55 (t, J=6.0 Hz, 1H), 8.31-8.23 (m, 2H), 8.20 (d, J=2.6 Hz, 1H), 7.96 (d, J=9.3 Hz, 1H), 7.79 (dd, J=8.8, 2.6 Hz, 1H), 7.40 (q, J=8.3 Hz, 4H), 6.99 (d, J=8.8 Hz, 1H), 5.13 (d, J=3.5 Hz, 1H), 4.56 (d, J=9.3 Hz, 1H), 4.48-4.39 (m, 2H), 4.35 (s, 1H), 4.30 (t, J=6.5 Hz, 2H), 4.22 (dd, J=15.8, 5.4 Hz, 1H), 3.74-3.61 (m, 2H), 2.47-2.39 (m, 4H), 2.36-2.29 (m, 1H), 2.10-1.85 (m, 4H), 1.52-1.50 (m, 6H), 0.94-0.92 (m, 9H).

Example A262
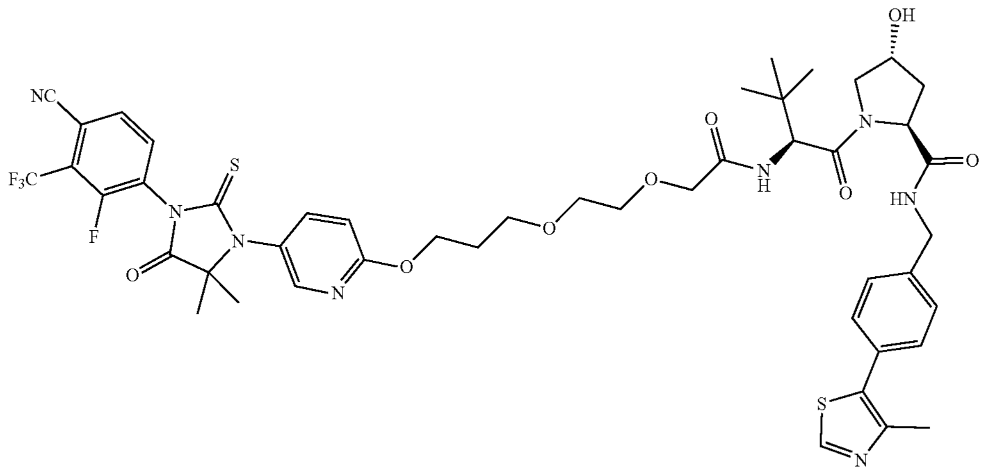 [SMILES: Cc1ncsc1-c1ccc(CNC(=O)[C@@H]2C[C@@H](O)CN2C(=O)[C@@H](NC(=O)COCCOCCCOc2ccc(N3C(=S)N(c4ccc(C#N)c(C(F)(F)F)c4F)C(=O)C3(C)C)cn2)C(C)(C)C)cc1]
LCMS ([M+H]+): 997.3
$^{1}$HNMR (400 MHz, DMSO-d6) δ8.97 (d, J=9.3 Hz, 1H), 8.59 (t, J=6.0 Hz, 1H), 8.30-8.23 (m, 2H), 8.19 (dd, J=7.2, 2.6 Hz, 1H), 7.77 (dd, J=8.8, 2.7 Hz, 1H), 7.48-7.35 (m, 5H), 6.97 (dd, J=17.2, 8.9 Hz, 1H), 5.15 (d, J=3.5 Hz, 1H), 4.56 (d, J=9.6 Hz, 1H), 4.49-4.31 (m, 5H), 4.24 (m, 1H), 3.95 (m, 2H), 3.71-3.53 (m, 8H), 2.44 (M, J=6.2 Hz, 3H), 2.10-1.95 (m, 3H), 1.90 (m, 1H), 1.51 (d, J=1.8 Hz, 6H), 0.92 (d, J=7.7 Hz, 9H).
Example A263
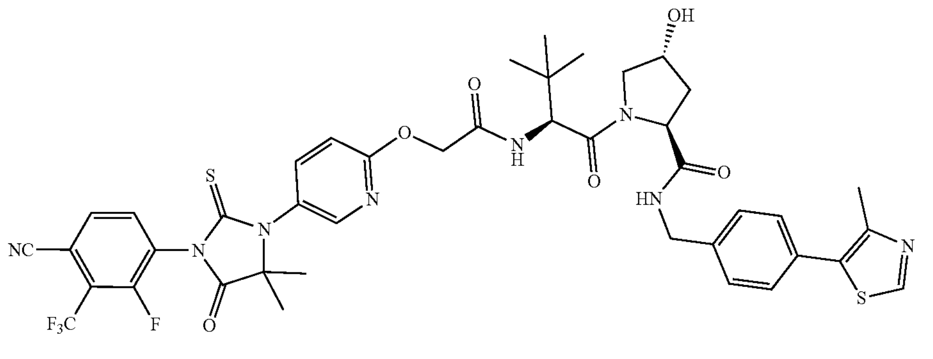 [SMILES: Cc1ncsc1-c1ccc(CNC(=O)[C@@H]2C[C@@H](O)CN2C(=O)[C@@H](NC(=O)COc2ccc(N3C(=S)N(c4ccc(C#N)c(C(F)(F)F)c4F)C(=O)C3(C)C)cn2)C(C)(C)C)cc1]
LCMS ([M+H]+): 895.2
$^{1}$HNMR (400 MHz, DMSO-d6) δ8.98 (d, J=0.8 Hz, 1H), 8.58 (t, J=6.0 Hz, 1H), 8.31-8.22 (m, 2H), 8.21-8.15 (m, 1H), 7.85 (ddd, J=8.5, 7.1, 5.6 Hz, 2H), 7.44-7.35 (m, 4H), 7.13 (d, J=8.8 Hz, 1H), 5.15 (d, J=3.4 Hz, 1H), 4.91 (q, J=14.9 Hz, 2H), 4.57 (d, J=9.5 Hz, 1H), 4.49-4.33 (m, 3H), 4.24 (dd, J=15.9, 5.5 Hz, 1H), 3.64 (dt, J=23.4, 7.3 Hz, 2H), 2.44 (s, 3H), 2.09-2.01 (m, 1H), 1.95-1.85 (m, 1H), 1.49 (dd, J=18.1, 7.2 Hz, 6H), 0.89 (d, J=15.8 Hz, 9H).

Example A264
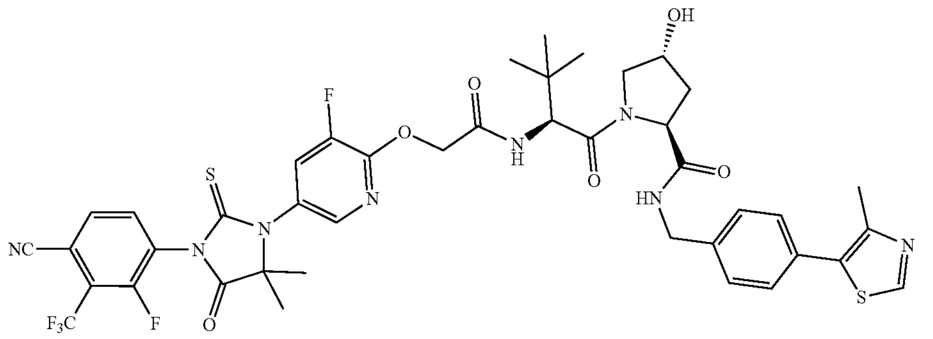 [SMILES: Cc1ncsc1-c1ccc(CNC(=O)[C@@H]2C[C@@H](O)CN2C(=O)[C@@H](NC(=O)COc2ncc(N3C(=S)N(c4ccc(C#N)c(C(F)(F)F)c4F)C(=O)C3(C)C)cc2F)C(C)(C)C)cc1]
LCMS ([M+H]+): 913.2
$^1$HNMR (400 MHz, DMSO-d6) δ8.98 (s, 1H), 8.59 (t, J=6.0 Hz, 1H), 8.28-8.22 (m, 2H), 8.11 (d, J=9.4 Hz, 1H), 8.03 (ddd, J=9.1, 5.9, 2.1 Hz, 2H), 7.41 (q, J=8.4 Hz, 4H), 5.08 (d, J=14.6 Hz, 2H), 5.01-4.95 (m, 1H), 4.58 (d, J=9.4 Hz, 1H), 4.43 (ddd, J=32.4, 19.0, 11.7 Hz, 3H), 4.24 (dd, J=15.8, 5.5 Hz, 1H), 3.70-3.58 (m, 2H), 2.45 (s, 3H), 2.11-2.02 (m, 1H), 1.91 (ddd, J=12.9, 8.7, 4.5 Hz, 1H), 1.56-1.45 (m, 6H), 0.92 (d, J=14.2 Hz, 9H).
Example A265
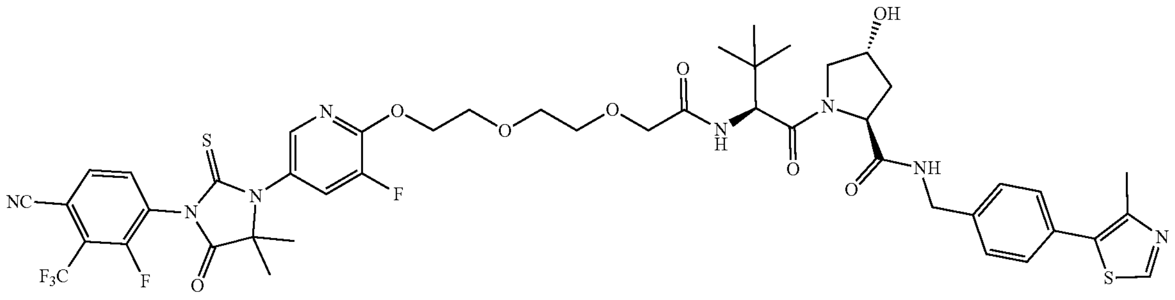 [SMILES: Cc1ncsc1-c1ccc(CNC(=O)[C@@H]2C[C@@H](O)CN2C(=O)[C@@H](NC(=O)COCCOCCOc2ncc(N3C(=S)N(c4ccc(C#N)c(C(F)(F)F)c4F)C(=O)C3(C)C)cc2F)C(C)(C)C)cc1]
LCMS ([M+H]+): 1001.3
$^1$HNMR (400 MHz, DMSO-d6) δ8.97 (d, J=9.6 Hz, 1H), 8.58 (t, J=6.0 Hz, 1H), 8.29-8.21 (m, 2H), 8.05 (t, J=1.9 Hz, 1H), 7.96 (dd, J=10.7, 2.1 Hz, 1H), 7.47-7.36 (m, 5H), 4.56 (dd, J=10.9, 6.1 Hz, 3H), 4.41 (ddd, J=24.7, 14.3, 8.5 Hz, 3H), 4.29-4.21 (m, 1H), 3.95 (d, J=17.0 Hz, 2H), 3.91-3.79 (m, 2H), 3.73-3.56 (m, 4H), 2.44 (d, J=6.2 Hz, 3H), 2.08-2.01 (m, 1H), 1.90 (ddd, J=13.0, 8.8, 4.5 Hz, 1H), 1.54 (s, 6H), 0.91 (d, J=8.3 Hz, 9H).

Example A266
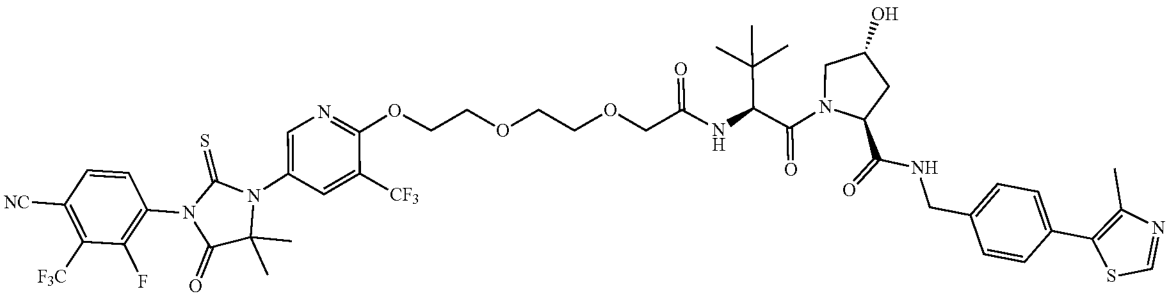 [SMILES: Cc1ncsc1-c1ccc(CNC(=O)[C@@H]2C[C@@H](O)CN2C(=O)[C@@H](NC(=O)COCCOCCOc2ncc(N3C(=S)N(c4ccc(C#N)c(C(F)(F)F)c4F)C(=O)C3(C)C)cc2C(F)(F)F)C(C)(C)C)cc1]
LCMS ([M+H]$^+$): 1051.3
$^1$HNMR (400 MHz, DMSO-d6) δ8.84 (d, J=6.8 Hz, 1H), 8.47 (t, J=2.5 Hz, 1H), 8.22 (d, J=2.5 Hz, 1H), 8.19-8.10 (m, 2H), 7.86 (t, J=5.9 Hz, 1H), 7.43 (ddd, J=23.9, 17.3, 8.9 Hz, 5H), 4.77-4.52 (m, 6H), 4.46-4.32 (m, 2H), 4.05-3.89 (m, 4H), 3.89-3.70 (m, 6H), 2.47 (d, J=3.3 Hz, 3H), 2.20-2.13 (m, 2H), 1.72 (d, J=4.2 Hz, 3H), 1.67 (d, J=4.6 Hz, 3H), 0.99 (s, 9H).
Example A267
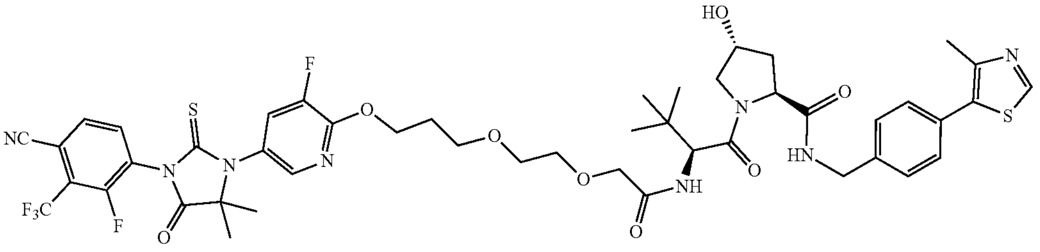 [SMILES: Cc1ncsc1-c1ccc(CNC(=O)[C@@H]2C[C@@H](O)CN2C(=O)[C@@H](NC(=O)COCCOCCCOc2ncc(N3C(=S)N(c4ccc(C#N)c(C(F)(F)F)c4F)C(=O)C3(C)C)cc2F)C(C)(C)C)cc1]
LCMS ([M+H]$^+$): 1015.3
$^1$HNMR (400 MHz, DMSO-d6) δ8.84 (d, J=7.8 Hz, 1H), 8.19-8.10 (m, 2H), 8.06 (dd, J=4.9, 3.0 Hz, 1H), 7.87 (t, J=5.8 Hz, 1H), 7.78 (dd, J=10.5, 2.2 Hz, 1H), 7.51-7.32 (m, 5H), 4.72-4.51 (m, 7H), 4.47 (d, J=3.5 Hz, 1H), 4.34 (dd, J=15.4, 5.2 Hz, 1H), 3.98 (m, 2H), 3.88-3.83 (m, 1H), 3.80-3.64 (m, 8H), 2.47 (d, J=2.7 Hz, 3H), 2.18-2.10 (m, 5H), 1.66 (d, J=13.8 Hz, 6H), 1.00 (s, 9H).

Example A268
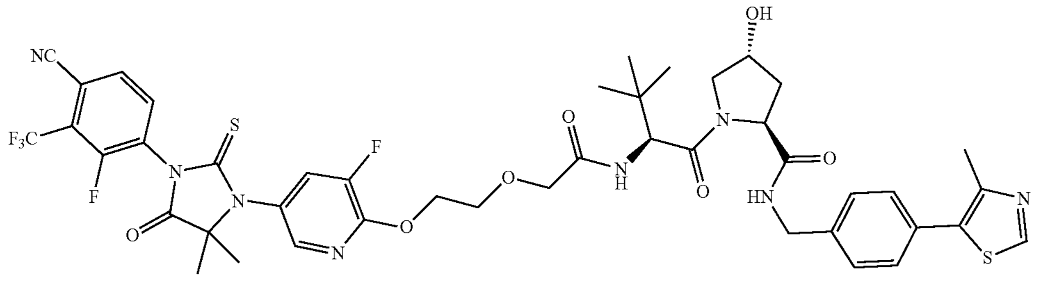 [SMILES: Cc1ncsc1-c1ccc(CNC(=O)[C@@H]2C[C@@H](O)CN2C(=O)[C@@H](NC(=O)COCCOc2ncc(N3C(=S)N(c4ccc(C#N)c(C(F)(F)F)c4F)C(=O)C3(C)C)cc2F)C(C)(C)C)cc1]
LCMS ($[M+H]^+$): 957.3
$^1$HNMR (400 MHz, DMSO-d6) δ8.98-8.97 (m, 1H), 8.58 (t, J=6.0 Hz, 1H), 8.31-8.21 (m, 2H), 8.08 (d, J=2.0 Hz, 1H), 7.95 (dt, J=10.7, 1.9 Hz, 1H), 7.51-7.33 (m, 5H), 5.16 (d, J=3.5 Hz, 1H), 4.67-4.52 (m, 3H), 4.48-4.33 (m, 3H), 4.25 (dd, J=15.8, 5.7 Hz, 1H), 4.07-4.03 (m, 2H), 3.92 (t, J=4.6 Hz, 2H), 3.69-3.60 (m, 2H), 2.45-2.43 (m, 3H), 2.08-2.01 (m, 1H), 1.96-1.85 (m, 1H), 1.54 (s, 6H), 0.92-0.90 (m, 9H).
Example A269
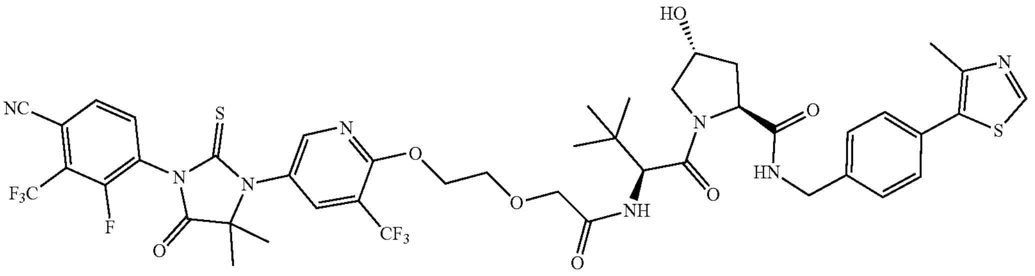 [SMILES: Cc1ncsc1-c1ccc(CNC(=O)[C@@H]2C[C@@H](O)CN2C(=O)[C@@H](NC(=O)COCCOc2ncc(N3C(=S)N(c4ccc(C#N)c(C(F)(F)F)c4F)C(=O)C3(C)C)cc2C(F)(F)F)C(C)(C)C)cc1]
LCMS ($[M+H]^+$): 1007.3
$^1$HNMR (400 MHz, DMSO-d6) δ8.97 (s, 1H), 8.64-8.49 (m, 2H), 8.36-8.17 (m, 3H), 7.43-7.39 (m, 5H), 5.14 (d, J=3.1 Hz, 1H), 4.72-4.52 (m, 3H), 4.47-4.32 (m, 3H), 4.25 (dd, J=15.4, 5.5 Hz, 1H), 4.07-4.03 (m, 2H), 3.92 (s, 2H), 3.64 (dd, J=25.7, 8.9 Hz, 2H), 2.43 (s, 3H), 2.05-2.03 (m, 1H), 1.90 (s, 1H), 1.56 (d, J=4.3 Hz, 6H), 0.92-0.90 (m, 9H).

Example A270
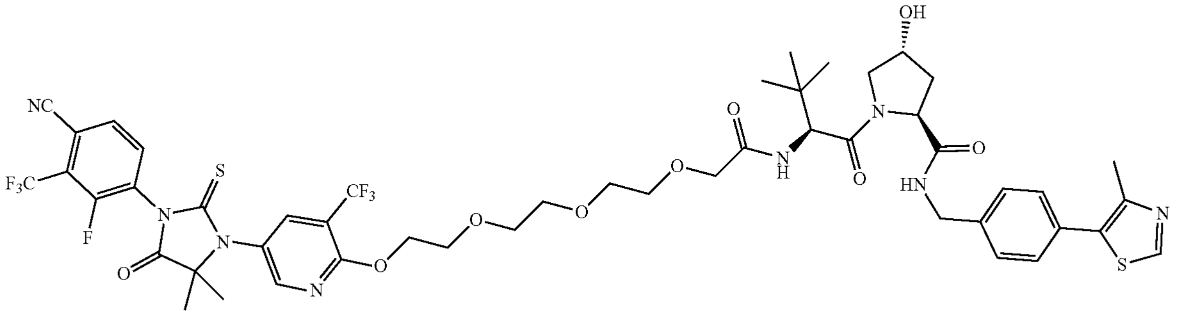 [SMILES: Cc1ncsc1-c1ccc(CNC(=O)[C@@H]2C[C@@H](O)CN2C(=O)[C@@H](NC(=O)COCCOCCOCCOc2ncc(N3C(=S)N(c4ccc(C#N)c(C(F)(F)F)c4F)C(=O)C3(C)C)cc2C(F)(F)F)C(C)(C)C)cc1]
LCMS ([M+H]$^+$): 1095.3
$^1$HNMR (400 MHz, DMSO-d6) δ8.96-8.95 (m, 1H), 8.58 (t, J=6.0 Hz, 1H), 8.50 (d, J=2.3 Hz, 1H), 8.30-8.19 (m, 3H), 7.46-7.34 (m, 5H), 5.18 (d, J=3.5 Hz, 1H), 4.58-4.54 (m, 3H), 4.47-4.31 (m, 3H), 4.24 (dd, J=15.8, 5.6 Hz, 1H), 3.95-3.91 (m, 2H), 3.81-3.75 (m, 2H), 3.65-3.54 (m, 12H), 2.44-2.43 (m, 3H), 2.06 (t, J=10.3 Hz, 1H), 1.95-1.84 (m, 1H), 1.55 (d, J=5.5 Hz, 6H), 0.93-0.91 (m, 9H).
Example A271
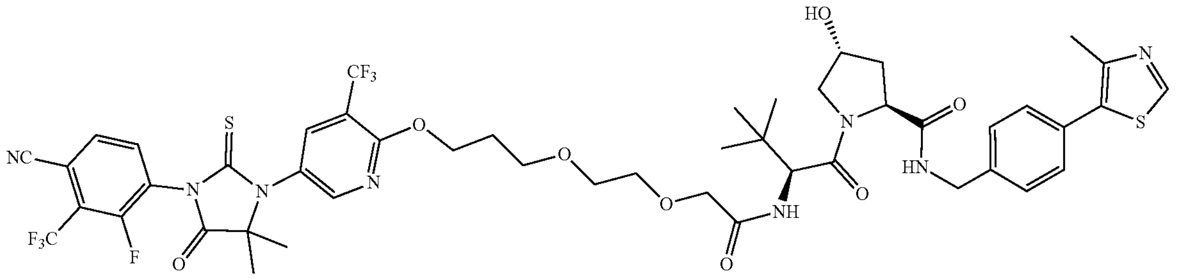 [SMILES: Cc1ncsc1-c1ccc(CNC(=O)[C@@H]2C[C@@H](O)CN2C(=O)[C@@H](NC(=O)COCCOCCCOc2ncc(N3C(=S)N(c4ccc(C#N)c(C(F)(F)F)c4F)C(=O)C3(C)C)cc2C(F)(F)F)C(C)(C)C)cc1]
LCMS ([M+H]$^+$): 1065.3
$^1$HNMR (400 MHz, DMSO-d6) δ8.96 (d, J=11.1 Hz, 1H), 8.57 (t, J=6.0 Hz, 1H), 8.50 (t, J=3.7 Hz, 1H), 8.32-8.19 (m, 3H), 7.47-7.33 (m, 5H), 5.14 (d, J=3.5 Hz, 1H), 4.59-4.48 (m, 3H), 4.48-4.32 (m, 3H), 4.24 (m, 1H), 3.94 (m, 2H), 3.70-3.52 (m, 8H), 2.44 (d, J=7.4 Hz, 3H), 2.09-1.96 (m, 3H), 1.90 (m, 1H), 1.56 (d, J=4.8 Hz, 6H), 0.91 (d, J=8.7 Hz, 9H).

Example A272
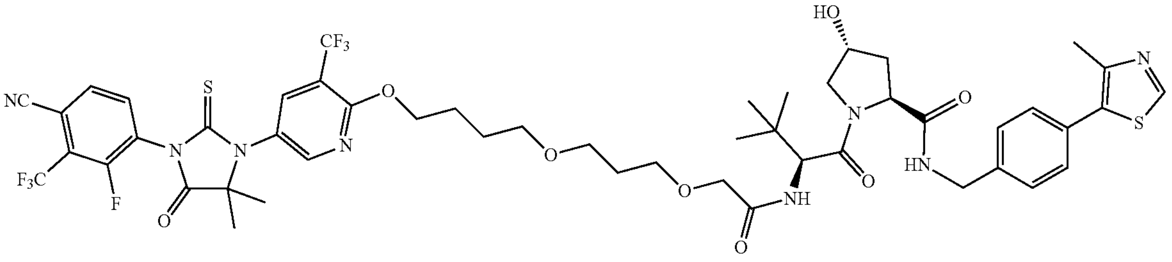 [SMILES: Cc1ncsc1-c1ccc(CNC(=O)[C@@H]2C[C@@H](O)CN2C(=O)[C@@H](NC(=O)COCCCOCCCCOc2ncc(N3C(=S)N(c4ccc(C#N)c(C(F)(F)F)c4F)C(=O)C3(C)C)cc2C(F)(F)F)C(C)(C)C)cc1]
LCMS ([M+H]$^+$): 1093.1
$^1$HNMR (400 MHz, DMSO-d6) δ8.97 (d, J=5.7 Hz, 1H), 8.59 (t, J=6.1 Hz, 1H), 8.51 (d, J=2.3 Hz, 1H), 8.31-8.20 (m, 3H), 7.46-7.33 (m, 5H), 5.14 (d, J=3.4 Hz, 1H), 4.55 (d, J=9.6 Hz, 1H), 4.50-4.33 (m, 6H), 4.25 (dd, J=15.8, 5.7 Hz, 2H), 3.91 (s, 2H), 3.69-3.59 (m, 3H), 3.53 (t, J=6.4 Hz, 2H), 3.45 (dd, J=14.1, 6.6 Hz, 5H), 2.68 (d, J=7.8 Hz, 2H), 2.43 (s, 3H), 2.10-1.94 (m, 3H), 1.90 (s, 2H), 1.84-1.73 (m, 4H), 1.69-1.60 (m, 2H), 1.56 (d, J=4.9 Hz, 5H), 0.92 (d, J=7.5 Hz, 9H).
Example A274
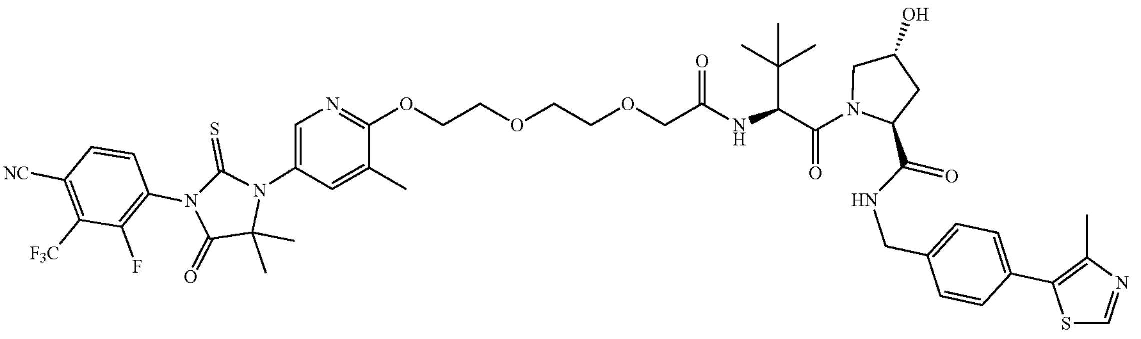 [SMILES: Cc1cc(N2C(=S)N(c3ccc(C#N)c(C(F)(F)F)c3F)C(=O)C2(C)C)cnc1OCCOCCOCC(=O)N[C@H](C(=O)N1C[C@H](O)C[C@H]1C(=O)NCc1ccc(-c2scnc2C)cc1)C(C)(C)C]
LCMS ([M+H]$^+$): 997.3
$^1$HNMR (400 MHz, DMSO-d6) δ8.96 (d, J=11.0 Hz, 1H), 8.58 (t, J=6.0 Hz, 1H), 8.32-8.20 (m, 2H), 8.00 (s, 1H), 7.65 (d, J=1.9 Hz, 1H), 7.48-7.31 (m, 5H), 5.15 (d, J=3.5 Hz, 1H), 4.56 (d, J=9.6 Hz, 1H), 4.52-4.31 (m, 5H), 4.24 (dd, J=15.8, 5.6 Hz, 1H), 3.97 (d, J=15.8 Hz, 2H), 3.90-3.76 (m, 2H), 3.74-3.58 (m, 6H), 2.44 (d, J=7.2 Hz, 3H), 2.19 (d, J=9.4 Hz, 3H), 2.13-2.01 (m, 1H), 1.91 (ddd, J=13.0, 8.8, 4.5 Hz, 1H), 1.51 (d, J=5.4 Hz, 6H), 0.92 (d, J=7.4 Hz, 9H).

Example A275
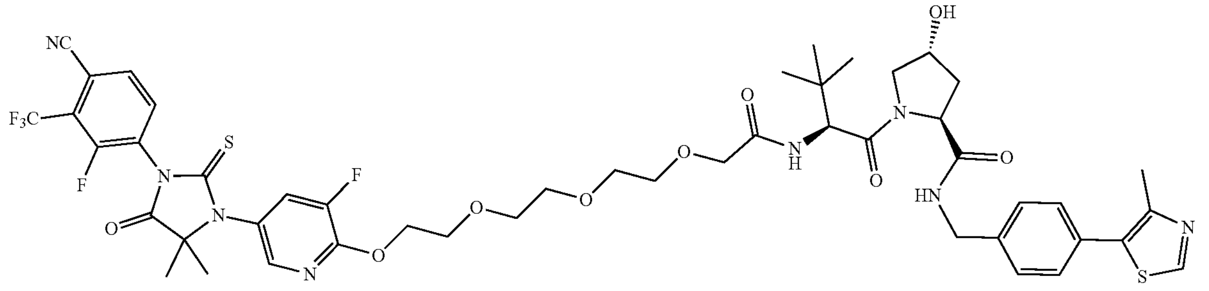 [SMILES: Cc1ncsc1-c1ccc(CNC(=O)[C@@H]2C[C@@H](O)CN2C(=O)[C@@H](NC(=O)COCCOCCOCCOc2ncc(N3C(=S)N(c4ccc(C#N)c(C(F)(F)F)c4F)C(=O)C3(C)C)cc2F)C(C)(C)C)cc1]
LCMS ([M+H]$^+$): 1045.3
$^1$HNMR (400 MHz, DMSO-d6) δ8.98-8.97 (m, 1H), 8.59 (t, J=6.0 Hz, 1H), 8.26-8.23 (m, 2H), 8.07 (d, J=2.1 Hz, 1H), 7.97 (dd, J=10.7, 2.1 Hz, 1H), 7.48-7.35 (m, 5H), 5.15 (d, J=3.5 Hz, 1H), 4.60-4.49 (m, 3H), 4.48-4.32 (m, 3H), 4.24 (dd, J=15.8, 5.5 Hz, 1H), 3.96-3.92 (m, 2H), 3.84-3.75 (m, 2H), 3.70-3.55 (m, 10H), 2.45-2.43 (m, 3H), 2.08-2.03 (m, 1H), 1.90 (ddd, J=12.7, 8.6, 4.4 Hz, 1H), 1.54 (d, J=1.2 Hz, 6H), 0.94-0.91 (d, J=8.6 Hz, 9H).
Example A276
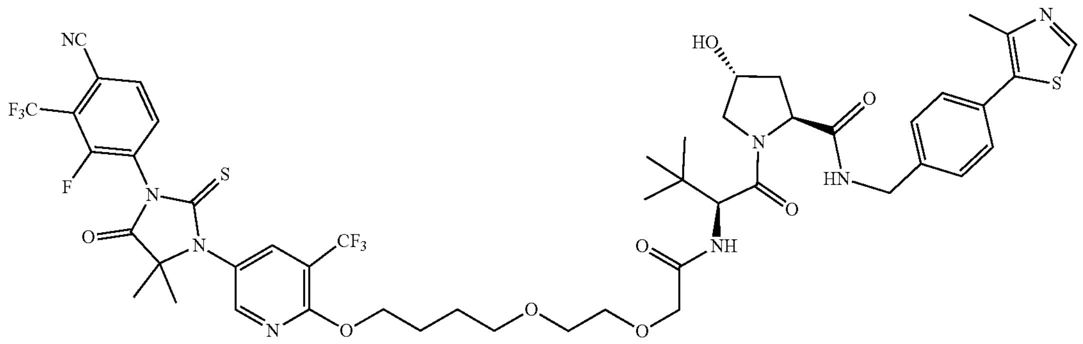 [SMILES: Cc1ncsc1-c1ccc(CNC(=O)[C@@H]2C[C@@H](O)CN2C(=O)[C@@H](NC(=O)COCCOCCCCOc2ncc(N3C(=S)N(c4ccc(C#N)c(C(F)(F)F)c4F)C(=O)C3(C)C)cc2C(F)(F)F)C(C)(C)C)cc1]
LCMS ([M+H]$^+$): 1079.3
$^1$HNMR (400 MHz, DMSO-d6) δ8.95 (s, 1H), 8.58 (t, J=6.0 Hz, 1H), 8.50 (d, J=2.3 Hz, 1H), 8.30-8.19 (m, 3H), 7.40 (d, J=6.6 Hz, 5H), 5.15 (d, J=3.5 Hz, 1H), 4.56 (d, J=9.6 Hz, 1H), 4.51-4.31 (m, 5H), 4.25 (dd, J=15.8, 5.6 Hz, 1H), 3.96 (s, 2H), 3.68-3.48 (m, 8H), 2.43 (s, 3H), 2.10-2.02 (m, 1H), 1.90 (ddd, J=12.9, 8.9, 4.5 Hz, 1H), 1.86-1.75 (m, 2H), 1.67 (p, J=6.5 Hz, 2H), 1.56 (d, J=5.1 Hz, 6H), 0.93 (s, 9H).

Example A277
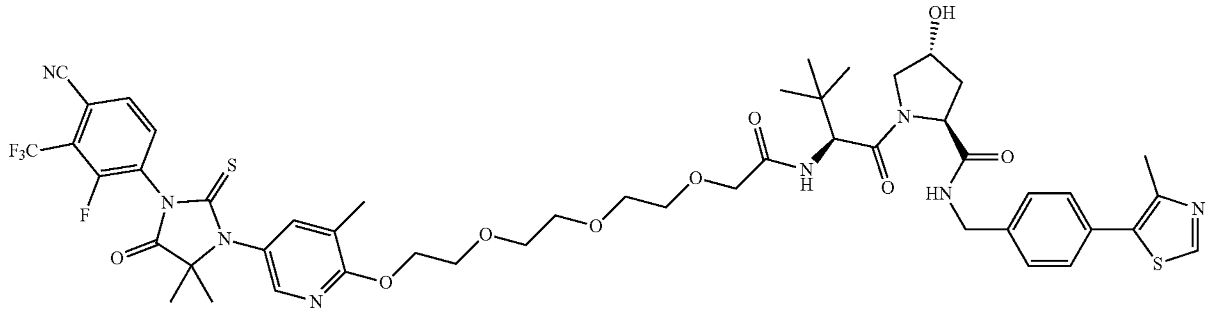 [SMILES: Cc1cc(N2C(=S)N(c3ccc(C#N)c(C(F)(F)F)c3F)C(=O)C2(C)C)cnc1OCCOCCOCCOCC(=O)N[C@H](C(=O)N1C[C@H](O)C[C@H]1C(=O)NCc1ccc(-c2scnc2C)cc1)C(C)(C)C]
LCMS ($[M+H]^+$): 1041.4
$^1$HNMR (400 MHz, DMSO-d6) δ8.98-8.96 (m, 1H), 8.60 (t, J=6.0 Hz, 1H), 8.31-8.22 (m, 2H), 8.02 (d, J=2.3 Hz, 1H), 7.66 (s, 1H), 7.47-7.34 (m, 5H), 5.18-5.17 (m, 1H), 4.56 (d, J=9.6 Hz, 1H), 4.46-4.36 (m, 5H), 4.24 (dd, J=15.8, 5.7 Hz, 1H), 3.96-3.92 (m, 2H), 3.80-3.74 (m, 2H), 3.66-3.58 (m, 10H), 2.44-2.43 (m, 3H), 2.19-2.18 (m, 3H), 2.11-1.97 (m, 2H), 1.94-1.85 (m, 1H), 1.51 (d, J=6.2 Hz, 6H), 0.93-0.91 (m, 9H).
Example A278
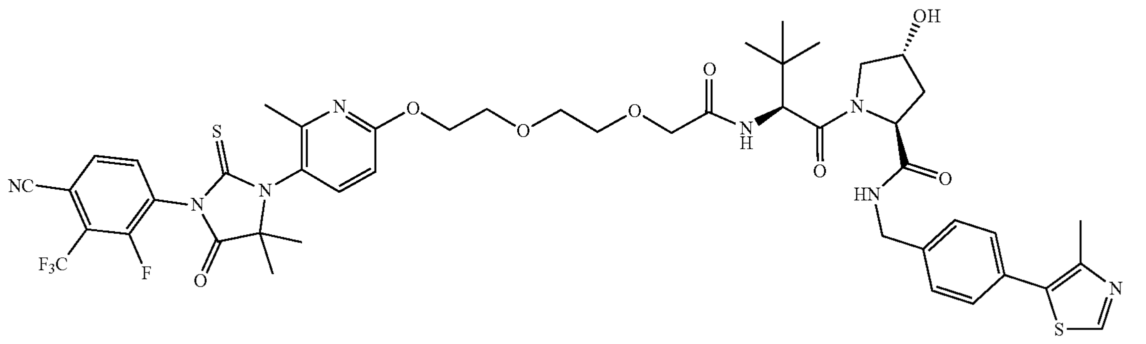 [SMILES: Cc1nc(OCCOCCOCC(=O)N[C@H](C(=O)N2C[C@H](O)C[C@H]2C(=O)NCc2ccc(-c3scnc3C)cc2)C(C)(C)C)ccc1N1C(=S)N(c2ccc(C#N)c(C(F)(F)F)c2F)C(=O)C1(C)C]
LCMS ($[M+H]^+$): 997.3
$^1$HNMR (400 MHz, DMSO-d6) δ8.97 (d, J=8.7 Hz, 1H), 8.59 (t, J=5.9 Hz, 1H), 8.31 (dt, J=40.9, 6.0 Hz, 2H), 7.74-7.55 (m, 1H), 7.48-7.36 (m, 5H), 6.85-6.73 (m, 1H), 5.15 (d, J=3.4 Hz, 1H), 4.56 (d, J=9.6 Hz, 1H), 4.48-4.31 (m, 5H), 4.29-4.17 (m, 1H), 3.96 (d, J=15.1 Hz, 2H), 3.85-3.74 (m, 2H), 3.70-3.57 (m, 6H), 2.44 (d, J=7.0 Hz, 3H), 2.33 (dd, J=19.2, 7.7 Hz, 3H), 2.06 (dd, J=14.3, 6.0 Hz, 1H), 1.90 (ddd, J=13.0, 8.8, 4.5 Hz, 1H), 1.63-1.55 (m, 3H), 1.50-1.41 (m, 3H), 0.92 (d, J=7.8 Hz, 9H).

Example A279
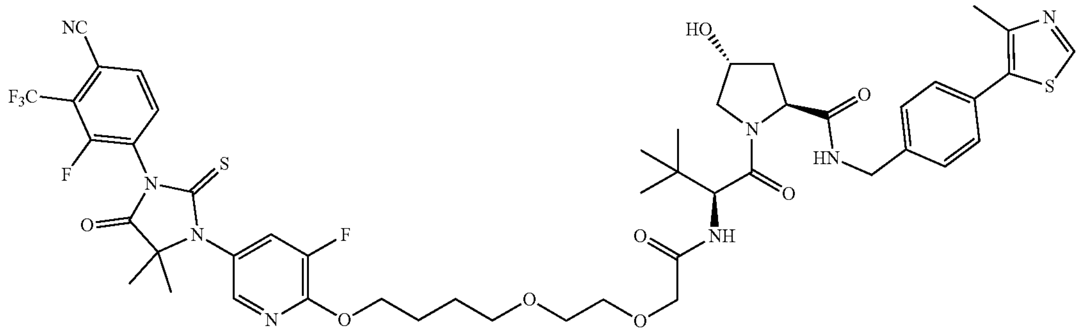 [SMILES: Cc1ncsc1-c1ccc(CNC(=O)[C@@H]2C[C@@H](O)CN2C(=O)[C@@H](NC(=O)COCCOCCCCOc2ncc(N3C(=S)N(c4ccc(C#N)c(C(F)(F)F)c4F)C(=O)C3(C)C)cc2F)C(C)(C)C)cc1]
LCMS ([M+H]$^+$): 1029.3
$^1$HNMR (400 MHz, DMSO-d6) δ8.96 (s, 1H), 8.58 (t, J=5.9 Hz, 1H), 8.25 (d, J=3.6 Hz, 2H), 8.06 (dd, J=6.2, 2.1 Hz, 1H), 7.95 (dd, J=10.7, 2.1 Hz, 1H), 7.39 (s, 5H), 5.15 (d, J=3.5 Hz, 1H), 4.56 (d, J=9.6 Hz, 1H), 4.41 (dq, J=14.3, 7.7, 7.3 Hz, 5H), 4.24 (dd, J=15.8, 5.6 Hz, 1H), 3.97 (s, 2H), 3.71-3.53 (m, 6H), 3.53-3.47 (m, 2H), 2.43 (s, 3H), 2.06 (dd, J=15.1, 6.4 Hz, 1H), 1.90 (ddd, J=13.0, 8.9, 4.6 Hz, 1H), 1.86-1.76 (m, 2H), 1.72-1.63 (m, 2H), 1.54 (s, 6H), 0.93 (d, J=9.4 Hz, 9H).
Example A280
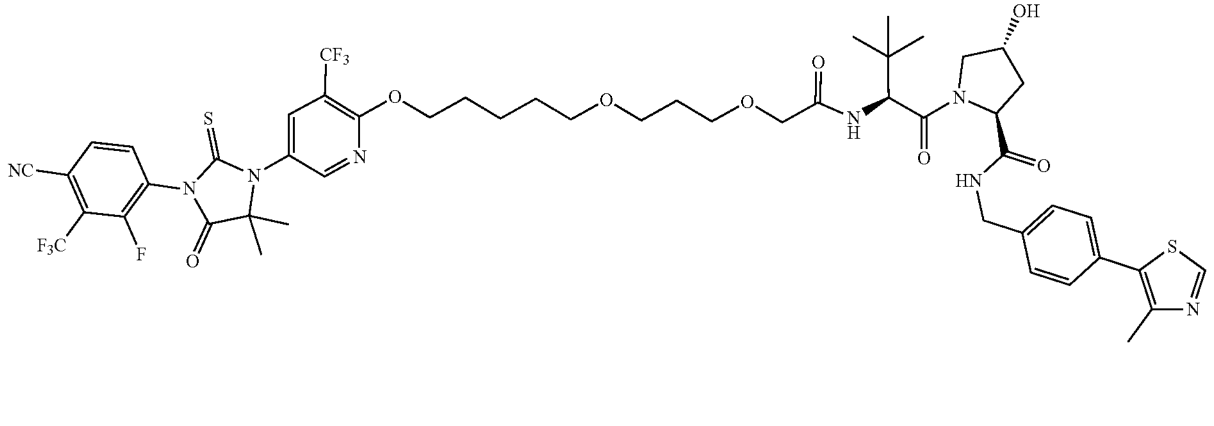 [SMILES: Cc1ncsc1-c1ccc(CNC(=O)[C@@H]2C[C@@H](O)CN2C(=O)[C@@H](NC(=O)COCCCOCCCCCOc2ncc(N3C(=S)N(c4ccc(C#N)c(C(F)(F)F)c4F)C(=O)C3(C)C)cc2C(F)(F)F)C(C)(C)C)cc1]
LCMS ([M+H]$^+$): 1107.3
$^1$HNMR (400 MHz, DMSO-d6) δ8.97 (d, J=5.0 Hz, 1H), 8.59 (t, J=6.0 Hz, 1H), 8.51 (d, J=2.3 Hz, 1H), 8.30-8.19 (m, 3H), 7.47-7.31 (m, 5H), 5.14 (d, J=3.5 Hz, 1H), 4.55 (d, J=9.6 Hz, 1H), 4.41 (m, 5H), 4.25 (m, 1H), 3.89 (m, 2H), 3.64 (m, 2H), 3.53 (m, 2H), 3.44 (m, 2H), 3.36 (m, 2H), 2.44 (d, J=5.1 Hz, 3H), 2.06 (m, 1H), 1.90 (m, 1H), 1.83-1.70 (m, 4H), 1.62-1.50 (m, 8H), 1.49-1.39 (m, 2H), 0.92 (d, J=7.4 Hz, 9H).

Example A281
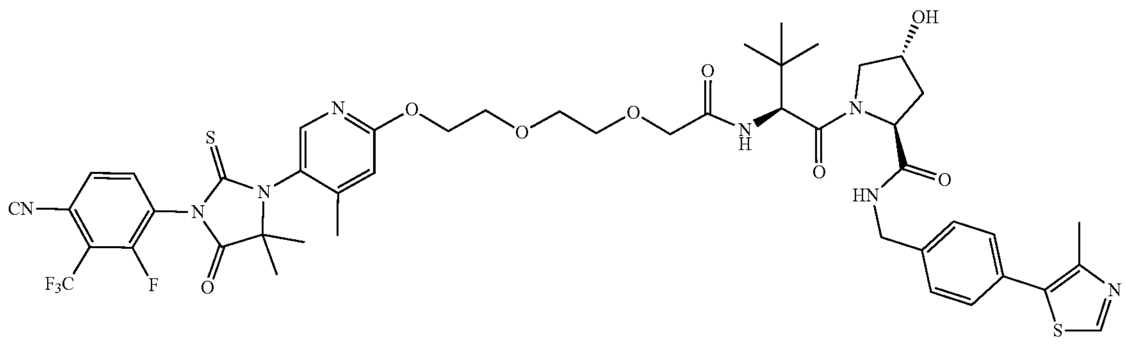
LCMS ([M+H]+): 997.3
$^1$HNMR (400 MHz, DMSO-d6) δ8.96 (s, 1H), 8.58 (t, J=6.0 Hz, 1H), 8.26 (s, 2H), 8.03 (s, 1H), 7.40 (s, 5H), 6.94-6.84 (m, 1H), 5.14 (d, J=3.5 Hz, 1H), 4.56 (d, J=8.7 Hz, 1H), 4.43 (s, 5H), 4.24 (dd, J=15.8, 5.6 Hz, 1H), 3.98 (s, 2H), 3.89-3.75 (m, 2H), 3.63 (d, J=9.7 Hz, 6H), 2.43 (s, 3H), 2.23 (d, J=17.3 Hz, 3H), 2.06 (dd, J=14.0, 6.3 Hz, 1H), 1.96-1.85 (m, 1H), 1.67-1.57 (m, 3H), 1.51-1.37 (m, 3H), 0.92 (d, J=8.2 Hz, 9H).
Example A282
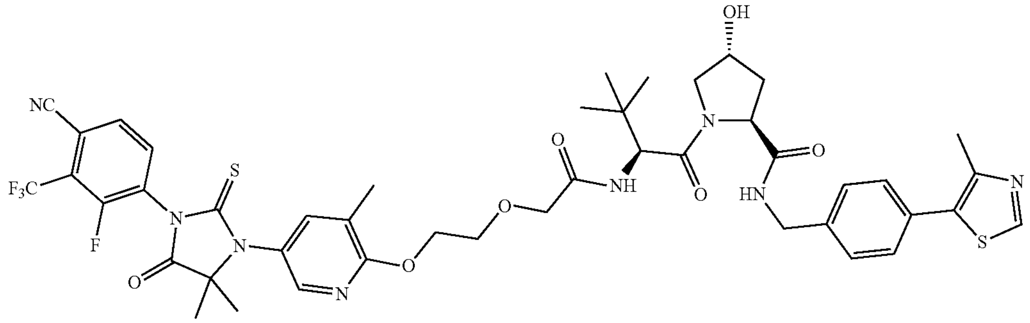 [SMILES: Cc1cc(N2C(=S)N(c3ccc(C#N)c(C(F)(F)F)c3F)C(=O)C2(C)C)cnc1OCCOCC(=O)N[C@H](C(=O)N1C[C@H](O)C[C@H]1C(=O)NCc1ccc(-c2scnc2C)cc1)C(C)(C)C]
LCMS ([M+H]+): 953.3
$^1$HNMR (400 MHz, DMSO-d6) δ8.98-8.97 (m, 1H), 8.58 (t, J=6.0 Hz, 1H), 8.29-8.23 (m, 2H), 8.03 (d, J=2.4 Hz, 1H), 7.68-7.65 (m, 1H), 7.46-7.37 (m, 6H), 5.16 (d, J=3.5 Hz, 1H), 4.61-4.48 (m, 3H), 4.48-4.36 (m, 3H), 4.25 (dd, J=15.7, 5.7 Hz, 1H), 4.08-4.03 (m, 2H), 3.90 (t, J=4.4 Hz, 2H), 3.69-3.59 (m, 2H), 2.45-2.43 (m, 3H), 2.24-2.22 (m, 3H), 2.08-2.02 (m, 1H), 1.90 (ddd, J=12.8, 8.7, 4.4 Hz, 1H), 1.51 (d, J=5.2 Hz, 6H), 0.92-0.90 (m, 11H).

Example A283
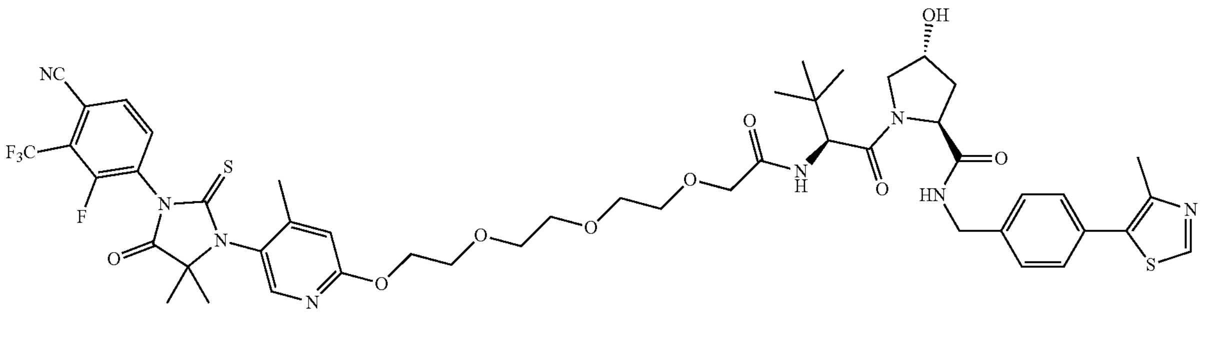 [SMILES: Cc1cc(OCCOCCOCCOCC(=O)N[C@H](C(=O)N2C[C@H](O)C[C@H]2C(=O)NCc2ccc(-c3scnc3C)cc2)C(C)(C)C)ncc1N1C(=S)N(c2ccc(C#N)c(C(F)(F)F)c2F)C(=O)C1(C)C]
LCMS ([M+H]$^+$): 1041.4
$^1$HNMR (400 MHz, DMSO-d6) δ8.98-8.27 (m, 1H), 8.59 (t, J=5.9 Hz, 1H), 8.39-8.23 (m, 2H), 8.09 (d, J=31.1 Hz, 1H), 7.48-7.36 (m, 5H), 6.90-6.87 (m, 1H), 5.16 (d, J=3.5 Hz, 1H), 4.56 (d, J=9.6 Hz, 1H), 4.47-4.33 (m, 5H), 4.24 (dd, J=15.8, 5.5 Hz, 1H), 3.96-3.92 (m, 2H), 3.73 (s, 2H), 3.61-3.57 (m, 10H), 2.44 (d, J=4.6 Hz, 3H), 2.24 (d, J=17.2 Hz, 3H), 2.07-1.99 (m, 2H), 1.95-1.86 (m, 1H), 1.63 (d, J=12.4 Hz, 3H), 1.43 (d, J=9.7 Hz, 3H), 0.94-0.92 (m, 9H).
Example A284
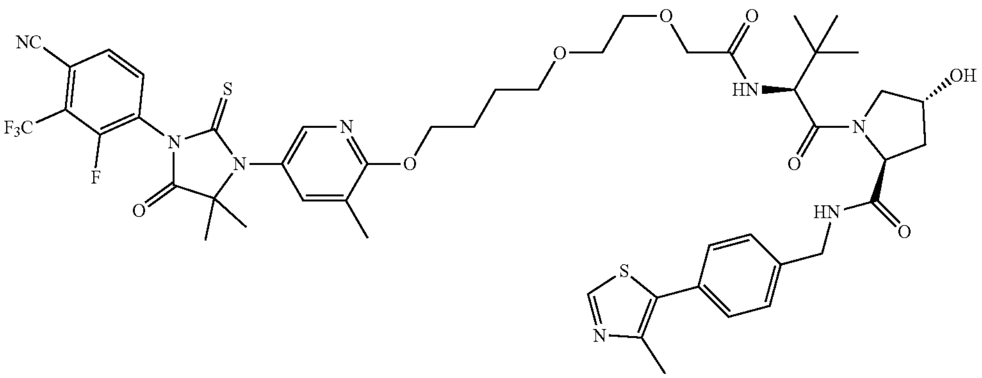 [SMILES: Cc1cc(N2C(=S)N(c3ccc(C#N)c(C(F)(F)F)c3F)C(=O)C2(C)C)cnc1OCCCCOCCOCC(=O)N[C@H](C(=O)N1C[C@H](O)C[C@H]1C(=O)NCc1ccc(-c2scnc2C)cc1)C(C)(C)C]
LCMS ([M+H]$^+$): 1025.3
$^1$HNMR (400 MHz, DMSO-d6) δ8.95 (s, 1H), 8.58 (t, J=6.0 Hz, 1H), 8.26 (d, J=4.2 Hz, 2H), 8.01 (d, J=2.4 Hz, 1H), 7.64 (d, J=1.8 Hz, 1H), 7.40 (d, J=9.6 Hz, 5H), 5.15 (d, J=3.5 Hz, 1H), 4.56 (d, J=9.6 Hz, 1H), 4.48-4.20 (m, 6H), 3.97 (s, 2H), 3.71-3.46 (m, 8H), 2.43 (s, 3H), 2.17 (s, 3H), 2.10-2.02 (m, 1H), 1.90 (ddd, J=12.9, 8.8, 4.5 Hz, 1H), 1.84-1.74 (m, 2H), 1.68 (dt, J=13.2, 6.4 Hz, 2H), 1.51 (d, J=6.0 Hz, 6H), 0.94 (s, 9H).

Example A285
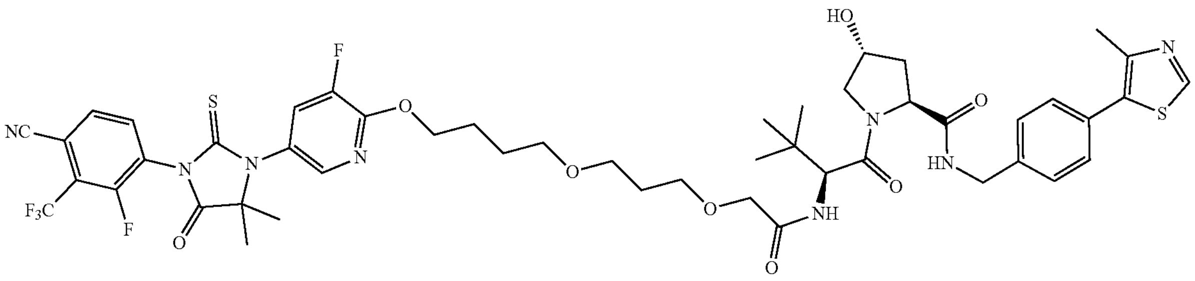 [SMILES: Cc1ncsc1-c1ccc(CNC(=O)[C@@H]2C[C@@H](O)CN2C(=O)[C@@H](NC(=O)COCCCOCCCCOc2ncc(N3C(=S)N(c4ccc(C#N)c(C(F)(F)F)c4F)C(=O)C3(C)C)cc2F)C(C)(C)C)cc1]
LCMS ($[M+H]^+$): 1043.1
$^1$HNMR (400 MHz, DMSO-d6) δ8.97 (d, J=5.3 Hz, 1H), 8.60 (t, J=6.0 Hz, 1H), 8.30-8.20 (m, 2H), 8.07 (d, J=2.1 Hz, 1H), 7.95 (dd, J=10.7, 2.1 Hz, 1H), 7.47-7.32 (m, 5H), 5.15 (d, J=3.5 Hz, 1H), 4.55 (d, J=9.6 Hz, 1H), 4.50-4.32 (m, 5H), 4.25 (dd, J=15.7, 5.6 Hz, 1H), 3.98-3.83 (m, 2H), 3.71-3.50 (m, 4H), 3.44 (dt, J=14.6, 6.3 Hz, 4H), 2.44 (d, J=4.7 Hz, 3H), 2.06 (dd, J=13.3, 6.7 Hz, 1H), 1.95-1.85 (m, 1H), 1.85-1.73 (m, 4H), 1.64 (dd, J=14.5, 6.4 Hz, 2H), 1.54 (d, J=1.7 Hz, 6H), 0.93 (d, J=7.6 Hz, 9H).
Example A286
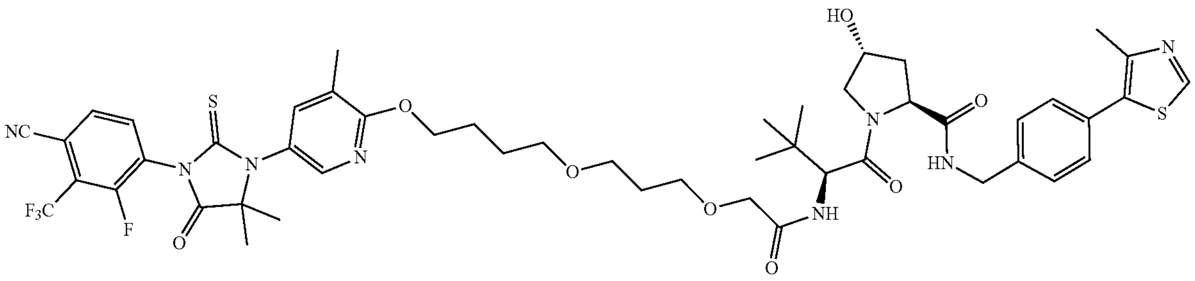 [SMILES: Cc1cc(N2C(=S)N(c3ccc(C#N)c(C(F)(F)F)c3F)C(=O)C2(C)C)cnc1OCCCCOCCCOCC(=O)N[C@H](C(=O)N1C[C@H](O)C[C@H]1C(=O)NCc1ccc(-c2scnc2C)cc1)C(C)(C)C]
LCMS ($[M+H]^+$): 1039.2
$^1$HNMR (400 MHz, DMSO-d6) δ8.97 (d, J=5.9 Hz, 1H), 8.60 (t, J=5.9 Hz, 1H), 8.31-8.22 (m, 2H), 8.02 (d, J=2.2 Hz, 1H), 7.64 (d, J=1.7 Hz, 1H), 7.47-7.32 (m, 5H), 5.15 (d, J=3.5 Hz, 1H), 4.55 (d, J=9.6 Hz, 1H), 4.49-4.20 (m, 6H), 3.90 (d, J=18.8 Hz, 2H), 3.71-3.50 (m, 4H), 3.50-3.39 (m, 4H), 2.44 (d, J=4.9 Hz, 3H), 2.18 (s, 3H), 2.11-2.02 (m, 1H), 1.96-1.84 (m, 1H), 1.84-1.72 (m, 4H), 1.65 (dd, J=14.5, 6.4 Hz, 2H), 1.51 (d, J=6.1 Hz, 6H), 0.92 (d, J=7.5 Hz, 9H).

Example A287
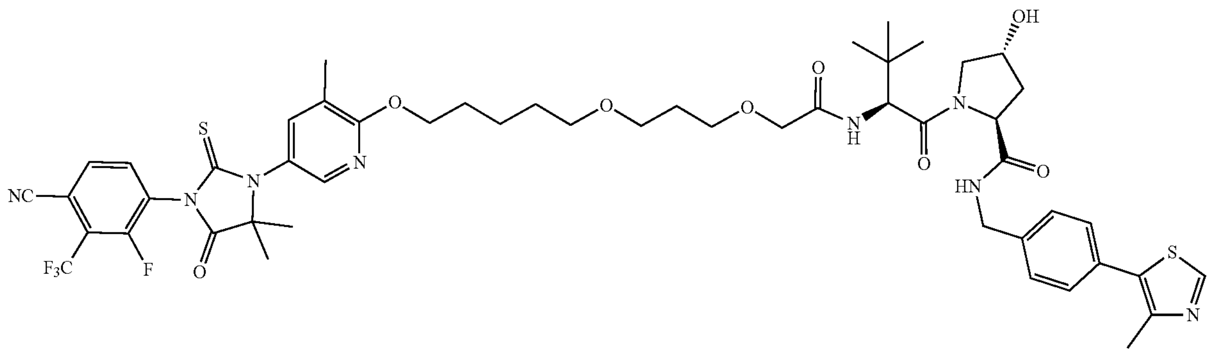 [SMILES: Cc1cc(N2C(=S)N(c3ccc(C#N)c(C(F)(F)F)c3F)C(=O)C2(C)C)cnc1OCCCCCOCCCOCC(=O)N[C@H](C(=O)N1C[C@H](O)C[C@H]1C(=O)NCc1ccc(-c2scnc2C)cc1)C(C)(C)C]
LCMS ([M+H]$^+$): 1053.3
$^1$HNMR (400 MHz, DMSO-d6) δ8.97 (d, J=4.7 Hz, 1H), 8.60 (t, J=6.0 Hz, 1H), 8.30-8.22 (m, 2H), 8.02 (d, J=2.3 Hz, 1H), 7.64 (d, J=1.8 Hz, 1H), 7.48-7.31 (m, 5H), 5.15 (d, J=3.5 Hz, 1H), 4.55 (d, J=9.6 Hz, 1H), 4.49-4.19 (m, 6H), 3.96-3.83 (m, 2H), 3.71-3.50 (m, 4H), 3.44 (m, 2H), 3.37 (m, 2H), 2.44 (d, J=5.1 Hz, 3H), 2.18 (m, 3H), 2.06 (m, 1H), 1.90 (m, 1H), 1.83-1.68 (m, 4H), 1.60-1.38 (m, 10H), 0.92 (d, J=7.4 Hz, 9H).
Example A288
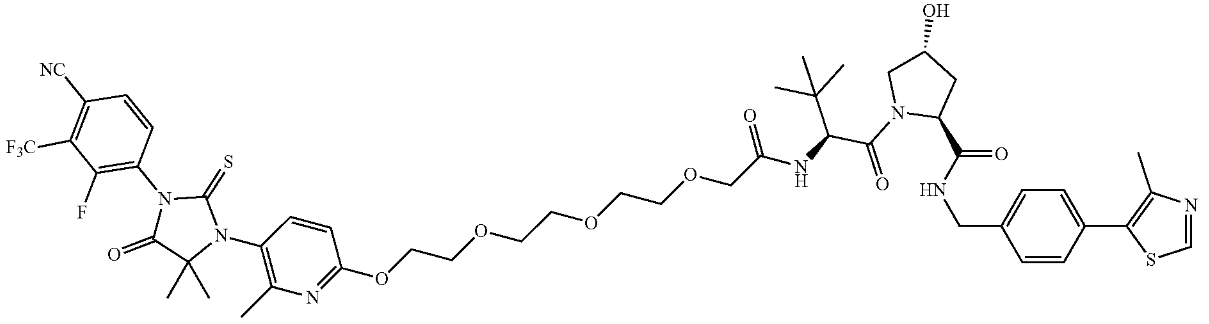 [SMILES: Cc1nc(OCCOCCOCCOCC(=O)N[C@H](C(=O)N2C[C@H](O)C[C@H]2C(=O)NCc2ccc(-c3scnc3C)cc2)C(C)(C)C)ccc1N1C(=S)N(c2ccc(C#N)c(C(F)(F)F)c2F)C(=O)C1(C)C]
LCMS ([M+H]$^+$): 1041.4
$^1$HNMR (400 MHz, DMSO-d6) δ8.98-8.97 (m, 1H), 8.59 (t, J=5.8 Hz, 1H), 8.40-8.21 (m, 2H), 7.66 (dd, J=42.8, 8.7 Hz, 1H), 7.48-7.33 (m, 5H), 6.80 (dd, J=13.4, 8.6 Hz, 1H), 5.15 (d, J=3.5 Hz, 1H), 4.56 (d, J=9.6 Hz, 1H), 4.48-4.32 (m, 5H), 4.24 (dd, J=15.8, 5.6 Hz, 1H), 3.96-3.92 (m, 2H), 3.77-3.71 (m, 2H), 3.67-3.55 (m, 10H), 2.44 (d, J=4.4 Hz, 3H), 2.34 (d, J=19.4 Hz, 3H), 2.10-2.02 (m, 1H), 1.94-1.85 (m, 1H), 1.60 (d, J=12.4 Hz, 3H), 1.46 (d, J=11.1 Hz, 3H), 0.94-0.92 (m, 9H).

Example A289
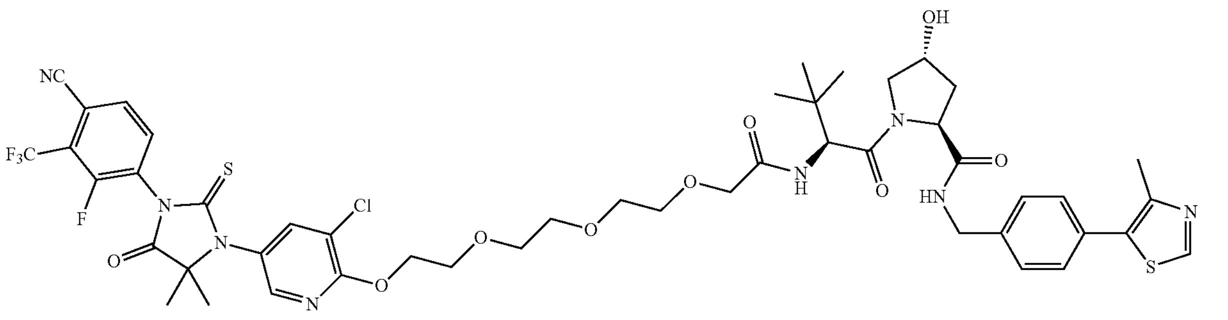 [SMILES: Cc1ncsc1-c1ccc(CNC(=O)[C@@H]2C[C@@H](O)CN2C(=O)[C@@H](NC(=O)COCCOCCOCCOc2ncc(N3C(=S)N(c4ccc(C#N)c(C(F)(F)F)c4F)C(=O)C3(C)C)cc2Cl)C(C)(C)C)cc1]
LCMS ([M+H]$^+$): 1061.3
$^1$HNMR (400 MHz, DMSO-d6) δ8.98-8.96 (m, 1H), 8.59 (t, J=5.9 Hz, 1H), 8.29-8.21 (m, 2H), 8.20 (d, J=2.3 Hz, 1H), 8.15 (d, J=2.3 Hz, 1H), 7.47-7.35 (m, 5H), 5.15 (d, J=3.5 Hz, 1H), 4.60-4.48 (m, 3H), 4.47-4.33 (m, 3H), 4.24 (dd, J=15.8, 5.5 Hz, 1H), 3.96-3.92 (m, 2H), 3.82-3.75 (m, 2H), 3.70-3.55 (m, 10H), 2.45-2.44 (m, 3H), 2.08-2.03 (m, 1H), 1.90 (ddd, J=12.8, 8.7, 4.4 Hz, 1H), 1.54 (s, 6H), 0.94-0.92 (m, 9H).
Example A290
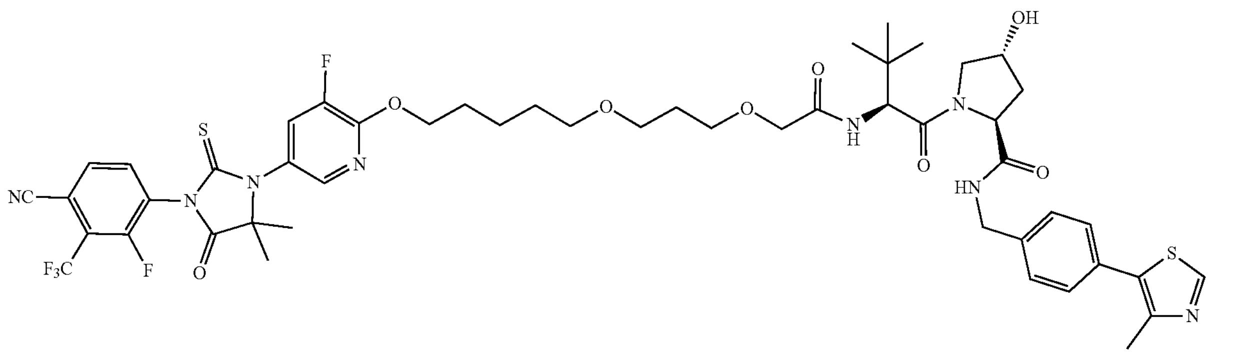 [SMILES: Cc1ncsc1-c1ccc(CNC(=O)[C@@H]2C[C@@H](O)CN2C(=O)[C@@H](NC(=O)COCCCOCCCCCOc2ncc(N3C(=S)N(c4ccc(C#N)c(C(F)(F)F)c4F)C(=O)C3(C)C)cc2F)C(C)(C)C)cc1]
LCMS ([M+H]$^+$): 1057.3
$^1$HNMR (400 MHz, DMSO-d6) δ8.96 (s, 1H), 8.61 (t, J=5.7 Hz, 1H), 8.25 (s, 2H), 8.07 (d, J=1.6 Hz, 1H), 7.95 (d, J=10.7 Hz, 1H), 7.48-7.31 (m, 5H), 5.16 (d, J=3.2 Hz, 1H), 4.62-4.19 (m, 7H), 3.90 (m, 2H), 3.71-3.58 (m, 2H), 3.54 (m, 2H), 3.45 (m, 2H), 3.38 (m, 2H), 2.44 (s, 3H), 2.07 (m, 1H), 1.97-1.86 (m, 1H), 1.77 (m, 4H), 1.54 (m, 8H), 1.49-1.38 (m, 2H), 0.94 (s, 9H).

Example A291
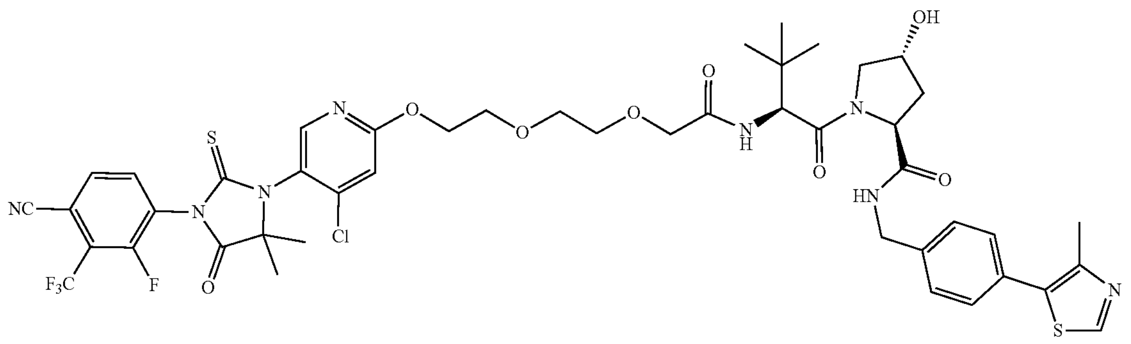 [SMILES: Cc1ncsc1-c1ccc(CNC(=O)[C@@H]2C[C@@H](O)CN2C(=O)[C@@H](NC(=O)COCCOCCOc2cc(Cl)c(N3C(=S)N(c4ccc(C#N)c(C(F)(F)F)c4F)C(=O)C3(C)C)cn2)C(C)(C)C)cc1]
LCMS ($[M+H]^+$): 1017.3
$^1$HNMR (400 MHz, DMSO-d6) δ8.96 (s, 1H), 8.58 (s, 1H), 8.26 (d, J=8.8 Hz, 2H), 7.46-7.38 (m, 4H), 7.31-7.19 (m, 3H), 5.37-5.27 (m, 1H), 5.14 (s, 1H), 4.56 (d, J=8.7 Hz, 1H), 4.51-4.40 (m, 3H), 4.36 (d, J=8.9 Hz, 2H), 4.26 (d, J=5.5 Hz, 2H), 3.98 (s, 2H), 3.81 (d, J=4.7 Hz, 3H), 3.68-3.58 (m, 6H), 2.46-2.29 (m, 1H), 1.68-1.61 (m, 4H), 1.52-1.46 (m, 3H), 1.02-0.84 (m, 9H).
Example A292
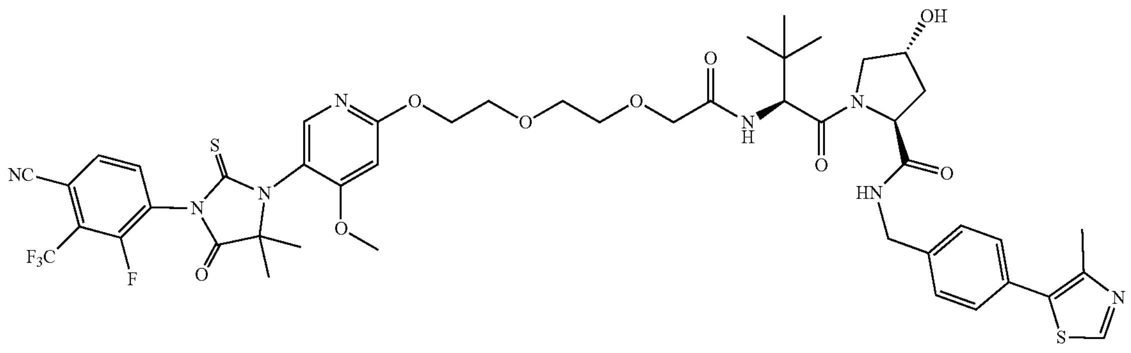 [SMILES: COc1cc(OCCOCCOCC(=O)N[C@H](C(=O)N2C[C@H](O)C[C@H]2C(=O)NCc2ccc(-c3scnc3C)cc2)C(C)(C)C)ncc1N1C(=S)N(c2ccc(C#N)c(C(F)(F)F)c2F)C(=O)C1(C)C]
LCMS ($[M+H]^+$): 1013.3
$^1$HNMR (400 MHz, DMSO-d6) δ8.97 (d, J=7.8 Hz, 1H), 8.58 (t, J=6.0 Hz, 1H), 8.33-8.19 (m, 2H), 8.08-7.90 (m, 1H), 7.49-7.35 (m, 5H), 6.67 (d, J=11.7 Hz, 1H), 5.15 (d, J=3.5 Hz, 1H), 4.56 (d, J=8.7 Hz, 1H), 4.41 (ddd, J=22.3, 12.2, 7.0 Hz, 5H), 4.25 (dd, J=15.7, 5.6 Hz, 1H), 3.97 (d, J=15.6 Hz, 2H), 3.86-3.74 (m, 5H), 3.72-3.58 (m, 6H), 2.44 (d, J=5.5 Hz, 3H), 2.10-2.00 (m, 1H), 1.90 (ddd, J=12.9, 8.8, 4.5 Hz, 1H), 1.55 (dd, J=7.8, 2.8 Hz, 3H), 1.39 (d, J=14.8 Hz, 3H), 0.92 (d, J=8.7 Hz, 9H).

Example A293
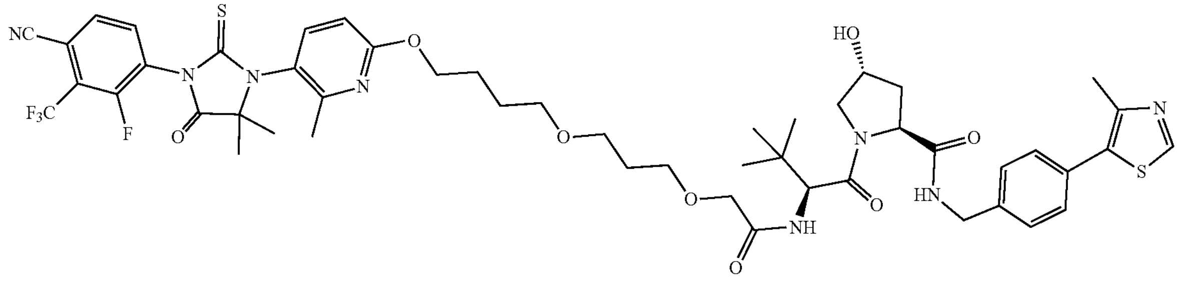 [SMILES: Cc1nc(OCCCCOCCCOCC(=O)N[C@H](C(=O)N2C[C@H](O)C[C@H]2C(=O)NCc2ccc(-c3scnc3C)cc2)C(C)(C)C)ccc1N1C(=S)N(c2ccc(C#N)c(C(F)(F)F)c2F)C(=O)C1(C)C]
LCMS ([M+H]$^+$): 1039.2
$^1$HNMR (400 MHz, DMSO-d6) δ8.97 (d, J=4.8 Hz, 1H), 8.60 (t, J=6.0 Hz, 1H), 8.32 (dt, J=40.6, 6.0 Hz, 2H), 7.65 (dd, J=42.9, 8.6 Hz, 1H), 7.46-7.32 (m, 5H), 6.77 (dd, J=13.7, 8.7 Hz, 1H), 5.15 (d, J=3.2 Hz, 1H), 4.55 (d, J=9.6 Hz, 1H), 4.48-4.32 (m, 3H), 4.31-4.20 (m, 3H), 3.95-3.86 (m, 2H), 3.64 (dt, J=23.6, 7.4 Hz, 2H), 3.54 (t, J=6.5 Hz, 2H), 3.44 (dt, J=18.1, 6.3 Hz, 4H), 2.44 (d, J=4.6 Hz, 3H), 2.33 (d, J=19.3 Hz, 3H), 2.06 (dd, J=14.1, 6.4 Hz, 1H), 1.90 (ddd, J=13.0, 8.9, 4.5 Hz, 1H), 1.83-1.69 (m, 4H), 1.66-1.55 (m, 5H), 1.46 (d, J=11.5 Hz, 3H), 0.93 (d, J=7.6 Hz, 9H).
Example A294
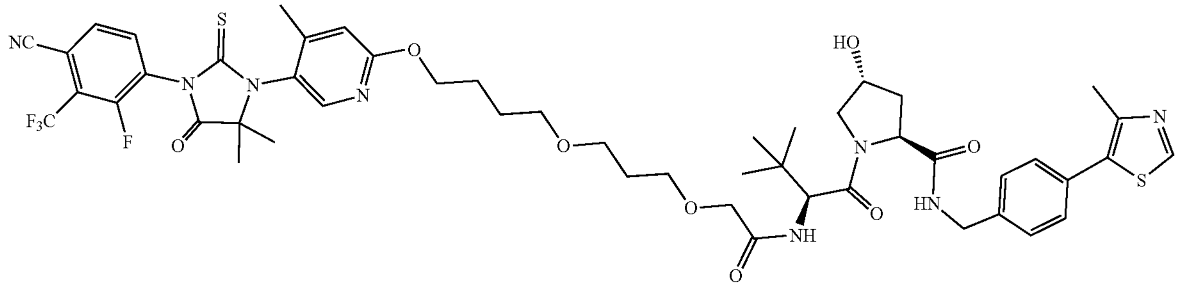 [SMILES: Cc1cc(OCCCCOCCCOCC(=O)N[C@H](C(=O)N2C[C@H](O)C[C@H]2C(=O)NCc2ccc(-c3scnc3C)cc2)C(C)(C)C)ncc1N1C(=S)N(c2ccc(C#N)c(C(F)(F)F)c2F)C(=O)C1(C)C]
LCMS ([M+H]$^+$): 1039.1
$^1$HNMR (400 MHz, DMSO-d6) δ8.97 (d, J=4.5 Hz, 1H), 8.60 (t, J=6.1 Hz, 1H), 8.40-8.23 (m, 2H), 8.09 (d, J=31.1 Hz, 1H), 7.47-7.33 (m, 5H), 6.86 (d, J=9.8 Hz, 1H), 5.15 (d, J=3.4 Hz, 1H), 4.55 (d, J=9.6 Hz, 1H), 4.48-4.32 (m, 3H), 4.31-4.20 (m, 3H), 3.96-3.86 (m, 2H), 3.64 (dt, J=23.6, 7.4 Hz, 2H), 3.54 (t, J=6.4 Hz, 2H), 3.43 (dt, J=18.8, 6.3 Hz, 5H), 2.44 (d, J=4.5 Hz, 3H), 2.24 (d, J=17.2 Hz, 3H), 2.10-2.02 (m, 1H), 1.90 (ddd, J=13.0, 8.8, 4.5 Hz, 1H), 1.83-1.69 (m, 4H), 1.62 (t, J=11.2 Hz, 5H), 1.43 (d, J=9.9 Hz, 3H), 0.93 (d, J=7.6 Hz, 9H).

Example A295
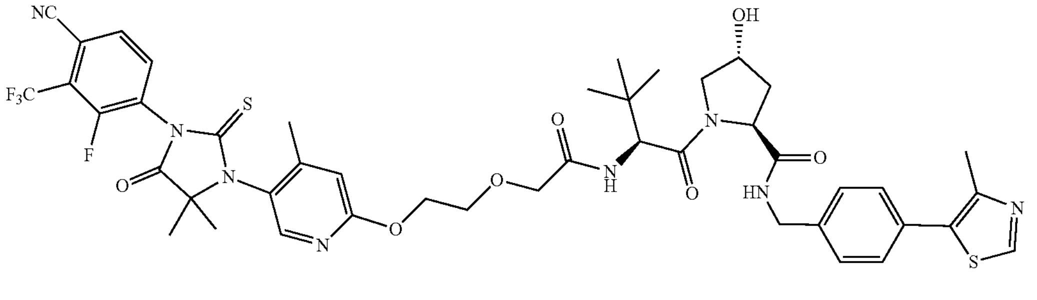 [SMILES: Cc1cc(OCCOCC(=O)N[C@H](C(=O)N2C[C@H](O)C[C@H]2C(=O)NCc2ccc(-c3scnc3C)cc2)C(C)(C)C)ncc1N1C(=S)N(c2ccc(C#N)c(C(F)(F)F)c2F)C(=O)C1(C)C]
LCMS ([M+H]$^+$): 953.3
$^1$HNMR (400 MHz, DMSO-d6) δ8.98-8.96 (m, 1H), 8.61-8.59 (m, 1H), 8.40-8.24 (m, 2H), 7.70-7.54 (m, 1H), 7.51-7.36 (m, 5H), 6.97-6.86 (m, 1H), 5.16 (d, J=3.4 Hz, 1H), 4.58 (d, J=9.5 Hz, 1H), 4.52-4.22 (m, 7H), 4.06 (s, 2H), 3.88-3.87 (m, 2H), 3.64 (dd, J=26.7, 8.8 Hz, 2H), 2.45-2.42 (m, 3H), 2.36-2.31 (m, 3H), 2.09-2.04 (m, 1H), 1.96-1.87 (m, 1H), 1.63-1.51 (m, 3H), 1.50-1.42 (m, 3H), 0.94 (s, 9H).
Example A296
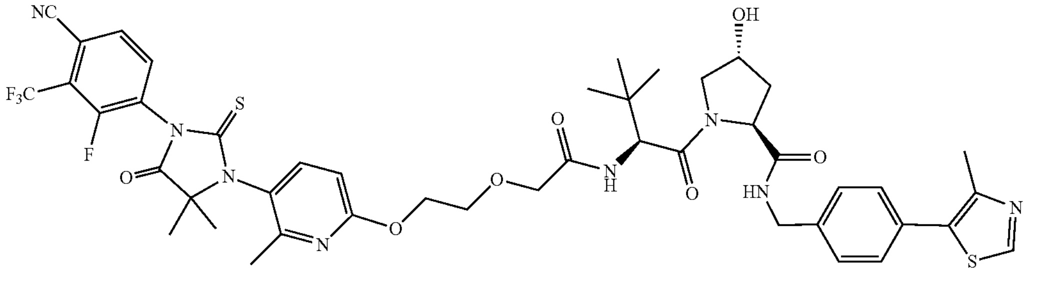 [SMILES: Cc1nc(OCCOCC(=O)N[C@H](C(=O)N2C[C@H](O)C[C@H]2C(=O)NCc2ccc(-c3scnc3C)cc2)C(C)(C)C)ccc1N1C(=S)N(c2ccc(C#N)c(C(F)(F)F)c2F)C(=O)C1(C)C]
LCMS ([M+H]$^+$): 953.3
$^1$HNMR (400 MHz, DMSO-d6) δ8.98-8.96 (m, 1H), 8.61-8.60 (m, 1H), 8.41-8.23 (m, 2H), 8.14-8.06 (m, 1H), 7.56-7.36 (m, 5H), 7.03 (dd, J=17.2, 8.2 Hz, 1H), 5.17 (d, J=3.4 Hz, 1H), 4.60 (dd, J=9.6, 4.8 Hz, 1H), 4.52-4.26 (m, 6H), 4.12-4.00 (m, 2H), 3.87-3.82 (m, 2H), 3.72-3.60 (m, 2H), 2.45-2.42 (m, 3H), 2.20 (dd, J=18.4, 5.6 Hz, 3H), 2.09-2.04 (m, 1H), 1.95-1.86 (m, 1H), 1.63 (dd, J=11.9, 3.5 Hz, 3H), 1.45-1.38 (m, 3H), 0.95-0.93 (m, 9H).

Example A297
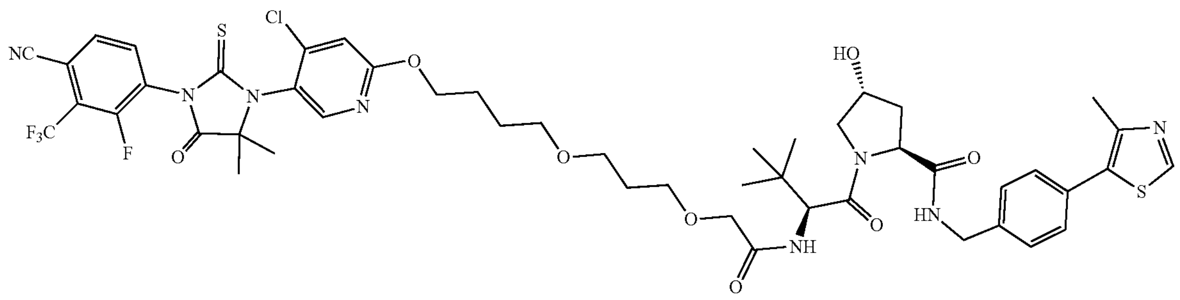 [SMILES: Cc1ncsc1-c1ccc(CNC(=O)[C@@H]2C[C@@H](O)CN2C(=O)[C@@H](NC(=O)COCCCOCCCCOc2cc(Cl)c(N3C(=S)N(c4ccc(C#N)c(C(F)(F)F)c4F)C(=O)C3(C)C)cn2)C(C)(C)C)cc1]
LCMS ([M+H]$^+$): 1059.5
$^1$HNMR (400 MHz, DMSO-d6) δ8.98 (d, J=4.1 Hz, 1H), 8.60 (t, J=6.0 Hz, 1H), 8.31 (dt, J=22.9, 12.5 Hz, 3H), 7.48-7.34 (m, 5H), 7.25 (dd, J=7.5, 1.5 Hz, 1H), 5.15 (d, J=3.3 Hz, 1H), 4.55 (d, J=9.6 Hz, 1H), 4.48-4.29 (m, 7H), 4.24 (dd, J=15.8, 5.8 Hz, 1H), 3.90 (d, J=16.2 Hz, 2H), 3.69-3.58 (m, 2H), 3.54 (t, J=6.5 Hz, 2H), 3.46 (t, J=6.4 Hz, 5H), 3.41 (t, J=6.3 Hz, 2H), 2.44 (d, J=4.5 Hz, 3H), 2.06 (dd, J=14.0, 6.2 Hz, 2H), 1.94-1.86 (m, 1H), 1.78 (dt, J=16.9, 8.4 Hz, 4H), 1.63 (dd, J=17.3, 8.5 Hz, 5H), 1.55-1.46 (m, 3H), 0.93 (d, J=7.7 Hz, 9H).
Example A298
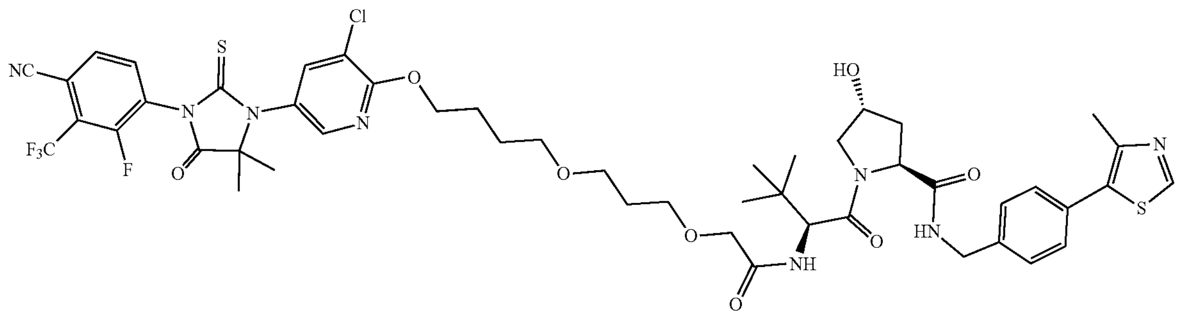 [SMILES: Cc1ncsc1-c1ccc(CNC(=O)[C@@H]2C[C@@H](O)CN2C(=O)[C@@H](NC(=O)COCCCOCCCCOc2ncc(N3C(=S)N(c4ccc(C#N)c(C(F)(F)F)c4F)C(=O)C3(C)C)cc2Cl)C(C)(C)C)cc1]
LCMS ([M+H]$^+$): 1059.5
$^1$HNMR (400 MHz, DMSO-d6) δ8.97 (d, J=5.4 Hz, 1H), 8.60 (t, J=5.9 Hz, 1H), 8.23 (dt, J=7.8, 5.4 Hz, 3H), 8.14 (d, J=2.3 Hz, 1H), 7.47-7.32 (m, 5H), 5.15 (d, J=3.5 Hz, 1H), 4.55 (d, J=9.6 Hz, 1H), 4.47-4.32 (m, 5H), 4.25 (dd, J=15.8, 5.5 Hz, 1H), 3.90 (d, J=16.7 Hz, 2H), 3.69-3.57 (m, 2H), 3.54 (t, J=6.4 Hz, 2H), 3.45 (dt, J=12.6, 6.4 Hz, 4H), 2.44 (d, J=4.6 Hz, 3H), 2.10-2.02 (m, 1H), 1.90 (ddd, J=12.9, 8.8, 4.3 Hz, 1H), 1.79 (dd, J=11.9, 5.9 Hz, 4H), 1.66 (dd, J=14.4, 6.4 Hz, 2H), 1.54 (s, 6H), 0.93 (d, J=7.6 Hz, 9H).

Example A299
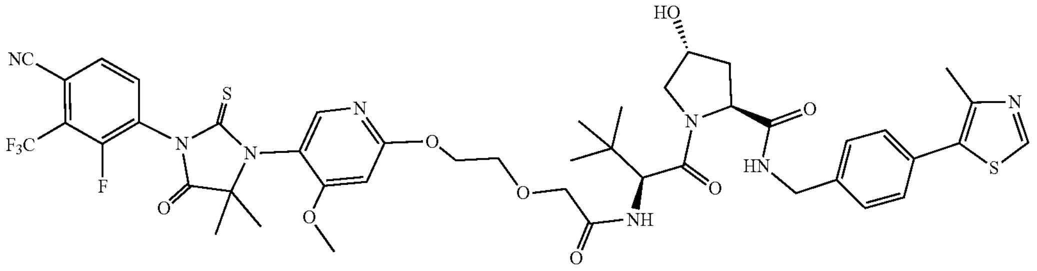 [SMILES: COc1cc(OCCOCC(=O)N[C@H](C(=O)N2C[C@H](O)C[C@H]2C(=O)NCc2ccc(-c3scnc3C)cc2)C(C)(C)C)ncc1N1C(=S)N(c2ccc(C#N)c(C(F)(F)F)c2F)C(=O)C1(C)C]
LCMS ([M+H]$^+$): 969.3
$^1$HNMR (400 MHz, DMSO-d6) δ8.97 (s, 1H), 8.57 (s, 1H), 8.26 (s, 2H), 7.98 (s, 1H), 7.55 (d, J=9.6 Hz, 1H), 7.40 (d, J=2.8 Hz, 4H), 6.95 (dd, J=21.2, 14.5 Hz, 1H), 5.11 (dd, J=60.7, 3.0 Hz, 1H), 4.73-4.58 (m, 1H), 4.47 (s, 6H), 4.07 (d, J=2.9 Hz, 2H), 3.85 (d, J=22.2 Hz, 5H), 3.73-3.61 (m, 2H), 2.51 (s, 3H), 2.22-1.84 (m, 2H), 1.56 (d, J=7.9 Hz, 3H), 1.44-1.30 (m, 3H), 0.97 (d, J=9.5 Hz, 9H).
Example A300
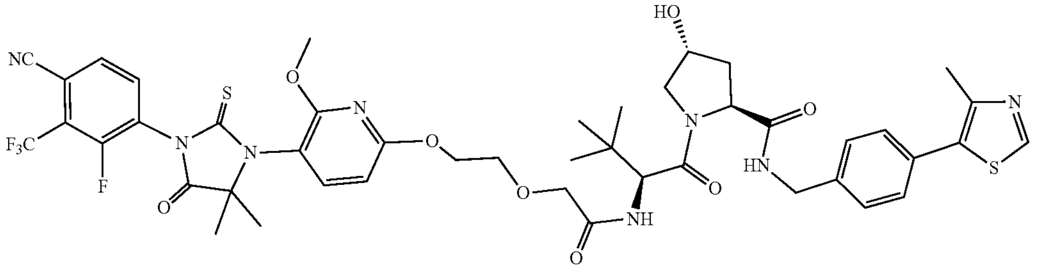 [SMILES: COc1nc(OCCOCC(=O)N[C@H](C(=O)N2C[C@H](O)C[C@H]2C(=O)NCc2ccc(-c3scnc3C)cc2)C(C)(C)C)ccc1N1C(=S)N(c2ccc(C#N)c(C(F)(F)F)c2F)C(=O)C1(C)C]
LCMS ([M+H]$^+$): 969.3
$^1$HNMR (400 MHz, DMSO-d6) δ8.97 (d, J=6.8 Hz, 1H), 8.60 (dd, J=12.2, 7.6 Hz, 1H), 8.37-8.19 (m, 2H), 7.74-7.56 (m, 1H), 7.53-7.35 (m, 5H), 6.70-6.57 (m, 1H), 5.16 (d, J=3.3 Hz, 1H), 4.63-4.55 (m, 1H), 4.55-4.32 (m, 5H), 4.27 (dd, J=15.5, 5.5 Hz, 1H), 4.04 (d, J=19.4 Hz, 2H), 3.88 (d, J=4.2 Hz, 5H), 3.66 (dt, J=24.3, 7.3 Hz, 2H), 2.44 (d, J=9.9 Hz, 3H), 2.06 (dd, J=12.6, 7.9 Hz, 1H), 1.98-1.85 (m, 1H), 1.58-1.35 (m, 6H), 0.94 (d, J=6.6 Hz, 9H).

Example A301
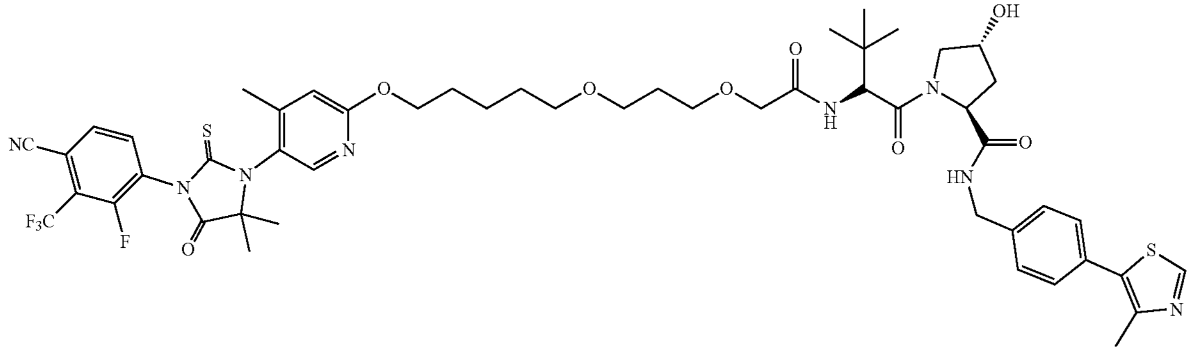
LCMS ([M+H]$^+$): 1053.3
$^1$HNMR (400 MHz, DMSO-d6) δ8.97 (s, 1H), 8.60 (t, J=6.0 Hz, 1H), 8.40-8.23 (m, 2H), 8.09 (d, J=31.0 Hz, 1H), 7.47-7.31 (m, 5H), 6.86 (t, J=7.0 Hz, 1H), 5.15 (d, J=3.4 Hz, 1H), 4.55 (m, 1H), 4.49-4.32 (m, 3H), 4.30-4.21 (m, 3H), 3.96-3.86 (m, 2H), 3.64 (m, 2H), 3.53 (m, 2H), 3.44 (m, 2H), 3.36 (m, 2H), 2.44 (d, J=4.7 Hz, 3H), 2.24 (d, J=17.5 Hz, 3H), 2.06 (m, 1H), 1.90 (m, 1H), 1.75 (m, 4H), 1.63 (d, J=12.4 Hz, 3H), 1.58-1.48 (m, 2H), 1.47-1.35 (m, 5H), 0.93 (d, J=7.1 Hz, 9H).
Example A302
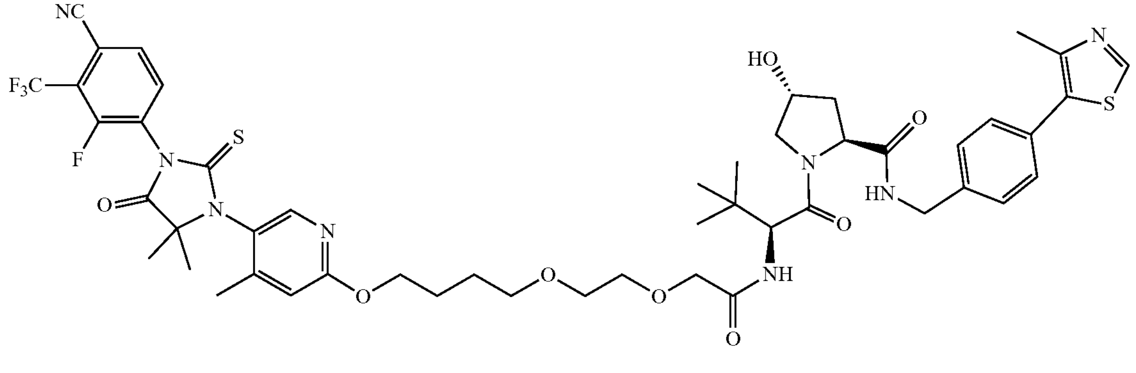 [SMILES: Cc1cc(OCCCCOCCOCC(=O)N[C@H](C(=O)N2C[C@H](O)C[C@H]2C(=O)NCc2ccc(-c3scnc3C)cc2)C(C)(C)C)ncc1N1C(=S)N(c2ccc(C#N)c(C(F)(F)F)c2F)C(=O)C1(C)C]
LCMS ([M+H]$^+$): 1025.3
$^1$HNMR (400 MHz, DMSO-d6) δ8.97 (d, J=7.8 Hz, 1H), 8.59 (t, J=6.0 Hz, 1H), 8.40-8.23 (m, 2H), 8.08 (d, J=31.1 Hz, 1H), 7.40 (d, J=10.0 Hz, 5H), 6.84 (d, J=9.5 Hz, 1H), 5.15 (d, J=3.5 Hz, 1H), 4.56 (d, J=9.6 Hz, 1H), 4.46-4.33 (m, 3H), 4.24 (d, J=12.7 Hz, 3H), 3.97 (s, 2H), 3.70-3.57 (m, 5H), 3.55 (d, J=4.7 Hz, 2H), 3.49 (s, 2H), 2.44 (d, J=6.7 Hz, 3H), 2.23 (d, J=17.1 Hz, 3H), 2.10-2.02 (m, 1H), 1.95-1.86 (m, 1H), 1.75 (d, J=6.8 Hz, 2H), 1.64 (t, J=12.0 Hz, 5H), 1.43 (d, J=9.8 Hz, 3H), 0.93 (d, J=8.8 Hz, 9H).

Example A303
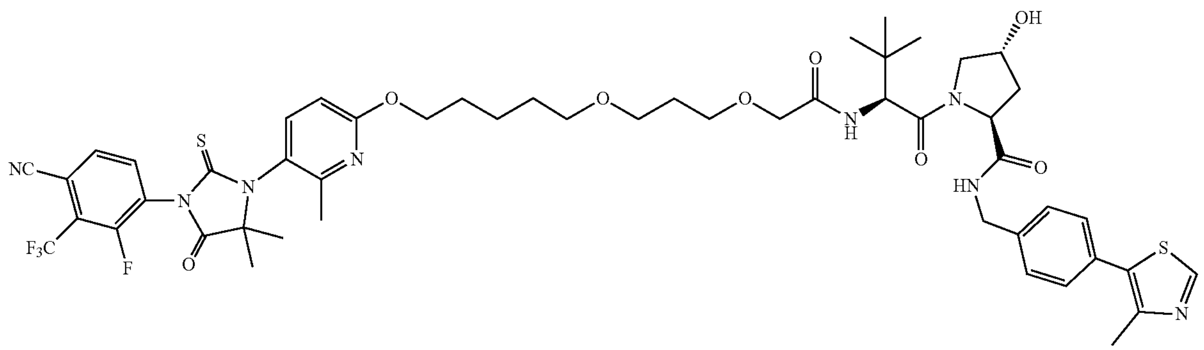 [SMILES: Cc1nc(OCCCCCOCCCOCC(=O)N[C@H](C(=O)N2C[C@H](O)C[C@H]2C(=O)NCc2ccc(-c3scnc3C)cc2)C(C)(C)C)ccc1N1C(=S)N(c2ccc(C#N)c(C(F)(F)F)c2F)C(=O)C1(C)C]
LCMS ([M+H]$^+$): 1053.3
$^1$HNMR (400 MHz, DMSO-d6) δ8.97 (d, J=4.0 Hz, 1H), 8.60 (t, J=6.0 Hz, 1H), 8.31 (dt, J=40.0, 5.8 Hz, 2H), 7.64 (dd, J=40.8, 8.7 Hz, 1H), 7.47-7.32 (m, 5H), 6.77 (dd, J=13.7, 8.7 Hz, 1H), 5.16 (d, J=2.8 Hz, 1H), 4.55 (d, J=9.6 Hz, 1H), 4.48-4.33 (m, 3H), 4.30-4.19 (m, 3H), 3.92 (m, 2H), 3.64 (m, 2H), 3.53 (m, 2H), 3.44 (m, 2H), 2.44 (d, J=4.7 Hz, 3H), 2.33 (m, 3H), 2.06 (m, 1H), 1.94-1.86 (m, 1H), 1.82-1.66 (m, 4H), 1.59 (d, J=12.5 Hz, 3H), 1.52 (m, 2H), 1.49-1.37 (m, 5H), 0.92 (d, J=7.3 Hz, 9H).
Example A304
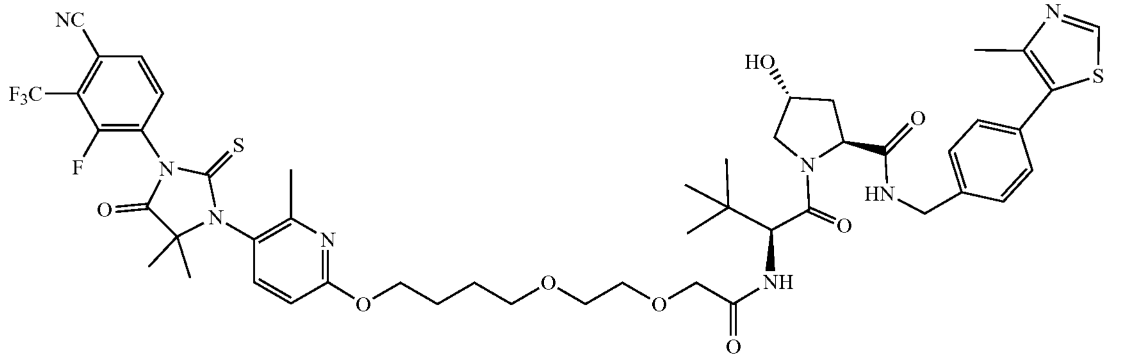 [SMILES: Cc1nc(OCCCCOCCOCC(=O)N[C@H](C(=O)N2C[C@H](O)C[C@H]2C(=O)NCc2ccc(-c3scnc3C)cc2)C(C)(C)C)ccc1N1C(=S)N(c2ccc(C#N)c(C(F)(F)F)c2F)C(=O)C1(C)C]
LCMS ([M+H]$^+$): 1025.3
$^1$HNMR (400 MHz, DMSO-d6) δ8.96 (s, 1H), 8.59 (t, J=5.9 Hz, 1H), 8.41-8.22 (m, 2H), 7.64 (dd, J=42.3, 8.7 Hz, 1H), 7.39 (s, 5H), 6.75 (dd, J=13.2, 8.7 Hz, 1H), 5.15 (d, J=3.1 Hz, 1H), 4.57 (d, J=9.6 Hz, 1H), 4.48-4.33 (m, 3H), 4.24 (dd, J=16.0, 5.3 Hz, 3H), 3.97 (s, 2H), 3.71-3.58 (m, 4H), 3.58-3.43 (m, 4H), 2.43 (s, 3H), 2.33 (dd, J=19.3, 5.0 Hz, 3H), 2.06 (dd, J=14.2, 6.9 Hz, 1H), 1.90 (ddd, J=13.0, 8.8, 4.5 Hz, 1H), 1.76 (p, J=6.7 Hz, 2H), 1.67 (q, J=6.3 Hz, 2H), 1.59 (d, J=12.6 Hz, 3H), 1.45 (d, J=11.3 Hz, 3H), 0.94 (s, 9H).

Example A305
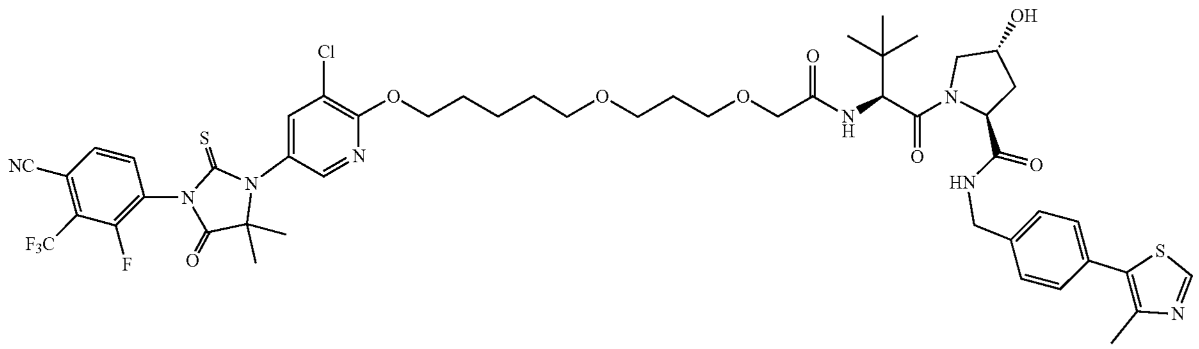 [SMILES: Cc1ncsc1-c1ccc(CNC(=O)[C@@H]2C[C@@H](O)CN2C(=O)[C@@H](NC(=O)COCCCOCCCCCOc2ncc(N3C(=S)N(c4ccc(C#N)c(C(F)(F)F)c4F)C(=O)C3(C)C)cc2Cl)C(C)(C)C)cc1]
LCMS ([M+H]$^+$): 1073.3
$^1$HNMR (400 MHz, DMSO-d6) δ8.97 (d, J=4.3 Hz, 1H), 8.60 (t, J=6.0 Hz, 1H), 8.28-8.21 (m, 2H), 8.20 (d, J=2.3 Hz, 1H), 8.13 (d, J=2.3 Hz, 1H), 7.49-7.30 (m, 5H), 5.16 (d, J=3.5 Hz, 1H), 4.55 (m, 1H), 4.48-4.33 (m, 5H), 4.24 (m, 1H), 3.95-3.86 (m, 2H), 3.64 (m, 2H), 3.53 (m, 2H), 3.45 (m, 2H), 3.38 (m, 2H), 2.44 (d, J=4.8 Hz, 3H), 2.06 (m, 1H), 1.90 (m, 1H), 1.82-1.72 (m, 4H), 1.60-1.50 (m, 8H), 1.50-1.39 (m, 2H), 0.92 (d, J=7.4 Hz, 9H).
Example A306
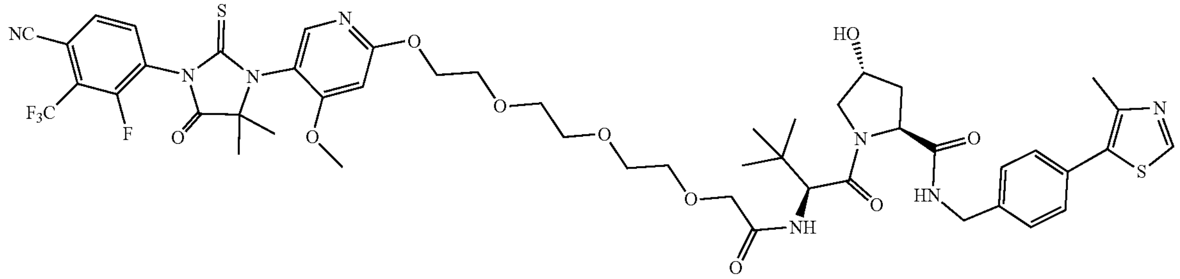 [SMILES: COc1cc(OCCOCCOCCOCC(=O)N[C@H](C(=O)N2C[C@H](O)C[C@H]2C(=O)NCc2ccc(-c3scnc3C)cc2)C(C)(C)C)ncc1N1C(=S)N(c2ccc(C#N)c(C(F)(F)F)c2F)C(=O)C1(C)C]
LCMS ([M+H]$^+$): 1057.3
$^1$HNMR (400 MHz, DMSO-d6) δ8.97 (d, J=4.7 Hz, 1H), 8.59 (t, J=5.9 Hz, 1H), 8.35-8.20 (m, 2H), 8.07-7.92 (m, 1H), 7.48-7.36 (m, 5H), 6.66 (d, J=9.7 Hz, 1H), 5.15 (d, J=3.5 Hz, 1H), 4.56 (d, J=9.6 Hz, 1H), 4.49-4.33 (m, 5H), 4.25 (dd, J=15.8, 5.6 Hz, 1H), 3.95 (d, J=16.2 Hz, 2H), 3.83 (d, J=3.6 Hz, 3H), 3.76-3.70 (m, 2H), 3.69-3.53 (m, 10H), 2.44 (d, J=4.3 Hz, 3H), 2.10-2.01 (m, 1H), 1.94-1.85 (m, 1H), 1.55 (d, J=10.3 Hz, 3H), 1.39 (d, J=14.7 Hz, 3H), 0.93 (d, J=8.9 Hz, 9H).

Example A307
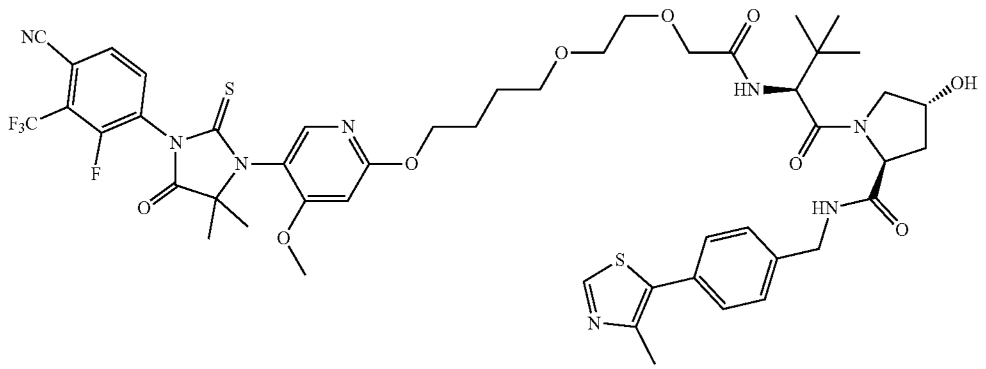 [SMILES: COc1cc(OCCCCOCCOCC(=O)N[C@H](C(=O)N2C[C@H](O)C[C@H]2C(=O)NCc2ccc(-c3scnc3C)cc2)C(C)(C)C)ncc1N1C(=S)N(c2ccc(C#N)c(C(F)(F)F)c2F)C(=O)C1(C)C]
LCMS ([M+H]$^+$): 1041.3
$^1$HNMR (400 MHz, DMSO-d6) δ8.96 (s, 1H), 8.59 (t, J=6.0 Hz, 1H), 8.36-8.21 (m, 2H), 8.06-7.92 (m, 1H), 7.47-7.35 (m, 5H), 6.58 (s, 1H), 5.15 (d, J=3.1 Hz, 1H), 4.56 (d, J=9.6 Hz, 1H), 4.48-4.33 (m, 3H), 4.31-4.20 (m, 3H), 3.97 (s, 2H), 3.82 (d, J=3.7 Hz, 3H), 3.71-3.46 (m, 9H), 2.43 (s, 3H), 2.11-2.01 (m, 1H), 1.90 (ddd, J=13.0, 8.9, 4.5 Hz, 1H), 1.75 (q, J=6.7 Hz, 2H), 1.67 (q, J=6.4 Hz, 2H), 1.54 (d, J=10.3 Hz, 3H), 1.39 (d, J=14.8 Hz, 3H), 0.94 (s, 9H).
Example A308
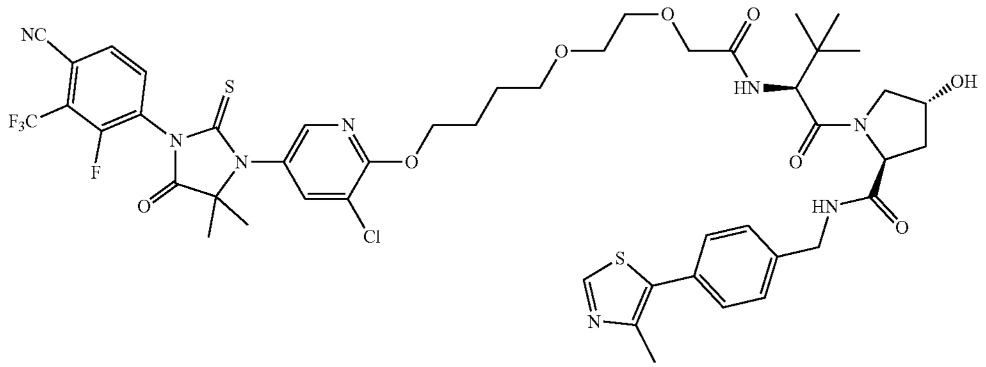 [SMILES: Cc1ncsc1-c1ccc(CNC(=O)[C@@H]2C[C@@H](O)CN2C(=O)[C@@H](NC(=O)COCCOCCCCOc2ncc(N3C(=S)N(c4ccc(C#N)c(C(F)(F)F)c4F)C(=O)C3(C)C)cc2Cl)C(C)(C)C)cc1]
LCMS ([M+H]$^+$): 1045.3
$^1$HNMR (400 MHz, DMSO-d6) δ8.95 (s, 1H), 8.59 (t, J=6.0 Hz, 1H), 8.29-8.16 (m, 3H), 8.13 (d, J=2.3 Hz, 1H), 7.40 (d, J=10.0 Hz, 5H), 5.16 (d, J=3.5 Hz, 1H), 4.56 (d, J=9.6 Hz, 1H), 4.42 (dt, J=21.3, 7.5 Hz, 5H), 4.24 (dd, J=15.8, 5.6 Hz, 1H), 3.97 (s, 2H), 3.64 (dtd, J=16.7, 11.7, 11.2, 4.5 Hz, 4H), 3.58-3.48 (m, 4H), 2.43 (s, 3H), 2.10-2.01 (m, 1H), 1.91 (ddd, J=13.0, 8.8, 4.5 Hz, 1H), 1.81 (dt, J=14.5, 6.3 Hz, 2H), 1.69 (q, J=6.4 Hz, 2H), 1.54 (s, 6H), 0.94 (s, 9H).

Example A309
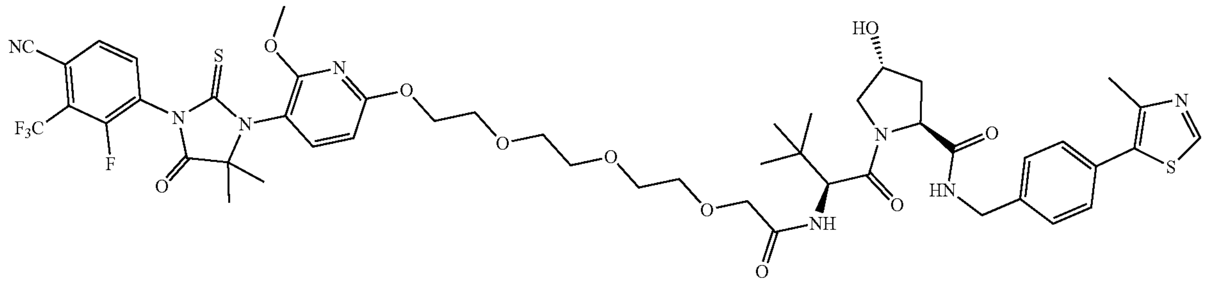 [SMILES: COc1nc(OCCOCCOCCOCC(=O)N[C@H](C(=O)N2C[C@H](O)C[C@H]2C(=O)NCc2ccc(-c3scnc3C)cc2)C(C)(C)C)ccc1N1C(=S)N(c2ccc(C#N)c(C(F)(F)F)c2F)C(=O)C1(C)C]
LCMS ($[M+H]^+$): 1057.3
$^1$HNMR (400 MHz, DMSO-d6) δ8.97 (d, J=5.3 Hz, 1H), 8.59 (t, J=6.0 Hz, 1H), 8.36-8.20 (m, 2H), 7.78-7.60 (m, 1H), 7.46-7.35 (m, 5H), 6.57-6.49 (m, 1H), 5.15 (d, J=3.5 Hz, 1H), 4.56 (d, J=9.6 Hz, 1H), 4.48-4.32 (m, 5H), 4.24 (dd, J=15.8, 5.6 Hz, 1H), 3.94 (d, J=16.1 Hz, 2H), 3.87 (t, J=4.1 Hz, 3H), 3.79-3.72 (m, 2H), 3.70-3.53 (m, 10H), 2.44 (d, J=4.7 Hz, 3H), 2.09-2.01 (m, 1H), 1.90 (ddd, J=13.0, 8.9, 4.5 Hz, 1H), 1.53 (d, J=11.0 Hz, 3H), 1.43 (d, J=16.0 Hz, 3H), 0.93 (d, J=8.8 Hz, 9H).
Example A310
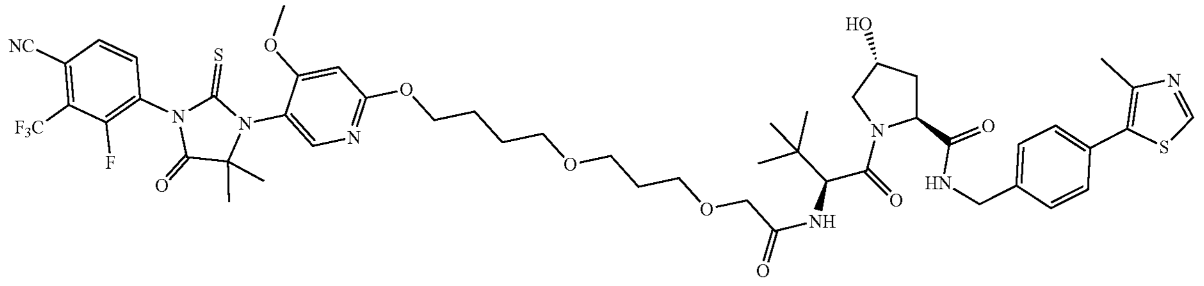 [SMILES: COc1cc(OCCCCOCCCOCC(=O)N[C@H](C(=O)N2C[C@H](O)C[C@H]2C(=O)NCc2ccc(-c3scnc3C)cc2)C(C)(C)C)ncc1N1C(=S)N(c2ccc(C#N)c(C(F)(F)F)c2F)C(=O)C1(C)C]
LCMS ($[M+H]^+$): 1055.1
$^1$HNMR (400 MHz, DMSO-d6) δ8.97 (s, 1H), 8.60 (t, J=5.7 Hz, 1H), 8.36-8.18 (m, 2H), 8.00 (d, J=35.8 Hz, 1H), 7.49-7.31 (m, 5H), 6.60 (s, 1H), 5.15 (d, J=3.1 Hz, 1H), 4.56 (d, J=9.6 Hz, 1H), 4.49-4.19 (m, 6H), 3.90 (d, J=16.7 Hz, 2H), 3.83 (d, J=3.3 Hz, 3H), 3.70-3.51 (m, 4H), 3.44 (dt, J=18.7, 6.0 Hz, 4H), 2.44 (s, 3H), 2.06 (dd, J=12.4, 7.4 Hz, 1H), 1.91 (dd, J=14.9, 6.2 Hz, 1H), 1.84-1.69 (m, 4H), 1.68-1.59 (m, 2H), 1.55 (d, J=10.5 Hz, 3H), 1.39 (d, J=14.9 Hz, 3H), 0.94 (s, 9H).

Example A311
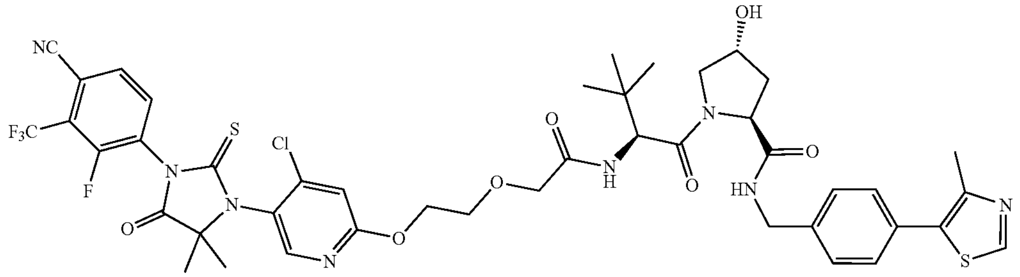 [SMILES: Cc1ncsc1-c1ccc(CNC(=O)[C@@H]2C[C@@H](O)CN2C(=O)[C@@H](NC(=O)COCCOc2cc(Cl)c(N3C(=S)N(c4ccc(C#N)c(C(F)(F)F)c4F)C(=O)C3(C)C)cn2)C(C)(C)C)cc1]
LCMS ([M+H]$^+$): 973.3
$^1$HNMR (400 MHz, DMSO-d6) δ8.98-8.96 (m, 1H), 8.58 (s, 1H), 8.36-8.23 (m, 3H), 7.50 (dd, J=9.5, 4.5 Hz, 1H), 7.46-7.36 (m, 5H), 5.16 (d, J=3.5 Hz, 1H), 4.60 (dd, J=9.6, 3.0 Hz, 1H), 4.55-4.44 (m, 4H), 4.38-4.26 (m, 4H), 4.06 (s, 2H), 3.88 (m, 2H), 3.68 (dd, J=10.6, 3.5 Hz, 2H), 3.61 (d, J=10.6 Hz, 2H), 2.42 (s, 3H), 2.09-2.04 (m, 1H), 1.93-1.88 (m, 1H), 1.64 (d, J=9.1 Hz, 3H), 1.48 (dd, J=13.3, 4.5 Hz, 3H), 0.94 (s, 9H).
Example A312
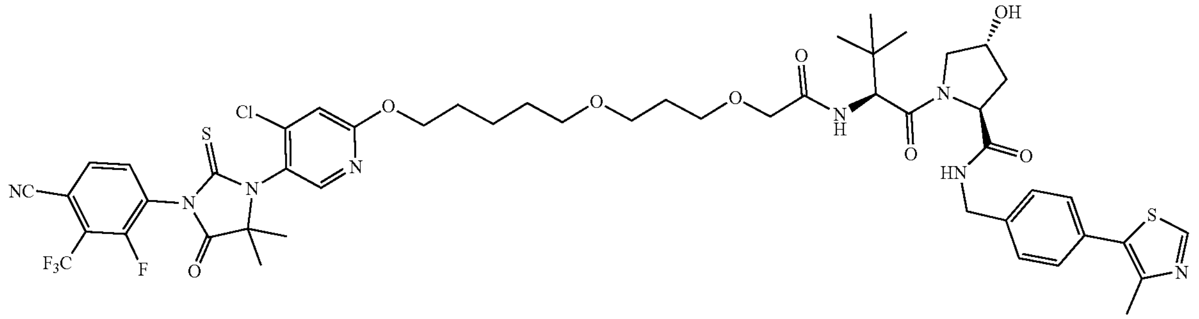 [SMILES: Cc1ncsc1-c1ccc(CNC(=O)[C@@H]2C[C@@H](O)CN2C(=O)[C@@H](NC(=O)COCCCOCCCCCOc2cc(Cl)c(N3C(=S)N(c4ccc(C#N)c(C(F)(F)F)c4F)C(=O)C3(C)C)cn2)C(C)(C)C)cc1]
LCMS ([M+H]$^+$): 1073.3
$^1$HNMR (400 MHz, DMSO-d6) δ8.97 (d, J=4.3 Hz, 1H), 8.60 (t, J=6.0 Hz, 1H), 8.28-8.21 (m, 2H), 8.20 (d, J=2.3 Hz, 1H), 8.13 (d, J=2.3 Hz, 1H), 7.49-7.30 (m, 5H), 5.16 (d, J=3.5 Hz, 1H), 4.55 (m, 1H), 4.48-4.33 (m, 5H), 4.24 (m, 1H), 3.95-3.86 (m, 2H), 3.64 (m, 2H), 3.53 (m, 2H), 3.45 (m, 2H), 3.38 (m, 2H), 2.44 (d, J=4.8 Hz, 3H), 2.06 (m, 1H), 1.90 (m, 1H), 1.82-1.72 (m, 4H), 1.60-1.50 (m, 8H), 1.50-1.39 (m, 2H), 0.92 (d, J=7.4 Hz, 9H).

Example A313
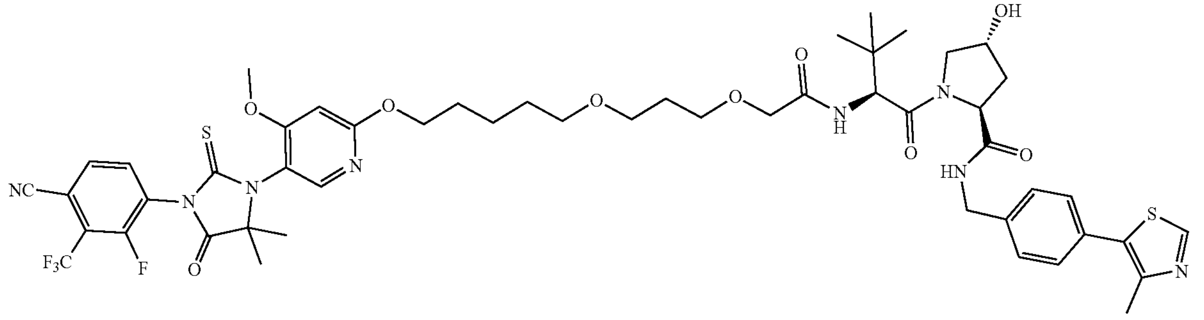 [SMILES: COc1cc(OCCCCCOCCCOCC(=O)N[C@H](C(=O)N2C[C@H](O)C[C@H]2C(=O)NCc2ccc(-c3scnc3C)cc2)C(C)(C)C)ncc1N1C(=S)N(c2ccc(C#N)c(C(F)(F)F)c2F)C(=O)C1(C)C]
LCMS ([M+H]$^+$): 1069.3
$^1$HNMR (400 MHz, DMSO-d6) δ8.97 (d, J=3.2 Hz, 1H), 8.60 (t, J=6.0 Hz, 1H), 8.35-8.20 (m, 2H), 8.00 (d, J=35.8 Hz, 1H), 7.48-7.32 (m, 5H), 6.61 (d, J=4.5 Hz, 1H), 5.15 (d, J=3.5 Hz, 1H), 4.55 (d, J=9.6 Hz, 1H), 4.48-4.33 (m, 3H), 4.31-4.20 (m, 3H), 3.95-3.87 (m, 2H), 3.83 (d, J=3.7 Hz, 3H), 3.64 (m, 2H), 3.54 (m, 2H), 3.45 (m, 2H), 3.37 (m, 2H), 2.44 (d, J=4.5 Hz, 3H), 2.06 (m, 1H), 1.90 (m, 1H), 1.82-1.75 (m, 2H), 1.70 (m, 2H), 1.59-1.48 (m, 5H), 1.42 (m, 5H), 0.93 (d, J=7.6 Hz, 9H).
Example A314
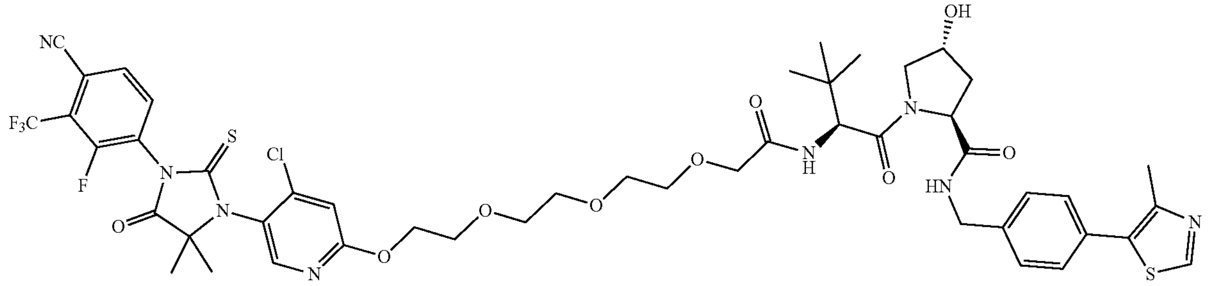 [SMILES: Cc1ncsc1-c1ccc(CNC(=O)[C@@H]2C[C@@H](O)CN2C(=O)[C@@H](NC(=O)COCCOCCOCCOc2cc(Cl)c(N3C(=S)N(c4ccc(C#N)c(C(F)(F)F)c4F)C(=O)C3(C)C)cn2)C(C)(C)C)cc1]
LCMS ([M+H]$^+$): 1061.3
$^1$HNMR (400 MHz, DMSO-d6) δ8.98-8.97 (m, 1H), 8.59 (t, J=6.0 Hz, 1H), 8.41-8.30 (m, 1H), 8.27-8.25 (m, 2H), 7.45-7.37 (m, 5H), 7.30 (dd, J=7.1, 1.8 Hz, 1H), 5.15 (d, J=3.5 Hz, 1H), 4.56 (d, J=9.6 Hz, 1H), 4.47-4.33 (m, 5H), 4.24 (dd, J=15.7, 5.5 Hz, 1H), 3.97-3.92 (m, 2H), 3.77-3.72 (m, 2H), 3.67-3.56 (m, 10H), 2.45-2.44 (m, 3H), 2.08-2.03 (m, 1H), 1.90 (ddd, J=13.0, 8.8, 4.5 Hz, 1H), 1.65 (d, J=9.9 Hz, 3H), 1.49 (d, J=12.6 Hz, 3H), 0.93 (d, J=8.7 Hz, 9H).

Example A315
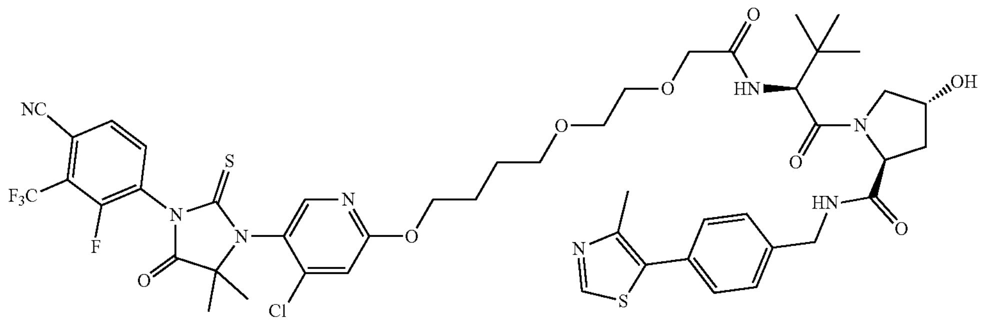 [SMILES: Cc1ncsc1-c1ccc(CNC(=O)[C@@H]2C[C@@H](O)CN2C(=O)[C@@H](NC(=O)COCCOCCCCOc2cc(Cl)c(N3C(=S)N(c4ccc(C#N)c(C(F)(F)F)c4F)C(=O)C3(C)C)cn2)C(C)(C)C)cc1]
LCMS ([M+H]$^+$): 1045.3
$^1$HNMR (400 MHz, DMSO-d6) δ8.96 (s, 1H), 8.59 (t, J=6.0 Hz, 1H), 8.41-8.23 (m, 3H), 7.40 (d, J=10.0 Hz, 5H), 7.29-7.19 (m, 1H), 5.15 (d, J=3.3 Hz, 1H), 4.57 (d, J=9.6 Hz, 1H), 4.48-4.20 (m, 6H), 3.97 (s, 2H), 3.71-3.46 (m, 8H), 2.43 (s, 3H), 2.06 (dd, J=13.6, 6.8 Hz, 1H), 1.90 (ddd, J=13.0, 8.8, 4.5 Hz, 1H), 1.78 (p, J=6.7 Hz, 2H), 1.66 (q, J=9.8, 8.0 Hz, 5H), 1.49 (d, J=12.6 Hz, 3H), 0.94 (s, 9H).
Example A316
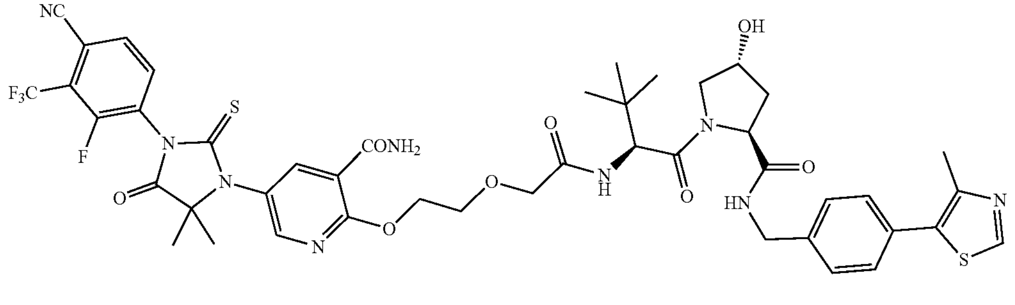 [SMILES: Cc1ncsc1-c1ccc(CNC(=O)[C@@H]2C[C@@H](O)CN2C(=O)[C@@H](NC(=O)COCCOc2ncc(N3C(=S)N(c4ccc(C#N)c(C(F)(F)F)c4F)C(=O)C3(C)C)cc2C(N)=O)C(C)(C)C)cc1]
LCMS ([M+H]$^+$): 982.3
$^1$HNMR (400 MHz, DMSO-d6) δ8.98-8.97 (m, 1H), 8.58 (t, J=6.0 Hz, 1H), 8.38 (d, J=2.7 Hz, 1H), 8.29-8.27 (m, 3H), 7.83 (d, J=11.8 Hz, 2H), 7.58 (d, J=9.4 Hz, 1H), 7.40 (s, 4H), 5.19 (d, J=3.5 Hz, 1H), 4.64 (m, 2H), 4.56 (d, J=9.4 Hz, 1H), 4.45 (d, J=8.0 Hz, 1H), 4.38-4.36 (m, 2H), 4.25 (d, J=10.1 Hz, 1H), 4.09 (s, 2H), 3.96-3.92 (m, 2H), 3.67 (m, 2H), 2.44 (d, J=3.0 Hz, 3H), 2.06-2.04 (m, 1H), 1.93-1.88 (m, 1H), 1.54 (d, J=5.4 Hz, 6H), 0.93-0.91 (m, 9H).

Example A317
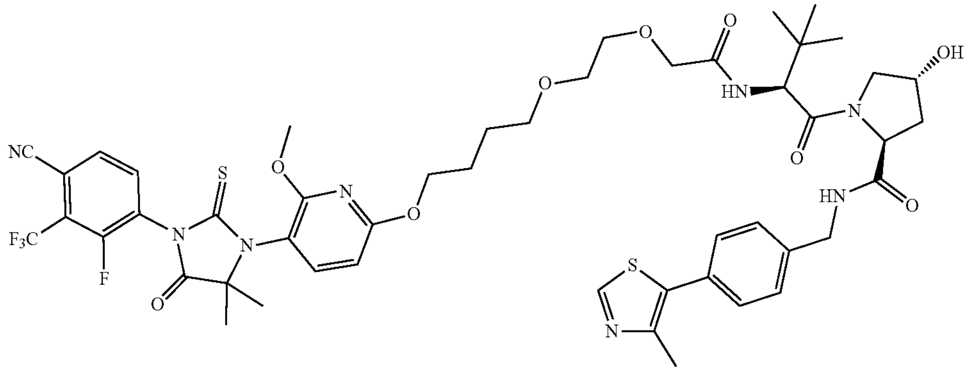 [SMILES: COc1nc(OCCCCOCCOCC(=O)N[C@H](C(=O)N2C[C@H](O)C[C@H]2C(=O)NCc2ccc(-c3scnc3C)cc2)C(C)(C)C)ccc1N1C(=S)N(c2ccc(C#N)c(C(F)(F)F)c2F)C(=O)C1(C)C]
LCMS ([M+H]$^+$): 1041.3
$^1$HNMR (400 MHz, DMSO-d6) δ8.96 (s, 1H), 8.59 (t, J=5.9 Hz, 1H), 8.36-8.20 (m, 2H), 7.78-7.57 (m, 1H), 7.40 (d, J=9.3 Hz, 5H), 6.55-6.44 (m, 1H), 5.15 (d, J=3.3 Hz, 1H), 4.57 (d, J=9.6 Hz, 1H), 4.49-4.33 (m, 3H), 4.27 (dt, J=17.6, 8.5 Hz, 3H), 3.97 (s, 2H), 3.86 (d, J=4.1 Hz, 3H), 3.72-3.46 (m, 8H), 2.43 (s, 3H), 2.06 (q, J=7.6 Hz, 1H), 1.91 (ddd, J=12.9, 8.9, 4.4 Hz, 1H), 1.78 (q, J=6.6 Hz, 2H), 1.73-1.61 (m, 2H), 1.53 (d, J=10.6 Hz, 3H), 1.42 (d, J=15.9 Hz, 3H), 0.93 (d, J=8.7 Hz, 9H).
Example A318
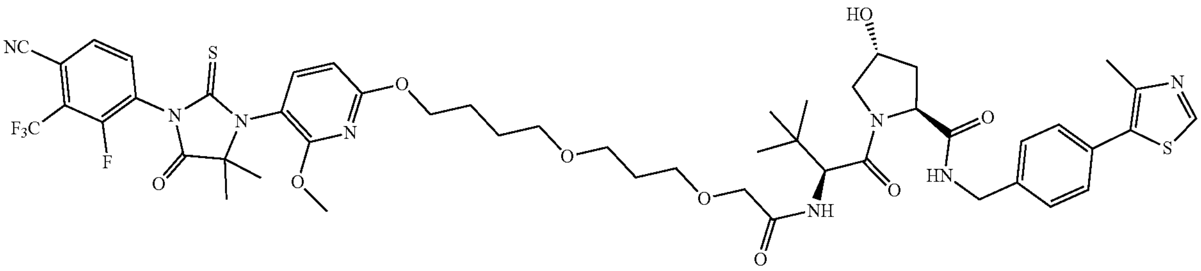 [SMILES: COc1nc(OCCCCOCCCOCC(=O)N[C@H](C(=O)N2C[C@H](O)C[C@H]2C(=O)NCc2ccc(-c3scnc3C)cc2)C(C)(C)C)ccc1N1C(=S)N(c2ccc(C#N)c(C(F)(F)F)c2F)C(=O)C1(C)C]
LCMS ([M+H]$^+$): 1055.1
$^1$HNMR (400 MHz, DMSO-d6) δ9.01-8.92 (m, 1H), 8.60 (t, J=5.9 Hz, 1H), 8.36-8.19 (m, 2H), 7.68 (dd, J=48.8, 8.3 Hz, 1H), 7.49-7.32 (m, 5H), 6.55-6.44 (m, 1H), 5.15 (d, J=3.4 Hz, 1H), 4.55 (d, J=9.6 Hz, 1H), 4.49-4.32 (m, 3H), 4.26 (dt, J=15.8, 6.1 Hz, 3H), 3.89 (dd, J=14.3, 7.8 Hz, 5H), 3.64 (dt, J=23.3, 7.2 Hz, 2H), 3.54 (t, J=6.4 Hz, 2H), 3.44 (dt, J=16.2, 6.3 Hz, 4H), 2.44 (d, J=4.9 Hz, 3H), 2.06 (dd, J=13.3, 7.1 Hz, 1H), 1.94-1.86 (m, 1H), 1.83-1.72 (m, 4H), 1.62 (dt, J=13.1, 6.4 Hz, 2H), 1.53 (d, J=11.1 Hz, 3H), 1.43 (d, J=16.2 Hz, 3H), 0.93 (d, J=7.5 Hz, 9H).

Example A319
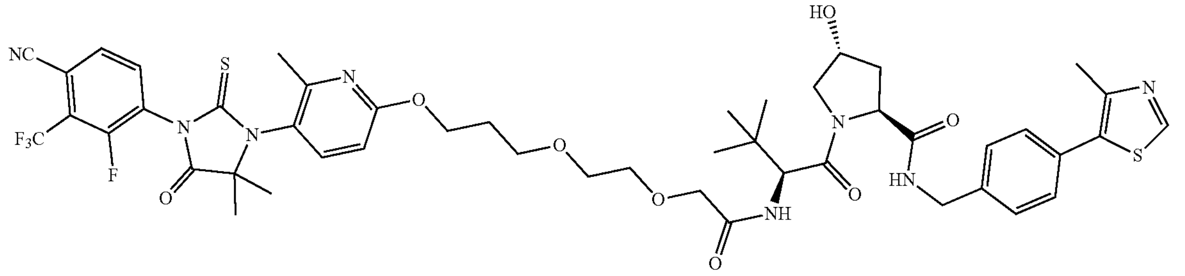 [SMILES: Cc1nc(OCCCOCCOCC(=O)N[C@H](C(=O)N2C[C@H](O)C[C@H]2C(=O)NCc2ccc(-c3scnc3C)cc2)C(C)(C)C)ccc1N1C(=S)N(c2ccc(C#N)c(C(F)(F)F)c2F)C(=O)C1(C)C]
LCMS ([M+H]$^+$): 1011.3
$^1$HNMR (400 MHz, DMSO-d6) δ8.97 (d, J=9.6 Hz, 1H), 8.59 (t, J=6.0 Hz, 1H), 8.32 (dt, J=40.7, 5.9 Hz, 2H), 7.74-7.55 (m, 1H), 7.48-7.34 (m, 5H), 6.80-6.62 (m, 1H), 5.15 (d, J=3.5 Hz, 1H), 4.56 (d, J=9.6 Hz, 1H), 4.33 (dddd, J=25.1, 21.4, 15.9, 6.8 Hz, 5H), 4.00-3.91 (m, 2H), 3.71-3.54 (m, 8H), 2.48-2.39 (m, 4H), 2.33 (dd, J=19.6, 5.7 Hz, 3H), 2.11-1.86 (m, 4H), 1.60 (d, J=11.8 Hz, 3H), 1.52-1.37 (m, 3H), 0.93 (d, J=7.9 Hz, 9H).
Example A320
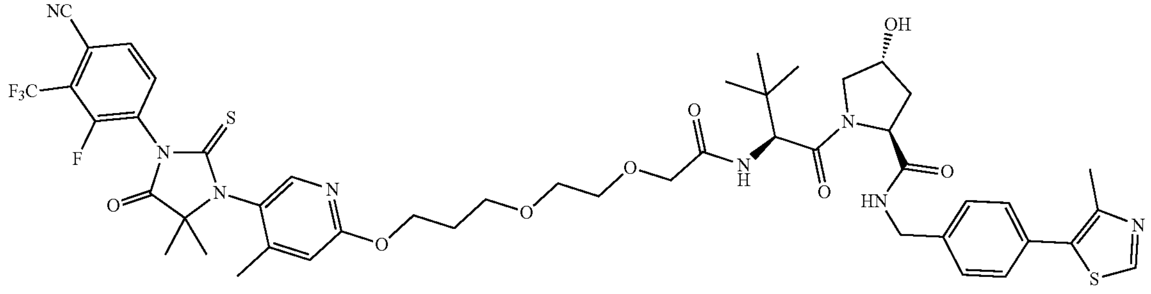 [SMILES: Cc1cc(OCCCOCCOCC(=O)N[C@H](C(=O)N2C[C@H](O)C[C@H]2C(=O)NCc2ccc(-c3scnc3C)cc2)C(C)(C)C)ncc1N1C(=S)N(c2ccc(C#N)c(C(F)(F)F)c2F)C(=O)C1(C)C]
LCMS ([M+H]$^+$): 1011.3
$^1$HNMR (400 MHz, DMSO-d6) δ8.95 (s, 1H), 8.59 (t, J=5.9 Hz, 1H), 8.41-8.23 (m, 2H), 8.17-8.02 (m, 1H), 7.41 (d, J=12.4 Hz, 5H), 6.84 (t, J=10.5 Hz, 1H), 5.16 (d, J=3.5 Hz, 1H), 4.57 (d, J=9.6 Hz, 1H), 4.49-4.29 (m, 5H), 4.24 (dd, J=15.9, 5.5 Hz, 1H), 3.97 (s, 2H), 3.71-3.53 (m, 8H), 2.43 (s, 3H), 2.24 (dd, J=17.6, 4.8 Hz, 3H), 2.11-1.86 (m, 4H), 1.63 (d, J=12.2 Hz, 3H), 1.48-1.38 (m, 3H), 0.93 (d, J=7.5 Hz, 9H).

Example A321
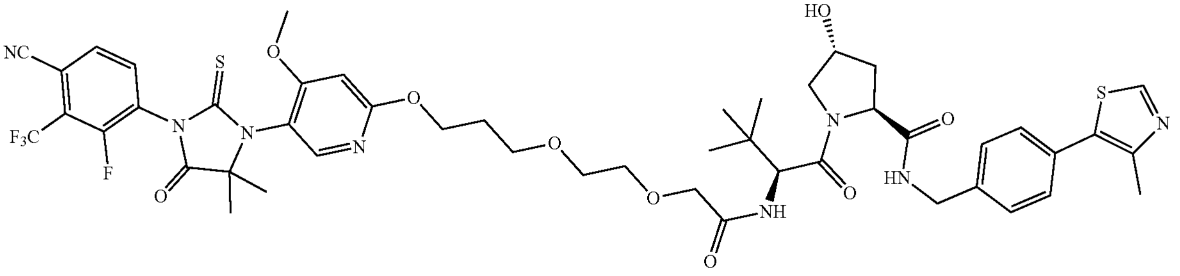 [SMILES: COc1cc(OCCCOCCOCC(=O)N[C@H](C(=O)N2C[C@H](O)C[C@H]2C(=O)NCc2ccc(-c3scnc3C)cc2)C(C)(C)C)ncc1N1C(=S)N(c2ccc(C#N)c(C(F)(F)F)c2F)C(=O)C1(C)C]
LCMS ([M+H]$^+$): 1027.3
$^1$HNMR (400 MHz, DMSO-d6) δ8.97 (d, J=8.8 Hz, 1H), 8.59 (t, J=5.9 Hz, 1H), 8.34-8.20 (m, 2H), 8.06-7.92 (m, 1H), 7.46-7.34 (m, 5H), 6.61 (d, J=16.7 Hz, 1H), 5.15 (m, 1H), 4.57 (m, 1H), 4.48-4.30 (m, 5H), 4.29-4.21 (m, 1H), 3.95 (m, 2H), 3.85-3.79 (m, 3H), 3.71-3.53 (m, 8H), 2.44 (d, J=5.9 Hz, 3H), 1.97 (m, 4H), 1.55 (d, J=10.2 Hz, 3H), 1.39 (d, J=14.7 Hz, 3H), 0.93 (d, J=8.2 Hz, 9H).
Example A322
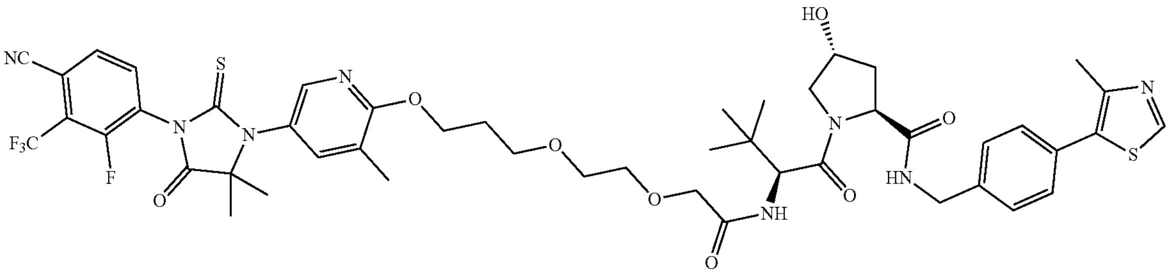 [SMILES: Cc1cc(N2C(=S)N(c3ccc(C#N)c(C(F)(F)F)c3F)C(=O)C2(C)C)cnc1OCCCOCCOCC(=O)N[C@H](C(=O)N1C[C@H](O)C[C@H]1C(=O)NCc1ccc(-c2scnc2C)cc1)C(C)(C)C]
LCMS ([M+H]$^+$): 1011.3
$^1$HNMR (400 MHz, DMSO-d6) δ8.96 (d, J=11.8 Hz, 1H), 8.59 (t, J=6.0 Hz, 1H), 8.32-8.20 (m, 2H), 8.02 (dd, J=7.0, 2.4 Hz, 1H), 7.64 (d, J=1.9 Hz, 1H), 7.47-7.31 (m, 5H), 5.08 (dd, J=62.4, 3.2 Hz, 1H), 4.56 (d, J=9.6 Hz, 1H), 4.50-4.30 (m, 5H), 4.24 (dd, J=15.9, 5.6 Hz, 1H), 3.95 (d, J=16.8 Hz, 2H), 3.71-3.51 (m, 8H), 2.44 (d, J=7.3 Hz, 3H), 2.18 (d, J=12.2 Hz, 3H), 2.10-1.86 (m, 4H), 1.51 (d, J=5.9 Hz, 6H), 0.92 (d, J=8.0 Hz, 9H).

Example A323
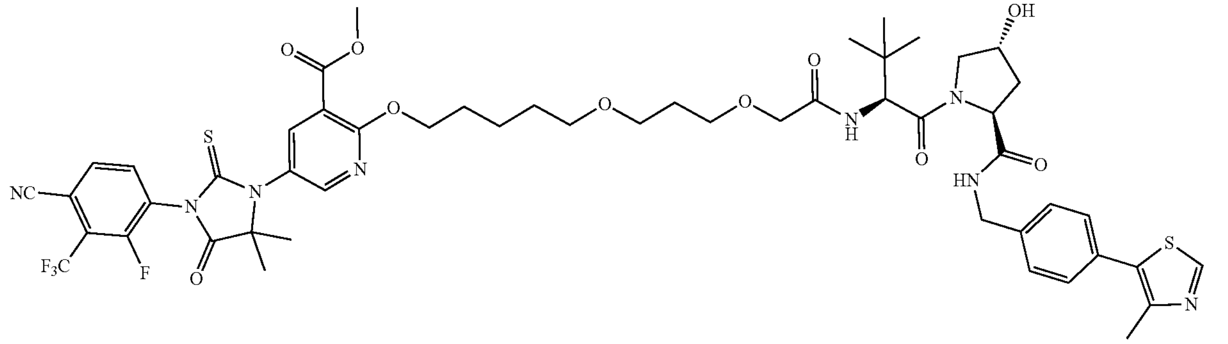 [SMILES: COC(=O)c1cc(N2C(=S)N(c3ccc(C#N)c(C(F)(F)F)c3F)C(=O)C2(C)C)cnc1OCCCCCOCCCOCC(=O)N[C@H](C(=O)N1C[C@H](O)C[C@H]1C(=O)NCc1ccc(-c2scnc2C)cc1)C(C)(C)C]
LCMS ([M+H]$^+$): 1097.3
$^1$HNMR (400 MHz, DMSO-d6) δ8.97 (d, J=4.6 Hz, 1H), 8.60 (t, J=6.1 Hz, 1H), 8.43 (d, J=2.6 Hz, 1H), 8.24 (dd, J=12.9, 3.3 Hz, 3H), 7.46-7.33 (m, 5H), 5.16 (s, 1H), 4.55 (d, J=9.6 Hz, 1H), 4.47-4.34 (m, 5H), 4.24 (m, 1H), 3.91 (m, 2H), 3.85 (d, J=18.4 Hz, 3H), 3.64 (m, 2H), 3.53 (m, 2H), 3.44 (m, 4H), 2.44 (d, J=4.9 Hz, 3H), 2.11-1.94 (m, 3H), 1.94-1.87 (m, 1H), 1.77 (m, 4H), 1.50 (m, 10H), 0.92 (d, J=7.6 Hz, 9H).
Example A324
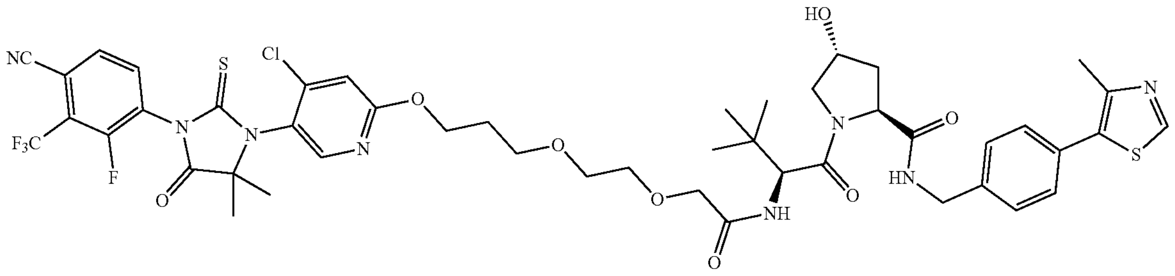 [SMILES: Cc1ncsc1-c1ccc(CNC(=O)[C@@H]2C[C@@H](O)CN2C(=O)[C@@H](NC(=O)COCCOCCCOc2cc(Cl)c(N3C(=S)N(c4ccc(C#N)c(C(F)(F)F)c4F)C(=O)C3(C)C)cn2)C(C)(C)C)cc1]
LCMS ([M+H]$^+$): 1031.5
$^1$HNMR (400 MHz, DMSO-d6) δ8.97 (d, J=9.3 Hz, 1H), 8.59 (t, J=5.8 Hz, 1H), 8.40-8.23 (m, 3H), 7.41 (d, J=10.3 Hz, 5H), 7.22 (d, J=7.2 Hz, 1H), 5.15 (s, 1H), 4.56 (d, J=9.6 Hz, 1H), 4.41 (dt, J=12.2, 7.3 Hz, 5H), 4.24 (dd, J=15.7, 5.4 Hz, 1H), 3.95 (d, J=16.9 Hz, 2H), 3.70-3.56 (m, 8H), 2.44 (d, J=6.0 Hz, 3H), 2.07-1.96 (m, 3H), 1.94-1.86 (m, 1H), 1.64 (d, J=9.7 Hz, 3H), 1.49 (d, J=11.8 Hz, 3H), 0.92 (d, J=8.4 Hz, 9H).

Example A325
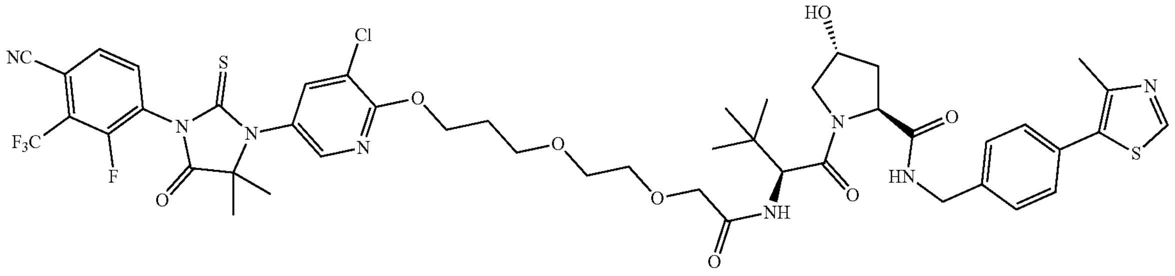 [SMILES: Cc1ncsc1-c1ccc(CNC(=O)[C@@H]2C[C@@H](O)CN2C(=O)[C@@H](NC(=O)COCCOCCCOc2ncc(N3C(=S)N(c4ccc(C#N)c(C(F)(F)F)c4F)C(=O)C3(C)C)cc2Cl)C(C)(C)C)cc1]
LCMS ([M+H]$^+$): 1031.5
$^1$HNMR (400 MHz, DMSO-d6) δ8.97 (d, J=10.8 Hz, 1H), 8.58 (t, J=6.1 Hz, 1H), 8.30-8.11 (m, 4H), 7.41 (d, J=9.4 Hz, 5H), 5.15 (d, J=3.2 Hz, 1H), 4.56 (d, J=9.6 Hz, 1H), 4.48-4.33 (m, 5H), 4.24 (dd, J=15.7, 5.4 Hz, 1H), 3.95 (d, J=17.1 Hz, 2H), 3.68-3.56 (m, 8H), 2.44 (d, J=6.4 Hz, 3H), 2.04 (dd, J=14.3, 8.1 Hz, 3H), 1.94-1.86 (m, 1H), 1.54 (s, 6H), 0.92 (d, J=7.9 Hz, 9H).
Example A326
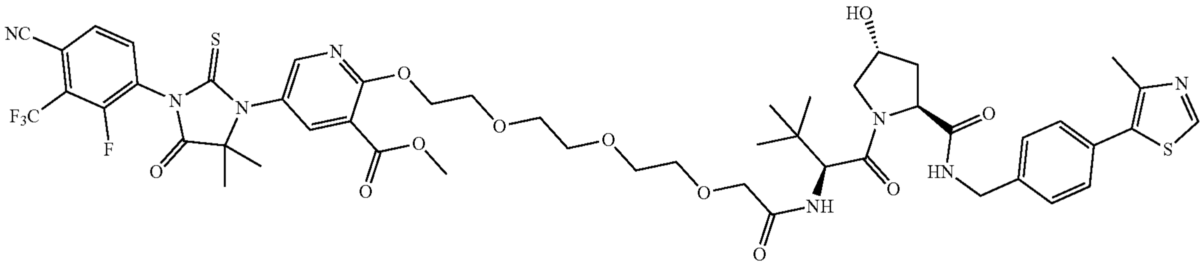 [SMILES: COC(=O)c1cc(N2C(=S)N(c3ccc(C#N)c(C(F)(F)F)c3F)C(=O)C2(C)C)cnc1OCCOCCOCCOCC(=O)N[C@H](C(=O)N1C[C@H](O)C[C@H]1C(=O)NCc1ccc(-c2scnc2C)cc1)C(C)(C)C]
LCMS ([M+H]$^+$): 1085.3
$^1$HNMR (400 MHz, DMSO-d6) δ8.97 (d, J=6.9 Hz, 1H), 8.59 (t, J=6.0 Hz, 1H), 8.43 (d, J=2.6 Hz, 1H), 8.30-8.21 (m, 3H), 7.47-7.35 (m, 5H), 5.15 (d, J=3.5 Hz, 1H), 4.60-4.49 (m, 3H), 4.48-4.33 (m, 3H), 4.25 (dd, J=15.7, 5.6 Hz, 1H), 3.94 (d, J=16.4 Hz, 2H), 3.86-3.75 (m, 5H), 3.71-3.54 (m, 10H), 2.44 (d, J=5.1 Hz, 3H), 2.10-2.02 (m, 1H), 1.90 (ddd, J=13.0, 8.9, 4.5 Hz, 1H), 1.55 (d, J=4.5 Hz, 6H), 0.93 (d, J=8.8 Hz, 9H).

Example A327
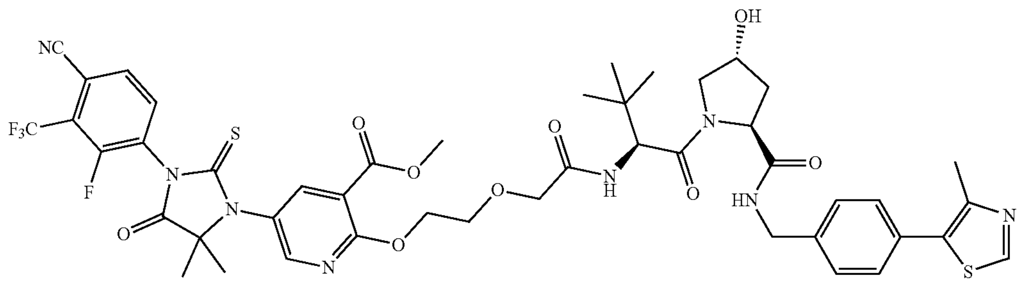 [SMILES: COC(=O)c1cc(N2C(=S)N(c3ccc(C#N)c(C(F)(F)F)c3F)C(=O)C2(C)C)cnc1OCCOCC(=O)N[C@H](C(=O)N1C[C@H](O)C[C@H]1C(=O)NCc1ccc(-c2scnc2C)cc1)C(C)(C)C]
LCMS ([M+H]+): 997.3
$^1$HNMR (400 MHz, DMSO-d6) δ8.97 (s, 1H), 8.58 (t, J=6.0 Hz, 1H), 8.44 (d, J=2.6 Hz, 1H), 8.31-8.22 (m, 3H), 7.47-7.36 (m, 5H), 5.16 (d, J=3.5 Hz, 1H), 4.64-4.54 (m, 3H), 4.48-4.32 (m, 3H), 4.25 (dd, J=15.7, 5.6 Hz, 1H), 4.17-4.08 (m, 2H), 3.96-3.90 (m, 2H), 3.84 (s, 3H), 3.68-3.59 (m, 2H), 2.45-2.44 (m, 3H), 2.08-2.03 (m, 1H), 1.95-1.85 (m, 1H), 1.54 (d, J=4.6 Hz, 6H), 0.97-0.86 (m, 9H).
Example A328
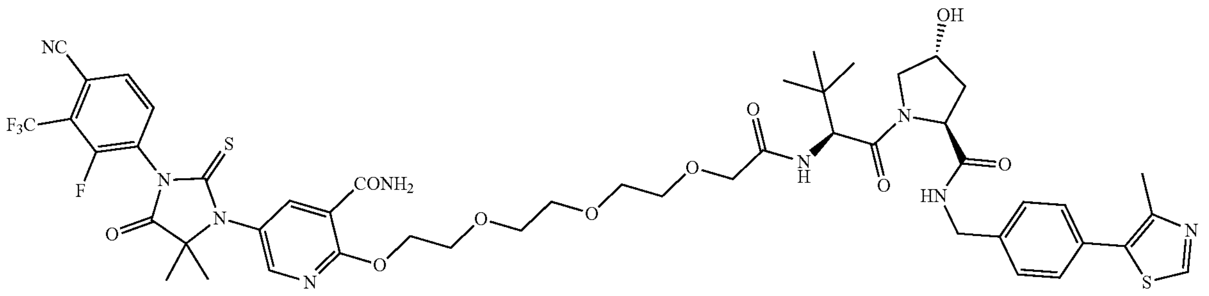 [SMILES: Cc1ncsc1-c1ccc(CNC(=O)[C@@H]2C[C@@H](O)CN2C(=O)[C@@H](NC(=O)COCCOCCOCCOc2ncc(N3C(=S)N(c4ccc(C#N)c(C(F)(F)F)c4F)C(=O)C3(C)C)cc2C(N)=O)C(C)(C)C)cc1]
LCMS ([M+H]+): 1070.3
$^1$HNMR (400 MHz, DMSO-d6) δ8.98-8.96 (m, 1H), 8.60 (t, J=6.0 Hz, 1H), 8.38 (d, J=2.6 Hz, 1H), 8.32-8.24 (m, 3H), 7.93 (s, 1H), 7.75 (s, 1H), 7.47-7.37 (m, 5H), 5.17 (d, J=3.5 Hz, 1H), 4.61-4.54 (m, 3H), 4.47-4.37 (m, 2H), 4.27-4.22 (m, 1H), 3.97 (s, 2H), 3.84-3.79 (m, 2H), 3.66-3.56 (m, 10H), 2.44-2.43 (m, 3H), 2.09-1.95 (m, 2H), 1.94-1.86 (m, 1H), 1.54 (d, J=5.2 Hz, 6H), 0.93-0.91 (m, 9H).

Example A329
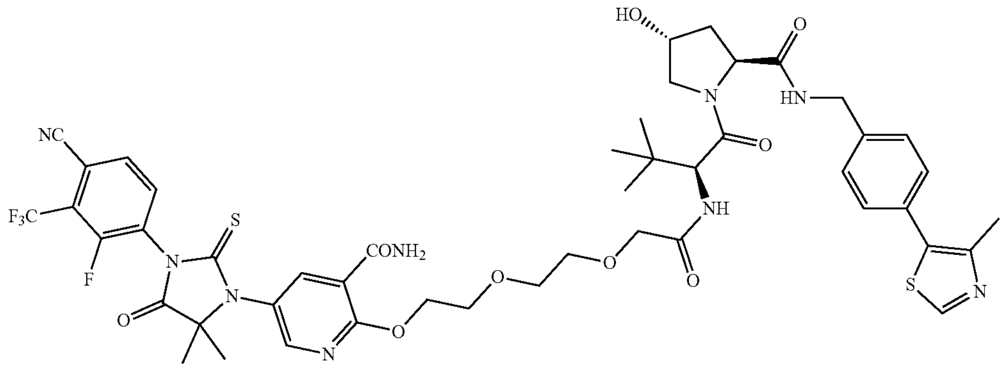 [SMILES: Cc1ncsc1-c1ccc(CNC(=O)[C@@H]2C[C@@H](O)CN2C(=O)[C@@H](NC(=O)COCCOCCOc2ncc(N3C(=S)N(c4ccc(C#N)c(C(F)(F)F)c4F)C(=O)C3(C)C)cc2C(N)=O)C(C)(C)C)cc1]
LCMS ([M+H]$^+$): 1026.3
$^1$HNMR (400 MHz, DMSO-d6) δ8.98-8.96 (m, 1H), 8.59 (t, J=5.9 Hz, 1H), 8.40-8.23 (m, 4H), 7.95 (s, 1H), 7.77 (s, 1H), 7.50-7.36 (m, 5H), 5.15 (d, J=3.5 Hz, 1H), 4.66-4.53 (m, 3H), 4.48-4.33 (m, 3H), 4.28-4.22 (m, 1H), 3.97 (s, 2H), 3.90-3.87 (m, 2H), 3.72-3.59 (m, 6H), 2.44-2.43 (m, 3H), 2.08-2.03 (m, 1H), 1.91 (ddd, J=13.0, 8.9, 4.5 Hz, 1H), 1.53 (d, J=4.7 Hz, 6H), 0.91-0.89 (m, 9H).
Example A330
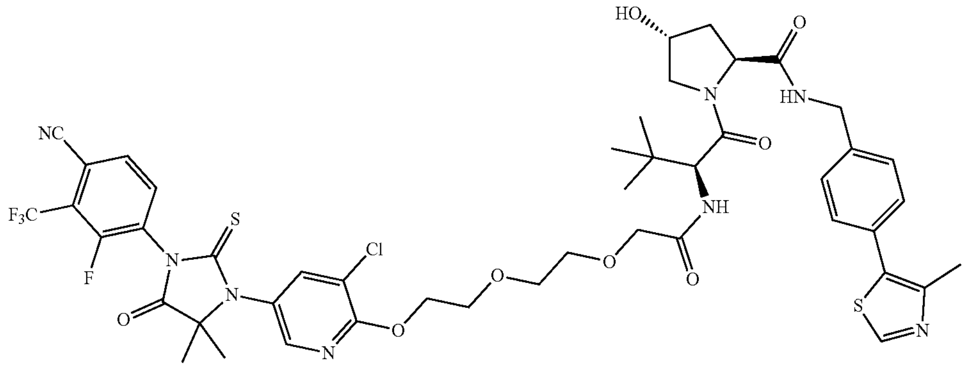 [SMILES: Cc1ncsc1-c1ccc(CNC(=O)[C@@H]2C[C@@H](O)CN2C(=O)[C@@H](NC(=O)COCCOCCOc2ncc(N3C(=S)N(c4ccc(C#N)c(C(F)(F)F)c4F)C(=O)C3(C)C)cc2Cl)C(C)(C)C)cc1]
LCMS ([M+H]$^+$): 1017.3
$^1$HNMR (400 MHz, DMSO-d6) δ8.97 (d, J=9.9 Hz, 1H), 8.59 (t, J=6.0 Hz, 1H), 8.30-8.19 (m, 2H), 8.19-8.11 (m, 2H), 7.49-7.35 (m, 5H), 5.15 (d, J=3.5 Hz, 1H), 4.55 (dd, J=9.4, 5.1 Hz, 3H), 4.49-4.32 (m, 3H), 4.24 (dd, J=15.8, 5.6 Hz, 1H), 3.98 (s, 2H), 3.92-3.78 (m, 2H), 3.75-3.57 (m, 6H), 2.44 (d, J=6.2 Hz, 3H), 2.11-2.01 (m, 1H), 1.91 (td, J=8.7, 4.5 Hz, 1H), 1.54 (s, 6H), 0.92 (d, J=7.9 Hz, 9H).

Example A331
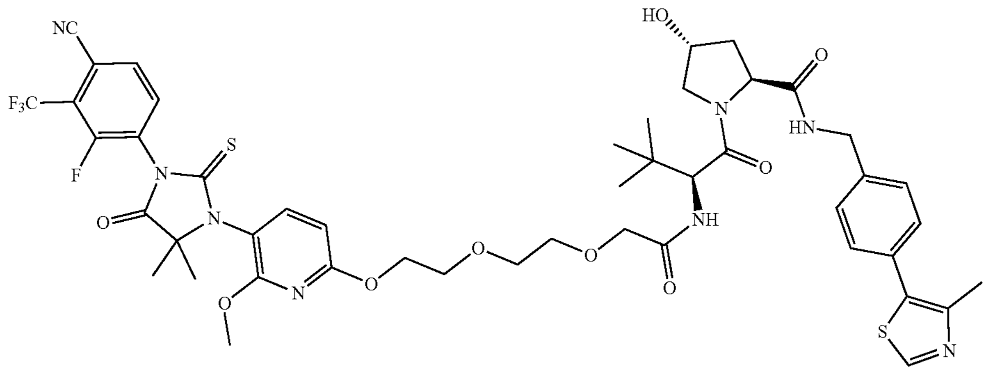 [SMILES: COc1nc(OCCOCCOCC(=O)N[C@H](C(=O)N2C[C@H](O)C[C@H]2C(=O)NCc2ccc(-c3scnc3C)cc2)C(C)(C)C)ccc1N1C(=S)N(c2ccc(C#N)c(C(F)(F)F)c2F)C(=O)C1(C)C]
LCMS ([M+H]$^+$): 1013.3
$^1$HNMR (400 MHz, DMSO-d6) δ8.96 (s, 1H), 8.58 (t, J=5.9 Hz, 1H), 8.37-8.20 (m, 2H), 7.79-7.58 (m, 1H), 7.52-7.33 (m, 5H), 6.53 (dd, J=5.9, 2.2 Hz, 1H), 5.15 (d, J=3.5 Hz, 1H), 4.57 (d, J=9.6 Hz, 1H), 4.42 (dd, J=26.1, 15.3 Hz, 5H), 4.26 (d, J=5.5 Hz, 1H), 3.99 (s, 2H), 3.84 (dd, J=13.9, 4.8 Hz, 5H), 3.64 (d, J=12.3 Hz, 6H), 2.44 (d, J=7.4 Hz, 3H), 2.11-2.00 (m, 1H), 1.95-1.85 (m, 1H), 1.58-1.47 (m, 3H), 1.47-1.37 (m, 3H), 0.92 (d, J=9.7 Hz, 9H).
Example A332
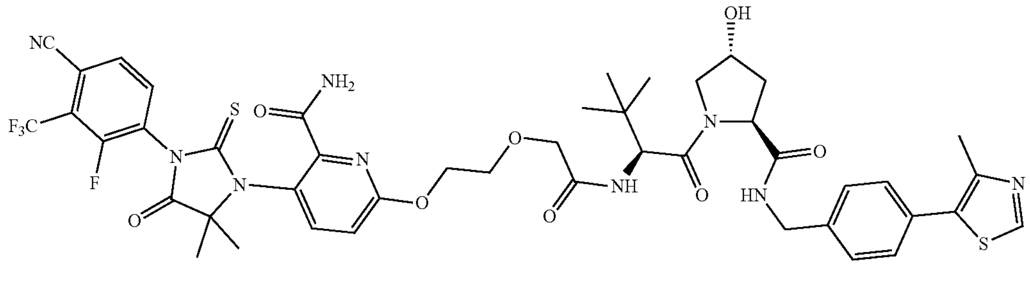 [SMILES: Cc1ncsc1-c1ccc(CNC(=O)[C@@H]2C[C@@H](O)CN2C(=O)[C@@H](NC(=O)COCCOc2ccc(N3C(=S)N(c4ccc(C#N)c(C(F)(F)F)c4F)C(=O)C3(C)C)c(C(N)=O)n2)C(C)(C)C)cc1]
LCMS ([M+H]$^+$): 982.3
$^1$HNMR (400 MHz, DMSO-d6) δ8.97 (t, J=5.0 Hz, 1H), 8.60 (d, J=5.7 Hz, 1H), 8.24 (d, J=7.5 Hz, 2H), 7.98 (d, J=18.4 Hz, 1H), 7.90-7.70 (m, 1H), 7.61 (d, J=9.8 Hz, 1H), 7.51 (d, J=9.6 Hz, 1H), 7.41 (d, J=7.6 Hz, 4H), 7.29 (dd, J=14.3, 8.9 Hz, 1H), 5.17 (d, J=3.4 Hz, 1H), 4.61 (d, J=9.3 Hz, 3H), 4.41 (d, J=37.2 Hz, 3H), 4.29 (d, J=5.0 Hz, 1H), 4.08 (s, 2H), 3.89 (s, 2H), 3.74-3.56 (m, 2H), 2.43 (s, 3H), 2.07 (dd, J=12.5, 8.3 Hz, 1H), 1.93 (dd, J=8.7, 4.4 Hz, 1H), 1.62 (dd, J=13.1, 4.1 Hz, 3H), 1.43 (dd, J=13.7, 7.5 Hz, 3H), 0.95 (s, 9H).

Example A333
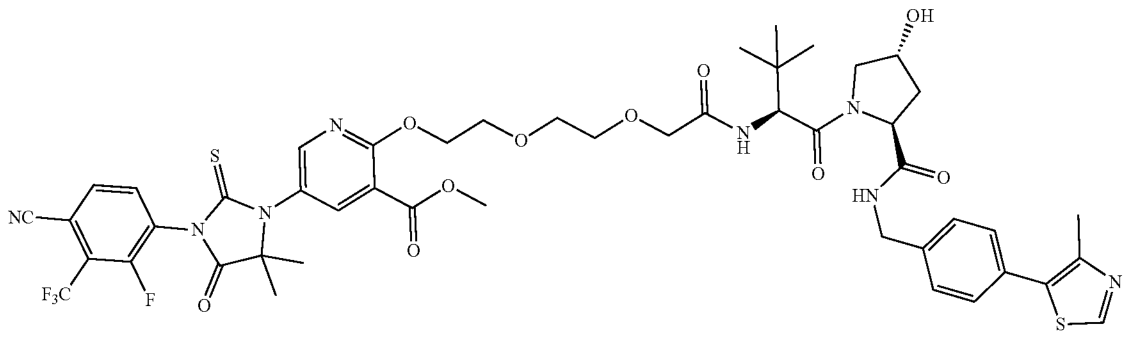 [SMILES: COC(=O)c1cc(N2C(=S)N(c3ccc(C#N)c(C(F)(F)F)c3F)C(=O)C2(C)C)cnc1OCCOCCOCC(=O)N[C@H](C(=O)N1C[C@H](O)C[C@H]1C(=O)NCc1ccc(-c2scnc2C)cc1)C(C)(C)C]
LCMS ([M+H]$^+$): 1041.3
$^1$HNMR (400 MHz, DMSO-d6) δ8.97 (d, J=10.3 Hz, 1H), 8.60 (t, J=5.9 Hz, 1H), 8.46-8.39 (m, 1H), 8.30-8.22 (m, 3H), 7.49-7.36 (m, 5H), 5.16 (d, J=3.5 Hz, 1H), 4.55 (dd, J=9.4, 5.0 Hz, 3H), 4.47-4.32 (m, 3H), 4.24 (dd, J=15.8, 5.6 Hz, 1H), 3.96 (d, J=17.0 Hz, 2H), 3.91-3.79 (m, 5H), 3.75-3.58 (m, 6H), 2.44 (d, J=6.5 Hz, 3H), 2.06 (dd, J=15.2, 5.9 Hz, 1H), 1.90 (ddd, J=12.9, 8.9, 4.4 Hz, 1H), 1.54 (d, J=4.2 Hz, 6H), 0.91 (d, J=8.5 Hz, 9H).
Example A334
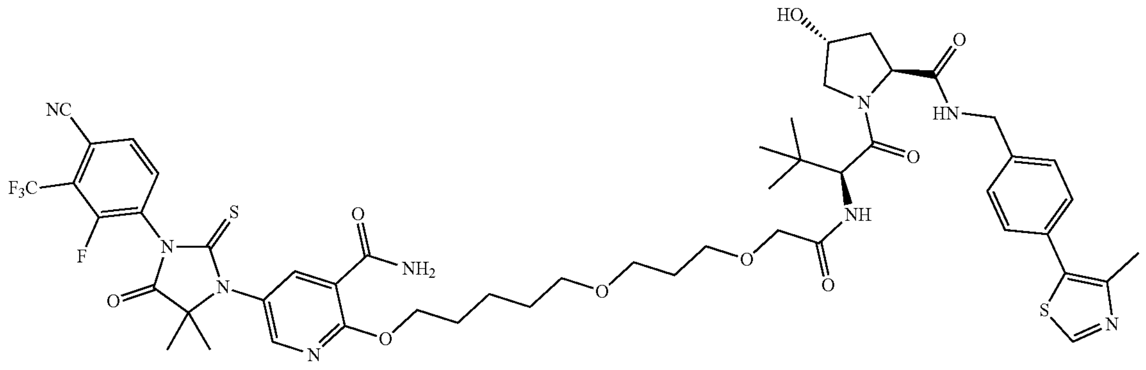 [SMILES: Cc1ncsc1-c1ccc(CNC(=O)[C@@H]2C[C@@H](O)CN2C(=O)[C@@H](NC(=O)COCCCOCCCCCOc2ncc(N3C(=S)N(c4ccc(C#N)c(C(F)(F)F)c4F)C(=O)C3(C)C)cc2C(N)=O)C(C)(C)C)cc1]
LCMS ([M+H]$^+$): 1082.4
$^1$HNMR (400 MHz, DMSO-d6) δ8.98-8.97 (m, 1H), 8.61 (t, J=5.9 Hz, 1H), 8.37 (d, J=2.6 Hz, 1H), 8.29-8.22 (m, 3H), 7.91 (s, 1H), 7.68 (s, 1H), 7.46-7.33 (m, 5H), 5.17 (d, J=3.4 Hz, 1H), 4.55 (d, J=9.6 Hz, 1H), 4.47-4.33 (m, 5H), 4.27-4.22 (m, 1H), 3.92-3.88 (m, 2H), 3.68-3.59 (m, 2H), 3.53 (t, J=6.3 Hz, 2H), 3.45 (d, J=6.3 Hz, 2H), 2.45-2.43 (m, 3H), 2.10-2.02 (m, 1H), 1.94-1.86 (m, 1H), 1.82-1.76 (m, 4H), 1.54 (d, J=5.2 Hz, 8H), 1.43 (dd, J=14.5, 7.8 Hz, 2H), 0.93-0.91 (m, 9H).

Example A335
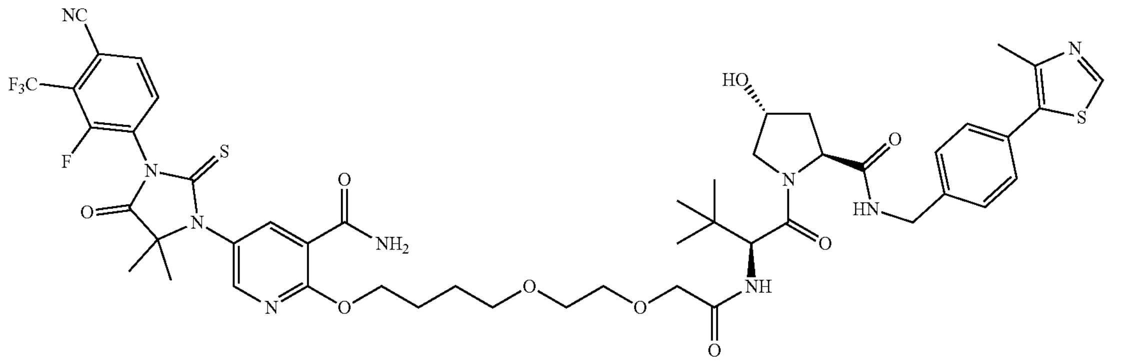 [SMILES: Cc1ncsc1-c1ccc(CNC(=O)[C@@H]2C[C@@H](O)CN2C(=O)[C@@H](NC(=O)COCCOCCCCOc2ncc(N3C(=S)N(c4ccc(C#N)c(C(F)(F)F)c4F)C(=O)C3(C)C)cc2C(N)=O)C(C)(C)C)cc1]
LCMS ([M+H]$^+$): 1054.4
$^1$HNMR (400 MHz, DMSO-d6) δ8.98-8.96 (m, 1H), 8.60 (t, J=5.9 Hz, 1H), 8.35 (d, J=2.5 Hz, 1H), 8.29-8.21 (m, 3H), 7.90 (s, 1H), 7.69 (s, 1H), 7.46-7.36 (m, 5H), 5.16 (d, J=3.4 Hz, 1H), 4.56 (d, J=9.6 Hz, 1H), 4.49-4.33 (m, 5H), 4.25 (dd, J=15.6, 5.4 Hz, 1H), 3.97 (s, 2H), 3.69-3.60 (m, 4H), 3.55 (m, 2H), 3.51-3.48 (m, 2H), 2.45-2.43 (m, 3H), 2.08-2.03 (m, 1H), 1.94-1.80 (m, 3H), 1.68 (dd, J=14.5, 6.6 Hz, 2H), 1.53 (d, J=4.8 Hz, 6H), 0.93-0.91 (m, 9H).
Example A336
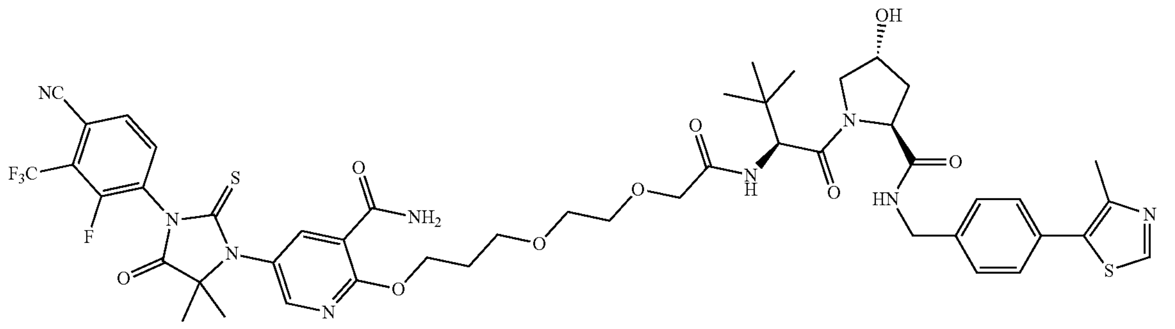 [SMILES: Cc1ncsc1-c1ccc(CNC(=O)[C@@H]2C[C@@H](O)CN2C(=O)[C@@H](NC(=O)COCCOCCCOc2ncc(N3C(=S)N(c4ccc(C#N)c(C(F)(F)F)c4F)C(=O)C3(C)C)cc2C(N)=O)C(C)(C)C)cc1]
LCMS ([M+H]$^+$): 1040.3
$^1$HNMR (400 MHz, DMSO-d6) δ8.98-8.96 (m, 1H), 8.60 (t, J=5.9 Hz, 1H), 8.35 (d, J=2.2 Hz, 1H), 8.26-8.25 (m, 3H), 7.90 (s, 1H), 7.80 (s, 1H), 7.49-7.35 (m, 5H), 5.16 (d, J=3.4 Hz, 1H), 4.60-4.48 (m, 3H), 4.47-4.31 (m, 3H), 4.27-4.22 (m, 1H), 3.98-3.93 (m, 2H), 3.70-3.54 (m, 8H), 2.44-2.43 (m, 3H), 2.08-2.05 (m, 3H), 1.94-1.85 (m, 1H), 1.53 (d, J=5.1 Hz, 6H), 0.92-0.90 (m, 9H).

Example A337
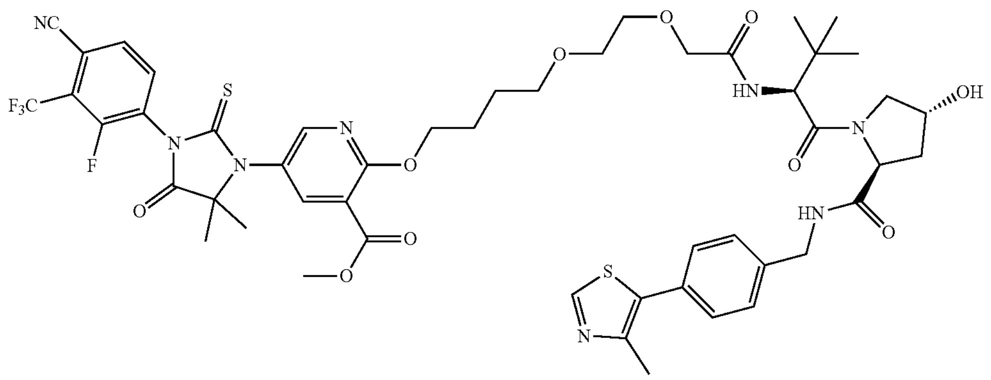 [SMILES: COC(=O)c1cc(N2C(=S)N(c3ccc(C#N)c(C(F)(F)F)c3F)C(=O)C2(C)C)cnc1OCCCCOCCOCC(=O)N[C@H](C(=O)N1C[C@H](O)C[C@H]1C(=O)NCc1ccc(-c2scnc2C)cc1)C(C)(C)C]
LCMS ([M+H]$^+$): 1069.3
$^1$HNMR (400 MHz, DMSO-d6) δ8.95 (s, 1H), 8.60 (t, J=6.0 Hz, 1H), 8.43 (dd, J=6.0, 2.5 Hz, 1H), 8.29-8.21 (m, 3H), 7.40 (d, J=5.5 Hz, 5H), 5.16 (d, J=3.5 Hz, 1H), 4.56 (d, J=9.6 Hz, 1H), 4.47-4.33 (m, 5H), 4.24 (dd, J=15.7, 5.5 Hz, 1H), 3.97 (s, 2H), 3.83 (d, J=5.6 Hz, 3H), 3.69-3.58 (m, 4H), 3.58-3.49 (m, 4H), 2.43 (s, 3H), 2.08-2.02 (m, 1H), 1.90 (ddd, J=12.9, 8.9, 4.4 Hz, 1H), 1.82-1.75 (m, 2H), 1.71 (q, J=6.3 Hz, 2H), 1.54 (d, J=4.2 Hz, 6H), 0.93 (s, 9H).
Example A338
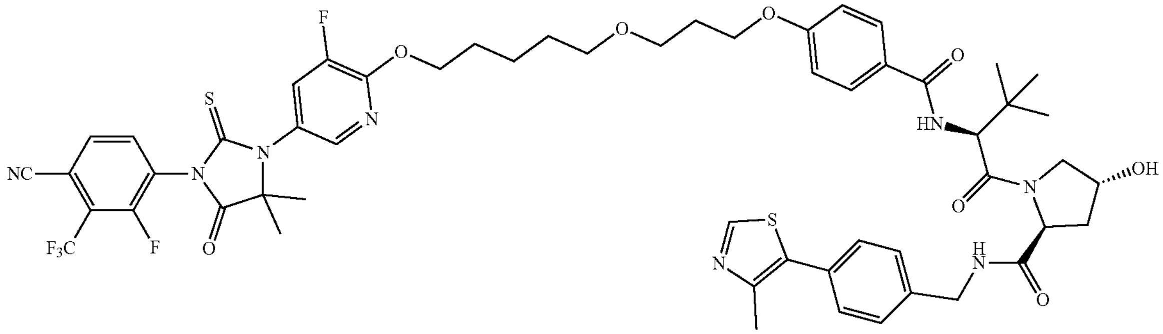 [SMILES: Cc1ncsc1-c1ccc(CNC(=O)[C@@H]2C[C@@H](O)CN2C(=O)[C@@H](NC(=O)c2ccc(OCCCOCCCCCOc3ncc(N4C(=S)N(c5ccc(C#N)c(C(F)(F)F)c5F)C(=O)C4(C)C)cc3F)cc2)C(C)(C)C)cc1]
LCMS ([M+H]$^+$): 1119.3
$^1$HNMR (400 MHz, DMSO-d6) δ8.98 (s, 1H), 8.59 (t, J=6.0 Hz, 1H), 8.28-8.22 (m, 2H), 8.07 (d, J=2.0 Hz, 1H), 7.96 (dd, J=10.7, 1.8 Hz, 1H), 7.86 (d, J=8.8 Hz, 2H), 7.79 (d, J=9.0 Hz, 1H), 7.44-7.37 (m, 4H), 6.97 (m, 2H), 5.16 (m, 1H), 4.75 (m, 1H), 4.42 (m, 5H), 4.24 (m, 1H), 4.08 (m, 2H), 3.72 (m, 2H), 3.52 (m, 2H), 3.41 (m, 2H), 2.46-2.42 (m, 3H), 2.09-1.87 (m, 5H), 1.83-1.74 (m, 2H), 1.62-1.51 (m, 8H), 1.46 (m, 2H), 1.00 (d, J=11.6 Hz, 9H).

Example A339
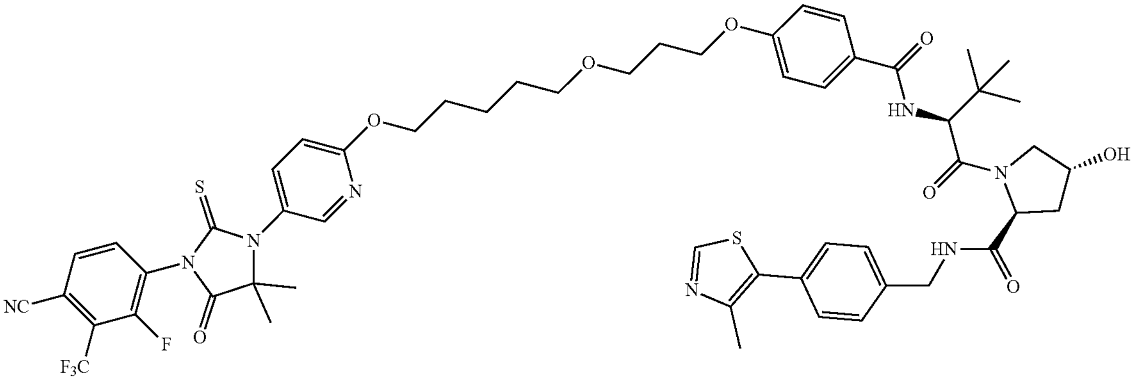 [SMILES: Cc1ncsc1-c1ccc(CNC(=O)[C@@H]2C[C@@H](O)CN2C(=O)[C@@H](NC(=O)c2ccc(OCCCOCCCCCOc3ccc(N4C(=S)N(c5ccc(C#N)c(C(F)(F)F)c5F)C(=O)C4(C)C)cn3)cc2)C(C)(C)C)cc1]
LCMS ([M+H]+): 1101.3
$^1$HNMR (400 MHz, DMSO-d6) δ8.98 (s, 1H), 8.59 (t, J=5.9 Hz, 1H), 8.30-8.23 (m, 2H), 8.20 (d, J=2.5 Hz, 1H), 7.86 (d, J=8.7 Hz, 2H), 7.78 (dd, J=13.5, 5.3 Hz, 2H), 7.44-7.37 (m, 4H), 6.97 (d, J=8.8 Hz, 3H), 5.16 (d, J=3.5 Hz, 1H), 4.75 (d, J=9.1 Hz, 1H), 4.42 (dt, J=13.9, 7.8 Hz, 3H), 4.32-4.22 (m, 3H), 4.08 (m, 2H), 3.72 (m, 2H), 3.52 (m, 2H), 3.41 (m, 2H), 2.43 (d, J=7.0 Hz, 3H), 2.09-1.88 (m, 5H), 1.78-1.70 (m, 2H), 1.61-1.40 (m, 10H), 1.00 (d, J=11.4 Hz, 9H).
Example A340
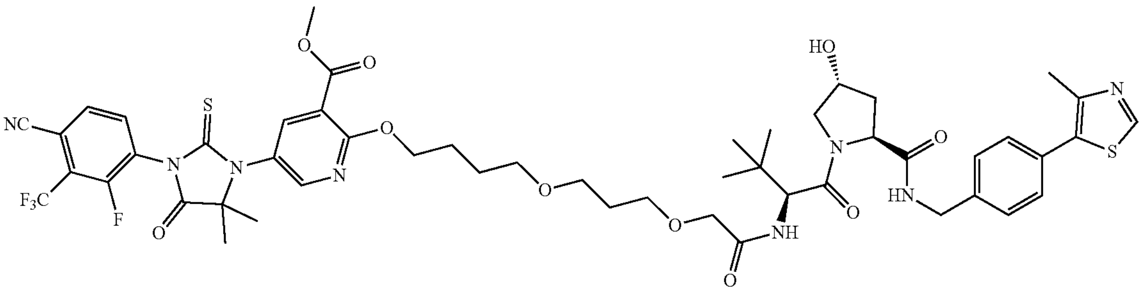 [SMILES: COC(=O)c1cc(N2C(=S)N(c3ccc(C#N)c(C(F)(F)F)c3F)C(=O)C2(C)C)cnc1OCCCCOCCCOCC(=O)N[C@H](C(=O)N1C[C@H](O)C[C@H]1C(=O)NCc1ccc(-c2scnc2C)cc1)C(C)(C)C]
LCMS ([M+H]+): 1083.1
$^1$HNMR (400 MHz, DMSO-d6) δ8.97 (d, J=5.6 Hz, 1H), 8.60 (t, J=6.0 Hz, 1H), 8.43 (d, J=2.6 Hz, 1H), 8.30-8.21 (m, 3H), 7.48-7.33 (m, 5H), 5.15 (d, J=3.4 Hz, 1H), 4.55 (d, J=9.6 Hz, 1H), 4.48-4.33 (m, 5H), 4.25 (dd, J=15.7, 5.5 Hz, 1H), 3.92 (s, 2H), 3.83 (s, 3H), 3.64 (dt, J=23.1, 7.2 Hz, 2H), 3.54 (t, J=6.4 Hz, 2H), 3.45 (dt, J=12.9, 6.3 Hz, 4H), 2.44 (d, J=4.7 Hz, 3H), 2.06 (dd, J=13.5, 6.8 Hz, 1H), 1.94-1.86 (m, 1H), 1.78 (dq, J=11.9, 6.1 Hz, 4H), 1.67 (dd, J=13.9, 6.5 Hz, 2H), 1.54 (d, J=4.3 Hz, 6H), 0.92 (d, J=7.7 Hz, 9H).

Example A341
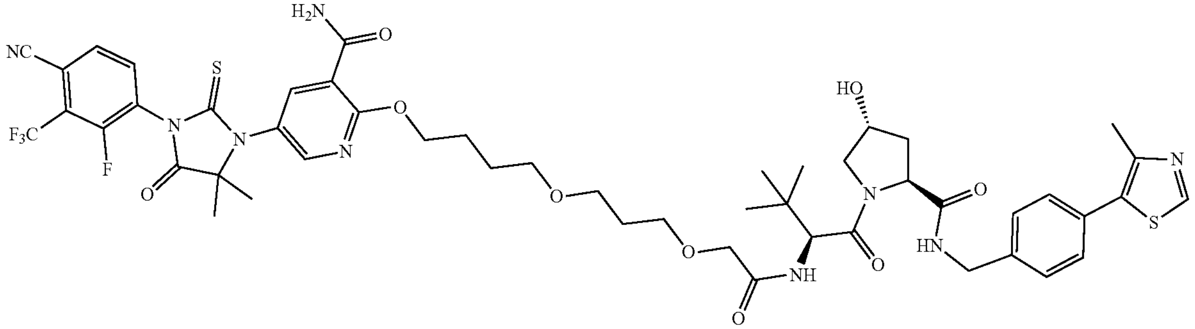 [SMILES: Cc1ncsc1-c1ccc(CNC(=O)[C@@H]2C[C@@H](O)CN2C(=O)[C@@H](NC(=O)COCCCOCCCCOc2ncc(N3C(=S)N(c4ccc(C#N)c(C(F)(F)F)c4F)C(=O)C3(C)C)cc2C(N)=O)C(C)(C)C)cc1]
LCMS ([M+H]+): 1068.1
$^1$HNMR (400 MHz, DMSO-d6) δ8.98 (d, J=5.0 Hz, 1H), 8.61 (t, J=5.9 Hz, 1H), 8.36 (d, J=2.5 Hz, 1H), 8.31-8.22 (m, 3H), 7.91 (s, 1H), 7.69 (s, 1H), 7.46-7.34 (m, 5H), 5.17 (d, J=3.4 Hz, 1H), 4.55 (d, J=9.5 Hz, 1H), 4.50-4.33 (m, 5H), 4.25 (dd, J=15.9, 5.5 Hz, 1H), 3.90 (d, J=16.1 Hz, 2H), 3.64 (dt, J=22.6, 7.3 Hz, 2H), 3.53 (t, J=6.4 Hz, 2H), 3.49-3.40 (m, 5H), 2.44 (d, J=4.3 Hz, 3H), 2.06 (dd, J=13.5, 6.6 Hz, 1H), 1.80 (ddt, J=18.7, 12.5, 6.4 Hz, 4H), 1.64 (dd, J=14.5, 6.5 Hz, 2H), 1.54 (d, J=5.2 Hz, 6H), 0.92 (d, J=8.1 Hz, 9H).
Example A347
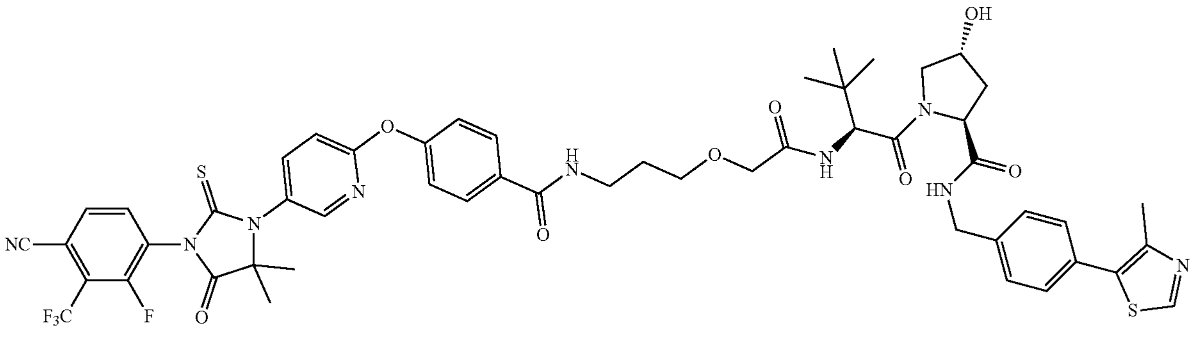 [SMILES: Cc1ncsc1-c1ccc(CNC(=O)[C@@H]2C[C@@H](O)CN2C(=O)[C@@H](NC(=O)COCCCNC(=O)c2ccc(Oc3ccc(N4C(=S)N(c5ccc(C#N)c(C(F)(F)F)c5F)C(=O)C4(C)C)cn3)cc2)C(C)(C)C)cc1]
LCMS ([M+H]+): 1072.3
$^1$HNMR (400 MHz, DMSO-d6) δ8.98 (d, J=7.8 Hz, 1H), 8.65-8.53 (m, 2H), 8.28 (d, J=3.8 Hz, 2H), 8.22 (d, J=2.6 Hz, 1H), 8.00 (dd, J=8.7, 2.6 Hz, 1H), 7.93 (d, J=8.7 Hz, 2H), 7.49 (d, J=9.6 Hz, 1H), 7.40 (s, 4H), 7.30 (dd, J=8.6, 4.1 Hz, 3H), 5.18 (d, J=3.4 Hz, 1H), 4.58 (d, J=9.6 Hz, 1H), 4.48-4.22 (m, 4H), 3.97 (s, 2H), 3.69-3.59 (m, 2H), 3.56 (t, J=6.3 Hz, 2H), 2.44 (s, 3H), 2.10-1.86 (m, 2H), 1.86-1.78 (m, 2H), 1.55 (s, 6H), 1.24 (s, 2H), 0.94 (s, 9H).

Example A348
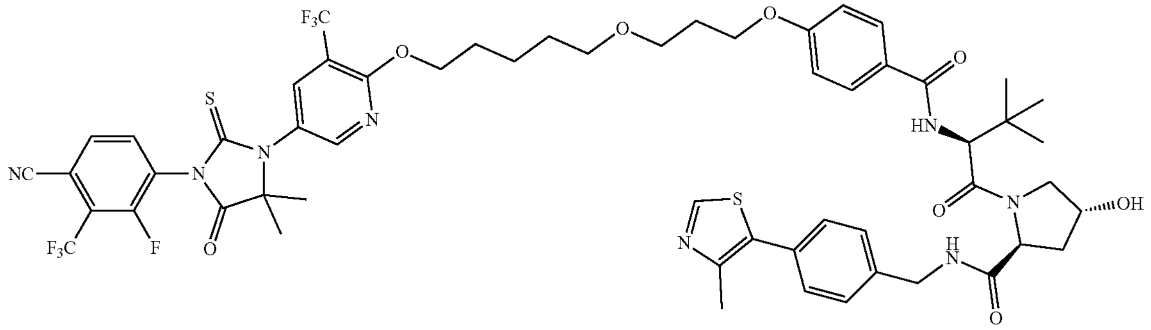 [SMILES: Cc1ncsc1-c1ccc(CNC(=O)[C@@H]2C[C@@H](O)CN2C(=O)[C@@H](NC(=O)c2ccc(OCCCOCCCCCOc3ncc(N4C(=S)N(c5ccc(C#N)c(C(F)(F)F)c5F)C(=O)C4(C)C)cc3C(F)(F)F)cc2)C(C)(C)C)cc1]
LCMS ([M+H]+): 1153.3
$^{1}$HNMR (400 MHz, DMSO-d6) δ8.99 (s, 1H), 8.60 (m, 1H), 8.52 (d, J=2.0 Hz, 1H), 8.31-8.21 (m, 3H), 7.84 (dd, J=24.7, 8.9 Hz, 3H), 7.41 (t, J=4.2 Hz, 4H), 6.98 (d, J=8.8 Hz, 2H), 5.17 (m, 1H), 4.76 (m, 1H), 4.46 (m, 5H), 4.25 (m, 1H), 4.09 (m, 2H), 3.73 (m, 2H), 3.52 (m, 2H), 3.40 (m, 2H), 2.45 (m, 3H), 2.08 (m, 1H), 1.96 (t, J=6.2 Hz, 3H), 1.77 (m, 2H), 1.57 (m, 8H), 1.48 (m, 2H), 1.01 (d, J=11.7 Hz, 9H).
Example A349
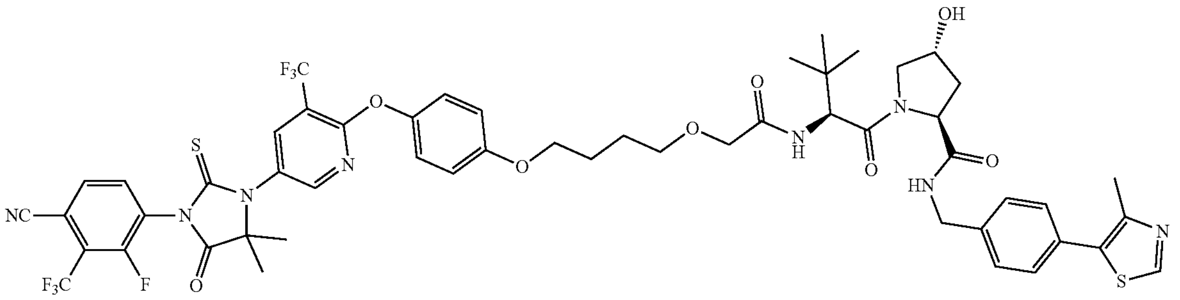 [SMILES: Cc1ncsc1-c1ccc(CNC(=O)[C@@H]2C[C@@H](O)CN2C(=O)[C@@H](NC(=O)COCCCCOc2ccc(Oc3ncc(N4C(=S)N(c5ccc(C#N)c(C(F)(F)F)c5F)C(=O)C4(C)C)cc3C(F)(F)F)cc2)C(C)(C)C)cc1]
LCMS ([M+H]+): 1127.3
$^{1}$HNMR (400 MHz, DMSO-d6) δ8.96 (s, 1H), 8.63 (s, 1H), 8.46 (d, J=5.2 Hz, 2H), 8.25 (d, J=6.5 Hz, 2H), 7.50-7.35 (m, 5H), 7.15 (d, J=9.0 Hz, 2H), 6.99 (d, J=9.0 Hz, 2H), 5.18 (d, J=3.4 Hz, 1H), 4.58 (d, J=9.6 Hz, 1H), 4.41 (dd, J=31.2, 7.2 Hz, 3H), 4.29 (d, J=5.6 Hz, 1H), 4.02 (t, J=6.2 Hz, 2H), 3.97 (d, J=1.2 Hz, 2H), 3.77-3.60 (m, 2H), 3.56 (t, J=6.2 Hz, 2H), 2.45 (d, J=6.9 Hz, 3H), 2.08 (s, 2H), 1.78 (dt, J=14.0, 6.6 Hz, 5H), 1.57 (d, J=4.0 Hz, 6H), 0.94 (d, J=6.7 Hz, 9H).

Example A350
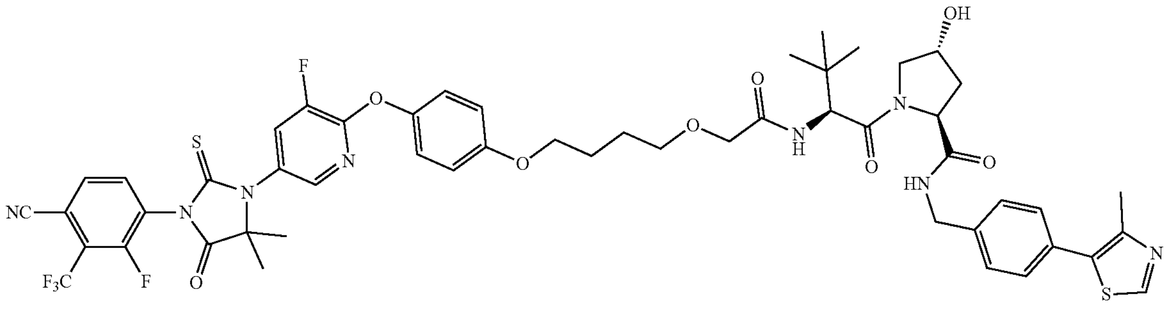 [SMILES: Cc1ncsc1-c1ccc(CNC(=O)[C@@H]2C[C@@H](O)CN2C(=O)[C@@H](NC(=O)COCCCCOc2ccc(Oc3ncc(N4C(=S)N(c5ccc(C#N)c(C(F)(F)F)c5F)C(=O)C4(C)C)cc3F)cc2)C(C)(C)C)cc1]
LCMS ($[M+H]^+$): 1077.3
$^1$HNMR (400 MHz, DMSO-d6) δ8.96 (s, 1H), 8.64 (s, 1H), 8.27 (s, 2H), 8.15 (dd, J=10.5, 1.6 Hz, 1H), 8.01 (d, J=1.6 Hz, 1H), 7.42 (d, J=10.9 Hz, 5H), 7.17 (d, J=8.9 Hz, 2H), 6.99 (d, J=8.9 Hz, 2H), 5.19 (d, J=3.2 Hz, 1H), 4.58 (d, J=9.6 Hz, 1H), 4.50-4.19 (m, 4H), 4.01 (dd, J=16.3, 10.5 Hz, 4H), 3.75-3.51 (m, 4H), 2.45 (d, J=6.9 Hz, 3H), 2.08 (s, 1H), 1.97-1.66 (m, 5H), 1.55 (s, 6H), 0.95 (s, 9H).
Example A351
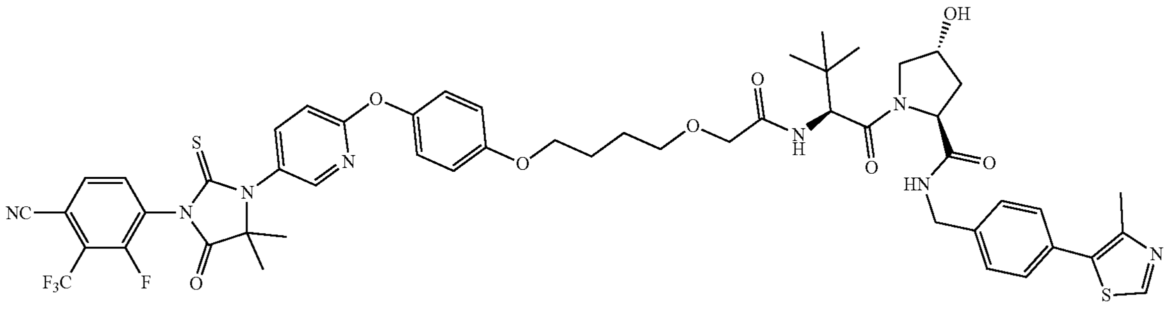 [SMILES: Cc1ncsc1-c1ccc(CNC(=O)[C@@H]2C[C@@H](O)CN2C(=O)[C@@H](NC(=O)COCCCCOc2ccc(Oc3ccc(N4C(=S)N(c5ccc(C#N)c(C(F)(F)F)c5F)C(=O)C4(C)C)cn3)cc2)C(C)(C)C)cc1]
LCMS ($[M+H]^+$): 1058.3
$^1$HNMR (400 MHz, DMSO-d6) δ8.97 (s, 1H), 8.63 (s, 1H), 8.28 (d, J=4.9 Hz, 2H), 8.19 (d, J=2.4 Hz, 1H), 7.93 (dd, J=8.7, 2.5 Hz, 1H), 7.42 (d, J=11.1 Hz, 5H), 7.14 (dd, J=17.8, 8.8 Hz, 3H), 6.98 (d, J=8.9 Hz, 2H), 5.18 (d, J=3.4 Hz, 1H), 4.58 (d, J=9.6 Hz, 1H), 4.41 (dd, J=30.8, 7.2 Hz, 3H), 4.28 (d, J=5.6 Hz, 1H), 4.00 (dd, J=15.5, 9.3 Hz, 4H), 3.61 (dt, J=12.3, 4.6 Hz, 4H), 2.45 (d, J=7.2 Hz, 3H), 2.08 (s, 1H), 1.78 (dt, J=13.9, 6.6 Hz, 5H), 1.53 (d, J=1.8 Hz, 6H), 0.94 (d, J=6.6 Hz, 9H).

Example A352
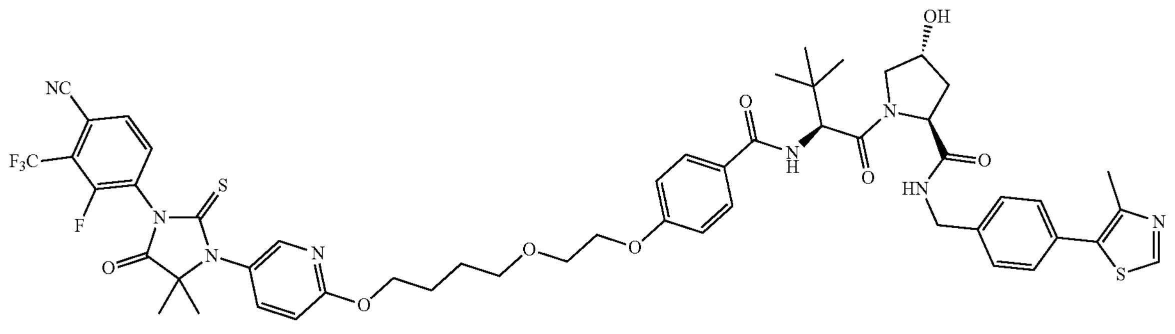 [SMILES: Cc1ncsc1-c1ccc(CNC(=O)[C@@H]2C[C@@H](O)CN2C(=O)[C@@H](NC(=O)c2ccc(OCCOCCCCOc3ccc(N4C(=S)N(c5ccc(C#N)c(C(F)(F)F)c5F)C(=O)C4(C)C)cn3)cc2)C(C)(C)C)cc1]
LCMS ([M+H]+): 1073.3
$^1$HNMR (400 MHz, DMSO-d6) δ8.99 (s, 1H), 8.59 (t, J=6.0 Hz, 1H), 8.27 (d, J=4.2 Hz, 2H), 8.21 (d, J=2.4 Hz, 1H), 7.86 (d, J=8.6 Hz, 2H), 7.84-7.76 (m, 2H), 7.45-7.36 (m, 4H), 7.00 (d, J=8.7 Hz, 3H), 5.32 (t, J=4.9 Hz, 1H), 5.16 (s, 1H), 4.76 (d, J=9.0 Hz, 1H), 4.45 (t, J=7.7 Hz, 2H), 4.42-4.35 (m, 2H), 4.32 (t, J=6.5 Hz, 2H), 4.24 (dd, J=15.7, 5.6 Hz, 1H), 4.16 (t, J=4.6 Hz, 2H), 3.74 (d, J=7.9 Hz, 3H), 3.53 (q, J=5.4, 4.4 Hz, 3H), 3.17 (d, J=3.9 Hz, 2H), 2.45 (s, 4H), 1.98 (ddd, J=29.2, 14.0, 7.9 Hz, 5H), 1.80 (t, J=7.4 Hz, 2H), 1.68 (t, J=7.4 Hz, 2H), 1.52 (d, J=2.3 Hz, 6H), 1.02 (s, 9H).
Example A353
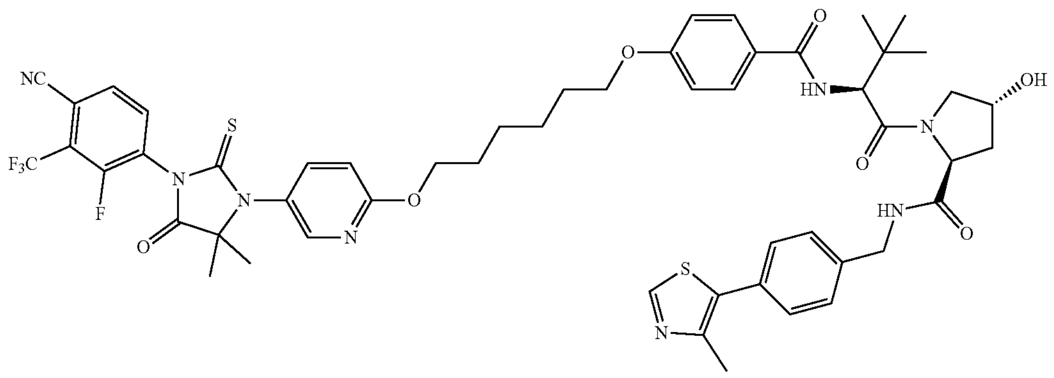 [SMILES: Cc1ncsc1-c1ccc(CNC(=O)[C@@H]2C[C@@H](O)CN2C(=O)[C@@H](NC(=O)c2ccc(OCCCCCCOc3ccc(N4C(=S)N(c5ccc(C#N)c(C(F)(F)F)c5F)C(=O)C4(C)C)cn3)cc2)C(C)(C)C)cc1]
LCMS ([M+H]+): 1057.4
$^1$HNMR (400 MHz, DMSO-d6) δ8.98 (s, 1H), 8.60 (t, J=6.0 Hz, 1H), 8.31-8.23 (m, 2H), 8.21 (d, J=2.5 Hz, 1H), 7.86 (d, J=8.7 Hz, 2H), 7.83-7.75 (m, 2H), 7.45-7.37 (m, 4H), 6.98 (t, J=8.6 Hz, 3H), 5.16 (d, J=3.5 Hz, 1H), 4.76 (d, J=9.1 Hz, 1H), 4.47-4.37 (m, 3H), 4.31 (t, J=6.5 Hz, 2H), 4.24 (dd, J=15.8, 5.5 Hz, 1H), 4.04 (t, J=6.3 Hz, 2H), 3.73 (s, 2H), 2.45-2.43 (m, 3H), 2.04 (d, J=8.2 Hz, 1H), 1.91 (ddd, J=12.7, 8.5, 4.5 Hz, 1H), 1.77 (d, J=5.8 Hz, 4H), 1.56-1.46 (m, 10H), 1.02-0.99 (m, 9H).

Example A354
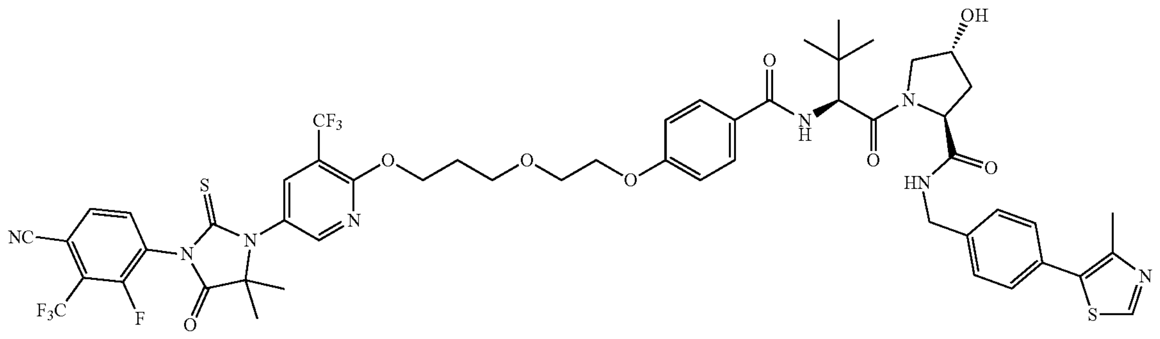 [SMILES: Cc1ncsc1-c1ccc(CNC(=O)[C@@H]2C[C@@H](O)CN2C(=O)[C@@H](NC(=O)c2ccc(OCCOCCCOc3ncc(N4C(=S)N(c5ccc(C#N)c(C(F)(F)F)c5F)C(=O)C4(C)C)cc3C(F)(F)F)cc2)C(C)(C)C)cc1]
LCMS ([M+H]$^+$): 1127.3
$^1$HNMR (400 MHz, DMSO-d6) δ8.99 (m, 1H), 8.60 (t, J=6.0 Hz, 1H), 8.53 (m, 1H), 8.26 (m, 3H), 7.84 (dd, J=21.0, 8.9 Hz, 3H), 7.41 (m, 4H), 6.99 (d, J=8.7 Hz, 2H), 5.17 (m, 1H), 4.76 (m, 1H), 4.55 (m, 2H), 4.43 (m, 3H), 4.25 (m, 1H), 4.20-4.11 (m, 2H), 3.79-3.69 (m, 4H), 3.65 (m, 2H), 2.45 (m, 3H), 2.05 (m, 3H), 1.92 (m, 1H), 1.57 (d, J=4.9 Hz, 6H), 1.02 (s, 9H).
Example A355
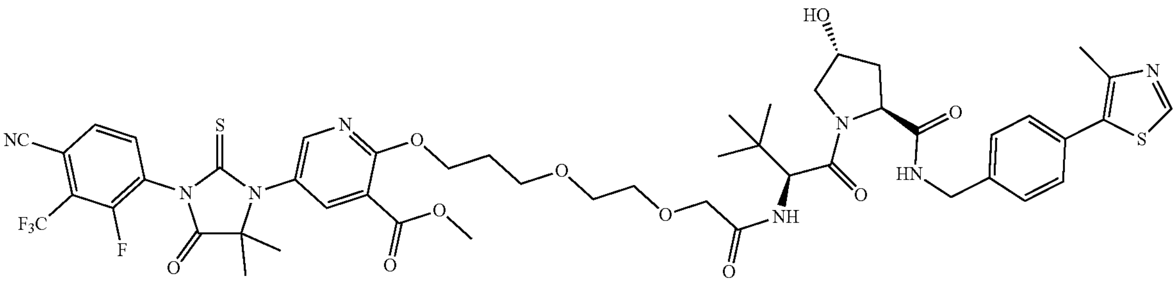 [SMILES: COC(=O)c1cc(N2C(=S)N(c3ccc(C#N)c(C(F)(F)F)c3F)C(=O)C2(C)C)cnc1OCCCOCCOCC(=O)N[C@H](C(=O)N1C[C@H](O)C[C@H]1C(=O)NCc1ccc(-c2scnc2C)cc1)C(C)(C)C]
LCMS ([M+H]$^+$): 1056.1
$^1$HNMR (400 MHz, DMSO-d6) δ8.96 (s, 1H), 8.61 (t, J=6.0 Hz, 1H), 8.42 (d, J=1.9 Hz, 1H), 8.25 (dd, J=9.4, 3.1 Hz, 3H), 7.48-7.34 (m, 5H), 5.17 (d, J=3.5 Hz, 1H), 4.56 (d, J=9.6 Hz, 1H), 4.45 (d, J=5.2 Hz, 6H), 3.98 (s, 2H), 3.83 (s, 3H), 3.72-3.53 (m, 8H), 2.43 (s, 3H), 2.01 (s, 4H), 1.55 (d, J=4.4 Hz, 6H), 0.92 (d, J=9.6 Hz, 9H).

Example A356
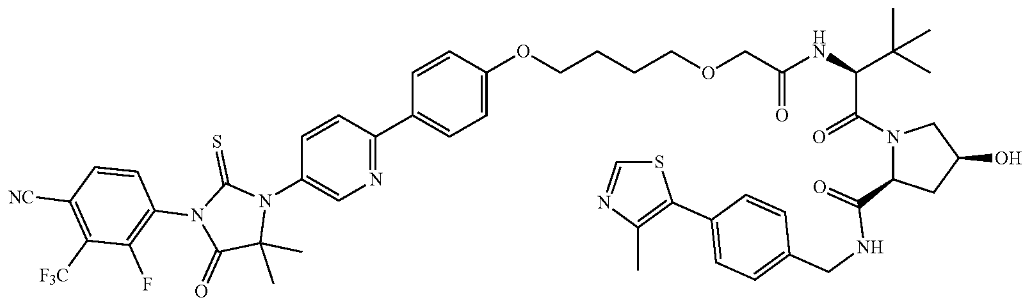 [SMILES: Cc1ncsc1-c1ccc(CNC(=O)[C@@H]2C[C@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2)C(C)(C)C)cc1]
LCMS ([M+H]$^+$): 1043.1
$^1$HNMR (400 MHz, DMSO-d6) δ8.97 (s, 1H), 8.70 (t, J=5.9 Hz, 1H), 8.66 (s, 1H), 8.29 (s, 2H), 8.14-8.07 (m, 3H), 7.95 (dd, J=8.5, 2.1 Hz, 1H), 7.41 (d, J=9.0 Hz, 5H), 7.06 (d, J=8.7 Hz, 2H), 5.47 (d, J=7.2 Hz, 1H), 4.53 (d, J=9.2 Hz, 1H), 4.41 (dt, J=14.7, 7.4 Hz, 2H), 4.33-4.20 (m, 2H), 4.09 (s, 2H), 3.95 (d, J=3.7 Hz, 2H), 3.89 (dd, J=10.0, 5.7 Hz, 1H), 3.56 (s, 2H), 3.47 (dd, J=9.9, 5.4 Hz, 1H), 2.43 (s, 3H), 2.40-2.31 (m, 1H), 1.87-1.80 (m, 2H), 1.77-1.70 (m, 3H), 1.59 (s, 6H), 0.96 (s, 9H).
Example A357
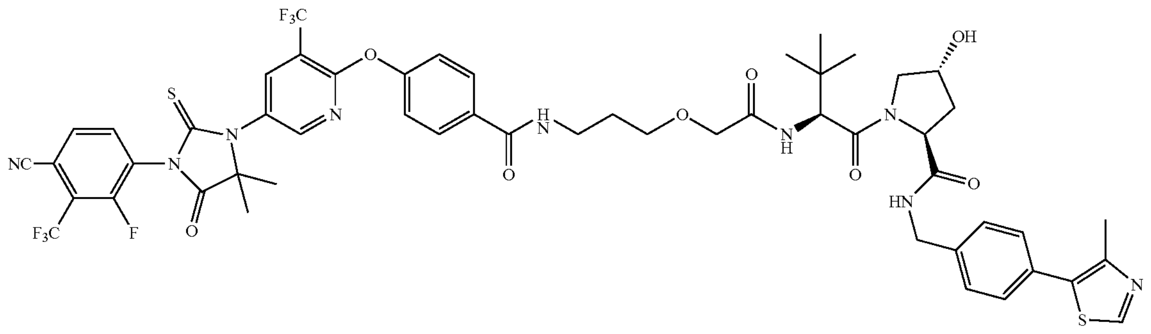
LCMS ([M+H]$^+$): 1040.1
$^1$HNMR (400 MHz, DMSO-d6) δ8.98 (d, J=8.3 Hz, 1H), 8.66-8.56 (m, 2H), 8.52 (s, 1H), 8.49 (s, 1H), 8.30-8.19 (m, 2H), 7.95 (d, J=8.6 Hz, 2H), 7.48 (d, J=9.4 Hz, 1H), 7.40 (s, 4H), 7.35 (d, J=8.6 Hz, 2H), 5.18 (d, J=3.4 Hz, 1H), 4.58 (d, J=9.5 Hz, 1H), 4.49-4.22 (m, 4H), 3.95 (d, J=12.1 Hz, 2H), 3.64 (dd, J=22.9, 8.9 Hz, 2H), 3.56 (t, J=6.2 Hz, 2H), 2.44 (s, 3H), 2.11-1.88 (m, 2H), 1.84 (dd, J=15.5, 9.0 Hz, 2H), 1.58 (d, J=4.2 Hz, 6H), 1.24 (s, 2H), 0.94 (s, 9H).

Example A358
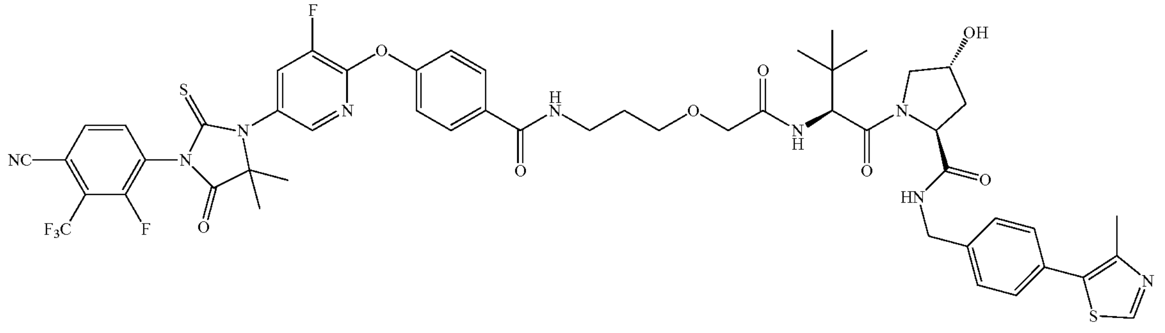 [SMILES: Cc1ncsc1-c1ccc(CNC(=O)[C@@H]2C[C@@H](O)CN2C(=O)[C@@H](NC(=O)COCCCNC(=O)c2ccc(Oc3ncc(N4C(=S)N(c5ccc(C#N)c(C(F)(F)F)c5F)C(=O)C4(C)C)cc3F)cc2)C(C)(C)C)cc1]
LCMS ([M+H]$^+$): 1090.2
$^1$HNMR (400 MHz, DMSO-d6) δ8.97 (s, 1H), 8.60 (d, J=17.4 Hz, 2H), 8.32-8.19 (m, 3H), 8.06 (s, 1H), 7.94 (d, J=8.6 Hz, 2H), 7.49 (d, J=9.8 Hz, 1H), 7.40 (s, 6H), 5.18 (s, 1H), 4.58 (d, J=9.5 Hz, 1H), 4.49-4.20 (m, 4H), 3.97 (s, 2H), 3.56 (s, 4H), 2.44 (s, 3H), 2.00 (d, J=52.2 Hz, 2H), 1.82 (s, 2H), 1.57 (s, 6H), 1.24 (s, 2H), 0.94 (s, 9H).
Example A359
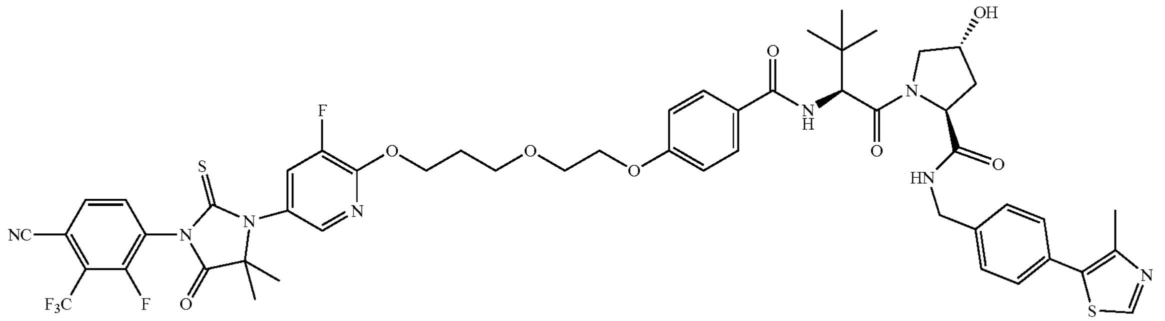 [SMILES: Cc1ncsc1-c1ccc(CNC(=O)[C@@H]2C[C@@H](O)CN2C(=O)[C@@H](NC(=O)c2ccc(OCCOCCCOc3ncc(N4C(=S)N(c5ccc(C#N)c(C(F)(F)F)c5F)C(=O)C4(C)C)cc3F)cc2)C(C)(C)C)cc1]
LCMS ([M+H]$^+$): 1077.3
$^1$HNMR (400 MHz, DMSO-d6) δ8.99 (m, 1H), 8.60 (t, J=6.0 Hz, 1H), 8.53 (s, 1H), 8.26 (s, 3H), 7.84 (dd, J=21.0, 8.9 Hz, 3H), 7.41 (s, 4H), 6.99 (d, J=8.7 Hz, 2H), 5.17 (m, 1H), 4.76 (m, 1H), 4.55 (m, 2H), 4.43 (m, 3H), 4.25 (m, 1H), 4.20-4.11 (m, 2H), 3.79-3.69 (m, 4H), 3.65 (m, 2H), 2.45 (m, 3H), 2.05 (dd, J=13.6, 7.6 Hz, 3H), 1.92 (m, 1H), 1.57 (d, J=4.9 Hz, 6H), 1.02 (s, 9H).

Example A360
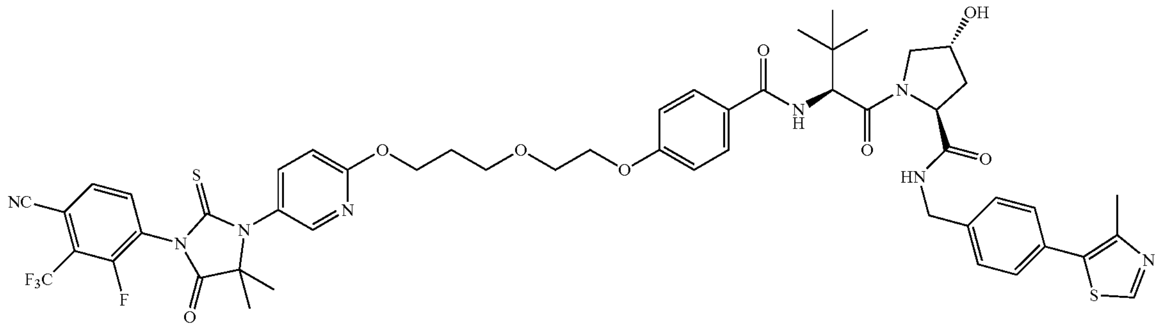 [SMILES: Cc1ncsc1-c1ccc(CNC(=O)[C@@H]2C[C@@H](O)CN2C(=O)[C@@H](NC(=O)c2ccc(OCCOCCCOc3ccc(N4C(=S)N(c5ccc(C#N)c(C(F)(F)F)c5F)C(=O)C4(C)C)cn3)cc2)C(C)(C)C)cc1]
LCMS ([M+H]$^+$): 1029.3
$^1$HNMR (400 MHz, DMSO-d6) δ8.99 (s, 1H), 8.60 (t, J=5.9 Hz, 1H), 8.25 (dd, J=22.4, 3.1 Hz, 3H), 7.91-7.73 (m, 4H), 7.48-7.35 (m, 4H), 7.00 (dd, J=8.7, 3.5 Hz, 3H), 5.17 (m, 1H), 4.76 (m, 1H), 4.51-4.33 (m, 5H), 4.30-4.21 (m, 1H), 4.21-4.13 (m, 2H), 3.76 (m, 4H), 3.65 (m, 2H), 2.45 (d, J=5.9 Hz, 3H), 2.11-1.97 (m, 3H), 1.92 (m, 1H), 1.53 (s, 6H), 1.01 (d, J=11.9 Hz, 9H).
Example A361
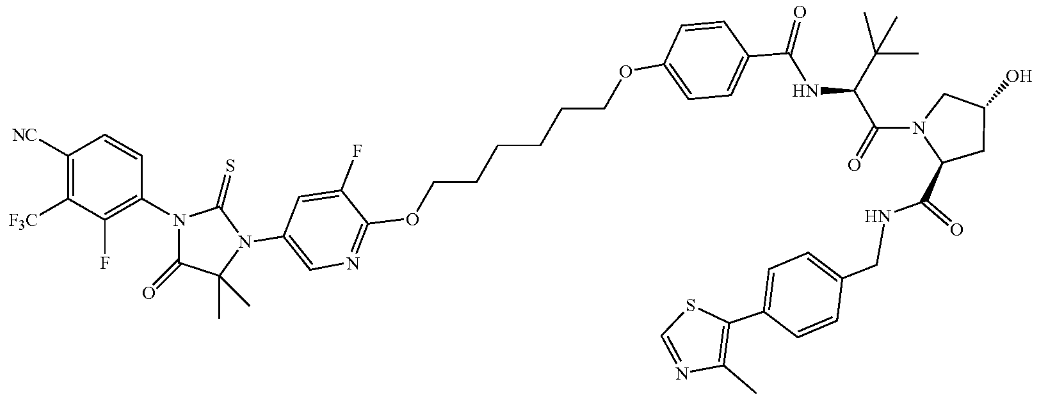 [SMILES: Cc1ncsc1-c1ccc(CNC(=O)[C@@H]2C[C@@H](O)CN2C(=O)[C@@H](NC(=O)c2ccc(OCCCCCCOc3ncc(N4C(=S)N(c5ccc(C#N)c(C(F)(F)F)c5F)C(=O)C4(C)C)cc3F)cc2)C(C)(C)C)cc1]
LCMS ([M+H]$^+$): 1075.4
$^1$HNMR (400 MHz, DMSO-d6) δ8.98 (s, 1H), 8.60 (t, J=6.0 Hz, 1H), 8.26-8.23 (m, 2H), 8.08 (d, J=1.9 Hz, 1H), 7.97 (dd, J=10.7, 1.9 Hz, 1H), 7.86 (d, J=8.7 Hz, 2H), 7.79 (d, J=9.0 Hz, 1H), 7.46-7.37 (m, 4H), 6.97 (d, J=8.7 Hz, 2H), 5.17 (d, J=3.5 Hz, 1H), 4.75 (d, J=9.1 Hz, 1H), 4.47-4.37 (m, 5H), 4.24 (dd, J=15.8, 5.5 Hz, 1H), 4.04 (t, J=6.3 Hz, 2H), 3.72 (s, 2H), 2.45-2.43 (m, 3H), 2.03 (d, J=8.0 Hz, 1H), 1.96-1.87 (m, 1H), 1.81-1.76 (m, 4H), 1.58-1.46 (m, 10H), 1.02-0.99 (m, 9H).

Example A362

-

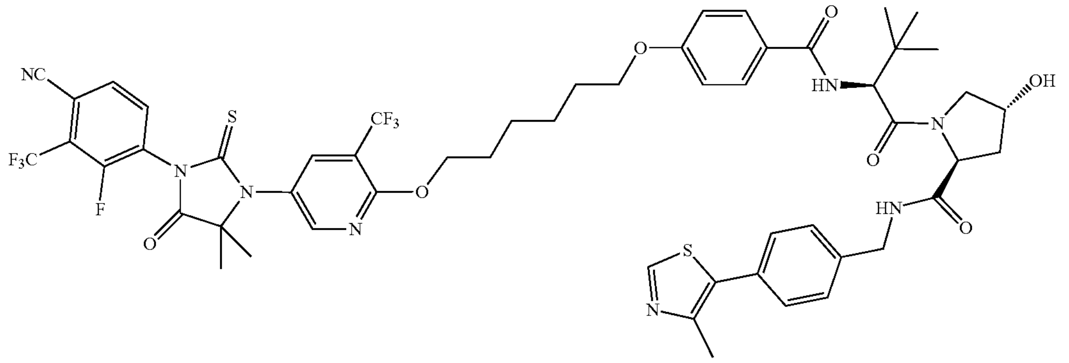 [SMILES: Cc1ncsc1-c1ccc(CNC(=O)[C@@H]2C[C@@H](O)CN2C(=O)[C@@H](NC(=O)c2ccc(OCCCCCCOc3ncc(N4C(=S)N(c5ccc(C#N)c(C(F)(F)F)c5F)C(=O)C4(C)C)cc3C(F)(F)F)cc2)C(C)(C)C)cc1]

LCMS ([M+H]+): 1125.4

$^1$HNMR (400 MHz, DMSO-d6) δ8.98 (s, 1H), 8.60 (t, J=6.0 Hz, 1H), 8.52 (d, J=2.0 Hz, 1H), 8.32-8.20 (m, 3H), 7.87-7.78 (m, 3H), 7.46-7.36 (m, 4H), 6.96 (d, J=8.8 Hz, 2H), 5.16 (d, J=3.5 Hz, 1H), 4.75 (d, J=9.1 Hz, 1H), 4.50-4.37 (m, 5H), 4.24 (dd, J=15.7, 5.5 Hz, 1H), 4.03 (t, J=6.3 Hz, 2H), 3.72 (s, 2H), 2.44-2.43 (m, 3H), 2.03 (d, J=8.0 Hz, 1H), 1.91 (ddd, J=12.7, 8.6, 4.5 Hz, 1H), 1.80-1.75 (m, 4H), 1.56 (d, J=4.7 Hz, 6H), 1.50 (m, 4H), 1.02-0.99 (m, 9H).

2. BIOLOGICAL ACTIVITY ASSAY

Activity Assay Example 1: Effects of Compounds on AR Expression in LNCaP Cells 1. Cell Line and Cell Culture Human prostate cancer cells LNCaP (Shanghai Chinese Academy of Sciences Cell Bank). LNCaP was cultured in 1640 medium containing 10% fetal bovine serum. The cells grow in clusters, with weak adhesion to the bottom of the culture flask, slow proliferation, with a multiplication time of 72 h. The cells are closely adhered to each other and need to be digested with 0.05% trypsin containing 0.025% EDTA. The cells were passaged every 3 days. The cells were cultured at 37° C. and 5% $CO_2$ in a humidified incubator 2. Cell plating: The supernatant was discarded, and the Lncap cells in the logarithmic growth phase were taken, washed with PBS once, and added with appropriate 0.05% trypsin digestion solution to be fully digested into single cell suspension, and centrifuged, resuspended and counted to make the number of cells about 15,000 per well, then inoculated in a 96-well plate, placed at 37° C., 5% $CO_2$ and cultured overnight for 24 h.

3. Preparation and Addition of Compound Solutions

About 2 mg of each compound was weighed and dissolved in DMSO to make the stock solution with a concentration of 10 mmol/L. Dilution process (final concentration dilution: 2, 0.667, 0.222, 0.074, 0.0245, 0.008, 0.003, 0.001, 0.0003, 0.0001 μmol/L): 10 centrifuge tubes with a volume of 1.5 mL were taken and numbered 1, 2, 3, 4, 5, 6, 7, 8, 9, and 10, 80 μL DMSO was added to tube No. 1, and 60 μL DMSO was added to tubes No. 2 to No. 10, 20 μL of the stock solution was pipetted to tube No. 1 and mixed well; 30 μL was pipetted from tube No. 1 into tube No. 2 and mixed well. 30 μL was pipetted from tube No. 2 into tube No. 3 and mixed well, and so forth, to obtain samples No. 4-10, and to obtain working solutions of compounds of different concentrations respectively. 2 μL was pipetted from the above-mentioned tubes No. 1-10 into each corresponding sterile deep-well plates, added with 198 μL of culture medium, and mixed well. 11 ul was added to each well of the 96-well cell plate cultured overnight to obtain the corresponding desired concentrations (2, 0.667, 0.222, 0.074, 0.0245, 0.008, 0.003, 0.001, 0.0003, 0.0001 μmol/L).

4. Measurement of the Effects of Drugs on the Expression of AR in Cells by ELISA Method After 24 hours of drug treatment, the supernatant was removed, and 200 μL of PBS was added to wash cells, and then the supernatant was removed, and 100 μL of cell lysate was added to lyse cells on ice for 20 min, then the cell lysate was centrifuged at 4000 rpm for 20 min at 4° C. and the supernatant was taken for later use. The measurement steps of the supernatant were according to the ELISA kit instructions:

4.1 The slats required for the test were taken out from the sealed bag that has been equilibrated to room temperature. Please put the unused slats and desiccant back into the aluminum foil bag and compress the self-sealing strip, seal the bag, and store at 4° C.

4.2 Standards and sample diluents were added to blank wells, and different concentrations of standards (10 ul/well) and sample diluents (90 ul/well) were added to the remaining corresponding wells, and the reaction wells were sealed with sealing tape, and refrigerated at 4° C. overnight.

4.3 Primary antibody was diluted with dilution buffer to the corresponding concentration and added to each well in 100 ul/well. The reaction wells were sealed with sealing tape and incubated at 37° C. for 60 min.

4.4 Secondary antibody was diluted with dilution buffer to the corresponding concentration and added to each well in 100 ul/well. The reaction wells were sealed with sealing tape and incubated at 37° C. for 30 min.

4.5 The reaction wells were added with 100 ul/well of substrate (TMB) and incubated at room temperature for 30 min.

4.6 The reaction wells were added with 100 ul/well of stop solution, mixed well and then the OD450 value was measured with a microplate reader.

5. Result Analysis $OD_{Tsample}$ was obtained from the test results. The medium group without cells added was the blank group ($OD_{Blank}$), and the cell treated with DMSO was the control group ($OD_{Control}$). Inhibition rate inhi %=(1−($OD_{Tsample}$−$OD_{Blank}$)/($OD_{Control}$−$OD_{Blank}$))*100%, and the $DC_{50}$ values of the compounds were calculated by software XLFit, and the detail results are shown in Table 1.

TABLE 1

| DC$_{50}$ values of compounds on LNCaP cells | | | | | |
|---|---|---|---|---|---|
| List of compound | LNCaP DC$_{50}$(nM) | List of compound | LNCaP DC$_{50}$(nM) | List of compound | LNCaP DC$_{50}$(nM) |
| A6 | >2000 | A69 | 39.4 | A106 | 402.0 |
| A22 | 73.7 | A70 | 62.1 | A107 | 107.1 |
| A23 | 720.6 | A71 | 62.1 | A108 | 136.0 |
| A24 | >2000 | A72 | 35.1 | A109 | 71.4 |
| A25 | >2000 | A73 | 49.3 | A110 | 56.4 |
| A26 | >2000 | A74 | 77.8 | A111 | 46.2 |
| A27 | 34.8 | A75 | 89.4 | A112 | 152.7 |
| A28 | >2000 | A76 | 40.0 | A113 | 193.0 |
| A34 | 835.1 | A77 | 114.5 | A114 | 79.3 |
| A35 | 117.4 | A78 | 57.4 | A115 | 213.9 |
| A36 | 93.0 | A79 | 128.6 | A116 | 370.4 |
| A37 | 18.6 | A80 | 116.4 | A117 | 111.2 |
| A38 | 58.6 | A81 | 63.3 | A118 | >2000 |
| A39 | 19.4 | A82 | 46.4 | A119 | 7.2 |
| A40 | 29.8 | A83 | 87.8 | A120 | 215.7 |
| A41 | 59.0 | A84 | 140.0 | A121 | 336.0 |
| A42 | 121.8 | A85 | 33.0 | A122 | 154.7 |
| A43 | 88.3 | A86 | 69.3 | A123 | 61.3 |
| A44 | >2000 | A87 | 54.6 | A124 | 188.3 |
| A45 | >2000 | A88 | 55.0 | A125 | >2000 |
| A48 | >2000 | A89 | 72.0 | A126 | 55.0 |
| A53 | 148.9 | A90 | 36.4 | A127 | 89.3 |
| A55 | 38.8 | A91 | 108.4 | A128 | 124.1 |
| A56 | 703.7 | A92 | 99.6 | A129 | 67.9 |
| A57 | 31.8 | A93 | 51.1 | A130 | 131.2 |
| A58 | 132.8 | A94 | 58.4 | A131 | 34.8 |
| A59 | 48.6 | A95 | 105.7 | A132 | 161.4 |
| A60 | 82.9 | A96 | 54.9 | A133 | 33.3 |
| A61 | 268.0 | A97 | 98.4 | A134 | 1128.3 |
| A62 | 80.0 | A98 | 280.5 | A135 | 1537.6 |
| A63 | 37.9 | A99 | 23.2 | A136 | 68.0 |
| A64 | 232.6 | A100 | 18.9 | A137 | 144.6 |
| A65 | 32.4 | A101 | 115.4 | A138 | 1499.4 |
| A65 | 32.4 | A102 | >2000 | A139 | 224.6 |
| A66 | 213.1 | A103 | 151.9 | A140 | 1500.6 |
| A67 | 247.6 | A104 | 241.3 | A141 | >2000 |
| A68 | >2000 | A105 | 187.8 | A142 | >2000 |
| A144 | 635.3 | A176 | 62.1 | A219 | 588.9 |
| A146 | 258.9 | A177 | 253.4 | A220 | 288.9 |
| A147 | 84.9 | A178 | 90.5 | A221 | 144.1 |
| A149 | 110.9 | A180 | 839.9 | A224 | 75.73 |
| A150 | 90.6 | A183 | 150.5 | A225 | 92.1 |
| A152 | 167.2 | A184 | 369.7 | A227 | 24.78 |
| A153 | 268.8 | A185 | 49.8 | A228 | 107.4 |
| A154 | 37.6 | A186 | 87.0 | A232 | 41.3 |
| A159 | 168.3 | A189 | 328.9 | A233 | 194.5 |
| A160 | 151.2 | A191 | 162.1 | A234 | 26.1 |
| A162 | 186.4 | A194 | 246.3 | A235 | 124.7 |
| A163 | 170.9 | A195 | 404.2 | A240 | 263.6 |
| A165 | 43.8 | A196 | 39.0 | A241 | 806.7 |
| A166 | 144.1 | A197 | 435.4 | A244 | 173.3 |
| A167 | 204.1 | A198 | 42.8 | A247 | 75.5 |
| A168 | 158.8 | A202 | 661.1 | A248 | 48.8 |
| A169 | 92.6 | A203 | 71.9 | A252 | 95.9 |
| A170 | 945.7 | A204 | 36.35 | A254 | 52.5 |
| A171 | 80.2 | A209 | 855.9 | A256 | 119.4 |
| A172 | 169.9 | A210 | 834.2 | A264 | 869.7 |
| A173 | 78.1 | A214 | 172.7 | A265 | 380.7 |
| A175 | 122.5 | A215 | 83.11 | A267 | 119.2 |
| A269 | 765.7 | | | | |

The above results show that the compounds provided by the present invention have a good inhibitory effect on the proliferation of LNCaP cells, indicating that the compounds of the present invention can be used as anti-tumor drugs, especially for the treatment of prostate cancer.

Activity Assay Example 2: Western Blot Assay

1. Cell Processing

The Lncap cells in the logarithmic growth phase were digested and the cells were plated into 6-well plates with $1\times10^6$ cells per well. After the cells grew by adherence to the wall for one day, they were cultured with drugs, and the protein was extracted after 24 hours of drug treatment.

2. Cellular Protein Extraction

The culture medium was removed from the 6-well plate, and the cells were washed with PBS, digested with trypsin, and collected by centrifugation in 1.5 mL centrifuge tubes. 100 μL RIPA lysis solution (containing 100 μM PMSF) was added to each tube, mixed thoroughly and left on ice for 30 min, and then centrifuged at 12000 rpm for 20 min at 4° C. The supernatant was taken for WB experiment, and the samples could be stored at −80° C.

3 Determination of Protein Concentration

The BCA protein concentration assay kit was used, and the BSA standard assay solution and the samples to be tested were prepared according to the following table (the samples to be tested can be tested after dilution). The samples were added to the 96-well plate. After each well was supplemented with PBS to 20 μl, 200 μl of BCA working solution (prepared according to the kit) was added. After mixed well, it was placed at 60° C. for 10 min, and then the absorbance at 562 nm was measured. After the readings were recorded, the standard curve was made according to the standard concentration gradient, and the sample protein concentration was calculated according to the sample absorbance.

4 Western Bloting Experiment Standard Process 4.1 Protein denaturation: The protein lysate was taken, added with 5×Loading Buffer, and denatured at 100° C. for 5 min.

4.2 Sample loading and electrophoresis: 10% precast gel and special electrophoresis solution were used. Protein marker and the same amount of protein sample were loaded into each well, and electrophoresis was performed at 200V for 30 min.

4.3 Blocking: After the gel was removed, the excess part was cut off, and the proteins were transferred to PVDF membrane through wet transfer method at 300 mA for 2 h (PVDF membrane needed to be activated with methanol for 1 min before use), and a large amount of heat was generated during the membrane transfer process, for which the ice box was needed for cooling.

4.4 Blocking: After membrane transferring, the PVDF membrane was placed in 5% skimmed milk and shaken for 1 hour at room temperature.

4.5 Incubation with the primary antibody: The PVDF membrane was cut according to the molecular weight indicated on the marker and placed in the primary antibodies of AR and GAPDH respectively. The antibodies were diluted with TBST at a ratio of 1:1000 and the membrane was blocked overnight at 4° C. on a shaker.

4.6 Incubation with secondary antibody: The PVDF membrane incubated with the primary antibody was washed 3 times with TBST on a shaker for 10 minutes each time. After washed, the membrane was placed in the secondary antibody of the corresponding species, respectively, and incubated with shaking on a shaker at room temperature for 2 h.

4.7 Membrane washing and exposure: After incubation with the secondary antibody, the membrane was placed in TBST and shaken for three times, and 10 min each time. After the membrane was washed, the ECL method was used to excite the fluorescence on the membrane.

The experimental results obtained are shown in FIG. 1, which shows that the compounds provided by the present invention have a good degradation effect on the AR protein in LNCaP cells, indicating that the compounds of the present invention have the potential to become anti-tumor drugs, especially for the treatment of prostate cancer.

Activity Assay Example 3: Pharmacokinetic Studies of Compounds in Mice

1. Experimental Design

In this test, 3 male mice were selected and divided into 1 group, 3 mice/group. All animals were fasted overnight before administration.

2. Experimental Method 2.1 Dosage

The intragastric administration dose was 10 mg/kg, and the administration volume was 10 mL/kg.

2.2 Preparation of Drug Solution

According to the animal body weight combined with the administration dose, the amount of the required drug solution was calculated. An appropriate amount of the test substance was weighed, added with 5% of the final volume of ethanol for dissolution, then added with 5% of the final volume of SolutolHS15, and finally added with PBS to the final volume, and mixed by vortex and fully dissolved to obtain a solution for intragastric administration (1 mg/mL). All solutions were prepared for immediate use.

2.3 Method of Administration

Before administration, the drug solution was placed on a magnetic stirrer in the animal laboratory and stirred for at least 10 min. During the administration process, vortex was continued to ensure uniformity of the drug solution. The theoretical volume of gavage administration was 10 mL/kg, which was administered with a syringe equipped with a gavage needle.

Before administration, the animals were weighed and the body weight of the animals involved in the experiment was recorded, and the administration volume of each animal was calculated according to the body weight. After administration, animals were promptly transferred back to the experimental cages to collect samples.

2.4 Observation of Animal Status

After administration, whether animals had abnormal reactions was observed immediately. If there were no abnormal reactions, animals were observed twice a day during the experiment. If abnormal reactions were found, they should be recorded in time, and the number of observations should be increased until the animals returned to normal or to the end of the experiment.

2.5 Sample Collection and Preservation

All experimental animals were fasted overnight before administration, and blood was collected at corresponding time points into blood collection tubes containing heparin sodium anticoagulant. After the whole blood was collected, the blood collection tube was gently shaken and placed on ice immediately, and then centrifuged (4° C., 4000 rpm, 10 min) to collect supernatant plasma samples, which were stored in a refrigerator at −80° C. before analysis.

2.6 Plasma Sample Processing and Analysis

The collected plasma samples were handed over to the Pharmacokinetic department for sample extraction, and the test substances in the plasma were extracted by protein precipitation method using organic reagents containing internal standards (acetonitrile:plasma=4:1, v/v). The extracted processed samples were submitted for quantitative concentration analysis by LC-MS/MS. According to the plasma concentration of each animal obtained by the analysis, software Kinetica (version 5.0) was used to calculate the main pharmacokinetic parameter $eAUC_{30-120}$ according to the non-compartment model to evaluate the exposure amount; the test results are shown in Table 2:

TABLE 2

Pharmacokinetic parameters of compounds of the present invention in mice

| Compound | $eAUC_{0.5-2\ h}$(ng · h/ml) |
|---|---|
| A35 | 71 ± 51 |
| A36 | 29 ± 12 |
| A37 | 98 ± 48 |
| A55 | 396 ± 79 |
| A57 | 182 ± 84 |
| A62 | 498 ± 124 |
| A63 | 373 ± 242 |
| A66 | 525 ± 106 |
| A70 | 1686 ± 938 |
| A71 | 287 ± 135 |
| A72 | 240 ± 68 |
| A73 | 189 ± 108 |
| A74 | 746 ± 158 |
| A77 | 1354 ± 205 |
| A78 | 187 ± 66 |
| A79 | 950 ± 114 |
| A82 | 191 ± 154 |
| A83 | 574 ± 176 |
| A84 | 774 ± 119 |
| A85 | 70 ± 23 |
| A89 | 501 ± 103.57 |
| A90 | 96 ± 28.51 |
| A91 | 3160 ± 2820 |
| A93 | 275 ± 116 |
| A94 | 410 ± 38 |
| A95 | 1234 ± 430 |
| A97 | 1690 ± 158 |
| A99 | 308 ± 288 |
| A100 | 720 ± 206 |
| A101 | 508 ± 171 |
| A103 | 984 ± 617 |
| A105 | 379 ± 300 |
| A108 | 993 ± 201 |
| A109 | 557 ± 108 |
| A110 | 1098 ± 208 |
| A111 | 297 ± 78 |
| A112 | 383 ± 165 |
| A115 | 1136 ± 164 |
| A123 | 287 ± 146 |
| A124 | 2776 ± 292 |
| A126 | 1110 ± 158 |
| A133 | 2253 ± 851 |
| A134 | 29 ± 22 |
| A136 | 697 ± 127 |
| A137 | 92 ± 34 |
| A138 | 471 ± 288 |
| A139 | 53 ± 30 |

Activity Assay Example 4: PK/PD Experimental Study of Compounds on LNCaP Mouse Xenograft Tumor 1. Experimental Materials 1.1 Test Sample The above compounds were weighed into a 2.5 mL centrifuge tube and added with the final volume of 5% EtOH and 5% solutolHS in PBS for preparation, and the prepared final concentration is 5 mg/mL.

1.2 Tumor Cells

LNCaP cells were purchased from Shanghai Chinese Academy of Sciences Cell Bank, and cultured in RPMI- 1640 medium containing 10% fetal bovine serum. The cells were grown to 80-90% confluency and passaged in about 2-3 days. After the cells had grown to a sufficient amount, SCID mice were inoculated.

1.3 Experimental Animals 21 male SCID mice aged 6-7 w were purchased from Beijing Vital River Laboratory Animal Technology Co., Ltd. The mice were kept in the SPF animal room of Suzhou Mabpharm Co., Ltd., in which the temperature was 20~25° C., and the humidity was 40%~70%, and the light/dark was 12 hours a day respectively. Animals were kept in separate cages, 5 per cage, with free access to food and water, in which the feed was sterilized by irradiation, and the water was autoclaved.

2. Research Methods 2.1 Tumor Model Establishment

LNCaP cells were cultured to a sufficient amount in vitro, digested with trypsin, centrifuged, resuspended in pre-cooled PBS and then centrifuged. An appropriate amount of pre-cooled PBS and matrigel was added to adjust the cell concentration to $7.5\times10^7$ cells/mL. Pre-cooled 1 mL syringe was used to aspirate the cell suspension and the cell suspension was injected into the right dorsal subcutis of nude mice in the shape of regular mounds, $1.5\times10^7$ cells/0.2 mL per mouse.

2.2 Grouping and Administration Method

After inoculation of tumor cells, tumor size was observed. When the tumor grew to about 200 $mm^3$, the mice with tumor of good shape and suitable size were selected and randomly systematically grouped according to the tumor volume. Several mice were selected and each group with 3 mice, and the compound was orally administered. After 3 days of administration, the tumors were collected for the measurement of the AR expression.

2.3 Measurement of Compound Concentration in Plasma

Blood collection: Before administration and 3 days after administration, 2 hours blood samples were collected for the measurement of the drug concentration. Blood samples were collected from the retro-orbital venous plexus of mice. 30 μL of blood (plasma) was collected into heparinized centrifuge tubes, and centrifuged at 4000 rpm for 10 min at 4° C., and then the upper plasma was transferred and stored at −80° C.

Figure 2:
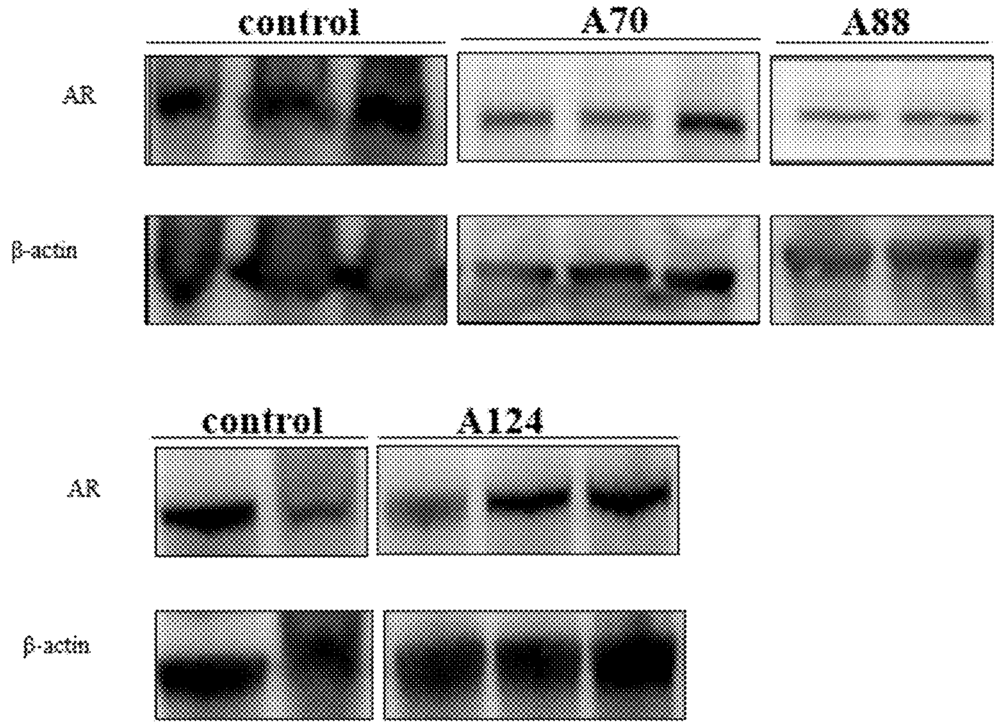
FIG. 2 is the result of the PK/PD experiment of the compounds of the present invention on transplanted tumors in LNCaP mice.

The experimental results obtained are shown in FIG. 2.

Activity Assay Example 5: Hormone-Dependent Prostate Cancer Long-Term Efficacy Test 1. Tumor Model Establishment 1.5*10^7 LNCaP (human prostate cancer) was purchased from the Chinese Academy of Sciences Cell Bank and cultured in RPMI-1640 medium containing 10% fetal bovine serum. The cells were grown to 80-90% confluence and passaged in about 4-5 days, and the cells were grown to a sufficient amount and then inoculated into nude mice.

2. Experimental Animals 18-20 g SCID nude mice aged 6-7 weeks old were purchased from Beijing Vital River Co., Ltd. Mice were kept in SPF animal room, in which the temperature was 20-25° C., and the humidity was 40%-70%, and light/dark was 12 hours a day respectively. Animals were kept in separate cages, 5 per cage, with free access to food and water, in which the feed was sterilized by irradiation, and the water was autoclaved. The mice were grouped for experiment when raised to 10~11 weeks old. LNCaP tumor cells were directly inoculated into the right back of nude mice.

3. Grouping and Administration Schedule Design

When the average tumor volume reached 200-300 $mm^3$, the tumors with good shape were selected for random number grouping according to the tumor volume, and the selected animals were marked and divided into 5 groups, 5 per group. Administration vehicle: 5% EtOH, 5% solutolHS15 in PBS. The corresponding dose of compound was administered by gavage.

4. Statistical Analysis

Data are presented as mean±standard deviation (Mean±SD). One-way multi-level analysis of variance was used for statistics, and the comparison between each drug group and the model group was performed by Stundent's t-test or rank sum test, and the p value was calculated. $p<0.05$ means there is a significant difference between the two groups. The tumor growth inhibition rate (TGI) results of compound A88 are shown in Table 3.

TABLE 3

Tumor growth inhibition rate of compound A88

| Dosage of administration | 3 days | 7 days | 10 days | 14 days |
|---|---|---|---|---|
| 10 mpk | 19.81% | 38.44% | 31.33% | 13.15% |
| 25 mpk | 14.98% | 36.36% | 37.51% | 24.68% |
| 50 mpk | 22.30% | 51.85% | 42.62% | 24.47% |

Activity Assay Example 6: Determination of the Degradation Effect of Compounds on AR Protein Activity in Prostate Cancer Cell Line Lncap by ELISA Method 1. Test Material LNCaP: 1.5*10^LNCaP (human prostate cancer) was purchased from the Chinese Academy of Sciences Cell Bank and cultured in RPMI-1640 medium containing 10% fetal bovine serum. Lncap cells were cultured at 37° C. and 5% $CO_2$ in a humidified incubator. When the coverage reached about 80%, the cells were passaged at a ratio of 1:3.

ELISA kit: Total Androgen Receptor Sandwich ELISA Kit (Brand CST, Cat #12850).

2. Test Method 2.1 Cell Plating

After the cells were centrifuged, they were diluted to $1.5\times10^4$ cells/100 ul with fresh medium and plated into a 96-well plate with 100 ul per well.

2.2 Cell Administration

Test compound preparation: The compounds were weighed and diluted with DMSO to stock solution with a concentration of 10 mM for later use. According to the experimental requirements, the drug was diluted from 2 uM, 3 fold dilution for 10 point series, and finally 2 μl of the drug was added to each well, and 2 μl of DMSO was added to the control group.

2.3 After 24 hours, the medium was removed, and the cells were washed once with ice-cold 1×PBS. Then the PBS was removed, and 0.5 ml ice-cold 1× Cell Lysis Buffer containing 1 mM PMSF was added to each well plate and incubated on ice for 20 minutes. It was centrifuged at 4000 rpm for 10 min at 4° C. and the supernatant was collected for later experiment.

2.4 Preparation of Reagents and Antibodies in ELISA Kit

Microwell plates: They were all placed to room temperature before use.

Detection antibody: The antibodies were freeze-dried, and in the form of a green cake or powder. 1.0 ml of detection antibody diluent (green solution) was added to produce a concentrated stock solution. It was incubated for 5 min at room temperature and mixed gently occasionally for complete dissolution. To make the final working solution, please add the entire 1.0 ml volume of the reconstituted detection antibody to 10.0 ml of detection antibody diluent in a clean tube and mix gently.

HRP antibody: The antibodies were freeze-dried, and in the form of a red cake or powder. 1.0 ml of HRP diluent (red solution) was added to produce a concentrated stock solution. It was incubated for 5 min at room temperature and mixed gently occasionally for complete dissolution. To make the final working solution, please add the complete 1.0 ml volume of recombinant HRP-Linked Antibody to 10.0 ml HRP Diluent in a clean tube.

Detection antibody diluent: green diluent, for reconstituting and diluting detection antibody.

HRP diluent: red diluent, for reconstituting and diluting HRP-linked antibody.

Sample diluent: blue diluent, for diluting cell lysates.

1× Washing buffer: by diluting 20× Washing buffer in purified water 3.5 ELISA 3.5.1 20 μl of the prepared cell lysate was added to the appropriate wells with 70 ul of antibody diluent sealed with tape and pressed firmly on top of the microwell. The plates were incubated at 37° C. for 2 h.

3.5.2 The tape was gently removed, and wells were washed: The plate contents were discarded into a container. Wells were washed 4 times with 1× Wash buffer, 200 μl per well per time. With each wash, please tap the microplate with sufficient strength on a fresh towel to remove residual solution from each well, but do not allow the wells to dry completely at any time. The bottoms of all wells were cleaned with a lint-free paper towel.

3.5.3 100 μl of reconstituted detection antibody (green) was added to each well. The wells were sealed with tape, and the plate was incubated at 37° C. for 1 h.

3.5.4 The washing program was repeated.

3.5.5 100 μl of reconstituted HRP-Linked secondary antibody (red) was added to each well, and the wells were sealed with tape, and the plate was incubated at 37° C. for 30 min.

3.5.6 The washing program was repeated.

3.5.7 100 μl of TMB substrate was added to each well. The wells were sealed with tape, and the plate was incubated for 10 min at 37° C. or 30 min at 25° C.

3.5.8 100 μl of STOP solution was added to each well. The plate was shaken gently for a few seconds. The absorbance at 450 nm was read by the microplate reader.

4. Test Results

Compound A46 was used as the test compound, and the results showed that the inhibition rate of AR protein in Lncap cell line varied with concentration, indicating that the compound had a good inhibitory effect on AR activity. According to the statistics of the data of this group, the $IC_{50}$ of compound A46 (the drug concentration at 50% inhibition) was 49 nM.

Activity Assay Example 7: In Vivo Efficacy of Compounds on Acne in Female Golden Hamsters 1. Test object: The flank sebaceous glands of golden hamster are androgen-dependent organs, and testosterone propionate (male hormone) promotes the enlargement of sebaceous glands. This experiment is mainly to study the inhibitory effect of CB-03-01 (positive drug), Flutamide (positive drug) and the compound on sebaceous gland enlargement in female golden hamster acne model (androgen dependence), to further observe the in vivo drug efficacy of the compound, to provide the basis for clinical trials of androgen-induced acne symptoms.

2. Test Material:

2.1 Test Article

Androgen (Testosterone Propionate-TP); CB-03-01 (Clascoterone, CAS No. 19608-29-8); □ Flutamide (Flutamide, CAS No. 13311-84-7); compound A46 of the present invention.

2.2 Experimental Animals, See Table 4 for Details

TABLE 4

| Experimental animal information | |
|---|---|
| Strain species: | Golden hamster |
| Animal class: | Clean |
| Gender and number[a]: | Female, 72 |
| Mice age(Weight)[b]: | 7-8 weeks, 90-110 g |
| Animal origin: | Beijing Vital River Laboratory Animal Technology Co., Ltd. |
| Animal identification: | Picric acid label |

2.3 Administration Vehicle: Acetone.

3. Experimental Design

In this experiment, from 72 female golden hamsters, according to the size and body weight of sebaceous glands, golden hamsters were evenly distributed to each group, 6 mice per group, a total of 7 groups, and they were administered continuously for 21 days. Details of animal grouping and dosing regimen and other information are shown in Table 5 below:

TABLE 5

Trial groups and dosing regimen

| Group | Test substance | Test substance content | Animal number/ gender | Individual golden hamster Sebaceous glands left/right | Route of adminis-tration |
|---|---|---|---|---|---|
| 1 | Acetone/ 25 μL | | 6/F | Left (blank)/ right (acetone) | Skin smear |
| 2 | 12 μgTP/ 25 μL | | 6/F | Left (acetone)/ right (TP) | |
| 3 | (12 μgTP + 400 μgCB-03-01)/25 μL | 1.6% | 6/F | Left (acetone)/ right (TP + CB-03-01) | |
| 4 | (12 μgTP + 400 μgFlutamide)/ 25 μL | 1.6% | 6/F | Left (acetone)/ right (TP + Flutamide) | |
| 5 | (12 μgTP + 100 μgA46)/ 25 μL | 0.4% | 6/F | Left (acetone)/ right (TP + A46) | |
| 6 | (12 μgTP + 200 μgA46)/ 25 μL | 0.8% | 6/F | Left (acetone)/ right (TP + A46) | |
| 7 | (12 μgTP + 400 μgA46)/ 25 μL | 1.6% | 6/F | Left (acetone)/ right (TP + A46) | |
| 8 | (12 μgTP + 800 μgA46)/ 25 μL | 3.2% | 6/F | Left (acetone)/ right (TP + A46) | |

Note:
TP stands for testosterone propionate.

According to the protocol in the table, 25 Ml of drug was administered each time, it was evenly smeared on the sebaceous glands, and administered once a day.

Animal grouping and status observation: Before grouping, the body weight was weighed, and the sebaceous glands on both sides were shaved for the observation of the size of sebaceous glands. Animals were observed twice a day in the morning and afternoon during the administration period. On the 21st day after administration, the size of sebaceous glands and the body weight of animals were observed and recorded.

The size of the sebaceous glands is expressed by the area, and the vernier caliper recorded its long side (a) and short side (b), and the area of the sebaceous glands (S) is obtained from the formula for calculating the area of a rectangle. In model group and administration group, ΔS=S−S(vehicle). Growth inhibition rate (%)=(ΔS(acetone testosterone group)−ΔS (administration group))/ΔS(acetone testosterone group)*100%.

Figure 3:
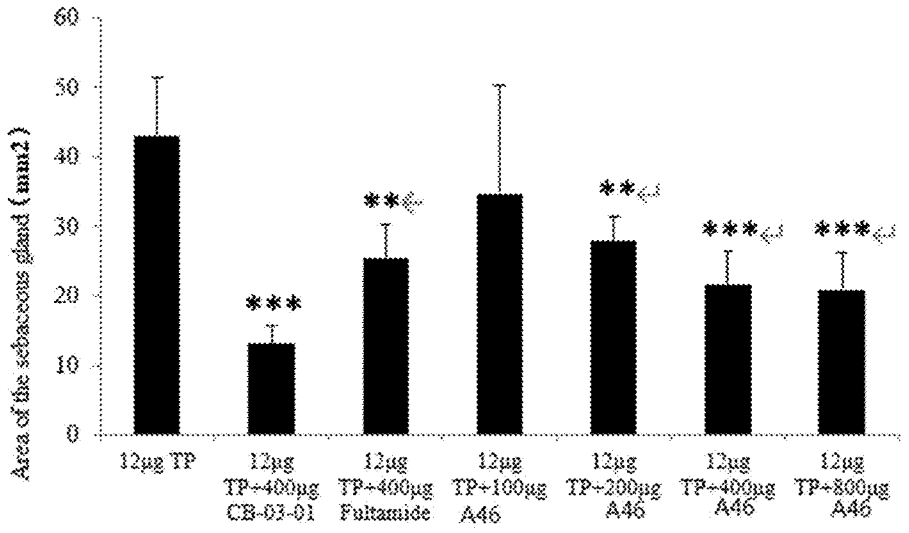
FIG. 3 is the inhibitory result of the compounds of the present invention on the growth of sebaceous gland plaques in female golden hamsters.

4. Test Results 4.1 Inhibitory Effect on the Growth of Sebaceous Plaques in Female Golden Hamsters The test results are shown in FIG. 3. From the experimental results in FIG. 3, it can be seen that after 21 days of testosterone propionate (TP) administration, the sebaceous plaques of female golden hamsters became significantly larger, and the area reached 40-50 $mm^2$. Compared with the model group, the growth inhibition rates of sebaceous gland plaques in the positive drug CB-03-01 (400 g, 1.6%) and Flutamide (400 g, 1.6%) groups were 69.53% (p<0.001) and 40.74% (P<0.01), respectively. The inhibition rate of the growth of sebaceous plaques in the 100 g (0.4%) dose group of A46 drug was 19.24% (P>0.05), and there was no obvious inhibitory effect. The growth inhibition rates of sebaceous plaques in the 200 g (0.8%), 400 g (1.6%) and 800 g (3.2%) dose groups of A46 were 35.20% (P<0.01), 49.54% (p<0.001), and 51.61% (P<0.001), respectively, and compared with the model group, there is a statistically significant difference. When the A46 was set as dose of 0.4%, 0.8%, 1.6%, and 3.2%, compared with the model group for acne efficacy, there was a statistically significant difference and an onset of efficacy at the 0.8% dose. Compared with the positive drugs, A46 drug 400 g (1.6%) and 800 g (3.2%) doses were both better than the drug Flutamide (400 g, 1.6%) in inhibiting the sebaceous plaque area.

The inhibitory effect of A46 compound on the increase of the sebaceous gland plaque area of golden hamster caused by androgen after 21 days of administration is shown in Table 6 below:

TABLE 6

| The inhibition rate of the compounds on the growth of sebaceous plaques in golden hamsters | The inhibition rate of the growth of sebaceous plaques (%) |
|---|---|
| Testosterone propionate (12 μg) + CB-03-01(400 μg) | 69.53 |
| Testosterone propionate(12 μg) + Flutamide(400 μg) | 40.74 |
| Testosterone propionate(12 μg) + A46(100 μg) | 19.24 |
| Testosterone propionate(12 μg) + A46(200 μg) | 35.20 |
| Testosterone propionate(12 μg) + A46(400 μg) | 49.54 |
| Testosterone propionate(12 μg) + A46(800 μg) | 51.61 |

4.2 Effects on Body Weight of Female Golden Hamsters

Figure 4:
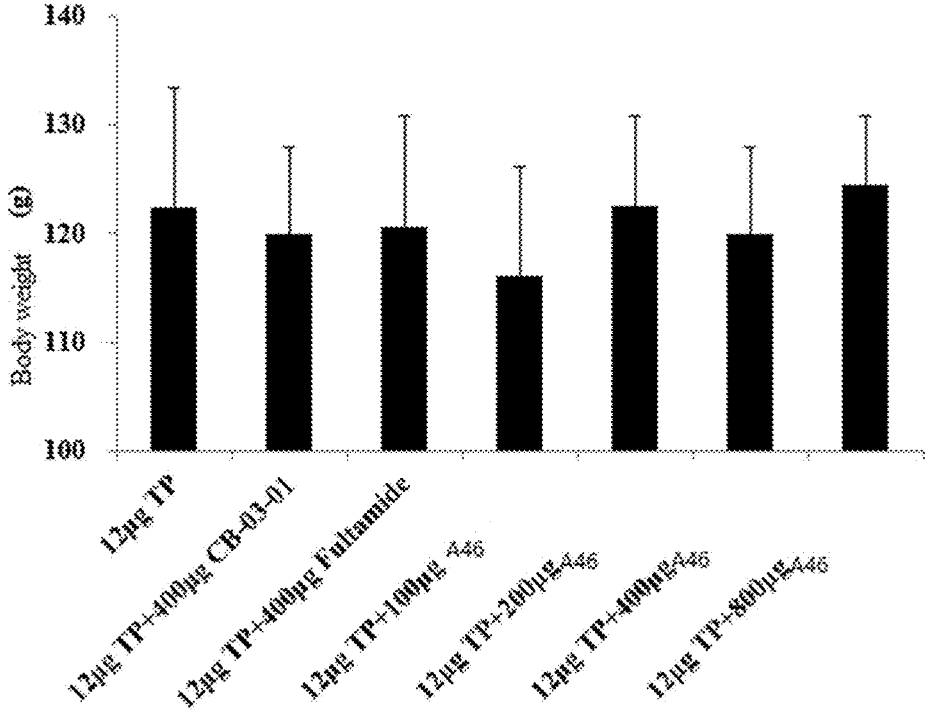
FIG. 4 shows the effect of the compounds of the present invention and their reference drugs on the body weight of golden hamsters on the 21st day after administration.

Before the start of the experiment, there was no significant difference in the body weight of the golden hamsters in each group. After the start of the experiment, the body weight of each group showed a slow increasing trend, and on the 21st day of the experiment, there was no significant difference in the body weight of the hamsters in each group. It is suggested that the transdermal administration of all subjects at the set concentrations does not significantly affect the body weight of mice (as shown in FIG. 4).

Activity Assay Example 8: Hair Regeneration Effects of Compounds on Androgenic Alopecia C57 Mouse Model 1. Objective The purpose of this study was to compare the effect of the compounds prepared by the present invention as AR protein degraders on hair regrowth in an androgenetic alopecia model in C57BL/6J mice by transdermal application route of administration, and to provide data to support subsequent clinical trials.

2. Experimental Principle

Subcutaneous injection of a dose of dihydrotestosterone (DHT) solution into mice after depilatory treatment with depilatory cream resulted in delayed hair regrowth, which is used to simulate AR-mediated androgenetic alopecia model. The compound of the present invention, as a degradation agent of AR protein, can reflect to some extent its efficacy in promoting hair growth in AR-mediated androgenetic alopecia models.

3. Test Compound

Name of test compound I: dihydrotestosterone DHT; name of test compound II: compound A46 of the present invention; name of test compound III: minoxidil.

4. Experimental animals: strain: C57BL/6N mice; age: 6-7 weeks; gender: male; number of animals: 70 (10 for later use); rearing environment: specific pathogen-free (SPF).

5. Experimental design 5.1 Model establishment 70 mice were deeply anesthetized, and the hair on the back of the mice was removed with an animal shaver, then the depilatory cream (Veet https://item.jd.com/6291245.html) was smeared evenly on the surface of the mice skin, and left 7-10 minutes. Then the hair was gently scraped off with a hair removal scraper against the direction of the hair, and finally the residual hair removal cream on the skin surface was fully washed with water to avoid burning the mice skin.

5.2 Grouping

This experiment was divided into 6 groups, and the DHT administration started on the day of hair removal, A46 is administered on day 2 after hair removal and is counted as day 1 (the day of hair removal is counted as day 0). 36 mice in good condition were randomly selected and grouped as shown in Table 7:

TABLE 7

Groups of mice and dose regimen

| Group | Number | Test substance | Administration dosage | Test substance concentration | Administration volume | Route of administration | Schedule |
|---|---|---|---|---|---|---|---|
| 1 | 6 | Vehicle | — | — | 150 μl | Skin smear | QD × 17 |
| 2 | 6 | DHT | 30 mg/kg | 6 mg/ml | 100 μl/20 g | Subcutaneous injection | QD × 17 |
| 3 | 6 | DHT | 30 mg/kg | 6 mg/ml | 100 μl/20 g | Subcutaneous injection | QD × 17 |
| | | Minoxidil | 5% | 50 mg/ml | 150 μl | Skin smear | BID × 17 |
| 4 | 6 | DHT | 30 mg/kg | 6 mg/ml | 100 μl/20 g | Subcutaneous injection | QD × 17 |
| | | A46 | 0.5% | 5 mg/ml | 150 μl | Skin smear | BID × 17 |
| 5 | 6 | DHT | 30 mg/kg | 6 mg/ml | 100 μl/20 g | Subcutaneous injection | QD × 17 |
| | | A46 | 1% | 10 mg/ml | 150 μl | Skin smear | BID × 17 |
| 6 | 6 | DHT | 30 mg/kg | 6 mg/ml | 100 μl/20 g | Subcutaneous injection | QD × 17 |
| | | A46 | 3% | 30 mg/ml | 150 μl | Skin smear | BID × 17 |

5.3 Test Compound Preparation Method

Drug preparation methods and storage conditions are shown in Table 8 below;

TABLE 8

Test drug preparation method

| Test drug | Preparation method | Concentration | Storage conditions | Frequency of preparation |
|---|---|---|---|---|
| Vehicle | 75% ethanol, 15% glyceryl tri(2-ethylhexanoate) and 10% glycerol were mixed by vortex. | — | 4° C. | Once a week |
| DHT | The quantitative DHT was weighed into a 2 ml centrifuge tube, first added with 50% of the final volume of DMSO for dissolution, and then added with 50% of the final volume of glycerol. | 6 mg/mL | 4° C. | Once a week |
| Minoxidil | 50 mg minoxidil was weighed into a 2 ml centrifuge tube, and added with 75% ethanol, 15% glyceryl tri(2-ethylhexanoate) and 10% glycerol. | 50 mg/mL | 4° C. | Prepare for immediate use |
| A46 | 5, 10, and 30 mg of three doses of A46 was weighed into a 2 ml centrifuge tube, added with 75% ethanol, 15% glyceryl tri(2-ethylhexanoate) and 10% glycerol, and ultrasonicated for 1 min to obtain a solution. | 5 mg/mL<br>10 mg/mL<br>30 mg/mL | 4° C. | Prepare for immediate use |

5.4 Observation and Measurement Indicators

1) Body weight/g: From the first day of administration, body weight was weighed and recorded twice a week.
2) Hair regeneration (anagen) score (0 points: no darkening of skin color in all areas; 1 point: darkening of gray skin color areas; 2 points: visible short hair; 3 points: thin hair; 4 points: thick hair; 5 points: full hair growth).

All mice were photographed on day 1 after hair removal, and then photographed and scored daily from day 4 until the end of the experiment.

3) At the end of the experiment, skin and blood collection operations were performed as needed.

5.5 Criteria for Drug Withdrawal and Experiment Termination

The in vivo experiment portion of an individual animal or the entire group of animals will be terminated when the following occurs. Animals will be euthanized before death or coma.

When the animal's health continues to deteriorate and the animal suffers continuous pain and is unable to eat or drink; or when the animal is emaciated and loses more than 20% of its body weight.

5.6 Statistical Analysis

Data are presented as average±standard error (AVE±SEM). One-way multi-level analysis of variance was used for statistics. The comparison between each drug group and the model group was performed by Stundent's t-test or rank sum test, and the p value was calculated. $p<0.05$ means there is a significant difference between the two groups, $p<0.01$ means there is a extremely significant difference between the two groups.

6. Experimental Results

There are 6 groups in this experiment, namely Vehicle, DHT (30 mg/kg) concentration group, DHT (30 mg/kg)+minoxidil 5% concentration group, DHT (30 mg/kg)+A46 0.5% concentration group, DHT (30 mg/kg)+A46 1% concentration group and DHT (30 mg/kg)+A46 3% concentration group. The results of hair regeneration effect on the C57 mouse androgenetic alopecia model are shown in Table 9 below:

TABLE 9

| Hair regeneration effect on C57 mouse androgenetic alopecia model (AVER, n = 6) | | | | | | | | |
|---|---|---|---|---|---|---|---|---|
| Group | 0 day | 3 days | 5 days | 7 days | 10 days | 12 days | 14 days | 17 days |
| Vehicle | 0.00 | 0.00 | 0.17 | 0.83 | 2.33 | 3.00 | 3.67 | 4.50 |
| DHT30 mpk | 0.00 | 0.00 | 0.00 | 0.00 | 0.00 | 0.00 | 0.17 | 0.50 |
| DHT30 mpk-minoxidil 5% | 0.00 | 0.00 | 0.00 | 0.00 | 0.33 | 0.67 | 1.67 | 2.33 |
| DHT30 mpk-A46 0.5% | 0.00 | 0.00 | 0.00 | 0.00 | 0.33 | 0.50 | 1.00 | 1.67 |
| DHT30 mpk-A46 1% | 0.00 | 0.00 | 0.00 | 0.00 | 0.33 | 0.83 | 1.50 | 2.00 |
| DHT30 mpk-A46 3% | 0.00 | 0.00 | 0.00 | 0.00 | 0.50 | 1.17 | 1.83 | 2.83 |

It can be seen from the results that the DHT (30 mg/kg) concentration group had a hair development score of 0.5 after 17 days of administration, with almost no hair development, which was significantly lower than the Vehicle group, indicating successful modeling. The average score of the DHT (30 mg/kg)+minoxidil 5% concentration group was 2.33, which was significantly higher than that of the DHT (30 mg/kg) model group, showing a good hair growth effect. Compared with the DHT (dihydrotestosterone) group in the model group, the DHT (30 mg/kg)+A46 0.5% concentration group had a slightly higher score, but there was no statistical difference. The scores of the A46 1% concentration dose and 3% concentration dose groups at Day 17 were roughly comparable to those of the 5% minoxidil group, and the scores were significantly different from those of the DHT (dihydrotestosterone) group ($p<0.05$; $p<0.01$).

(2) Body Weight Change

Figure 5:
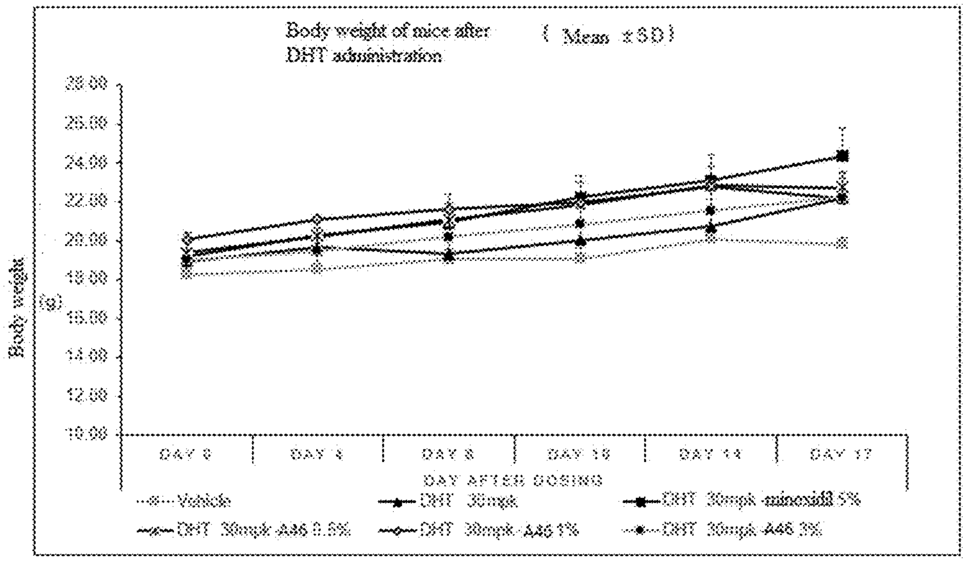
FIG. 5 is a graph showing the effect of the compounds of the present invention and their reference drugs on the body weight of C57BL/6 mice after administration.
Figure 6:
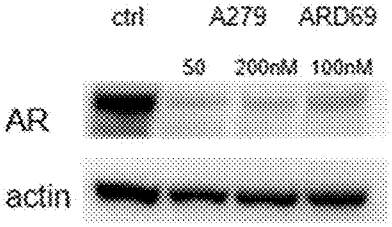
FIG. 6 is a comparison of the results of the degradation experiment of the compound A279 of the present invention and the positive compound ARD-69 on the AR protein of LNCaP cells.
Figure 7:
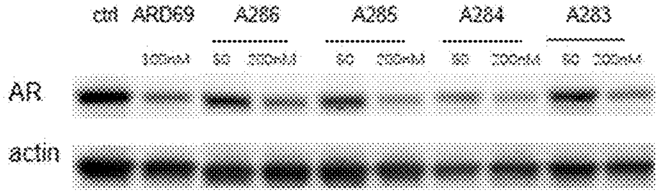
FIG. 7 is a comparison of the results of the degradation experiment of the compounds A283-A286 of the present invention and the positive compound ARD-69 on the AR protein in LNCaP cells.
Figure 8:
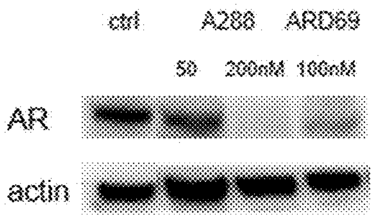
FIG. 8 is a comparison of the results of the degradation experiment of the compound A288 of the present invention and the positive compound ARD-69 on the AR protein in LNCaP cells.
Figure 9:
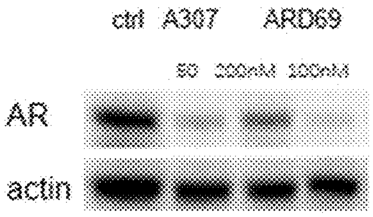
FIG. 9 is a comparison of the results of the degradation experiment of the compound A307 of the present invention and the positive compound ARD-69 on the AR protein in LNCaP cells.
Figure 10:
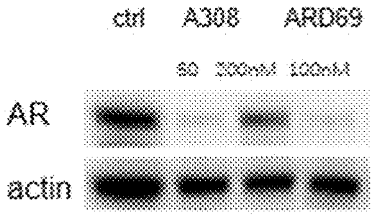
FIG. 10 is a comparison of the results of the degradation experiment of the compound A308 of the present invention and the positive compound ARD-69 on the AR protein in LNCaP cells.
Figure 11:
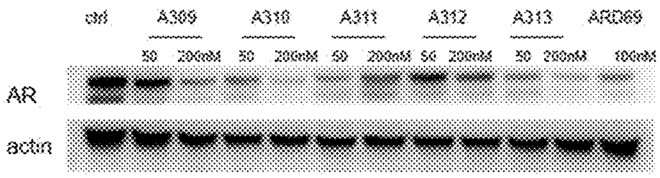
FIG. 11 is a comparison of the results of the degradation experiment of the compounds A309-A313 of the present invention and the positive compound ARD-69 on the AR protein in LNCaP cells.
Figure 12:
FIG. 12 is a comparison of the results of the degradation experiment of the compounds A314, A315, A317 and A318 of the present invention and the positive compound ARD-69 on the AR protein in LNCaP cells.
Figure 13:
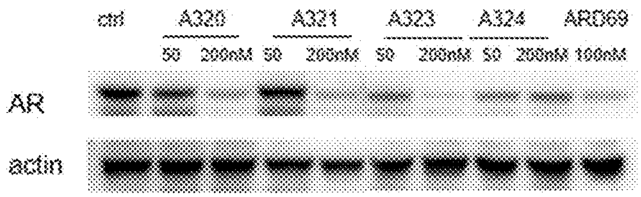
FIG. 13 is a comparison of the results of the degradation experiment of the compounds A320-A324 and A318 of the present invention and the positive compound ARD-69 on the AR protein in LNCaP cells.
Figure 14:
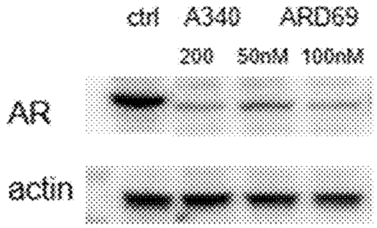
FIG. 14 is a comparison of the results of the degradation experiment of the compounds A340 of the present invention and the positive compound ARD-69 on the AR protein in LNCaP cells.
Figure 15:
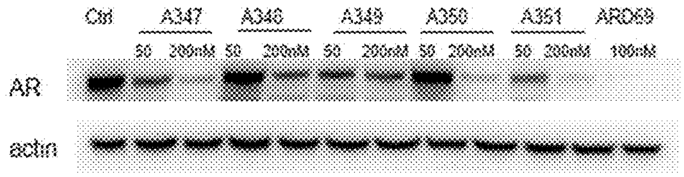
FIG. 15 is a comparison of the results of the degradation experiments of the compounds A347-A351 and A318 of the present invention and the positive compound ARD-69 on the AR protein in LNCaP cells.
Figure 16:
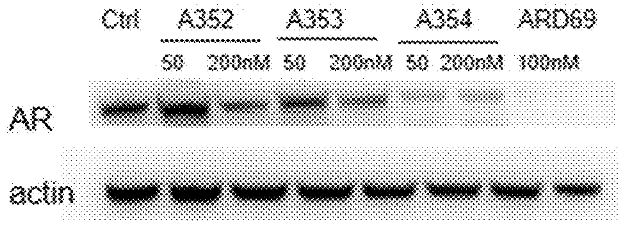
FIG. 16 is a comparison of the results of the degradation experiments of the compounds A352-A354 and A318 of the present invention and the positive compound ARD-69 on the AR protein in LNCaP cells.
Figure 17:
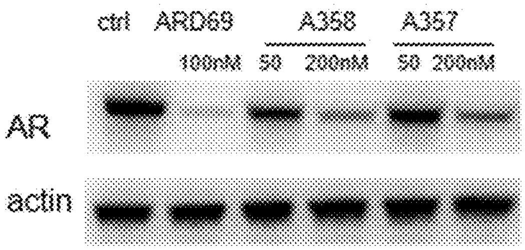
FIG. 17 is a comparison of the results of the degradation experiments of the compounds A357-A358 and A318 of the present invention and the positive compound ARD-69 on the AR protein in LNCaP cells.

The results of the changes in the body weight of the mice during the entire administration period are shown in FIG. 5. It can be seen from the figure that during the entire administration period, the body weight of all the subject groups and the control groups remained stable and increased slightly, indicating that transdermal administration of all the subjects at the set concentration did not affect the body weight of the mice, indicating that the drug is safe.

Activity Assay Example 9: Distribution of Compounds in Sebaceous Glands and Blood in Golden Hamsters 6 male golden hamsters were selected for the experiment and divided into two groups (three in each group). The drug was administered by a single smear route. All animals fasted overnight before administration. The specific animal grouping, administration and sampling schedule are shown in Table 8-1 below:

TABLE 10

| Animal grouping, administration and sampling schedule | | | | | |
|---|---|---|---|---|---|
| | | | Dosage of administration [a] | | |
| Grouping | Animal No. | Route of adminis-tration | Adminis-tration volume (ml) | Drug concen-tration mg/ml | Blood Collection Time Point (h) |
| 1 | 1, 2, 3 | Single smear | 0.02*2 | 30 | 0.25, 0.5, 1, 2, 4, 6, 8 h |
| 2 | 4, 5, 6 | Single smear | 0.02*2 | 100 | 0.25, 0.5, 1, 2, 4, 6, 8 h |

1.1 Experimental Method 1.1.1 Dosage of Administration

A46 was weighed into a 50 ml centrifuge tube, added with mixed solvent (75% ethanol, 15% glyceryl tri(2-ethylhexanoate) and 10% glycerol), vortexed and heated at 60° C. until A46 was completely dissolved. A46 was prepared at a concentration of 30 mg/mL, 100 mg/mL, and stored at room temperature in the dark.

In group 1, the dosage for smear administration was 1.2 mg, corresponding to an administration volume of 30 mL/kg. In group 2, the dosage for smear administration was 4 mg, and the administration volume was 100 mL/kg.

1.1.2 Method of Administration

During the experiment, the 2 sebaceous glands of all the hamsters were coated with the corresponding medicinal solution (the dosage was about 0.02 mL).

1.1.3 Observation of Animal Status

Immediately after administration, whether the animals have abnormal reactions was observed. If there were no abnormal reactions, the animals were observed twice during the experiment. If any abnormal reactions were found, the number of observations was recorded and increased in time until the animals returned to normal, or the experiment ended.

1.1.4 Sample Collection and Storage

All experimental animals were fasted overnight before administration, and blood was collected at corresponding time points into blood collection tubes containing heparin sodium anticoagulant after administration. After collection of whole blood, the blood collection tube was immediately shook gently and placed on ice, then centrifuged (4° C., 4000 rpm, 10 min) to collect the supernatant plasma sample (plasma volume ≥100 μL), and the supernatant plasma sample was stored at −80° C. before analysis. Plasma sample was collected for 8 h.

1.2 Experimental Results

The experimental results showed that even in group 2 (that is, the dosage of administration was 4 mg), only one out of 3 animals had a maximum blood concentration of 10.6 ng/ml at each sampling time point of 0.25, 0.5, 1, 2, 4, 6, and 8 h, and the remaining 2 were below the detection limit of 2 ng/ml.

The mean drug concentration in sebaceous glands after 8 h was 13513 (ng/ml) in group 1 (i.e., dose of 1.2 mg) and 24223 (ng/ml) in group 2 (i.e., dose of 4 mg) when the left and right sebaceous gland sites were collected. Comparing the concentrations of the drug in blood and sebaceous glands, it can be concluded that the compounds of the present invention can enter into the sebaceous glands, but cannot enter the blood. It is shown that, while achieving efficacy by dermal application, the compounds of the present invention are also effective in avoiding systemic exposure in order to reduce or avoid the side effects of oral androgen signal pathway inhibitors.

Activity Assay Example 10: Comparison of Degradation Effect of the Compound and the Positive Control Compound on AR Protein in LNCaP Cells 1. Experimental Materials LNCaP: LNCaP (human prostate cancer) was purchased from the Chinese Academy of Sciences Cell Bank and cultured in RPMI-1640 medium containing 10% fetal bovine serum. Lncap cells were routinely cultured in a $CO_2$ incubator at 37° C. with 5% saturated humidity. When cultured to about 80% coverage, the cells were passaged at a ratio of 1:3.

2. Experimental Reagents

| Experimental reagents | Brand | Catalogue number |
|---|---|---|
| Phosphate buffer (PBS) | Hyclone | SH30256.01 |
| High efficiency RIPA tissue/ cell rapid lysate | Solarbio | R0010 |
| Proteasome inhibitor PMSF | meilunbio | MA0001 |
| Skim milk powder | BioFROXX | 1172GR500 |
| Polyvinylidene fluoride (PVDF) membrane | Immobilon | ISEQ00010 |
| BCA protein quantification kit (Pierce BCA protein assay kit) | Thermo | VK312555 |
| SDS-PAGE protein loading buffer (5X) | Btosharp | 681274 BL502A |
| Polyacrylamide fast protein electrophoresis precast gels | GenScript | M00666 |
| Androgen receptor rabbit mAb | CST | 5153S |
| β-Actin Mouse mAb | CST | 3700S |
| Goat Anti-Rabbit IgG H&L | Abcam | ab6721 |
| Goat Anti-Mouse IgG H&L | Abcam | ab6789 |
| Horseradish Peroxidase Chemiluminescent Substrate (Immobilon Western Chemiluminescent HRP Substrate) | Millipore | WBKLS0100 |
| ARD-69 | Homemade | CAS# 2316837-10-0 |

Note:
Synthesis of ARD-69 with reference to the article J. Med. Chem. 2019. 62, 2, 941-964

3. Instrument for Use

| Instrument for use | Model |
|---|---|
| Microplate reader | BioTek Synergy H1 Hybrid reader |
| Chemiluminescence gel imager | AllianceQ9 Advance |

4. Western Blot Steps 4.1 Cell Culture:

The Lncap cells cryopreserved in a liquid nitrogen tank was taken, and the cells were recovered and cultured to the logarithmic phase of growth and plated into a 6-well plate (about 10^6 cells per well), and treated with drug 4.2 Drug Treatment An appropriate amount of the compound was weighed and dissolved in DMSO solvent, mixed by vortex, and configured into a 10 mM stock solution. Drugs were added to Lncap cells respectively. The control group was treated with DMSO only, and the drug treatment groups were treated with the corresponding compounds respectively, and the final action concentrations were 50 nM and 200 nM, respectively, and the concentration of ARD-69 in the positive control group was 100 nM. Cells were collected after 24 h.

4.3 Cell Collection

The six-well plate of cells treated with compounds and other untreated cell lines were taken out, and the medium was discarded. The cells were washed with PBS, digested by trypsin, digestion terminated, blown, centrifuged, and washed with PBS again, and PBS was completely discarded.

4.4 Cell Lysis and Protein Collection

The collected cells were added with an appropriate amount of lysis solution (the proteasome inhibitor PMSF was added to the lysis solution), lysed on ice for 30 min, and centrifuged at 12,000 rpm for 20 min, and the supernatant was taken.

4.5 Determination of Total Protein by BCA Method

① Standard protein with gradient concentrations was prepared, and 20 μL was taken into a 96-well plate, and a duplicate well for each standard was made.

② 2 μL of protein lysate was taken and dissolved in 18 μL of PBS, and a duplicate well for each sample was made.

③ 200 μL of BCA working solution was added to each well and incubated at 37° C. for 30 min.

④ the absorbance at 562 nm was measured.

⑤ the protein concentration of each sample was calculated, and the required protein lysate volume for 50 μg protein was calculated.

4.6 Measurement of Protein Expression Level by Western Blot

Denaturation: The protein lysate was taken, added with an appropriate amount of 5× protein loading buffer, and denatured at 100° C. for 5 min.

Electrophoresis: 10% precast gel was used for electrophoresis at 200V for 30 min;

Membrane transfer: The stacking gel was cut off, and the proteins on the separation gel were transferred to PVDF membrane by wet transfer method at 270 mA for 2 h.

Blocking: The PVDF membrane was blocked in 5% skim milk at room temperature for 1 h.

Primary antibody: The PVDF membrane was cut according to the molecular weight of Mark, put in AR and 3-Actin antibodies, and incubated overnight at 4° C. on a shaker.

Membrane washing: The PVDF membrane was placed in PBST and washed 4 times with shaking on a shaker, 6 min each time.

Secondary antibody: The PVDF membrane was put in the secondary antibodies (goat anti-rabbit and goat anti-mouse) solution corresponding to AR and 3-Actin antibodies, and incubated at room temperature for 1-2 hours with shaking on a shaker.

Membrane washing: The PVDF membrane was placed in PBST and washed 4 times with shaking on a shaker, 6 min each time.

Exposure: The developer excites the fluorescence on PVDF.

The obtained experimental results are shown in FIG. 6-17, which shows that the compounds provided by the present invention have a good degradation effect on the AR protein in LNCaP cells (basically reaching or better than the degradation effect of ARD-69), indicating that the compounds of the present invention have the ability to become anti-tumor medicines, especially for prostate cancer treatment.

The content of the present invention merely illustrates some specific examples claimed, wherein the technical features recorded in one or more technical solutions can be combined with any one or more technical solutions, and the technical solutions obtained by the combination of these technical solutions are also within the protection scope of the present application, just as the technical solutions obtained by the combination have been specifically described in the disclosure of the present invention.

The invention claimed is:

1. Bifunctional compounds represented by formula (III) or pharmaceutically acceptable salts, stereoisomers thereof:

ABM-L-VLM (III), wherein ABM is selected from the following structures, wherein  represents the point of attachment of the linking moiety:

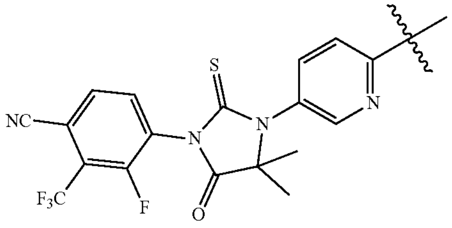

and

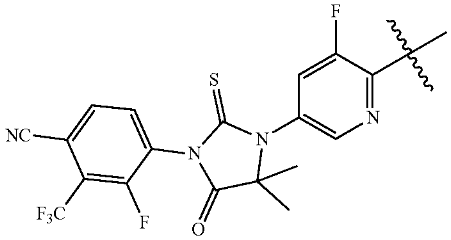

,

L is the chemical linking moiety connecting ABM and VLM, and L is selected from $—O—(CH_2)_m—O—(CH_2)_n—CO—$, $—O—(CH_2)_m—O—(CH_2)_n—O—(CH_2)_o—CO—$, $-(Cy)_q-O—(CH_2)_m—O—(CH_2)_n—CO—$, and $-(Cy)_q-O—(CH_2)_m—O—(CH_2)_n—O—(CH_2)_o—CO—$, wherein Cy is selected from $C_{6-10}$ aryl, $C_{3-6}$ heteroaryl, $C_{3-6}$ cycloalkyl and $C_{3-6}$ heterocycloalkyl, and Cy is optionally substituted with 1, 2 or 3 $R^{Cy}$, and each $R^{Cy}$ is independently selected from: hydrogen, halogen, cyano, $C_{1-3}$ alkyl or $C_{1-3}$ alkoxy optionally substituted with halogen;

wherein m, n, o are each independently selected from: 1, 2, 3, 4; and

VLM is

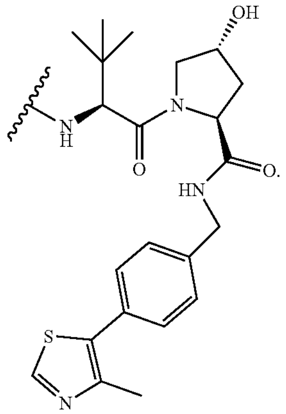 [SMILES: *N[C@H](C(=O)N1C[C@H](O)C[C@H]1C(=O)NCc1ccc(-c2scnc2C)cc1)C(C)(C)C]

2. The bifunctional compounds according to claim 1, wherein L is selected from the following groups:

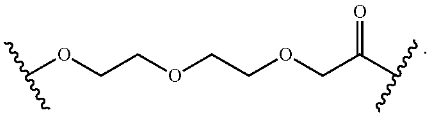 [SMILES: *OCCOCCOCC(*)=O]

3. The bifunctional compounds of claim 1, wherein the compounds are selected from:

A46

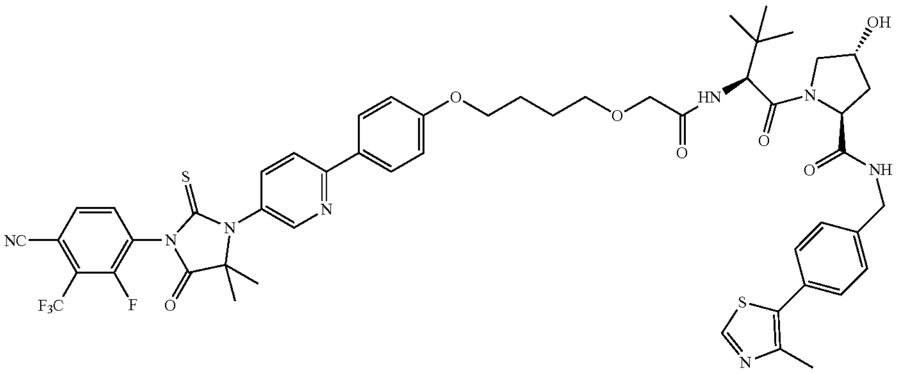 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2)C(C)(C)C)cc1]

-continued

A99

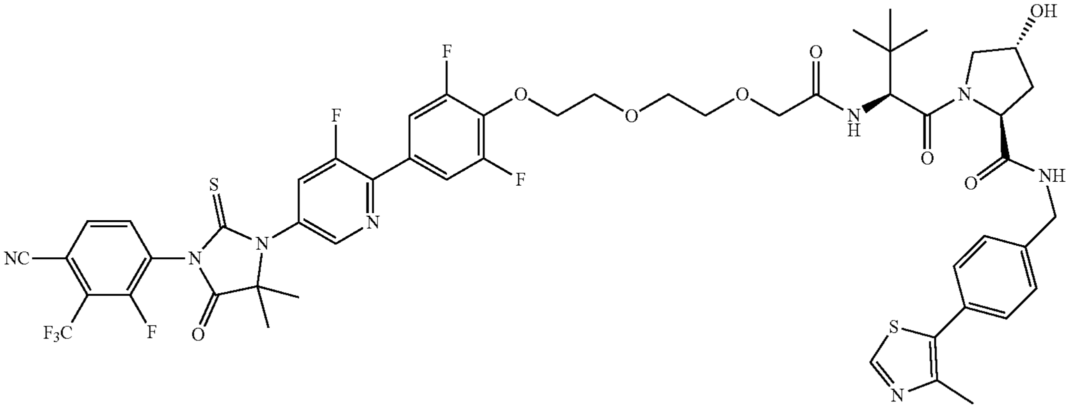 [SMILES: Cc1ncsc1-c1ccc(CNC(=O)[C@@H]2C[C@@H](O)CN2C(=O)[C@@H](NC(=O)COCCOCCOc2c(F)cc(-c3ncc(N4C(=S)N(c5ccc(C#N)c(C(F)(F)F)c5F)C(=O)C4(C)C)cc3F)cc2F)C(C)(C)C)cc1]

A100

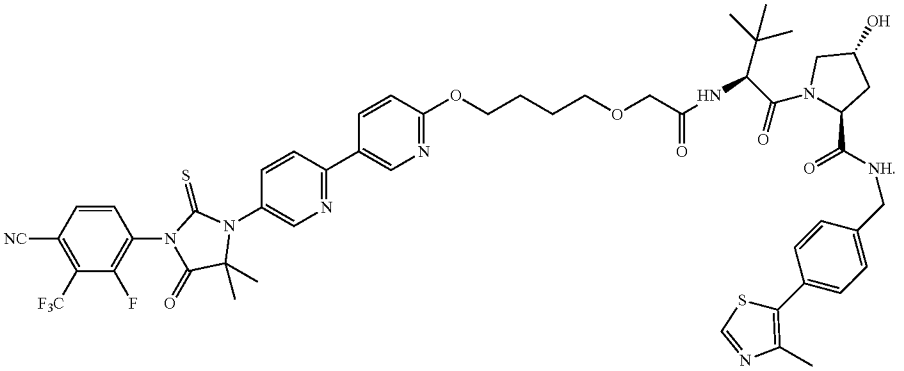 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cn2)C(C)(C)C)cc1]

4. The bifunctional compounds of claim 1, wherein the compound is:

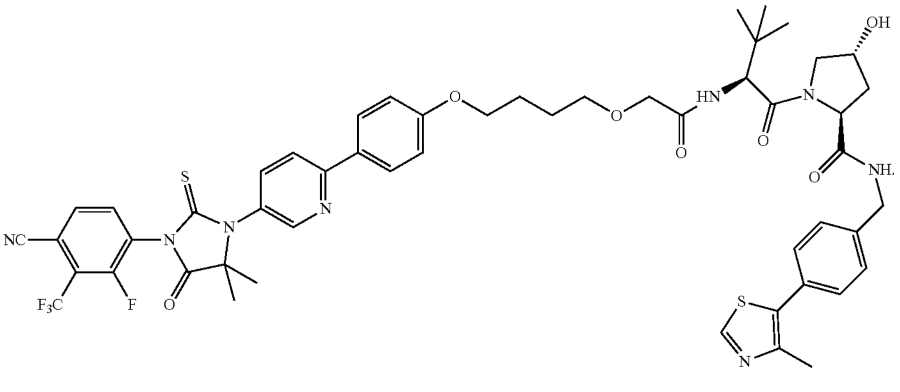 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5F)C(=O)C4(C)C)cn3)cc2)C(C)(C)C)cc1]

5. A pharmaceutical composition comprising an effective amount of the bifunctional compounds according to claim 1 or the pharmaceutically acceptable salts, stereoisomers thereof, and pharmaceutically acceptable carriers.

6. The pharmaceutical composition according to claim 5, further comprising at least one other biologically active agent.

7. The pharmaceutical composition according to claim 6, wherein the other biologically active agent is an anticancer agent.

8. A method of recruiting endogenous proteins to E3 ubiquitin ligases for degradation in a subject in need thereof, the method comprising administrating the bifunctional compounds according to claim 1 or the pharmaceutically available salts, stereoisomers thereof.

9. A method of degrading or inhibiting androgen receptors in a subject in need thereof, the method comprising administrating the bifunctional compounds according to claim 1 or the pharmaceutically available salts, stereoisomers thereof.

10. A method of treating or preventing a disease associated with recruitment of endogenous proteins to E3 ubiquitin ligases or androgen receptors in a subject in need thereof, the method comprising administrating the bifunctional compounds according to claim 1 or the pharmaceutically available salts, stereoisomers thereof.

11. The method according to claim 10, wherein the disease associated with the recruitment of endogenous proteins to E3 ubiquitin ligases or androgen receptors is selected from: acne, hirsutism, sebaceous gland enlargement, alopecia, asthma, multiple sclerosis, cancer, Kenney's disease, ciliopathies, cleft palate, diabetes, heart disease, high blood pressure, inflammatory bowel disease, mental retardation, mood disorders, obesity, refractive errors, infertility, Angelman syndrome, Canavan disease, celiac disease, Charcot-Marie-Tooth disease, cystic fibrosis, Duchenne muscular dystrophy, hemochromatosis, hemophilia, Klinefelter's syndrome, neurofibromatosis, phenylketonuria, polycystic kidney disease (PKD1) or 4 (PKD2), Prader-Willi syndrome, sickle cell disease, Tay-Sachs disease, Turner syndrome;

the cancers are squamous cell carcinoma, basal cell carcinoma, adenocarcinoma, hepatocellular carcinoma and renal cell carcinoma; cancers of bladder, bowel, breast, cervix, colon, esophagus, head, kidney, liver, lung, neck, ovary, pancreas, prostate and stomach; leukemia; benign and malignant lymphomas, especially Burkitt's lymphoma and Non-Hodgkin's lymphoma; benign and malignant melanoma; myeloproliferative diseases; sarcomas, including Ewing's sarcoma, hemangioendothelioma, Kaposi's sarcoma, liposarcoma, sarcoma, peripheral neuroepithelial tumor, synovial sarcoma, glioma, astrocytoma, oligodendroglioma, ependymoma, glioblastoma, neuroblastoma, ganglioglioma, medulloblastoma, pineal cell tumor, meningioma, meningiosarcoma, neurofibromas and Schwannomas; intestinal cancer, breast cancer, prostate cancer, cervix cancer, uterine cancer, lung cancer, ovarian cancer, testicular cancer, thyroid cancer, astrocytoma, esophageal cancer, pancreatic cancer, gastric cancer, liver cancer, colon cancer, melanoma; carcinosarcoma, Hodgkin's disease, Wilms tumor or teratoma.

12. The method according to claim 11, wherein the disease is cancer, acne, sebaceous gland enlargement, alopecia, or Kennedy's disease.

13. The method according to claim 12, wherein the disease is prostate cancer, acne, or alopecia.

* * * * *